US007371837B2

(12) United States Patent
Yuen et al.

(10) Patent No.: US 7,371,837 B2
(45) Date of Patent: May 13, 2008

(54) HUMAN VIRUS CAUSING RESPIRATORY TRACT INFECTION AND USES THEREOF

(75) Inventors: Kwok Yung Yuen, Hong Kong (CN); Chiu Yat Patrick Woo, Hong Kong (CN); Kar Pui Susanna Lau, Hong Kong (CN); Kwok Hung Chan, Hong Kong (CN)

(73) Assignee: The University of Hong Kong, Hong Kong (HK)

(*) Notice: Subject to any disclaimer, the term of this patent is extended or adjusted under 35 U.S.C. 154(b) by 212 days.

(21) Appl. No.: 11/129,741

(22) Filed: May 16, 2005

(65) Prior Publication Data

US 2006/0034853 A1 Feb. 16, 2006

Related U.S. Application Data

(63) Continuation-in-part of application No. 10/895,064, filed on Jul. 21, 2004.

(51) Int. Cl.

*C07H 21/02* (2006.01)
*C12N 15/00* (2006.01)
*A61K 39/00* (2006.01)
*A61K 39/12* (2006.01)

(52) U.S. Cl. ............... 536/23.1; 435/320.1; 530/185.1; 530/186.1

(58) Field of Classification Search ..................... None
See application file for complete search history.

(56) References Cited

U.S. PATENT DOCUMENTS

2005/0266397 A1* 12/2005 Exker et al. ................... 435/5

OTHER PUBLICATIONS

Zhao et al., "DNA Vaccine of SARS-Cov S Gene Induces Antibody Response in Mice"; Acta Biochim et Biophysica Sinica 2004, 36(1):37-41 CN 31-1300/Q.

Yount et al., "Systematic assembly of a full-length infectious cDNA of mouse hepatitis virus strain A59", Journal of Virology, vol. 76, No. 21, pp. 11065-11078 (Nov. 2002).

Entraz Accession No. NC 001846, Jul. 7, 1997.

Woo et al., "Phylogenetic and recombination analysis of coronavirus HKU1, a novel coronavirus from patients with pneumonia", Arch Virol., vol. 150, pp. 2299-2311 (2005).

* cited by examiner

*Primary Examiner*—Bruce Campell
*Assistant Examiner*—Bo Peng
(74) *Attorney, Agent, or Firm*—Dickstein Shapiro LLP

(57) ABSTRACT

The present invention provides the complete genomic sequence of a novel human coronavirus, coined as human coronavirus-HKU1 ("CoV-HKU1"), isolated in Hong Kong. The virus belongs to the order Nidovirales of the family Coronaviridae, being a single-stranded RNA virus of positive polarity. Further study on nasopharyngeal aspirates from patients with community-acquired pneumonia has revealed that there are two genotypes, genotype A and genotype B, for this virus. In addition to the genomic sequences of these two genotypes, the invention provides the deduced amino acid sequences of the complete genome of the CoV-HKU1. The nucleotide sequences and deduced amino acid sequences of the CoV-HKU1 are useful in preventing, diagnosing and/or treating the infection by CoV-HKU1. Furthermore, the invention provides immunogenic and vaccine preparations using recombinant and chimeric forms as well as subunits of the CoV-HKU1 based on the nucleotide sequences and deduced amino acid sequences of the CoV-HKU1.

8 Claims, 201 Drawing Sheets

Figure 4:
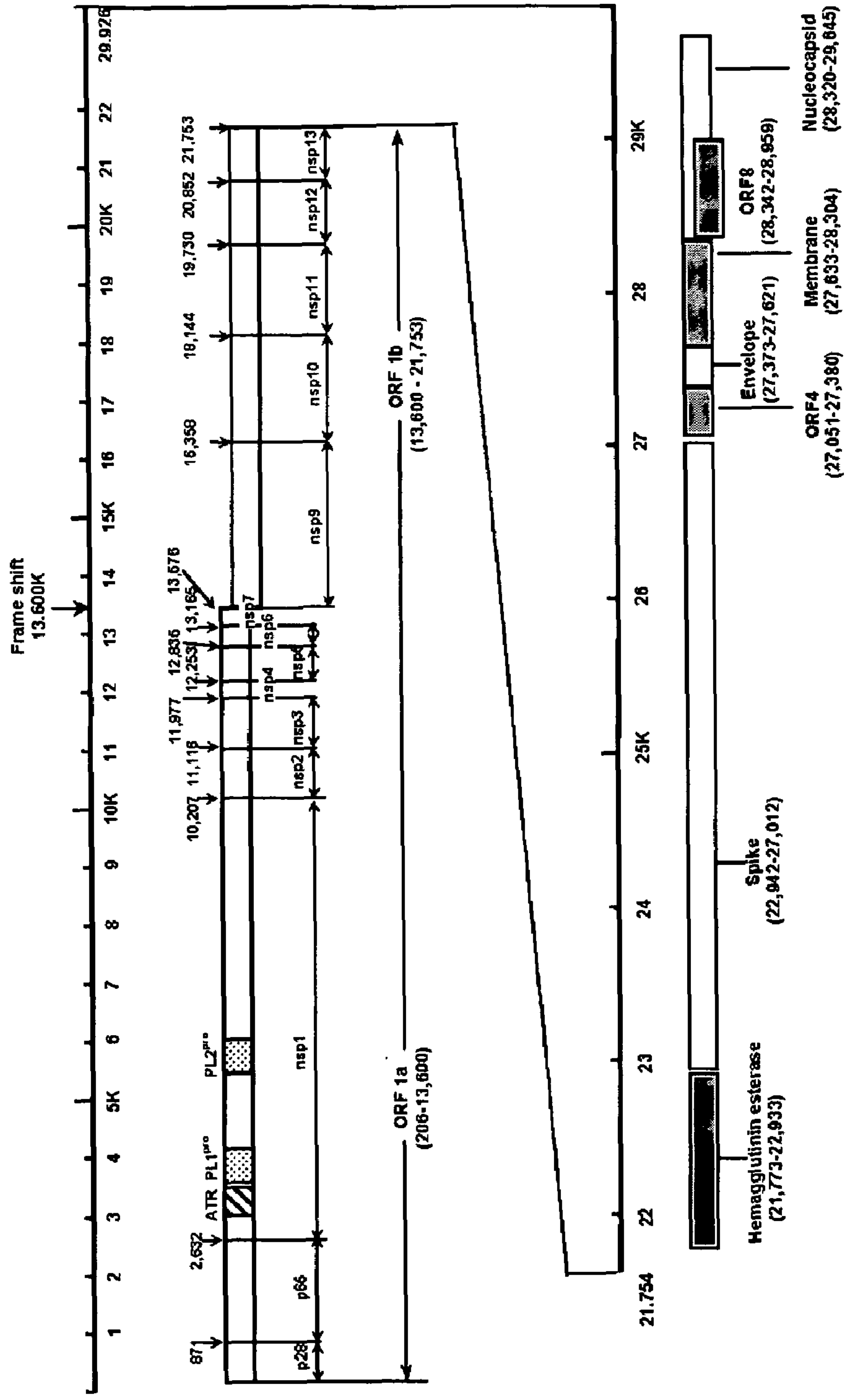

| | | | |
|---|---|---|---|
| SEQ:1 | 1 | TCGTGCTATGCCAAATATTTTGCGTATTGTTAGTAGTTTAGTTTTGGCCCGCAAACAT | 58 |
| SEQ:2 | 1 | R A M P N I L R I V S S L V L A R K H | 19 |
| | 59 | GAATTTTGTTGTTCACATGGTGATAGATTTTATCGCCTTGCGAATGAATGTGCTCAAGTT | 118 |
| | 20 | E F C C S H G D R F Y R L A N E C A Q V | 39 |
| | 119 | TTGAGTGAAATAGTTATGTGTGGCGGTTGCTATTATGTTAAGCCTGGTGGTACTAGCAGT | 178 |
| | 40 | L S E I V M C G G C Y Y V K P G G T S S | 59 |
| | 179 | GGTGATGCAACTACTGCTTTTGCTAATTCTGTTTTTAATATATGTCAGGCTGTTACTGCT | 238 |
| | 60 | G D A T T A F A N S V F N I C Q A V T A | 79 |
| | 239 | AATGTTTGTTCTCTTATGGCCTGTAATGGCCATAAGATTGAAGATTTAAGTATACGCAAT | 298 |
| | 80 | N V C S L M A C N G H K I E D L S I R N | 99 |
| | 299 | TTACAAAAACGCTTATACTCTAATGTTTATCGTACAGATTATGTTGATTATACATTTGTT | 358 |
| | 100 | L Q K R L Y S N V Y R T D Y V D Y T F V | 119 |
| | 359 | AATGAGTATTATGAATTTTTATGTAAGCATTTTAG | 393 |
| | 120 | N E Y Y E F L C K H F | 130 |

FIG. 1

```
SEQ:3   1   GAATAAGAGCGAATTGCGTCCGTACCGTCTATCAGCTTACGATCTCTTGTCAGATCTCAT   60
            E  *  E  R  I  A  S  V  P  S  I  S  L  R  S  L  V  R  S  H
             N  K  S  E  L  R  P  Y  R  L  S  A  Y  D  L  L  S  D  L  I
              I  R  A  N  C  V  R  T  V  Y  Q  L  T  I  S  C  Q  I  S  L

       61   TAAATCTAAACTTTTTAAACAAGATTCCCTGTTATCCATGCTTGTGAGTGTGGTTTAATC   120
            *  I  *  T  F  *  T  R  F  P  V  I  H  A  C  E  C  G  L  I
             K  S  K  L  F  K  Q  D  S  L  L  S  M  L  V  S  V  V  *  S
              N  L  N  F  L  N  K  I  P  C  Y  P  C  L  *  V  W  F  N  H

      121   ATAATCTTGTATTTTACTTTCCACACTTTTCATCTCTCTGCCAGTGACGTGTTGGTTGTC   180
            I  I  L  Y  F  T  F  H  T  F  H  L  S  A  S  D  V  L  V  V
             *  S  C  I  L  L  S  T  L  F  I  S  L  P  V  T  C  W  L  S
              N  L  V  F  Y  F  P  H  F  S  S  L  C  Q  *  R  V  G  C  P

      181   CTCAGCGTCCCTCCCATAGGTCGCAATGATTAAAACCAGCAAATACGGTCTCGGCTTCAA   240
            L  S  V  P  P  I  G  R  N  D  *  N  Q  Q  I  R  S  R  L  Q
             S  A  S  L  P  *  V  A  M  I  K  T  S  K  Y  G  L  G  F  K
              Q  R  P  S  H  R  S  Q  *  L  K  P  A  N  T  V  S  A  S  S

      241   GTGGGCGCCAGAATTTCGTTGGCTGCTTCCGGATGCAGCGGAGGAGTTGGCTAGTCCTAT   300
            V  G  A  R  I  S  L  A  A  S  G  C  S  G  G  V  G  *  S  Y
             W  A  P  E  F  R  W  L  L  P  D  A  A  E  E  L  A  S  P  M
              G  R  Q  N  F  V  G  C  F  R  M  Q  R  R  S  W  L  V  L  *

      301   GAAGTCAGATGAGGGTGGGTTATGCCCCTCTACTGGTCAAGCGATGGAAAGTGTTGGATT   360
            E  V  R  *  G  W  V  M  P  L  Y  W  S  S  D  G  K  C  W  I
             K  S  D  E  G  G  L  C  P  S  T  G  Q  A  M  E  S  V  G  F
              S  Q  M  R  V  G  Y  A  P  L  L  V  K  R  W  K  V  L  D  S

      361   CGTTTATGATAATCATGTGAAGATAGATTGTCGCTGCATTCTTGGACAAGAATGGCATGT   420
            R  L  *  *  S  C  E  D  R  L  S  L  H  S  W  T  R  M  A  C
             V  Y  D  N  H  V  K  I  D  C  R  C  I  L  G  Q  E  W  H  V
              F  M  I  I  M  *  R  *  I  V  A  A  F  L  D  K  N  G  M  C

      421   GCAGTCAAATCTTATCCGTGATATTTTTGTTCATGAAGATCTACATGTTGTAGAAGTTCT   480
            A  V  K  S  Y  P  *  Y  F  C  S  *  R  S  T  C  C  R  S  S
             Q  S  N  L  I  R  D  I  F  V  H  E  D  L  H  V  V  E  V  L
              S  Q  I  L  S  V  I  F  L  F  M  K  I  Y  M  L  *  K  F  *

      481   AACTAAAACAGCCGTAAAGTCCGGTACGGCAATTTTAATTAAATCACCTTTGCATAGCTT   540
            N  *  N  S  R  K  V  R  Y  G  N  F  N  *  I  T  F  A  *  L
             T  K  T  A  V  K  S  G  T  A  I  L  I  K  S  P  L  H  S  L
              L  K  Q  P  *  S  P  V  R  Q  F  *  L  N  H  L  C  I  A  W
```

FIG. 2

```
541   GGGTGGTTTTCCTAAAGGGTATGTTATGGGCTTGTTCCGTTCATACAAGACTAAACGTTA   600
      G  W  F  S  *  R  V  C  Y  G  L  V  P  F  I  Q  D  *  T  L
       G  G  F  P  K  G  Y  V  M  G  L  F  R  S  Y  K  T  K  R  Y
        V  V  F  L  K  G  M  L  W  A  C  S  V  H  T  R  L  N  V  M

601   TGTTGTACATCATCTTTCTATGACTACATCTACTACTAATTTTGGTGAAGATTTTTTGGG   660
      C  C  T  S  S  F  Y  D  Y  I  Y  Y  *  F  W  *  R  F  F  G
       V  V  H  H  L  S  M  T  T  S  T  T  N  F  G  E  D  F  L  G
        L  Y  I  I  F  L  *  L  H  L  L  L  I  L  V  K  I  F  W  V

661   TTGGATTGTACCTTTTGGTTTTATGCCATCTTATGTTCACAAATGGTTTCAATTCTGTAG   720
      L  D  C  T  F  W  F  Y  A  I  L  C  S  Q  M  V  S  I  L  *
       W  I  V  P  F  G  F  M  P  S  Y  V  H  K  W  F  Q  F  C  R
        G  L  Y  L  L  V  L  C  H  L  M  F  T  N  G  F  N  S  V  G

721   GTTGTATATTGAAGAGAGTGATTTAATAATTTCAAATTTTAAATTTGATGATTATGATTT   780
      V  V  Y  *  R  E  *  F  N  N  F  K  F  *  I  *  *  L  *  F
       L  Y  I  E  E  S  D  L  I  I  S  N  F  K  F  D  D  Y  D  F
        C  I  L  K  R  V  I  *  *  F  Q  I  L  N  L  M  I  M  I  L

781   TAGTGTAGAAGATGCTTATGCTGAGGTTCATGCTGAGCCTAAAGGTAAATATTCACAAAA   840
      *  C  R  R  C  L  C  *  G  S  C  *  A  *  R  *  I  F  T  K
       S  V  E  D  A  Y  A  E  V  H  A  E  P  K  G  K  Y  S  Q  K
        V  *  K  M  L  M  L  R  F  M  L  S  L  K  V  N  I  H  K  K

841   AGCTTATGCTTTACTTAGACAATATCGTGGTATTAAACCCGTACTTTTTGTAGACCAGTA   900
      S  L  C  F  T  *  T  I  S  W  Y  *  T  R  T  F  C  R  P  V
       A  Y  A  L  L  R  Q  Y  R  G  I  K  P  V  L  F  V  D  Q  Y
        L  M  L  Y  L  D  N  I  V  V  L  N  P  Y  F  L  *  T  S  M

901   TGGTTGTGACTATTCTGGTAAATTAGCAGATTGTCTTCAAGCTTATGGTCATTATTCTTT   960
      W  L  *  L  F  W  *  I  S  R  L  S  S  S  L  W  S  L  F  F
       G  C  D  Y  S  G  K  L  A  D  C  L  Q  A  Y  G  H  Y  S  L
        V  V  T  I  L  V  N  *  Q  I  V  F  K  L  M  V  I  I  L  C

961   GCAAGATATGAGACAAAAGCAGTCTGTATGGCTTGCCAATTGTGACTTTGATATTGTAGT   1020
      A  R  Y  E  T  K  A  V  C  M  A  C  Q  L  *  L  *  Y  C  S
       Q  D  M  R  Q  K  Q  S  V  W  L  A  N  C  D  F  D  I  V  V
        K  I  *  D  K  S  S  L  Y  G  L  P  I  V  T  L  I  L  *  W

1021  GGCTTGGCATGTAGTTCGTGATTCACGATTTGTTATGCGCCTGCAGACTATAGCTACTAT   1080
      G  L  A  C  S  S  *  F  T  I  C  Y  A  P  A  D  Y  S  Y  Y
       A  W  H  V  V  R  D  S  R  F  V  M  R  L  Q  T  I  A  T  I
        L  G  M  *  F  V  I  H  D  L  L  C  A  C  R  L  *  L  L  F
```

FIG. 2 CONT.

```
1081   TTGTGGTATTAAATATGTTGCACAACCTACAGAAGATGTAGTAGATGGAGATGTAGTTAT   1140
       L  W  Y  *  I  C  C  T  T  Y  R  R  C  S  R  W  R  C  S  Y
        C  G  I  K  Y  V  A  Q  P  T  E  D  V  V  D  G  D  V  V  I
         V  V  L  N  M  L  H  N  L  Q  K  M  *  *  M  E  M  *  L  Y

1141   ACGTGAACCTGTACATTTATTATCTGCTGATGCAATAGTTTTAAAGCTTCCTAGTTTGAT   1200
       T  *  T  C  T  F  I  I  C  *  C  N  S  F  K  A  S  *  F  D
        R  E  P  V  H  L  L  S  A  D  A  I  V  L  K  L  P  S  L  M
         V  N  L  Y  I  Y  Y  L  L  M  Q  *  F  *  S  F  L  V  *  *

1201   GAAAGTTATGACTCATATGGATGATTTTTCTATTAAATCTATATATAATGTTGATTTGTG   1260
       E  S  Y  D  S  Y  G  *  F  F  Y  *  I  Y  I  *  C  *  F  V
        K  V  M  T  H  M  D  D  F  S  I  K  S  I  Y  N  V  D  L  C
         K  L  *  L  I  W  M  I  F  L  L  N  L  Y  I  M  L  I  C  V

1261   TGATTGTGGTTTTGTTATGCAGTATGGTTATGTAGATTGTTTTAATGATAATTGTGATTT   1320
       *  L  W  F  C  Y  A  V  W  L  C  R  L  F  *  *  *  L  *  F
        D  C  G  F  V  M  Q  Y  G  Y  V  D  C  F  N  D  N  C  D  F
         I  V  V  L  L  C  S  M  V  M  *  I  V  L  M  I  I  V  I  F

1321   TTATGGTTGGGTTTCAGGTAATATGATGGATGGTTTTTCTTGTCCATTGTGTTGTACAGT   1380
       L  W  L  G  F  R  *  Y  D  G  W  F  F  L  S  I  V  L  Y  S
        Y  G  W  V  S  G  N  M  M  D  G  F  S  C  P  L  C  C  T  V
         M  V  G  F  Q  V  I  *  W  M  V  F  L  V  H  C  V  V  Q  F

1381   TTATGACTCTAGCGAAGTTAAAGCCCAATCATCTGGTGTTATTCCTGAAAATCCTGTGTT   1440
       L  *  L  *  R  S  *  S  P  I  I  W  C  Y  S  *  K  S  C  V
        Y  D  S  S  E  V  K  A  Q  S  S  G  V  I  P  E  N  P  V  L
         M  T  L  A  K  L  K  P  N  H  L  V  L  F  L  K  I  L  C  Y

1441   ATTTACTAATAGTACTGATACTGTTAACCATGATTCTTTTAATTTGTATGGTTATTCTGT   1500
       I  Y  *  *  Y  *  Y  C  *  P  *  F  F  *  F  V  W  L  F  C
        F  T  N  S  T  D  T  V  N  H  D  S  F  N  L  Y  G  Y  S  V
         L  L  I  V  L  I  L  L  T  M  I  L  L  I  C  M  V  I  L  S

1501   CACACCATTTGGTTCTTGTATATATTGGTCGCCGCGTCCTGGATTGTGGATTCCTATAAT   1560
       H  T  I  W  F  L  Y  I  L  V  A  A  S  W  I  V  D  S  Y  N
        T  P  F  G  S  C  I  Y  W  S  P  R  P  G  L  W  I  P  I  I
         H  H  L  V  L  V  Y  I  G  R  R  V  L  D  C  G  F  L  *  L

1561   TAAATCTTCAGTCAAGTCTTATGATGATTTGGTTTATTCAGGTGTAGTAGGTTGTAAATC   1620
       *  I  F  S  Q  V  L  *  *  F  G  L  F  R  C  S  R  L  *  I
        K  S  S  V  K  S  Y  D  D  L  V  Y  S  G  V  V  G  C  K  S
         N  L  Q  S  S  L  M  M  I  W  F  I  Q  V  *  *  V  V  N  L
```

FIG. 2 CONT.

```
1621   TATTGTTAAAGAAACTGCTCTTATTACTCATGCACTTTACTTAGATTATGTTCAATGTAA   1680
       Y  C  *  R  N  C  S  Y  Y  S  C  T  L  L  R  L  C  S  M  *
        I  V  K  E  T  A  L  I  T  H  A  L  Y  L  D  Y  V  Q  C  K
         L  L  K  K  L  L  L  L  L  M  H  F  T  *  I  M  F  N  V  S

1681   GTGTGGTAATCTTGAACAAAATCATATTCTTGGCGTTAATAATTCTTGGTGTAGGCAACT   1740
       V  W  *  S  *  T  K  S  Y  S  W  R  *  *  F  L  V  *  A  T
        C  G  N  L  E  Q  N  H  I  L  G  V  N  N  S  W  C  R  Q  L
         V  V  I  L  N  K  I  I  F  L  A  L  I  I  L  G  V  G  N  C

1741   GTTGCTTAATAGAGGTGATTATAATATGCTTCTAAAAAATATTGACTTGTTTGTTAAGCG   1800
       V  A  *  *  R  *  L  *  Y  A  S  K  K  Y  *  L  V  C  *  A
        L  L  N  R  G  D  Y  N  M  L  L  K  N  I  D  L  F  V  K  R
         C  L  I  E  V  I  I  I  C  F  *  K  I  L  T  C  L  L  S  V

1801   TCGTGCTGATTTTGCTTGCAAGTTTGCAGTTTGTGGAGATGGTTTTGTACCTTTTTTACT   1860
       S  C  *  F  C  L  Q  V  C  S  L  W  R  W  F  C  T  F  F  T
        R  A  D  F  A  C  K  F  A  V  C  G  D  G  F  V  P  F  L  L
         V  L  I  L  L  A  S  L  Q  F  V  E  M  V  L  Y  L  F  Y  *

1861   AGATGGTTTAATTCCCCGTAGTTATTATCTAATTCAGAGTGGTATTTTCTTTACATCTTT   1920
       R  W  F  N  S  P  *  L  L  S  N  S  E  W  Y  F  L  Y  I  F
        D  G  L  I  P  R  S  Y  Y  L  I  Q  S  G  I  F  F  T  S  L
         M  V  *  F  P  V  V  I  I  *  F  R  V  V  F  S  L  H  L  *

1921   GATGTCTCAATTTTCACAAGAAGTTTCTGATATGTGTTTAAAAATGTGTATTTTGTTTAT   1980
       D  V  S  I  F  T  R  S  F  *  Y  V  F  K  N  V  Y  F  V  Y
        M  S  Q  F  S  Q  E  V  S  D  M  C  L  K  M  C  I  L  F  M
         C  L  N  F  H  K  K  F  L  I  C  V  *  K  C  V  F  C  L  W

1981   GGACAGAGTTTCAGTTGCTACATTTTATATAGAGCATTATGTTAATAGGTTGGTTACTCA   2040
       G  Q  S  F  S  C  Y  I  L  Y  R  A  L  C  *  *  V  G  Y  S
        D  R  V  S  V  A  T  F  Y  I  E  H  Y  V  N  R  L  V  T  Q
         T  E  F  Q  L  L  H  F  I  *  S  I  M  L  I  G  W  L  L  N

2041   ATTTAAGTTATTGGGTACTACACTTGTTAATAAAATGGTTAATTGGTTTAATACCATGTT   2100
       I  *  V  I  G  Y  Y  T  C  *  *  N  G  *  L  V  *  Y  H  V
        F  K  L  L  G  T  T  L  V  N  K  M  V  N  W  F  N  T  M  L
         L  S  Y  W  V  L  H  L  L  I  K  W  L  I  G  L  I  P  C  *

2101   AGATGCTAGTGCACCTGCTACAGGCTGGCTTCTTTACCAATTATTGAATGGTCTTTTTGT   2160
       R  C  *  C  T  C  Y  R  L  A  S  L  P  I  I  E  W  S  F  C
        D  A  S  A  P  A  T  G  W  L  L  Y  Q  L  L  N  G  L  F  V
         M  L  V  H  L  L  Q  A  G  F  F  T  N  Y  *  M  V  F  L  *
```

FIG. 2 CONT.

```
2161  AGTATCTCAAGCCAACTTTAATTTTGTTGCTTTAATACCTGATTATGCTAAAATTTTAGT  2220
      S  I  S  S  Q  L  *  F  C  C  F  N  T  *  L  C  *  N  F  S
       V  S  Q  A  N  F  N  F  V  A  L  I  P  D  Y  A  K  I  L  V
        Y  L  K  P  T  L  I  L  L  L  *  Y  L  I  M  L  K  F  *  L

2221  TAATAAATTTTACACTTTTTTTAAGTTATTATTAGAGTGTGTTACAGTTGATGTTTTAAA  2280
      *  *  I  L  H  F  F  *  V  I  I  R  V  C  Y  S  *  C  F  K
       N  K  F  Y  T  F  F  K  L  L  L  E  C  V  T  V  D  V  L  K
        I  N  F  T  L  F  L  S  Y  Y  *  S  V  L  Q  L  M  F  *  K

2281  AGATATGCCTGTTCTTAAAACTATTAATGGTTTAGTTTGTATTGTAGGCAATAAGTTTTA  2340
      R  Y  A  C  S  *  N  Y  *  W  F  S  L  Y  C  R  Q  *  V  L
       D  M  P  V  L  K  T  I  N  G  L  V  C  I  V  G  N  K  F  Y
        I  C  L  F  L  K  L  L  M  V  *  F  V  L  *  A  I  S  F  I

2341  TAACGTTAGTACAGGGTTAATTCCTGGTTTTGTTTTACCATGTAATGCACAGGAACAACA  2400
      *  R  *  Y  R  V  N  S  W  F  C  F  T  M  *  C  T  G  T  T
       N  V  S  T  G  L  I  P  G  F  V  L  P  C  N  A  Q  E  Q  Q
        T  L  V  Q  G  *  F  L  V  L  F  Y  H  V  M  H  R  N  N  K

2401  AATTTATTTTTTTGAAGGCGTTGCAGAATCTGTTATAGTAGAAGATGATGTTATTGAGAA  2460
      N  L  F  F  *  R  R  C  R  I  C  Y  S  R  R  *  C  Y  *  E
       I  Y  F  F  E  G  V  A  E  S  V  I  V  E  D  D  V  I  E  N
        F  I  F  L  K  A  L  Q  N  L  L  *  *  K  M  M  L  L  R  M

2461  TGTCAAATCTTCTTTATCATCTTATGAGTATTGTCAACCACCTAAATCTGTAGAAAAAAT  2520
      C  Q  I  F  F  I  I  L  *  V  L  S  T  T  *  I  C  R  K  N
       V  K  S  S  L  S  S  Y  E  Y  C  Q  P  P  K  S  V  E  K  I
        S  N  L  L  Y  H  L  M  S  I  V  N  H  L  N  L  *  K  K  F

2521  TTGTATTATAGATAATATGTACATGGGTAAGTGTGGTGATAAATTTTTCCCTATTGTCAT  2580
      L  Y  Y  R  *  Y  V  H  G  *  V  W  *  *  I  F  P  Y  C  H
       C  I  I  D  N  M  Y  M  G  K  C  G  D  K  F  F  P  I  V  M
        V  L  *  I  I  C  T  W  V  S  V  V  I  N  F  S  L  L  S  *

2581  GAATGATAAAAATATTTGTCTTTTAGATCAGGCTTGGCGTTTTCCATGTGCAGGTAGAAA  2640
      E  *  *  K  Y  L  S  F  R  S  G  L  A  F  S  M  C  R  *  K
       N  D  K  N  I  C  L  L  D  Q  A  W  R  F  P  C  A  G  R  K
        M  I  K  I  F  V  F  *  I  R  L  G  V  F  H  V  Q  V  E  K

2641  AGTTAATTTTAACGAGAAACCTGTTGTTATGGAGATTCCGTCTTTGATGACAGTTAAGGT  2700
      S  *  F  *  R  E  T  C  C  Y  G  D  S  V  F  D  D  S  *  G
       V  N  F  N  E  K  P  V  V  M  E  I  P  S  L  M  T  V  K  V
        L  I  L  T  R  N  L  L  L  W  R  F  R  L  *  *  Q  L  R  L
```

FIG. 2 CONT.

```
2701   TATGTTTGATTTAGATTCTACTTTTGATGATATTTTAGGTAAAGTTTGTTCAGAATTTGA   2760
       Y  V  *  F  R  F  Y  F  *  *  Y  F  R  *  S  L  F  R  I  *
        M  F  D  L  D  S  T  F  D  D  I  L  G  K  V  C  S  E  F  E
         C  L  I  *  I  L  L  L  M  I  F  *  V  K  F  V  Q  N  L  K

2761   AGTAGAAAAGGGTGTTACTGTAGATGATTTTGTTGCTGTTGTTTGTGATGCTATAGAGAA   2820
       S  R  K  G  C  Y  C  R  *  F  C  C  C  C  L  *  C  Y  R  E
        V  E  K  G  V  T  V  D  D  F  V  A  V  V  C  D  A  I  E  N
         *  K  R  V  L  L  *  M  I  L  L  L  L  F  V  M  L  *  R  M

2821   TGCTTTAAACTCTTGTAAAGAGCATCCAGTGGTTGGTTATCAAGTTCGTGCATTTTTAAA   2880
       C  F  K  L  L  *  R  A  S  S  G  W  L  S  S  S  C  I  F  K
        A  L  N  S  C  K  E  H  P  V  V  G  Y  Q  V  R  A  F  L  N
         L  *  T  L  V  K  S  I  Q  W  L  V  I  K  F  V  H  F  *  I

2881   TAAACTTAATGAGAATGTTGTTTATTTATTTGATGAGGCTGGTGATGAAGCAATGGCCTC   2940
       *  T  *  *  E  C  C  L  F  I  *  *  G  W  *  *  S  N  G  L
        K  L  N  E  N  V  V  Y  L  F  D  E  A  G  D  E  A  M  A  S
         N  L  M  R  M  L  F  I  Y  L  M  R  L  V  M  K  Q  W  P  L

2941   TCGTATGTATTGTACTTTTGCTATTGAGGATGTTGAAGACGTTATCAGTAGTGAAGCTGT   3000
       S  Y  V  L  Y  F  C  Y  *  G  C  *  R  R  Y  Q  *  *  S  C
        R  M  Y  C  T  F  A  I  E  D  V  E  D  V  I  S  S  E  A  V
         V  C  I  V  L  L  L  L  R  M  L  K  T  L  S  V  V  K  L  S

3001   CGAAGATACTATTGATGGTGTCGTTGAAGACACTATTAATGACGATGAAGATGTTGTTAC   3060
       R  R  Y  Y  *  W  C  R  *  R  H  Y  *  *  R  *  R  C  C  Y
        E  D  T  I  D  G  V  V  E  D  T  I  N  D  D  E  D  V  V  T
         K  I  L  L  M  V  S  L  K  T  L  L  M  T  M  K  M  L  L  L

3061   TGGTGACAATGACGATGAAGATGTTGTTACTGGTGACAATGACGATGAAGATGTTGTTAC   3120
       W  *  Q  *  R  *  R  C  C  Y  W  *  Q  *  R  *  R  C  C  Y
        G  D  N  D  D  E  D  V  V  T  G  D  N  D  D  E  D  V  V  T
         V  T  M  T  M  K  M  L  L  L  V  T  M  T  M  K  M  L  L  L

3121   TGGTGACAATGACGATGAAGATGTTGTTACTGGTGACAATGACGATGAAGATGTTGTTAC   3180
       W  *  Q  *  R  *  R  C  C  Y  W  *  Q  *  R  *  R  C  C  Y
        G  D  N  D  D  E  D  V  V  T  G  D  N  D  D  E  D  V  V  T
         V  T  M  T  M  K  M  L  L  L  V  T  M  T  M  K  M  L  L  L

3181   TGGTGACAATGACGATGAAGATGTTGTTACTGGTGACAATGACGATGAAGATGTTGTTAC   3240
       W  *  Q  *  R  *  R  C  C  Y  W  *  Q  *  R  *  R  C  C  Y
        G  D  N  D  D  E  D  V  V  T  G  D  N  D  D  E  D  V  V  T
         V  T  M  T  M  K  M  L  L  L  V  T  M  T  M  K  M  L  L  L
```

FIG. 2 CONT.

```
3241    TGGTGACAATGACGATGAAGATGTTGTTACTGGTGACAATGACGATGAAGATGTTGTTAC    3300
        W  *  Q  *  R  *  R  C  C  Y  W  *  Q  *  R  *  R  C  C  Y
         G  D  N  D  D  E  D  V  V  T  G  D  N  D  D  E  D  V  V  T
          V  T  M  T  M  K  M  L  L  L  V  T  M  T  M  K  M  L  L  L

3301    TGGTGACAATGACGATGAAGATGTTGTTACTGGTGACAATGACGATGAAGATGTTGTTAC    3360
        W  *  Q  *  R  *  R  C  C  Y  W  *  Q  *  R  *  R  C  C  Y
         G  D  N  D  D  E  D  V  V  T  G  D  N  D  D  E  D  V  V  T
          V  T  M  T  M  K  M  L  L  L  V  T  M  T  M  K  M  L  L  L

3361    TGGTGACAATGACGATGAAGATGTTGTTACTGGTGACAATGACGATGAAGATGTTGTTAC    3420
        W  *  Q  *  R  *  R  C  C  Y  W  *  Q  *  R  *  R  C  C  Y
         G  D  N  D  D  E  D  V  V  T  G  D  N  D  D  E  D  V  V  T
          V  T  M  T  M  K  M  L  L  L  V  T  M  T  M  K  M  L  L  L

3421    TGGTGACAATGACGATGAAGATGTTGTTACTGGTGACAATAACGATGAAGAGATTGTTAC    3480
        W  *  Q  *  R  *  R  C  C  Y  W  *  Q  *  R  *  R  D  C  Y
         G  D  N  D  D  E  D  V  V  T  G  D  N  N  D  E  E  I  V  T
          V  T  M  T  M  K  M  L  L  L  V  T  I  T  M  K  R  L  L  L

3481    TGGTGACAATGATGACCAAATTGTTGTTACTGGTGATGATGTAGATGATATTGAAAGTAT    3540
        W  *  Q  *  *  P  N  C  C  Y  W  *  *  C  R  *  Y  *  K  Y
         G  D  N  D  D  Q  I  V  V  T  G  D  D  V  D  D  I  E  S  I
          V  T  M  M  T  K  L  L  L  L  V  M  M  *  M  I  L  K  V  F

3541    TTATGACTTTGATACTTATAAAGCTCTTTTAGTTTTTAATGATGTCTATAATGATGCTTT    3600
        L  *  L  *  Y  L  *  S  S  F  S  F  *  *  C  L  *  *  C  F
         Y  D  F  D  T  Y  K  A  L  L  V  F  N  D  V  Y  N  D  A  L
          M  T  L  I  L  I  K  L  F  *  F  L  M  M  S  I  M  M  L  C

3601    GTTTGTTAGTTATGGTTCTAGTGTTGAAACAGAAACATATTTTAAAGTTAATGGTTTATG    3660
        V  C  *  L  W  F  *  C  *  N  R  N  I  F  *  S  *  W  F  M
         F  V  S  Y  G  S  S  V  E  T  E  T  Y  F  K  V  N  G  L  W
          L  L  V  M  V  L  V  L  K  Q  K  H  I  L  K  L  M  V  Y  G

3661    GTCACCTACTATTACACATACTAATTGTTGGTTGCGTTCTGTGTTACTTGTAATGCAGAA    3720
        V  T  Y  Y  Y  T  Y  *  L  L  V  A  F  C  V  T  C  N  A  E
         S  P  T  I  T  H  T  N  C  W  L  R  S  V  L  L  V  M  Q  K
          H  L  L  L  H  I  L  I  V  G  C  V  L  C  Y  L  *  C  R  N

3721    ATTACCTTTTAAGTTTAAGGATTTAGCTATTGAAAATATGTGGTTATCTTATAAGGTGGG    3780
        I  T  F  *  V  *  G  F  S  Y  *  K  Y  V  V  I  L  *  G  G
         L  P  F  K  F  K  D  L  A  I  E  N  M  W  L  S  Y  K  V  G
          Y  L  L  S  L  R  I  *  L  L  K  I  C  G  Y  L  I  R  W  V
```

FIG. 2 CONT.

```
3781  TTATAATCAAAGTTTTGTTGATTATTTACTGACCACTATTCCTAAAGCTATTGTTTTGCC  3840
       L * S K F C * L F T D H Y S * S Y C F A
        Y N Q S F V D Y L L T T I P K A I V L P
         I I K V L L I I Y * P L F L K L L F C L

3841  TCAAGGTGGTTTTGTAGCTGATTTTGCTTATTGGTTTTTAAACCAGTTTGATATTAATGC  3900
       S R W F C S * F C L L V F K P V * Y * C
        Q G G F V A D F A Y W F L N Q F D I N A
         K V V L * L I L L I G F * T S L I L M R

3901  GTATGCTAATTGGTGTTGTTTAAAATGTGGTTTTTCTTTTGATTTAAATGGTTTGGATGC  3960
       V C * L V L F K M W F F F * F K W F G C
        Y A N W C C L K C G F S F D L N G L D A
         M L I G V V * N V V F L L I * M V W M L

3961  TTTGTTTTTTTATGGAGATATTGTGTCTCATGTTTGTAAGTGTGGACATAATATGACTCT  4020
       F V F L W R Y C V S C L * V W T * Y D S
        L F F Y G D I V S H V C K C G H N M T L
         C F F M E I L C L M F V S V D I I . * L *

4021  AATAGCAGCGGACTTACCTTGTACATTACATTTTTCATTATTTGATGACAATTTTTGTGC  4080
       N S S G L T L Y I T F F I I * * Q F L C
        I A A D L P C T L H F S L F D D N F C A
         * Q R T Y L V H Y I F H Y L M T I F V L

4081  TTTTTGCACCCCTAAAAAAATTTTTATTGCTGCATGTGCTGTGGATGTAAACGTTTGTCA  4140
       F L H P * K N F Y C C M C C G C K R L S
        F C T P K K I F I A A C A V D V N V C H
         F A P L K K F L L L H V L W M * T F V I

4141  TTCTGTAGCTGTTATAGGTGATGAACAAATAGATGGTAAGTTTGTTACTAAATTTAGTGG  4200
       F C S C Y R * * T N R W * V C Y * I * W
        S V A V I G D E Q I D G K F V T K F S G
         L * L L * V M N K * M V S L L L N L V V

4201  TGATAAATTTGATTTTATAGTAGGTTATGGAATGTCATTTAGTATGTCTTCTTTTGAGTT  4260
       * * I * F Y S R L W N V I * Y V F F * V
        D K F D F I V G Y G M S F S M S S F E L
         I N L I L * * V M E C H L V C L L L S Y

4261  ACCTCAATTGTATGGTTTGTGTATAACACCTAATGTATGTTTTGTTAAAGGTGATATTAT  4320
       T S I V W F V Y N T * C M F C * R * Y Y
        P Q L Y G L C I T P N V C F V K G D I I
         L N C M V C V * H L M Y V L L K V I L *
```

FIG. 2 CONT.

```
4321   AAATGTTGCTAGACTTGTTAAAGCTGATGTTATTGTTAATCCTGCTAATGGGCATATGCT   4380
       K  C  C  *  T  C  *  S  *  C  Y  C  *  S  C  *  W  A  Y  A
        N  V  A  R  L  V  K  A  D  V  I  V  N  P  A  N  G  H  M  L
         M  L  L  D  L  L  K  L  M  L  L  L  I  L  L  M  G  I  C  S

4381   CCATGGTGGTGGAGTTGCAAAAGCTATAGCTGTAGCTGCAGGTAAAAAATTTTCTAAAGA   4440
       P  W  W  W  S  C  K  S  Y  S  C  S  C  R  *  K  I  F  *  R
        H  G  G  G  V  A  K  A  I  A  V  A  A  G  K  K  F  S  K  E
         M  V  V  E  L  Q  K  L  *  L  *  L  Q  V  K  N  F  L  K  K

4441   AACTGCTGCTATGGTTAAATCTAAAGGTGTTTGCCAAGTAGGAGATTGTTATGTTTCTAC   4500
       N  C  C  Y  G  *  I  *  R  C  L  P  S  R  R  L  L  C  F  Y
        T  A  A  M  V  K  S  K  G  V  C  Q  V  G  D  C  Y  V  S  T
         L  L  L  W  L  N  L  K  V  F  A  K  *  E  I  V  M  F  L  P

4501   CGGTGGTAAATTATGTAAAACAATTCTTAATATTGTAGGCCCTGATGCTAGACAAGATGG   4560
       R  W  *  I  M  *  N  N  S  *  Y  C  R  P  *  C  *  T  R  W
        G  G  K  L  C  K  T  I  L  N  I  V  G  P  D  A  R  Q  D  G
         V  V  N  Y  V  K  Q  F  L  I  L  *  A  L  M  L  D  K  M  E

4561   AAGACAATCTTATGTTTTGTTAGCACGTGCTTATAAGCATCTTAATAATTATGATTGTTG   4620
       K  T  I  L  C  F  V  S  T  C  L  *  A  S  *  *  L  *  L  L
        R  Q  S  Y  V  L  L  A  R  A  Y  K  H  L  N  N  Y  D  C  C
         D  N  L  M  F  C  *  H  V  L  I  S  I  L  I  I  M  I  V  V

4621   TTTGTCTACTCTCATATCGGCTGGTATATTTAGTGTTCCTGCTGATGTGTCATTAACTTA   4680
       F  V  Y  S  H  I  G  W  Y  I  *  C  S  C  *  C  V  I  N  L
        L  S  T  L  I  S  A  G  I  F  S  V  P  A  D  V  S  L  T  Y
         C  L  L  S  Y  R  L  V  Y  L  V  F  L  L  M  C  H  *  L  T

4681   CCTTCTAGGTGTTGTTGATAAACAAGTTATCCTTGTTAGTAATAATAAAGAAGATTTTGA   4740
       P  S  R  C  C  *  *  T  S  Y  P  C  *  *  *  *  R  R  F  *
        L  L  G  V  V  D  K  Q  V  I  L  V  S  N  N  K  E  D  F  D
         F  *  V  L  L  I  N  K  L  S  L  L  V  I  I  K  K  I  L  I

4741   TATTATTCAAAAATGTCAAATTACTTCAGTTGTTGGTACTAAAGCATTGGCTGTTAGATT   4800
       Y  Y  S  K  M  S  N  Y  F  S  C  W  Y  *  S  I  G  C  *  I
        I  I  Q  K  C  Q  I  T  S  V  V  G  T  K  A  L  A  V  R  L
         L  F  K  N  V  K  L  L  Q  L  L  V  L  K  H  W  L  L  D  *

4801   AACTGCTAATGTAGGCCGTGTTATTAAATTTGAGACAGATGCATACAAACTTTTTTTGAG   4860
       N  C  *  C  R  P  C  Y  *  I  *  D  R  C  I  Q  T  F  F  E
        T  A  N  V  G  R  V  I  K  F  E  T  D  A  Y  K  L  F  L  S
         L  L  M  *  A  V  L  L  N  L  R  Q  M  H  T  N  F  F  *  V
```

FIG. 2 CONT.

```
4861   TGGTGATGATTGTTTTGTTTCAAATTCTTCTGTTATACAAGAAGTTTTATTGCTTCGTCA   4920
       W  *  *  L  F  C  F  K  F  F  C  Y  T  R  S  F  I  A  S  S
        G  D  D  C  F  V  S  N  S  S  V  I  Q  E  V  L  L  L  R  H
         V  M  I  V  L  F  Q  I  L  L  L  Y  K  K  F  Y  C  F  V  M

4921   TGATATACAATTGAATAATGACGTTCGTGATTATTTGTTGTCTAAGATGACTAGTCTTCC   4980
       *  Y  T  I  E  *  *  R  S  *  L  F  V  V  *  D  D  *  S  S
        D  I  Q  L  N  N  D  V  R  D  Y  L  L  S  K  M  T  S  L  P
         I  Y  N  *  I  M  T  F  V  I  I  C  C  L  R  *  L  V  F  L

4981   TAAAGATTGGCGTCTTATCAATAAATTTGATGTTATTAACGGTGTTAAAACTGTTAAGTA   5040
       *  R  L  A  S  Y  Q  *  I  *  C  Y  *  R  C  *  N  C  *  V
        K  D  W  R  L  I  N  K  F  D  V  I  N  G  V  K  T  V  K  Y
         K  I  G  V  L  S  I  N  L  M  L  L  T  V  L  K  L  L  S  I

5041   TTTTGAGTGTCCTAATTCTATTTATATATGTAGTCAGGGTAAAGACTTTGGTTATGTATG   5100
       F  *  V  S  *  F  Y  L  Y  M  *  S  G  *  R  L  W  L  C  M
        F  E  C  P  N  S  I  Y  I  C  S  Q  G  K  D  F  G  Y  V  C
         L  S  V  L  I  L  F  I  Y  V  V  R  V  K  T  L  V  M  Y  V

5101   TGATGGTTCTTTTTATAAAGCAACTGTTAATCAAGTTTGTGTTTTATTAGCTAAGAAGAT   5160
       *  W  F  F  L  *  S  N  C  *  S  S  L  C  F  I  S  *  E  D
        D  G  S  F  Y  K  A  T  V  N  Q  V  C  V  L  L  A  K  K  I
         M  V  L  F  I  K  Q  L  L  I  K  F  V  F  Y  *  L  R  R  *

5161   AGATGTTTTGCTTACTGTAGATGGTGTTAATTTTAAATCTATTTCTCTTACTGTAGGTGA   5220
       R  C  F  A  Y  C  R  W  C  *  F  *  I  Y  F  S  Y  C  R  *
        D  V  L  L  T  V  D  G  V  N  F  K  S  I  S  L  T  V  G  E
         M  F  C  L  L  *  M  V  L  I  L  N  L  F  L  L  L  *  V  K

5221   AGTTTTTGGTAAAATACTTGGTAATGTTTTCTGTGATGGCATTGATGTTACTAAGTTAAA   5280
       S  F  W  *  N  T  W  *  C  F  L  *  W  H  *  C  Y  *  V  K
        V  F  G  K  I  L  G  N  V  F  C  D  G  I  D  V  T  K  L  K
         F  L  V  K  Y  L  V  M  F  S  V  M  A  L  M  L  L  S  *  S

5281   GTGTAGTGATTTTTATGCCGATAAAATTTTATATCAGTATGAAAATTTGTCTTTAGCTGA   5340
       V  *  *  F  L  C  R  *  N  F  I  S  V  *  K  F  V  F  S  *
        C  S  D  F  Y  A  D  K  I  L  Y  Q  Y  E  N  L  S  L  A  D
         V  V  I  F  M  P  I  K  F  Y  I  S  M  K  I  C  L  *  L  I

5341   TATTTCTGCTGTACAAAGTTCATTTGGGTTTGATCAGCAACAATTGCTTGCTTATTATAA   5400
       Y  F  C  C  T  K  F  I  W  V  *  S  A  T  I  A  C  L  L  *
        I  S  A  V  Q  S  S  F  G  F  D  Q  Q  Q  L  L  A  Y  Y  N
         F  L  L  Y  K  V  H  L  G  L  I  S  N  N  C  L  L  I  I  I
```

FIG. 2 CONT.

```
5401   TTTTTTAACAGTATGTAAATGGTCTGTAGTTGTTAACGGTCCATTTTTTTCTTTTGAACA   5460
       F  F  N  S  M  *  M  V  C  S  C  *  R  S  I  F  F  F  *  T
        F  L  T  V  C  K  W  S  V  V  V  N  G  P  F  F  S  F  E  Q
         F  *  Q  Y  V  N  G  L  *  L  L  T  V  H  F  F  L  L  N  S

5461   GTCTCATAATAATTGTTATGTGAATGTAGCTTGTCTTATGTTGCAGCATATTAATCTTAA   5520
       V  S  *  *  L  L  C  E  C  S  L  S  Y  V  A  A  Y  *  S  *
        S  H  N  N  C  Y  V  N  V  A  C  L  M  L  Q  H  I  N  L  K
         L  I  I  I  V  M  *  M  *  L  V  L  C  C  S  I  L  I  L  N

5521   ATTTAATAAATGGCAGTGGCAGGAAGCATGGTATGAATTTCGTGCTGGCAGACCACATAG   5580
       I  *  *  M  A  V  A  G  S  M  V  *  I  S  C  W  Q  T  T  *
        F  N  K  W  Q  W  Q  E  A  W  Y  E  F  R  A  G  R  P  H  R
         L  I  N  G  S  G  R  K  H  G  M  N  F  V  L  A  D  H  I  G

5581   GTTAGTTGCTCTTGTTTTAGCTAAAGGTCATTTTAAATTTGATGAACCATCAGATGCTAC   5640
       V  S  C  S  C  F  S  *  R  S  F  *  I  *  *  T  I  R  C  Y
        L  V  A  L  V  L  A  K  G  H  F  K  F  D  E  P  S  D  A  T
         *  L  L  L  F  *  L  K  V  I  L  N  L  M  N  H  Q  M  L  L

5641   TGATTTTATTCGTGTTGTTTTGAAACAAGCTGATTTATCAGGTGCAATTTGTGAATTAGA   5700
       *  F  Y  S  C  C  F  E  T  S  *  F  I  R  C  N  L  *  I  R
        D  F  I  R  V  V  L  K  Q  A  D  L  S  G  A  I  C  E  L  E
         I  L  F  V  L  F  *  N  K  L  I  Y  Q  V  Q  F  V  N  *  N

5701   ACTTATTTGTGATTGTGGTATTAAACAAGAAAGTCGTGTTGGTGTTGATGCTGTTATGCA   5760
       T  Y  L  *  L  W  Y  *  T  R  K  S  C  W  C  *  C  C  Y  A
        L  I  C  D  C  G  I  K  Q  E  S  R  V  G  V  D  A  V  M  H
         L  F  V  I  V  V  L  N  K  K  V  V  L  V  L  M  L  L  C  I

5761   TTTTGGTACATTAGCAAAGACTGATCTTTTTAATGGTTATAAGATTGGCTGTAATTGTGC   5820
       F  W  Y  I  S  K  D  *  S  F  *  W  L  *  D  W  L  *  L  C
        F  G  T  L  A  K  T  D  L  F  N  G  Y  K  I  G  C  N  C  A
         L  V  H  *  Q  R  L  I  F  L  M  V  I  R  L  A  V  I  V  Q

5821   AGGTAGAATTGTCCATTGTACTAAATTGAATGTACCATTTTTGATTTGTTCTAATACTCC   5880
       R  *  N  C  P  L  Y  *  I  E  C  T  I  F  D  L  F  *  Y  S
        G  R  I  V  H  C  T  K  L  N  V  P  F  L  I  C  S  N  T  P
         V  E  L  S  I  V  L  N  *  M  Y  H  F  *  F  V  L  I  L  L

5881   TCTGAGTAAGGATTTACCTGATGATGTTGTTGCAGCTAACATGTTTATGGGTGTAGGTGT   5940
       S  E  *  G  F  T  *  *  C  C  C  S  *  H  V  Y  G  C  R  C
        L  S  K  D  L  P  D  D  V  V  A  A  N  M  F  M  G  V  G  V
         *  V  R  I  Y  L  M  M  L  L  Q  L  T  C  L  W  V  *  V  *
```

FIG. 2 CONT.

```
5941  AGGCCATTATACACATTTGAAATGTGGTTCACCTTACCAACATTATGATGCTTGTAGTGT  6000
      R  P  L  Y  T  F  E  M  W  F  T  L  P  T  L  *  C  L  *  C
       G  H  Y  T  H  L  K  C  G  S  P  Y  Q  H  Y  D  A  C  S  V
        A  I  I  H  I  *  N  V  V  H  L  T  N  I  M  M  L  V  V  L

6001  TAAAAAATATACAGGTGTTAGTGGTTGTTTAACTGACTGCTTGTATCTTAAAAATTTAAC  6060
      *  K  I  Y  R  C  *  W  L  F  N  *  L  L  V  S  *  K  F  N
       K  K  Y  T  G  V  S  G  C  L  T  D  C  L  Y  L  K  N  L  T
        K  N  I  Q  V  L  V  V  V  *  L  T  A  C  I  L  K  I  *  P

6061  CCAGACTTTTACATCTATGTTGACTAATTATTTTTTGGATGATGTTGAAATGGTTGCTTA  6120
      P  D  F  Y  I  Y  V  D  *  L  F  F  G  *  C  *  N  G  C  L
       Q  T  F  T  S  M  L  T  N  Y  F  L  D  D  V  E  M  V  A  Y
        R  L  L  H  L  C  *  L  I  I  F  W  M  M  L  K  W  L  L  I

6121  TAACCCTGATCTTTCACAATATTATTGTGATAATGGTAAGTATTATACAAAACCTATTAT  6180
      *  P  *  S  F  T  I  L  L  *  *  W  *  V  L  Y  K  T  Y  Y
       N  P  D  L  S  Q  Y  Y  C  D  N  G  K  Y  Y  T  K  P  I  I
        T  L  I  F  H  N  I  I  V  I  M  V  S  I  I  Q  N  L  L  *

6181  AAAGGCTCAGTTTAAACCATTTGCTAAAGTTGACGGTGTTTATACTAACTTTAAGTTAGT  6240
      K  G  S  V  *  T  I  C  *  S  *  R  C  L  Y  *  L  *  V  S
       K  A  Q  F  K  P  F  A  K  V  D  G  V  Y  T  N  F  K  L  V
        R  L  S  L  N  H  L  L  K  L  T  V  F  I  L  T  L  S  *  L

6241  TGGACATGATATTTGTGCTCAATTGAATGATAAGTTAGGTTTTAATGTAGATTTGCCGTT  6300
      W  T  *  Y  L  C  S  I  E  *  *  V  R  F  *  C  R  F  A  V
       G  H  D  I  C  A  Q  L  N  D  K  L  G  F  N  V  D  L  P  F
        D  M  I  F  V  L  N  *  M  I  S  *  V  L  M  *  I  C  R  L

6301  TGTTGAGTACAAAGTAACAGTCTGGCCTGTAGCTACTGGTGATGTTGTTTTGGCATCTGA  6360
      C  *  V  Q  S  N  S  L  A  C  S  Y  W  *  C  C  F  G  I  *
       V  E  Y  K  V  T  V  W  P  V  A  T  G  D  V  V  L  A  S  D
        L  S  T  K  *  Q  S  G  L  *  L  L  V  M  L  F  W  H  L  M

6361  TGATTTATATGTGAAACGTTATTTTAAAGGATGTGAAACTTTTGGTAAGCCTGTTATTTG  6420
      *  F  I  C  E  T  L  F  *  R  M  *  N  F  W  *  A  C  Y  L
       D  L  Y  V  K  R  Y  F  K  G  C  E  T  F  G  K  P  V  I  W
        I  Y  M  *  N  V  I  L  K  D  V  K  L  L  V  S  L  L  F  G

6421  GTTTTGTCATGATGAAGCATCATTGAATTCTCTTACTTATTTTAATAAACCTAGTTTTAA  6480
      V  L  S  *  *  S  I  I  E  F  S  Y  L  F  *  *  T  *  F  *
       F  C  H  D  E  A  S  L  N  S  L  T  Y  F  N  K  P  S  F  K
        F  V  M  M  K  H  H  *  I  L  L  L  I  L  I  N  L  V  L  N
```

FIG. 2 CONT.

```
6481   ATCTGAAAATAGATATAGTGTTTTGTCTGTTGATTCTGTATCTGAGGAGTCACAAGGTAA   6540
       I  *  K  *  I  *  C  F  V  C  *  F  C  I  *  G  V  T  R  *
        S  E  N  R  Y  S  V  L  S  V  D  S  V  S  E  E  S  Q  G  N
         L  K  I  D  I  V  F  C  L  L  I  L  Y  L  R  S  H  K  V  M

6541   TGTGGTTACTTCTGTTATGGAATCGCAGATTAGTACTAAAGAGGTTAAGTTAAAGGGTGT   6600
       C  G  Y  F  C  Y  G  I  A  D  *  Y  *  R  G  *  V  K  G  C
        V  V  T  S  V  M  E  S  Q  I  S  T  K  E  V  K  L  K  G  V
         W  L  L  L  L  W  N  R  R  L  V  L  K  R  L  S  *  R  V  L

6601   TAGAAAGACTGTTAAAATAGAAGATGCTATTATTGTTAATGATGAAAATAGTTCTATTAA   6660
       *  K  D  C  *  N  R  R  C  Y  Y  C  *  *  *  K  *  F  Y  *
        R  K  T  V  K  I  E  D  A  I  I  V  N  D  E  N  S  S  I  K
         E  R  L  L  K  *  K  M  L  L  L  L  M  M  K  I  V  L  L  R

6661   GGTTGTTAAAAGTTTATCTTTAGTTGATGTTTGGGATATGTATTTGACAGGTTGTGATTA   6720
       G  C  *  K  F  I  F  S  *  C  L  G  Y  V  F  D  R  L  *  L
        V  V  K  S  L  S  L  V  D  V  W  D  M  Y  L  T  G  C  D  Y
         L  L  K  V  Y  L  *  L  M  F  G  I  C  I  *  Q  V  V  I  M

6721   TGTTGTTTGGGTTGCTAATGAATTGTCACGCCTAGTTAAATCACCAACAGTTAGGGAATA   6780
       C  C  L  G  C  *  *  I  V  T  P  S  *  I  T  N  S  *  G  I
        V  V  W  V  A  N  E  L  S  R  L  V  K  S  P  T  V  R  E  Y
         L  F  G  L  L  M  N  C  H  A  *  L  N  H  Q  Q  L  G  N  I

6781   TATACGATATGGTATTAAACCTATTACTATACCTATAGATTTGTTATGTTTAAGAGATGA   6840
       Y  T  I  W  Y  *  T  Y  Y  Y  T  Y  R  F  V  M  F  K  R  *
        I  R  Y  G  I  K  P  I  T  I  P  I  D  L  L  C  L  R  D  D
         Y  D  M  V  L  N  L  L  L  Y  L  *  I  C  Y  V  *  E  M  I

6841   TAATCAAACTCTTTTAGTTCCTAAAATTTTTAAAGCAAGAGCTATAGAATTTTATGGTTT   6900
       *  S  N  S  F  S  S  *  N  F  *  S  K  S  Y  R  I  L  W  F
        N  Q  T  L  L  V  P  K  I  F  K  A  R  A  I  E  F  Y  G  F
         I  K  L  F  *  F  L  K  F  L  K  Q  E  L  *  N  F  M  V  F

6901   TTTGAAGTGGTTGTTTATTTATGTTTTTAGTTTATTACATTTTACAAATGATAAAACCAT   6960
       F  E  V  V  V  Y  L  C  F  *  F  I  T  F  Y  K  *  *  N  H
        L  K  W  L  F  I  Y  V  F  S  L  L  H  F  T  N  D  K  T  I
         *  S  G  C  L  F  M  F  L  V  Y  Y  I  L  Q  M  I  K  P  F

6961   TTTTTATACTACAGAAATAGCTTCTAAGTTTACTTTTAATTTGTTTTGTTTGGCTCTTAA   7020
       F  L  Y  Y  R  N  S  F  *  V  Y  F  *  F  V  L  F  G  S  *
        F  Y  T  T  E  I  A  S  K  F  T  F  N  L  F  C  L  A  L  K
         F  I  L  Q  K  *  L  L  S  L  L  L  I  C  F  V  W  L  L  K
```

FIG. 2 CONT.

```
7021    AAATGCTTTTCAGACATTTAGATGGAGTATATTTATAAAAGGTTTTCTTGTTGTAGCCAC    7080
        K  C  F  S  D  I  *  M  E  Y  I  Y  K  R  F  S  C  C  S  H
         N  A  F  Q  T  F  R  W  S  I  F  I  K  G  F  L  V  V  A  T
          M  L  F  R  H  L  D  G  V  Y  L  *  K  V  F  L  L  *  P  L

7081    TGTGTTTTTGTTTTGGTTTAATTTTTTGTATATAAATGTTATTTTTAGTGACTTTTATCT    7140
        C  V  F  V  L  V  *  F  F  V  Y  K  C  Y  F  *  *  L  L  S
         V  F  L  F  W  F  N  F  L  Y  I  N  V  I  F  S  D  F  Y  L
          C  F  C  F  G  L  I  F  C  I  *  M  L  F  L  V  T  F  I  F

7141    TCCTAATATTAGTGTTTTTCCTATTTTTGTGGGAAGAATTGTTATGTGGATAAAGGCTAC    7200
        S  *  Y  *  C  F  S  Y  F  C  G  K  N  C  Y  V  D  K  G  Y
         P  N  I  S  V  F  P  I  F  V  G  R  I  V  M  W  I  K  A  T
          L  I  L  V  F  F  L  F  L  W  E  E  L  L  C  G  *  R  L  L

7201    TTTTGGTTTGGTTACAATTTGTGATTTTTATTCTAAGTTAGGTGTAGGTTTTACAAGTCA    7260
        F  W  F  G  Y  N  L  *  F  L  F  *  V  R  C  R  F  Y  K  S
         F  G  L  V  T  I  C  D  F  Y  S  K  L  G  V  G  F  T  S  H
          L  V  W  L  Q  F  V  I  F  I  L  S  *  V  *  V  L  Q  V  I

7261    TTTTTGTAATGGTAGTTTTATATGTGAATTGTGTCATTCTGGTTTTGATATGTTGGATAC    7320
        F  L  *  W  *  F  Y  M  *  I  V  S  F  W  F  *  Y  V  G  Y
         F  C  N  G  S  F  I  C  E  L  C  H  S  G  F  D  M  L  D  T
          F  V  M  V  V  L  Y  V  N  C  V  I  L  V  L  I  C  W  I  H

7321    ATATGCAGCTATAGATTTTGTTCAGTATGAAGTAGATAGACGTGTTTTATTTGATTATGT    7380
        I  C  S  Y  R  F  C  S  V  *  S  R  *  T  C  F  I  *  L  C
         Y  A  A  I  D  F  V  Q  Y  E  V  D  R  R  V  L  F  D  Y  V
          M  Q  L  *  I  L  F  S  M  K  *  I  D  V  F  Y  L  I  M  L

7381    TAGTTTAGTCAAATTAATTGTTGAACTCGTTATTGGTTATTCATTATACACAGTATGGTT    7440
        *  F  S  Q  I  N  C  *  T  R  Y  W  L  F  I  I  H  S  M  V
         S  L  V  K  L  I  V  E  L  V  I  G  Y  S  L  Y  T  V  W  F
          V  *  S  N  *  L  L  N  S  L  L  V  I  H  Y  T  Q  Y  G  F

7441    TTATCCATTATTTTGTCTTATTGGTTTACAATTATTTACTACATGGTTGCCTGATTTGTT    7500
        L  S  I  I  L  S  Y  W  F  T  I  I  Y  Y  M  V  A  *  F  V
         Y  P  L  F  C  L  I  G  L  Q  L  F  T  T  W  L  P  D  L  F
          I  H  Y  F  V  L  L  V  Y  N  Y  L  L  H  G  C  L  I  C  L

7501    TATGTTAGAAACTATGCATTGGTTGATTAGATTTATTGTATTTGTAGCTAATATGTTACC    7560
        Y  V  R  N  Y  A  L  V  D  *  I  Y  C  I  C  S  *  Y  V  T
         M  L  E  T  M  H  W  L  I  R  F  I  V  F  V  A  N  M  L  P
          C  *  K  L  C  I  G  *  L  D  L  L  Y  L  *  L  I  C  Y  L
```

FIG. 2 CONT.

```
7561   TGCTTTTGTCTTGTTGCGGTTTTATATAGTTGTTACTGCTATGTATAAAGTAGTTGGTTT   7620
       C  F  C  L  V  A  V  L  Y  S  C  Y  C  Y  V  *  S  S  W  F
        A  F  V  L  L  R  F  Y  I  V  V  T  A  M  Y  K  V  V  G  F
         L  L  S  C  C  G  F  I  *  L  L  L  L  C  I  K  *  L  V  L

7621   TATTAGGCATATTGTCTATGGTTGTAATAAAGCTGGTTGTTTATTTTGTTATAAACGAAA   7680
       Y  *  A  Y  C  L  W  L  *  *  S  W  L  F  I  L  L  *  T  K
        I  R  H  I  V  Y  G  C  N  K  A  G  C  L  F  C  Y  K  R  N
         L  G  I  L  S  M  V  V  I  K  L  V  V  Y  F  V  I  N  E  I

7681   TTGTAGTGTTCGTGTTAAGTGTAGTACTATTGTTGGTGGTGTAATTCGTTATTATGATAT   7740
       L  *  C  S  C  *  V  *  Y  Y  C  W  W  C  N  S  L  L  *  Y
        C  S  V  R  V  K  C  S  T  I  V  G  G  V  I  R  Y  Y  D  I
         V  V  F  V  L  S  V  V  L  L  L  V  V  *  F  V  I  M  I  L

7741   TACTGCTAATGGTGGTACTGGTTTTTGTGTTAAACATCAATGGAATTGTTTTAATTGCCA   7800
       Y  C  *  W  W  Y  W  F  L  C  *  T  S  M  E  L  F  *  L  P
        T  A  N  G  G  T  G  F  C  V  K  H  Q  W  N  C  F  N  C  H
         L  L  M  V  V  L  V  F  V  L  N  I  N  G  I  V  L  I  A  I

7801   TTCTTTTAAACCAGGTAACACTTTTATAACTGTAGAAGCTGCTATAGAACTTTCTAAAGA   7860
       F  F  *  T  R  *  H  F  Y  N  C  R  S  C  Y  R  T  F  *  R
        S  F  K  P  G  N  T  F  I  T  V  E  A  A  I  E  L  S  K  E
         L  L  N  Q  V  T  L  L  *  L  *  K  L  L  *  N  F  L  K  S

7861   GCTTAAACGACCTGTAAATCCAACTGATGCTTCACATTATGTAGTTACTGATATTAAGCA   7920
       A  *  T  T  C  K  S  N  *  C  F  T  L  C  S  Y  *  Y  *  A
        L  K  R  P  V  N  P  T  D  A  S  H  Y  V  V  T  D  I  K  Q
         L  N  D  L  *  I  Q  L  M  L  H  I  M  *  L  L  I  L  S  K

7921   AGTTGGTTGTATGATGCGTTTGTTCTATGATAGAGATGGACAGCGTGTTTACGATGATGT   7980
       S  W  L  Y  D  A  F  V  L  *  *  R  W  T  A  C  L  R  *  C
        V  G  C  M  M  R  L  F  Y  D  R  D  G  Q  R  V  Y  D  D  V
         L  V  V  *  C  V  C  S  M  I  E  M  D  S  V  F  T  M  M  L

7981   TGATGCTAGTTTATTTGTAGATATTAATAATCTGTTACATTCTAAAGTTAAAGTTGTTCC   8040
       *  C  *  F  I  C  R  Y  *  *  S  V  T  F  *  S  *  S  C  S
        D  A  S  L  F  V  D  I  N  N  L  L  H  S  K  V  K  V  V  P
         M  L  V  Y  L  *  I  L  I  I  C  Y  I  L  K  L  K  L  F  L

8041   TAATTTGTATGTAGTTGTAGTAGAGAGTGATGCTGATAGAGCTAATTTTCTGAATGCTGT   8100
       *  F  V  C  S  C  S  R  E  *  C  *  *  S  *  F  S  E  C  C
        N  L  Y  V  V  V  V  E  S  D  A  D  R  A  N  F  L  N  A  V
         I  C  M  *  L  *  *  R  V  M  L  I  E  L  I  F  *  M  L  L
```

FIG. 2 CONT.

```
8101  TGTGTTTTATGCACAATCATTGTATAGGCCTATATTACTTGTAGACAAAAAGTTAATTAC  8160
      C V L C T I I V * A Y I T C R Q K V N Y
       V F Y A Q S L Y R P I L L V D K K L I T
        C F M H N H C I G L Y Y L * T K S * L L

8161  TACAGCTTGTAATGGTATCTCTGTAACCCAGACTATGTTTGATGTTTATGTTGATACTTT  8220
      Y S L * W Y L C N P D Y V * C L C * Y F
       T A C N G I S V T Q T M F D V Y V D T F
        Q L V M V S L * P R L C L M F M L I L L

8221  TATGTCTCATTTTGATGTTGATAGAAAGAGTTTTAATAATTTTGTTAACATTGCTCATGC  8280
      Y V S F * C * * K E F * * F C * H C S C
       M S H F D V D R K S F N N F V N I A H A
        C L I L M L I E R V L I I L L T L L M L

8281  TTCTCTTAGAGAGGGTGTGCAATTAGAAAAGGTTTTAGATACTTTTGTGGGATGTGTACG  8340
      F S * R G C A I R K G F R Y F C G M C T
       S L R E G V Q L E K V L D T F V G C V R
        L L E R V C N * K R F * I L L W D V Y V

8341  TAAATGTTGTTCCATTGATTCAGATGTTGAAACAAGATTTATTACTAAATCTATGATATC  8400
      * M L F H * F R C * N K I Y Y * I Y D I
       K C C S I D S D V E T R F I T K S M I S
        N V V P L I Q M L K Q D L L L N L * Y L

8401  TGCAGTAGCTGCTGGTTTGGAATTTACTGATGAAAATTATAACAATTTGGTACCTACATA  8460
      C S S C W F G I Y * * K L * Q F G T Y I
       A V A A G L E F T D E N Y N N L V P T Y
        Q * L L V W N L L M K I I T I W Y L H I

8461  TTTAAAGAGTGATAATATTGTAGCTGCTGATTTAGGTGTTCTTATACAGAATGGTGCTAA  8520
      F K E * * Y C S C * F R C S Y T E W C *
       L K S D N I V A A D L G V L I Q N G A K
        * R V I I L * L L I * V F L Y R M V L S

8521  GCATGTACAGGGTAATGTTGCTAAGGCAGCTAATATTTCTTGTATATGGTTTATTGATGC  8580
      A C T G * C C * G S * Y F L Y M V Y * C
       H V Q G N V A K A A N I S C I W F I D A
        M Y R V M L L R Q L I F L V Y G L L M L

8581  TTTTAATCAACTTACTGCTGATTTACAGCATAAATTAAAAAAAGCATGTGTTAAAACTGG  8640
      F * S T Y C * F T A * I K K S M C * N W
       F N Q L T A D L Q H K L K K A C V K T G
        L I N L L L I Y S I N * K K H V L K L A
```

FIG. 2 CONT.

```
8641   CTTGAAGTTAAAATTGACTTTTAATAAGCAAGAGGCAAGTGTCCCTATTCTTACAACACC   8700
       L  E  V  K  I  D  F  *  *  A  R  G  K  C  P  Y  S  Y  N  T
        L  K  L  K  L  T  F  N  K  Q  E  A  S  V  P  I  L  T  T  P
         *  S  *  N  *  L  L  I  S  K  R  Q  V  S  L  F  L  Q  H  P

8701   CTTTTCACTTAAAGGAGGTGTTGTATTGAGTAATTTGTTATATATATTATTTTTTGTTAG   8760
       L  F  T  *  R  R  C  C  I  E  *  F  V  I  Y  I  I  F  C  *
        F  S  L  K  G  G  V  V  L  S  N  L  L  Y  I  L  F  F  V  S
         F  H  L  K  E  V  L  Y  *  V  I  C  Y  I  Y  Y  F  L  L  V

8761   TTTAATCTGTTTTATATTATTGTGGGCTTTATTGCCTACATATAGTGTTTATAAGTCTGA   8820
       F  N  L  F  Y  I  I  V  G  F  I  A  Y  I  *  C  L  *  V  *
        L  I  C  F  I  L  L  W  A  L  L  P  T  Y  S  V  Y  K  S  D
         *  S  V  L  Y  Y  C  G  L  Y  C  L  H  I  V  F  I  S  L  I

8821   TATTCATTTGCCTGCTTATGCTAGTTTTAAAGTTATTGATAATGGTGTTGTTAGAGATAT   8880
       Y  S  F  A  C  L  C  *  F  *  S  Y  *  *  W  C  C  *  R  Y
        I  H  L  P  A  Y  A  S  F  K  V  I  D  N  G  V  V  R  D  I
         F  I  C  L  L  M  L  V  L  K  L  L  I  M  V  L  L  E  I  F

8881   TTCAGTTAATGATTTATGTTTTGCTAATAAATTTTTCCAATTTGATCAATGGTATGAGTC   8940
       F  S  *  *  F  M  F  C  *  *  I  F  P  I  *  S  M  V  *  V
        S  V  N  D  L  C  F  A  N  K  F  F  Q  F  D  Q  W  Y  E  S
         Q  L  M  I  Y  V  L  L  I  N  F  S  N  L  I  N  G  M  S  P

8941   CACTTTTGGGTCTGTTTACTATCATAATTCTATGGATTGCCCTATTGTAGTGGCAGTTAT   9000
       H  F  W  V  C  L  L  S  *  F  Y  G  L  P  Y  C  S  G  S  Y
        T  F  G  S  V  Y  Y  H  N  S  M  D  C  P  I  V  V  A  V  M
         L  L  G  L  F  T  I  I  I  L  W  I  A  L  L  *  W  Q  L  W

9001   GGATGAAGATATCGGTTCTACTATGTTTAATGTTCCTACTAAAGTTTTGAGACATGGCTT   9060
       G  *  R  Y  R  F  Y  Y  V  *  C  S  Y  *  S  F  E  T  W  L
        D  E  D  I  G  S  T  M  F  N  V  P  T  K  V  L  R  H  G  F
         M  K  I  S  V  L  L  C  L  M  F  L  L  K  F  *  D  M  A  F

9061   TCATGTTTTACATTTTTTAACTTATGCATTTGCTAGTGATAGTGTTCAGTGCTATACACC   9120
       S  C  F  T  F  F  N  L  C  I  C  *  *  *  C  S  V  L  Y  T
        H  V  L  H  F  L  T  Y  A  F  A  S  D  S  V  Q  C  Y  T  P
         M  F  Y  I  F  *  L  M  H  L  L  V  I  V  F  S  A  I  H  H

9121   ACATATTCAGATTTCTTATAATGATTTTTATGCTAGTGGTTGTGTTTTATCATCTTTGTG   9180
       T  Y  S  D  F  L  *  *  F  L  C  *  W  L  C  F  I  I  F  V
        H  I  Q  I  S  Y  N  D  F  Y  A  S  G  C  V  L  S  S  L  C
         I  F  R  F  L  I  M  I  F  M  L  V  V  V  F  Y  H  L  C  V
```

FIG. 2 CONT.

```
9181   TACTATGTTTAAAAGAGGTGATGGTACACCACATCCTTATTGTTATTCAGATGGTGTTAT   9240
       Y  Y  V  *  K  R  *  W  Y  T  T  S  L  L  L  F  R  W  C  Y
        T  M  F  K  R  G  D  G  T  P  H  P  Y  C  Y  S  D  G  V  M
         L  C  L  K  E  V  M  V  H  H  I  L  I  V  I  Q  M  V  L  *

9241   GAAGAATGCTTCTTTGTATACATCTTTGGTTCCACATACACGTTATAGCCTTGCTAATTC   9300
       E  E  C  F  F  V  Y  I  F  G  S  T  Y  T  L  *  P  C  *  F
        K  N  A  S  L  Y  T  S  L  V  P  H  T  R  Y  S  L  A  N  S
         R  M  L  L  C  I  H  L  W  F  H  I  H  V  I  A  L  L  I  L

9301   TAATGGTTTTATAAGATTTCCTGATGTTATTAGTGAAGGTATTGTACGTATTGTAAGAAC   9360
       *  W  F  Y  K  I  S  *  C  Y  *  *  R  Y  C  T  Y  C  K  N
        N  G  F  I  R  F  P  D  V  I  S  E  G  I  V  R  I  V  R  T
         M  V  L  *  D  F  L  M  L  L  V  K  V  L  Y  V  L  *  E  R

9361   GCGCTCTATGACTTATTGTAGAGTGGGTGCATGTGAATACGCCGAAGAGGGTATATGTTT   9420
       A  L  Y  D  L  L  *  S  G  C  M  *  I  R  R  R  G  Y  M  F
        R  S  M  T  Y  C  R  V  G  A  C  E  Y  A  E  E  G  I  C  F
         A  L  *  L  I  V  E  W  V  H  V  N  T  P  K  R  V  Y  V  L

9421   TAATTTTAATAGTTCCTGGGTTTTGAATAATGATTATTATAGAAGTATGCCTGGAACTTT   9480
       *  F  *  *  F  L  G  F  E  *  *  L  L  *  K  Y  A  W  N  F
        N  F  N  S  S  W  V  L  N  N  D  Y  Y  R  S  M  P  G  T  F
         I  L  I  V  P  G  F  *  I  M  I  I  I  E  V  C  L  E  L  F

9481   TTGTGGTAGAGATCTTTTTGATTTGTTTTATCAATTTTTTAGTAGTTTAATTCGTCCTAT   9540
       L  W  *  R  S  F  *  F  V  L  S  I  F  *  *  F  N  S  S  Y
        C  G  R  D  L  F  D  L  F  Y  Q  F  F  S  S  L  I  R  P  I
         V  V  E  I  F  L  I  C  F  I  N  F  L  V  V  *  F  V  L  *

9541   AGATTTCTTTTCTCTTACTGCTAGTTCTATTTTTGGAGCTATATTGGCTATAGTTGTTGT   9600
       R  F  L  F  S  Y  C  *  F  Y  F  W  S  Y  I  G  Y  S  C  C
        D  F  F  S  L  T  A  S  S  I  F  G  A  I  L  A  I  V  V  V
         I  S  F  L  L  L  L  V  L  F  L  E  L  Y  W  L  *  L  L  S

9601   CTTGGTTTTTTATTATTTAATAAAACTTAAGCGTGCTTTTGGAGATTATACTAGTGTTGT   9660
       L  G  F  L  L  F  N  K  T  *  A  C  F  W  R  L  Y  *  C  C
        L  V  F  Y  Y  L  I  K  L  K  R  A  F  G  D  Y  T  S  V  V
         W  F  F  I  I  *  *  N  L  S  V  L  L  E  I  I  L  V  L  *

9661   AGTTATAAATGTTGTTGTTTGGTGTATTAATTTTCTTATGCTTTTTGTTTTTCAAGTTTA   9720
       S  Y  K  C  C  C  L  V  Y  *  F  S  Y  A  F  C  F  S  S  L
        V  I  N  V  V  V  W  C  I  N  F  L  M  L  F  V  F  Q  V  Y
         L  *  M  L  L  F  G  V  L  I  F  L  C  F  L  F  F  K  F  I
```

FIG. 2 CONT.

```
9721   TCCTATTTGTGCATGTGTTTATGCTTGTTTTTATTTTTATGTAACATTGTATTTTCCTTC   9780
       S  Y  L  C  M  C  L  C  L  F  L  F  L  C  N  I  V  F  S  F
        P  I  C  A  C  V  Y  A  C  F  Y  F  Y  V  T  L  Y  F  P  S
         L  F  V  H  V  F  M  L  V  F  I  F  M  *  H  C  I  F  L  L

9781   TGAAATTAGTGTAATTATGCATTTGCAATGGATTGTTATGTATGGTGCTATAATGCCTTT   9840
       *  N  *  C  N  Y  A  F  A  M  D  C  Y  V  W  C  Y  N  A  F
        E  I  S  V  I  M  H  L  Q  W  I  V  M  Y  G  A  I  M  P  F
         K  L  V  *  L  C  I  C  N  G  L  L  C  M  V  L  *  C  L  F

9841   TTGGTTTTGTGTCACATATGTAGCTATGGTTATTGCAAACCATGTTTTATGGTTATTTTC   9900
       L  V  L  C  H  I  C  S  Y  G  Y  C  K  P  C  F  M  V  I  F
        W  F  C  V  T  Y  V  A  M  V  I  A  N  H  V  L  W  L  F  S
         G  F  V  S  H  M  *  L  W  L  L  Q  T  M  F  Y  G  Y  F  H

9901   ATATTGTAGGAAAATTGGTGTTAATGTATGTAGTGATAGTACATTTGAAGAAACATCTCT   9960
       I  L  *  E  N  W  C  *  C  M  *  *  *  Y  I  *  R  N  I  S
        Y  C  R  K  I  G  V  N  V  C  S  D  S  T  F  E  E  T  S  L
         I  V  G  K  L  V  L  M  Y  V  V  I  V  H  L  K  K  H  L  L

9961   TACTACTTTTATGATTACTAAAGATTCTTATTGTAGATTAAAGAATTCTGTTTCTGATGT   10020
       Y  Y  F  Y  D  Y  *  R  F  L  L  *  I  K  E  F  C  F  *  C
        T  T  F  M  I  T  K  D  S  Y  C  R  L  K  N  S  V  S  D  V
         L  L  L  *  L  L  K  I  L  I  V  D  *  R  I  L  F  L  M  L

10021  TGCCTACAATAGATATTTGAGTTTGTATAATAAGTATCGTTACTATAGTGGTAAAATGGA   10080
       C  L  Q  *  I  F  E  F  V  *  *  V  S  L  L  *  W  *  N  G
        A  Y  N  R  Y  L  S  L  Y  N  K  Y  R  Y  Y  S  G  K  M  D
         P  T  I  D  I  *  V  C  I  I  S  I  V  T  I  V  V  K  W  I

10081  TACTGCTGCCTATAGAGAAGCGGCGTGTTCTCAGTTAGCTAAAGCTATGGAAACATTTAA   10140
       Y  C  C  L  *  R  S  G  V  F  S  V  S  *  S  Y  G  N  I  *
        T  A  A  Y  R  E  A  A  C  S  Q  L  A  K  A  M  E  T  F  N
         L  L  P  I  E  K  R  R  V  L  S  *  L  K  L  W  K  H  L  I

10141  TCACAATAATGGTAATGATGTCTTATACCAACCTCCTACAGCATCTGTTTCTACATCTTT   10200
       S  Q  *  W  *  *  C  L  I  P  T  S  Y  S  I  C  F  Y  I  F
        H  N  N  G  N  D  V  L  Y  Q  P  P  T  A  S  V  S  T  S  F
         T  I  M  V  M  M  S  Y  T  N  L  L  Q  H  L  F  L  H  L  F

10201  TTTGCAATCAGGTATTGTAAAGATGGTATCTCCTACGTCAAAAATTGAACCTTGTATTGT   10260
       F  A  I  R  Y  C  K  D  G  I  S  Y  V  K  N  *  T  L  Y  C
        L  Q  S  G  I  V  K  M  V  S  P  T  S  K  I  E  P  C  I  V
         C  N  Q  V  L  *  R  W  Y  L  L  R  Q  K  L  N  L  V  L  L
```

FIG. 2 CONT.

```
10261  TAGTGTTACTTATGGTAGTATGACTTTGAATGGTTTATGGTTAGATGACAAAGTTTATTG  10320
       *  C  Y  L  W  *  Y  D  F  E  W  F  M  V  R  *  Q  S  L  L
        S  V  T  Y  G  S  M  T  L  N  G  L  W  L  D  D  K  V  Y  C
         V  L  L  M  V  V  *  L  *  M  V  Y  G  *  M  T  K  F  I  V

10321  TCCTCGTCATGTTATATGTTCATCCTCTAATATGAACGAACCTGATTATTCTGCCTTATT  10380
       S  S  S  C  Y  M  F  I  L  *  Y  E  R  T  *  L  F  C  L  I
        P  R  H  V  I  C  S  S  S  N  M  N  E  P  D  Y  S  A  L  L
         L  V  M  L  Y  V  H  P  L  I  *  T  N  L  I  I  L  P  Y  C

10381  GTGTAGAGTTACTCTAGGTGATTTTACTATAATGTCTGGTCGGATGAGTTTAACAGTTGT  10440
       V  *  S  Y  S  R  *  F  Y  Y  N  V  W  S  D  E  F  N  S  C
        C  R  V  T  L  G  D  F  T  I  M  S  G  R  M  S  L  T  V  V
         V  E  L  L  *  V  I  L  L  *  C  L  V  G  *  V  *  Q  L  C

10441  GTCTTACCAGATGCAGGGCTGTCAACTTGTTTTGACAGTCTCTTTACAAAATCCTTACAC  10500
       V  L  P  D  A  G  L  S  T  C  F  D  S  L  F  T  K  S  L  H
        S  Y  Q  M  Q  G  C  Q  L  V  L  T  V  S  L  Q  N  P  Y  T
         L  T  R  C  R  A  V  N  L  F  *  Q  S  L  Y  K  I  L  T  L

10501  TCCAAAATATACTTTTGGTAATGTTAAACCTGGTGAAACTTTTACTGTTTTAGCTGCGTA  10560
       S  K  I  Y  F  W  *  C  *  T  W  *  N  F  Y  C  F  S  C  V
        P  K  Y  T  F  G  N  V  K  P  G  E  T  F  T  V  L  A  A  Y
         Q  N  I  L  L  V  M  L  N  L  V  K  L  L  L  F  *  L  R  I

10561  TAATGGCCGACCACAAGGGGCATTTCATGTTACTATGCGTAGTAGTTATACTATTAAAGG  10620
       *  W  P  T  T  R  G  I  S  C  Y  Y  A  *  *  L  Y  Y  *  R
        N  G  R  P  Q  G  A  F  H  V  T  M  R  S  S  Y  T  I  K  G
         M  A  D  H  K  G  H  F  M  L  L  C  V  V  V  I  L  L  K  V

10621  TTCTTTTTTGTGTGGGTCATGTGGATCTGTTGGTTATGTATTAACAGGTGATAGTGTTAA  10680
       F  F  F  V  W  V  M  W  I  C  W  L  C  I  N  R  *  *  C  *
        S  F  L  C  G  S  C  G  S  V  G  Y  V  L  T  G  D  S  V  K
         L  F  C  V  G  H  V  D  L  L  V  M  Y  *  Q  V  I  V  L  S

10681  GTTTGTATATATGCATCAATTAGAGCTCAGTACTGGTTGTCACACTGGCACTGATTTTAC  10740
       V  C  I  Y  A  S  I  R  A  Q  Y  W  L  S  H  W  H  *  F  Y
        F  V  Y  M  H  Q  L  E  L  S  T  G  C  H  T  G  T  D  F  T
         L  Y  I  C  I  N  *  S  S  V  L  V  V  T  L  A  L  I  L  L

10741  TGGTAATTTTTATGGTCCATATAGAGATGCTCAAGTTGTACAGTTGCCAGTTAAGGACTA  10800
       W  *  F  L  W  S  I  *  R  C  S  S  C  T  V  A  S  *  G  L
        G  N  F  Y  G  P  Y  R  D  A  Q  V  V  Q  L  P  V  K  D  Y
         V  I  F  M  V  H  I  E  M  L  K  L  Y  S  C  Q  L  R  T  T
```

FIG. 2 CONT.

```
10801   CGTCCAGACTGTTAATGTTATTGCTTGGCTCTATGCAGCTATACTTAATAATTGTGCTTG   10860
        R  P  D  C  *  C  Y  C  L  A  L  C  S  Y  T  *  *  L  C  L
         V  Q  T  V  N  V  I  A  W  L  Y  A  A  I  L  N  N  C  A  W
          S  R  L  L  M  L  L  L  G  S  M  Q  L  Y  L  I  I  V  L  G

10861   GTTTGTACAAAATGATGTTTGTTCTACTGAAGATTTTAATGTTTGGGCTATGGCAAATGG   10920
        V  C  T  K  *  C  L  F  Y  *  R  F  *  C  L  G  Y  G  K  W
         F  V  Q  N  D  V  C  S  T  E  D  F  N  V  W  A  M  A  N  G
          L  Y  K  M  M  F  V  L  L  K  I  L  M  F  G  L  W  Q  M  V

10921   TTTTAGCCAAGTAAAAGCAGATCTTGTCTTAGATGCTTTGGCTTCAATGACAGGTGTTTC   10980
        F  *  P  S  K  S  R  S  C  L  R  C  F  G  F  N  D  R  C  F
         F  S  Q  V  K  A  D  L  V  L  D  A  L  A  S  M  T  G  V  S
          L  A  K  *  K  Q  I  L  S  *  M  L  W  L  Q  *  Q  V  F  L

10981   TATTGAAACTTTATTGGCTGCTATTAAGCGTCTATATATGGGATTTCAAGGTCGTCAAAT   11040
        Y  *  N  F  I  G  C  Y  *  A  S  I  Y  G  I  S  R  S  S  N
         I  E  T  L  L  A  A  I  K  R  L  Y  M  G  F  Q  G  R  Q  I
          L  K  L  Y  W  L  L  L  S  V  Y  I  W  D  F  K  V  V  K  Y

11041   ACTAGGAAGTTGTACTTTTGAAGATGAATTGGCACCTTCTGACGTTTATCAACAATTGGC   11100
        T  R  K  L  Y  F  *  R  *  I  G  T  F  *  R  L  S  T  I  G
         L  G  S  C  T  F  E  D  E  L  A  P  S  D  V  Y  Q  Q  L  A
          *  E  V  V  L  L  K  M  N  W  H  L  L  T  F  I  N  N  W  L

11101   TGGTGTTAAATTGCAATCTAAAACAAAAAGATTTATTAAAGAAACAATTTATTGGATTTT   11160
        W  C  *  I  A  I  *  N  K  K  I  Y  *  R  N  N  L  L  D  F
         G  V  K  L  Q  S  K  T  K  R  F  I  K  E  T  I  Y  W  I  L
          V  L  N  C  N  L  K  Q  K  D  L  L  K  K  Q  F  I  G  F  *

11161   GATATCTACATTTTTGTTTAGTTGTATAATTTCTGCATTTGTTAAATGGACTATATTTAT   11220
        D  I  Y  I  F  V  *  L  Y  N  F  C  I  C  *  M  D  Y  I  Y
         I  S  T  F  L  F  S  C  I  I  S  A  F  V  K  W  T  I  F  M
          Y  L  H  F  C  L  V  V  *  F  L  H  L  L  N  G  L  Y  L  C

11221   GTATATTAATACACATATGATTGGTGTTACATTATGTGTACTTTGTTTTGTTAGTTTTAT   11280
        V  Y  *  Y  T  Y  D  W  C  Y  I  M  C  T  L  F  C  *  F  Y
         Y  I  N  T  H  M  I  G  V  T  L  C  V  L  C  F  V  S  F  M
          I  L  I  H  I  *  L  V  L  H  Y  V  Y  F  V  L  L  V  L  *

11281   GATGTTACTAGTTAAACATAAGCATTTTTATTTGACTATGTATATAATTCCTGTACTCTG   11340
        D  V  T  S  *  T  *  A  F  L  F  D  Y  V  Y  N  S  C  T  L
         M  L  L  V  K  H  K  H  F  Y  L  T  M  Y  I  I  P  V  L  C
          C  Y  *  L  N  I  S  I  F  I  *  L  C  I  *  F  L  Y  S  V
```

FIG. 2 CONT.

```
11341  TACCTTGTTTTATGTAAATTATTTAGTTGTTTATAAGGAAGGTTTTAGAGGTTTTACTTA  11400
       Y  L  V  L  C  K  L  F  S  C  L  *  G  R  F  *  R  F  Y  L
        T  L  F  Y  V  N  Y  L  V  V  Y  K  E  G  F  R  G  F  T  Y
         P  C  F  M  *  I  I  *  L  F  I  R  K  V  L  E  V  L  L  M

11401  TGTCTGGCTCTCATATTTTGTTCCTGCTGTGAATTTTACTTATGTTTATGAAGTATTTTA  11460
       C  L  A  L  I  F  C  S  C  C  E  F  Y  L  C  L  *  S  I  L
        V  W  L  S  Y  F  V  P  A  V  N  F  T  Y  V  Y  E  V  F  Y
         S  G  S  H  I  L  F  L  L  *  I  L  L  M  F  M  K  Y  F  M

11461  TGGTTGTATTTTATGTGTTTTTGCTATTTTTATAACTATGCATAGTATTAATCATGACAT  11520
       W  L  Y  F  M  C  F  C  Y  F  Y  N  Y  A  *  Y  *  S  *  H
        G  C  I  L  C  V  F  A  I  F  I  T  M  H  S  I  N  H  D  I
         V  V  F  Y  V  F  L  L  F  L  *  L  C  I  V  L  I  M  T  F

11521  TTTTTCTTTGATGTTTTTGGTTGGTAGAATAGTTACTTTAATTTCTATGTGGTATTTTGG  11580
       F  F  F  D  V  F  G  W  *  N  S  Y  F  N  F  Y  V  V  F  W
        F  S  L  M  F  L  V  G  R  I  V  T  L  I  S  M  W  Y  F  G
         F  L  *  C  F  W  L  V  E  *  L  L  *  F  L  C  G  I  L  G

11581  GTCGAATTTAGAAGAGGATGTTTTGTTATTTATTACAGCCTTTTTAGGTACTTATACATG  11640
       V  E  F  R  R  G  C  F  V  I  Y  Y  S  L  F  R  Y  L  Y  M
        S  N  L  E  E  D  V  L  L  F  I  T  A  F  L  G  T  Y  T  W
         R  I  *  K  R  M  F  C  Y  L  L  Q  P  F  *  V  L  I  H  G

11641  GACCACTATTTTGTCATTAGCTATAGCAAAAATTGTTGCTAATTGGTTGTCTGTTAATAT  11700
       D  H  Y  F  V  I  S  Y  S  K  N  C  C  *  L  V  V  C  *  Y
        T  T  I  L  S  L  A  I  A  K  I  V  A  N  W  L  S  V  N  I
         P  L  F  C  H  *  L  *  Q  K  L  L  L  I  G  C  L  L  I  Y

11701  ATTTTATTTTACAGATGTACCTTATATTAAATTGATTCTCTTGAGTTACTTATTTATAGG  11760
       I  L  F  Y  R  C  T  L  Y  *  I  D  S  L  E  L  L  I  Y  R
        F  Y  F  T  D  V  P  Y  I  K  L  I  L  L  S  Y  L  F  I  G
         F  I  L  Q  M  Y  L  I  L  N  *  F  S  *  V  T  Y  L  *  G

11761  GTATATTTTATCTTGTTATTGGGGATTTTTCTCTCTTTTAAACAGTGTTTTTAGAATGCC  11820
       V  Y  F  I  L  L  L  G  I  F  L  S  F  K  Q  C  F  *  N  A
        Y  I  L  S  C  Y  W  G  F  F  S  L  L  N  S  V  F  R  M  P
         I  F  Y  L  V  I  G  D  F  S  L  F  *  T  V  F  L  E  C  L

11821  TATGGGTGTTTATAATTATAAAATTTCTGTTCAAGAATTGCGTTATATGAATGCTAATGG  11880
       Y  G  C  L  *  L  *  N  F  C  S  R  I  A  L  Y  E  C  *  W
        M  G  V  Y  N  Y  K  I  S  V  Q  E  L  R  Y  M  N  A  N  G
         W  V  F  I  I  I  K  F  L  F  K  N  C  V  I  *  M  L  M  A
```

FIG. 2 CONT.

```
11881   CTTACGTCCACCTCGTAATAGTTTTGAGGCTATTTTGTTAAATTTAAAACTGCTTGGAAT   11940
        L  T  S  T  S  *  *  F  *  G  Y  F  V  K  F  K  T  A  W  N
         L  R  P  P  R  N  S  F  E  A  I  L  L  N  L  K  L  L  G  I
          Y  V  H  L  V  I  V  L  R  L  F  C  *  I  *  N  C  L  E  *

11941   AGGTGGCGTGCCAGTTATTGAAGTCTCCCAAATTCAATCAAAATTGACTGATGTGAAATG   12000
        R  W  R  A  S  Y  *  S  L  P  N  S  I  K  I  D  *  C  E  M
         G  G  V  P  V  I  E  V  S  Q  I  Q  S  K  L  T  D  V  K  C
          V  A  C  Q  L  L  K  S  P  K  F  N  Q  N  *  L  M  *  N  V

12001   TGCTAATGTTGTTTTGTTAAATTGTTTACAGCATTTGCATGTTGCTTCTAATTCTAAGTT   12060
        C  *  C  C  F  V  K  L  F  T  A  F  A  C  C  F  *  F  *  V
         A  N  V  V  L  L  N  C  L  Q  H  L  H  V  A  S  N  S  K  L
          L  M  L  F  C  *  I  V  Y  S  I  C  M  L  L  L  I  L  S  C

12061   GTGGCAGTATTGTAGTGTTTTACATAATGAAATACTATCTACTTCAGATTTGAGTGTAGC   12120
        V  A  V  L  *  C  F  T  *  *  N  T  I  Y  F  R  F  E  C  S
         W  Q  Y  C  S  V  L  H  N  E  I  L  S  T  S  D  L  S  V  A
          G  S  I  V  V  F  Y  I  M  K  Y  Y  L  L  Q  I  *  V  *  L

12121   TTTTGATAAGCTTGCTCAATTATTGATTGTTTTATTCGCCAATCCTGCTGCAGTTGATAC   12180
        F  *  *  A  C  S  I  I  D  C  F  I  R  Q  S  C  C  S  *  Y
         F  D  K  L  A  Q  L  L  I  V  L  F  A  N  P  A  A  V  D  T
          L  I  S  L  L  N  Y  *  L  F  Y  S  P  I  L  L  Q  L  I  L

12181   TAAGTGTCTTGCAAGTATAGATGAAGTTAGCGATGATTATGTTCAAGATAGTACCGTTTT   12240
        *  V  S  C  K  Y  R  *  S  *  R  *  L  C  S  R  *  Y  R  F
         K  C  L  A  S  I  D  E  V  S  D  D  Y  V  Q  D  S  T  V  L
          S  V  L  Q  V  *  M  K  L  A  M  I  M  F  K  I  V  P  F  C

12241   GCAGGCTTTGCAAAGTGAGTTTGTAAATATGGCTAGTTTTGTTGAATATGAAGTCGCAAA   12300
        A  G  F  A  K  *  V  C  K  Y  G  *  F  C  *  I  *  S  R  K
         Q  A  L  Q  S  E  F  V  N  M  A  S  F  V  E  Y  E  V  A  K
          R  L  C  K  V  S  L  *  I  W  L  V  L  L  N  M  K  S  Q  R

12301   GAAAAATTTGGCTGATGCTAAAAATAGTGGTTCTGTTAATCAACAACAGATAAAACAGTT   12360
        E  K  F  G  *  C  *  K  *  W  F  C  *  S  T  T  D  K  T  V
         K  N  L  A  D  A  K  N  S  G  S  V  N  Q  Q  Q  I  K  Q  L
          K  I  W  L  M  L  K  I  V  V  L  L  I  N  N  R  *  N  S  *

12361   AGAAAAAGCATGTAATATAGCTAAGTCTGTGTATGAACGTGATAAAGCTGTAGCTCGCAA   12420
        R  K  S  M  *  Y  S  *  V  C  V  *  T  *  *  S  C  S  S  Q
         E  K  A  C  N  I  A  K  S  V  Y  E  R  D  K  A  V  A  R  K
          K  K  H  V  I  *  L  S  L  C  M  N  V  I  K  L  *  L  A  N
```

FIG. 2 CONT.

12421 ACTTGAACGTATGGCAGACCTAGCACTTACTAACATGTATAAAGAGGCTCGGATTAATGA 12480
T * T Y G R P S T Y * H V * R G S D * *
L E R M A D L A L T N M Y K E A R I N D
L N V W Q T * H L L T C I K R L G L M I

12481 TAAGAAGAGTAAAGTTGTTTCCGCTTTGCAGACAATGCTTTTTAGCATGGTTCGTAAATT 12540
* E E * S C F R F A D N A F * H G S * I
K K S K V V S A L Q T M L F S M V R K L
R R V K L F P L C R Q C F L A W F V N W

12541 GGATAATCAGGCTTTAAATTCTATTCTGGATAATGCTGTTAAAGGTTGTGTACCTTTGAG 12600
G * S G F K F Y S G * C C * R L C T F E
D N Q A L N S I L D N A V K G C V P L S
I I R L * I L F W I M L L K V V Y L * V

12601 TGCTATTCCAGCATTGGCTGCTAATACTTTAACTATAGTAATACCAGATAAACAAGTTTT 12660
C Y S S I G C * Y F N Y S N T R * T S F
A I P A L A A N T L T I V I P D K Q V F
L F Q H W L L I L * L * * Y Q I N K F L

12661 TGATAAAGTTGTTGATAATGTTTATGTTACATATGCTGGTAGTGTATGGCATATACAGAC 12720
* * S C * * C L C Y I C W * C M A Y T D
D K V V D N V Y V T Y A G S V W H I Q T
I K L L I M F M L H M L V V Y G I Y R L

12721 TGTTCAAGATGCTGATGGTATTAATAAACAGTTAACTGATATTAGTGTTGATTCTAATTG 12780
C S R C * W Y * * T V N * Y * C * F * L
V Q D A D G I N K Q L T D I S V D S N W
F K M L M V L I N S * L I L V L I L I G

12781 GCCTCTTGTTATCATTGCGAACAGGTATAATGAAGTTGCTAATGCTGTTATGCAGAATAA 12840
A S C Y H C E Q V * * S C * C C Y A E *
P L V I I A N R Y N E V A N A V M Q N N
L L L S L R T G I M K L L M L L C R I M

12841 TGAGTTGATGCCTCATAAATTAAAAATACAAGTTGTTAATAGTGGTTCTGATATGAATTG 12900
* V D A S * I K N T S C * * W F * Y E L
E L M P H K L K I Q V V N S G S D M N C
S * C L I N * K Y K L L I V V L I * I V

12901 TAATATTCCTACTCAATGTTATTATAATAATGGTAGTAGTGGTAGAATAGTTTATGCTGT 12960
* Y S Y S M L L * * W * * W * N S L C C
N I P T Q C Y Y N N G S S G R I V Y A V
I F L L N V I I I M V V V V E * F M L F

FIG. 2 CONT.

```
12961  TCTTAGTGATGTTGATGGTCTTAAGTATACTAAGATAATGAAAGATGATGGAAATTGTGT  13020
        S  *  *  C  *  W  S  *  V  Y  *  D  N  E  R  *  W  K  L  C
         L  S  D  V  D  G  L  K  Y  T  K  I  M  K  D  D  G  N  C  V
          L  V  M  L  M  V  L  S  I  L  R  *  *  K  M  M  E  I  V  L

13021  TGTTTTAGAGCTTGATCCTCCTTGTAAATTTTCTATACAAGATGTTAAGGGACTTAAAAT  13080
        C  F  R  A  *  S  S  L  *  I  F  Y  T  R  C  *  G  T  *  N
         V  L  E  L  D  P  P  C  K  F  S  I  Q  D  V  K  G  L  K  I
          F  *  S  L  I  L  L  V  N  F  L  Y  K  M  L  R  D  L  K  L

13081  TAAGTATCTTTATTTTATTAAAGGATGTAACACTTTAGCTAGAGGGTGGGTTGTTGGTAC  13140
        *  V  S  L  F  Y  *  R  M  *  H  F  S  *  R  V  G  C  W  Y
         K  Y  L  Y  F  I  K  G  C  N  T  L  A  R  G  W  V  V  G  T
          S  I  F  I  L  L  K  D  V  T  L  *  L  E  G  G  L  L  V  L

13141  TTTATCTTCAACAATTAGATTGCAGGCTGGTGTTGCTACTGAGTATGCAGCTAATTCTTC  13200
        F  I  F  N  N  *  I  A  G  W  C  C  Y  *  V  C  S  *  F  F
         L  S  S  T  I  R  L  Q  A  G  V  A  T  E  Y  A  A  N  S  S
          Y  L  Q  Q  L  D  C  R  L  V  L  L  L  S  M  Q  L  I  L  L

13201  TATACTTTCATTATGTGCATTTTCTGTAGATCCTAAGAAAACTTATTTAGATTATATACA  13260
        Y  T  F  I  M  C  I  F  C  R  S  *  E  N  L  F  R  L  Y  T
         I  L  S  L  C  A  F  S  V  D  P  K  K  T  Y  L  D  Y  I  Q
          Y  F  H  Y  V  H  F  L  *  I  L  R  K  L  I  *  I  I  Y  N

13261  ACAAGGTGGTGTACCTATAATTAATTGTGTTAAAATGCTCTGTGATCATGCTGGTACTGG  13320
        T  R  W  C  T  Y  N  *  L  C  *  N  A  L  *  S  C  W  Y  W
         Q  G  G  V  P  I  I  N  C  V  K  M  L  C  D  H  A  G  T  G
          K  V  V  Y  L  *  L  I  V  L  K  C  S  V  I  M  L  V  L  V

13321  TATGGCCATTACTATTAAACCTGAGGCTACTATTAACCAAGATTCTTATGGTGGTGCCTC  13380
        Y  G  H  Y  Y  *  T  *  G  Y  Y  *  P  R  F  L  W  W  C  L
         M  A  I  T  I  K  P  E  A  T  I  N  Q  D  S  Y  G  G  A  S
          W  P  L  L  L  N  L  R  L  L  L  T  K  I  L  M  V  V  P  Q

13381  AGTTTGTATTTATTGCCGTGCACGTGTAGAGCATCCAGATGTAGATGGTATATGTAAATT  13440
        S  L  Y  L  L  P  C  T  C  R  A  S  R  C  R  W  Y  M  *  I
         V  C  I  Y  C  R  A  R  V  E  H  P  D  V  D  G  I  C  K  L
          F  V  F  I  A  V  H  V  *  S  I  Q  M  *  M  V  Y  V  N  Y

13441  ACGTGGTAAATTTGTACAAGTCCCTTTGGGTATAAAAGATCCTATTCTTTATGTGTTAAC  13500
        T  W  *  I  C  T  S  P  F  G  Y  K  R  S  Y  S  L  C  V  N
         R  G  K  F  V  Q  V  P  L  G  I  K  D  P  I  L  Y  V  L  T
          V  V  N  L  Y  K  S  L  W  V  *  K  I  L  F  F  M  C  *  H
```

FIG. 2 CONT.

```
13501   ACATGATGTTTGTCAAGTCTGTGGTTTTTGGAGAGATGGCAGTTGTTCCTGTGTAGGTTC   13560
        T  *  C  L  S  S  L  W  F  L  E  R  W  Q  L  F  L  C  R  F
         H  D  V  C  Q  V  C  G  F  W  R  D  G  S  C  S  C  V  G  S
          M  M  F  V  K  S  V  V  F  G  E  M  A  V  V  P  V  *  V  Q

13561   AAGTGTCGCTGTTCAATCTAAAGATTTAAATTTTTTAAACGGGTTCGGGGTACTAGTGTG   13620
        K  C  R  C  S  I  *  R  F  K  F  F  K  R  V  R  G  T  S  V
         S  V  A  V  Q  S  K  D  L  N  F  L  N  G  F  G  V  L  V  *
          V  S  L  F  N  L  K  I  *  I  F  *  T  G  S  G  Y  *  C  E

13621   AATGCCCGGCTAGTACCCTGTGCTAGTGGTTTATCTACTGATGTTCAATTAAGGGCATTT   13680
        N  A  R  L  V  P  C  A  S  G  L  S  T  D  V  Q  L  R  A  F
         M  P  G  *  Y  P  V  L  V  V  Y  L  L  M  F  N  *  G  H  L
          C  P  A  S  T  L  C  *  W  F  I  Y  *  C  S  I  K  G  I  *

13681   GACATTTGTAATACCAATAGAGCTGGTATAGGTTTATATTATAAAGTGAATTGTTGCCGT   13740
        D  I  C  N  T  N  R  A  G  I  G  L  Y  Y  K  V  N  C  C  R
         T  F  V  I  P  I  E  L  V  *  V  Y  I  I  K  *  I  V  A  V
          H  L  *  Y  Q  *  S  W  Y  R  F  I  L  *  S  E  L  L  P  F

13741   TTTCAGCGTATAGATGACGACGGTAATAAATTGGATAAGTTCTTTGTTGTCAAAAGAACT   13800
        F  Q  R  I  D  D  D  G  N  K  L  D  K  F  F  V  V  K  R  T
         F  S  V  *  M  T  T  V  I  N  W  I  S  S  L  L  S  K  E  L
          S  A  Y  R  *  R  R  *  *  I  G  *  V  L  C  C  Q  K  N  *

13801   AATTTAGAAGTTTATAATAAAGAGAAAACTTATTATGAGTTGACTAAAAGTTGTGGTGTT   13860
        N  L  E  V  Y  N  K  E  K  T  Y  Y  E  L  T  K  S  C  G  V
         I  *  K  F  I  I  K  R  K  L  I  M  S  *  L  K  V  V  V  L
          F  R  S  L  *  *  R  E  N  L  L  *  V  D  *  K  L  W  C  C

13861   GTGGCTGAACATGATTTCTTTACATTTGATATTGATGGTAGTCGCGTGCCACATATAGTT   13920
        V  A  E  H  D  F  F  T  F  D  I  D  G  S  R  V  P  H  I  V
         W  L  N  M  I  S  L  H  L  I  L  M  V  V  A  C  H  I  *  F
          G  *  T  *  F  L  Y  I  *  Y  *  W  *  S  R  A  T  Y  S  S

13921   CGTAGGAATCTTTCAAAGTATACTATGTTAGATCTTTGCTATGCATTGCGTCATTTTGAT   13980
        R  R  N  L  S  K  Y  T  M  L  D  L  C  Y  A  L  R  H  F  D
         V  G  I  F  Q  S  I  L  C  *  I  F  A  M  H  C  V  I  L  I
          *  E  S  F  K  V  Y  Y  V  R  S  L  L  C  I  A  S  F  *  S

13981   CGTAATGATTGTTCAATATTGTGTGAAATTCTTTGTGAGTATGCTGATTGTAAAGAATCC   14040
        R  N  D  C  S  I  L  C  E  I  L  C  E  Y  A  D  C  K  E  S
         V  M  I  V  Q  Y  C  V  K  F  F  V  S  M  L  I  V  K  N  P
          *  *  L  F  N  I  V  *  N  S  L  *  V  C  *  L  *  R  I  L
```

FIG. 2 CONT.

```
14041  TACTTTTCTAAGAAAGATTGGTATGATTTTGTTGAAAATCCTGATATTATTAATATATAT  14100
       Y  F  S  K  K  D  W  Y  D  F  V  E  N  P  D  I  I  N  I  Y
        T  F  L  R  K  I  G  M  I  L  L  K  I  L  I  L  L  I  Y  I
         L  F  *  E  R  L  V  *  F  C  *  K  S  *  Y  Y  *  Y  I  *

14101  AAAAAATTAGGCCCTATTTTTAATAGAGCTTTACTTAATACTGTCATTTTTGCAGACACC  14160
       K  K  L  G  P  I  F  N  R  A  L  L  N  T  V  I  F  A  D  T
        K  N  *  A  L  F  L  I  E  L  Y  L  I  L  S  F  L  Q  T  P
         K  I  R  P  Y  F  *  *  S  F  T  *  Y  C  H  F  C  R  H  L

14161  TTAGTTGAAGTAGGTTTAGTTGGTGTTTTAACTTTAGATAACCAAGATTTGTATGGTCAA  14220
       L  V  E  V  G  L  V  G  V  L  T  L  D  N  Q  D  L  Y  G  Q
        *  L  K  *  V  *  L  V  F  *  L  *  I  T  K  I  C  M  V  N
         S  *  S  R  F  S  W  C  F  N  F  R  *  P  R  F  V  W  S  M

14221  TGGTATGATTTTGGTGATTTTATACAAACAGCCCCAGGGTTTGGTGTGGCAGTTGCAGAT  14280
       W  Y  D  F  G  D  F  I  Q  T  A  P  G  F  G  V  A  V  A  D
        G  M  I  L  V  I  L  Y  K  Q  P  Q  G  L  V  W  Q  L  Q  I
         V  *  F  W  *  F  Y  T  N  S  P  R  V  W  C  G  S  C  R  F

14281  TCTTACTATTCTTATATGATGCCTATGTTGACTATGTGTCATGTATTAGATTGTGAATTA  14340
       S  Y  Y  S  Y  M  M  P  M  L  T  M  C  H  V  L  D  C  E  L
        L  T  I  L  I  *  C  L  C  *  L  C  V  M  Y  *  I  V  N  Y
         L  L  F  L  Y  D  A  Y  V  D  Y  V  S  C  I  R  L  *  I  I

14341  TTTGTTAATGATAGTTATAGACAATTCGATCTTGTACAGTATGATTTTACTGATTACAAG  14400
       F  V  N  D  S  Y  R  Q  F  D  L  V  Q  Y  D  F  T  D  Y  K
        L  L  M  I  V  I  D  N  S  I  L  Y  S  M  I  L  L  I  T  S
         C  *  *  *  L  *  T  I  R  S  C  T  V  *  F  Y  *  L  Q  V

14401  TTAGAGTTGTTTAATAAGTATTTTAAGTATTGGGGTATGAAGTATCATCCTAATACTGTG  14460
       L  E  L  F  N  K  Y  F  K  Y  W  G  M  K  Y  H  P  N  T  V
        *  S  C  L  I  S  I  L  S  I  G  V  *  S  I  I  L  I  L  W
         R  V  V  *  *  V  F  *  V  L  G  Y  E  V  S  S  *  Y  C  G

14461  GATTGTGATAATGATAGGTGTATTATTCATTGTGCTAATTTTAATATACTATTTAGTATG  14520
       D  C  D  N  D  R  C  I  I  H  C  A  N  F  N  I  L  F  S  M
        I  V  I  M  I  G  V  L  F  I  V  L  I  L  I  Y  Y  L  V  W
         L  *  *  *  *  V  Y  Y  S  L  C  *  F  *  Y  T  I  *  Y  G

14521  GTTTTACCTAATACTTGTTTTGGTCCCCTTGTTAGACAAATTTTTGTAGATGGTGTACCG  14580
       V  L  P  N  T  C  F  G  P  L  V  R  Q  I  F  V  D  G  V  P
        F  Y  L  I  L  V  L  V  P  L  L  D  K  F  L  *  M  V  Y  R
         F  T  *  Y  L  F  W  S  P  C  *  T  N  F  C  R  W  C  T  V
```

FIG. 2 CONT.

```
14581  TTTGTTGTTTCTATTGGTTACCATTACAAAGAGTTAGGTGTAGTTATGAACTTAGATGTT  14640
       F  V  V  S  I  G  Y  H  Y  K  E  L  G  V  V  M  N  L  D  V
        L  L  F  L  L  V  T  I  T  K  S  *  V  *  L  *  T  *  M  L
         C  C  F  Y  W  L  P  L  Q  R  V  R  C  S  Y  E  L  R  C  *

14641  GACACACACCGTTATCGTTTGTCTCTTAAAGATTTACTTCTTTATGCAGCAGATCCTGCT  14700
       D  T  H  R  Y  R  L  S  L  K  D  L  L  L  Y  A  A  D  P  A
        T  H  T  V  I  V  C  L  L  K  I  Y  F  F  M  Q  Q  I  L  L
         H  T  P  L  S  F  V  S  *  R  F  T  S  L  C  S  R  S  C  Y

14701  ATGCACGTTGCATCTGCTAGTGCTCTGCTTGATTTACGAACTTGTTGTTTTAGTGTAGCT  14760
       M  H  V  A  S  A  S  A  L  L  D  L  R  T  C  C  F  S  V  A
        C  T  L  H  L  L  V  L  C  L  I  Y  E  L  V  V  L  V  *  L
         A  R  C  I  C  *  C  S  A  *  F  T  N  L  L  F  *  C  S  C

14761  GCCATTACAAGTGGTATAAAATTTCAAACTGTAAAACCAGGTAACTTTAACCAAGACTTT  14820
       A  I  T  S  G  I  K  F  Q  T  V  K  P  G  N  F  N  Q  D  F
        P  L  Q  V  V  *  N  F  K  L  *  N  Q  V  T  L  T  K  T  F
         H  Y  K  W  Y  K  I  S  N  C  K  T  R  *  L  *  P  R  L  L

14821  TACGAGTTTGTTAAAAGTAAAGGCTTGTTTAAAGAGGGTAGTACAGTTGATTTGAAACAT  14880
       Y  E  F  V  K  S  K  G  L  F  K  E  G  S  T  V  D  L  K  H
        T  S  L  L  K  V  K  A  C  L  K  R  V  V  Q  L  I  *  N  I
         R  V  C  *  K  *  R  L  V  *  R  G  *  Y  S  *  F  E  T  F

14881  TTTTTCTTTACTCAAGATGGTAATGCTGCAATTACTGATTATAATTATTATAAGTATAAT  14940
       F  F  F  T  Q  D  G  N  A  A  I  T  D  Y  N  Y  Y  K  Y  N
        F  S  L  L  K  M  V  M  L  Q  L  L  I  I  I  I  I  S  I  I
         F  L  Y  S  R  W  *  C  C  N  Y  *  L  *  L  L  *  V  *  F

14941  TTACCTACTATGGTTGATATTAAGCAGTTATTGTTTGTATTAGAAGTTGTTTATAAATAT  15000
       L  P  T  M  V  D  I  K  Q  L  L  F  V  L  E  V  V  Y  K  Y
        Y  L  L  W  L  I  L  S  S  Y  C  L  Y  *  K  L  F  I  N  I
         T  Y  Y  G  *  Y  *  A  V  I  V  C  I  R  S  C  L  *  I  F

15001  TTTGAAATTTATGATGGTGGTTGTATACCAGCATCACAAGTTATTGTTAATAATTATGAT  15060
       F  E  I  Y  D  G  G  C  I  P  A  S  Q  V  I  V  N  N  Y  D
        L  K  F  M  M  V  V  V  Y  Q  H  H  K  L  L  L  I  I  M  I
         *  N  L  *  W  W  L  Y  T  S  I  T  S  Y  C  *  *  L  *  *

15061  AAAAGTGCTGGTTATCCATTTAATAAATTTGGTAAAGCCAGACTTTATTATGAGGCATTA  15120
       K  S  A  G  Y  P  F  N  K  F  G  K  A  R  L  Y  Y  E  A  L
        K  V  L  V  I  H  L  I  N  L  V  K  P  D  F  I  M  R  H  Y
         K  C  W  L  S  I  *  *  I  W  *  S  Q  T  L  L  *  G  I  I
```

FIG. 2 CONT.

```
15121  TCATTTGAGGAACAGAATGAAATTTATGCATATACTAAACGTAATGTTCTGCCCACCTTA  15180
       S  F  E  E  Q  N  E  I  Y  A  Y  T  K  R  N  V  L  P  T  L
        H  L  R  N  R  M  K  F  M  H  I  L  N  V  M  F  C  P  P  *
         I  *  G  T  E  *  N  L  C  I  Y  *  T  *  C  S  A  H  L  N

15181  ACTCAAATGAATTTAAAATATGCTATCAGTGCTAAGAATAGAGCTCGCACTGTAGCAGGT  15240
       T  Q  M  N  L  K  Y  A  I  S  A  K  N  R  A  R  T  V  A  G
        L  K  *  I  *  N  M  L  S  V  L  R  I  E  L  A  L  *  Q  V
         S  N  E  F  K  I  C  Y  Q  C  *  E  *  S  S  H  C  S  R  C

15241  GTTTCTATTCTTAGTACTATGACAGGCCGAATGTTCCATCAAAAATGTTTGAAGAGTATA  15300
       V  S  I  L  S  T  M  T  G  R  M  F  H  Q  K  C  L  K  S  I
        F  L  F  L  V  L  *  Q  A  E  C  S  I  K  N  V  *  R  V  *
         F  Y  S  *  Y  Y  D  R  P  N  V  P  S  K  M  F  E  E  Y  S

15301  GCAGCTACCCGAGGTGTTCCTGTTGTTATAGGAACCACTAAATTTTATGGTGGTTGGGAC  15360
       A  A  T  R  G  V  P  V  V  I  G  T  T  K  F  Y  G  G  W  D
        Q  L  P  E  V  F  L  L  L  *  E  P  L  N  F  M  V  V  G  T
         S  Y  P  R  C  S  C  C  Y  R  N  H  *  I  L  W  W  L  G  R

15361  GATATGTTACGTCATCTTATAAAGGATGTTGACAACCCTGTTCTTATGGGTTGGGATTAT  15420
       D  M  L  R  H  L  I  K  D  V  D  N  P  V  L  M  G  W  D  Y
        I  C  Y  V  I  L  *  R  M  L  T  T  L  F  L  W  V  G  I  I
         Y  V  T  S  S  Y  K  G  C  *  Q  P  C  S  Y  G  L  G  L  S

15421  CCTAAATGTGATCGTGCTATGCCAAATATTTTGCGTATTGTTAGTAGTTTAGTTTTGGCC  15480
       P  K  C  D  R  A  M  P  N  I  L  R  I  V  S  S  L  V  L  A
        L  N  V  I  V  L  C  Q  I  F  C  V  L  L  V  V  *  F  W  P
         *  M  *  S  C  Y  A  K  Y  F  A  Y  C  *  *  F  S  F  G  P

15481  CGCAAACATGAATTTTGTTGTTCACATGGTGATAGATTTTATCGCCTTGCGAATGAATGT  15540
       R  K  H  E  F  C  C  S  H  G  D  R  F  Y  R  L  A  N  E  C
        A  N  M  N  F  V  V  H  M  V  I  D  F  I  A  L  R  M  N  V
         Q  T  *  I  L  L  F  T  W  *  *  I  L  S  P  C  E  *  M  C

15541  GCTCAAGTTTTGAGTGAAATAGTTATGTGTGGCGGTTGCTATTATGTTAAGCCTGGTGGT  15600
       A  Q  V  L  S  E  I  V  M  C  G  G  C  Y  Y  V  K  P  G  G
        L  K  F  *  V  K  *  L  C  V  A  V  A  I  M  L  S  L  V  V
         S  S  F  E  *  N  S  Y  V  W  R  L  L  L  C  *  A  W  W  Y

15601  ACTAGCAGTGGTGATGCAACTACTGCTTTTGCTAATTCTGTTTTTAATATATGTCAGGCT  15660
       T  S  S  G  D  A  T  T  A  F  A  N  S  V  F  N  I  C  Q  A
        L  A  V  V  M  Q  L  L  L  L  L  I  L  F  L  I  Y  V  R  L
         *  Q  W  *  C  N  Y  C  F  C  *  F  C  F  *  Y  M  S  G  C
```

FIG. 2 CONT.

15661 GTTACTGCTAATGTTTGTTCTCTTATGGCCTGTAATGGCCATAAGATTGAAGATTTAAGT 15720
V T A N V C S L M A C N G H K I E D L S
L L L M F V L L W P V M A I R L K I * V
Y C * C L F S Y G L * W P * D * R F K Y

15721 ATACGCAATTTACAAAAACGCTTATACTCTAATGTTTATCGTACAGATTATGTTGATTAT 15780
I R N L Q K R L Y S N V Y R T D Y V D Y
Y A I Y K N A Y T L M F I V Q I M L I I
T Q F T K T L I L * C L S Y R L C * L Y

15781 ACATTTGTTAATGAGTATTATGAATTTTTATGTAAGCATTTTAGTATGATGATTTTGAGT 15840
T F V N E Y Y E F L C K H F S M M I L S
H L L M S I M N F Y V S I L V * * F * V
I C * * V L * I F M * A F * Y D D F E *

15841 GATGATGGTGTTGTCTGTTATAACTCTGATTATGCTAGTAAGGGTTATATAGCTAATATA 15900
D D G V V C Y N S D Y A S K G Y I A N I
M M V L S V I T L I M L V R V I * L I *
* W C C L L * L * L C * * G L Y S * Y K

15901 AGTGTTTTTCAACAAGTTTTGTACTATCAGAATAATGTCTTTATGTCTGAATCTAAATGT 15960
S V F Q Q V L Y Y Q N N V F M S E S K C
V F F N K F C T I R I M S L C L N L N V
C F S T S F V L S E * C L Y V * I * M L

15961 TGGGTTGAAAATGATATTACTAATGGTCCTCATGAATTTTGTTCCCAACATACTATGTTA 16020
W V E N D I T N G P H E F C S Q H T M L
G L K M I L L M V L M N F V P N I L C *
G * K * Y Y * W S S * I L F P T Y Y V S

16021 GTTAAGATAGATGGTGATTATGTTTATTTACCATATCCAGATCCTTCTAGAATTTTAGGA 16080
V K I D G D Y V Y L P Y P D P S R I L G
L R * M V I M F I Y H I Q I L L E F * E
* D R W * L C L F T I S R S F * N F R S

16081 GCTGGTTGTTTTGTTGATGATTTATTGAAGACTGACAGTGTTCTTTTGATAGAGCGCTTT 16140
A G C F V D D L L K T D S V L L I E R F
L V V L L M I Y * R L T V F F * * S A L
W L F C * * F I E D * Q C S F D R A L C

16141 GTAAGTCTAGCTATAGATGCTTACCCTTTAGTACATCATGAAAATGAAGAATACCAAAAA 16200
V S L A I D A Y P L V H H E N E E Y Q K
* V * L * M L T L * Y I M K M K N T K K
K S S Y R C L P F S T S * K * R I P K S

FIG. 2 CONT.

```
16201   GTCTTTCGTGTATATTTAGAATATATAAAAAAACTGTATAATGATCTTGGTACTCAGATC   16260
        V  F  R  V  Y  L  E  Y  I  K  K  L  Y  N  D  L  G  T  Q  I
         S  F  V  Y  I  *  N  I  *  K  N  C  I  M  I  L  V  L  R  S
          L  S  C  I  F  R  I  Y  K  K  T  V  *  *  S  W  Y  S  D  L

16261   TTAGATAGTTATAGTGTTATTTTAAGTACTTGTGATGGTTTAAAGTTTACTGAAGAATCA   16320
        L  D  S  Y  S  V  I  L  S  T  C  D  G  L  K  F  T  E  E  S
         *  I  V  I  V  L  F  *  V  L  V  M  V  *  S  L  L  K  N  H
          R  *  L  *  C  Y  F  K  Y  L  *  W  F  K  V  Y  *  R  I  I

16321   TTTTACAAGAATATGTATTTAAAAAGTGCCGTGATGCAGAGTGTAGGTGCATGCGTTGTT   16380
        F  Y  K  N  M  Y  L  K  S  A  V  M  Q  S  V  G  A  C  V  V
         F  T  R  I  C  I  *  K  V  P  *  C  R  V  *  V  H  A  L  F
          L  Q  E  Y  V  F  K  K  C  R  D  A  E  C  R  C  M  R  C  L

16381   TGTTCATCACAAACTTCTTTGCGTTGTGGCAGTTGTATACGTAAGCCTTTGTTATGTTGT   16440
        C  S  S  Q  T  S  L  R  C  G  S  C  I  R  K  P  L  L  C  C
         V  H  H  K  L  L  C  V  V  A  V  V  Y  V  S  L  C  Y  V  V
          F  I  T  N  F  F  A  L  W  Q  L  Y  T  *  A  F  V  M  L  *

16441   AAATGTTGTTATGACCATGTTATGGCAACTAATCATAAATATGTTTTGAGTGTCTCACCT   16500
        K  C  C  Y  D  H  V  M  A  T  N  H  K  Y  V  L  S  V  S  P
         N  V  V  M  T  M  L  W  Q  L  I  I  N  M  F  *  V  S  H  L
          M  L  L  *  P  C  Y  G  N  *  S  *  I  C  F  E  C  L  T  L

16501   TACGTTTGTAATGCACCTAACTGTGATGTGAGTGATGTCACCAAATTATATTTGGGCGGT   16560
        Y  V  C  N  A  P  N  C  D  V  S  D  V  T  K  L  Y  L  G  G
         T  F  V  M  H  L  T  V  M  *  V  M  S  P  N  Y  I  W  A  V
          R  L  *  C  T  *  L  *  C  E  *  C  H  Q  I  I  F  G  R  Y

16561   ATGTCTTACTATTGTGAAAACCATAAACCCCATTATTCATTTAAGTTAGTTATGAATGGT   16620
        M  S  Y  Y  C  E  N  H  K  P  H  Y  S  F  K  L  V  M  N  G
         C  L  T  I  V  K  T  I  N  P  I  I  H  L  S  *  L  *  M  V
          V  L  L  L  *  K  P  *  T  P  L  F  I  *  V  S  Y  E  W  Y

16621   ATGGTCTTTGGTTTGTATAAACAATCTTGCACGGGTTCACCTTATATAGATGATTTTAAT   16680
        M  V  F  G  L  Y  K  Q  S  C  T  G  S  P  Y  I  D  D  F  N
         W  S  L  V  C  I  N  N  L  A  R  V  H  L  I  *  M  I  L  I
          G  L  W  F  V  *  T  I  L  H  G  F  T  L  Y  R  *  F  *  *

16681   AAGATAGCTAGTTGTAAATGGACAGAAGTTGATGATTATGTTCTGGCAAATGAGTGTATT   16740
        K  I  A  S  C  K  W  T  E  V  D  D  Y  V  L  A  N  E  C  I
         R  *  L  V  V  N  G  Q  K  L  M  I  M  F  W  Q  M  S  V  L
          D  S  *  L  *  M  D  R  S  *  *  L  C  S  G  K  *  V  Y  *
```

FIG. 2 CONT.

16741 GAACGTTTAAAGTTATTTGCTGCAGAAACTCAAAAGGCAACTGAAGAGGCTTTTAAACAA 16800
E R L K L F A A E T Q K A T E E A F K Q
N V * S Y L L Q K L K R Q L K R L L N K
T F K V I C C R N S K G N * R G F * T K

16801 AGCTATGCTTCTGCTACCATTCAAGAGATTGTTAGTGATAGAGAAGTTATTTTGTGTTGG 16860
S Y A S A T I Q E I V S D R E V I L C W
A M L L L P F K R L L V I E K L F C V G
L C F C Y H S R D C * * * R S Y F V L G

16861 GAGACAGGTAAAGTTAAACCACCACTTAATAAAAATTATGTTTTCACAGGCTACCATTTT 16920
E T G K V K P P L N K N Y V F T G Y H F
R Q V K L N H H L I K I M F S Q A T I L
D R * S * T T T * * K L C F H R L P F Y

16921 ACTAGTACTGGTAAGACAGTTTTAGGTGAGTATGTTTTTGATAAAAGTGAATTAACTAAC 16980
T S T G K T V L G E Y V F D K S E L T N
L V L V R Q F * V S M F L I K V N * L T
* Y W * D S F R * V C F * * K * I N * R

16981 GGTGTGTATTACCGCGCTACAACTACTTATAAACTTTCTATAGGTGATGTTTTTGTTTTA 17040
G V Y Y R A T T T Y K L S I G D V F V L
V C I T A L Q L L I N F L * V M F L F *
C V L P R Y N Y L * T F Y R * C F C F N

17041 ACATCACATTCTGTAGCTAGTTTAAGTGCACCTACACTTGTCCCACAAGAGAACTATGCT 17100
T S H S V A S L S A P T L V P Q E N Y A
H H I L * L V * V H L H L S H K R T M L
I T F C S * F K C T Y T C P T R E L C *

17101 AGTATAAGATTTTCTAGTGTTTATAGTGTTCCATTGGTGTTTCAAAATAATGTTGCTAAT 17160
S I R F S S V Y S V P L V F Q N N V A N
V * D F L V F I V F H W C F K I M L L I
Y K I F * C L * C S I G V S K * C C * L

17161 TATCAGCACATTGGAATGAAACGTTATTGCACTGTTCAAGGTCCCCCTGGTACGGGAAAG 17220
Y Q H I G M K R Y C T V Q G P P G T G K
I S T L E * N V I A L F K V P L V R E S
S A H W N E T L L H C S R S P W Y G K V

17221 TCTCATCTTGCTATAGGTCTAGCTGTTTATTACTACACAGCACGTGTAGTTTATACTGCT 17280
S H L A I G L A V Y Y Y T A R V V Y T A
L I L L * V * L F I T T Q H V * F I L L
S S C Y R S S C L L L H S T C S L Y C C

FIG. 2 CONT.

```
17281    GCTAGTCATGCTGCTGTAGATGCATTGTGTGAAAAAGCTTATAAGTTTTTAAATATTAAC    17340
         A  S  H  A  A  V  D  A  L  C  E  K  A  Y  K  F  L  N  I  N
          L  V  M  L  L  *  M  H  C  V  K  K  L  I  S  F  *  I  L  T
           *  S  C  C  C  R  C  I  V  *  K  S  L  *  V  F  K  Y  *  R

17341    GATTGTACACGTATTATTCCTGCTAAAGTTCGTGTAGATTGTTATGATAAGTTTAAAATT    17400
         D  C  T  R  I  I  P  A  K  V  R  V  D  C  Y  D  K  F  K  I
          I  V  H  V  L  F  L  L  K  F  V  *  I  V  M  I  S  L  K  L
           L  Y  T  Y  Y  S  C  *  S  S  C  R  L  L  *  *  V  *  N  *

17401    AATGATACCACTTGTAAGTATGTTTTTACCACAATAAATGCATTACCAGAGTTGGTTACA    17460
         N  D  T  T  C  K  Y  V  F  T  T  I  N  A  L  P  E  L  V  T
          M  I  P  L  V  S  M  F  L  P  Q  *  M  H  Y  Q  S  W  L  Q
           *  Y  H  L  *  V  C  F  Y  H  N  K  C  I  T  R  V  G  Y  R

17461    GATATTGTTGTTGTTGATGAAGTTAGTATGCTTACTAATTATGAATTGTCTGTTATAAAT    17520
         D  I  V  V  V  D  E  V  S  M  L  T  N  Y  E  L  S  V  I  N
          I  L  L  L  L  M  K  L  V  C  L  L  I  M  N  C  L  L  *  M
           Y  C  C  C  *  *  S  *  Y  A  Y  *  L  *  I  V  C  Y  K  C

17521    GCTCGTATTAAAGCTAAACATTATGTATATATTGGAGATCCTGCTCAATTACCTGCACCA    17580
         A  R  I  K  A  K  H  Y  V  Y  I  G  D  P  A  Q  L  P  A  P
          L  V  L  K  L  N  I  M  Y  I  L  E  I  L  L  N  Y  L  H  H
           S  Y  *  S  *  T  L  C  I  Y  W  R  S  C  S  I  T  C  T  T

17581    CGTGTGCTGTTGAGCAAGGGTTCTTTAGAACCTAGGCACTTCAATTCTATTACTAAAATA    17640
         R  V  L  L  S  K  G  S  L  E  P  R  H  F  N  S  I  T  K  I
          V  C  C  *  A  R  V  L  *  N  L  G  T  S  I  L  L  L  K  *
           C  A  V  E  Q  G  F  F  R  T  *  A  L  Q  F  Y  Y  *  N  N

17641    ATGTGTTGTTTAGGTCCTGATATCTTTTTGGGAAATTGTTATAGGTGTCCTAAAGAAATT    17700
         M  C  C  L  G  P  D  I  F  L  G  N  C  Y  R  C  P  K  E  I
          C  V  V  *  V  L  I  S  F  W  E  I  V  I  G  V  L  K  K  L
           V  L  F  R  S  *  Y  L  F  G  K  L  L  *  V  S  *  R  N  C

17701    GTAGAAACTGTTTCAGCATTGGTTTATGATAATAAACTCAAGGCTAAAAATGATAATAGT    17760
         V  E  T  V  S  A  L  V  Y  D  N  K  L  K  A  K  N  D  N  S
          *  K  L  F  Q  H  W  F  M  I  I  N  S  R  L  K  M  I  I  V
           R  N  C  F  S  I  G  L  *  *  *  T  Q  G  *  K  *  *  *  F

17761    TCATTATGTTTTAAAGTATATTTTAAGGGACAGACAACACATGAGAGTTCAAGTGCTGTA    17820
         S  L  C  F  K  V  Y  F  K  G  Q  T  T  H  E  S  S  S  A  V
          H  Y  V  L  K  Y  I  L  R  D  R  Q  H  M  R  V  Q  V  L  *
           I  M  F  *  S  I  F  *  G  T  D  N  T  *  E  F  K  C  C  K
```

FIG. 2 CONT.

```
17821   AATATTCAACAGATATATCTAATTAGTAAATTTTTAAAAGCTAATCCAGTTTGGAATAGT   17880
        N  I  Q  Q  I  Y  L  I  S  K  F  L  K  A  N  P  V  W  N  S
         I  F  N  R  Y  I  *  L  V  N  F  *  K  L  I  Q  F  G  I  V
          Y  S  T  D  I  S  N  *  *  I  F  K  S  *  S  S  L  E  *  C

17881   GCTGTTTTTATTAGTCCTTATAATAGTCAGAATTATGTTGCTAAGCGTGTTTTAGGTGTT   17940
        A  V  F  I  S  P  Y  N  S  Q  N  Y  V  A  K  R  V  L  G  V
         L  F  L  L  V  L  I  I  V  R  I  M  L  L  S  V  F  *  V  F
          C  F  Y  *  S  L  *  *  S  E  L  C  C  *  A  C  F  R  C  S

17941   CAAACACAAACTGTAGATTCTGCTCAAGGTTCGGAATATGATTATGTTATATATTCACAA   18000
        Q  T  Q  T  V  D  S  A  Q  G  S  E  Y  D  Y  V  I  Y  S  Q
         K  H  K  L  *  I  L  L  K  V  R  N  M  I  M  L  Y  I  H  K
          N  T  N  C  R  F  C  S  R  F  G  I  *  L  C  Y  I  F  T  N

18001   ACAGCAGAAACAGCCCATTCTGTTAATGTTAATCGATTTAATGTTGCCATAACTAGAGCC   18060
        T  A  E  T  A  H  S  V  N  V  N  R  F  N  V  A  I  T  R  A
         Q  Q  K  Q  P  I  L  L  M  L  I  D  L  M  L  P  *  L  E  P
          S  R  N  S  P  F  C  *  C  *  S  I  *  C  C  H  N  *  S  Q

18061   AAGAAGGGCATTTTTTGTGTTATGAGTAATATGCAATTATTTGAATCTCTTAATTTTATT   18120
        K  K  G  I  F  C  V  M  S  N  M  Q  L  F  E  S  L  N  F  I
         R  R  A  F  F  V  L  *  V  I  C  N  Y  L  N  L  L  I  L  L
          E  G  H  F  L  C  Y  E  *  Y  A  I  I  *  I  S  *  F  Y  Y

18121   ACTCTACCTTTAGATAAAATTCAAAATCAAACTTTACCTCGTTTGCATTGCACAACTAAT   18180
        T  L  P  L  D  K  I  Q  N  Q  T  L  P  R  L  H  C  T  T  N
         L  Y  L  *  I  K  F  K  I  K  L  Y  L  V  C  I  A  Q  L  I
          S  T  F  R  *  N  S  K  S  N  F  T  S  F  A  L  H  N  *  S

18181   CTTTTTAAAGATTGTAGTAAAAGTTGCTTAGGTTATCATCCAGCGCATGCCCCCTCATTT   18240
        L  F  K  D  C  S  K  S  C  L  G  Y  H  P  A  H  A  P  S  F
         F  L  K  I  V  V  K  V  A  *  V  I  I  Q  R  M  P  P  H  F
          F  *  R  L  *  *  K  L  L  R  L  S  S  S  A  C  P  L  I  F

18241   TTAGCAGTTGATGATAAATATAAGGTTAATGAAAATTTGGCTGTAAATTTAAATATTTGT   18300
        L  A  V  D  D  K  Y  K  V  N  E  N  L  A  V  N  L  N  I  C
         *  Q  L  M  I  N  I  R  L  M  K  I  W  L  *  I  *  I  F  V
          S  S  *  *  *  I  *  G  *  *  K  F  G  C  K  F  K  Y  L  *

18301   GAACCTGTTTTAACATATTCTCGTTTAATATCTCTTATGGGTTTTAAATTAGATTTGACT   18360
        E  P  V  L  T  Y  S  R  L  I  S  L  M  G  F  K  L  D  L  T
         N  L  F  *  H  I  L  V  *  Y  L  L  W  V  L  N  *  I  *  L
          T  C  F  N  I  F  S  F  N  I  S  Y  G  F  *  I  R  F  D  S
```

FIG. 2 CONT.

18361 CTTGATGGTTATTCTAAATTGTTTATTACTAAAGATGAAGCCATTAAACGTGTTAGAGGT 18420
L D G Y S K L F I T K D E A I K R V R G
L M V I L N C L L L K M K P L N V L E V
* W L F * I V Y Y * R * S H * T C * R L

18421 TGGGTTGGTTTTGATGTTGAGGGCGCTCATGCTACTCGCGAAAACATTGGAACAAACTTT 18480
W V G F D V E G A H A T R E N I G T N F
G L V L M L R A L M L L A K T L E Q T F
G W F * C * G R S C Y S R K H W N K L S

18481 CCACTGCAAATAGGTTTTTCAACTGGTGTGGATTTTGTAGTTGAAGCTACTGGCTTATTT 18540
P L Q I G F S T G V D F V V E A T G L F
H C K * V F Q L V W I L * L K L L A Y L
T A N R F F N W C G F C S * S Y W L I C

18541 GCTGAGAGAGATTGTTATACTTTTAAAAAAACTGTAGCTAAAGCTCCTCCTGGTGAAAAA 18600
A E R D C Y T F K K T V A K A P P G E K
L R E I V I L L K K L * L K L L L V K N
* E R L L Y F * K N C S * S S S W * K I

18601 TTTAAACATTTAATACCCCTTATGTCAAAAGGTCAAAAGTGGGATATTGTTAGAATTAGA 18660
F K H L I P L M S K G Q K W D I V R I R
L N I * Y P L C Q K V K S G I L L E L E
* T F N T P Y V K R S K V G Y C * N * N

18661 ATTGTTCAAATGTTATCTGATTATCTTTTAGACCTTTCTGATAGTGTAGTATTTATTACT 18720
I V Q M L S D Y L L D L S D S V V F I T
L F K C Y L I I F * T F L I V * Y L L L
C S N V I * L S F R P F * * C S I Y Y L

18721 TGGTCTGCCAGTTTTGAACTTACTTGTTTAAGGTATTTTGCTAAATTAGGCAGAGAGCTT 18780
W S A S F E L T C L R Y F A K L G R E L
G L P V L N L L V * G I L L N * A E S L
V C Q F * T Y L F K V F C * I R Q R A *

18781 AATTGTAATGTGTGTTCTAATCGTGCTACATGCTACAATTCTAGAACTGGTTATTATGGT 18840
N C N V C S N R A T C Y N S R T G Y Y G
I V M C V L I V L H A T I L E L V I M V
L * C V F * S C Y M L Q F * N W L L W L

18841 TGTTGGCGCCATAGTTATACTTGTGATTATGTGTATAATCCACTTATTGTAGATATACAA 18900
C W R H S Y T C D Y V Y N P L I V D I Q
V G A I V I L V I M C I I H L L * I Y N
L A P * L Y L * L C V * S T Y C R Y T T

FIG. 2 CONT.

```
18901   CAGTGGGGTTATACAGGTTCTTTAACTAGTAATCACGATATAATTTGTAATGTACATAAA   18960
        Q  W  G  Y  T  G  S  L  T  S  N  H  D  I  I  C  N  V  H  K
         S  G  V  I  Q  V  L  *  L  V  I  T  I  *  F  V  M  Y  I  K
          V  G  L  Y  R  F  F  N  *  *  S  R  Y  N  L  *  C  T  *  R

18961   GGTGCACATGTTGCGTCAGCTGATGCAATTATGACTCGTTGTTTAGCAATCTATGATTGT   19020
        G  A  H  V  A  S  A  D  A  I  M  T  R  C  L  A  I  Y  D  C
         V  H  M  L  R  Q  L  M  Q  L  *  L  V  V  *  Q  S  M  I  V
          C  T  C  C  V  S  *  C  N  Y  D  S  L  F  S  N  L  *  L  F

19021   TTTTGTAAATCTGTTAATTGGAATTTAGAGTATCCAATAATTTCTAATGAGGTCAGTATA   19080
        F  C  K  S  V  N  W  N  L  E  Y  P  I  I  S  N  E  V  S  I
         F  V  N  L  L  I  G  I  *  S  I  Q  *  F  L  M  R  S  V  *
          L  *  I  C  *  L  E  F  R  V  S  N  N  F  *  *  G  Q  Y  K

19081   AATACATCTTGTAGGTTATTGCAGCGTGTCATGCTTAAAGCTGCCATGCTATGTAATAGA   19140
        N  T  S  C  R  L  L  Q  R  V  M  L  K  A  A  M  L  C  N  R
         I  H  L  V  G  Y  C  S  V  S  C  L  K  L  P  C  Y  V  I  D
          Y  I  L  *  V  I  A  A  C  H  A  *  S  C  H  A  M  *  *  I

19141   TACAACTTATGTTATGACATAGGCAATCCTAAAGGTTTAGCTTGTGTCAAAGATTATGAA   19200
        Y  N  L  C  Y  D  I  G  N  P  K  G  L  A  C  V  K  D  Y  E
         T  T  Y  V  M  T  *  A  I  L  K  V  *  L  V  S  K  I  M  N
          Q  L  M  L  *  H  R  Q  S  *  R  F  S  L  C  Q  R  L  *  I

19201   TTTAAATTTTATGATGCTTTTCCTGTAGCCAAGTCTGTTAAACAGTTATTTTATGTCTAT   19260
        F  K  F  Y  D  A  F  P  V  A  K  S  V  K  Q  L  F  Y  V  Y
         L  N  F  M  M  L  F  L  *  P  S  L  L  N  S  Y  F  M  S  M
          *  I  L  *  C  F  S  C  S  Q  V  C  *  T  V  I  L  C  L  *

19261   GATGTGCATAAAGATAATTTTAAAGATGGTTTATGTATGTTTTGGAATTGTAATGTTGAT   19320
        D  V  H  K  D  N  F  K  D  G  L  C  M  F  W  N  C  N  V  D
         M  C  I  K  I  I  L  K  M  V  Y  V  C  F  G  I  V  M  L  I
          C  A  *  R  *  F  *  R  W  F  M  Y  V  L  E  L  *  C  *  *

19321   AAATATCCATCTAATTCAATTGTTTGTAGATTTGACACTCGAGTGTTAAATAAATTAAAC   19380
        K  Y  P  S  N  S  I  V  C  R  F  D  T  R  V  L  N  K  L  N
         N  I  H  L  I  Q  L  F  V  D  L  T  L  E  C  *  I  N  *  T
          I  S  I  *  F  N  C  L  *  I  *  H  S  S  V  K  *  I  K  P

19381   CTTCCTGGATGTAATGGTGGTAGTTTGTATGTTAATAAACATGCATTCCATACTAATCCT   19440
        L  P  G  C  N  G  G  S  L  Y  V  N  K  H  A  F  H  T  N  P
         F  L  D  V  M  V  V  V  C  M  L  I  N  M  H  S  I  L  I  L
          S  W  M  *  W  W  *  F  V  C  *  *  T  C  I  P  Y  *  S  F
```

FIG. 2 CONT.

```
19441  TTTACTAGAACTGTTTTTGAAAATCTTAAGCCTATGCCTTTTTTCTATTATTCAGATACG  19500
       F  T  R  T  V  F  E  N  L  K  P  M  P  F  F  Y  Y  S  D  T
        L  L  E  L  F  L  K  I  L  S  L  C  L  F  S  I  I  Q  I  R
         Y  *  N  C  F  *  K  S  *  A  Y  A  F  F  L  L  F  R  Y  A

19501  CCTTGTGTGTACGTAGATGGTTTAGAATCTAAACAAGTTGATTACGTTCCTTTAAGAAGC  19560
       P  C  V  Y  V  D  G  L  E  S  K  Q  V  D  Y  V  P  L  R  S
        L  V  C  T  *  M  V  *  N  L  N  K  L  I  T  F  L  *  E  A
         L  C  V  R  R  W  F  R  I  *  T  S  *  L  R  S  F  K  K  R

19561  GCCACTTGTATCACACGGTGTAATCTAGGTGGAGCTGTTTGTTCAAAGCATGCTGAAGAA  19620
       A  T  C  I  T  R  C  N  L  G  G  A  V  C  S  K  H  A  E  E
        P  L  V  S  H  G  V  I  *  V  E  L  F  V  Q  S  M  L  K  N
         H  L  Y  H  T  V  *  S  R  W  S  C  L  F  K  A  C  *  R  I

19621  TATTGTAACTACCTTGAGTCTTATAATATAGTTACTACAGCAGGCTTTACTTTTTGGGTT  19680
       Y  C  N  Y  L  E  S  Y  N  I  V  T  T  A  G  F  T  F  W  V
        I  V  T  T  L  S  L  I  I  *  L  L  Q  Q  A  L  L  F  G  F
         L  *  L  P  *  V  L  *  Y  S  Y  Y  S  R  L  Y  F  L  G  L

19681  TATAAGAATTTTGATTTTTATAATTTATGGAACACTTTTACTACGTTACAGAGTTTAGAA  19740
       Y  K  N  F  D  F  Y  N  L  W  N  T  F  T  T  L  Q  S  L  E
        I  R  I  L  I  F  I  I  Y  G  T  L  L  L  R  Y  R  V  *  K
         *  E  F  *  F  L  *  F  M  E  H  F  Y  Y  V  T  E  F  R  K

19741  AACGTAATATATAACTTGGTTAATGTTGGTCATTATGATGGACGTACAGGTGAATTACCT  19800
       N  V  I  Y  N  L  V  N  V  G  H  Y  D  G  R  T  G  E  L  P
        T  *  Y  I  T  W  L  M  L  V  I  M  M  D  V  Q  V  N  Y  L
         R  N  I  *  L  G  *  C  W  S  L  *  W  T  Y  R  *  I  T  L

19801  TGTGCTATTATGAATGACAAAGTTGTTGTTAAGATTAATAATGTAGATACTGTTATTTTT  19860
       C  A  I  M  N  D  K  V  V  V  K  I  N  N  V  D  T  V  I  F
        V  L  L  *  M  T  K  L  L  L  R  L  I  M  *  I  L  L  F  L
         C  Y  Y  E  *  Q  S  C  C  *  D  *  *  C  R  Y  C  Y  F  *

19861  AAAAATAATACATCATTTCCTACTAATATAGCTGTTGAATTGTTTACAAAACGTAGTATC  19920
       K  N  N  T  S  F  P  T  N  I  A  V  E  L  F  T  K  R  S  I
        K  I  I  H  H  F  L  L  I  *  L  L  N  C  L  Q  N  V  V  S
         K  *  Y  I  I  S  Y  *  Y  S  C  *  I  V  Y  K  T  *  Y  P

19921  CGGCACCACCCTGAACTTAAGATTCTTAGAAATTTGAACATTGATATTTGTTGGAAGCAT  19980
       R  H  H  P  E  L  K  I  L  R  N  L  N  I  D  I  C  W  K  H
        G  T  T  L  N  L  R  F  L  E  I  *  T  L  I  F  V  G  S  M
         A  P  P  *  T  *  D  S  *  K  F  E  H  *  Y  L  L  E  A  C
```

FIG. 2 CONT.

```
19981  GTCCTGTGGGATTATGTTAAAGATAGTTTGTTTTGTAGTTCCACTTATGGTGTTTGTAAA  20040
       V  L  W  D  Y  V  K  D  S  L  F  C  S  S  T  Y  G  V  C  K
        S  C  G  I  M  L  K  I  V  C  F  V  V  P  L  M  V  F  V  N
         P  V  G  L  C  *  R  *  F  V  L  *  F  H  L  W  C  L  *  I

20041  TACACAGATTTGAAGTTCATCGAAAATTTGAATATACTTTTTGATGGTCGTGACACTGGC  20100
       Y  T  D  L  K  F  I  E  N  L  N  I  L  F  D  G  R  D  T  G
        T  Q  I  *  S  S  S  K  I  *  I  Y  F  L  M  V  V  T  L  A
         H  R  F  E  V  H  R  K  F  E  Y  T  F  *  W  S  *  H  W  R

20101  GCTTTAGAAGCTTTTAGAAAAGCAAGAAATGGTGTTTTTATTAGTACTGAAAAATTAAGT  20160
       A  L  E  A  F  R  K  A  R  N  G  V  F  I  S  T  E  K  L  S
        L  *  K  L  L  E  K  Q  E  M  V  F  L  L  V  L  K  N  *  V
         F  R  S  F  *  K  S  K  K  W  C  F  Y  *  Y  *  K  I  K  *

20161  AGGTTATCAATGATTAAAGGTCCGCAACGAGCTGATTTAAATGGTGTGATTGTGGATAAA  20220
       R  L  S  M  I  K  G  P  Q  R  A  D  L  N  G  V  I  V  D  K
        G  Y  Q  *  L  K  V  R  N  E  L  I  *  M  V  *  L  W  I  K
         V  I  N  D  *  R  S  A  T  S  *  F  K  W  C  D  C  G  *  S

20221  GTTGGAGAACTCAAAGTTGAGTTTTGGTTCGCTATGAGAAAAGATGGTGACGATGTTATC  20280
       V  G  E  L  K  V  E  F  W  F  A  M  R  K  D  G  D  D  V  I
        L  E  N  S  K  L  S  F  G  S  L  *  E  K  M  V  T  M  L  S
         W  R  T  Q  S  *  V  L  V  R  Y  E  K  R  W  *  R  C  Y  L

20281  TTCAGCCGAACAGACAGCCTATGCTCAAGCCATTACTGGAGCCCACAAGGTAATCTAGGT  20340
       F  S  R  T  D  S  L  C  S  S  H  Y  W  S  P  Q  G  N  L  G
        S  A  E  Q  T  A  Y  A  Q  A  I  T  G  A  H  K  V  I  *  V
         Q  P  N  R  Q  P  M  L  K  P  L  L  E  P  T  R  *  S  R  W

20341  GGTAATTGCGCGGGTAATGTCATTGGTAATGATGCTCTAACACGTTTTACTATCTTTACT  20400
       G  N  C  A  G  N  V  I  G  N  D  A  L  T  R  F  T  I  F  T
        V  I  A  R  V  M  S  L  V  M  M  L  *  H  V  L  L  S  L  L
         *  L  R  G  *  C  H  W  *  *  C  S  N  T  F  Y  Y  L  Y  S

20401  CAGAGTCGTGTATTGTCAAGTTTTGAACCTCGCTCAGATTTAGAACGGGATTTTATTGAT  20460
       Q  S  R  V  L  S  S  F  E  P  R  S  D  L  E  R  D  F  I  D
        R  V  V  Y  C  Q  V  L  N  L  A  Q  I  *  N  G  I  L  L  I
         E  S  C  I  V  K  F  *  T  S  L  R  F  R  T  G  F  Y  *  Y

20461  ATGGATGATAATCTGTTTATTGCTAAATATGGTTTAGAAGACTATGCATTTGATCATATA  20520
       M  D  D  N  L  F  I  A  K  Y  G  L  E  D  Y  A  F  D  H  I
        W  M  I  I  C  L  L  L  N  M  V  *  K  T  M  H  L  I  I  *
         G  *  *  S  V  Y  C  *  I  W  F  R  R  L  C  I  *  S  Y  S
```

FIG. 2 CONT.

```
20521   GTTTATGGTAGTTTTAACCATAAAGTTATAGGAGGTTTGCATTTGCTTATAGGCTTATTT   20580
        V  Y  G  S  F  N  H  K  V  I  G  G  L  H  L  L  I  G  L  F
         F  M  V  V  L  T  I  K  L  *  E  V  C  I  C  L  *  A  Y  F
          L  W  *  F  *  P  *  S  Y  R  R  F  A  F  A  Y  R  L  I  S

20581   CGTAGGAAAAAAAAATCTAATTTGTTAATTCAAGAGTTTTTACAGTATGATTCTAGTATT   20640
        R  R  K  K  K  S  N  L  L  I  Q  E  F  L  Q  Y  D  S  S  I
         V  G  K  K  N  L  I  C  *  F  K  S  F  Y  S  M  I  L  V  F
          *  E  K  K  I  *  F  V  N  S  R  V  F  T  V  *  F  *  Y  S

20641   CATTCATATTTTATTACTGATCAGGAGTGTGGTAGTAGTAAGAGTGTTTGTACAGTTATT   20700
        H  S  Y  F  I  T  D  Q  E  C  G  S  S  K  S  V  C  T  V  I
         I  H  I  L  L  L  I  R  S  V  V  V  V  R  V  F  V  Q  L  L
          F  I  F  Y  Y  *  S  G  V  W  *  *  *  E  C  L  Y  S  Y  *

20701   GATTTATTATTAGATGATTTTGTTTCTATTGTTAAGTCATTAAATTTGAGTTGTGTTAGT   20760
        D  L  L  L  D  D  F  V  S  I  V  K  S  L  N  L  S  C  V  S
         I  Y  Y  *  M  I  L  F  L  L  L  S  H  *  I  *  V  V  L  V
          F  I  I  R  *  F  C  F  Y  C  *  V  I  K  F  E  L  C  *  *

20761   AAAGTTGTTAATATTAATGTTGATTTTAAGGATTTTCAATTTATGTTGTGGTGTAATGAT   20820
        K  V  V  N  I  N  V  D  F  K  D  F  Q  F  M  L  W  C  N  D
         K  L  L  I  L  M  L  I  L  R  I  F  N  L  C  C  G  V  M  I
          S  C  *  Y  *  C  *  F  *  G  F  S  I  Y  V  V  V  *  *  *

20821   AATAAAATTATGACTTTTTATCCTAAAATGCAAGCCACTAATGATTGGAAACCTGGCTAT   20880
        N  K  I  M  T  F  Y  P  K  M  Q  A  T  N  D  W  K  P  G  Y
         I  K  L  *  L  F  I  L  K  C  K  P  L  M  I  G  N  L  A  I
          *  N  Y  D  F  L  S  *  N  A  S  H  *  *  L  E  T  W  L  F

20881   TCTATGCCTGTTTTGTATAAGTATTTGAATGTTCCATTAGAGAGAGTCTCTTTATGGAAT   20940
        S  M  P  V  L  Y  K  Y  L  N  V  P  L  E  R  V  S  L  W  N
         L  C  L  F  C  I  S  I  *  M  F  H  *  R  E  S  L  Y  G  I
          Y  A  C  F  V  *  V  F  E  C  S  I  R  E  S  L  F  M  E  L

20941   TATGGTAAACCTATTAATTTGCCTACAGGCTGTATGATGAATGTTGCTAAGTACACTCAA   21000
        Y  G  K  P  I  N  L  P  T  G  C  M  M  N  V  A  K  Y  T  Q
         M  V  N  L  L  I  C  L  Q  A  V  *  *  M  L  L  S  T  L  N
          W  *  T  Y  *  F  A  Y  R  L  Y  D  E  C  C  *  V  H  S  I

21001   TTATGTCAGTATTTGAATACTACAACATTAGCTGTTCCTGTTAATATGCGTGTTTTACAT   21060
        L  C  Q  Y  L  N  T  T  T  L  A  V  P  V  N  M  R  V  L  H
         Y  V  S  I  *  I  L  Q  H  *  L  F  L  L  I  C  V  F  Y  I
          M  S  V  F  E  Y  Y  N  I  S  C  S  C  *  Y  A  C  F  T  F
```

FIG. 2 CONT.

```
21061   TTAGGTGCAGGGTCTGATAAAGAAGTAGCTCCAGGTTCTGCTGTTTTAAGACAGTGGTTA   21120
        L  G  A  G  S  D  K  E  V  A  P  G  S  A  V  L  R  Q  W  L
         *  V  Q  G  L  I  K  K  *  L  Q  V  L  L  F  *  D  S  G  Y
          R  C  R  V  *  *  R  S  S  S  R  F  C  C  F  K  T  V  V  T

21121   CCATCTGGTAGTATTCTTGTAGATAATGATTTAAACCCATTTGTTAGCGATAGTTTAGTT   21180
        P  S  G  S  I  L  V  D  N  D  L  N  P  F  V  S  D  S  L  V
         H  L  V  V  F  L  *  I  M  I  *  T  H  L  L  A  I  V  *  L
          I  W  *  Y  S  C  R  *  *  F  K  P  I  C  *  R  *  F  S  Y

21181   ACTTATTTTGGAGATTGTATGACTTTACCATTTGATTGTCATTGGGATTTGATAATATCT   21240
        T  Y  F  G  D  C  M  T  L  P  F  D  C  H  W  D  L  I  I  S
         L  I  L  E  I  V  *  L  Y  H  L  I  V  I  G  I  *  *  Y  L
          L  F  W  R  L  Y  D  F  T  I  *  L  S  L  G  F  D  N  I  *

21241   GATATGTATGATCCTCTTACTAAAAATATTGGTGATTATAATGTGAGTAAGGATGGGTTT   21300
        D  M  Y  D  P  L  T  K  N  I  G  D  Y  N  V  S  K  D  G  F
         I  C  M  I  L  L  L  K  I  L  V  I  I  M  *  V  R  M  G  F
          Y  V  *  S  S  Y  *  K  Y  W  *  L  *  C  E  *  G  W  V  F

21301   TTTACTTACATTTGTCATTTAATTCGTGATAAATTATCTTTGGGTGGTAGTGTAGCTATA   21360
        F  T  Y  I  C  H  L  I  R  D  K  L  S  L  G  G  S  V  A  I
         L  L  T  F  V  I  *  F  V  I  N  Y  L  W  V  V  V  *  L  *
          Y  L  H  L  S  F  N  S  *  *  I  I  F  G  W  *  C  S  Y  K

21361   AAAATTACAGAGTTTTCTTGGAATGCTGATTTATATAAATTAATGAGTTGTTTTGCATTT   21420
        K  I  T  E  F  S  W  N  A  D  L  Y  K  L  M  S  C  F  A  F
         K  L  Q  S  F  L  G  M  L  I  Y  I  N  *  *  V  V  L  H  F
          N  Y  R  V  F  L  E  C  *  F  I  *  I  N  E  L  F  C  I  L

21421   TGGACAGTTTTTTGTACTAATGTAAATGCTTCTTCTAGTGAAGGGTTTTTAATAGGTATA   21480
        W  T  V  F  C  T  N  V  N  A  S  S  S  E  G  F  L  I  G  I
         G  Q  F  F  V  L  M  *  M  L  L  L  V  K  G  F  *  *  V  *
          D  S  F  L  Y  *  C  K  C  F  F  *  *  R  V  F  N  R  Y  K

21481   AATTACCTGGGTAAATCTTCTTTTGAAATAGATGGCAATGTTATGCATGCTAACTATTTG   21540
        N  Y  L  G  K  S  S  F  E  I  D  G  N  V  M  H  A  N  Y  L
         I  T  W  V  N  L  L  L  K  *  M  A  M  L  C  M  L  T  I  C
          L  P  G  *  I  F  F  *  N  R  W  Q  C  Y  A  C  *  L  F  V

21541   TTTTGGAGAAATAGTACAACATGGAATGGCGGTGCTTATAGTTTATTTGATATGACTAAA   21600
        F  W  R  N  S  T  T  W  N  G  G  A  Y  S  L  F  D  M  T  K
         F  G  E  I  V  Q  H  G  M  A  V  L  I  V  Y  L  I  *  L  N
          L  E  K  *  Y  N  M  E  W  R  C  L  *  F  I  *  Y  D  *  I
```

FIG. 2 CONT.

```
21601  TTTTCTTTGAAATTGGCTGGCACTGCTGTTGTTAATTTAAGACCAGATCAATTAAATGAT  21660
       F  S  L  K  L  A  G  T  A  V  V  N  L  R  P  D  Q  L  N  D
        F  L  *  N  W  L  A  L  L  L  L  I  *  D  Q  I  N  *  M  I
         F  F  E  I  G  W  H  C  C  C  *  F  K  T  R  S  I  K  *  F

21661  TTAGTTTATTCTCTTATTGAAAGAGGTAAATTATTAGTTCGCGATACGCGTAAAGAGATT  21720
       L  V  Y  S  L  I  E  R  G  K  L  L  V  R  D  T  R  K  E  I
        *  F  I  L  L  L  K  E  V  N  Y  *  F  A  I  R  V  K  R  F
         S  L  F  S  Y  *  K  R  *  I  I  S  S  R  Y  A  *  R  D  F

21721  TTTGTTGGTGATAGTCTTGTAAATACTTGTTAGATCTCATTAAATCTAAACTATGTTAAT  21780
       F  V  G  D  S  L  V  N  T  C  *  I  S  L  N  L  N  Y  V  N
        L  L  V  I  V  L  *  I  L  V  R  S  H  *  I  *  T  M  L  I
         C  W  *  *  S  C  K  Y  L  L  D  L  I  K  S  K  L  C  *  L

21781  TATTTTTTTATTTTTTTATTTCTGTTATGGTTTTAATGAACCTCTTAATGTTGTGTCTCA  21840
       Y  F  F  I  F  L  F  L  L  W  F  *  *  T  S  *  C  C  V  S
        I  F  L  F  F  Y  F  C  Y  G  F  N  E  P  L  N  V  V  S  H
         F  F  Y  F  F  I  S  V  M  V  L  M  N  L  L  M  L  C  L  I

21841  TTTAAACCATGACTGGTTTTTATTTGGTGATAGTCGTTCTGATTGTAACCATATTAATAA  21900
       F  K  P  *  L  V  F  I  W  *  *  S  F  *  L  *  P  Y  *  *
        L  N  H  D  W  F  L  F  G  D  S  R  S  D  C  N  H  I  N  N
         *  T  M  T  G  F  Y  L  V  I  V  V  L  I  V  T  I  L  I  I

21901  TTTAAAAATTAAAAATTTTGATTATTTGGATATTCACCCTAGTTTGTGCAACAATGGTAA  21960
       F  K  N  *  K  F  *  L  F  G  Y  S  P  *  F  V  Q  Q  W  *
        L  K  I  K  N  F  D  Y  L  D  I  H  P  S  L  C  N  N  G  K
         *  K  L  K  I  L  I  I  W  I  F  T  L  V  C  A  T  M  V  R

21961  GATTTCATCTAGTGCCGGTGATTCTATTTTAAGAGTTTTCATTTCACTCGATTTTATAA  22020
       D  F  I  *  C  R  *  F  Y  F  *  E  F  S  F  H  S  I  L  *
        I  S  S  S  A  G  D  S  I  F  K  S  F  H  F  T  R  F  Y  N
         F  H  L  V  P  V  I  L  F  L  R  V  F  I  S  L  D  F  I  I

22021  TTACACTGGCGAAGGTGATCAAATTATTTTTTATGAGGGTGTTAATTTTAATCCTTATCA  22080
       L  H  W  R  R  *  S  N  Y  F  L  *  G  C  *  F  *  S  L  S
        Y  T  G  E  G  D  Q  I  I  F  Y  E  G  V  N  F  N  P  Y  H
         T  L  A  K  V  I  K  L  F  F  M  R  V  L  I  L  I  L  I  I

22081  TAGATTTAAGTGTTTTCCTAATGGTAGTAATGATGTATGGCTTCTTAACAAGGTAAGATT  22140
       *  I  *  V  F  S  *  W  *  *  *  C  M  A  S  *  Q  G  K  I
        R  F  K  C  F  P  N  G  S  N  D  V  W  L  L  N  K  V  R  F
         D  L  S  V  F  L  M  V  V  M  M  Y  G  F  L  T  R  *  D  F
```

FIG. 2 CONT.

```
22141  TTATCGTGCCTTATATTCTAATATGGCCTTTTTTCGTTATCTTACTTTTGTTGATATTCC  22200
       L  S  C  L  I  F  *  Y  G  L  F  S  L  S  Y  F  C  *  Y  S
        Y  R  A  L  Y  S  N  M  A  F  F  R  Y  L  T  F  V  D  I  P
         I  V  P  Y  I  L  I  W  P  F  F  V  I  L  L  L  L  I  F  L

22201  TTATAATGTTTCTCTTTCTAAGTTTAATTCTTGTAAAAGTGATATTTTATCACTTAACAA  22260
       L  *  C  F  S  F  *  V  *  F  L  *  K  *  Y  F  I  T  *  Q
        Y  N  V  S  L  S  K  F  N  S  C  K  S  D  I  L  S  L  N  N
         I  M  F  L  F  L  S  L  I  L  V  K  V  I  F  Y  H  L  T  I

22261  TCCTATTTTTATTAATTATTCTAAGGAAGTTTATTTTACTTTATTAGGTTGTTCTCTTTA  22320
       S  Y  F  Y  *  L  F  *  G  S  L  F  Y  F  I  R  L  F  S  L
        P  I  F  I  N  Y  S  K  E  V  Y  F  T  L  L  G  C  S  L  Y
         L  F  L  L  I  I  L  R  K  F  I  L  L  Y  *  V  V  L  F  I

22321  TTTAGTACCGCTTTGCCTTTTTAAATCTAACTTTAGTCAGTACTATTATAACATAGATAC  22380
       F  S  T  A  L  P  F  *  I  *  L  *  S  V  L  L  *  H  R  Y
        L  V  P  L  C  L  F  K  S  N  F  S  Q  Y  Y  Y  N  I  D  T
         *  Y  R  F  A  F  L  N  L  T  L  V  S  T  I  I  T  *  I  L

22381  TGGCTCTGTTTATGGTTTTTCTAATGTTGTTTATCCTGATTTAGACTGTATTTATATTTC  22440
       W  L  C  L  W  F  F  *  C  C  L  S  *  F  R  L  Y  L  Y  F
        G  S  V  Y  G  F  S  N  V  V  Y  P  D  L  D  C  I  Y  I  S
         A  L  F  M  V  F  L  M  L  F  I  L  I  *  T  V  F  I  F  L

22441  TCTTAAACCAGGTTCTTATAAAGTTTCCACCACTGCACCTTTTTTATCCTTACCTACTAA  22500
       S  *  T  R  F  L  *  S  F  H  H  C  T  F  F  I  L  T  Y  *
        L  K  P  G  S  Y  K  V  S  T  T  A  P  F  L  S  L  P  T  K
         L  N  Q  V  L  I  K  F  P  P  L  H  L  F  Y  P  Y  L  L  K

22501  AGCTCTCTGTTTTGATAAATCTAAACAATTTGTACCTGTACAGGTTGTTGATTCTAGATG  22560
       S  S  L  F  *  *  I  *  T  I  C  T  C  T  G  C  *  F  *  M
        A  L  C  F  D  K  S  K  Q  F  V  P  V  Q  V  V  D  S  R  W
         L  S  V  L  I  N  L  N  N  L  Y  L  Y  R  L  L  I  L  D  G

22561  GAACAACGAGCGTGCCTCAGATATTTCTTTATCTGTTGCATGTCAATTGCCATATTGTTA  22620
       E  Q  R  A  C  L  R  Y  F  F  I  C  C  M  S  I  A  I  L  L
        N  N  E  R  A  S  D  I  S  L  S  V  A  C  Q  L  P  Y  C  Y
         T  T  S  V  P  Q  I  F  L  Y  L  L  H  V  N  C  H  I  V  I

22621  TTTTCGCAATTCTTCTGCTAATTATGTTGGCAAGTATGATATTAACCACGGTGATAGTGG  22680
       F  S  Q  F  F  C  *  L  C  W  Q  V  *  Y  *  P  R  *  *  W
        F  R  N  S  S  A  N  Y  V  G  K  Y  D  I  N  H  G  D  S  G
         F  A  I  L  L  L  I  M  L  A  S  M  I  L  T  T  V  I  V  V
```

FIG. 2 CONT.

```
22681   TTTTATTTCTATTTTATCTGGTCTTTTATATAATGTTTCTTGTATTTCATATTATGGTGT   22740
        F  Y  F  Y  F  I  W  S  F  I  *  C  F  L  Y  F  I  L  W  C
         F  I  S  I  L  S  G  L  L  Y  N  V  S  C  I  S  Y  Y  G  V
          L  F  L  F  Y  L  V  F  Y  I  M  F  L  V  F  H  I  M  V  Y

22741   ATTTTTATATGATAATTTTACATCCATTTGGCCCTATTATTCTTTTGGTAGGTGTCCTAC   22800
        I  F  I  *  *  F  Y  I  H  L  A  L  L  F  F  W  *  V  S  Y
         F  L  Y  D  N  F  T  S  I  W  P  Y  Y  S  F  G  R  C  P  T
          F  Y  M  I  I  L  H  P  F  G  P  I  I  L  L  V  G  V  L  H

22801   ATCTTCTATTATTAAACATCCAATTTGTGTTTATGATTTTTTGCCTATTATTTTACAAGG   22860
        I  F  Y  Y  *  T  S  N  L  C  L  *  F  F  A  Y  Y  F  T  R
         S  S  I  I  K  H  P  I  C  V  Y  D  F  L  P  I  I  L  Q  G
          L  L  L  L  N  I  Q  F  V  F  M  I  F  C  L  L  F  Y  K  V

22861   TATTTTATTATGTTTAGCTTTACTTTTTGTTGTTTTTCTATTATTTTTGTTATATAACGA   22920
        Y  F  I  M  F  S  F  T  F  C  C  F  S  I  I  F  V  I  *  R
         I  L  L  C  L  A  L  L  F  V  V  F  L  L  F  L  L  Y  N  D
          F  Y  Y  V  *  L  Y  F  L  L  F  F  Y  Y  F  C  Y  I  T  I

22921   TAAATCTCATTAAATCTAAACATGTTATTAATTATTTTTATTTTGCCTACAACATTAGCT   22980
        *  I  S  L  N  L  N  M  L  L  I  I  F  I  L  P  T  T  L  A
         K  S  H  *  I  *  T  C  Y  *  L  F  L  F  C  L  Q  H  *  L
          N  L  I  K  S  K  H  V  I  N  Y  F  Y  F  A  Y  N  I  S  C

22981   GTTATAGGTGATTTTAATTGTACTAATTTTGCTATTAATGATTTAAACACCACAGTTCCT   23040
        V  I  G  D  F  N  C  T  N  F  A  I  N  D  L  N  T  T  V  P
         L  *  V  I  L  I  V  L  I  L  L  L  M  I  *  T  P  Q  F  L
          Y  R  *  F  *  L  Y  *  F  C  Y  *  *  F  K  H  H  S  S  S

23041   CGCATAAGTGAGTATGTTGTGGATGTTTCTTATGGTTTGGGTACATATTATATACTTGAT   23100
        R  I  S  E  Y  V  V  D  V  S  Y  G  L  G  T  Y  Y  I  L  D
         A  *  V  S  M  L  W  M  F  L  M  V  W  V  H  I  I  Y  L  I
          H  K  *  V  C  C  G  C  F  L  W  F  G  Y  I  L  Y  T  *  S

23101   CGTGTTTATTTAAATACTACTATATTATTTACTGGTTATTTCCCTAAATCTGGTGCCAAT   23160
        R  V  Y  L  N  T  T  I  L  F  T  G  Y  F  P  K  S  G  A  N
         V  F  I  *  I  L  L  Y  Y  L  L  V  I  S  L  N  L  V  P  I
          C  L  F  K  Y  Y  Y  I  I  Y  W  L  F  P  *  I  W  C  Q  F

23161   TTTAGGGATCTATCTTTAAAAGGTACTACATATTTGAGTACTCTTTGGTATCAGAAACCC   23220
        F  R  D  L  S  L  K  G  T  T  Y  L  S  T  L  W  Y  Q  K  P
         L  G  I  Y  L  *  K  V  L  H  I  *  V  L  F  G  I  R  N  P
          *  G  S  I  F  K  R  Y  Y  I  F  E  Y  S  L  V  S  E  T  L
```

FIG. 2 CONT.

```
23221  TTTTTATCTGATTTTAATAATGGTATTTTTTCTAGAGTTAAGAATACTAAGTTGTATGTT  23280
       F  L  S  D  F  N  N  G  I  F  S  R  V  K  N  T  K  L  Y  V
        F  Y  L  I  L  I  M  V  F  F  L  E  L  R  I  L  S  C  M  L
         F  I  *  F  *  *  W  Y  F  F  *  S  *  E  Y  *  V  V  C  *

23281  AATAAAACTTTGTATAGTGAGTTTAGTACTATAGTTATAGGTAGTGTTTTTATTAACAAC  23340
       N  K  T  L  Y  S  E  F  S  T  I  V  I  G  S  V  F  I  N  N
        I  K  L  C  I  V  S  L  V  L  *  L  *  V  V  F  L  L  T  T
         *  N  F  V  *  *  V  *  Y  Y  S  Y  R  *  C  F  Y  *  Q  L

23341  TCTTATACTATTGTTGTTCAACCTCATAATGGTGTTTTGGAGATTACAGCTTGTCAATAC  23400
       S  Y  T  I  V  V  Q  P  H  N  G  V  L  E  I  T  A  C  Q  Y
        L  I  L  L  L  F  N  L  I  M  V  F  W  R  L  Q  L  V  N  T
         L  Y  Y  C  C  S  T  S  *  W  C  F  G  D  Y  S  L  S  I  H

23401  ACTATGTGTGAGTATCCTCATACTATTTGTAAATCTAAAGGTAGTTCTCGTAATGAATCT  23460
       T  M  C  E  Y  P  H  T  I  C  K  S  K  G  S  S  R  N  E  S
        L  C  V  S  I  L  I  L  F  V  N  L  K  V  V  L  V  M  N  L
         Y  V  *  V  S  S  Y  Y  L  *  I  *  R  *  F  S  *  *  I  L

23461  TGGCATTTTGATAAATCTGAACCTTTGTGTCTGTTCAAGAAAAATTTTACTTATAATGTT  23520
       W  H  F  D  K  S  E  P  L  C  L  F  K  K  N  F  T  Y  N  V
        G  I  L  I  N  L  N  L  C  V  C  S  R  K  I  L  L  I  M  F
         A  F  *  *  I  *  T  F  V  S  V  Q  E  K  F  Y  L  *  C  F

23521  TCTACAGATTGGTTGTATTTTCATTTTTATCAAGAACGTGGCACTTTTTATGCTTATTAT  23580
       S  T  D  W  L  Y  F  H  F  Y  Q  E  R  G  T  F  Y  A  Y  Y
        L  Q  I  G  C  I  F  I  F  I  K  N  V  A  L  F  M  L  I  M
         Y  R  L  V  V  F  S  F  L  S  R  T  W  H  F  L  C  L  L  C

23581  GCTGATTCTGGCATGCCTACTACTTTTTTATTTAGTTTGTATCTTGGTACTCTTTTATCT  23640
       A  D  S  G  M  P  T  T  F  L  F  S  L  Y  L  G  T  L  L  S
        L  I  L  A  C  L  L  L  F  Y  L  V  C  I  L  V  L  F  Y  L
         *  F  W  H  A  Y  Y  F  F  I  *  F  V  S  W  Y  S  F  I  S

23641  CATTATTATGTTTTGCCTTTGACTTGTAATGCTATATCTTCTAATACTGATAATGAGACT  23700
       H  Y  Y  V  L  P  L  T  C  N  A  I  S  S  N  T  D  N  E  T
        I  I  M  F  C  L  *  L  V  M  L  Y  L  L  I  L  I  M  R  L
         L  L  C  F  A  F  D  L  *  C  Y  I  F  *  Y  *  *  *  D  F

23701  TTACAATATTGGGTCACACCTTTGTCTAAACGCCAATATCTTCTTAAATTTGACAACCGT  23760
       L  Q  Y  W  V  T  P  L  S  K  R  Q  Y  L  L  K  F  D  N  R
        Y  N  I  G  S  H  L  C  L  N  A  N  I  F  L  N  L  T  T  V
         T  I  L  G  H  T  F  V  *  T  P  I  S  S  *  I  *  Q  P  W
```

FIG. 2 CONT.

```
23761  GGTGTTATTACTAATGCTGTTGATTGTTCTAGTAGTTTCTTTAGCGAGATTCAATGTAAA  23820
       G  V  I  T  N  A  V  D  C  S  S  S  F  F  S  E  I  Q  C  K
        V  L  L  L  M  L  L  I  V  L  V  V  S  L  A  R  F  N  V  K
         C  Y  Y  *  C  C  *  L  F  *  *  F  L  *  R  D  S  M  *  N

23821  ACTAAATCTTTATTACCTAATACTGGTGTTTATGACTTATCTGGTTTTACTGTTAAGCCT  23880
       T  K  S  L  L  P  N  T  G  V  Y  D  L  S  G  F  T  V  K  P
        L  N  L  Y  Y  L  I  L  V  F  M  T  Y  L  V  L  L  L  S  L
         *  I  F  I  T  *  Y  W  C  L  *  L  I  W  F  Y  C  *  A  C

23881  GTTGCAACTGTACATCGTCGTATTCCTGATTTACCTGATTGTGACATTGATAAATGGCTT  23940
       V  A  T  V  H  R  R  I  P  D  L  P  D  C  D  I  D  K  W  L
        L  Q  L  Y  I  V  V  F  L  I  Y  L  I  V  T  L  I  N  G  L
         C  N  C  T  S  S  Y  S  *  F  T  *  L  *  H  *  *  M  A  *

23941  AACAATTTTAATGTACCCTCACCTCTTAATTGGGAACGTAAAATTTTTTCTAATTGCAAC  24000
       N  N  F  N  V  P  S  P  L  N  W  E  R  K  I  F  S  N  C  N
        T  I  L  M  Y  P  H  L  L  I  G  N  V  K  F  F  L  I  A  T
         Q  F  *  C  T  L  T  S  *  L  G  T  *  N  F  F  *  L  Q  L

24001  TTTAATTTGAGTACTTTGCTTCGTTTAGTTCATACTGATTCTTTTTCTTGTAATAATTTT  24060
       F  N  L  S  T  L  L  R  L  V  H  T  D  S  F  S  C  N  N  F
        L  I  *  V  L  C  F  V  *  F  I  L  I  L  F  L  V  I  I  L
         *  F  E  Y  F  A  S  F  S  S  Y  *  F  F  F  L  *  *  F  *

24061  GATGAATCTAAGATATATGGTAGTTGTTTTAAGAGTATTGTTTTAGATAAATTTGCCATA  24120
       D  E  S  K  I  Y  G  S  C  F  K  S  I  V  L  D  K  F  A  I
        M  N  L  R  Y  M  V  V  V  L  R  V  L  F  *  I  N  L  P  Y
         *  I  *  D  I  W  *  L  F  *  E  Y  C  F  R  *  I  C  H  T

24121  CCCAACTCCAGACGATCTGATTTGCAGTTGGGCAGTTCTGGTTTTCTGCAATCTTCTAAT  24180
       P  N  S  R  R  S  D  L  Q  L  G  S  S  G  F  L  Q  S  S  N
        P  T  P  D  D  L  I  C  S  W  A  V  L  V  F  C  N  L  L  I
         Q  L  Q  T  I  *  F  A  V  G  Q  F  W  F  S  A  I  F  *  L

24181  TATAAAATTGACACTACTTCTAGTTCTTGTCAATTGTATTATAGTTTGCCTGCAATTAAT  24240
       Y  K  I  D  T  T  S  S  S  C  Q  L  Y  Y  S  L  P  A  I  N
        I  K  L  T  L  L  L  V  L  V  N  C  I  I  V  C  L  Q  L  M
         *  N  *  H  Y  F  *  F  L  S  I  V  L  *  F  A  C  N  *  C

24241  GTTACTATTAATAATTATAATCCTTCTTCTTGGAATAGAAGGTATGGTTTTAATAATTTT  24300
       V  T  I  N  N  Y  N  P  S  S  W  N  R  R  Y  G  F  N  N  F
        L  L  L  I  I  I  I  L  L  L  G  I  E  G  M  V  L  I  I  L
         Y  Y  *  *  L  *  S  F  F  L  E  *  K  V  W  F  *  *  F  *
```

FIG. 2 CONT.

```
24301  AATTTGAGCTCTCATAGTGTTGTTTACTCACGTTATTGTTTTTCTGTTAATAATACTTTT  24360
       N  L  S  S  H  S  V  V  Y  S  R  Y  C  F  S  V  N  N  T  F
        I  *  A  L  I  V  L  F  T  H  V  I  V  F  L  L  I  I  L  F
         F  E  L  S  *  C  C  L  L  T  L  L  F  F  C  *  *  Y  F  L

24361  TGTCCTTGTGCTAAACCTTCTTTTGCTTCAAGTTGCAAGAGTCATAAACCACCTTCTGCT  24420
       C  P  C  A  K  P  S  F  A  S  S  C  K  S  H  K  P  P  S  A
        V  L  V  L  N  L  L  L  L  Q  V  A  R  V  I  N  H  L  L  L
         S  L  C  *  T  F  F  C  F  K  L  Q  E  S  *  T  T  F  C  F

24421  TCCTGTCCTATTGGTACTAATTATCGTTCTTGTGAGAGTACTACTGTACTCGACCACACT  24480
       S  C  P  I  G  T  N  Y  R  S  C  E  S  T  T  V  L  D  H  T
        P  V  L  L  V  L  I  I  V  L  V  R  V  L  L  Y  S  T  T  L
         L  S  Y  W  Y  *  L  S  F  L  *  E  Y  Y  C  T  R  P  H  *

24481  GACTGGTGTAGGTGTTCTTGTTTACCTGATCCTATAACTGCTTATGACCCTAGGTCTTGT  24540
       D  W  C  R  C  S  C  L  P  D  P  I  T  A  Y  D  P  R  S  C
        T  G  V  G  V  L  V  Y  L  I  L  *  L  L  M  T  L  G  L  V
         L  V  *  V  F  L  F  T  *  S  Y  N  C  L  *  P  *  V  L  F

24541  TCTCAAAAAAAGTCTCTGGTTGGTGTTGGTGAACATTGTGCAGGGTTCGGTGTTGATGAA  24600
       S  Q  K  K  S  L  V  G  V  G  E  H  C  A  G  F  G  V  D  E
        L  K  K  S  L  W  L  V  L  V  N  I  V  Q  G  S  V  L  M  K
         S  K  K  V  S  G  W  C  W  *  T  L  C  R  V  R  C  *  *  R

24601  GAAAAGTGTGGTGTATTGGATGGATCATATAATGTTTCTTGTCTTTGTAGTACTGATGCC  24660
       E  K  C  G  V  L  D  G  S  Y  N  V  S  C  L  C  S  T  D  A
        K  S  V  V  Y  W  M  D  H  I  M  F  L  V  F  V  V  L  M  P
         K  V  W  C  I  G  W  I  I  *  C  F  L  S  L  *  Y  *  C  L

24661  TTTCTAGGTTGGTCTTATGACACTTGCGTCAGTAACAACCGTTGTAATATTTTTTCTAAT  24720
       F  L  G  W  S  Y  D  T  C  V  S  N  N  R  C  N  I  F  S  N
        F  *  V  G  L  M  T  L  A  S  V  T  T  V  V  I  F  F  L  I
         S  R  L  V  L  *  H  L  R  Q  *  Q  P  L  *  Y  F  F  *  F

24721  TTTATTTTAAATGGTATCAATAGTGGTACCACTTGTTCTAATGATTTATTGCAGCCTAAT  24780
       F  I  L  N  G  I  N  S  G  T  T  C  S  N  D  L  L  Q  P  N
        L  F  *  M  V  S  I  V  V  P  L  V  L  M  I  Y  C  S  L  I
         Y  F  K  W  Y  Q  *  W  Y  H  L  F  *  *  F  I  A  A  *  Y

24781  ACTGAAGTTTTTACTGATGTTTGTGTTGATTACGACCTTTATGGTATTACAGGACAAGGT  24840
       T  E  V  F  T  D  V  C  V  D  Y  D  L  Y  G  I  T  G  Q  G
        L  K  F  L  L  M  F  V  L  I  T  T  F  M  V  L  Q  D  K  V
         *  S  F  Y  *  C  L  C  *  L  R  P  L  W  Y  Y  R  T  R  Y
```

FIG. 2 CONT.

```
24841   ATTTTTAAAGAAGTTTCTGCTGTTTATTATAATAGTTGGCAAAATCTTTTGTATGATTCT   24900
        I  F  K  E  V  S  A  V  Y  Y  N  S  W  Q  N  L  L  Y  D  S
         F  L  K  K  F  L  L  F  I  I  I  V  G  K  I  F  C  M  I  L
          F  *  R  S  F  C  C  L  L  *  *  L  A  K  S  F  V  *  F  *

24901   AATGGCAACATTATTGGTTTTAAAGATTTTGTTACTAATAAAACATATAATATTTTCCCT   24960
        N  G  N  I  I  G  F  K  D  F  V  T  N  K  T  Y  N  I  F  P
         M  A  T  L  L  V  L  K  I  L  L  L  I  K  H  I  I  F  S  L
          W  Q  H  Y  W  F  *  R  F  C  Y  *  *  N  I  *  Y  F  P  L

24961   TGTTATGCAGGAAGAGTTTCTGCTGCTTTTCATCAAAATGCTTCCTCTTTGGCTTTACTT   25020
        C  Y  A  G  R  V  S  A  A  F  H  Q  N  A  S  S  L  A  L  L
         V  M  Q  E  E  F  L  L  L  F  I  K  M  L  P  L  W  L  Y  F
          L  C  R  K  S  F  C  C  F  S  S  K  C  F  L  F  G  F  T  L

25021   TATCGTAATTTAAAATGTAGCTATGTTTTGAATAATATTTCTTTAACTACTCAGCCATAT   25080
        Y  R  N  L  K  C  S  Y  V  L  N  N  I  S  L  T  T  Q  P  Y
         I  V  I  *  N  V  A  M  F  *  I  I  F  L  *  L  L  S  H  I
          S  *  F  K  M  *  L  C  F  E  *  Y  F  F  N  Y  S  A  I  F

25081   TTTGATAGTTATCTTGGTTGCGTTTTTAATGCTGATAATTTAACTGATTATTCTGTTTCT   25140
        F  D  S  Y  L  G  C  V  F  N  A  D  N  L  T  D  Y  S  V  S
         L  I  V  I  L  V  A  F  L  M  L  I  I  *  L  I  I  L  F  L
          *  *  L  S  W  L  R  F  *  C  *  *  F  N  *  L  F  C  F  F

25141   TCTTGTGCTCTTCGCATGGGTAGTGGTTTTTGTGTTGATTATAACTCACCTTCTTCTTCC   25200
        S  C  A  L  R  M  G  S  G  F  C  V  D  Y  N  S  P  S  S  S
         L  V  L  F  A  W  V  V  V  F  V  L  I  I  T  H  L  L  L  P
          L  C  S  S  H  G  *  W  F  L  C  *  L  *  L  T  F  F  F  L

25201   TCTTCGCGTCGTAAACGTAGAAGTATTTCTGCTTCTTATCGTTTTGTTACTTTTGAACCC   25260
        S  S  R  R  K  R  R  S  I  S  A  S  Y  R  F  V  T  F  E  P
         L  R  V  V  N  V  E  V  F  L  L  L  I  V  L  L  L  L  N  P
          F  A  S  *  T  *  K  Y  F  C  F  L  S  F  C  Y  F  *  T  L

25261   TTTAATGTCAGTTTTGTTAATGACAGTATTGAGTCTGTGGGTGGTCTTTATGAGATCAAA   25320
        F  N  V  S  F  V  N  D  S  I  E  S  V  G  G  L  Y  E  I  K
         L  M  S  V  L  L  M  T  V  L  S  L  W  V  V  F  M  R  S  K
          *  C  Q  F  C  *  *  Q  Y  *  V  C  G  W  S  L  *  D  Q  N

25321   ATTCCCACTAACTTTACTATAGTTGGTCAAGAGGAATTTATTCAAACTAATTCTCCTAAA   25380
        I  P  T  N  F  T  I  V  G  Q  E  E  F  I  Q  T  N  S  P  K
         F  P  L  T  L  L  *  L  V  K  R  N  L  F  K  L  I  L  L  K
          S  H  *  L  Y  Y  S  W  S  R  G  I  Y  S  N  *  F  S  *  S
```

FIG. 2 CONT.

```
25381     GTTACTATTGATTGTTCTTTATTTGTCTGTTCTAATTATGCAGCTTGCCATGACTTATTG     25440
          V  T  I  D  C  S  L  F  V  C  S  N  Y  A  A  C  H  D  L  L
           L  L  L  I  V  L  Y  L  S  V  L  I  M  Q  L  A  M  T  Y  C
            Y  Y  *  L  F  F  I  C  L  F  *  L  C  S  L  P  *  L  I  V

25441     TCAGAGTATGGCACTTTTTGTGATAATATTAATAGTATTTTAGATGAAGTTAATGGTTTA     25500
          S  E  Y  G  T  F  C  D  N  I  N  S  I  L  D  E  V  N  G  L
           Q  S  M  A  L  F  V  I  I  L  I  V  F  *  M  K  L  M  V  Y
            R  V  W  H  F  L  *  *  Y  *  *  Y  F  R  *  S  *  W  F  T

25501     CTTGATACTACTCAATTGCATGTAGCTGATACTCTTATGCAAGGTGTCACACTTAGCTCC     25560
          L  D  T  T  Q  L  H  V  A  D  T  L  M  Q  G  V  T  L  S  S
           L  I  L  L  N  C  M  *  L  I  L  L  C  K  V  S  H  L  A  P
            *  Y  Y  S  I  A  C  S  *  Y  S  Y  A  R  C  H  T  *  L  Q

25561     AATCTTAATACTAATTTGCATTTTGATGTTGATAATATTAATTTTAAATCCCTAGTTGGA     25620
          N  L  N  T  N  L  H  F  D  V  D  N  I  N  F  K  S  L  V  G
           I  L  I  L  I  C  I  L  M  L  I  I  L  I  L  N  P  *  L  D
            S  *  Y  *  F  A  F  *  C  *  *  Y  *  F  *  I  P  S  W  M

25621     TGTTTAGGTCCACACTGCGGTTCTTCTTCTCGTTCTTTTTTTGAAGATTTATTGTTTGAC     25680
          C  L  G  P  H  C  G  S  S  S  R  S  F  F  E  D  L  L  F  D
           V  *  V  H  T  A  V  L  L  L  V  L  F  L  K  I  Y  C  L  T
            F  R  S  T  L  R  F  F  F  S  F  F  F  *  R  F  I  V  *  Q

25681     AAAGTTAAACTTTCAGATGTTGGTTTTGTTGAAGCTTATAACAATTGTACTGGTGGTAGT     25740
          K  V  K  L  S  D  V  G  F  V  E  A  Y  N  N  C  T  G  G  S
           K  L  N  F  Q  M  L  V  L  L  K  L  I  T  I  V  L  V  V  V
            S  *  T  F  R  C  W  F  C  *  S  L  *  Q  L  Y  W  W  *  *

25741     GAAATTAGAGATCTTCTTTGTGTACAATCCTTTAATGGTATTAAAGTTTTGCCTCCTATT     25800
          E  I  R  D  L  L  C  V  Q  S  F  N  G  I  K  V  L  P  P  I
           K  L  E  I  F  F  V  Y  N  P  L  M  V  L  K  F  C  L  L  F
            N  *  R  S  S  L  C  T  I  L  *  W  Y  *  S  F  A  S  Y  F

25801     TTGTCTGAATCTCAAATTTCTGGTTACACCACAGCCGCTACTGTTGCTGCTATGTTTCCA     25860
          L  S  E  S  Q  I  S  G  Y  T  T  A  A  T  V  A  A  M  F  P
           C  L  N  L  K  F  L  V  T  P  Q  P  L  L  L  L  L  C  F  H
            V  *  I  S  N  F  W  L  H  H  S  R  Y  C  C  C  Y  V  S  T

25861     CCATGGTCAGCAGCAGCTGGCATACCATTTTCTCTTAATGTACAATATAGAATTAATGGT     25920
          P  W  S  A  A  A  G  I  P  F  S  L  N  V  Q  Y  R  I  N  G
           H  G  Q  Q  Q  L  A  Y  H  F  L  L  M  Y  N  I  E  L  M  V
            M  V  S  S  S  W  H  T  I  F  S  *  C  T  I  *  N  *  W  F
```

FIG. 2 CONT.

```
25921   TTGGGTGTTACTATGGATGTTCTTAATAAAAATCAAAAGTTGATAGCTACTGCTTTTAAT   25980
        L  G  V  T  M  D  V  L  N  K  N  Q  K  L  I  A  T  A  F  N
         W  V  L  L  W  M  F  L  I  K  I  K  S  *  *  L  L  L  L  I
          G  C  Y  Y  G  C  S  *  *  K  S  K  V  D  S  Y  C  F  *  *

25981   AATGCTCTTCTTTCTATTCAGAATGGTTTTAGTGCTACCAACTCTGCACTTGCTAAAATA   26040
        N  A  L  L  S  I  Q  N  G  F  S  A  T  N  S  A  L  A  K  I
         M  L  F  F  L  F  R  M  V  L  V  L  P  T  L  H  L  L  K  Y
          C  S  S  F  Y  S  E  W  F  *  C  Y  Q  L  C  T  C  *  N  T

26041   CAAAGTGTTGTTAATTCTAATGCTCAAGCACTTAATAGTTTGTTACAGCAATTATTTAAT   26100
        Q  S  V  V  N  S  N  A  Q  A  L  N  S  L  L  Q  Q  L  F  N
         K  V  L  L  I  L  M  L  K  H  L  I  V  C  Y  S  N  Y  L  I
          K  C  C  *  F  *  C  S  S  T  *  *  F  V  T  A  I  I  *  *

26101   AAATTTGGTGCAATTAGTTCTTCTTTACAAGAAATTTTATCTCGTCTCGATGCTTTAGAG   26160
        K  F  G  A  I  S  S  S  L  Q  E  I  L  S  R  L  D  A  L  E
         N  L  V  Q  L  V  L  L  Y  K  K  F  Y  L  V  S  M  L  *  R
          I  W  C  N  *  F  F  F  T  R  N  F  I  S  S  R  C  F  R  G

26161   GCTCAGGTTCAGATTGATAGGCTTATTAATGGTCGTTTAACTGCTTTAAATGCTTATGTC   26220
        A  Q  V  Q  I  D  R  L  I  N  G  R  L  T  A  L  N  A  Y  V
         L  R  F  R  L  I  G  L  L  M  V  V  *  L  L  *  M  L  M  S
          S  G  S  D  *  *  A  Y  *  W  S  F  N  C  F  K  C  L  C  L

26221   TCTCAACAGCTTAGTGATATTTCTCTTGTAAAATTTGGTGCTGCTTTAGCTATGGAGAAG   26280
        S  Q  Q  L  S  D  I  S  L  V  K  F  G  A  A  L  A  M  E  K
         L  N  S  L  V  I  F  L  L  *  N  L  V  L  L  *  L  W  R  R
          S  T  A  *  *  Y  F  S  C  K  I  W  C  C  F  S  Y  G  E  G

26281   GTTAATGAGTGTGTTAAAAGTCAATCTCCTCGTATTAATTTTTGTGGTAATGGTAATCAT   26340
        V  N  E  C  V  K  S  Q  S  P  R  I  N  F  C  G  N  G  N  H
         L  M  S  V  L  K  V  N  L  L  V  L  I  F  V  V  M  V  I  I
          *  *  V  C  *  K  S  I  S  S  Y  *  F  L  W  *  W  *  S  Y

26341   ATTTTGTCATTAGTTCAAAATGCTCCTTATGGTTTGTTGTTTATGCATTTTAGTTATAAA   26400
        I  L  S  L  V  Q  N  A  P  Y  G  L  L  F  M  H  F  S  Y  K
         F  C  H  *  F  K  M  L  L  M  V  C  C  L  C  I  L  V  I  N
          F  V  I  S  S  K  C  S  L  W  F  V  V  Y  A  F  *  L  *  T

26401   CCTATTTCTTTTAAAACTGTTTTAGTAAGTCCTGGTTTGTGTATATCAGGTGATGTAGGT   26460
        P  I  S  F  K  T  V  L  V  S  P  G  L  C  I  S  G  D  V  G
         L  F  L  L  K  L  F  *  *  V  L  V  C  V  Y  Q  V  M  *  V
          Y  F  F  *  N  C  F  S  K  S  W  F  V  Y  I  R  *  C  R  Y
```

FIG. 2 CONT.

```
26461  ATTGCACCTAAACAAGGGTATTTTATTAAACATAATGATCATTGGATGTTCACTGGTAGT  26520
       I  A  P  K  Q  G  Y  F  I  K  H  N  D  H  W  M  F  T  G  S
        L  H  L  N  K  G  I  L  L  N  I  M  I  I  G  C  S  L  V  V
         C  T  *  T  R  V  F  Y  *  T  *  *  S  L  D  V  H  W  *  F

26521  TCTTACTATTATCCTGAACCAATTTCAGATAAAAATGTTGTTTTTATGAATACTTGTTCT  26580
       S  Y  Y  Y  P  E  P  I  S  D  K  N  V  V  F  M  N  T  C  S
        L  T  I  I  L  N  Q  F  Q  I  K  M  L  F  L  *  I  L  V  L
         L  L  L  S  *  T  N  F  R  *  K  C  C  F  Y  E  Y  L  F  C

26581  GTTAATTTTACTAAAGCGCCTCTTGTTTATTTGAATCATTCTGTACCAAAATTGTCTGAT  26640
       V  N  F  T  K  A  P  L  V  Y  L  N  H  S  V  P  K  L  S  D
        L  I  L  L  K  R  L  L  F  I  *  I  I  L  Y  Q  N  C  L  I
         *  F  Y  *  S  A  S  C  L  F  E  S  F  C  T  K  I  V  *  F

26641  TTTGAATCTGAGTTATCTCATTGGTTTAAAAATCAAACATCCATTGCGCCTAATTTGACT  26700
       F  E  S  E  L  S  H  W  F  K  N  Q  T  S  I  A  P  N  L  T
        L  N  L  S  Y  L  I  G  L  K  I  K  H  P  L  R  L  I  *  L
         *  I  *  V  I  S  L  V  *  K  S  N  I  H  C  A  *  F  D  F

26701  TTAAATCTTCATACTATTAATGCTACTTTTTTAGATTTGTATTATGAGATGAATCTTATT  26760
       L  N  L  H  T  I  N  A  T  F  L  D  L  Y  Y  E  M  N  L  I
        *  I  F  I  L  L  M  L  L  F  *  I  C  I  M  R  *  I  L  F
         K  S  S  Y  Y  *  C  Y  F  F  R  F  V  L  *  D  E  S  Y  S

26761  CAAGAGTCTATTAAGTCTTTGAATAATAGTTATATCAATCTTAAAGATATAGGTACATAT  26820
       Q  E  S  I  K  S  L  N  N  S  Y  I  N  L  K  D  I  G  T  Y
        K  S  L  L  S  L  *  I  I  V  I  S  I  L  K  I  *  V  H  M
         R  V  Y  *  V  F  E  *  *  L  Y  Q  S  *  R  Y  R  Y  I  *

26821  GAAATGTATGTAAAATGGCCTTGGTATGTTTGGCTACTAATTTCTTTTTCATTTATAATA  26880
       E  M  Y  V  K  W  P  W  Y  V  W  L  L  I  S  F  S  F  I  I
        K  C  M  *  N  G  L  G  M  F  G  Y  *  F  L  F  H  L  *  Y
         N  V  C  K  M  A  L  V  C  L  A  T  N  F  F  F  I  Y  N  I

26881  TTCCTTGTATTGCTCTTTTTTATATGTTGTTGTACTGGTTGTGGTTCTGCATGTTTTAGT  26940
       F  L  V  L  L  F  F  I  C  C  C  T  G  C  G  S  A  C  F  S
        S  L  Y  C  S  F  L  Y  V  V  V  L  V  V  V  L  H  V  L  V
         P  C  I  A  L  F  Y  M  L  L  Y  W  L  W  F  C  M  F  *  *

26941  AAATGTCATAATTGTTGTGATGAGTATGGTGGTCATCATGATTTTGTTATCAAAACATCT  27000
       K  C  H  N  C  C  D  E  Y  G  G  H  H  D  F  V  I  K  T  S
        N  V  I  I  V  V  M  S  M  V  V  I  M  I  L  L  S  K  H  L
         M  S  *  L  L  *  *  V  W  W  S  S  *  F  C  Y  Q  N  I  S
```

FIG. 2 CONT.

```
27001   CATGATGATTAGAATCTCTTGTCAGATCTCATTAAATCTAAACTTTATTTATGGACGTTT   27060
        H  D  D  *  N  L  L  S  D  L  I  K  S  K  L  Y  L  W  T  F
         M  M  I  R  I  S  C  Q  I  S  L  N  L  N  F  I  Y  G  R  L
          *  *  L  E  S  L  V  R  S  H  *  I  *  T  L  F  M  D  V  W

27061   GGAGACCTAGCTACACACATTCTCTTGTTATTAGAGAATTTGGTGTTACAAACCTTGAAG   27120
        G  D  L  A  T  H  I  L  L  L  L  E  N  L  V  L  Q  T  L  K
         E  T  *  L  H  T  F  S  C  Y  *  R  I  W  C  Y  K  P  *  R
          R  P  S  Y  T  H  S  L  V  I  R  E  F  G  V  T  N  L  E  D

27121   ATTTGTGTCTAAAGTATAATTACTGTCAACCTATTGTTGGTTACTGTATTGTACCTTTAA   27180
        I  C  V  *  S  I  I  T  V  N  L  L  L  V  T  V  L  Y  L  *
         F  V  S  K  V  *  L  L  S  T  Y  C  W  L  L  Y  C  T  F  K
          L  C  L  K  Y  N  Y  C  Q  P  I  V  G  Y  C  I  V  P  L  N

27181   ATGTTTGGTGTCGCAAGTTTGGCAAATTTGCTTCTCACTTTACATTACGTAGTCACGATA   27240
        M  F  G  V  A  S  L  A  N  L  L  L  T  L  H  Y  V  V  T  I
         C  L  V  S  Q  V  W  Q  I  C  F  S  L  Y  I  T  *  S  R  Y
          V  W  C  R  K  F  G  K  F  A  S  H  F  T  L  R  S  H  D  I

27241   TTTCCCATAGTAATAATTTTGGTGTTGTAACTAGTTTTACTACTTATGGTAATACTGTTT   27300
        F  P  I  V  I  I  L  V  L  *  L  V  L  L  L  M  V  I  L  F
         F  P  *  *  *  F  W  C  C  N  *  F  Y  Y  L  W  *  Y  C  F
          S  H  S  N  N  F  G  V  V  T  S  F  T  T  Y  G  N  T  V  S

27301   CTGAGGCTGTGTCTAGATTAGTTGAATCAGCTTCTGAATTTATTGTTTGGCGTGCAGAGG   27360
        L  R  L  C  L  D  *  L  N  Q  L  L  N  L  L  F  G  V  Q  R
         *  G  C  V  *  I  S  *  I  S  F  *  I  Y  C  L  A  C  R  G
          E  A  V  S  R  L  V  E  S  A  S  E  F  I  V  W  R  A  E  A

27361   CACTTAATAAGTATGGTTGATTTATTTTTCAATGATACTGCTTGGTACATAGGACAGATT   27420
        H  L  I  S  M  V  D  L  F  F  N  D  T  A  W  Y  I  G  Q  I
         T  *  *  V  W  L  I  Y  F  S  M  I  L  L  G  T  *  D  R  F
          L  N  K  Y  G  *  F  I  F  Q  *  Y  C  L  V  H  R  T  D  F

27421   TTAGTTTTAGTTTTATTTTGTCTTATTTCTTTAATCTTTGTTGTTGCTTTTTTAGCAACT   27480
        L  V  L  V  L  F  C  L  I  S  L  I  F  V  V  A  F  L  A  T
         *  F  *  F  Y  F  V  L  F  L  *  S  L  L  L  L  F  *  Q  L
          S  F  S  F  I  L  S  Y  F  F  N  L  C  C  C  F  F  S  N  Y

27481   ATTAAGCTTTGTATGCAACTTTGTGGTTTTTGTAATTTCTTTATTATTTCACCTTCGGCT   27540
        I  K  L  C  M  Q  L  C  G  F  C  N  F  F  I  I  S  P  S  A
         L  S  F  V  C  N  F  V  V  F  V  I  S  L  L  F  H  L  R  L
          *  A  L  Y  A  T  L  W  F  L  *  F  L  Y  Y  F  T  F  G  L
```

FIG. 2 CONT.

```
27541    TACGTTTATAAAAGAGGTATGCAGTTGTATAAGTCTTATAGTGAACAAGTTATACCACCC    27600
         Y  V  Y  K  R  G  M  Q  L  Y  K  S  Y  S  E  Q  V  I  P  P
          T  F  I  K  E  V  C  S  C  I  S  L  I  V  N  K  L  Y  H  P
           R  L  *  K  R  Y  A  V  V  *  V  L  *  *  T  S  Y  T  T  H

27601    ACTTCAGATTATTTAATCTAAATCTAAACATTATGAATAAATCTTTTCTTCCTCAATTTA    27660
         T  S  D  Y  L  I  *  I  *  T  L  *  I  N  L  F  F  L  N  L
          L  Q  I  I  *  S  K  S  K  H  Y  E  *  I  F  S  S  S  I  Y
           F  R  L  F  N  L  N  L  N  I  M  N  K  S  F  L  P  Q  F  T

27661    CTTCTGATCAAGCTGTTACATTCTTAAAAGAATGGAATTTCTCTTTGGGTGTAATACTAC    27720
         L  L  I  K  L  L  H  S  *  K  N  G  I  S  L  W  V  *  Y  Y
          F  *  S  S  C  Y  I  L  K  R  M  E  F  L  F  G  C  N  T  T
           S  D  Q  A  V  T  F  L  K  E  W  N  F  S  L  G  V  I  L  L

27721    TTTTTATTACTATCATATTGCAGTTCGGTTATACGAGCCGTAGTATGTTTGTTTATCTTA    27780
         F  L  L  L  S  Y  C  S  S  V  I  R  A  V  V  C  L  F  I  L
          F  Y  Y  Y  H  I  A  V  R  L  Y  E  P  *  Y  V  C  L  S  Y
           F  I  T  I  I  L  Q  F  G  Y  T  S  R  S  M  F  V  Y  L  I

27781    TCAAGATGATTATTCTTTGGCTTATGTGGCCATTGACTATCACCTTGACTATATTTAATT    27840
         S  R  *  L  F  F  G  L  C  G  H  *  L  S  P  *  L  Y  L  I
          Q  D  D  Y  S  L  A  Y  V  A  I  D  Y  H  L  D  Y  I  *  L
           K  M  I  I  L  W  L  M  W  P  L  T  I  T  L  T  I  F  N  C

27841    GTTTTTATGCTTTGAATAATGCTTTTCTTGCATTTTCTATAGTGTTTACTATTATTTCTA    27900
         V  F  M  L  *  I  M  L  F  L  H  F  L  *  C  L  L  L  F  L
          F  L  C  F  E  *  C  F  S  C  I  F  Y  S  V  Y  Y  Y  F  Y
           F  Y  A  L  N  N  A  F  L  A  F  S  I  V  F  T  I  I  S  I

27901    TTGTTATATGGATTCTTTATTTTGTTAATAGTATTCGGCTTTTTATTAGAACTGGCAGTT    27960
         L  L  Y  G  F  F  I  L  L  I  V  F  G  F  L  L  E  L  A  V
          C  Y  M  D  S  L  F  C  *  *  Y  S  A  F  Y  *  N  W  Q  L
           V  I  W  I  L  Y  F  V  N  S  I  R  L  F  I  R  T  G  S  W

27961    GGTGGAGTTTTAATCCAGAGACCAATAATCTTATGTGTATTGATATGAAAGGCAAGATGT    28020
         G  G  V  L  I  Q  R  P  I  I  L  C  V  L  I  *  K  A  R  C
          V  E  F  *  S  R  D  Q  *  S  Y  V  Y  *  Y  E  R  Q  D  V
           W  S  F  N  P  E  T  N  N  L  M  C  I  D  M  K  G  K  M  F

28021    TTGTTAGGCCAGTTATTGAGGACTATCACACATTAACTGCTACTGTTATTCGTGGTCATC    28080
         L  L  G  Q  L  L  R  T  I  T  H  *  L  L  L  L  F  V  V  I
          C  *  A  S  Y  *  G  L  S  H  I  N  C  Y  C  Y  S  W  S  S
           V  R  P  V  I  E  D  Y  H  T  L  T  A  T  V  I  R  G  H  L
```

FIG. 2 CONT.

```
28081   TTTATATACAGGGTGTCAAACTTGGCACTGGTTATACTCTTTCAGATTTGCCCGTATATG   28140
        F  I  Y  R  V  S  N  L  A  L  V  I  L  F  Q  I  C  P  Y  M
         L  Y  T  G  C  Q  T  W  H  W  L  Y  S  F  R  F  A  R  I  C
          Y  I  Q  G  V  K  L  G  T  G  Y  T  L  S  D  L  P  V  Y  V

28141   TTACTGTAGCTAAGGTGCAAGTACTTTGTACCTATAAACGTGCCTTTTTAGATAAGTTAG   28200
        L  L  *  L  R  C  K  Y  F  V  P  I  N  V  P  F  *  I  S  *
         Y  C  S  *  G  A  S  T  L  Y  L  *  T  C  L  F  R  *  V  R
          T  V  A  K  V  Q  V  L  C  T  Y  K  R  A  F  L  D  K  L  D

28201   ATGTTAATAGTGGTTTTGCTGTTTTTGTTAAGTCTAAAGTTGGTAACTATCGTTTACCGT   28260
        M  L  I  V  V  L  L  F  L  L  S  L  K  L  V  T  I  V  Y  R
         C  *  *  W  F  C  C  F  C  *  V  *  S  W  *  L  S  F  T  V
          V  N  S  G  F  A  V  F  V  K  S  K  V  G  N  Y  R  L  P  S

28261   CTAGTAAACCTAGTGGTATGGATACTGCCTTGTTAAGAGCTTAAATCTAAACTATTAGGA   28320
        L  V  N  L  V  V  W  I  L  P  C  *  E  L  K  S  K  L  L  G
         *  *  T  *  W  Y  G  Y  C  L  V  K  S  L  N  L  N  Y  *  D
          S  K  P  S  G  M  D  T  A  L  L  R  A  *  I  *  T  I  R  M

28321   TGTCTTATACTCCCGGTCATTATGCTGGAAGTAGAAGCTCCTCTGGAAATCGTTCAGGAA   28380
        C  L  I  L  P  V  I  M  L  E  V  E  A  P  L  E  I  V  Q  E
         V  L  Y  S  R  S  L  C  W  K  *  K  L  L  W  K  S  F  R  N
          S  Y  T  P  G  H  Y  A  G  S  R  S  S  S  G  N  R  S  G  I

28381   TCCTCAAGAAAACTTCTTGGGCTGACCAATCTGAGCGAAATTACCAAACCTTTAATAGAG   28440
        S  S  R  K  L  L  G  L  T  N  L  S  E  I  T  K  P  L  I  E
         P  Q  E  N  F  L  G  *  P  I  *  A  K  L  P  N  L  *  *  R
          L  K  K  T  S  W  A  D  Q  S  E  R  N  Y  Q  T  F  N  R  G

28441   GCAGAAAAACCCAACCTAAATTCACTGTGTCTACTCAACCACAAGGAAATACTATCCCAC   28500
        A  E  K  P  N  L  N  S  L  C  L  L  N  H  K  E  I  L  S  H
         Q  K  N  P  T  *  I  H  C  V  Y  S  T  T  R  K  Y  Y  P  T
          R  K  T  Q  P  K  F  T  V  S  T  Q  P  Q  G  N  T  I  P  H

28501   ATTATTCCTGGTTCTCCGGGATCACTCAATTTCAAAAAGGTAGAGACTTTAAATTTTCAG   28560
        I  I  P  G  S  P  G  S  L  N  F  K  K  V  E  T  L  N  F  Q
         L  F  L  V  L  R  D  H  S  I  S  K  R  *  R  L  *  I  F  R
          Y  S  W  F  S  G  I  T  Q  F  Q  K  G  R  D  F  K  F  S  D

28561   ATGGTCAAGGAGTTCCCATTGCTTTCGGAGTACCCCCTTCTGAAGCAAAAGGATATTGGT   28620
        M  V  K  E  F  P  L  L  S  E  Y  P  L  L  K  Q  K  D  I  G
         W  S  R  S  S  H  C  F  R  S  T  P  F  *  S  K  R  I  L  V
          G  Q  G  V  P  I  A  F  G  V  P  P  S  E  A  K  G  Y  W  Y
```

FIG. 2 CONT.

```
28621   ATAGACACAGCCGGCGTTCTTTTAAAACAGCTGATGGTCAACAAAAGCAGTTGTTACCGA   28680
        I  D  T  A  G  V  L  L  K  Q  L  M  V  N  K  S  S  C  Y  R
         *  T  Q  P  A  F  F  *  N  S  *  W  S  T  K  A  V  V  T  E
          R  H  S  R  R  S  F  K  T  A  D  G  Q  Q  K  Q  L  L  P  R

28681   GATGGTATTTCTACTATCTCGGTACCGGCCCATATGCCAATGCATCCTATGGTGAATCCC   28740
        D  G  I  S  T  I  S  V  P  A  H  M  P  M  H  P  M  V  N  P
         M  V  F  L  L  S  R  Y  R  P  I  C  Q  C  I  L  W  *  I  P
          W  Y  F  Y  Y  L  G  T  G  P  Y  A  N  A  S  Y  G  E  S  L

28741   TCGAAGGGGTCTTCTGGGTTGCTAATCACCAAGCTGACACTTCTACTCCCTCCGATGTTT   28800
        S  K  G  S  S  G  L  L  I  T  K  L  T  L  L  L  P  P  M  F
         R  R  G  L  L  G  C  *  S  P  S  *  H  F  Y  S  L  R  C  F
          E  G  V  F  W  V  A  N  H  Q  A  D  T  S  T  P  S  D  V  S

28801   CGTCAAGGGATCCTACTACTCAAGAAGCTATCCCTACTAGGTTTCCGCCTGGTACGATTT   28860
        R  Q  G  I  L  L  L  K  K  L  S  L  L  G  F  R  L  V  R  F
         V  K  G  S  Y  Y  S  R  S  Y  P  Y  *  V  S  A  W  Y  D  F
          S  R  D  P  T  T  Q  E  A  I  P  T  R  F  P  P  G  T  I  L

28861   TGCCTCAAGGCTATTATGTTGAAGGCTCAGGAAGGTCTGCTTCTAATAGTCGACCAGGTT   28920
        C  L  K  A  I  M  L  K  A  Q  E  G  L  L  L  I  V  D  Q  V
         A  S  R  L  L  C  *  R  L  R  K  V  C  F  *  *  S  T  R  F
          P  Q  G  Y  Y  V  E  G  S  G  R  S  A  S  N  S  R  P  G  S

28921   CACGTTCTCAATCACGTGGACCCAATAATCGTTCATTAAGTAGAAGTAATTCTAATTTTA   28980
        H  V  L  N  H  V  D  P  I  I  V  H  *  V  E  V  I  L  I  L
         T  F  S  I  T  W  T  Q  *  S  F  I  K  *  K  *  F  *  F  *
          R  S  Q  S  R  G  P  N  N  R  S  L  S  R  S  N  S  N  F  R

28981   GACATTCAGATTCTATAGTAAAACCTGATATGGCTGATGAGATCGCTAATCTTGTTTTAG   29040
        D  I  Q  I  L  *  *  N  L  I  W  L  M  R  S  L  I  L  F  *
         T  F  R  F  Y  S  K  T  *  Y  G  *  *  D  R  *  S  C  F  S
          H  S  D  S  I  V  K  P  D  M  A  D  E  I  A  N  L  V  L  A

29041   CCAAGCTTGGTAAAGATTCTAAACCTCAGCAAGTCACTAAGCAAAATGCCAAGGAAATCA   29100
        P  S  L  V  K  I  L  N  L  S  K  S  L  S  K  M  P  R  K  S
         Q  A  W  *  R  F  *  T  S  A  S  H  *  A  K  C  Q  G  N  Q
          K  L  G  K  D  S  K  P  Q  Q  V  T  K  Q  N  A  K  E  I  R

29101   GGCATAAAATTTTAACAAAACCTCGCCAAAAGCGAACTCCTAATAAACATTGTAATGTTC   29160
        G  I  K  F  *  Q  N  L  A  K  S  E  L  L  I  N  I  V  M  F
         A  *  N  F  N  K  T  S  P  K  A  N  S  *  *  T  L  *  C  S
          H  K  I  L  T  K  P  R  Q  K  R  T  P  N  K  H  C  N  V  Q
```

FIG. 2 CONT.

```
29161   AACAGTGTTTTGGTAAAAGAGGACCTTCTCAAAATTTTGGTAATGCTGAAATGTTAAAGC   29220
        N  S  V  L  V  K  E  D  L  L  K  I  L  V  M  L  K  C  *  S
         T  V  F  W  *  K  R  T  F  S  K  F  W  *  C  *  N  V  K  A
          Q  C  F  G  K  R  G  P  S  Q  N  F  G  N  A  E  M  L  K  L

29221   TTGGTACTAATGATCCTCAGTTTCCTATTCTTGCAGAATTAGCTCCTACACCAGGTGCTT   29280
        L  V  L  M  I  L  S  F  L  F  L  Q  N  *  L  L  H  Q  V  L
         W  Y  *  *  S  S  V  S  Y  S  C  R  I  S  S  Y  T  R  C  F
          G  T  N  D  P  Q  F  P  I  L  A  E  L  A  P  T  P  G  A  F

29281   TTTTCTTTGGTTCTAAATTAGACTTGGTTAAAAGAGATTCCGAGGCTGACTCACCTGTTA   29340
        F  S  L  V  L  N  *  T  W  L  K  E  I  P  R  L  T  H  L  L
         F  L  W  F  *  I  R  L  G  *  K  R  F  R  G  *  L  T  C  *
          F  F  G  S  K  L  D  L  V  K  R  D  S  E  A  D  S  P  V  K

29341   AAGATGTTTTTGAACTTCATTATTCTGGTTCTATTAGGTTTGATAGTACTTTACCAGGCT   29400
        K  M  F  L  N  F  I  I  L  V  L  L  G  L  I  V  L  Y  Q  A
         R  C  F  *  T  S  L  F  W  F  Y  *  V  *  *  Y  F  T  R  L
          D  V  F  E  L  H  Y  S  G  S  I  R  F  D  S  T  L  P  G  F

29401   TTGAGACAATTATGAAAGTTCTTGAAGAGAATTTAAATGCTTACGTTAATTCTAATCAGA   29460
        L  R  Q  L  *  K  F  L  K  R  I  *  M  L  T  L  I  L  I  R
         *  D  N  Y  E  S  S  *  R  E  F  K  C  L  R  *  F  *  S  E
          E  T  I  M  K  V  L  E  E  N  L  N  A  Y  V  N  S  N  Q  N

29461   ACACTGATTCTGATTCGTTGAGTTCTAAACCTCAGCGTAAAAGAGGTGTTAAACAATTAC   29520
        T  L  I  L  I  R  *  V  L  N  L  S  V  K  E  V  L  N  N  Y
         H  *  F  *  F  V  E  F  *  T  S  A  *  K  R  C  *  T  I  T
          T  D  S  D  S  L  S  S  K  P  Q  R  K  R  G  V  K  Q  L  P

29521   CAGAACAGTTTGACTCTCTTAATTTAAGTGCTGGTACTCAGCACATTTCAAATGATTTTA   29580
        Q  N  S  L  T  L  L  I  *  V  L  V  L  S  T  F  Q  M  I  L
         R  T  V  *  L  S  *  F  K  C  W  Y  S  A  H  F  K  *  F  Y
          E  Q  F  D  S  L  N  L  S  A  G  T  Q  H  I  S  N  D  F  T

29581   CTCCTGAGGATCATAGTTTACTTGCTACTCTTGATGATCCTTATGTAGAAGACTCTGTTG   29640
        L  L  R  I  I  V  Y  L  L  L  L  M  I  L  M  *  K  T  L  L
         S  *  G  S  *  F  T  C  Y  S  *  *  S  L  C  R  R  L  C  C
          P  E  D  H  S  L  L  A  T  L  D  D  P  Y  V  E  D  S  V  A

29641   CTTAATGAGAATGAATCCTAATTCGACACTAGGTGGTAACCCCTCGCTATTATTCGGAAT   29700
        L  N  E  N  E  S  *  F  D  T  R  W  *  P  L  A  I  I  R  N
         L  M  R  M  N  P  N  S  T  L  G  G  N  P  S  L  L  F  G  I
          *  *  E  *  I  L  I  R  H  *  V  V  T  P  R  Y  Y  S  E  *
```

FIG. 2 CONT.

```
29701   AGGACACTCTCTATCAGAATGAATTCTTGCTGTAATAACAGATAGAGTAGGTTGTTACAG   29760
        R  T  L  S  I  R  M  N  S  C  C  N  N  R  *  S  R  L  L  Q
         G  H  S  L  S  E  *  I  L  A  V  I  T  D  R  V  G  C  Y  R
          D  T  L  Y  Q  N  E  F  L  L  *  *  Q  I  E  *  V  V  T  D

29761   ACTATATATTAATTAGTAGAAATTTTATATTTAGACATTTGATTGTTAGAGTAGTTATAA   29820
        T  I  Y  *  L  V  E  I  L  Y  L  D  I  *  L  L  E  *  L  *
         L  Y  I  N  *  *  K  F  Y  I  *  T  F  D  C  *  S  S  Y  K
          Y  I  L  I  S  R  N  F  I  F  R  H  L  I  V  R  V  V  I  R

29821   GGTTTAGCTGTAGTATAAACGCCTCCGGGAAGAGCTATCAATTGTAGTGTTTAATATATA   29880
        G  L  A  V  V  *  T  P  P  G  R  A  I  N  C  S  V  *  Y  I
         V  *  L  *  Y  K  R  L  R  E  E  L  S  I  V  V  F  N  I  Y
          F  S  C  S  I  N  A  S  G  K  S  Y  Q  L  *  C  L  I  Y  I

29881   TATTAGTATATGATTGAAATTAATTATAGCCTTTTGGAGGAATTACAAAAAAAAAAAAAA   29940
        Y  *  Y  M  I  E  I  N  Y  S  L  L  E  E  L  Q  K  K  K  K
         I  S  I  *  L  K  L  I  I  A  F  W  R  N  Y  K  K  K  K  K
          L  V  Y  D  *  N  *  L  *  P  F  G  G  I  T  K  K  K  K  K

29941   AA                                                             29942
```

FIG. 2 CONT.

```
1   CTTATTCTCGCTTAACGCAGGCATGGCAGATAGTCGAATGCTAGAGAACAGTCTAGAGTA  60
      Y  S  R  I  A  D  T  G  D  I  L  K  R  D  R  T  L  D  *
     I  L  A  F  Q  T  R  V  T  *  *  S  V  I  E  Q  *  I  E
    F  L  L  S  N  R  G  Y  R  R  D  A  *  S  R  K  D  S  R  M

61  ATTTAGATTTGAAAAATTTGTTCTAAGGGACAATAGGTACGAACACTCACACCAAATTAG  120
     *  I  *  V  K  *  V  L  N  G  T  I  W  A  Q  S  H  P  K  I
    N  F  R  F  K  K  F  L  I  G  Q  *  G  H  K  H  T  H  N  L
     L  D  L  S  K  L  C  S  E  R  N  D  M  S  T  L  T  T  *  D

121 TATTAGAACATAAAATGAAAGGTGTGAAAAGTAGAGAGACGGTCACTGCACAACCAACAG  180
     M  I  K  Y  K  V  K  W  V  K  *  R  E  A  L  S  T  N  T  T
    *  L  R  T  N  *  K  G  C  K  E  D  R  Q  W  H  R  T  P  Q
     Y  D  Q  I  K  S  E  V  S  K  M  E  R  G  T  V  H  Q  N  D

181 GAGTCGCAGGGAGGGTATCCAGCGTTACTAATTTTGGTCGTTTATGCCAGAGCCGAAGTT  240
     R  L  T  G  G  M  P  R  L  S  *  F  W  C  I  R  D  R  S  *
    G  *  R  G  E  W  L  D  C  H  N  F  G  A  F  V  T  E  A  E
     E  A  D  R  G  Y  T  A  I  I  L  V  L  L  Y  P  R  P  K  L

241 CACCCGCGGTCTTAAAGCAACCGACGAAGGCCTACGTCGCCTCCTCAACCGATCAGGATA  300
     T  P  A  L  I  E  N  A  A  E  P  H  L  P  P  T  P  *  D  *
    L  P  R  W  F  K  T  P  Q  K  R  I  C  R  L  L  Q  S  T  R
     H  A  G  S  N  R  Q  S  S  G  S  A  A  S  S  N  A  L  G  I

301 CTTCAGTCTACTCCCACCCAATACGGGGAGATGACCAGTTCGCTACCTTTCACAACCTAA  360
     S  T  L  H  P  H  T  I  G  R  *  Q  D  L  S  P  F  H  Q  I
    H  L  *  I  L  T  P  *  A  G  R  S  T  L  R  H  F  T  N  S
     F  D  S  S  P  P  N  H  G  E  V  P  *  A  I  S  L  T  P  N

361 GCAAATACTATTAGTACACTTCTATCTAACAGCGACGTAAGAACCTGTTCTTACCGTACA  420
     R  K  H  Y  D  H  S  S  L  N  D  S  C  E  Q  V  L  I  A  H
    E  N  I  I  I  M  H  L  Y  I  T  A  A  N  K  S  L  F  P  M
     T  *  S  L  *  T  F  I  S  Q  R  Q  M  R  P  C  S  H  C  T

421 CGTCAGTTTAGAATAGGCACTATAAAAACAAGTACTTCTAGATGTACAACATCTTCAAGA  480
     A  T  L  D  *  G  H  Y  K  Q  E  H  L  D  V  H  Q  L  L  E
    H  L  *  I  K  D  T  I  N  K  N  M  F  I  *  M  N  Y  F  N
     C  D  F  R  I  R  S  I  K  T  *  S  S  R  C  T  T  S  T  R

481 TTGATTTTGTCGGCATTTCAGGCCATGCCGTTAAAATTAATTTAGTGGAAACGTATCGAA  540
     L  *  F  L  R  L  T  R  Y  P  L  K  L  *  I  V  K  A  Y  S
    *  S  F  C  G  Y  L  G  T  R  C  N  *  N  F  *  R  Q  M  A
     V  L  V  A  T  F  D  P  V  A  I  K  I  L  D  G  K  C  L  K
```

FIG. 3

```
541   CCCACCAAAAGGATTTCCCATACAATACCCGAACAAGGCAAGTATGTTCTGATTTGCAAT   600
       P  H  N  E  *  L  T  H  *  P  S  T  G  N  M  C  S  *  V  N
      Q  T  T  K  R  F  P  I  N  H  A  Q  E  T  *  V  L  S  F  T
        P  P  K  G  L  P  Y  T  I  P  K  N  R  E  Y  L  V  L  R  *

601   ACAACATGTAGTAGAAAGATACTGATGTAGATGATGATTAAAACCACTTCTAAAAAACCC   660
       H  Q  V  D  D  K  *  S  *  M  *  *  *  N  Q  H  L  N  K  P
      I  N  Y  M  M  K  R  H  S  C  R  S  S  I  K  T  F  I  K  Q
        T  T  C  *  R  E  I  V  V  D  V  V  L  K  P  S  S  K  K  P

661   AACCTAACATGGAAAACCAAAATACGGTAGAATACAAGTGTTTACCAAAGTTAAGACATC   720
       N  S  Q  V  K  Q  N  *  A  M  K  H  E  C  I  T  E  I  R  Y
      T  P  N  Y  R  K  T  K  H  W  R  I  N  V  F  P  K  L  E  T
        Q  I  T  G  K  P  K  I  G  D  *  T  *  L  H  N  *  N  Q  L

721   CAACATATAACTTCTCTCACTAAATTATTAAAGTTTAAAATTTAAACTACTAATACTAAA   780
       T  T  Y  Q  L  S  H  N  L  L  K  L  N  *  I  Q  H  N  H  N
      P  Q  I  N  F  L  T  I  *  Y  N  *  I  K  F  K  I  I  I  I
        N  Y  I  S  S  L  S  K  I  I  E  F  K  L  N  S  S  *  S  K

781   ATCACATCTTCTACGAATACGACTCCAAGTACGACTCGGATTTCCATTTATAAGTGTTTT   840
       *  H  L  L  H  K  H  Q  P  E  H  Q  A  *  L  Y  I  N  V  F
      K  T  Y  F  I  S  I  S  L  N  M  S  L  R  F  T  F  I  *  L
        L  T  S  S  A  *  A  S  T  *  A  S  G  L  P  L  Y  E  C  F

841   TCGAATACGAAATGAATCTGTTATAGCACCATAATTTGGGCATGAAAAACATCTGGTCAT   900
       L  K  H  K  V  *  V  I  D  H  Y  *  V  R  V  K  Q  L  G  T
      F  S  I  S  *  K  S  L  I  T  T  N  F  G  Y  K  K  Y  V  L
        A  *  A  K  S  L  C  Y  R  P  I  L  G  T  S  K  T  S  W  Y

901   ACCAACACTGATAAGACCATTTAATCGTCTAACAGAAGTTCGAATACCAGTAATAAGAAA   960
       H  N  H  S  N  Q  Y  I  L  L  N  D  E  L  K  H  D  N  N  K
      I  T  T  V  I  R  T  F  *  C  I  T  K  L  S  I  T  M  I  R
        P  Q  S  *  E  P  L  N  A  S  Q  R  *  A  *  P  *  *  E  K

961   CGTTCTATACTCTGTTTTCGTCAGACATACCGAACGGTTAACACTGAAACTATAACATCA   1020
       A  L  Y  S  V  F  A  T  Q  I  A  Q  W  N  H  S  Q  Y  Q  L
      Q  L  I  H  S  L  L  L  R  Y  P  K  G  I  T  V  K  I  N  Y
        C  S  I  L  C  F  C  D  T  H  S  A  L  Q  S  K  S  I  T  T

1021  CCGAACCGTACATCAAGCACTAAGTGCTAAACAATACGCGGACGTCTGATATCGATGATA   1080
       P  K  A  H  L  E  H  N  V  I  Q  *  A  G  A  S  *  L  *  *
      H  S  P  M  Y  N  T  I  *  S  K  N  H  A  Q  L  S  Y  S  S
        A  Q  C  T  T  R  S  E  R  N  T  I  R  R  C  V  I  A  V  I
```

FIG. 3 CONT'D

```
1081 AACACCATAATTTATACAACGTGTTGGATGTCTTCTACATCATCTACCTCTACATCAATA 1140
      K  H  Y  *  I  H  Q  V  V  *  L  L  H  L  L  H  L  H  L  *
     N  T  T  N  F  I  N  C  L  R  C  F  I  Y  Y  I  S  I  Y  N
       Q  P  I  L  Y  T  A  C  G  V  S  S  T  T  S  P  S  T  T  I

1141 TGCACTTGGACATGTAAATAATAGACGACTACGTTATCAAAATTTCGAAGGATCAAACTA 1200
      V  H  V  Q  V  N  I  I  Q  Q  H  L  L  K  L  A  E  *  N  S
     Y  T  F  R  Y  M  *  *  R  S  I  C  Y  N  *  L  K  R  T  Q
       R  S  G  T  C  K  N  D  A  S  A  I  T  K  F  S  G  L  K  I

1201 CTTTCAATACTGAGTATACCTACTAAAAAGATAATTTAGATATATATTACAACTAAACAC 1260
      S  L  *  S  E  Y  P  H  N  K  *  *  I  *  I  Y  H  Q  N  T
     H  F  N  H  S  M  H  I  I  K  R  N  F  R  Y  I  I  N  I  Q
       F  T  I  V  *  I  S  S  K  E  I  L  D  I  Y  L  T  S  K  H

1261 ACTAACACCAAAACAATACGTCATACCAATACATCTAACAAAATTACTATTAACACTAAA 1320
      H  N  H  N  Q  *  A  T  H  N  H  L  N  N  *  H  Y  N  H  N
     T  I  T  T  K  N  H  L  I  T  I  Y  I  T  K  I  I  I  T  I
       S  Q  P  K  T  I  C  Y  P  *  T  S  Q  K  L  S  L  Q  S  K

1321 AATACCAACCCAAAGTCCATTATACTACCTACCAAAAAGAACAGGTAACACAACATGTCA 1380
      K  H  N  P  K  L  Y  Y  S  P  H  N  K  K  D  M  T  N  Y  L
     K  I  T  P  N  *  T  I  H  H  I  T  K  R  T  W  Q  T  T  C
       *  P  Q  T  E  P  L  I  I  S  P  K  E  Q  G  N  H  Q  V  T

1381 AATACTGAGATCGCTTCAATTTCGGGTTAGTAGACCACAATAAGGACTTTTAGGACACAA 1440
      K  H  S  *  R  L  *  L  G  I  M  Q  H  *  E  Q  F  D  Q  T
     N  I  V  R  A  F  N  F  G  L  *  R  T  N  N  R  F  I  R  H
       *  S  E  L  S  T  L  A  W  D  D  P  T  I  G  S  F  G  T  N

1441 TAAATGATTATCATGACTATGACAATTGGTACTAAGAAAATTAAACATACCAATAAGACA 1500
      I  *  *  Y  Y  Q  Y  Q  *  G  H  N  K  *  N  T  H  N  N  Q
     *  K  S  I  T  S  I  S  N  V  M  I  R  K  I  Q  I  T  I  R
       N  V  L  L  V  S  V  T  L  W  S  E  K  L  K  Y  P  *  E  T

1501 GTGTGGTAAACCAAGAACATATATAACCAGCGGCGCAGGACCTAACACCTAAGGATATTA 1560
      *  V  M  Q  N  K  Y  I  N  T  A  A  D  Q  I  T  S  E  *  L
     D  C  W  K  T  R  T  Y  I  P  R  R  T  R  S  Q  P  N  R  Y
       V  G  N  P  E  Q  I  Y  Q  D  G  R  G  P  N  H  I  G  I  I

1561 ATTTAGAAGTCAGTTCAGAATACTACTAAACCAAATAAGTCCACATCATCCAACATTTAG 1620
      *  I  K  L  *  T  K  H  H  N  P  K  N  L  H  L  L  N  Y  I
     N  F  R  *  D  L  R  I  I  I  Q  N  I  *  T  Y  Y  T  T  F
       L  D  E  T  L  D  *  S  S  K  T  *  E  P  T  T  P  Q  L  D
```

FIG. 3 CONT'D

```
1621  ATAACAATTTCTTTGACGAGAATAATGAGTACGTGAAATGAATCTAATACAAGTTACATT  1680
         *  Q  *  L  F  Q  E  *  *  E  H  V  K  S  L  N  H  E  I  Y
        R  N  N  F  F  S  S  K  N  S  M  C  K  V  *  I  I  N  L  T
          I  T  L  S  V  A  R  I  V  *  A  S  *  K  S  *  T  *  H  L

1681  CACACCATTAGAACTTGTTTTAGTATAAGAACCGCAATTATTAAGAACCACATCCGTTGA  1740
         T  H  Y  D  Q  V  F  D  Y  E  Q  R  *  Y  N  K  T  Y  A  V
        L  T  T  I  K  F  L  I  M  N  K  A  N  I  I  R  P  T  P  L
          H  P  L  R  S  C  F  *  I  R  P  T  L  L  E  Q  H  L  C  S

1741  CAACGAATTATCTCCACTAATATTATACGAAGATTTTTTATAACTGAACAAACAATTCGC  1800
         T  A  *  Y  L  H  N  Y  Y  A  E  L  F  Y  Q  S  T  Q  *  A
        Q  Q  K  I  S  T  I  I  I  H  K  *  F  I  N  V  Q  K  N  L
          N  S  L  L  P  S  *  L  I  S  R  F  F  I  S  K  N  T  L  R

1801  AGCACGACTAAAACGAACGTTCAAACGTCAAACACCTCTACCAAAACATGGAAAAAATGA  1860
         D  H  Q  N  Q  K  C  T  Q  L  K  H  L  H  N  Q  V  K  K  V
        T  T  S  I  K  S  A  L  K  C  N  T  S  I  T  K  Y  R  K  *
          R  A  S  K  A  Q  L  N  A  T  Q  P  S  P  K  T  G  K  K  S

1861  TCTACCAAATTAAGGGGCATCAATAATAGATTAAGTCTCACCATAAAAGAAATGTAGAAA  1920
         L  H  N  L  E  G  Y  N  N  D  L  E  S  H  Y  K  R  *  M  K
        *  I  T  *  N  G  T  T  I  I  *  N  L  T  T  N  E  K  C  R
          S  P  K  I  G  R  L  *  *  R  I  *  L  P  I  K  K  V  D  K

1921  CTACAGAGTTAAAAGTGTTCTTCAAAGACTATACACAAATTTTTACACATAAAACAAATA  1980
         S  T  E  I  K  V  L  L  K  Q  Y  T  N  L  F  T  Y  K  T  *
        Q  H  R  L  K  *  L  F  N  R  I  H  T  *  F  H  T  N  Q  K
          I  D  *  N  E  C  S  T  E  S  I  H  K  F  I  H  I  K  N  I

1981  CCTGTCTCAAAGTCAACGATGTAAAATATATCTCGTAATACAATTATCCAACCAATGAGT  2040
         P  C  L  K  L  Q  *  M  K  Y  L  A  N  H  *  Y  T  P  *  E
        H  V  S  N  *  N  S  C  K  I  Y  L  M  I  N  I  P  Q  N  S
          S  L  T  E  T  A  V  N  *  I  S  C  *  T  L  L  N  T  V  *

2041  TAAATTCAATAACCCATGATGTGAACAATTATTTTACCAATTAACCAAATTATGGTACAA  2100
         I  *  T  I  P  Y  *  V  Q  *  Y  F  P  *  N  T  *  Y  W  T
        L  K  L  *  Q  T  S  C  K  N  I  F  H  N  I  P  K  I  G  H
          N  L  N  N  P  V  V  S  T  L  L  I  T  L  Q  N  L  V  M  N

2101  TCTACGATCACGTGGACGATGTCCGACCGAAGAAATGGTTAATAACTTACCAGAAAAACA  2160
         L  H  *  H  V  Q  *  L  S  A  E  K  G  I  I  S  H  D  K  Q
        *  I  S  T  C  R  S  C  A  P  K  K  V  L  *  Q  I  T  K  K
          S  A  L  A  G  A  V  P  Q  S  R  *  W  N  N  F  P  R  K  T
```

FIG. 3 CONT'D

```
2161 TCATAGAGTTCGGTTGAAATTAAAACAACGAAATTATGGACTAATACGATTTTAAAATCA 2220
      L  I  E  L  W  S  *  N  Q  Q  K  L  V  Q  N  H  *  F  K  L
     Y  Y  R  L  G  V  K  I  K  N  S  *  Y  R  I  I  S  F  N  *
       T  D  *  A  L  K  L  K  T  A  K  I  G  S  *  A  L  I  K  T

2221 ATTATTTAAAATGTGAAAAAAATTCAATAATAATCTCACACAATGTCAACTACAAAATTT 2280
      *  Y  I  K  C  K  K  *  T  I  I  L  T  H  *  L  Q  H  K  L
     N  I  F  K  V  S  K  K  L  *  *  *  L  T  N  C  N  I  N  *
       L  L  N  *  V  K  K  L  N  N  N  S  H  T  V  T  S  T  K  F

2281 TCTATACGGACAAGAATTTTGATAATTACCAAATCAAACATAACATCCGTTATTCAAAAT 2340
      L  Y  A  Q  E  *  F  *  *  H  N  L  K  Y  Q  L  C  Y  T  K
     F  I  H  R  N  K  F  S  N  I  T  *  N  T  N  Y  A  I  L  K
       S  I  G  T  R  L  V  I  L  P  K  T  Q  I  T  P  L  L  N  *

2341 ATTGCAATCATGTCCCAATTAAGGACCAAAACAAAATGGTACATTACGTGTCCTTGTTGT 2400
      Y  R  *  Y  L  T  L  E  Q  N  Q  K  V  M  Y  H  V  P  V  V
     I  V  N  T  C  P  *  N  R  T  K  N  *  W  T  I  C  L  F  L
       L  T  L  V  P  N  I  G  P  K  T  K  G  H  L  A  C  S  C  C

2401 TTAAATAAAAAAACTTCCGCAACGTCTTAGACAATATCATCTTCTACTACAATAACTCTT 2460
      F  K  N  K  Q  L  R  Q  L  I  Q  *  L  L  L  H  H  *  Q  S
     L  N  I  K  K  F  A  N  C  F  R  N  Y  Y  F  I  I  N  N  L
       I  *  K  K  S  P  T  A  S  D  T  I  T  S  S  S  T  I  S  F

2461 ACAGTTTAGAAGAAATAGTAGAATACTCATAACAGTTGGTGGATTTAGACATCTTTTTTA 2520
      H  *  I  K  K  I  M  K  H  T  N  D  V  V  *  I  Q  L  F  F
     I  D  F  R  R  *  *  R  I  L  I  T  L  W  R  F  R  Y  F  F
       T  L  D  E  K  D  D  *  S  Y  Q  *  G  G  L  D  T  S  F  I

2521 AACATAATATCTATTATACATGTACCCATTCACACCACTATTTAAAAAGGGATAACAGTA 2580
      K  Y  *  L  Y  Y  T  C  P  Y  T  H  H  Y  I  K  G  *  Q  *
     N  T  N  Y  I  I  H  V  H  T  L  T  T  I  F  K  E  R  N  D
       Q  I  I  S  L  I  Y  M  P  L  H  P  S  L  N  K  G  I  T  M

2581 CTTACTATTTTTATAAACAGAAAATCTAGTCCGAACCGCAAAAGGTACACGTCCATCTTT 2640
      S  H  Y  F  Y  K  D  K  L  D  P  K  A  N  E  M  H  L  Y  F
     H  I  I  F  I  N  T  K  *  I  L  S  P  T  K  W  T  C  T  S
       F  S  L  F  I  Q  R  K  S  *  A  Q  R  K  G  H  A  P  L  F

2641 TCAATTAAAATTGCTCTTTGGACAACAATACCTCTAAGGCAGAAACTACTGTCAATTCCA 2700
      L  *  N  *  R  S  V  Q  Q  *  P  S  E  T  K  S  S  L  *  P
     F  N  I  K  V  L  F  R  N  N  H  L  N  R  R  Q  H  C  N  L
       T  L  K  L  S  F  G  T  T  I  S  I  G  D  K  I  V  T  L  T
```

FIG. 3 CONT'D

```
2701 ATACAAACTAAATCTAAGATGAAAACTACTATAAAATCCATTTCAAACAAGTCTTAAACT 2760
      *  T  Q  N  L  N  *  K  Q  H  Y  K  L  Y  L  K  N  L  I  Q
     N  H  K  I  *  I  R  S  K  I  I  N  *  T  F  N  T  *  F  K
       I  N  S  K  S  E  V  K  S  S  I  K  P  L  T  Q  E  S  N  S

2761 TCATCTTTTCCCACAATGACATCTACTAAAACAACGACAACAAACACTACGATATCTCTT 2820
      L  L  F  P  H  *  Q  L  H  N  Q  Q  Q  Q  K  H  H  *  L  S
     F  Y  F  L  T  N  S  Y  I  I  K  N  S  N  N  T  I  S  Y  L
       T  S  F  P  T  V  T  S  S  K  T  A  T  T  Q  S  A  I  S  F

2821 ACGAAATTTGAGAACATTTCTCGTAGGTCACCAACCAATAGTTCAAGCACGTAAAAATTT 2880
      H  K  L  S  K  Y  L  A  D  L  P  Q  N  D  L  E  H  M  K  L
     I  S  *  V  R  T  F  L  M  W  H  N  T  I  L  N  T  C  K  *
       A  K  F  E  Q  L  S  C  G  T  T  P  *  *  T  R  A  N  K  F

2881 ATTTGAATTACTCTTACAACAAATAAATAAACTACTCCGACCACTACTTCGTTACCGGAG 2940
      Y  V  *  H  S  H  Q  K  N  I  Q  H  P  Q  H  H  L  L  P  R
     I  F  K  I  L  I  N  N  I  *  K  I  L  S  T  I  F  C  H  G
       L  S  L  S  F  T  T  *  K  N  S  S  A  P  S  S  A  I  A  E

2941 AGCATACATAACATGAAAACGATAACTCCTACAACTTCTGCAATAGTCATCACTTCGACA 3000
      E  Y  T  N  Y  K  Q  *  Q  P  H  Q  L  R  *  *  Y  H  L  Q
     R  T  H  I  T  S  K  S  N  L  I  N  F  V  N  D  T  T  F  S
       R  I  Y  Q  V  K  A  I  S  S  T  S  S  T  I  L  L  S  A  T

3001 GCTTCTATGATAACTACCACAGCAACTTCTGTGATAATTACTGCTACTTCTACAACAATG 3060
      R  L  Y  *  Q  H  H  R  Q  L  C  *  *  H  R  H  L  H  Q  *
     D  F  I  S  N  I  T  D  N  F  V  S  N  I  V  I  F  I  N  N
       S  S  V  I  S  P  T  T  S  S  V  I  L  S  S  S  S  T  T  V

3061 ACCACTGTTACTGCTACTTCTACAACAATGACCACTGTTACTGCTACTTCTACAACAATG 3120
      Q  H  C  H  R  H  L  H  Q  *  Q  H  C  H  R  H  L  H  Q  *
     S  T  V  I  V  I  F  I  N  N  S  T  V  I  V  I  F  I  N  N
       P  S  L  S  S  S  S  T  T  V  P  S  L  S  S  S  S  T  T  V

3121 ACCACTGTTACTGCTACTTCTACAACAATGACCACTGTTACTGCTACTTCTACAACAATG 3180
      Q  H  C  H  R  H  L  H  Q  *  Q  H  C  H  R  H  L  H  Q  *
     S  T  V  I  V  I  F  I  N  N  S  T  V  I  V  I  F  I  N  N
       P  S  L  S  S  S  S  T  T  V  P  S  L  S  S  S  S  T  T  V

3181 ACCACTGTTACTGCTACTTCTACAACAATGACCACTGTTACTGCTACTTCTACAACAATG 3240
      Q  H  C  H  R  H  L  H  Q  *  Q  H  C  H  R  H  L  H  Q  *
     S  T  V  I  V  I  F  I  N  N  S  T  V  I  V  I  F  I  N  N
       P  S  L  S  S  S  S  T  T  V  P  S  L  S  S  S  S  T  T  V
```

FIG. 3 CONT'D

```
3241  ACCACTGTTACTGCTACTTCTACAACAATGACCACTGTTACTGCTACTTCTACAACAATG  3300
       Q  H  C  H  R  H  L  H  Q  *  Q  H  C  H  R  H  L  H  Q  *
      S  T  V  I  V  I  F  I  N  N  S  T  V  I  V  I  F  I  N  N
        P  S  L  S  S  S  S  T  T  V  P  S  L  S  S  S  S  T  T  V

3301  ACCACTGTTACTGCTACTTCTACAACAATGACCACTGTTACTGCTACTTCTACAACAATG  3360
       Q  H  C  H  R  H  L  H  Q  *  Q  H  C  H  R  H  L  H  Q  *
      S  T  V  I  V  I  F  I  N  N  S  T  V  I  V  I  F  I  N  N
        P  S  L  S  S  S  S  T  T  V  P  S  L  S  S  S  S  T  T  V

3361  ACCACTGTTACTGCTACTTCTACAACAATGACCACTGTTACTGCTACTTCTACAACAATG  3420
       Q  H  C  H  R  H  L  H  Q  *  Q  H  C  H  R  H  L  H  Q  *
      S  T  V  I  V  I  F  I  N  N  S  T  V  I  V  I  F  I  N  N
        P  S  L  S  S  S  S  T  T  V  P  S  L  S  S  S  S  T  T  V

3421  ACCACTGTTACTGCTACTTCTACAACAATGACCACTGTTATTGCTACTTCTCTAACAATG  3480
       Q  H  C  H  R  H  L  H  Q  *  Q  H  C  Y  R  H  L  S  Q  *
      S  T  V  I  V  I  F  I  N  N  S  T  V  I  V  I  F  L  N  N
        P  S  L  S  S  S  S  T  T  V  P  S  L  L  S  S  S  I  T  V

3481  ACCACTGTTACTACTGGTTTAACAACAATGACCACTACTACATCTACTATAACTTTCATA  3540
       Q  H  C  H  H  G  F  Q  Q  *  Q  H  H  H  L  H  Y  Q  F  Y
      S  T  V  I  I  V  L  N  N  N  S  T  I  I  Y  I  I  N  F  T
        P  S  L  S  S  W  I  T  T  V  P  S  S  T  S  S  I  S  L  I

3541  AATACTGAAACTATGAATATTTCGAGAAAATCAAAAATTACTACAGATATTACTACGAAA  3600
       K  H  S  Q  Y  K  Y  L  E  K  L  K  *  H  H  R  Y  H  H  K
      N  I  V  K  I  S  I  F  S  K  *  N  K  I  I  D  I  I  I  S
        *  S  K  S  V  *  L  A  R  K  T  K  L  S  T  *  L  S  A  K

3601  CAAACAATCAATACCAAGATCACAACTTTGTCTTTGTATAAAATTTCAATTACCAAATAC  3660
       T  Q  *  N  H  N  *  H  Q  F  L  F  M  N  *  L  *  H  N  I
      Q  K  N  T  I  T  R  T  N  F  C  F  C  I  K  F  N  I  T  *
        N  T  L  *  P  E  L  T  S  V  S  V  Y  K  L  T  L  P  K  H

3661  CAGTGGATGATAATGTGTATGATTAACAACCAACGCAAGACACAATGAACATTACGTCTT  3720
       T  V  *  *  *  V  Y  *  N  N  T  A  N  Q  T  V  Q  L  A  S
      P  *  R  S  N  C  M  S  I  T  P  Q  T  R  H  *  K  Y  H  L
        D  G  V  I  V  C  V  L  Q  Q  N  R  E  T  N  S  T  I  C  F

3721  TAATGGAAAATTCAAATTCCTAAATCGATAACTTTTATACACCAATAGAATATTCCACCC  3780
       I  V  K  *  T  *  P  N  L  *  Q  F  Y  T  T  I  K  Y  P  P
      F  *  R  K  L  K  L  I  *  S  N  F  I  H  P  *  R  I  L  H
        N  G  K  L  N  L  S  K  A  I  S  F  I  H  N  D  *  L  T  P
```

FIG. 3 CONT'D

```
3781 AATATTAGTTTCAAAACAACTAATAAATGACTGGTGATAAGGATTTCGATAACAAAACGG 3840
      N  Y  D  F  N  Q  Q  N  N  V  S  W  *  E  *  L  *  Q  K  A
     T  I  I  L  T  K  N  I  I  *  Q  G  S  N  R  F  S  N  N  Q
       *  L  *  L  K  T  S  *  K  S  V  V  I  G  L  A  I  T  K  G

3841 AGTTCCACCAAAACATCGACTAAAACGAATAACCAAAAATTTGGTCAAACTATAATTACG 3900
      E  L  H  N  Q  L  Q  N  Q  K  N  T  K  L  G  T  Q  Y  *  H
     R  L  T  T  K  Y  S  I  K  S  I  P  K  *  V  L  K  I  N  I
       *  P  P  K  T  A  S  K  A  *  Q  N  K  F  W  N  S  I  L  A

3901 CATACGATTAACCACAACAAATTTTACACCAAAAAGAAAACTAAATTTACCAAACCTACG 3960
      T  H  *  N  T  N  N  L  I  H  N  K  K  Q  N  L  H  N  P  H
     R  I  S  I  P  T  T  *  F  T  T  K  R  K  I  *  I  T  Q  I
       Y  A  L  Q  H  Q  K  F  H  P  K  E  K  S  K  F  P  K  S  A

3961 AAACAAAAAAATACCTCTATAACACAGAGTACAAACATTCACACCTGTATTATACTGAGA 4020
      K  T  K  K  H  L  Y  Q  T  E  H  K  Y  T  H  V  Y  Y  S  E
     S  Q  K  K  I  S  I  N  H  R  M  N  T  L  T  S  M  I  H  S
       K  N  K  *  P  S  I  T  D  *  T  Q  L  H  P  C  L  I  V  R

4021 TTATCGTCGCCTGAATGGAACATGTAATGTAAAAAGTAATAAACTACTGTTAAAAACACG 4080
      L  L  L  P  S  V  K  Y  M  V  N  K  M  I  Q  H  C  N  K  H
     *  Y  C  R  V  *  R  T  C  *  M  K  *  *  K  I  V  I  K  T
       I  A  A  S  K  G  Q  V  N  C  K  E  N  N  S  S  L  K  Q  A

4081 AAAAACGTGGGGATTTTTTTAAAAATAACGACGTACACGACACCTACATTTGCAAACAGT 4140
      K  K  C  G  *  F  F  K  *  Q  Q  M  H  Q  P  H  L  R  K  D
     S  K  A  G  R  F  F  N  K  N  S  C  T  S  H  I  Y  V  N  T
       K  Q  V  G  L  F  I  K  I  A  A  H  A  T  S  T  F  T  Q  *

4141 AAGACATCGACAATATCCACTACTTGTTTATCTACCATTCAAACAATGATTTAAATCACC 4200
      N  Q  L  Q  *  L  H  H  V  F  L  H  Y  T  Q  *  *  I  *  H
     M  R  Y  S  N  Y  T  I  F  L  Y  I  T  L  K  N  S  F  K  T
       E  T  A  T  I  P  S  S  C  I  S  P  L  N  T  V  L  N  L  P

4201 ACTATTTAAACTAAAATATCATCCAATACCTTACAGTAAATCATACAGAAGAAAACTCAA 4260
      H  Y  I  Q  N  *  L  L  N  H  F  T  M  *  Y  T  K  K  Q  T
     T  I  F  K  I  K  Y  Y  T  I  S  H  *  K  T  H  R  R  K  L
       S  L  N  S  K  I  T  P  *  P  I  D  N  L  I  D  E  K  S  N

4261 TGGAGTTAACATACCAAACACATATTGTGGATTACATACAAAACAATTTCCACTATAATA 4320
      V  E  I  T  H  N  T  Y  L  V  *  H  I  N  Q  *  L  H  Y  *
     *  R  L  Q  I  T  Q  T  Y  C  R  I  Y  T  K  N  F  T  I  N
       G  *  N  Y  P  K  H  I  V  G  L  T  H  K  T  L  P  S  I  I
```

FIG. 3 CONT'D

```
4321  TTTACAACGATCTGAACAATTTCGACTACAATAACAATTAGGACGATTACCCGTATACGA  4380
       L  H  Q  *  V  Q  *  L  Q  H  *  Q  *  D  Q  *  H  A  Y  A
      Y  I  N  S  S  K  N  F  S  I  N  N  N  I  R  S  I  P  M  H
        F  T  A  L  S  T  L  A  S  T  I  T  L  G  A  L  P  C  I  S

4381  GGTACCACCACCTCAACGTTTTCGATATCGACATCGACGTCCATTTTTTAAAAGATTTCT  4440
       G  H  H  H  L  Q  L  L  *  L  Q  L  Q  L  Y  F  I  K  *  L
      E  M  T  T  S  N  C  F  S  Y  S  Y  S  C  T  F  F  K  R  F
        W  P  P  P  T  A  F  A  I  A  T  A  A  P  L  F  N  E  L  S

4441  TTGACGACGATACCAATTTAGATTTCCACAAACGGTTCATCCTCTAACAATACAAAGATG  4500
       F  Q  Q  *  P  *  I  *  L  H  K  G  L  L  L  N  N  H  K  *
      F  S  S  S  H  N  F  R  F  T  N  A  L  Y  S  I  T  I  N  R
        V  A  A  I  T  L  D  L  P  T  Q  W  T  P  S  Q  *  T  E  V

4501  GCCACCATTTAATACATTTTGTTAAGAATTATAACATCCGGGACTACGATCTGTTCTACC  4560
       R  H  Y  I  I  Y  F  L  E  *  Y  Q  L  G  Q  H  *  V  L  H
      G  T  T  F  *  T  F  C  N  K  I  N  Y  A  R  I  S  S  L  I
        P  P  L  N  H  L  V  I  R  L  I  T  P  G  S  A  L  C  S  P

4561  TTCTGTTAGAATACAAAACAATCGTGCACGAATATTCGTAGAATTATTAATACTAACAAC  4620
       F  V  I  K  H  K  T  L  V  H  K  Y  A  D  *  Y  N  H  N  N
      S  S  L  R  I  N  Q  *  C  T  S  I  L  M  K  I  I  I  I  T
        L  C  D  *  T  K  N  A  R  A  *  L  C  R  L  L  *  S  Q  Q

4621  AAACAGATGAGAGTATAGCCGACCATATAAATCACAAGGACGACTACACAGTAATTGAAT  4680
       N  T  *  E  *  I  P  Q  Y  I  *  H  E  Q  Q  H  T  M  L  K
      T  Q  R  S  E  Y  R  S  T  Y  K  T  N  R  S  I  H  *  *  S
        K  D  V  R  M  D  A  P  I  N  L  T  G  A  S  T  D  N  V  *

4681  GGAAGATCCACAACAACTATTTGTTCAATAGGAACAATCATTATTATTTCTTCTAAAACT  4740
       G  E  L  H  Q  Q  Y  V  L  *  G  Q  *  Y  Y  Y  L  L  N  Q
      V  K  *  T  N  N  I  F  L  N  D  K  N  T  I  I  F  F  I  K
        R  R  P  T  T  S  L  C  T  I  R  T  L  L  L  L  S  S  K  S

4741  ATAATAAGTTTTTACAGTTTAATGAAGTCAACAACCATGATTTCGTAACCGACAATCTAA  4800
       Y  *  E  F  I  D  F  *  K  L  Q  Q  Y  *  L  M  P  Q  *  I
      I  N  N  L  F  T  L  N  S  *  N  N  T  S  F  C  Q  S  N  S
        I  I  *  F  H  *  I  V  E  T  T  P  V  L  A  N  A  T  L  N

4801  TTGACGATTACATCCGGCACAATAATTTAAACTCTGTCTACGTATGTTTGAAAAAAACTC  4860
       L  Q  *  H  L  G  H  *  *  I  Q  S  L  H  M  C  V  K  K  S
      *  S  S  I  Y  A  T  N  N  F  K  L  C  I  C  V  F  K  K  Q
        V  A  L  T  P  R  T  I  L  N  S  V  S  A  Y  L  S  K  K  L
```

FIG. 3 CONT'D

```
4861 ACCACTACTAACAAAACAAAGTTTAAGAAGACAATATGTTCTTCAAAATAACGAAGCAGT 4920
      H  H  H  N  N  Q  K  L  N  K  Q  *  V  L  L  K  I  A  E  D
     T  T  I  I  T  K  N  *  I  R  R  N  Y  L  F  N  *  Q  K  T
       P  S  S  Q  K  T  E  F  E  E  T  I  C  S  T  K  N  S  R  *

4921 ACTATATGTTAACTTATTACTGCAAGCACTAATAAACAACAGATTCTACTGATCAGAAGG 4980
      H  Y  V  I  S  Y  H  R  E  H  N  N  T  T  *  S  S  *  D  E
     M  I  Y  L  Q  I  I  V  N  T  I  I  Q  Q  R  L  H  S  T  K
       S  I  C  N  F  L  S  T  R  S  *  K  N  D  L  I  V  L  R  G

4981 ATTTCTAACCGCAGAATAGTTATTTAAACTACAATAATTGCCACAATTTTGACAATTCAT 5040
      *  L  N  A  D  *  *  Y  I  Q  H  *  *  R  H  *  F  Q  *  T
     R  F  I  P  T  K  D  I  F  K  I  N  N  V  T  N  F  S  N  L
       L  S  Q  R  R  I  L  L  N  S  T  I  L  P  T  L  V  T  L  Y

5041 AAAACTCACAGGATTAAGATAAATATATACATCAGTCCCATTTCTGAAACCAATACATAC 5100
      N  Q  T  D  *  N  *  K  Y  I  Y  D  P  Y  L  S  Q  N  H  I
     I  K  L  T  R  I  R  N  I  Y  T  T  L  T  F  V  K  T  I  Y
       K  S  H  G  L  E  I  *  I  H  L  *  P  L  S  K  P  *  T  H

5101 ACTACCAAGAAAAATATTTCGTTGACAATTAGTTCAAACACAAAATAATCGATTCTTCTA 5160
      H  H  N  K  K  Y  L  L  Q  *  D  L  K  H  K  I  L  *  S  S
     T  I  T  R  K  I  F  C  S  N  I  L  N  T  N  *  *  S  L  L
       S  P  E  K  *  L  A  V  T  L  *  T  Q  T  K  N  A  L  F  I

5161 TCTACAAAACGAATGACATCTACCACAATTAAAATTTAGATAAAGAGAATGACATCCACT 5220
      L  H  K  A  *  Q  L  H  H  *  N  *  I  *  K  E  *  Q  L  H
     Y  I  N  Q  K  S  Y  I  T  N  I  K  F  R  N  R  K  S  Y  T
       S  T  K  S  V  T  S  P  T  L  K  L  D  I  E  R  V  T  P  S

5221 TCAAAAACCATTTTATGAACCATTACAAAAGACACTACCGTAACTACAATGATTCAATTT 5280
      L  K  Q  Y  F  V  Q  Y  H  K  R  H  H  C  Q  H  *  *  T  L
     F  N  K  T  F  Y  K  T  I  N  E  T  I  A  N  I  N  S  L  *
       T  K  P  L  I  S  P  L  T  K  Q  S  P  M  S  T  V  L  N  F

5281 CACATCACTAAAAATACGGCTATTTTAAAATATAGTCATACTTTTAAACAGAAATCGACT 5340
      T  Y  H  N  K  H  R  Y  F  K  I  D  T  H  F  N  T  K  L  Q
     L  T  T  I  K  I  G  I  F  N  *  I  L  I  F  I  Q  R  *  S
       H  L  S  K  *  A  S  L  I  K  Y  *  Y  S  F  K  D  K  A  S

5341 ATAAAGACGACATGTTTCAAGTAAACCCAAACTAGTCGTTGTTAACGAACGAATAATATT 5400
      Y  K  Q  Q  V  F  N  M  Q  T  Q  D  A  V  I  A  Q  K  N  Y
     I  N  R  S  Y  L  T  *  K  P  K  I  L  L  L  Q  K  S  I  I
       I  E  A  T  C  L  E  N  P  N  S  *  C  C  N  S  A  *  *  L
```

FIG. 3 CONT'D

```
5401  AAAAAATTGTCATACATTTACCAGACATCAACAATTGCCAGGTAAAAAAAGAAAACTTGT  5460
       N  K  L  L  I  Y  I  T  Q  L  Q  *  R  D  M  K  K  K  Q  V
      I  K  *  C  Y  T  F  P  R  Y  N  N  V  T  W  K  K  R  K  F
        K  K  V  T  H  L  H  D  T  T  T  L  P  G  N  K  E  K  S  C

5461  CAGAGTATTATTAACAATACACTTACATCGAACAGAATACAACGTCGTATAATTAGAATT  5520
       T  E  Y  Y  N  N  H  S  H  L  K  D  *  T  A  A  Y  *  D  *
      L  R  M  I  I  T  I  H  I  Y  S  T  K  H  Q  L  M  N  I  K
        D  *  L  L  Q  *  T  F  T  A  Q  R  I  N  C  C  I  L  R  L

5521  TAAATTATTTACCGTCACCGTCCTTCGTACCATACTTAAAGCACGACCGTCTGGTGTATC  5580
       I  *  Y  I  A  T  A  P  L  M  T  H  I  E  H  Q  C  V  V  Y
      F  K  I  F  P  L  P  L  F  C  P  I  F  K  T  S  A  S  W  M
        N  L  L  H  C  H  C  S  A  H  Y  S  N  R  A  P  L  G  C  L

5581  CAATCAACGAGAACAAAATCGATTTCCAGTAAAATTTAAACTACTTGGTAGTCTACGATG  5640
       T  L  Q  E  Q  K  L  *  L  D  N  *  I  Q  H  V  M  L  H  *
      P  *  N  S  K  N  *  S  F  T  M  K  F  K  I  F  W  *  I  S
        N  T  A  R  T  K  A  L  P  *  K  L  N  S  S  G  D  S  A  V

5641  ACTAAAATAAGCACAACAAAACTTTGTTCGACTAAATAGTCCACGTTAAACACTTAATCT  5700
       Q  N  *  E  H  Q  K  S  V  L  Q  N  I  L  H  L  K  H  I  L
      S  I  K  N  T  N  N  Q  F  L  S  I  *  *  T  C  N  T  F  *
        S  K  I  R  T  T  K  F  C  A  S  K  D  P  A  I  Q  S  N  S

5701  TGAATAAACACTAACACCATAATTTGTTCTTTCAGCACAACCACAACTACGACAATACGT  5760
       V  *  K  H  N  H  Y  *  V  L  F  D  H  Q  H  Q  H  Q  *  A
      F  K  N  T  I  T  T  N  F  L  F  T  T  N  T  N  I  S  N  H
        S  I  Q  S  Q  P  I  L  C  S  L  R  T  P  T  S  A  T  I  C

5761  AAAACCATGTAATCGTTTCTGACTAGAAAAATTACCAATATTCTAACCGACATTAACACG  5820
       N  Q  Y  M  L  L  S  Q  D  K  *  H  N  Y  S  Q  S  Y  N  H
      M  K  T  C  *  C  L  S  I  K  K  I  T  I  L  N  A  T  I  T
        K  P  V  N  A  F  V  S  R  K  L  P  *  L  I  P  Q  L  Q  A

5821  TCCATCTTAACAGGTAACATGATTTAACTTACATGGTAAAAACTAAACAAGATTATGAGG  5880
       L  Y  F  Q  G  N  Y  *  I  S  H  V  M  K  S  K  N  *  Y  E
      C  T  S  N  D  M  T  S  F  Q  I  Y  W  K  Q  N  T  R  I  S
        P  L  I  T  W  Q  V  L  N  F  T  G  N  K  I  Q  E  L  V  G

5881  AGACTCATTCCTAAATGGACTACTACAACAACGTCGATTGTACAAATACCCACATCCACA  5940
       E  S  Y  P  N  V  Q  H  H  Q  Q  L  *  C  T  *  P  H  L  H
      R  Q  T  L  I  *  R  I  I  N  N  C  S  V  H  K  H  T  Y  T
        R  L  L  S  K  G  S  S  T  T  A  A  L  M  N  I  P  T  P  T
```

FIG. 3 CONT'D

5941 TCCGGTAATATGTGTAAACTTTACACCAAGTGGAATGGTTGTAATACTACGAACATCACA 6000
L G N Y V N S I H N V K G V N H H K Y H
Y A M I C M Q F T T * R V L M I I S T T
P W * V C K F H P E G * W C * S A Q L T

6001 ATTTTTTATATGTCCACAATCACCAACAAATTGACTGACGAACATAGAATTTTTAAATTG 6060
* F I Y L H * H N N L Q S S T D * F N L
N F F I C T N T T T * S V A Q I K F I *
L F Y V P T L P Q K V S Q K Y R L F K V

6061 GGTCTGAAAATGTAGATACAACTGATTAATAAAAAACCTACTACAACTTTACCAACGAAT 6120
G S K * M * T S * N N K P H H Q F P Q K
G L S K C R H Q S I I K Q I I N F H N S
W V K V D I N V L * K K S S T S I T A *

6121 ATTGGGACTAGAAAGTGTTATAATAACACTATTACCATTCATAATATGTTTTGGATAATA 6180
Y G Q D K V I N N H Y H Y T N Y L V * *
I V R I K * L I I T I I T L I I C F R N
L G S R E C Y * Q S L P L Y * V F G I I

6181 TTTCCGAGTCAAATTTGGTAAACGATTTCAACTGCCACAAATATGATTGAAATTCAATCA 6240
L P E T * V M Q * L Q R H K Y * S * T L
Y L S L K F W K S F N V T N I S V K L *
F A * N L G N A L T S P T * V L K L N T

6241 ACCTGTACTATAAACACGAGTTAACTTACTATTCAATCCAAAATTACATCTAAACGGCAA 6300
Q V H Y K H E I S H Y T L N * H L N A T
N S M I N T S L Q I I L * T K I Y I Q R
P C S I Q A * N F S L N P K L T S K G N

6301 ACAACTCATGTTTCATTGTCAGACCGGACATCGATGACCACTACAACAAAACCGTAGACT 6360
Q Q T C L L L R A Q L * Q H H Q K P M Q
K N L V F Y C D P R Y S S T I N N Q C R
T S Y L T V T Q G T A V P S T T K A D S

6361 ACTAAATATACACTTTGCAATAAAATTTCCTACACTTTGAAAACCATTCGGACAATAAAC 6420
H N I H S V N N * L I H F K Q Y A Q * K
I I * I H F T I K F S T F S K T L R N N
S K Y T F R * K L P H S V K P L G T I Q

6421 CAAAACAGTACTACTTCGTAGTAACTTAAGAGAATGAATAAAATTATTTGGATCAAAATT 6480
T K D H H L M M S N E * K N * Y V * N *
P K T M I F C * Q I R K S I K I F R T K
N Q * S S A D N F E R V * K L L G L K L

FIG. 3 CONT'D

```
6481 TAGACTTTTATCTATATCACAAAACAGACAACTAAGACATAGACTCCTCAGTGTTCCATT 6540
      I  Q  F  Y  I  Y  H  K  T  Q  Q  N  Q  I  Q  P  T  V  L  Y
     F  R  F  I  S  I  T  N  Q  R  N  I  R  Y  R  L  L  *  L  T
       D  S  F  L  Y  L  T  K  D  T  S  E  T  D  S  S  D  C  P  L

6541 ACACCAATGAAGACAATACCTTAGCGTCTAATCATGATTTCTCCAATTCAATTTCCCACA 6600
      H  P  *  K  Q  *  P  I  A  S  *  Y  *  L  P  *  T  L  P  H
     I  H  N  S  R  N  H  F  R  L  N  T  S  F  L  N  L  *  L  T
       T  T  V  E  T  I  S  D  C  I  L  V  L  S  T  L  N  F  P  T

6601 ATCTTTCTGACAATTTTATCTTCTACGATAATAACAATTACTACTTTTATCAAGATAATT 6660
      *  F  S  Q  *  F  L  L  H  *  *  Q  *  H  H  F  Y  N  *  *
     N  S  L  S  N  F  Y  F  I  S  N  N  N  I  I  F  I  T  R  N
       L  F  V  T  L  I  S  S  A  I  I  T  L  S  S  F  L  E  I  L

6661 CCAACAATTTTCAAATAGAAATCAACTACAAACCCTATACATAAACTGTCCAACACTAAT 6720
      P  Q  *  F  N  I  K  L  Q  H  K  P  Y  T  N  S  L  N  H  N
     L  N  N  F  T  *  R  *  N  I  N  P  I  H  I  Q  C  T  T  I
       T  T  L  L  K  D  K  T  S  T  Q  S  I  Y  K  V  P  Q  S  *

6721 ACAACAAACCCAACGATTACTTAACAGTGCGGATCAATTTAGTGGTTGTCAATCCCTTAT 6780
      H  Q  K  P  Q  *  H  I  T  V  G  L  *  I  V  L  L  *  P  I
     I  N  N  P  N  S  I  F  Q  *  A  *  N  F  *  W  C  N  P  F
       T  T  Q  T  A  L  S  N  D  R  R  T  L  D  G  V  T  L  S  Y

6781 ATATGCTATACCATAATTTGGATAATGATATGGATATCTAAACAATACAAATTCTCTACT 6840
      Y  V  I  H  Y  *  V  *  *  *  V  *  L  N  T  I  N  L  L  H
     I  Y  S  I  T  N  F  R  N  S  Y  R  Y  I  Q  *  T  *  S  I
       I  R  Y  P  I  L  G  I  V  I  G  I  S  K  N  H  K  L  S  S

6841 ATTAGTTTGAGAAAATCAAGGATTTTAAAAATTTCGTTCTCGATATCTTAAAATACCAAA 6900
      Y  D  F  E  K  L  E  *  F  K  *  L  L  L  *  L  I  K  H  N
     I  I  L  S  K  *  N  R  F  N  K  F  C  S  S  Y  F  K  I  T
       L  *  V  R  K  T  G  L  I  K  L  A  L  A  I  S  N  *  P  K

6901 AAACTTCACCAACAAATAAATACAAAAATCAAATAATGTAAAATGTTTACTATTTTGGTA 6960
      K  S  T  T  T  *  K  H  K  *  N  I  V  N  *  L  H  Y  F  W
     K  Q  L  P  Q  K  N  I  N  K  T  *  *  M  K  C  I  I  F  G
       K  F  H  N  N  I  *  T  K  L  K  N  C  K  V  F  S  L  V  M

6961 AAAAATATGATGTCTTTATCGAAGATTCAAATGAAAATTAAACAAAACAAACCGAGAATT 7020
      K  K  Y  *  L  F  L  K  *  T  *  K  *  N  T  K  N  P  E  *
     N  K  I  S  C  F  Y  S  R  L  K  S  K  I  Q  K  T  Q  S  K
       K  *  V  V  S  I  A  E  L  N  V  K  L  K  N  Q  K  A  R  L
```

FIG. 3 CONT'D

```
7021  TTTACGAAAAGTCTGTAAATCTACCTCATATAAATATTTTCCAAAAGAACAACATCGGTG  7080
       F  H  K  E  S  M  *  I  S  Y  I  *  L  L  N  E  Q  Q  L  W
      F  I  S  K  L  C  K  S  P  T  Y  K  Y  F  T  K  K  N  Y  G
        F  A  K  *  V  N  L  H  L  I  N  I  F  P  K  R  T  T  A  V

7081  ACACAAAAACAAAACCAAATTAAAAAACATATATTTACAATAAAAATCACTGAAAATAGA  7140
       Q  T  K  T  K  T  *  N  K  T  Y  L  H  *  K  *  H  S  K  D
      S  H  K  Q  K  P  K  I  K  Q  I  Y  I  N  N  K  T  V  K  I
        T  N  K  N  Q  N  L  K  K  Y  I  F  T  I  K  L  S  K  *  R

7141  AGGATTATAATCACAAAAAGGATAAAAACACCCTTCTTAACAATACACCTATTTCCGATG  7200
       E  *  Y  *  H  K  E  *  K  Q  P  F  F  Q  *  T  S  L  P  *
      K  R  I  N  T  N  K  R  N  K  H  S  S  N  N  H  P  Y  L  S
        G  L  I  L  T  K  G  I  K  T  P  L  I  T  I  H  I  F  A  V

7201  AAAACCAAACCAATGTTAAACACTAAAAATAAGATTCAATCCACATCCAAAATGTTCAGT  7260
       K  Q  N  P  *  L  K  H  N  K  N  *  T  L  H  L  N  *  L  D
      S  K  T  Q  N  C  N  T  I  K  I  R  L  *  T  Y  T  K  C  T
        K  P  K  T  V  I  Q  S  K  *  E  L  N  P  T  P  K  V  L  *

7261  AAAAACATTACCATCAAAATATACACTTAACACAGTAAGACCAAAACTATACAACCTATG  7320
       N  K  Y  H  Y  N  *  I  H  I  T  D  N  Q  N  Q  Y  T  P  Y
      M  K  T  I  T  T  K  Y  T  F  Q  T  M  R  T  K  I  H  Q  I
        K  Q  L  P  L  K  I  H  S  N  H  *  E  P  K  S  I  N  S  V

7321  TATACGTCGATATCTAAAACAAGTCATACTTCATCTATCTGCACAAAATAAACTAATACA  7380
       M  H  L  *  L  N  Q  E  T  H  L  L  Y  V  H  K  I  Q  N  H
      C  I  C  S  Y  I  K  N  L  I  F  Y  I  S  T  N  *  K  I  I
        Y  A  A  I  S  K  T  *  Y  S  T  S  L  R  T  K  N  S  *  T

7381  ATCAAATCAGTTTAATTAACAACTTGAGCAATAACCAATAAGTAATATGTGTCATACCAA  7440
       *  N  L  *  I  L  Q  Q  V  R  *  Q  N  N  M  I  C  L  I  T
      N  T  *  D  F  *  N  N  F  E  N  N  T  I  *  *  V  C  Y  P
        L  K  T  L  N  I  T  S  S  T  I  P  *  E  N  Y  V  T  H  N

7441  AATAGGTAATAAAACAGAATAACCAAATGTTAATAAATGATGTACCAACGGACTAAACAA  7500
       K  D  M  I  K  D  *  Q  N  V  I  I  *  *  M  T  A  Q  N  T
      K  I  W  *  K  T  K  N  T  *  L  *  K  S  C  P  Q  R  I  Q
        *  G  N  N  Q  R  I  P  K  C  N  N  V  V  H  N  G  S  K  N

7501  ATACAATCTTTGATACGTAACCAACTAATCTAAATAACATAAACATCGATTATACAATGG  7560
       *  T  L  F  *  A  N  T  S  *  I  *  Q  I  Q  L  *  Y  T  V
      K  H  *  F  S  H  M  P  Q  N  S  K  N  Y  K  Y  S  I  H  *
        I  N  S  V  I  C  Q  N  I  L  N  I  T  N  T  A  L  I  N  G
```

FIG. 3 CONT'D

```
7561  ACGAAAACAGAACAACGCCAAAATATATCAACAATGACGATACATATTTCATCAACCAAA  7620
       Q  K  Q  R  T  A  T  K  Y  L  Q  *  Q  *  T  Y  L  L  Q  N
      R  S  K  D  Q  Q  P  K  I  Y  N  N  S  S  H  I  F  Y  N  T
        A  K  T  K  N  R  N  *  I  T  T  V  A  I  Y  L  T  T  P  K

7621  ATAATCCGTATAACAGATACCAACATTATTTCGACCAACAAATAAAACAATATTTGCTTT  7680
       *  *  A  Y  Q  R  H  N  Y  Y  L  Q  N  N  I  K  N  Y  V  F
      K  N  P  M  N  D  I  T  T  I  F  S  T  T  *  K  T  I  F  S
        I  L  C  I  T  *  P  Q  L  L  A  P  Q  K  N  Q  *  L  R  F

7681  AACATCACAAGCACAATTCACATCATGATAACAACCACCACATTAAGCAATAATACTATA  7740
       N  Y  H  E  H  *  T  Y  Y  *  Q  Q  H  H  L  E  N  N  H  Y
      I  T  T  N  T  N  L  T  T  S  N  N  T  T  Y  N  T  I  I  I
        Q  L  T  R  T  L  H  L  V  I  T  P  P  T  I  R  *  *  S  I

7741  ATGACGATTACCACCATGACCAAAAACACAATTTGTAGTTACCTTAACAAAATTAACGGT  7800
       *  Q  *  H  H  Y  Q  N  K  H  *  V  D  I  S  N  N  *  N  G
      N  S  S  I  T  T  S  T  K  T  N  F  M  L  P  I  T  K  I  A
        V  A  L  P  P  V  P  K  Q  T  L  C  *  H  F  Q  K  L  Q  W

7801  AAGAAAATTTGGTCCATTGTGAAAATATTGACATCTTCGACGATATCTTGAAAGATTTCT  7860
       N  K  *  V  L  Y  C  K  *  L  Q  L  L  Q  *  L  V  K  *  L
      M  R  K  F  W  T  V  S  K  Y  S  Y  F  S  S  Y  F  K  R  F
        E  K  L  G  P  L  V  K  I  V  T  S  A  A  I  S  S  E  L  S

7861  CGAATTTGCTGGACATTTAGGTTGACTACGAAGTGTAATACATCAATGACTATAATTCGT  7920
       A  *  V  V  Q  L  D  L  Q  H  K  V  N  H  L  *  Q  Y  *  A
      L  K  F  S  R  Y  I  W  S  I  S  *  M  I  Y  N  S  I  N  L
        S  L  R  G  T  F  G  V  S  A  E  C  *  T  T  V  S  I  L  C

7921  TCAACCAACATACTACGCAAACAAGATACTATCTCTACCTGTCGCACAAATGCTACTACA  7980
       L  Q  N  Y  S  A  N  T  R  H  Y  L  H  V  A  H  K  R  H  H
      L  N  T  T  H  H  T  Q  E  I  I  S  I  S  L  T  N  V  I  I
        T  P  Q  I  I  R  K  N  *  S  L  S  P  C  R  T  *  S  S  T

7981  ACTACGATCAAATAAACATCTATAATTATTAGACAATGTAAGATTTCAATTTCAACAAGG  8040
       Q  H  *  N  I  Q  L  Y  *  Y  D  T  V  N  *  L  *  L  Q  E
      N  I  S  T  *  K  Y  I  N  I  I  Q  *  M  R  F  N  F  N  N
        S  A  L  K  N  T  S  I  L  L  R  N  C  E  L  T  L  T  T  G

8041  ATTAAACATACATCAACATCATCTCTCACTACGACTATCTCGATTAAAAGACTTACGACA  8100
       *  N  T  H  L  Q  L  L  S  H  H  Q  Y  L  *  N  E  S  H  Q
      R  I  Q  I  Y  N  Y  Y  L  T  I  S  I  S  S  I  K  Q  I  S
        L  K  Y  T  T  T  T  S  L  S  A  S  L  A  L  K  R  F  A  T
```

FIG. 3 CONT'D

8101 ACACAAAATACGTGTTAGTAACATATCCGGATATAATGAACATCTGTTTTTCAATTAATG 8160
Q T K H V I M T Y A * I V Q L C F T L *
N H K I C L * Q I P R Y * K Y V F L * N
T N * A C D N Y L G I N S T S L F N I V

8161 ATGTCGAACATTACCATAGAGACATTGGGTCTGATACAAACTACAAATACAACTATGAAA 8220
* L K Y H Y R Q L G S * T Q H K H Q Y K
S C S T I T D R Y G L S H K I N I N I S
V A Q L P I E T V W V I N S T * T S V K

8221 ATACAGAGTAAAACTACAACTATCTTTCTCAAAATTATTAAAACAATTGTAACGAGTACG 8280
* T E N Q H Q Y F S N * Y N Q * C Q E H
K H R M K I N I S L T K I I K N V N S M
I D * K S T S L F L K L L K T L M A * A

8281 AAGAGAATCTCTCCCACACGTTAATCTTTTCCAAAATCTATGAAAACACCCTACACATGC 8340
K E * L P H A I L F P K L Y K Q P I H V
S R K S L T H L * F L N * I S K H S T Y
E R L S P T C N S F T K S V K T P H T R

8341 ATTTACAACAAGGTAACTAAGTCTACAACTTTGTTCTAAATAATGATTTAGATACTATAG 8400
Y I N N W Q N L H Q F L I * * * I * S I
T F T T G N I * I N F C S K N S F R H Y
L H Q E M S E S T S V L N I V L D I I D

8401 ACGTCATCGACGACCAAACCTTAAATGACTACTTTTAATATTGTTAAACCATGGATGTAT 8460
Q L L Q Q N P I * Q H F N Y C N P V * M
R C Y S S T Q F K S I F I I V I Q Y R C
A T A A P K S N V S S F * L L K T G V Y

8461 AAATTTCTCACTATTATAACATCGACGACTAAATCCACAAGAATATGTCTTACCACGATT 8520
N L S H Y Y Q L Q Q N L H E * V S H H *
I * L T I I N Y S S I * T N K Y L I T S
K F L S L I T A A S K P T R I C F P A L

8521 CGTACATGTCCCATTACAACGATTCCGTCGATTATAAAGAACATATACCAAATAACTACG 8580
A H V P Y H Q * P L * Y K K Y I T * Q H
L M Y L T I N S L C S I N R T Y P K N I
C T C P L T A L A A L I E Q I H N I S A

8581 AAAATTAGTTGAATGACGACTAAATGTCGTATTTAATTTTTTTCGTACACAATTTTGACC 8640
K * D V * Q Q N V A Y I L F L M H * F Q
S K I L K S S I * L M F * F F C T N F S
K L * S V A S K C C L N F F A H T L V P

FIG. 3 CONT'D

8641 GAACTTCAATTTTAACTGAAAATTATTCGTTCTCCGTTCACAGGGATAAGAATGTTGTGG 8700
S S T L I S K * Y A L P L H G * E * L V
A Q L * F Q S K I L L L C T D R N K C C
K F N F N V K L L C S A L T G I R V V G

8701 GAAAAGTGAATTTCCTCCACAACATAACTCATTAAACAATATATATAATAAAAAACAATC 8760
R K V * L L H Q I S Y N T I Y I I K Q *
G K * K F S T N Y Q T I Q * I Y * K K N
K E S L P P T T N L L K N Y I N N K T L

8761 AAATTAGACAAAATATAATAACACCCGAAATAACGGATGTATATCACAAATATTCAGACT 8820
N L R N * I I T P K I A * M Y H K Y T Q
T * D T K Y * Q P S * Q R C I T N I L R
K I Q K I N N H A K N G V Y L T * L D S

8821 ATAAGTAAACGGACGAATACGATCAAAATTTCAATAACTATTACCACAACAATCTCTATA 8880
Y E N A Q K H * N * L * Q Y H H Q * L Y
I N M Q R S I S T K F N N I I T N N S I
I * K G A * A L K L T I S L P T T L S I

8881 AAGTCAATTACTAAATACAAAACGATTATTTAAAAAGGTTAAACTAGTTACCATACTCAG 8940
K L * H N I N Q * Y I K G I Q D I T H T
N * N I I * T K S I F K E L K I L P I L
E T L S K H K A L L N K W N S * H Y S D

8941 GTGAAAACCCAGACAAATGATAGTATTAAGATACCTAACGGGATAACATCACCGTCAATA 9000
W K Q T Q K S D Y N * P N G * Q L P L *
G S K P R N V I M I R H I A R N Y H C N
V K P D T * * * L E I S Q G I T T A T I

9001 CCTACTTCTATAGCCAAGATGATACAAATTACAAGGATGATTTCAAAACTCTGTACCGAA 9060
P H L Y R N * * T * H E * * L K S V H S
H I F I D T R S H K I N R S F N Q S M A
S S S I P E V I N L T G V L T K L C P K

9061 AGTACAAAATGTAAAAAATTGAATACGTAAACGATCACTATCACAAGTCACGATATGTGG 9120
E H K V N K L K H M Q * H Y H E T S Y V
K M N * M K * S I C K S T I T N L A I C
* T K C K K V * A N A L S L T * H * V G

9121 TGTATAAGTCTAAAGAATATTACTAAAAATACGATCACCAACACAAAATAGTAGAAACAC 9180
V Y E S K K Y H N K H * H N H K I M K T
W M N L N R I I I K I S T T T N * * R Q
C I * I E * L S K * A L P Q T K D D K H

FIG. 3 CONT'D

```
9181  ATGATACAAATTTTCTCCACTACCATGTGGTGTAGGAATAACAATAAGTCTACCACAATA  9240
       Y  *  T  *  F  L  H  H  Y  V  V  D  K  N  N  N  L  H  H  *
      T  S  H  K  F  S  T  I  T  C  W  M  R  I  T  I  *  I  T  N
        V  I  N  L  L  P  S  P  V  G  C  G  *  Q  *  E  S  P  T  I

9241  CTTCTTACGAAGAAACATATGTAGAAACCAAGGTGTATGTGCAATATCGGAACGATTAAG  9300
       S  S  H  K  K  T  Y  M  K  P  E  V  Y  V  N  Y  G  Q  *  N
      H  L  I  S  R  Q  I  C  R  Q  N  W  M  C  T  I  A  K  S  I
        F  F  A  E  K  Y  V  D  K  T  G  C  V  R  *  L  R  A  L  E

9301  ATTACCAAAATATTCTAAAGGACTACAATAATCACTTCCATAACATGCATAACATTCTTG  9360
       *  H  N  *  L  I  E  Q  H  *  *  H  L  Y  Q  V  Y  Q  L  F
      R  I  T  K  Y  S  K  R  I  N  N  T  F  T  N  Y  T  N  Y  S
        L  P  K  I  L  N  G  S  T  I  L  S  P  I  T  R  I  T  L  V

9361  CGCGAGATACTGAATAACATCTCACCCACGTACACTTATGCGGCTTCTCCCATATACAAA  9420
       A  S  *  S  K  N  Y  L  P  H  M  H  I  R  R  L  P  Y  I  N
      R  A  R  H  S  I  T  S  H  T  C  T  F  V  G  F  L  T  Y  T
        R  E  I  V  *  Q  L  T  P  A  H  S  Y  A  S  S  P  I  H  K

9421  ATTAAAATTATCAAGGACCCAAAACTTATTACTAATAATATCTTCATACGGACCTTGAAA  9480
       *  N  *  Y  N  R  P  K  S  Y  H  N  N  Y  F  Y  A  Q  F  K
      K  I  K  I  T  G  P  N  Q  I  I  I  I  I  S  T  H  R  S  S
        L  K  L  L  E  Q  T  K  F  L  S  *  *  L  L  I  G  P  V  K

9481  AACACCATCTCTAGAAAAACTAAACAAAATAGTTAAAAAATCATCAAATTAAGCAGGATA  9540
       K  H  Y  L  D  K  Q  N  T  K  D  I  K  *  Y  N  L  E  D  *
      K  T  T  S  I  K  K  I  Q  K  I  L  K  K  T  T  *  N  T  R
        Q  P  L  S  R  K  S  K  N  *  *  N  K  L  L  K  I  R  G  I

9541  TCTAAAGAAAAGAGAATGACGATCAAGATAAAAACCTCGATATAACCGATATCAACAACA  9600
       L  N  R  K  E  *  Q  *  N  *  K  Q  L  *  I  P  *  L  Q  Q
      Y  I  E  K  R  K  S  S  T  R  N  K  S  S  Y  Q  S  Y  N  N
        S  K  K  E  R  V  A  L  E  I  K  P  A  I  N  A  I  T  T  T

9601  GAACCAAAAAAATAATAAATTATTTTGAATTCGCACGAAAACCTCTAATATGATCACAACA  9660
       R  P  K  K  N  N  L  L  V  *  A  H  K  Q  L  N  Y  *  H  Q
      D  Q  N  K  I  I  *  Y  F  K  L  T  S  K  S  I  I  S  T  N
        K  T  K  *  *  K  I  F  S  L  R  A  K  P  S  *  V  L  T  T

9661  TCAATATTTACAACAACAAACCACATAATTAAAAGAATACGAAAAACAAAAAGTTCAAAT  9720
       L  *  L  H  Q  Q  K  T  Y  *  N  E  *  A  K  Q  K  E  L  K
      Y  N  Y  I  N  N  N  P  T  N  I  K  K  H  K  K  N  K  L  N
        T  I  F  T  T  T  Q  H  I  L  K  R  I  S  K  T  K  *  T  *
```

FIG. 3 CONT'D

```
9721   AGGATAAACACGTACACAAATACGAACAAAAATAAAAATACATTGTAACATAAAAGGAAG   9780
        D  *  K  H  M  H  K  H  K  N  K  N  K  H  L  M  T  N  E  K
       I  R  N  T  C  T  N  I  S  T  K  I  K  I  Y  C  Q  I  K  R
         G  I  Q  A  H  T  *  A  Q  K  *  K  *  T  V  N  Y  K  G  E

9781   ACTTTAATCACATTAATACGTAAACGTTACCTAACAATACATACCACGATATTACGGAAA   9840
        Q  F  *  H  L  *  A  N  A  I  S  Q  *  T  H  H  *  L  A  K
       R  F  N  T  Y  N  H  M  Q  L  P  N  N  H  I  T  S  Y  H  R
         S  I  L  T  I  I  C  K  C  H  I  T  I  Y  P  A  I  I  G  K

9841   AACCAAAACACAGTGTATACATCGATACCAATAACGTTTGGTACAAAATACCAATAAAAG   9900
        K  T  K  H  *  M  H  L  *  P  *  Q  L  G  H  K  I  T  I  K
       K  P  K  T  D  C  I  Y  S  H  N  N  C  V  M  N  *  P  *  K
         Q  N  Q  T  V  Y  T  A  I  T  I  A  F  W  T  K  H  N  N  E

9901   TATAACATCCTTTTAACCACAATTACATACATCACTATCATGTAAACTTCTTTGTAGAGA   9960
        M  N  Y  S  F  Q  H  *  H  I  Y  H  Y  Y  M  Q  L  F  M  E
       *  I  T  P  F  N  T  N  I  Y  T  T  I  T  C  K  F  F  C  R
         Y  Q  L  F  I  P  T  L  T  H  L  S  L  V  N  S  S  V  D  R

9961   ATGATGAAAATACTAATGATTTCTAAGAATAACATCTAATTTCTTAAGACAAAGACTACA   10020
        *  *  K  *  S  *  *  L  N  K  N  Y  I  L  S  N  Q  K  Q  H
       K  S  S  K  H  N  S  F  I  R  I  T  S  *  L  I  R  N  R  I
         V  V  K  I  I  V  L  S  E  *  Q  L  N  F  F  E  T  E  S  T

10021  ACGGATGTTATCTATAAACTCAAACATATTATTCATAGCAATGATATCACCATTTTACCT   10080
        Q  R  C  Y  I  N  S  N  T  Y  Y  T  D  N  S  Y  H  Y  F  P
       N  G  V  I  S  I  Q  T  Q  I  I  L  I  T  V  I  T  T  F  H
         A  *  L  L  Y  K  L  K  Y  L  L  Y  R  *  *  L  P  L  I  S

10081  ATGACGACGGATATCTCTTCGCCGCACAAGAGTCAATCGATTTCGATACCTTTGTAAATT   10140
        Y  Q  Q  R  Y  L  L  P  T  N  E  T  L  *  L  *  P  F  M  *
       I  S  S  G  I  S  F  R  R  T  R  L  *  S  F  S  H  F  C  K
         V  A  A  *  L  S  A  A  H  E  *  N  A  L  A  I  S  V  N  L

10141  AGTGTTATTACCATTACTACAGAATATGGTTGGAGGATGTCGTAGACAAAGATGTAGAAA   10200
        D  C  Y  H  Y  H  H  R  I  G  V  E  *  L  M  Q  K  *  M  K
       I  V  I  I  T  I  I  D  *  V  L  R  R  C  C  R  N  R  C  R
         *  L  L  P  L  S  T  K  Y  W  G  G  V  A  D  T  E  V  D  K

10201  AAACGTTAGTCCATAACATTTCTACCATAGAGGATGCAGTTTTTAACTTGGAACATAACA   10260
        K  A  I  L  Y  Q  L  S  P  I  E  *  T  L  F  Q  V  K  Y  Q
       K  Q  L  *  T  N  Y  L  H  Y  R  R  R  *  F  N  F  R  T  N
         K  C  D  P  I  T  F  I  T  D  G  V  D  F  I  S  G  Q  I  T
```

FIG. 3 CONT'D

10261 ATCACAATGAATACCATCATACTGAAACTTACCAAATACCAATCTACTGTTTCAAATAAC 10320
* H * K H Y Y S K S H N I T L H C L K N
N T N S I T T H S Q I T * P * I V F N I
L T V * P L I V K F P K H N S S L T * Q

10321 AGGAGCAGTACAATATACAAGTAGGAGATTATACTTGCTTGGACTAATAAGACGGAATAA 10380
D E D H * I N M R * Y S R V Q N N Q R I
T R T M N Y T * G R I H V F R I I R G *
G R * T I H E D E L I F S G S * E A K N

10381 CACATCTCAATGAGATCCACTAAAATGATATTACAGACCAGCCTACTCAAATTGTCAACA 10440
T Y L * E L H N * * L T Q D S S N L L Q
Q T S N S * T I K S Y H R T P H T * C N
H L T V R P S K V I I D P R I L K V T T

10441 CAGAATGGTCTACGTCCCGACAGTTGAACAAAACTGTCAGAGAAATGTTTTAGGAATGTG 10500
T K G S A P S D V Q K S L R K V F D K C
H R V L H L A T L K N Q C D R * L I R V
D * W I C P Q * S T K V T E K C F G * V

10501 AGGTTTTATATGAAAACCATTACAATTTGGACCACTTTGAAAATGACAAAATCGACGCAT 10560
E L I Y K Q Y H * V Q H F K * Q K L Q T
S W F I S K T I N F R T F S K S N * S R
G F Y V K P L T L G P S V K V T K A A Y

10561 ATTACCGGCTGGTGTTCCCCGTAAAGTACAATGATACGCATCATCAATATGATAATTTCC 10620
Y H G V V L P M E H * * A Y Y N Y * * L
I I A S W L P C K M N S H T T T I S N F
L P R G C P A N * T V I R L L * V I L P

10621 AAGAAAAAACACACCCAGTACACCTAGACAACCAATACATAATTGTCCACTATCACAATT 10680
N K K T H T M H I Q Q N H I L L H Y H *
T R K Q T P * T S R N T I Y * C T I T N
E K K H P D H P D T P * T N V P S L T L

10681 CAAACATATATACGTAGTTAATCTCGAGTCATGACCAACAGTGTGACCGTGACTAAAATG 10740
T Q I Y A D I L A * Y Q N D C Q C Q N *
L K Y I H M L * L E T S T T V S A S I K
N T Y I C * N S S L V P Q * V P V S K V

10741 ACCATTAAAAATACCAGGTATATCTCTACGAGTTCAACATGTCAACGGTCAATTCCTGAT 10800
Q Y N K H D M Y L H E L Q V T A L * P S
S T I K I T W I S I S L N Y L Q W N L V
P L K * P G Y L S A * T T C N G T L S *

FIG. 3 CONT'D

```
10801 GCAGGTCTGACAATTACAATAACGAACCGAGATACGTCGATATGAATTATTAACACGAAC 10860
       R  G  S  Q  *  H  *  Q  K  A  R  H  L  *  V  *  Y  N  H  K
      V  D  L  S  N  I  N  N  S  P  E  I  C  S  Y  K  I  I  T  S
        T  W  V  T  L  T  I  A  Q  S  *  A  A  I  S  L  L  Q  A  Q

10861 CAAACATGTTTTACTACAAACAAGATGACTTCTAAAATTACAAACCCGATACCGTTTACC 10920
       T  Q  V  F  H  H  K  N  *  Q  L  N  *  H  K  P  *  P  L  H
      P  K  Y  L  I  I  N  T  R  S  F  I  K  I  N  P  S  H  C  I
        N  T  C  F  S  T  Q  E  V  S  S  K  L  T  Q  A  I  A  F  P

10921 AAAATCGGTTCATTTTCGTCTAGAACAGAATCTACGAAACCGAAGTTACTGTCCACAAAG 10980
       N  *  G  L  L  L  L  D  Q  R  L  H  K  P  K  L  S  L  H  K
      T  K  A  L  Y  F  C  I  K  D  *  I  S  Q  S  *  H  C  T  N
        K  L  W  T  F  A  S  R  T  K  S  A  K  A  E  I  V  P  T  E

10981 ATAACTTTGAAATAACCGACGATAATTCGCAGATATATACCCTAAAGTTCCAGCAGTTTA 11040
       *  Q  F  K  I  P  Q  *  *  A  D  I  Y  P  I  E  L  D  D  F
      R  N  F  S  *  Q  S  S  N  L  T  *  I  H  S  K  L  T  T  L
        I  S  V  K  N  A  A  I  L  R  R  Y  I  P  N  *  P  R  *  I

11041 TGATCCTTCAACATGAAAACTTCTACTTAACCGTGGAAGACTGCAAATAGTTGTTAACCG 11100
       V  L  F  N  Y  K  Q  L  H  I  P  V  K  Q  R  K  D  V  I  P
      Y  *  S  T  T  S  K  F  I  F  Q  C  R  R  V  N  I  L  L  Q
        S  P  L  Q  V  K  S  S  S  N  A  G  E  S  T  *  *  C  N  A

11101 ACCACAATTTAACGTTAGATTTTGTTTTTCTAAATAATTTCTTTGTTAAATAACCTAAAA 11160
       Q  H  *  I  A  I  *  F  L  F  I  *  *  L  F  L  K  N  S  K
      S  T  N  F  Q  L  R  F  C  F  S  K  N  F  F  C  N  I  P  N
        P  T  L  N  C  D  L  V  F  L  N  I  L  S  V  I  *  Q  I  K

11161 CTATAGATGTAAAAACAAATCAACATATTAAAGACGTAAACAATTTACCTGATATAAATA 11220
       S  I  *  M  K  T  *  N  Y  L  K  Q  M  Q  *  I  S  *  I  *
      Q  Y  R  C  K  Q  K  T  T  Y  N  R  C  K  N  F  P  S  Y  K
        I  D  V  N  K  N  L  Q  I  I  E  A  N  T  L  H  V  I  N  I

11221 CATATAATTATGTGTATACTAACCACAATGTAATACACATGAAACAAAACAATCAAAATA 11280
       T  Y  *  Y  V  Y  S  Q  H  *  M  I  H  V  K  N  Q  *  N  *
      H  I  N  I  C  M  H  N  T  N  C  *  T  Y  K  T  K  N  T  K
        Y  I  L  V  C  I  I  P  T  V  N  H  T  S  Q  K  T  L  K  I

11281 CTACAATGATCAATTTGTATTCGTAAAAATAAACTGATACATATATTAAGGACATGAGAC 11340
       S  T  V  L  *  V  Y  A  N  K  N  S  *  T  Y  L  E  Q  V  R
      H  H  *  *  N  F  M  L  M  K  I  Q  S  H  I  Y  N  R  Y  E
        I  N  S  T  L  C  L  C  K  *  K  V  I  Y  I  I  G  T  S  Q
```

FIG. 3 CONT'D

11341 ATGGAACAAAATACATTTAATAAATCAACAAATATTCCTTCCAAAATCTCCAAAATGAAT 11400
Y R T K H L N N L Q K Y P L N * L N * K
T G Q K I Y I I * N N I L F T K S T K S
V K N * T F * K T T * L S P K L P K V *

11401 ACAGACCGAGAGTATAAAACAAGGACGACACTTAAAATGAATACAAATACTTCATAAAAT 11460
H R A R M N Q E Q Q S N * K H K H L I K
I D P E * I K N R S H I K S I N I F Y K
T Q S E Y K T G A T F K V * T * S T N *

11461 ACCAACATAAAATACACAAAAACGATAAAAATATTGATACGTATCATAATTAGTACTGTA 11520
H N Y K I H K Q * K * L * A Y Y * D H C
I T T N * T N K S N K Y S H M T N I M V
P Q I K H T K A I K I V I C L I L * S M

11521 AAAAAGAAACTACAAAAACCAACCATCTTATCAATGAAATTAAAGATACACCATAAAACC 11580
K K K S T K P Q Y F L * K L K * T T N Q
N K R Q H K Q N T S Y N S * N R H P I K
K E K I N K T P L I T V K I E I H Y K P

11581 CAGCTTAAATCTTCTCCTACAAAACAATAAATAATGTCGGAAAAATCCATGAATATGTAC 11640
T S N L L P H K T I * * L R K L Y K Y M
P R I * F L I N Q * K N C G K * T S I C
D F K S S S T K N N I V A K K P V * V H

11641 CTGGTGATAAAACAGTAATCGATATCGTTTTTAACAACGATTAACCAACAGACAATTATA 11700
S W * K T M L * L L F Q Q * N T T Q * Y
P G S N Q * * S Y C F N N S I P Q R N I
V V I K D N A I A F I T A L Q N D T L I

11701 TAAAATAAAATGTCTACATGGAATATAATTTAACTAAGAGAACTCAATGAATAAATATCC 11760
I K N * L H V K Y * I S E R S N S I * L
Y K I K C I Y R I N F Q N E Q T V * K Y
N * K V S T G * I L N I R K L * K N I P

11761 CATATAAAATAGAACAATAACCCCTAAAAAGAGAGAAAATTTGTCACAAAAATCTTACGG 11820
T Y K I K N N P I K R E K L C H K * F A
P I N * R T I P S K E R K * V T N K S H
Y I K D Q * Q P N K E R K F L T K L I G

11821 ATACCCACAAATATTAATATTTTAAAGACAAGTTCTTAACGCAATATACTTACGATTACC 11880
* P H K Y N Y F K Q E L I A N Y S H * H
R H T N I I I F N R N L F Q T I H I S I
I P T * L * L I E T * S N R * I F A L P

FIG. 3 CONT'D

```
11881 GAATGCAGGTGGAGCATTATCAAAACTCCGATAAAACAATTTAAATTTTGACGAACCTTA 11940
       S  V  D  V  E  Y  Y  N  Q  P  *  K  T  L  N  L  V  A  Q  F
      A  *  T  W  R  T  I  T  K  L  S  N  Q  *  I  *  F  Q  K  S
        K  R  G  G  R  L  L  K  S  A  I  K  N  F  K  F  S  S  P  I

11941 TCCACCGCACGGTCAATAACTTCAGAGGGTTTAAGTTAGTTTTAACTGACTACACTTTAC 12000
       L  H  R  A  L  *  Q  L  R  G  F  E  I  L  I  S  Q  H  S  I
      Y  T  A  H  W  N  N  F  D  G  L  N  L  *  F  Q  S  I  H  F
        P  P  T  G  T  I  S  T  E  W  I  *  D  F  N  V  S  T  F  H

12001 ACGATTACAACAAAACAATTTAACAAATGTCGTAAACGTACAACGAAGATTAAGATTCAA 12060
       H  *  H  Q  K  T  L  N  N  V  A  N  A  H  Q  K  *  N  *  T
      T  S  I  N  N  Q  *  I  T  *  L  M  Q  M  N  S  R  I  R  L
        A  L  T  T  K  N  F  Q  K  C  C  K  C  T  A  E  L  E  L  N

12061 CACCGTCATAACATCACAAAATGTATTACTTTATGATAGATGAAGTCTAAACTCACATCG 12120
       T  A  T  N  Y  H  K  V  Y  H  F  V  I  *  K  L  N  S  H  L
      Q  P  L  I  T  T  N  *  M  I  F  Y  *  R  S  *  I  Q  T  Y
        H  C  Y  Q  L  T  K  C  L  S  I  S  D  V  E  S  K  L  T  A

12121 AAAACTATTCGAACGAGTTAATAACTAACAAAATAAGCGGTTAGGACGACGTCAACTATG 12180
       K  Q  Y  A  Q  E  I  I  S  Q  K  I  R  W  D  Q  Q  L  Q  Y
      S  K  I  L  K  S  L  *  Q  N  N  *  E  G  I  R  S  C  N  I
        K  S  L  S  A  *  N  N  I  T  K  N  A  L  G  A  A  T  S  V

12181 ATTCACAGAACGTTCATATCTACTTCAATCGCTACTAATACAAGTTCTATCATGGCAAAA 12240
       *  T  D  Q  L  Y  L  H  L  *  R  H  N  H  E  L  Y  Y  R  K
      S  L  T  K  C  T  Y  I  F  N  A  I  I  I  N  L  I  T  G  N
        L  H  R  A  L  I  S  S  T  L  S  S  *  T  *  S  L  V  T  K

12241 CGTCCGAAACGTTTCACTCAAACATTTATACCGATCAAAACAACTTATACTTCAGCGTTT 12300
       A  P  K  A  F  H  T  Q  L  Y  P  *  N  Q  Q  I  H  L  R  L
      Q  L  S  Q  L  T  L  K  Y  I  H  S  T  K  N  F  I  F  D  C
        C  A  K  C  L  S  N  T  F  I  A  L  K  T  S  Y  S  T  A  F

12301 CTTTTTAAACCGACTACGATTTTTATCACCAAGACAATTAGTTGTTGTCTATTTTGTCAA 12360
       S  F  N  P  Q  H  *  F  Y  H  N  Q  *  D  V  V  S  L  V  T
      L  F  I  Q  S  I  S  F  I  T  T  R  N  I  L  L  L  Y  F  L
        F  F  K  A  S  A  L  F  L  P  E  T  L  *  C  C  I  F  C  N

12361 TCTTTTTCGTACATTATATCGATTCAGACACATACTTGCACTATTTCGACATCGAGCGTT 12420
       L  F  L  M  Y  Y  L  *  T  Q  T  H  V  H  Y  L  Q  L  E  C
      *  F  F  C  T  I  Y  S  L  R  H  I  F  T  I  F  S  Y  S  A
        S  F  A  H  L  I  A  L  D  T  Y  S  R  S  L  A  T  A  R  L
```

FIG. 3 CONT'D

12421 TGAACTTGCATACCGTCTGGATCGTGAATGATTGTACATATTTCTCCGAGCCTAATTACT 12480
V Q V Y P L G L V * * C T Y L P E S * H
F K F T H C V * C K S V H I F L S P N I
S S R I A S R A S V L M Y L S A R I L S

12481 ATTCTTCTCATTTCAACAAAGGCGAAACGTCTGTTACGAAAAATCGTACCAAGCATTTAA 12540
Y S S Y L Q K R K A S L A K * C P E Y I
I L L T F N N G S Q L C H K K A H N T F
L F L L T T E A K C V I S K L M T R L N

12541 CCTATTAGTCCGAAATTTAAGATAAGACCTATTACGACAATTTCCAACACATGGAAACTC 12600
P Y D P K L N * E P Y H Q * L N H V K S
Q I I L S * I R N Q I I S N F T T Y R Q
S L * A K F E I R S L A T L P Q T G K L

12601 ACGATAAGGTCGTAACCGACGATTATGAAATTGATATCATTATGGTCTATTTGTTCAAAA 12660
H * E L M P Q * Y K L * L L V L Y V L K
T S N W C Q S S I S * S Y Y Y W I F L N
A I G A N A A L V K V I T I G S L C T K

12661 ACTATTTCAACAACTATTACAAATACAATGTATACGACCATCACATACCGTATATGTCTG 12720
Q Y L Q Q Y H K H * M H Q Y H I A Y V S
K I F N N I I N I N C I S T T Y P M Y L
S L T T S L T * T V Y A P L T H C I C V

12721 ACAAGTTCTACGACTACCATAATTATTTGTCAATTGACTATAATCACAACTAAGATTAAC 12780
Q E L H Q H Y * Y V T L Q Y * H Q N * N
S N L I S I T N I F L * S I N T N I R I
T * S A S P I L L C N V S I L T S E L Q

12781 CGGAGAACAATAGTAACGCTTGTCCATATTACTTCAACGATTACGACAATACGTCTTATT 12840
A E Q * * Q S C T Y H L Q * H Q * A S Y
P R K N D N R V P I I F N S I S N H L I
G R T I M A F L Y L S T A L A T I C F L

12841 ACTCAACTACGGAGTATTTAATTTTTATGTTCAACAATTATCACCAAGACTATACTTAAC 12900
H T S A E Y I L F V L Q * Y H N Q Y S N
I L Q H R M F * F Y L N N I T T R I H I
S N I G * L N F I C T T L L P E S I F Q

12901 ATTATAAGGATGAGTTACAATAATATTATTACCATCATCACCATCTTATCAAATACGACA 12960
Y Y E * E I N N Y Y H Y Y H Y F L K H Q
T I N R S L T I I I I T T T T S Y N I S
L I G V * H * * L L P L L P L I T * A T

FIG. 3 CONT'D

```
12961  AGAATCACTACAACTACCAGAATTCATATGATTCTATTACTTTCTACTACCTTTAACACA  13020
        E  *  H  H  Q  H  D  *  T  Y  *  S  L  S  L  H  H  F  N  H
       N  K  T  I  N  I  T  K  L  I  S  L  Y  H  F  I  I  S  I  T
         R  L  S  T  S  P  R  L  Y  V  L  I  I  F  S  S  P  F  Q  T

13021  ACAAAATCTCGAACTAGGAGGAACATTTAAAAGATATGTTCTACAATTCCCTGAATTTTA  13080
        Q  K  L  A  Q  D  E  K  Y  I  K  *  V  L  H  *  P  V  *  F
       N  N  *  L  K  I  R  R  T  F  K  R  Y  L  I  N  L  S  K  F
         T  K  S  S  S  G  G  Q  L  N  E  I  C  S  T  L  P  S  L  I

13081  ATTCATAGAAATAAAATAATTTCCTACATTGTGAAATCGATCTCCCACCCAACAACCATG  13140
        *  T  D  K  N  *  *  L  I  Y  C  K  L  *  L  T  P  Q  Q  Y
       N  L  I  K  I  K  N  F  S  T  V  S  *  S  S  P  P  N  N  T
         L  Y  R  *  K  I  L  P  H  L  V  K  A  L  P  H  T  T  P  V

13141  AAATAGAAGTTGTTAATCTAACGTCCGACCACAACGATGACTCATACGTCGATTAAGAAG  13200
        K  I  K  L  L  *  I  A  P  Q  H  Q  *  Q  T  H  L  *  N  K
       S  *  R  *  C  N  S  Q  L  S  T  N  S  S  L  I  C  S  I  R
         K  D  E  V  I  L  N  C  A  P  T  A  V  S  Y  A  A  L  E  E

13201  ATATGAAAGTAATACACGTAAAAGACATCTAGGATTCTTTTGAATAAATCTAATATATGT  13260
        *  V  K  M  I  H  M  K  Q  L  D  *  S  F  K  N  L  N  Y  V
       R  Y  K  *  *  T  C  K  R  Y  I  R  L  F  S  I  *  I  I  Y
         I  S  E  N  H  A  N  E  T  S  G  L  F  V  *  K  S  *  I  C

13261  TGTTCCACCACATGGATATTAATTAACACAATTTTACGAGACACTAGTACGACCATGACC  13320
        V  L  H  H  V  *  L  *  N  H  *  F  A  R  H  D  H  Q  Y  Q
       L  L  T  T  Y  R  Y  N  I  T  N  F  H  E  T  I  M  S  T  S
         C  P  P  T  G  I  I  L  Q  T  L  I  S  Q  S  *  A  P  V  P

13321  ATACCGGTAATGATAATTTGGACTCCGATGATAATTGGTTCTAAGAATACCACCACGGAG  13380
        Y  P  W  *  *  *  V  Q  P  *  *  *  G  L  N  K  H  H  H  R
       T  H  G  N  S  N  F  R  L  S  S  N  V  L  I  R  I  T  T  G
         I  A  M  V  I  L  G  S  A  V  I  L  W  S  E  *  P  P  A  E

13381  TCAAACATAAATAACGGCACGTGCACATCTCGTAGGTCTACATCTACCATATACATTTAA  13440
        L  K  Y  K  N  G  H  V  H  L  A  D  L  H  L  H  Y  I  Y  I
       *  N  T  N  I  A  T  C  T  Y  L  M  W  I  Y  I  T  Y  T  F
         T  Q  I  *  Q  R  A  R  T  S  C  G  S  T  S  P  I  H  L  N

13441  TGCACCATTTAAACATGTTCAGGGAAACCCATATTTTCTAGGATAAGAAATACACAATTG  13500
        V  H  Y  I  Q  V  L  G  K  P  Y  L  L  D  *  E  K  H  T  L
       *  T  T  F  K  Y  L  D  R  Q  T  Y  F  I  R  N  K  I  H  *
         R  P  L  N  T  C  T  G  K  P  I  F  S  G  I  R  *  T  N  V
```

FIG. 3 CONT'D

13501 TGTACTACAAACAGTTCAGACACCAAAAACCTCTCTACCGTCAACAAGGACACATCCAAG 13560
V H H K D L R H N K S L H C N N R H L N
C M I N T L D T T K P S I A T T G T Y T
C S T Q * T Q P K Q L S P L Q E Q T P E

13561 TTCACAGCGACAAGTTAGATTTCTAAATTTAAAAAATTTGCCCAAGCCCCATGATCACAC 13620
L H R Q E I * L N L N K L R T R P V L T
* T D S N L R F I * I K * V P E P Y * H
L T A T * D L S K F K K F P N P T S T H

13621 TTACGGGCCGATCATGGGACACGATCACCAAATAGATGACTACAAGTTAATTCCCGTAAA 13680
F A R S T G Q A L P K D V S T * N L A N
S H G A L V R H * H N I * Q H E I L P M
I G P * Y G T S T T * R S I N L * P C K

13681 CTGTAAACATTATGGTTATCTCGACCATATCCAAATATAATATTTCACTTAACAACGGCA 13740
S M Q L V L L A P I P K Y * L T F Q Q R
Q C K Y Y W Y L Q Y L N I N Y L S N N G
V N T I G I S S T Y T * I I F H I T A T

13741 AAAGTCGCATATCTACTGCTGCCATTATTTAACCTATTCAAGAAACAACAGTTTTCTTGA 13800
K * R I S S S P L L N S L N K T T L L V
N E A Y L H R R Y Y I P Y T R Q Q * F F
K L T Y I V V T I F Q I L E K N D F S S

13801 TTAAATCTTCAAATATTATTTCTCTTTTGAATAATACTCAACTGATTTTCAACACCACAA 13860
L K S T * L L S F V * * S N V L L Q P T
* N L L K Y Y L S F K N H T S * F N H H
I * F N I I F L F S I I L Q S F T T T N

13861 CACCGACTTGTACTAAAGAAATGTAAACTATAACTACCATCAGCGCACGGTGTATATCAA 13920
T A S C S K K V N S I S P L R T G C I T
Q P Q V H N R * M Q Y Q H Y D R A V Y L
H S F M I E K C K I N I T T A H W M Y N

13921 GCATCCTTAGAAAGTTTCATATGATACAATCTAGAAACGATACGTAACGCAGTAAAACTA 13980
R L F R E F Y V I N S R Q * A N R * K S
E Y S D K L T Y * T L D K S H M A D N Q
T P I K * L I S H * I K A I C Q T M K I

13981 GCATTACTAACAAGTTATAACACACTTTAAGAAACACTCATACGACTAACATTTCTTAGG 14040
R L S Q E I N H S I R Q S Y A S Q L S D
D Y H N N L I T H F E K H T H Q N Y L I
T I I T * Y Q T F N K T L I S I T F F G

FIG. 3 CONT'D

```
14041  ATGAAAAGATTCTTTCTAACCATACTAAAACAACTTTTAGGACTATAATAATTATATATA  14100
        * K E L F S Q Y S K T S F G S I I L I Y
       R S K * S L N T H N Q Q F D Q Y * * Y I
         V K R L F I P I I K N F I R I N N I Y I

14101  TTTTTAATCCGGGATAAAAATTATCTCGAAATGAATTATGACAGTAAAAACGTCTGTGG  14160
        L F N P G I K L L A K S L V T M K A S V
       Y F I L G * K * Y L K V * Y Q * K Q L C
         F F * A R N K I S S * K I S D N K C V G

14161  AATCAACTTCATCCAAATCAACCACAAAATTGAAATCTATTGGTTCTAAACATACCAGTT  14220
        K T S T P K T P T K V K S L W S K Y P *
       R L Q L L N L Q H K L K L Y G L N T H D
         * N F Y T * N T N * S * I V L I Q I T L

14221  ACCATACTAAAACCACTAAAATATGTTTGTCGGGGTCCCAAACCACACCGTCAACGTCTA  14280
        H Y S K P S K I C V A G P N P T A T A S
       I T H N Q H N * V F L G L T Q H P L Q L
         P I I K T I K Y L C G W P K T H C N C I

14281  AGAATGATAAGAATATACTACGGATACAACTGATACACAGTACATAATCTAACACTTAAT  14340
        E * * E * I I G I N V I H * T N S Q S N
       N K S N K Y S A * T S * T D H I L N H I
         R V I R I H H R H Q S H T M Y * I T F *

14341  AAACAATTACTATCAATATCTGTTAAGCTAGAACATGTCATACTAAAATGACTAATGTTC  14400
        N T L S L * L C N S R T C Y S K V S * L
       I Q * H Y N Y V I R D Q V T H N * Q N C
         K N I I T I S L E I K Y L I I K S I V L

14401  AATCTCAACAAATTATTCATAAAATTCATAACCCCATACTTCATAGTAGGATTATGACAC  14460
        N S N N L L Y K L Y Q P I F Y * G L V T
       T L T T * Y T N * T N P Y S T D D * Y Q
         * L Q K I L I K L I P T H L I M R I S H

14461  CTAACACTATTACTATCCACATAATAAGTAACACGATTAAAATTATATGATAAATCATAC  14520
        S Q S L S L H I I * Q A L K L I S N L I
       P N H Y H Y T Y * E N H * N * Y V I * Y
         I T I I I P T N N M T S I K I Y * K T H

14521  CAAAATGGATTATGAACAAAACCAGGGGAACAATCTGTTTAAAAACATCTACCACATGGC  14580
        T K G L V Q K P G R T L C I K T S P T G
       P K V * Y K N Q D G Q * V F K Q L H H V
         N * R I S T K T G K N S L N K Y I T Y R
```

FIG. 3 CONT'D

```
14581  AAACAACAAAGATAACCAATGGTAATGTTTCTCAATCCACATCAATACTTGAATCTACAA  14640
        N  T  T  E  I  P  *  W  *  L  S  N  P  T  T  I  F  K  S  T
       T  Q  Q  K  *  Q  N  G  N  C  L  T  L  H  L  *  S  S  L  H
         K  N  N  R  N  T  V  M  V  F  L  *  T  Y  N  H  V  *  I  N

14641  CTGTGTGTGGCAATAGCAAACAGAGAATTTCTAAATGAAGAAATACGTCGTCTAGGACGA  14700
        S  V  C  R  *  R  K  D  R  L  S  K  S  R  *  A  A  S  G  A
       Q  C  V  G  N  D  N  T  E  *  L  N  V  E  K  H  L  L  D  Q
         V  C  V  T  I  T  Q  R  K  F  I  *  K  K  I  C  C  I  R  S

14701  TACGTGCAACGTAGACGATCACGAGACGAACTAAATGCTTGAACAACAAAATCACATCGA  14760
        I  C  T  A  D  A  L  A  R  S  S  K  R  V  Q  Q  K  L  T  A
       *  A  R  Q  M  Q  *  H  E  A  Q  N  V  F  K  N  N  *  H  L
         H  V  N  C  R  S  T  S  Q  K  I  *  S  S  T  T  K  T  Y  S

14761  CGGTAATGTTCACCATATTTTAAAGTTTGACATTTTGGTCCATTGAAATTGGTTCTGAAA  14820
        A  M  V  L  P  I  F  N  *  V  T  F  G  P  L  K  L  W  S  K
       Q  W  *  L  H  Y  L  I  E  F  Q  L  V  L  Y  S  *  G  L  S
         G  N  C  T  T  Y  F  K  L  S  Y  F  W  T  V  K  V  L  V  K

14821  ATGCTCAAACAATTTTCATTTCCGAACAAATTTCTCCCATCATGTCAACTAAACTTTGTA  14880
        *  S  N  T  L  L  L  P  K  N  L  S  P  L  V  T  S  K  F  C
       K  R  T  Q  *  F  Y  L  S  T  *  L  P  Y  Y  L  Q  N  S  V
         V  L  K  N  F  T  F  A  Q  K  F  L  T  T  C  N  I  Q  F  M

14881  AAAAAGAAATGAGTTCTACCATTACGACGTTAATGACTAATATTAATAATATTCATATTA  14940
        K  K  K  V  *  S  P  L  A  A  I  V  S  *  L  *  *  L  Y  L
       N  K  R  *  E  L  H  Y  H  Q  L  *  Q  N  Y  N  N  Y  T  Y
         K  E  K  S  L  I  T  I  S  C  N  S  I  I  I  I  I  L  I  I

14941  AATGGATGATACCAACTATAATTCGTCAATAACAAACATAATCTTCAACAAATATTTATA  15000
        K  G  V  I  T  S  I  L  C  N  N  N  T  N  S  T  T  *  L  Y
       N  V  *  *  P  Q  Y  *  A  T  I  T  Q  I  L  L  Q  K  Y  I
         *  R  S  H  N  I  N  L  L  *  Q  K  Y  *  F  N  N  I  F  I

15001  AAACTTTAAATACTACCACCAACATATGGTCGTAGTGTTCAATAACAATTATTAATACTA  15060
        K  S  I  *  S  P  P  Q  I  G  A  D  C  T  I  T  L  L  *  S
       N  Q  F  K  H  H  H  N  Y  V  L  M  V  L  *  Q  *  Y  N  H
         K  F  N  I  I  T  T  T  Y  W  C  *  L  N  N  N  I  I  I  I

15061  TTTTCACGACCAATAGGTAAATTATTTAAACCATTTCGGTCTGAAATAATACTCCGTAAT  15120
        L  L  A  P  *  G  N  L  L  N  P  L  A  L  S  *  *  S  A  N
       Y  F  H  Q  N  D  M  *  Y  I  Q  Y  L  W  V  K  N  H  P  M
         F  T  S  T  I  W  K  I  F  K  T  F  G  S  K  I  I  L  C  *
```

FIG. 3 CONT'D

```
15121  AGTAAACTCCTTGTCTTACTTTAAATACGTATATGATTTGCATTACAAGACGGGTGGAAT  15180
        D  N  S  S  C  F  S  I  *  A  Y  V  L  R  L  T  R  G  V  K
       I  M  Q  P  V  S  H  F  K  H  M  Y  *  V  Y  H  E  A  W  R
         *  K  L  F  L  I  F  N  I  C  I  S  F  T  I  N  Q  G  G  *

15181  TGAGTTTACTTAAATTTTATACGATAGTCACGATTCTTATCTCGAGCGTGACATCGTCCA  15240
        V  *  I  F  K  F  Y  A  I  L  A  L  F  L  A  R  V  T  A  P
       L  E  F  S  N  L  I  H  *  *  H  *  S  Y  L  E  C  Q  L  L
         S  L  H  I  *  F  I  S  D  T  S  L  I  S  S  A  S  Y  C  T

15241  CAAAGATAAGAATCATGATACTGTCCGGCTTACAAGGTAGTTTTTACAAACTTCTCATAT  15300
        T  E  I  R  L  V  I  V  P  R  I  N  W  *  F  H  K  F  L  I
       H  K  *  E  *  Y  *  S  L  G  F  T  G  D  F  I  N  S  S  Y
         N  R  N  K  T  S  H  C  A  S  H  E  M  L  F  T  Q  L  T  Y

15301  CGTCGATGGGCTCCACAAGGACAACAATATCCTTGGTGATTTAAAATACCACCAACCCTG  15360
        A  A  V  R  P  T  G  T  T  I  P  V  V  L  N  *  P  P  Q  S
       L  L  *  G  L  H  E  Q  Q  *  L  F  W  *  I  K  H  H  N  P
         C  S  G  S  T  N  R  N  N  Y  S  G  S  F  K  I  T  T  P  V

15361  CTATACAATGCAGTAGAATATTTCCTACAACTGTTGGGACAAGAATACCCAACCCTAATA  15420
        S  I  N  R  *  R  I  F  S  T  S  L  G  T  R  I  P  Q  S  *
       R  Y  T  V  D  D  *  L  P  H  Q  C  G  Q  E  *  P  N  P  N
         I  H  *  T  M  K  Y  L  I  N  V  V  R  N  K  H  T  P  I  I

15421  GGATTTACACTAGCACGATACGGTTTATAAAACGCATAACAATCATCAAATCAAAACCGG  15480
        G  L  H  S  R  A  I  G  F  I  K  R  I  T  L  L  K  T  K  A
       D  *  I  H  D  H  *  A  L  Y  K  A  Y  Q  *  Y  N  L  K  P
         R  F  T  I  T  S  H  W  I  N  Q  T  N  N  T  T  *  N  Q  G

15481  GCGTTTGTACTTAAAACAACAAGTGTACCACTATCTAAAATAGCGGAACGCTTACTTACA  15540
        R  L  C  S  N  Q  Q  E  C  P  S  L  N  *  R  R  A  F  S  H
       G  C  V  H  I  K  N  N  V  H  H  Y  I  K  D  G  Q  S  H  I
         A  F  M  F  K  T  T  *  M  T  I  S  K  I  A  K  R  I  F  T

15541  CGAGTTCAAAACTCACTTTATCAATACACACCGCCAACGATAATACAATTCGGACCACCA  15600
        A  *  T  K  L  S  I  T  I  H  P  P  Q  *  *  T  L  G  P  P
       H  E  L  K  S  H  F  L  *  T  H  R  N  S  N  H  *  A  Q  H
         S  L  N  Q  T  F  Y  N  H  T  A  T  A  I  I  N  L  R  T  T

15601  TGATCGTCACCACTACGTTGATGACGAAAACGATTAAGACAAAAATTATATACAGTCCGA  15660
        V  L  L  P  S  A  V  V  A  K  A  L  E  T  K  L  I  H  *  A
       Y  *  C  H  H  H  L  *  Q  K  Q  *  N  Q  K  *  Y  I  D  P
         S  A  T  T  I  C  S  S  S  K  S  I  R  N  K  I  Y  T  L  S
```

FIG. 3 CONT'D

```
15661 CAATGACGATTACAAACAAGAGAATACCGGACATTACCGGTATTCTAACTTCTAAATTCA 15720
       T  V  A  L  T  Q  E  R  I  A  Q  L  P  W  L  I  S  S  K  L
      Q  *  Q  *  H  K  N  E  *  P  R  Y  H  G  Y  S  Q  L  N  L
        N  S  S  I  N  T  R  K  H  G  T  I  A  M  L  N  F  I  *  T

15721 TATGCGTTAAATGTTTTTGCGAATATGAGATTACAAATAGCATGTCTAATACAACTAATA 15780
       I  R  L  K  C  F  R  K  Y  E  L  T  *  R  V  S  *  T  S  *
      Y  V  C  N  V  F  V  S  I  S  *  H  K  D  Y  L  N  H  Q  N
        Y  A  I  *  L  F  A  *  V  R  I  N  I  T  C  I  I  N  I  I

15781 TGTAAACAATTACTCATAATACTTAAAAATACATTCGTAAAATCATACTACTAAAACTCA 15840
       V  N  T  L  S  Y  *  S  N  K  H  L  C  K  L  I  I  I  K  L
      Y  M  Q  *  H  T  N  H  I  K  I  Y  A  N  *  Y  S  S  K  S
        C  K  N  I  L  I  I  F  K  *  T  L  M  K  T  H  H  N  Q  T

15841 CTACTACCACAACAGACAATATTGAGACTAATACGATCATTCCCAATATATCGATTATAT 15900
       S  S  P  T  T  Q  *  L  E  S  *  A  L  L  P  *  I  A  L  I
      H  H  H  H  Q  R  N  Y  S  Q  N  H  *  Y  P  N  Y  L  *  Y
        I  I  T  N  D  T  I  V  R  I  I  S  T  L  T  I  Y  S  I  Y

15901 TCACAAAAAGTTGTTCAAAACATGATAGTCTTATTACAGAAATACAGACTTAGATTTACA 15960
       L  T  K  *  C  T  K  Y  *  *  F  L  T  K  I  D  S  D  L  H
      L  H  K  E  V  L  K  T  S  D  S  Y  H  R  *  T  Q  I  *  I
        T  N  K  L  L  N  Q  V  I  L  I  I  D  K  H  R  F  R  F  T

15961 ACCCAACTTTTACTATAATGATTACCAGGAGTACTTAAAACAAGGGTTGTATGATACAAT 16020
       Q  T  S  F  S  I  V  L  P  G  *  S  N  Q  E  W  C  V  I  N
      N  P  Q  F  H  Y  *  *  H  D  E  H  I  K  N  G  V  Y  *  T
        P  N  F  I  I  N  S  I  T  R  M  F  K  T  G  L  M  S  H  *

16021 CAATTCTATCTACCACTAATACAAATAAATGGTATAGGTCTAGGAAGATCTTAAAATCCT 16080
       T  L  I  S  P  S  *  T  *  K  G  Y  G  S  G  E  L  I  K  P
      L  *  S  L  H  H  N  H  K  N  V  M  D  L  D  K  *  F  K  L
        N  L  Y  I  T  I  I  N  I  *  W  I  W  I  R  R  S  N  *  S

16081 CGACCAACAAAACAACTACTAAATAACTTCTGACTGTCACAAGAAAACTATCTCGCGAAA 16140
       A  P  Q  K  T  S  S  K  N  F  V  S  L  T  R  K  I  S  R  K
      L  Q  N  N  Q  Q  H  N  I  S  S  Q  C  H  E  K  S  L  A  S
        S  T  T  K  N  I  I  *  Q  L  S  V  T  N  K  Q  Y  L  A  K

16141 CATTCAGATCGATATCTACGAATGGGAAATCATGTAGTACTTTTACTTCTTATGGTTTTT 16200
       T  L  R  A  I  S  A  *  G  K  T  C  *  S  F  S  S  Y  W  F
      Q  L  D  L  *  L  H  K  G  K  L  V  D  H  F  H  L  I  G  F
        Y  T  *  S  Y  I  S  V  R  *  Y  M  M  F  I  F  F  V  L  F
```

FIG. 3 CONT'D

```
16201  CAGAAAGCACATATAAATCTTATATATTTTTTTGACATATTACTAGAACCATGAGTCTAG  16260
        T  K  R  T  Y  K  S  Y  I  F  F  S  Y  L  S  R  P  V  *  I
       L  R  E  H  I  N  L  I  Y  L  F  V  T  Y  H  D  Q  Y  E  S
         D  K  T  Y  I  *  F  I  Y  F  F  Q  I  I  I  K  T  S  L  D

16261  AATCTATCAATATCACAATAAAATTCATGAACACTACCAAATTTCAAATGACTTCTTAGT  16320
        K  S  L  *  L  T  I  K  L  V  Q  S  P  K  F  N  V  S  S  D
       R  L  Y  N  Y  H  *  K  L  Y  K  H  H  N  L  T  *  Q  L  I
         *  I  T  I  T  N  N  *  T  S  T  I  T  *  L  K  S  F  F  *

16321  AAAATGTTCTTATACATAAATTTTTCACGGCACTACGTCTCACATCCACGTACGCAACAA  16380
        N  *  L  F  I  Y  K  F  L  A  T  I  C  L  T  P  A  H  T  T
       M  K  C  S  Y  T  N  L  F  H  R  S  A  S  H  L  H  M  R  Q
         K  V  L  I  H  I  *  F  T  G  H  H  L  T  Y  T  C  A  N  N

16381  ACAAGTAGTGTTTGAAGAAACGCAACACCGTCAACATATGCATTCGGAAACAATACAACA  16440
        Q  E  D  C  V  E  K  R  Q  P  L  Q  I  R  L  G  K  N  H  Q
       K  N  M  V  F  K  K  A  N  H  C  N  Y  V  Y  A  K  T  I  N
         T  *  *  L  S  R  Q  T  T  A  T  T  Y  T  L  R  Q  *  T  T

16441  TTTACAACAATACTGGTACAATACCGTTGATTAGTATTTATACAAAACTCACAGAGTGGA  16500
        L  H  Q  *  S  W  T  I  A  V  L  *  L  Y  T  K  L  T  E  G
       Y  I  N  N  H  G  H  *  P  L  *  D  Y  I  H  K  S  H  R  V
         F  T  T  I  V  M  N  H  C  S  I  M  F  I  N  Q  T  D  *  R

16501  ATGCAAACATTACGTGGATTGACACTACACTCACTACAGTGGTTTAATATAAACCCGCCA  16560
        *  T  Q  L  A  G  L  Q  S  T  L  S  T  V  L  N  Y  K  P  P
       K  R  K  Y  H  V  *  S  H  H  S  H  H  *  W  I  I  N  P  R
         V  N  T  I  C  R  V  T  I  H  T  I  D  G  F  *  I  Q  A  T

16561  TACAGAATGATAACACTTTTGGTATTTGGGGTAATAAGTAAATTCAATCAATACTTACCA  16620
        I  D  *  *  Q  S  F  W  L  G  W  *  E  N  L  N  T  I  F  P
       Y  T  K  S  N  H  F  G  Y  V  G  N  N  M  *  T  L  *  S  H
         H  R  V  I  T  F  V  M  F  G  M  I  *  K  L  *  N  H  I  T

16621  TACCAGAAACCAAACATATTTGTTAGAACGTGCCCAAGTGGAATATATCTACTAAAATTA  16680
        I  T  K  P  K  Y  L  C  D  Q  V  P  E  G  *  I  S  S  K  L
       Y  P  R  Q  N  T  Y  V  I  K  C  P  N  V  K  Y  L  H  N  *
         H  D  K  T  Q  I  F  L  R  A  R  T  *  R  I  Y  I  I  K  I

16681  TTCTATCGATCAACATTTACCTGTCTTCAACTACTAATACAAGACCGTTTACTCACATAA  16740
        L  I  A  L  Q  L  H  V  S  T  S  S  *  T  R  A  F  S  H  I
       Y  S  L  *  N  Y  I  S  L  L  Q  H  N  H  E  P  L  H  T  Y
         L  Y  S  T  T  F  P  C  F  N  I  I  I  N  Q  C  I  L  T  N
```

FIG. 3 CONT'D

16741 CTTGCAAATTTCAATAAACGACGTCTTTGAGTTTTCCGTTGACTTCTCCGAAAATTTGTT 16800
S R K F N N A A S V * F A V S S A K L C
Q V N L T I Q Q L F E F P L Q L P K * V
F T * L * K S C F S L L C S F L S K F L

16801 TCGATACGAAGACGATGGTAAGTTCTCTAACAATCACTATCTCTTCAATAAAACACAACC 16860
L * A E A V M * S I T L S L S T I K H Q
F S H K Q * W E L S Q * H Y L L * K T N
A I S R S G N L L N N T I S F N N Q T P

16861 CTCTGTCCATTTCAATTTGGTGGTGAATTATTTTTAATACAAAAGTGTCCGATGGTAAAA 16920
S V P L T L G G S L L F * T K V P * W K
P S L Y L * V V V * Y F N H K * L S G N
L C T F N F W W K I F I I N E C A V M K

16921 TGATCATGACCATTCTGTCAAAATCCACTCATACAAAAACTATTTTCACTTAATTGATTG 16980
V L V P L V T K P S Y T K S L L S N V L
* * Y Q Y S L K L H T H K Q Y F H I L *
S T S T L C N * T L I N K I F T F * S V

16981 CCACACATAATGGCGCGATGTTGATGAATATTTGAAAGATATCCACTACAAAAACAAAAT 17040
P T Y * R A V V V * L S E I P S T K T K
R H T N G R * L * K Y V K * L H H K Q K
T H I V A S C S S I F K R Y T I N K N *

17041 TGTAGTGTAAGACATCGATCAAATTCACGTGGATGTGAACAGGGTGTTCTCTTGATACGA 17100
V D C E T A L K L A G V S T G C S F * A
L M V N Q L * N L H V * V Q G V L S S H
C * M R Y S T * T C R C K D W L L V I S

17101 TCATATTCTAAAAGATCACAAATATCACAAGGTAACCACAAAGTTTTATTACAACGATTA 17160
L I L N E L T * L T G N T N * F L T A L
* Y L I K * H K Y H E M P T E F Y H Q *
T Y S K R T N I T N W Q H K L I I N S I

17161 ATAGTCGTGTAACCTTACTTTGCAATAACGTGACAAGTTCCAGGGGGACCATGCCCTTTC 17220
* * C M P I F R * Q V T * P G G P V P F
N D A C Q F S V N N C Q E L D G Q Y P F
I L V N S H F T I A S N L T G R T R S L

17221 AGAGTAGAACGATATCCAGATCGACAAATAATGATGTGTCGTGCACATCAAATATGACGA 17280
D * R A I P R A T * * * V A R T T * V A
T E D Q * L D L Q K N S C L V H L K Y Q
R M K S Y T * S N I V V C C T Y N I S S

FIG. 3 CONT'D

```
17281  CGATCAGTACGACGACATCTACGTAACACACTTTTTCGAATATTCAAAAATTTATAATTG  17340
        A  L  *  A  A  T  S  A  N  H  S  F  A  *  L  N  K  F  I  L
       Q  *  D  H  Q  Q  L  H  M  T  H  F  L  K  Y  T  K  L  Y  *
         S  T  M  S  S  Y  I  C  Q  T  F  F  S  I  L  K  *  I  N  V

17341  CTAACATGTGCATAATAAGGACGATTTCAAGCACATCTAACAATACTATTCAAATTTTAA  17400
        S  Q  V  R  I  I  G  A  L  T  R  T  S  Q  *  S  L  N  L  I
       R  N  Y  V  Y  *  E  Q  *  L  E  H  L  N  N  H  Y  T  *  F
         I  T  C  T  N  N  R  S  F  N  T  Y  I  T  I  I  L  K  F  N

17401  TTACTATGGTGAACATTCATACAAAAATGGTGTTATTTACGTAATGGTCTCAACCAATGT  17460
        L  S  V  V  Q  L  Y  T  K  V  V  I  F  A  N  G  S  N  T  V
       *  H  Y  W  K  Y  T  H  K  *  W  L  L  H  M  V  L  T  P  *
         I  I  G  S  T  L  I  N  K  G  C  Y  I  C  *  W  L  Q  N  C

17461  CTATAACAACAACAACTACTTCAATCATACGAATGATTAATACTTAACAGACAATATTTA  17520
        S  I  T  T  T  S  S  T  L  I  S  V  L  *  S  N  D  T  I  F
       L  Y  Q  Q  Q  Q  H  L  *  Y  A  *  *  N  H  I  T  Q  *  L
         I  N  N  N  N  I  F  N  T  H  K  S  I  I  F  Q  R  N  Y  I

17521  CGAGCATAATTTCGATTTGTAATACATATATAACCTCTAGGACGAGTTAATGGACGTGGT  17580
        A  R  I  L  A  L  C  *  T  Y  I  P  S  G  A  *  N  G  A  G
       H  E  Y  *  L  *  V  N  H  I  Y  Q  L  D  Q  E  I  V  Q  V
         S  T  N  F  S  F  M  I  Y  I  N  S  I  R  S  L  *  R  C  W

17581  GCACACGACAACTCGTTCCCAAGAAATCTTGGATCCGTGAAGTTAAGATAATGATTTTAT  17640
        R  T  S  N  L  L  P  E  K  S  G  L  C  K  L  E  I  V  L  I
       V  H  A  T  S  C  P  N  K  L  V  *  A  S  *  N  *  *  *  F
         T  H  Q  Q  A  L  T  R  *  F  R  P  V  E  I  R  N  S  F  Y

17641  TACACAACAAATCCAGGACTATAGAAAAACCCTTTAACAATATCCACAGGATTTCTTTAA  17700
        I  H  Q  K  P  G  S  I  K  K  P  F  Q  *  L  H  G  L  S  I
       L  T  N  N  L  D  Q  Y  R  K  P  F  N  N  Y  T  D  *  L  F
         H  T  T  *  T  R  I  D  K  Q  S  I  T  I  P  T  R  F  F  N

17701  CATCTTTGACAAAGTCGTAACCAAATACTATTATTTGAGTTCCGATTTTTACTATTATCA  17760
        T  S  V  T  E  A  N  T  *  S  L  L  S  L  A  L  F  S  L  L
       Q  L  F  Q  K  L  M  P  K  H  Y  Y  V  *  P  *  F  H  Y  Y
         Y  F  S  N  *  C  Q  N  I  I  I  F  E  L  S  F  I  I  I  T

17761  AGTAATACAAAATTTCATATAAAATTCCCTGTCTGTTGTGTACTCTCAAGTTCACGACAT  17820
        E  N  H  K  L  T  Y  K  L  P  C  V  V  C  S  L  E  L  A  T
       N  M  I  N  *  L  I  N  *  P  V  S  L  V  H  S  N  L  H  Q
         *  *  T  K  F  Y  I  K  L  S  L  C  C  M  L  T  *  T  S  Y
```

FIG. 3 CONT'D

17821 TTATAAGTTGTCTATATAGATTAATCATTTAAAAATTTTCGATTAGGTCAAACCTTATCA 17880
F I * C I Y R I L L N K F A L G T Q F L
L Y E V S I D L * Y I K L L * D L K S Y
I N L L Y I * N T F K * F S I W N P I T

17881 CGACAAAAATAATCAGGAATATTATCAGTCTTAATACAACGATTCGCACAAAATCCACAA 17940
A T K I L G * L L * F * T A L R T K P T
H Q K * * D K Y Y D S N H Q * A H K L H
S N K N T R I I T L I I N S L T N * T N

17941 GTTTGTGTTTGACATCTAAGACGAGTTCCAAGCCTTATACTAATACAATATATAAGTGTT 18000
* V C V T S E A * P E S Y S * T I Y E C
E F V F Q L N Q E L N P I H N H * I N V
L C L S Y I R S L T R F I I I N Y I * L

18001 TGTCGTCTTTGTCGGGTAAGACAATTACAATTAGCTAAATTACAACGGTATTGATCTCGG 18060
V A S V A W E T L T L R N L T A M V L A
F L L F L G N Q * H * D I * H Q W L * L
C C F C G M R N I N I S K I N G Y S S G

18061 TTCTTCCCGTAAAAAACACAATACTCATTATACGTTAATAAACTTAGAGAATTAAAATAA 18120
L F P M K Q T I L L I C N N S D R L K I
W S P C K K H * S Y Y A I I Q I E * N *
L L A N K T N H T I H L * K F R K I K N

18121 TGAGATGGAAATCTATTTTAAGTTTTAGTTTGAAATGGAGCAAACGTAACGTGTTGATTA 18180
V R G K S L I * F * V K G R K C Q V V L
* E V K L Y F E F D F K V E N A N C L *
S * R * I F N L I L S * R T Q M A C S I

18181 GAAAAATTTCTAACATCATTTTCAACGAATCCAATAGTAGGTCGCGTACGGGGGAGTAAA 18240
R K L S Q L L L Q K P * * G A C A G E N
D K * L N Y Y F N S L N D D L A H G R M
K K F I T T F T A * T I M W R M G G * K

18241 AATCGTCAACTACTATTTATATTCCAATTACTTTTAAACCGACATTTAAATTTATAAACA 18300
K A T S S L Y L T L S F K A T F K F I Q
K L L Q H Y I Y P * H F N P Q L N L Y K
* C N I I F I L N I F I Q S Y I * I N T

18301 CTTGGACAAAATTGTATAAGAGCAAATTATAGAGAATACCCAAAATTTAATCTAAACTGA 18360
S G T K V Y E R K I D R I P K L N S K V
H V Q K L M N E N L I E * P N * I L N S
F R N * C I R T * Y R K H T K F * I Q S

FIG. 3 CONT'D

```
18361  GAACTACCAATAAGATTTAACAAATAATGATTTCTACTTCGGTAATTTGCACAATCTCCA  18420
        R  S  P  *  E  L  N  N  I  V  L  S  S  A  M  L  R  T  L  P
       E  Q  H  N  N  *  I  T  *  *  *  L  H  L  W  *  V  H  *  L
         K  I  T  I  R  F  Q  K  N  S  F  I  F  G  N  F  T  N  S  T

18421  ACCCAACCAAAACTACAACTCCCGCGAGTACGATGAGCGCTTTTGTAACCTTGTTTGAAA  18480
        Q  T  P  K  S  T  S  P  A  *  A  V  R  S  F  M  P  V  F  K
       N  P  Q  N  Q  H  Q  P  R  E  H  *  E  R  F  C  Q  F  L  S
         P  N  T  K  I  N  L  A  S  M  S  S  A  F  V  N  S  C  V  K

18481  GGTGACGTTTATCCAAAAAGTTGACCACACCTAAAACATCAACTTCGATGACCGAATAAA  18540
        G  S  C  I  P  K  E  V  P  T  S  K  T  T  S  A  V  P  K  N
       E  V  A  F  L  N  K  L  Q  H  P  N  Q  L  Q  L  *  Q  S  I
         W  Q  L  Y  T  K  *  S  T  H  I  K  Y  N  F  S  S  A  *  K

18541  CGACTCTCTCTAACAATATGAAAATTTTTTTGACATCGATTTCGAGGAGGACCACTTTTT  18600
        A  S  L  S  Q  *  V  K  L  F  V  T  A  L  A  G  G  P  S  F
       Q  Q  S  L  N  N  Y  K  *  F  F  Q  L  *  L  E  E  Q  H  F
         S  L  S  I  T  I  S  K  F  F  S  Y  S  F  S  R  R  T  F  F

18601  AAATTTGTAAATTATGGGGAATACAGTTTTCCAGTTTTCACCCTATAACAATCTTAATCT  18660
        N  L  C  K  I  G  R  I  D  F  P  *  F  H  S  I  T  L  I  L
       I  *  V  N  L  V  G  *  T  L  L  D  F  T  P  Y  Q  *  F  *
         K  F  M  *  Y  G  K  H  *  F  T  L  L  P  I  N  N  S  N  S

18661  TAACAAGTTTACAATAGACTAATAGAAAATCTGGAAAGACTATCACATCATAAATAATGA  18720
        I  T  *  I  N  D  S  *  R  K  S  R  E  S  L  T  T  N  I  V
       F  Q  E  F  T  I  Q  N  D  K  L  G  K  Q  Y  H  L  I  *  *
         N  N  L  H  *  R  I  I  K  *  V  K  R  I  T  Y  Y  K  N  S

18721  ACCAGACGGTCAAAACTTGAATGAACAAATTCCATAAAACGATTTAATCCGTCTCTCGAA  18780
        Q  D  A  L  K  S  S  V  Q  K  L  Y  K  A  L  N  P  L  S  S
       K  T  Q  W  N  Q  V  *  K  N  L  T  N  Q  *  I  L  C  L  A
         P  R  G  T  K  F  K  S  T  *  P  I  K  S  F  *  A  S  L  K

18781  TTAACATTACACACAAGATTAGCACGATGTACGATGTTAAGATCTTGACCAATAATACCA  18840
        L  Q  L  T  H  E  L  R  A  V  H  *  L  E  L  V  P  *  *  P
       *  N  Y  H  T  N  *  D  H  *  M  S  C  N  *  F  Q  N  N  H
         I  T  I  H  T  R  I  T  S  C  A  V  I  R  S  S  T  I  I  T

18841  ACAACCGCGGTATCAATATGAACACTAATACACATATTAGGTGAATAACATCTATATGTT  18900
        Q  Q  R  W  L  *  V  Q  S  *  T  Y  L  G  S  I  T  S  I  C
       N  N  A  G  Y  N  Y  K  H  N  H  T  Y  D  V  *  Q  L  Y  V
         T  P  A  M  T  I  S  T  I  I  H  I  I  W  K  N  Y  I  Y  L
```

FIG. 3 CONT'D

18901 GTCACCCCAATATGTCCAAGAAATTGATCATTAGTGCTATATTAAACATTACATGTATTT 18960
C H P * V P E K V L L * S I I Q L T C L
V T P N Y L N K L * Y D R Y L K Y H V Y
L P T I C T R * S T I V I Y N T I Y M F

18961 CCACGTGTACAACGCAGTCGACTACGTTAATACTGAGCAACAAATCGTTAGATACTAACA 19020
P A C T A D A S A I I V R Q K A I * S Q
L H V H Q T L Q H L * S E N N L L R H N
T C M N R * S I C N H S T T * C D I I T

19021 AAAACATTTAGACAATTAACCTTAAATCTCATAGGTTATTAAAGATTACTCCAGTCATAT 19080
K Q L D T L Q F K S Y G I I E L S T L I
N K Y I Q * N S N L T D L L K * H P * Y
K T F R N I P I * L I W Y N R I L D T Y

19081 TTATGTAGAACATCCAATAACGTCGCACAGTACGAATTTCGACGGTACGATACATTATCT 19140
F V D Q L N N C R T M S L A A M S H L L
L Y M K Y T I A A H * A * L Q W A I Y Y
I C R T P * Q L T D H K F S G H * T I S

19141 ATGTTGAATACAATACTGTATCCGTTAGGATTTCCAAATCGAACACAGTTTCTAATACTT 19200
Y L K H * S M P L G L P K A Q T L S * S
I C S I N H C L C D * L N L K H * L N H
V V * T I V Y A I R F T * S T D F I I F

19201 AAATTTAAAATACTACGAAAAGGACATCGGTTCAGACAATTTGTCAATAAAATACAGATA 19260
N L N * S A K G T A L D T L C N N * T *
I * I K H H K E Q L W T Q * V T I K H R
K F K I I S K R Y G L R N F L * K I D I

19261 CTACACGTATTTCTATTAAAATTTCTACCAAATACATACAAAACCTTAACATTACAACTA 19320
S T C L S L K L S P K H I N Q F Q L T S
H H A Y L Y N * L H N I Y T K S N Y H Q
I H M F I I K F I T * T H K P I T I N I

19321 TTTATAGGTAGATTAAGTTAACAAACATCTAAACTGTGAGCTCACAATTTATTTAATTTG 19380
L Y G D L E I T Q L N S V R T N F L N F
Y I D M * N L Q K Y I Q C E L T L Y I L
F I W R I * N N T S K V S S H * I F * V

19381 GAAGGACCTACATTACCACCATCAAACATACAATTATTTGTACGTAAGGTATGATTAGGA 19440
R G P H L P P L K Y T L L C A N W V L G
G E Q I Y H H Y N T H * Y V H M G Y * D
K R S T I T T T Q I N I F M C E M S I R

FIG. 3 CONT'D

```
19441  AAATGATCTTGACAAAAACTTTTAGAATTCGGATACGGAAAAAAGATAATAAGTCTATGC  19500
        K  V  L  V  T  K  S  F  R  L  G  I  G  K  K  *  *  E  S  V
       K  *  *  F  Q  K  Q  F  D  *  A  *  A  K  K  R  N  N  L  Y
         K  S  S  S  N  K  F  I  K  L  R  H  R  K  E  I  I  *  I  R

19501  GGAACACACATGCATCTACCAAATCTTAGATTTGTTCAACTAATGCAAGGAAATTCTTCG  19560
        G  Q  T  Y  T  S  P  K  S  D  L  C  T  S  *  T  G  K  L  L
       A  K  H  T  R  L  H  N  L  I  *  V  L  Q  N  R  E  K  L  F
         R  T  H  V  Y  I  T  *  F  R  F  L  N  I  V  N  R  *  S  A

19561  CGGTGAACATAGTGTGCCACATTAGATCCACCTCGACAAACAAGTTTCGTACGACTTCTT  19620
        A  V  Q  I  V  R  H  L  R  P  P  A  T  Q  E  F  C  A  S  S
       R  W  K  Y  *  V  T  Y  D  L  H  L  Q  K  N  L  A  H  Q  L
         G  S  T  D  C  P  T  I  *  T  S  S  N  T  *  L  M  S  F  F

19621  ATAACATTGATGGAACTCAGAATATTATATCAATGATGTCGTCCGAAATGAAAAACCCAA  19680
        Y  Q  L  *  R  S  D  *  L  I  T  V  V  A  P  K  V  K  Q  T
       I  N  Y  S  G  Q  T  K  Y  Y  L  *  *  L  L  S  *  K  K  P
         I  T  V  V  K  L  R  I  I  Y  N  S  C  C  A  K  S  K  P  N

19681  ATATTCTTAAAACTAAAAATATTAAATACCTTGTGAAAATGATGCAATGTCTCAAATCTT  19740
        *  L  F  K  S  K  *  L  K  H  F  V  K  V  V  N  C  L  K  S
       K  Y  S  N  Q  N  K  Y  N  I  S  C  K  *  *  T  V  S  N  L
         I  L  I  K  I  K  I  I  *  P  V  S  K  S  R  *  L  T  *  F

19741  TTGCATTATATATTGAACCAATTACAACCAGTAATACTACCTGCATGTCCACTTAATGGA  19800
        F  T  I  Y  L  K  T  L  T  P  *  *  S  P  R  V  P  S  N  G
       F  R  L  I  Y  S  P  *  H  Q  D  N  H  H  V  Y  L  H  I  V
         V  Y  Y  I  V  Q  N  I  N  T  M  I  I  S  T  C  T  F  *  R

19801  ACACGATAATACTTACTGTTTCAACAACAATTCTAATTATTACATCTATGACAATAAAAA  19860
        Q  A  I  I  F  S  L  T  T  T  L  I  L  L  T  S  V  T  I  K
       K  H  *  *  S  H  C  L  Q  Q  *  S  *  Y  H  L  Y  Q  *  K
         T  S  N  H  I  V  F  N  N  N  L  N  I  I  Y  I  S  N  N  K

19861  TTTTTATTATGTAGTAAAGGATGATTATATCGACAACTTAACAAATGTTTTGCATCATAG  19920
        L  F  L  V  D  N  G  V  L  I  A  T  S  N  N  V  F  R  L  I
       *  F  Y  Y  M  M  E  *  *  Y  L  Q  Q  I  T  *  L  V  Y  Y
         F  I  I  C  *  K  R  S  I  Y  S  N  F  Q  K  C  F  T  T  D

19921  GCCGTGGTGGGACTTGAATTCTAAGAATCTTTAAACTTGTAACTATAAACAACCTTCGTA  19980
        R  C  W  G  S  S  L  I  R  L  F  K  F  M  S  I  Q  Q  F  C
       G  A  G  G  Q  V  *  S  E  *  F  N  S  C  Q  Y  K  N  S  A
         P  V  V  R  F  K  L  N  K  S  I  Q  V  N  I  N  T  P  L  M
```

FIG. 3 CONT'D

```
19981 CAGGACACCCTAATACAATTTCTATCAAACAAAACATCAAGGTGAATACCACAAACATTT 20040
       T  R  H  S  *  T  L  S  L  K  N  Q  L  E  V  *  P  T  Q  L
      H  G  T  P  N  H  *  L  Y  N  T  K  Y  N  W  K  H  H  K  Y
        D  Q  P  I  I  N  F  I  T  Q  K  T  T  G  S  I  T  N  T  F

20041 ATGTGTCTAAACTTCAAGTAGCTTTTAAACTTATATGAAAAACTACCAGCACTGTGACCG 20100
       Y  V  S  K  F  N  M  S  F  K  F  I  S  K  S  P  R  S  V  P
      I  C  L  N  S  T  *  R  F  N  S  Y  V  K  Q  H  D  H  C  Q
        V  C  I  Q  L  E  D  F  I  Q  I  Y  K  K  I  T  T  V  S  A

20101 CGAAATCTTCGAAAATCTTTTCGTTCTTTACCACAAAAATAATCATGACTTTTTAATTCA 20160
       A  K  S  A  K  L  F  A  L  F  P  T  K  I  L  V  S  F  N  L
      R  K  L  L  K  *  F  L  L  F  H  H  K  *  *  Y  Q  F  I  L
        S  *  F  S  K  S  F  C  S  I  T  N  K  N  T  S  F  F  *  T

20161 TCCAATAGTTACTAATTTCCAGGCGTTGCTCGACTAAATTTACCACACTAACACCTATTT 20220
       L  N  D  I  I  L  P  G  C  R  A  S  K  F  P  T  I  T  S  L
      Y  T  I  L  S  *  L  D  A  V  L  Q  N  L  H  H  S  Q  P  Y
        P  *  *  H  N  F  T  R  L  S  S  I  *  I  T  H  N  H  I  F

20221 CAACCTCTTGAGTTTCAACTCAAAACCAAGCGATACTCTTTTCTACCACTGCTACAATAG 20280
       T  P  S  S  L  T  S  N  Q  N  A  I  L  F  S  P  S  S  T  I
      L  Q  L  V  *  L  Q  T  K  T  R  *  S  F  L  H  H  R  H  *
        N  S  F  E  F  N  L  K  P  E  S  H  S  F  I  T  V  I  N  D

20281 AAGTCGGCTTGTCTGTCGGATACGAGTTCGGTAATGACCTCGGGTGTTCCATTAGATCCA 20340
       K  L  R  V  S  L  R  H  E  L  W  *  Q  L  G  C  P  L  R  P
      R  *  G  F  L  C  G  I  S  L  G  N  S  S  G  V  L  Y  D  L
        E  A  S  C  V  A  *  A  *  A  M  V  P  A  W  L  T  I  *  T

20341 CCATTAACGCGCCCATTACAGTAACCATTACTACGAGATTGTGCAAAATGATAGAAATGA 20400
       P  L  Q  A  P  L  T  M  P  L  S  A  R  V  R  K  V  I  K  V
      H  Y  N  R  P  Y  H  *  Q  Y  H  H  E  L  V  N  *  *  R  *
        T  I  A  R  T  I  D  N  T  I  I  S  *  C  T  K  S  D  K  S

20401 GTCTCAGCACATAACAGTTCAAAACTTGGAGCGAGTCTAAATCTTGCCCTAAAATAACTA 20460
       *  L  R  T  N  D  L  K  S  G  R  E  S  K  S  R  S  K  I  S
      E  S  D  H  I  T  L  N  Q  V  E  S  L  N  L  V  P  N  *  Q
        L  T  T  Y  Q  *  T  K  F  R  A  *  I  *  F  P  I  K  N  I

20461 TACCTACTATTAGACAAATAACGATTTATACCAAATCTTCTGATACGTAAACTAGTATAT 20520
       I  S  S  L  R  N  I  A  L  Y  P  K  S  S  *  A  N  S  *  I
      Y  P  H  Y  D  T  *  Q  *  I  H  N  L  L  S  H  M  Q  D  Y
        H  I  I  I  Q  K  N  S  F  I  T  *  F  V  I  C  K  I  M  Y
```

FIG. 3 CONT'D

```
20521 CAAATACCATCAAAATTGGTATTTCAATATCCTCCAAACGTAAACGAATATCCGAATAAA 20580
       T  *  P  L  K  L  W  L  T  I  P  P  K  C  K  S  I  P  K  N
      L  K  H  Y  N  *  G  Y  L  *  L  L  N  A  N  A  *  L  S  I
        N  I  T  T  K  V  M  F  N  Y  S  T  Q  M  Q  K  Y  A  *  K

20581 GCATCCTTTTTTTTTAGATTAAACAATTAAGTTCTCAAAAATGTCATACTAAGATCATAA 20640
       R  L  F  F  F  D  L  K  N  I  *  S  N  K  C  Y  S  E  L  I
      E  Y  S  F  F  I  *  N  T  L  E  L  T  K  V  T  H  N  *  Y
        T  P  F  F  F  R  I  Q  *  N  L  L  K  *  L  I  I  R  T  N

20641 GTAAGTATAAAATAATGACTAGTCCTCACACCATCATCATTCTCACAAACATGTCAATAA 20700
       *  E  Y  K  I  V  S  *  S  H  P  L  L  L  L  T  Q  V  T  I
      E  N  M  N  *  *  Q  D  P  T  H  Y  Y  Y  S  H  K  Y  L  *
        M  *  I  K  N  S  I  L  L  T  T  T  T  L  T  N  T  C  N  N

20701 CTAAATAATAATCTACTAAAACAAAGATAACAATTCAGTAATTTAAACTCAACACAATCA 20760
       S  K  N  N  S  S  K  T  E  I  T  L  D  N  F  K  L  Q  T  L
      Q  N  I  I  L  H  N  Q  K  *  Q  *  T  M  L  N  S  N  H  *
        I  *  *  *  I  I  K  N  R  N  N  L  *  *  I  Q  T  T  N  T

20761 TTTCAACAATTATAATTACAACTAAAATTCCTAAAAGTTAAATACAACACCACATTACTA 20820
       L  T  T  L  I  L  T  S  K  L  S  K  *  N  I  N  H  H  L  S
      Y  L  Q  *  Y  *  H  Q  N  *  P  N  E  I  *  T  T  T  Y  H
        F  N  N  I  N  I  N  I  K  L  I  K  L  K  H  Q  P  T  I  I

20821 TTATTTTAATACTGAAAAATAGGATTTTACGTTCGGTGATTACTAACCTTTGGACCGATA 20880
       L  L  I  I  V  K  *  G  L  I  C  A  V  L  S  Q  F  G  P  *
      Y  Y  F  *  S  K  K  D  *  F  A  L  W  *  H  N  S  V  Q  S
        I  F  N  H  S  K  I  R  F  H  L  G  S  I  I  P  F  R  A  I

20881 AGATACGGACAAAACATATTCATAAACTTACAAGGTAATCTCTCTCAGAGAAATACCTTA 20940
       E  I  G  T  K  Y  L  Y  K  F  T  G  N  S  L  T  E  K  H  F
      N  *  A  Q  K  T  Y  T  N  S  H  E  M  L  S  L  R  K  I  S
        R  H  R  N  Q  I  L  I  Q  I  N  W  *  L  S  D  R  *  P  I

20941 ATACCATTTGGATAATTAAACGGATGTCCGACATACTACTTACAACGATTCATGTGAGTT 21000
       *  P  L  G  I  L  K  G  V  P  Q  I  I  F  T  A  L  Y  V  *
      N  H  Y  V  *  *  N  A  *  L  S  Y  S  S  H  Q  *  T  C  E
        I  T  F  R  N  I  Q  R  C  A  T  H  H  I  N  S  L  V  S  L

21001 AATACAGTCATAAACTTATGATGTTGTAATCGACAAGGACAATTATACGCACAAAATGTA 21060
       N  H  *  Y  K  F  V  V  V  N  A  T  G  T  L  I  R  T  K  C
      I  I  D  T  N  S  Y  *  L  M  L  Q  E  Q  *  Y  A  H  K  V
        *  T  L  I  Q  I  S  C  C  *  S  N  R  N  I  H  T  N  *  M
```

FIG. 3 CONT'D

```
21061 AATCCACGTCCCAGACTATTTCTTCATCGAGGTCCAAGACGACAAAATTCTGTCACCAAT 21120
       K  P  A  P  D  S  L  S  T  A  G  P  E  A  T  K  L  C  H  N
      N  L  H  L  T  Q  Y  L  L  L  E  L  N  Q  Q  K  L  V  T  T
        *  T  C  P  R  I  F  F  Y  S  W  T  R  S  N  *  S  L  P  *

21121 GGTAGACCATCATAAGAACATCTATTACTAAATTTGGGTAAACAATCGCTATCAAATCAA 21180
       G  D  P  L  I  R  T  S  L  S  K  F  G  N  T  L  S  L  K  T
      V  M  Q  Y  Y  E  Q  L  Y  H  N  L  G  M  Q  *  R  Y  N  L
        W  R  T  T  N  K  Y  I  I  I  *  V  W  K  N  A  I  T  *  N

21181 TGAATAAAACCTCTAACATACTGAAATGGTAAACTAACAGTAACCCTAAACTATTATAGA 21240
       V  *  K  P  S  Q  I  V  K  G  N  S  Q  *  Q  S  K  I  I  D
      *  K  N  Q  L  N  Y  S  K  V  M  Q  N  D  N  P  N  S  L  I
        S  I  K  S  I  T  H  S  *  W  K  I  T  M  P  I  Q  Y  Y  R

21241 CTATACATACTAGGAGAATGATTTTTATAACCACTAATATTACACTCATTCCTACCCAAA 21300
       S  I  Y  S  G  R  V  L  F  I  P  S  *  L  T  L  L  S  P  N
      Q  Y  T  H  D  E  *  *  F  Y  Q  H  N  Y  H  S  Y  P  H  T
        I  H  I  I  R  K  S  F  I  N  T  I  I  I  H  T  L  I  P  K

21301 AAATGAATGTAAACAGTAAATTAAGCACTATTTAATAGAAACCCACCATCACATCGATAT 21360
       K  V  *  M  Q  *  K  I  R  S  L  N  D  K  P  P  L  T  A  I
      K  *  K  C  K  D  N  L  E  H  Y  I  I  K  P  H  Y  H  L  *
        K  S  V  N  T  M  *  N  T  I  F  *  R  Q  T  T  T  Y  S  Y

21361 TTTTAATGTCTCAAAAGAACCTTACGACTAAATATATTTAATTACTCAACAAAACGTAAA 21420
       F  I  V  S  N  E  Q  F  A  S  K  Y  L  N  I  L  Q  K  A  N
      L  F  *  L  T  K  K  S  H  Q  N  I  Y  I  L  S  N  N  Q  M
        F  N  C  L  K  R  P  I  S  I  *  I  F  *  H  T  T  K  C  K

21421 ACCTGTCAAAAAACATGATTACATTTACGAAGAAGATCACTTCCCAAAAATTATCCATAT 21480
       Q  V  T  K  Q  V  L  T  F  A  E  E  L  S  P  N  K  I  P  I
      K  S  L  K  K  Y  *  H  L  H  K  K  *  H  L  T  K  L  L  Y
        P  C  N  K  T  S  I  Y  I  S  R  R  T  F  P  K  *  Y  T  Y

21481 TTAATGGACCCATTTAGAAGAAAACTTTATCTACCGTTACAATACGTACGATTGATAAAC 21540
       F  *  R  P  L  D  E  K  S  I  S  P  L  T  I  C  A  L  *  K
      L  N  G  P  Y  I  K  K  Q  F  L  H  C  H  *  A  H  *  S  N
        I  V  Q  T  F  R  R  K  F  Y  I  A  I  N  H  M  S  V  I  Q

21541 AAAACCTCTTTATCATGTTGTACCTTACCGCCACGAATATCAAATAAACTATACTGATTT 21600
       N  Q  L  F  L  V  V  H  F  P  P  A  *  L  K  N  S  I  V  L
      T  K  S  F  Y  Y  L  M  S  H  R  H  K  Y  N  I  Q  Y  S  *
        K  P  S  I  T  C  C  P  I  A  T  S  I  T  *  K  I  H  S  F
```

FIG. 3 CONT'D

```
21601  AAAAGAAACTTTAACCGACCGTGACGACAACAATTAAATTCTGGTCTAGTTAATTTACTA  21660
        N  E  K  F  N  A  P  V  A  T  T  L  K  L  G  S  *  N  F  S
       I  K  K  S  I  P  Q  C  Q  Q  Q  *  N  L  V  L  D  I  L  H
         K  R  Q  F  Q  S  A  S  S  N  N  I  *  S  W  I  L  *  I  I

21661  AATCAAATAAGAGAATAACTTTCTCCATTTAATAATCAAGCGCTATGCGCATTTCTCTAA  21720
        K  T  *  E  R  I  S  L  P  L  N  N  T  R  S  V  R  L  S  I
       N  L  K  N  E  *  Q  F  L  Y  I  I  L  E  R  Y  A  Y  L  S
         *  N  I  R  K  N  F  S  T  F  *  *  N  A  I  R  T  F  L  N

21721  AAACAACCACTATCAGAACATTTATGAACAATCTAGAGTAATTTAGATTTGATACAATTA  21780
        K  T  P  S  L  R  T  F  V  Q  *  I  E  N  F  R  F  *  T  L
       K  Q  Q  H  Y  D  Q  L  Y  K  N  S  R  M  L  D  L  S  H  *
         K  N  T  I  T  K  Y  I  S  T  L  D  *  *  I  *  V  I  N  I

21781  ATAAAAAAATAAAAAAATAAAGACAATACCAAAATTACTTGGAGAATTACAACACAGAGT  21840
        *  K  K  I  K  K  N  R  N  H  N  *  H  V  E  *  H  Q  T  E
       N  N  K  *  K  K  I  E  T  I  T  K  I  F  R  K  I  N  H  R
         I  K  K  N  K  *  K  Q  *  P  K  L  S  G  R  L  T  T  D  *

21841  AAATTTGGTACTGACCAAAAATAAACCACTATCAGCAAGACTAACATTGGTATAATTATT  21900
        N  L  G  H  S  T  K  I  Q  H  Y  D  N  Q  N  Y  G  Y  *  Y
       M  *  V  M  V  P  K  *  K  T  I  T  T  R  I  T  V  M  N  I
         K  F  W  S  Q  N  K  N  P  S  L  R  E  S  Q  L  W  I  L  L

21901  AAATTTTTAATTTTTAAAACTAATAAACCTATAAGTGGGATCAAACACGTTGTTACCATT  21960
        N  L  F  *  F  N  Q  N  N  P  Y  E  G  *  N  T  C  C  H  Y
       I  *  F  N  F  I  K  I  I  Q  I  N  V  R  T  Q  A  V  I  T
         K  F  I  L  F  K  S  *  K  S  I  *  G  L  K  H  L  L  P  L

21961  CTAAAGTAGATCACGGCCACTAAGATAAAAATTCTCAAAAGTAAAGTGAGCTAAAATATT  22020
        S  K  M  *  H  R  H  N  *  K  *  S  N  E  N  *  E  I  K  Y
       L  N  *  R  T  G  T  I  R  N  K  L  T  K  M  E  S  S  K  I
         I  E  D  L  A  P  S  E  I  K  L  L  K  *  K  V  R  N  *  L

22021  AATGTGACCGCTTCCACTAGTTTAATAAAAAATACTCCCACAATTAAAATTAGGAATAGT  22080
        N  C  Q  R  L  H  D  F  *  K  K  H  P  H  *  N  *  D  K  D
       I  V  S  A  F  T  I  L  N  N  K  I  L  T  N  I  K  I  R  I
         *  V  P  S  P  S  *  I  I  K  *  S  P  T  L  K  L  G  *  *

22081  ATCTAAATTCACAAAAGGATTACCATCATTACTACATACCGAAGAATTGTTCCATTCTAA  22140
        Y  I  *  T  N  E  *  H  Y  Y  H  H  I  A  E  *  C  P  L  I
       M  S  K  L  T  K  R  I  T  T  I  I  Y  P  K  K  V  L  Y  S
         L  N  L  H  K  G  L  P  L  L  S  T  H  S  R  L  L  T  L  N
```

FIG. 3 CONT'D

```
22141  AATAGCACGGAATATAAGATTATACCGGAAAAAAGCAATAGAATGAAAACAACTATAAGG  22200
        K  D  H  R  I  N  *  Y  P  R  K  E  N  D  *  K  Q  Q  Y  E
       K  I  T  G  *  I  R  I  H  G  K  K  T  I  K  S  K  N  I  N
         *  R  A  K  Y  E  L  I  A  K  K  R  *  R  V  K  T  S  I  G

22201  AATATTACAAAGAGAAAGATTCAAATTAAGAACATTTTCACTATAAAATAGTGAATTGTT  22260
        K  Y  H  K  E  K  *  T  *  N  K  Y  F  H  Y  K  I  V  *  C
       R  I  I  N  R  K  R  L  K  I  R  T  F  T  I  N  *  *  K  V
         *  L  T  E  R  E  L  N  L  E  Q  L  L  S  I  K  D  S  L  L

22261  AGGATAAAAATAATTAATAAGATTCCTTCAAATAAAATGAAATAATCCAACAAGAGAAAT  22320
        D  *  K  *  *  N  N  *  P  L  K  N  *  K  I  L  N  N  E  K
       I  R  N  K  N  I  I  R  L  F  N  I  K  S  *  *  T  T  R  K
         G  I  K  I  L  *  E  L  S  T  *  K  V  K  N  P  Q  E  R  *

22321  AAATCATGGCGAAACGGAAAAATTTAGATTGAAATCAGTCATGATAATATTGTATCTATG  22380
        N  L  V  A  K  G  K  *  I  *  S  *  D  T  S  N  Y  C  L  Y
       I  *  Y  R  K  A  K  K  F  R  V  K  T  L  V  I  I  V  Y  I
         K  T  G  S  Q  R  K  L  D  L  K  L  *  Y  *  *  L  M  S  V

22381  ACCGAGACAAATACCAAAAAGATTACAACAAATAGGACTAAATCTGACATAAATATAAAG  22440
        Q  S  Q  K  H  N  K  *  H  Q  K  D  Q  N  L  S  Y  K  Y  K
       S  A  R  N  I  T  K  R  I  N  N  I  R  I  *  V  T  N  I  N
         P  E  T  *  P  K  E  L  T  T  *  G  S  K  S  Q  I  *  I  E

22441  AGAATTTGGTCCAAGAATATTTCAAAGGTGGTGACGTGGAAAAAATAGGAATGGATGATT  22500
        E  *  V  L  N  K  Y  L  K  W  W  Q  V  K  K  I  R  V  *  *
       R  K  F  W  T  R  I  F  N  G  G  S  C  R  K  *  G  *  R  S
         R  L  G  P  E  *  L  T  E  V  V  A  G  K  K  D  K  G  V  L

22501  TCGAGAGACAAAACTATTTAGATTTGTTAAACATGGACATGTCCAACAACTAAGATCTAC  22560
        L  E  R  N  Q  Y  I  *  V  I  Q  V  Q  V  P  Q  Q  N  *  I
       F  S  E  T  K  I  F  R  F  L  K  Y  R  Y  L  N  N  I  R  S
         A  R  Q  K  S  L  D  L  C  N  T  G  T  C  T  T  S  E  L  H

22561  CTTGTTGCTCGCACGGAGTCTATAAAGAAATAGACAACGTACAGTTAACGGTATAACAAT  22620
        S  C  R  A  H  R  L  Y  K  K  I  Q  Q  M  D  I  A  M  N  N
       P  V  V  L  T  G  *  I  N  R  *  R  N  C  T  L  Q  W  I  T
         F  L  S  R  A  E  S  I  E  K  D  T  A  H  *  N  G  Y  Q  *

22621  AAAAGCGTTAAGAAGACGATTAATACAACCGTTCATACTATAATTGGTGCCACTATCACC  22680
        N  E  C  N  K  Q  *  N  H  Q  C  T  H  Y  *  G  R  H  Y  H
       I  K  A  I  R  R  S  I  I  N  A  L  I  I  N  V  V  T  I  T
         K  R  L  E  E  A  L  *  T  P  L  Y  S  I  L  W  P  S  L  P
```

FIG. 3 CONT'D

```
22681 AAAATAAAGATAAAATAGACCAGAAAATATATTACAAAGAACATAAAGTATAATACCACA 22740
       N  *  K  *  K  I  Q  D  K  I  Y  H  K  K  Y  K  M  N  H  H
      T  K  N  R  N  *  R  T  K  *  I  I  N  R  T  N  *  I  I  T
        K  I  E  I  K  D  P  R  K  Y  L  T  E  Q  I  E  Y  *  P  T

22741 TAAAAATATACTATTAAAATGTAGGTAAACCGGGATAATAAGAAAACCATCCACAGGATG 22800
       I  K  I  H  Y  N  *  M  W  K  A  R  N  N  K  Q  Y  T  D  *
      Y  K  *  I  I  I  K  C  G  N  P  G  I  I  R  K  T  P  T  R
        N  K  Y  S  L  K  V  D  M  Q  G  *  *  E  K  P  L  H  G  V

22801 TAGAAGATAATAATTTGTAGGTTAAACACAAATACTAAAAAACGGATAATAAAATGTTCC 22860
       M  K  *  *  *  V  D  L  K  H  K  H  N  K  A  *  *  K  V  L
      C  R  R  N  N  F  M  W  N  T  N  I  I  K  Q  R  N  N  *  L
        D  E  I  I  L  C  G  I  Q  T  *  S  K  K  G  I  I  K  C  P

22861 ATAAAATAATACAAATCGAAATGAAAAACAACAAAAAGATAATAAAAACAATATATTGCT 22920
       Y  K  I  I  N  L  K  V  K  Q  Q  K  E  I  I  K  T  I  Y  R
      T  N  *  *  T  *  S  *  K  K  N  N  K  *  *  K  Q  *  I  V
        I  K  N  H  K  A  K  S  K  T  T  K  R  N  N  K  N  Y  L  S

22921 ATTTAGAGTAATTTAGATTTGTACAATAATTAATAAAAATAAAACGGATGTTGTAATCGA 22980
       Y  I  E  N  F  R  F  M  N  N  I  I  K  I  K  G  V  V  N  A
      I  F  R  M  L  D  L  C  T  I  L  *  K  *  K  A  *  L  M  L
        L  D  *  *  I  *  V  H  *  *  N  N  K  N  Q  R  C  C  *  S

22981 CAATATCCACTAAAATTAACATGATTAAAACGATAATTACTAAATTTGTGGTGTCAAGGA 23040
       T  I  P  S  K  L  Q  V  L  K  A  I  L  S  K  F  V  V  T  G
      Q  *  L  H  N  *  N  Y  *  N  Q  *  *  H  N  L  C  W  L  E
        N  Y  T  I  K  I  T  S  I  K  S  N  I  I  *  V  G  C  N  R

23041 GCGTATTCACTCATACAACACCTACAAAGAATACCAAACCCATGTATAATATATGAACTA 23100
       R  M  L  S  Y  T  T  S  T  E  *  P  K  P  V  Y  *  I  S  S
      E  C  L  H  T  H  Q  P  H  K  K  H  N  P  Y  M  N  Y  V  Q
        A  Y  T  L  I  N  H  I  N  R  I  T  Q  T  C  I  I  Y  K  I

23101 GCACAAATAAATTTATGATGATATAATAAATGACCAATAAAGGGATTTAGACCACGGTTA 23160
       R  T  *  K  F  V  V  I  N  N  V  P  *  K  G  L  D  P  A  L
      D  H  K  N  L  Y  *  *  I  I  *  Q  N  N  G  *  I  Q  H  W
        T  N  I  *  I  S  S  Y  *  K  S  T  I  E  R  F  R  T  G  I

23161 AAATCCCTAGATAGAAATTTTCCATGATGTATAAACTCATGAGAAACCATAGTCTTTGGG 23220
       K  L  S  R  D  K  F  P  V  V  Y  K  L  V  R  Q  Y  *  F  G
      N  *  P  D  I  K  L  L  Y  *  M  N  S  Y  E  K  T  D  S  V
        K  P  I  *  R  *  F  T  S  C  I  Q  T  S  K  P  I  L  F  G
```

FIG. 3 CONT'D

23221 AAAAATAGACTAAAATTATTACCATAAAAAAGATCTCAATTCTTATGATTCAACATACAA 23280
K K D S K L L P I K E L T L F V L N Y T
R K I Q N * Y H Y K K * L * S Y * T T H
K * R I K I I T N K R S N L I S L Q I N

23281 TTATTTTGAAACATATCACTCAAATCATGATATCAATATCCATCACAAAAATAATTGTTG 23340
L L V K Y L S N L V I T I P L T K I L L
* Y F K T Y H T * Y * L * L Y H K * * C
I F S Q I T L K T S Y N Y T T N K N V V

23341 AGAATATGATAACAACAAGTTGGAGTATTACCACAAAACCTCTAATGTCGAACAGTTATG 23400
E * V I T T * G * L P T K S I V A Q * Y
S K Y * Q Q E V E Y H H K P S * L K D I
R I S N N N L R M I T N Q L N C S T L V

23401 TGATACACACTCATAGGAGTATGATAAACATTTAGATTTCCATCAAGAGCATTACTTAGA 23460
V I H S Y G * V I Q L D L P L E R L S D
C * T H T D E Y * K Y I * L Y N E Y H I
S H T L I R M S N T F R F T T R T I F R

23461 ACCGTAAAACTATTTAGACTTGGAAACACAGACAAGTTCTTTTTAAAATGAATATTACAA 23520
Q C K S L D S G K H R N L F F K V * L T
K A N Q Y I Q V K T D T * S F N * K Y H
P M K I F R F R Q T Q E L F I K S I I N

23521 AGATGTCTAACCAACATAAAAGTAAAAATAGTTCTTGCACCGTGAAAAATACGAATAATA 23580
E V S Q N Y K * K * * S R P V K * A * *
K * L N T T N E N K D L V H C K K H K N
R C I P Q I K M K I L F T A S K I S I I

23581 CGACTAAGACCGTACGGATGATGAAAAAATAAATCAAACATAGAACCATGAGAAAATAGA 23640
A S E P M G V V K K N L K Y R P V R K D
H Q N Q C A * * K K I * N T D Q Y E K I
S I R A H R S S K * K T Q I K T S K * R

23641 GTAATAATACAAAACGGAAACTGAACATTACGATATAGAAGATTATGACTATTACTCTGA 23700
* * * T K G K V Q L A I D E L V S L S V
E N N H K A K S K Y H * I K * Y Q Y H S
M I I N Q R Q S T I S Y R R I S I I L S

23701 AATGTTATAACCCAGTGTGGAAACAGATTTGCGGTTATAGAAGAATTTAAACTGTTGGCA 23760
K C Y Q T V G K D L R W Y R R L N S L R
K V I N P * V K T * V G I D E * I Q C G
* L I P D C R Q R F A L I K K F K V V T

FIG. 3 CONT'D

```
23761  CCACAATAATGATTACGACAACTAACAAGATCATCAAAGAAATCGCTCTAAGTTACATTT  23820
        P  T  I  V  L  A  T  S  Q  E  L  L  K  K  L  S  I  *  H  L
       H  H  *  *  *  H  Q  Q  N  N  *  Y  N  R  *  R  S  E  I  Y
         T  N  N  S  I  S  N  I  T  R  T  T  E  K  A  L  N  L  T  F

23821  TGATTTAGAAATAATGGATTATGACCACAAATACTGAATAGACCAAAATGACAATTCGGA  23880
        V  L  D  K  N  G  L  V  P  T  *  S  K  D  P  K  V  T  L  G
       F  *  I  K  I  V  *  Y  Q  H  K  H  S  I  Q  N  *  Q  *  A
         S  F  R  *  *  R  I  S  T  N  I  V  *  R  T  K  S  N  L  R

23881  CAACGTTGACATGTAGCAGCATAAGGACTAAATGGACTAACACTGTAACTATTTACCGAA  23940
        T  A  V  T  C  R  R  I  G  S  K  G  S  Q  S  M  S  L  H  S
       Q  Q  L  Q  V  D  D  Y  E  Q  N  V  Q  N  H  C  Q  Y  I  A
         N  C  S  Y  M  T  T  N  R  I  *  R  I  T  V  N  I  F  P  K

23941  TTGTTAAAATTACATGGGAGTGGAGAATTAACCCTTGCATTTTAAAAAAGATTAACGTTG  24000
        L  L  K  L  T  G  E  G  R  L  Q  S  R  L  I  K  E  L  Q  L
       *  C  N  *  H  V  R  V  E  *  N  P  V  Y  F  K  K  *  N  C
         V  I  K  I  Y  G  *  R  K  I  P  F  T  F  N  K  R  I  A  V

24001  AAATTAAACTCATGAAACGAAGCAAATCAAGTATGACTAAGAAAAAGAACATTATTAAAA  24060
        K  L  K  L  V  K  S  R  K  T  *  V  S  E  K  E  Q  L  L  K
       S  *  N  S  Y  K  A  E  N  L  E  Y  Q  N  K  K  K  Y  Y  N
         K  I  Q  T  S  Q  K  T  *  N  M  S  I  R  K  R  T  I  I  K

24061  CTACTTAGATTCTATATACCATCAACAAAATTCTCATAACAAAATCTATTTAAACGGTAT  24120
        S  S  D  L  I  Y  P  L  Q  K  L  L  I  T  K  S  L  N  A  M
       Q  H  I  *  S  I  H  Y  N  N  *  S  Y  Q  K  L  Y  I  Q  W
         I  F  R  L  Y  I  T  T  T  K  L  T  N  N  *  I  F  K  G  Y

24121  GGGTTGAGGTCTGCTAGACTAAACGTCAACCCGTCAAGACCAAAAGACGTTAGAAGATTA  24180
        G  L  E  L  R  D  S  K  C  N  P  L  E  P  K  R  C  D  E  L
       V  W  S  W  V  I  Q  N  A  T  P  C  N  Q  N  E  A  I  K  *
         G  V  G  S  S  R  I  Q  L  Q  A  T  R  T  K  Q  L  R  R  I

24181  ATATTTTAACTGTGATGAAGATCAAGAACAGTTAACATAATATCAAACGGACGTTAATTA  24240
        *  L  I  S  V  V  E  L  E  Q  *  N  Y  *  L  K  G  A  I  L
       N  Y  F  Q  C  *  K  *  N  K  D  I  T  N  Y  N  A  Q  L  *
         I  F  N  V  S  S  R  T  R  T  L  Q  I  I  T  Q  R  C  N  I

24241  CAATGATAATTATTAATATTAGGAAGAAGAACCTTATCTTCCATACCAAAATTATTAAAA  24300
        T  V  I  L  L  *  L  G  E  E  Q  F  L  L  Y  P  K  L  L  K
       H  *  *  *  Y  N  Y  D  K  K  K  S  Y  F  T  H  N  *  Y  N
         N  S  N  I  I  I  I  R  R  R  P  I  S  P  I  T  K  I  I  K
```

FIG. 3 CONT'D

```
24301 TTAAACTCGAGAGTATCACAACAAATGAGTGCAATAACAAAAAGACAATTATTATGAAAA 24360
       L  K  L  E  *  L  T  T  *  E  R  *  Q  K  E  T  L  L  V  K
      *  N  S  S  E  Y  H  Q  K  S  V  N  N  N  K  Q  *  Y  Y  K
        I  Q  A  R  M  T  N  N  V  *  T  I  T  K  R  N  I  I  S  K

24361 ACAGGAACACGATTTGGAAGAAAACGAAGTTCAACGTTCTCAGTATTTGGTGGAAGACGA 24420
       Q  G  Q  A  L  G  E  K  A  E  L  Q  L  L  *  L  G  G  E  A
      K  D  K  H  *  V  K  K  Q  K  L  N  C  S  D  Y  V  V  K  Q
        T  R  T  S  F  R  R  K  S  *  T  A  L  T  M  F  W  R  R  S

24421 AGGACAGGATAACCATGATTAATAGCAAGAACACTCTCATGATGACATGAGCTGGTGTGA 24480
       E  Q  G  I  P  V  L  *  R  E  Q  S  L  V  V  T  S  S  W  V
      K  R  D  *  Q  Y  *  N  D  N  K  H  S  Y  *  Q  V  R  G  C
        G  T  R  N  T  S  I  I  T  R  T  L  T  S  S  Y  E  V  V  S

24481 CTGACCACATCCACAAGAACAAATGGACTAGGATATTGACGAATACTGGGATCCAGAACA 24540
       S  Q  H  L  H  E  Q  K  G  S  G  I  V  A  *  S  G  L  D  Q
      Q  S  T  Y  T  N  K  N  V  Q  D  *  L  Q  K  H  G  *  T  K
        V  P  T  P  T  R  T  *  R  I  R  Y  S  S  I  V  R  P  R  T

24541 AGAGTTTTTTTCAGAGACCAACCACAACCACTTGTAACACGTCCCAAGCCACAACTACTT 24600
       E  *  F  F  D  R  T  P  T  P  S  C  Q  A  P  N  P  T  S  S
      N  E  F  F  T  E  P  Q  H  Q  H  V  N  H  L  T  R  H  Q  H
        R  L  F  L  R  Q  N  T  N  T  F  M  T  C  P  E  T  N  I  F

24601 CTTTTCACACCACATAACCTACCTAGTATATTACAAAGAACAGAAACATCATGACTACGG 24660
       S  F  H  P  T  N  S  P  D  Y  L  T  E  Q  R  Q  L  V  S  A
      L  F  T  H  H  I  P  H  I  M  Y  H  K  K  D  K  Y  Y  Q  H
        F  L  T  T  Y  Q  I  S  *  I  I  N  R  T  K  T  T  S  I  G

24661 AAAGATCCAACCAGAATACTGTGAACGCAGTCATTGTTGGCAACATTATAAAAAAGATTA 24720
       K  R  P  Q  D  *  S  V  Q  T  L  L  L  R  Q  L  I  K  E  L
      R  E  L  N  T  K  H  C  K  R  *  Y  C  G  N  Y  Y  K  K  *
        K  *  T  P  R  I  V  S  A  D  T  V  V  T  T  I  N  K  R  I

24721 AAATAAAATTTACCATAGTTATCACCATGGTGAACAAGATTACTAAATAACGTCGGATTA 24780
       K  I  K  F  P  I  L  L  P  V  V  Q  E  L  S  K  N  C  G  L
      N  *  K  L  H  Y  *  Y  H  Y  W  K  N  *  H  N  I  A  A  *
        K  N  *  I  T  D  I  T  T  G  S  T  R  I  I  *  Q  L  R  I

24781 TGACTTCAAAAATGACTACAAACACAACTAATGCTGGAAATACCATAATGTCCTGTTCCA 24840
       V  S  T  K  V  S  T  Q  T  S  *  S  R  *  P  I  V  P  C  P
      Y  Q  L  K  *  Q  H  K  H  Q  N  R  G  K  H  Y  *  L  V  L
        S  F  N  K  S  I  N  T  N  I  V  V  K  I  T  N  C  S  L  T
```

FIG. 3 CONT'D

24841 TAAAAATTTCTTCAAAGACGACAAATAATATTATCAACCGTTTTAGAAAACATACTAAGA 24900
I K L S T E A T * * L L Q C F R K Y S E
Y K * L L K Q Q K N Y Y N A F D K T H N
N K F F N R S N I I I T P L I K Q I I R

24901 TTACCGTTGTAATAACCAAAATTTCTAAAACAATGATTATTTTGTATATTATAAAAGGGA 24960
L P L M I P K L S K T V L L V Y L I K G
* H C C * Q N * L N Q * * Y F M Y Y K G
I A V N N T K F I K N S I F C I I N E R

24961 ACAATACGTCCTTCTCAAAGACGACGAAAAGTAGTTTTACGAAGGAGAAACCGAAATGAA 25020
Q * A P L T E A A K * * F A E E K A K S
K N H L F L K Q Q K E D F H K R K P K V
T I C S S N R S S K M L I S G R Q S * K

25021 ATAGCATTAAATTTTACATCGATACAAAACTTATTATAAAGAAATTGATGAGTCGGTATA 25080
* R L K F H L * T K F L I E K V V * G Y
K D Y N L I Y S H K S Y Y K K L * E A M
I T I * F T A I N Q I I N R * S S L W I

25081 AAACTATCAATAGAACCAACGCAAAAATTACGACTATTAAATTGACTAATAAGACAAAGA 25140
K S L * R P Q T K L A S L K V S * E T E
N Q Y N D Q N R K * H Q Y N L Q N N Q K
K I T I K T A N K I S I I * S I I R N R

25141 AGAACACGAGAAGCGTACCCATCACCAAAAACACAACTAATATTGAGTGGAAGAAGAAGG 25200
E Q A R R M P L P K Q T S * L E G E E E
K K H E E C P Y H N K H Q N Y S V K K K
R T S K A H T T T K T N I I V * R R R G

25201 AGAAGCGCAGCATTTGCATCTTCATAAAGACGAAGAATAGCAAAACAATGAAAACTTGGG 25260
E E R R L R L L I E A E * R K T V K S G
R K A D Y V Y F Y K Q K K D N Q * K Q V
R R T T F T S T N R S R I T K N S K F G

25261 AAATTACAGTCAAAACAATTACTGTCATAACTCAGACACCCACCAGAAATACTCTAGTTT 25320
K L T L K T L S L I S D T P P R * S I L
R * H * N Q * H C Y Q T Q P H D K H S *
K I D T K N I V T N L R H T T K I L D F

25321 TAAGGGTGATTGAAATGATATCAACCAGTTCTCCTTAAATAAGTTTGATTAAGAGGATTT 25380
I G V L K V I T P * S S N I * V L E G L
F E W * S * * L Q D L P I * E F * N E *
N G S V K S Y N T L L F K N L S I R R F

FIG. 3 CONT'D

```
25381  CAATGATAACTAACAAGAAATAAACAGACAAGATTAATACGTCGAACGGTACTGAATAAC  25440
        T  V  I  S  Q  E  K  N  T  Q  E  L  *  A  A  Q  W  S  K  N
       L  *  *  Q  N  N  K  I  Q  R  N  *  N  H  L  K  G  H  S  I
         N  S  N  I  T  R  *  K  D  T  R  I  I  C  S  A  M  V  *  Q

25441  AGTCTCATACCGTGAAAAACACTATTATAATTATCATAAAATCTACTTCAATTACCAAAT  25500
        D  S  Y  P  V  K  Q  S  L  I  L  L  I  K  S  S  T  L  P  K
       T  L  T  H  C  K  K  H  Y  Y  *  Y  Y  K  L  H  L  *  H  N
         *  L  I  A  S  K  T  I  I  N  I  T  N  *  I  F  N  I  T  *

25501  GAACTATGATGAGTTAACGTACATCGACTATGAGAATACGTTCCACAGTGTGAATCGAGG  25560
        S  S  V  V  *  N  C  T  A  S  V  R  I  C  P  T  V  S  L  E
       V  Q  Y  *  E  I  A  H  L  Q  Y  E  *  A  L  H  *  V  *  S
         K  I  S  S  L  Q  M  Y  S  I  S  K  H  L  T  D  C  K  A  G

25561  TTAGAATTATGATTAAACGTAAAACTACAACTATTATAATTAAAATTTAGGGATCAACCT  25620
        L  R  L  V  L  K  C  K  S  T  S  L  I  L  K  L  D  R  T  P
       W  D  *  Y  *  N  A  N  Q  H  Q  Y  Y  *  N  *  I  G  L  Q
         I  K  I  S  I  Q  M  K  I  N  I  I  N  I  K  F  G  *  N  S

25621  ACAAATCCAGGTGTGACGCCAAGAAGAAGAGCAAGAAAAAAACTTCTAAATAACAAACTG  25680
        H  K  P  G  C  Q  P  E  E  E  R  E  K  K  S  S  K  N  N  S
       I  N  L  D  V  S  R  N  K  K  E  N  K  K  Q  L  N  I  T  Q
         T  *  T  W  V  A  T  R  R  R  T  R  K  K  F  I  *  Q  K  V

25681  TTTCAATTTGAAAGTCTACAACCAAAACAACTTCGAATATTGTTAACATGACCACCATCA  25740
        L  T  L  S  E  S  T  P  K  T  S  A  *  L  L  Q  V  P  P  L
       C  L  *  V  K  L  H  Q  N  Q  Q  L  K  Y  C  N  Y  Q  H  Y
         F  N  F  K  *  I  N  T  K  N  F  S  I  V  I  T  S  T  T  T

25741  CTTTAATCTCTAGAAGAAACACATGTTAGGAAATTACCATAATTTCAAAACGGAGGATAA  25800
        S  I  L  S  R  R  Q  T  C  D  K  L  P  I  L  T  K  G  G  I
       H  F  *  L  D  E  K  H  V  I  R  *  H  Y  *  L  K  A  E  *
         F  N  S  I  K  K  T  Y  L  G  K  I  T  N  F  N  Q  R  R  N

25801  AACAGACTTAGAGTTTAAAGACCAATGTGGTGTCGGCGATGACAACGACGATACAAAGGT  25860
        K  D  S  D  *  I  E  P  *  V  V  A  A  V  T  A  A  I  N  G
       K  T  Q  I  E  F  K  Q  N  C  W  L  R  *  Q  Q  Q  *  T  E
         Q  R  F  R  L  N  R  T  V  G  C  G  S  S  N  S  S  H  K  W

25861  GGTACCAGTCGTCGTCGACCGTATGGTAAAAGAGAATTACATGTTATATCTTAATTACCA  25920
        G  H  D  A  A  A  P  M  G  N  E  R  L  T  C  Y  L  I  L  P
       V  M  T  L  L  L  Q  C  V  M  K  E  *  H  V  I  Y  F  *  H
         W  P  *  C  C  S  A  Y  W  K  R  K  I  Y  L  I  S  N  I  T
```

FIG. 3 CONT'D

```
25921  AACCCACAATGATACCTACAAGAATTATTTTTAGTTTTCAACTATCGATGACGAAAATTA  25980
        K  P  T  V  I  S  T  R  L  L  F  *  F  N  I  A  V  A  K  L
       N  P  H  *  *  P  H  E  *  Y  F  D  F  T  S  L  *  Q  K  *
         Q  T  N  S  H  I  N  K  I  F  I  L  L  Q  Y  S  S  S  K  I

25981  TTACGAGAAGAAAGATAAGTCTTACCAAAATCACGATGGTTGAGACGTGAACGATTTTAT  26040
        L  A  R  R  E  I  *  F  P  K  L  A  V  L  E  A  S  A  L  I
       Y  H  E  E  K  *  E  S  H  N  *  H  *  W  S  Q  V  Q  *  F
         I  S  K  K  R  N  L  I  T  K  T  S  G  V  R  C  K  S  F  Y

26041  GTTTCACAACAATTAAGATTACGAGTTCGTGAATTATCAAACAATGTCGTTAATAAATTA  26100
        C  L  T  T  L  E  L  A  *  A  S  L  L  K  N  C  C  N  N  L
       V  F  H  Q  *  N  *  H  E  L  V  *  Y  N  T  V  A  I  I  *
         L  T  N  N  I  R  I  S  L  C  K  I  T  Q  *  L  L  *  K  I

26101  TTTAAACCACGTTAATCAAGAAGAAATGTTCTTTAAAATAGAGCAGAGCTACGAAATCTC  26160
        L  N  P  A  I  L  E  E  K  C  S  I  K  D  R  R  S  A  K  S
       Y  I  Q  H  L  *  N  K  K  V  L  F  K  I  E  D  R  H  K  L
         F  K  T  C  N  T  R  R  *  L  F  N  *  R  T  E  I  S  *  L

26161  CGAGTCCAAGTCTAACTATCCGAATAATTACCAGCAAATTGACGAAATTTACGAATACAG  26220
        A  *  T  *  I  S  L  S  I  L  P  R  K  V  A  K  F  A  *  T
       P  E  P  E  S  Q  Y  A  *  *  H  D  N  L  Q  K  L  H  K  H
         S  L  N  L  N  I  P  K  N  I  T  T  *  S  S  *  I  S  I  D

26221  AGAGTTGTCGAATCACTATAAAGAGAACATTTTAAACCACGACGAAATCGATACCTCTTC  26280
        E  *  C  S  L  S  I  E  R  T  F  N  P  A  A  K  A  I  S  F
       R  E  V  A  *  H  Y  K  E  Q  L  I  Q  H  Q  K  L  *  P  S
         R  L  L  K  T  I  N  R  K  Y  F  K  T  S  S  *  S  H  L  L

26281  CAATTACTCACACAATTTTCAGTTAGAGGAGCATAATTAAAAACACCATTACCATTAGTA  26340
        T  L  S  H  T  L  L  *  D  G  R  I  L  K  Q  P  L  P  L  *
       P  *  H  T  H  *  F  D  I  E  E  Y  *  N  K  H  Y  H  Y  D
         N  I  L  T  N  F  T  L  R  R  T  N  I  K  T  T  I  T  I  M

26341  TAAAACAGTAATCAAGTTTTACGAGGAATACCAAACAACAAATACGTAAAATCAATATTT  26400
        I  K  D  N  T  *  F  A  G  *  P  K  N  N  I  C  K  L  *  L
       Y  K  T  M  L  E  F  H  E  K  H  N  T  T  *  A  N  *  N  Y
         N  Q  *  *  N  L  I  S  R  I  T  Q  Q  K  H  M  K  T  I  F

26401  GGATAAAGAAAATTTTGACAAAATCATTCAGGACCAAACACATATAGTCCACTACATCCA  26460
        G  I  E  K  L  V  T  K  T  L  G  P  K  H  I  D  P  S  T  P
       V  *  K  K  *  F  Q  K  L  L  D  Q  N  T  Y  I  L  H  H  L
         R  N  R  K  F  S  N  *  Y  T  R  T  Q  T  Y  *  T  I  Y  T
```

FIG. 3 CONT'D

```
26461  TAACGTGGATTTGTTCCCATAAAATAATTTGTATTACTAGTAACCTACAAGTGACCATCA  26520
        I  A  G  L  C  P  Y  K  I  L  C  L  S  *  Q  I  N  V  P  L
       Y  Q  V  *  V  L  T  N  *  *  V  Y  H  D  N  S  T  *  Q  Y
         N  C  R  F  L  P  I  K  N  F  M  I  I  M  P  H  E  S  T  T

26521  AGAATGATAATAGGACTTGGTTAAAGTCTATTTTTACAACAAAAATACTTATGAACAAGA  26580
        E  *  *  *  G  S  G  I  E  S  L  F  T  T  K  I  F  V  Q  E
       N  K  S  N  D  Q  V  L  K  L  Y  F  H  Q  K  *  S  Y  K  N
         R  V  I  I  R  F  W  N  *  I  F  I  N  N  K  H  I  S  T  R

26581  CAATTAAAATGATTTCGCGGAGAACAAATAAACTTAGTAAGACATGGTTTTAACAGACTA  26640
        T  L  K  V  L  A  G  R  T  *  K  F  *  E  T  G  F  N  D  S
       Q  *  N  *  *  L  A  E  Q  K  N  S  D  N  Q  V  L  I  T  Q
         N  I  K  S  F  R  R  K  N  I  Q  I  M  R  Y  W  F  Q  R  I

26641  AAACTTAGACTCAATAGAGTAACCAAATTTTTAGTTTGTAGGTAACGCGGATTAAACTGA  26700
        K  S  D  S  N  D  *  Q  N  L  F  *  V  D  M  A  G  L  K  V
       N  Q  I  Q  T  I  E  N  T  *  F  D  F  M  W  Q  A  *  N  S
         K  F  R  L  *  R  M  P  K  F  I  L  C  G  N  R  R  I  Q  S

26701  AATTTAGAAGTATGATAATTACGATGAAAAAATCTAAACATAATACTCTACTTAGAATAA  26760
        K  F  R  *  V  I  L  A  V  K  K  S  K  Y  *  S  I  F  R  I
       K  L  D  E  Y  *  *  H  *  K  K  L  N  T  N  H  S  S  D  *
         *  I  K  M  S  N  I  S  S  K  *  I  Q  I  I  L  H  I  K  N

26761  GTTCTCAGATAATTCAGAAACTTATTATCAATATAGTTAGAATTTCTATATCCATGTATA  26820
        *  S  D  I  L  D  K  F  L  L  *  I  L  R  L  S  I  P  V  Y
       E  L  T  *  *  T  K  S  Y  Y  N  Y  *  D  *  L  Y  L  Y  M
         L  L  R  N  L  R  Q  I  I  T  I  D  I  K  F  I  Y  T  C  I

26821  CTTTACATACATTTTACCGGAACCATACAAACCGATGATTAAAGAAAAAGTAAATATTAT  26880
        S  I  Y  T  F  H  G  Q  Y  T  Q  S  S  I  E  K  E  N  I  I
       H  F  T  H  L  I  A  K  T  H  K  A  V  L  K  K  K  M  *  L
         F  H  I  Y  F  P  R  P  I  N  P  *  *  N  R  K  *  K  Y  Y

26881  AAGGAACATAACGAGAAAAAATATACAACAACATGACCAACACCAAGACGTACAAAATCA  26940
        N  R  T  N  S  K  K  I  H  Q  Q  V  P  Q  P  E  A  H  K  L
       I  G  Q  I  A  R  K  *  I  N  N  Y  Q  N  H  N  Q  M  N  *
         E  K  Y  Q  E  K  K  Y  T  T  T  S  T  T  T  R  C  T  K  T

26941  TTTACAGTATTAACAACACTACTCATACCACCAGTAGTACTAAAACAATAGTTTTGTAGA  27000
        L  H  *  L  Q  Q  S  S  Y  P  P  *  *  S  K  T  I  L  V  D
       Y  I  D  Y  N  N  H  H  T  H  H  D  D  H  N  Q  *  *  F  M
         F  T  M  I  T  T  I  L  I  T  T  M  M  I  K  N  D  F  C  R
```

FIG. 3 CONT'D

27001 GTACTACTAATCTTAGAGAACAGTCTAGAGTAATTTAGATTTGAAATAAATACCTGCAAA 27060
* S S * F R K D S R M L D L S * K H V N
E H H N S D R T L D * * I * V K N I S T
M I I L I E Q * I E N F R F K I * P R K

27061 CCTCTGGATCGATGTGTGTAAGAGAACAATAATCTCTTAAACCACAATGTTTGGAACTTC 27120
P S R A V C M R K N N S F K T N C V K F
Q L G L * V C E R T I L S N P T V F R S
S V * S C V N E Q * * L I Q H * L G Q L

27121 TAAACACAGATTTCATATTAATGACAGTTGGATAACAACCAATGACATAACATGGAAATT 27180
I Q T * L I I V T L R N N T V T N Y R *
S K H R F Y L * Q * G I T P * Q I T G K
N T D L T Y N S D V * Q Q N S Y Q V K L

27181 TACAAACCACAGCGTTCAAACCGTTTAAACGAAGAGTGAAATGTAATGCATCAGTGCTAT 27240
I N P T A L K A F K S R V K C * T T V I
F T Q H R L N P L N A E * K V N R L * S
H K T D C T Q C I Q K E S * M V Y D R Y

27241 AAAGGGTATCATTATTAAAACCACAACATTGATCAAAATGATGAATACCATTATGACAAA 27300
N G M T I I K T N Y S T K S S I T I S N
I E W L L L K P T T V L K V V * P L V T
K G Y Y Y N Q H Q L * N * * K H Y Y Q K

27301 GACTCCGACACAGATCTAATCAACTTAGTCGAAGACTTAAATAACAAACCGCACGTCTCC 27360
R L S H R S * N F * S R F K N N P T C L
E S A T D L N T S D A E S N I T Q R A S
Q P Q T * I L Q I L K Q I * Q K A H L P

27361 GTGAATTATTCATACCAACTAAATAAAAAGTTACTATGACGAACCATGTATCCTGTCTAA 27420
C K I L I T S K N K L S V A Q Y M P C I
A S L L Y P Q N I K * H Y Q K T C L V S
V * Y T H N I * K E I I S S P V Y S L N

27421 AATCAAAATCAAAATAAAACAGAATAAAGAAATTAGAAACAACAACGAAAAAATCGTTGA 27480
K T K T K N Q R I E K I K T T A K K A V
K L K L K I K D * K K L R Q Q Q K K L L
* N * N * K T K N R * D K N N S K * C S

27481 TAATTCGAAACATACGTTGAAACACCAAAAACATTAAAGAAATAATAAAGTGGAAGCCGA 27540
I L S Q I C S Q P K Q L K K I I E G E A
* * A K Y A V K H N K Y N R * * K V K P
N L K T H L K T T K T I E K N N * R R S

FIG. 3 CONT'D

27541 ATGCAAATATTTTCTCCATACGTCAACATATTCAGAATATCACTTGTTCAATATGGTGGG 27600
* T * L L P I C N Y L D * L S C T I G G
K R K Y F L Y A T T Y T K Y H V L * V V
V N I F S T H L Q I L R I T F L N Y W G

27601 TGAAGTCTAATAAATTAGATTTAGATTTGTAATACTTATTTAGAAAAGAAGGAGTTAAAT 27660
V E S * K I * I * V N H I F R K K R L K
W K L N N L R F R F M I F L D K R G * N
S * I I * D L D L C * S Y I K E E E I *

27661 GAAGACTAGTTCGACAATGTAAGAATTTTCTTACCTTAAAGAGAAACCCACATTATGATG 27720
S R I L S N C E * F F P I E R Q T Y Y *
V E S * A T V N K F S H F K E K P T I S
K Q D L Q * M R L L I S N R K P H L V V

27721 AAAAATAATGATAGTATAACGTCAAGCCAATATGCTCGGCATCATACAAACAAATAGAAT 27780
K K N S D Y Q L E T I R A T T H K N I K
S K I V I M N C N P * V L R L I N T * R
K * * * * I A T R N Y S G Y Y T Q K D *

27781 AGTTCTACTAATAAGAAACCGAATACACCGGTAACTGATAGTGGAACTGATATAAATTAA 27840
D L H N N K P K H P W Q S D G Q S Y K I
I L I I I R Q S I H G N V I V K V I N L
* S S * E K A * T A M S * * R S * I * N

27841 CAAAAATACGAAACTTATTACGAAAAGAACGTAAAAGATATCACAAATGATAATAAAGAT 27900
T K I S Q I I S K K C K R Y H K S N N R
Q K * A K F L A K R A N E I T N V I I E
N K H K S Y H K E Q M K * L T * * * K *

27901 AACAATATACCTAAGAAATAAAACAATTATCATAAGCCGAAAAAATAATCTTGACCGTCAA 27960
N N Y P N K I K N I T N P K K N S S A T
I T I H I R * K T L L I R S K I L V P L
Q * I S E K N Q * Y Y E A K * * F Q C N

27961 CCACCTCAAAATTAGGTCTCTGGTTATTAGAATACACATAACTATACTTTCCGTTCTACA 28020
P P T K I W L G I I K H T N I H F A L H
Q H L K L G S V L L R I H I S I F P L I
T S N * D L S W Y D * T Y Q Y S L C S T

28021 AACAATCCGGTCAATAACTCCTGATAGTGTGTAATTGACGATGACAATAAGCACCAGTAG 28080
K N P W N N L V I V C * S S S N N T T M
N T L G T I S S * * V N V A V T I R P *
Q * A L * Q P S D C M L Q * Q * E H D D

FIG. 3 CONT'D

28081 AAATATATGTCCCACAGTTTGAACCGTGACCAATATGAGAAAGTCTAAACGGGCATATAC 28140
K I Y L T D F K A S T I S K * I Q G Y I
R * I C P T L S P V P * V R E S K G T Y
K Y V P H * V Q C Q N Y E K L N A R I H

28141 AATGACATCGATTCCACGTTCATGAAACATGGATATTTGCACGGAAAAATCTATTCAATC 28200
N S Y S L H L Y K T G I F T G K * I L *
T V T A L T C T S Q V * L R A K K S L N
* Q L * P A L V K Y R Y V H R K L Y T L

28201 TACAATTATCACCAAAACGACAAAAACAATTCAGATTTCAACCATTGATAGCAAATGGCA 28260
I N I T T K S N K N L R F N T V I T * R
S T L L P K A T K T L D L T P L * R K G
H * Y H N Q Q K Q * T * L Q Y S D N V T

28261 GATCATTTGGATCACCATACCTATGACGGAACAATTCTCGAATTTAGATTTGATAATCCT 28320
R T F R T T H I S G Q * S S L D L S N P
D L L G L P I S V A K N L A * I * V I L
* Y V * H Y P Y Q R T L L K F R F * * S

28321 ACAGAATATGAGGGCCAGTAATACGACCTTCATCTTCGAGGAGACCTTTAGCAAGTCCTT 28380
H R I S G T M I S S T S A G R S I T * S
I D * V G P * * A P L L L E E P F R E P
T K Y E R D N H Q F Y F S R Q F D N L F

28381 AGGAGTTCTTTTGAAGAACCCGACTGGTTAGACTCGCTTTAATGGTTTGGAAATTATCTC 28440
D E L F S R P S V L R L S I V L G K I S
I R L F V E Q A S W D S R F * W V K L L
G * S F K K P Q G I Q A F N G F R * Y L

28441 CGTCTTTTTGGGTTGGATTTAAGTGACACAGATGAGTTGGTGTTCCTTTATGATAGGGTG 28500
A S F G L R F E S H R S L W L S I S D W
P L F V W G L N V T D V * G C P F V I G
C F F G V * I * Q T * E V V L F Y * G V

28501 TAATAAGGACCAAGAGGCCCTAGTGAGTTAAAGTTTTTCCATCTCTGAAATTTAAAAGTC 28560
M I G P E G P D S L K L F T S V K F K *
C * E Q N E P I V * N * F P L S K L N E
N N R T R R S * E I E F L Y L S * I K L

28561 TACCAGTTCCTCAAGGGTAACGAAAGCCTCATGGGGGAAGACTTCGTTTTCCTATAACCA 28620
I T L S N G N S E S Y G R R F C F S I P
S P * P T G M A K P T G G E S A F P Y Q
H D L L E W Q K R L V G K Q L L L I N T

FIG. 3 CONT'D

28621 TATCTGTGTCGGCCGCAAGAAAATTTTGTCGACTACCAGTTGTTTTCGTCAACAATGGCT 28680
I S V A P T R K F C S I T L L L L Q * R
Y L C L R R E K L V A S P * C F C N N G
Y V C G A N K * F L Q H D V F A T T V S

28681 CTACCATAAAGATGATAGAGCCATGGCCGGGTATACGGTTACGTAGGATACCACTTAGGG 28740
S P I E V I E T G A W I G I C G I T F G
L H Y K * * R P V P G Y A L A D * P S D
I T N R S D R Y R G M H W H M R H H I G

28741 AGCTTCCCCAGAAGACCCAACGATTAGTGGTTCGACTGTGAAGATGAGGGAGGCTACAAA 28800
E F P D E P N S I V L S V S R S G G I N
R S P T K Q T A L * W A S V E V G E S T
R L P R R P Q * D G L Q C K * E R R H K

28801 GCAGTTCCCTAGGATGATGAGTTCTTCGATAGGGATGATCCAAAGGCGGACCATGCTAAA 28860
R * P I R S S L F S D R S P K R R T R N
E D L S G V V * S A I G V L N G G P V I
T L P D * * E L L * G * * T E A Q Y S K

28861 ACGGAGTTCCGATAATACAACTTCCGAGTCCTTCCAGACGAAGATTATCAGCTGGTCCAA 28920
Q R L A I I N F A * S P R S R I T S W T
K G * P * * T S P E P L D A E L L R G P
A E L S N H Q L S L F T Q K * Y D V L N

28921 GTGCAAGAGTTAGTGCACCTGGGTTATTAGCAAGTAATTCATCTTCATTAAGATTAAAAT 28980
* T R L * T S G I I T * * T S T I R I K
E R E * D R P G L L R E N L L L L E L K
V N E I V H V W Y D N M L Y F Y N * N *

28981 CTGTAAGTCTAAGATATCATTTTGGACTATACCGACTACTCTAGCGATTAGAACAAAATC 29040
S M * I R Y Y F R I H S I L D S I K N *
L C E S E I T F G S I A S S I A L R T K
V N L N * L L V Q Y P Q H S R * D Q K L

29041 GGTTCGAACCATTTCTAAGATTTGGAGTCGTTCAGTGATTCGTTTTACGGTTCCTTTAGT 29100
G L K T F I R F R L L D S L L I G L F D
A L S P L S E L G * C T V L C F A L S I
W A Q Y L N * V E A L * * A F H W P F *

29101 CCGTATTTTAAAATTGTTTTGGAGCGGTTTTCGCTTGAGGATTATTTGTAACATTACAAG 29160
P M F N * C F R A L L S S R I F M T I N
L C L I K V F G R W F R V G L L C Q L T
A Y F K L L V E G F A F E * Y V N Y H E

FIG. 3 CONT'D

```
29161  TTGTCACAAAACCATTTTCTCCTGGAAGAGTTTTAAAACCATTACGACTTTACAATTTCG  29220
        L  L  T  K  T  F  S  S  R  R  L  I  K  T  I  S  F  H  *  L
       *  C  H  K  P  L  L  P  G  E  *  F  K  P  L  A  S  I  N  F
         V  T  N  Q  Y  F  L  V  K  E  F  N  Q  Y  H  Q  F  T  L  A

29221  AACCATGATTACTAGGAGTCAAAGGATAAGAACGTCTTAATCGAGGATGTGGTCCACGAA  29280
        K  T  S  I  I  R  L  K  R  N  K  C  F  *  S  R  C  W  T  S
       S  P  V  L  S  G  *  N  G  I  R  A  S  N  A  G  V  G  P  A
         Q  Y  *  H  D  E  T  E  *  E  Q  L  I  L  E  *  V  L  H  K

29281  AAAAGAAACCAAGATTTAATCTGAACCAATTTTCTCTAAGGCTCCGACTGAGTGGACAAT  29340
        K  E  K  T  R  F  *  V  Q  N  F  S  I  G  L  S  V  *  R  N
       K  K  K  P  E  L  N  S  K  T  L  L  S  E  S  A  S  E  G  T
         K  R  Q  N  *  I  L  S  P  *  F  L  N  R  P  Q  S  V  Q  *

29341  TTCTACAAAAACTTGAAGTAATAAGACCAAGATAATCCAAACTATCATGAAATGGTCCGA  29400
        F  I  N  K  F  K  M  I  R  T  R  N  P  K  I  T  S  *  W  A
       L  S  T  K  S  S  *  *  E  P  E  I  L  N  S  L  V  K  G  P
         L  H  K  Q  V  E  N  N  Q  N  *  *  T  Q  Y  Y  K  V  L  S

29401  AACTCTGTTAATACTTTCAAGAACTTCTCTTAAATTTACGAATGCAATTAAGATTAGTCT  29460
        K  L  C  N  H  F  N  K  F  L  I  *  I  S  V  N  I  R  I  L
       K  S  V  I  I  F  T  R  S  S  F  K  F  A  *  T  L  E  L  *
         Q  S  L  *  S  L  E  Q  L  S  N  L  H  K  R  *  N  *  D  S

29461  TGTGACTAAGACTAAGCAACTCAAGATTTGGAGTCGCATTTTCTCCACAATTTGTTAATG  29520
        V  S  I  R  I  R  Q  T  R  F  R  L  T  F  S  T  N  F  L  *
       F  V  S  E  S  E  N  L  E  L  G  *  R  L  L  P  T  L  C  N
         C  Q  N  Q  N  T  S  N  *  V  E  A  Y  F  L  H  *  V  I  V

29521  GTCTTGTCAAACTGAGAGAATTAAATTCACGACCATGAGTCGTGTAAAGTTTACTAAAAT  29580
        W  F  L  K  V  R  K  I  *  T  S  T  S  L  V  N  *  I  I  K
       G  S  C  N  S  E  R  L  K  L  A  P  V  *  C  M  E  F  S  K
         L  V  T  Q  S  E  *  N  L  H  Q  Y  E  A  C  K  L  H  N  *

29581  GAGGACTCCTAGTATCAAATGAACGATGAGAACTACTAGGAATACATCTTCTGAGACAAC  29640
        S  R  L  I  M  T  *  K  S  S  K  I  I  R  I  Y  F  V  R  N
       V  G  S  S  *  L  K  S  A  V  R  S  S  G  *  T  S  S  E  T
         E  Q  P  D  Y  N  V  Q  *  E  Q  H  D  K  H  L  L  S  Q  Q

29641  GAATTACTCTTACTTAGGATTAAGCTGTGATCCACCATTGGGGAGCGATAATAAGCCTTA  29700
        S  L  S  F  S  D  *  N  S  V  L  H  Y  G  R  A  I  I  R  F
       A  *  H  S  H  I  R  I  R  C  *  T  T  V  G  R  *  *  E  S
         K  I  L  I  F  G  L  E  V  S  P  P  L  G  E  S  N  N  P  I
```

FIG. 3 CONT'D

```
29701  TCCTGTGAGAGATAGTCTTACTTAAGAACGACATTATTGTCTATCTCATCCAACAATGTC  29760
        L  V  S  E  I  L  I  F  E  Q  Q  L  L  L  Y  L  L  N  N  C
       Y  S  V  R  *  *  F  S  N  K  S  Y  Y  C  I  S  Y  T  T  V
         P  C  E  R  D  S  H  I  R  A  T  I  V  S  L  T  P  Q  *  L

29761  TGATATATAATTAATCATCTTTAAAATATAAATCTGTAAACTAACAATCTCATCAATATT  29820
        V  I  Y  *  N  T  S  I  K  Y  K  S  M  Q  N  N  S  Y  N  Y
       S  *  I  N  I  L  L  F  K  I  N  L  C  K  I  T  L  T  T  I
         S  Y  I  L  *  Y  F  N  *  I  *  V  N  S  Q  *  L  L  *  L

29821  CCAAATCGACATCATATTTGCGGAGGCCCTTCTCGATAGTTAACATCACAAATTATATAT  29880
        P  K  A  T  T  Y  V  G  G  P  L  A  I  L  Q  L  T  *  Y  I
       L  N  L  Q  L  I  F  A  E  P  F  L  *  *  N  Y  H  K  I  Y
         T  *  S  Y  Y  L  R  R  R  S  S  S  D  I  T  T  N  L  I  Y

29881  ATAATCATATACTAACTTTAATTAATATCGGAAAACCTCCTTAATGTTTTTTTTTTTTTT  29940
        Y  *  Y  I  I  S  I  L  *  L  R  K  S  S  N  C  F  F  F  F
       I  N  T  Y  S  Q  F  *  N  Y  G  K  P  P  I  V  F  F  F  F
         I  L  I  H  N  F  N  I  I  A  K  Q  L  F  *  L  F  F  F  F

29941  TT                                                            29942
        F
       F
```

FIG. 3 CONT'D

```
  1 GAATAAGAGCGAATTGCGTCCGTACCGTCTATCAGCTTACGATCTCTTGTCAGATCTCAT 60
    E  *  E  R  I  A  S  V  P  S  I  S  L  R  S  L  V  R  S  H
     N  K  S  E  L  R  P  Y  R  L  S  A  Y  D  L  L  S  D  L  I
      I  R  A  N  C  V  R  T  V  Y  Q  L  T  I  S  C  Q  I  S  L

 61 TAAATCTAAACTTTTTAAACAAGATTCCCTGTTATCCATGCTTGTGAGTGTGGTTTAATC 120
    *  I  *  T  F  *  T  R  F  P  V  I  H  A  C  E  C  G  L  I
     K  S  K  L  F  K  Q  D  S  L  L  S  M  L  V  S  V  V  *  S
      N  L  N  F  L  N  K  I  P  C  Y  P  C  L  *  V  W  F  N  H

121 ATAATCTTGTATTTTACTTTCCACACTTTTCATCTCTCTGCCAGTGACGTGTTGGTTGTC 180
    I  I  L  Y  F  T  F  H  T  F  H  L  S  A  S  D  V  L  V  V
     *  S  C  I  L  L  S  T  L  F  I  S  L  P  V  T  C  W  L  S
      N  L  V  F  Y  F  P  H  F  S  S  L  C  Q  *  R  V  G  C  P

181 CTCAGCGTCCCTCCCATAGGTCGCAATGATTAAAACCAGCAAATACGGTCTCGGCTTCAA 240
    L  S  V  P  P  I  G  R  N  D  *  N  Q  Q  I  R  S  R  L  Q
     S  A  S  L  P  *  V  A  M  I  K  T  S  K  Y  G  L  G  F  K
      Q  R  P  S  H  R  S  Q  *  L  K  P  A  N  T  V  S  A  S  S

241 GTGGGCGCCAGAATTTCGTTGGCTGCTTCCGGATGCAGCGGAGGAGTTGGCTAGTCCTAT 300
    V  G  A  R  I  S  L  A  A  S  G  C  S  G  G  V  G  *  S  Y
     W  A  P  E  F  R  W  L  L  P  D  A  A  E  E  L  A  S  P  M
      G  R  Q  N  F  V  G  C  F  R  M  Q  R  R  S  W  L  V  L  *

301 GAAGTCAGATGAGGGTGGGTTATGCCCCTCTACTGGTCAAGCGATGGAAAGTGTTGGATT 360
    E  V  R  *  G  W  V  M  P  L  Y  W  S  S  D  G  K  C  W  I
     K  S  D  E  G  G  L  C  P  S  T  G  Q  A  M  E  S  V  G  F
      S  Q  M  R  V  G  Y  A  P  L  L  V  K  R  W  K  V  L  D  L

361 TGTTTATGATAATCATGTGAAGATAGATTGTCGCTGCATTCTTGGACAAGAATGGCATGT 420
    C  L  *  *  S  C  E  D  R  L  S  L  H  S  W  T  R  M  A  C
     V  Y  D  N  H  V  K  I  D  C  R  C  I  L  G  Q  E  W  H  V
      F  M  I  I  M  *  R  *  I  V  A  A  F  L  D  K  N  G  M  C

421 GCAGTCAAATCTTATCCGTGATATTTTTGTTCATGAAGATCTACATGTTGTAGAAGTTCT 480
    A  V  K  S  Y  P  *  Y  F  C  S  *  R  S  T  C  C  R  S  S
     Q  S  N  L  I  R  D  I  F  V  H  E  D  L  H  V  V  E  V  L
      S  Q  I  L  S  V  I  F  L  F  M  K  I  Y  M  L  *  K  F  *

481 AACTAAAACAGCCGTAAAGTCCGGTACGGCAATTTTAATTAAATCACCTTTGCATAGCTT 540
    N  *  N  S  R  K  V  R  Y  G  N  F  N  *  I  T  F  A  *  L
     T  K  T  A  V  K  S  G  T  A  I  L  I  K  S  P  L  H  S  L
      L  K  Q  P  *  S  P  V  R  Q  F  *  L  N  H  L  C  I  A  W
```

FIG. 9

```
541 GGGTGGTTTTCCTAAAGGGTATGTTATGGGCTTGTTCCGTTCATACAAGACTAAACGTTA 600
     G  W  F  S  *  R  V  C  Y  G  L  V  P  F  I  Q  D  *  T  L
      G  G  F  P  K  G  Y  V  M  G  L  F  R  S  Y  K  T  K  R  Y
    .  V  V  F  L  K  G  M  L  W  A  C  S  V  H  T  R  L  N  V  M

601 TGTTGTACATCATCTTTCTATGACTACATCTACTACTAATTTTGGTGAAGATTTTTTGGG 660
     C  C  T  S  S  F  Y  D  Y  I  Y  Y  *  F  W  *  R  F  F  G
      V  V  H  H  L  S  M  T  T  S  T  T  N  F  G  E  D  F  L  G
       L  Y  I  I  F  L  *  L  H  L  L  L  I  L  V  K  I  F  W  V

661 TTGGATTGTACCTTTTGGTTTTATGCCATCTTATGTTCACAAATGGTTTCAATTCTGTAG 720
     L  D  C  T  F  W  F  Y  A  I  L  C  S  Q  M  V  S  I  L  *
      W  I  V  P  F  G  F  M  P  S  Y  V  H  K  W  F  Q  F  C  R
       G  L  Y  L  L  V  L  C  H  L  M  F  T  N  G  F  N  S  V  G

721 GTTGTATATTGAAGAGAGTGATTTAATAATTTCAAATTTTAAATTTGATGATTATGATTT 780
     V  V  Y  *  R  E  *  F  N  N  F  K  F  *  I  *  *  L  *  F
      L  Y  I  E  E  S  D  L  I  I  S  N  F  K  F  D  D  Y  D  F
       C  I  L  K  R  V  I  *  *  F  Q  I  L  N  L  M  I  M  I  L

781 TAGTGTAGAAGATGCTTATGCTGAGGTTCATGCTGAGCCTAAAGGTAAATATTCACAAAA 840
     *  C  R  R  C  L  C  *  G  S  C  *  A  *  R  *  I  F  T  K
      S  V  E  D  A  Y  A  E  V  H  A  E  P  K  G  K  Y  S  Q  K
       V  *  K  M  L  M  L  R  F  M  L  S  L  K  V  N  I  H  K  K

841 AGCTTATGCTTTACTTAGACAATATCGTGGTATTAAACCCGTACTCTTTGTAGACCAGTA 900
     S  L  C  F  T  *  T  I  S  W  Y  *  T  R  T  L  C  R  P  V
      A  Y  A  L  L  R  Q  Y  R  G  I  K  P  V  L  F  V  D  Q  Y
       L  M  L  Y  L  D  N  I  V  V  L  N  P  Y  S  L  *  T  S  M

901 TGGTTGTGACTATTCTGGTAAATTAGCAGATTGTCTTCAAGCTTATGGTCATTATTCTTT 960
     W  L  *  L  F  W  *  I  S  R  L  S  S  S  L  W  S  L  F  F
      G  C  D  Y  S  G  K  L  A  D  C  L  Q  A  Y  G  H  Y  S  L
       V  V  T  I  L  V  N  *  Q  I  V  F  K  L  M  V  I  I  L  C

961 GCAAGATATGAGACAAAAGCAGTCTGTATGGCTTGCCAATTGCGACTTTGATATTGTAGT 1020
     A  R  Y  E  T  K  A  V  C  M  A  C  Q  L  R  L  *  Y  C  S
      Q  D  M  R  Q  K  Q  S  V  W  L  A  N  C  D  F  D  I  V  V
       K  I  *  D  K  S  S  L  Y  G  L  P  I  A  T  L  I  L  *  W

1021 GGCTTGGCATGTAGTTCGTGATTCACGATTTGTTATGCGCCTGCAGACTATAGCTACTAT 1080
      G  L  A  C  S  S  *  F  T  I  C  Y  A  P  A  D  Y  S  Y  Y
       A  W  H  V  V  R  D  S  R  F  V  M  R  L  Q  T  I  A  T  I
        L  G  M  *  F  V  I  H  D  L  L  C  A  C  R  L  *  L  L  F
```

FIG. 9 CONT.

```
1081 TTGTGGTATTAAATATGTTGCACAACCTACAGAAGATGTAGTAGATGGAGCTGTAGTTAT 1140
     L  W  Y  *  I  C  C  T  T  Y  R  R  C  S  R  W  S  C  S  Y
      C  G  I  K  Y  V  A  Q  P  T  E  D  V  V  D  G  A  V  V  I
       V  V  L  N  M  L  H  N  L  Q  K  M  *  *  M  E  L  *  L  Y

1141 ACGTGAACCTGTACATTTATTATCTGCTGATGCAATAGTTTTAAAGCTTCCTAGTTTGAT 1200
     T  *  T  C  T  F  I  I  C  *  C  N  S  F  K  A  S  *  F  D
      R  E  P  V  H  L  L  S  A  D  A  I  V  L  K  L  P  S  L  M
       V  N  L  Y  I  Y  Y  L  L  M  Q  *  F  *  S  F  L  V  *  *

1201 GAAAGTTATGACTCATATGGATGATTTTTCTATTAAATCTATATACAATGTTGATTTGTG 1260
     E  S  Y  D  S  Y  G  *  F  F  Y  *  I  Y  I  Q  C  *  F  V
      K  V  M  T  H  M  D  D  F  S  I  K  S  I  Y  N  V  D  L  C
       K  L  *  L  I  W  M  I  F  L  L  N  L  Y  T  M  L  I  C  V

1261 TGATTGTGGTTTTGTTATGCAGTATGGTTATGTAGATTGTTTTAATGATAATTGTGATTT 1320
     *  L  W  F  C  Y  A  V  W  L  C  R  L  F  *  *  *  L  *  F
      D  C  G  F  V  M  Q  Y  G  Y  V  D  C  F  N  D  N  C  D  F
       I  V  V  L  L  C  S  M  V  M  *  I  V  L  M  I  I  V  I  F

1321 TTATGGTTGGGTTTCAGGTAATATGATGGATGGTTTTTCTTGTCCATTGTGTTGTACAGT 1380
     L  W  L  G  F  R  *  Y  D  G  W  F  F  L  S  I  V  L  Y  S
      Y  G  W  V  S  G  N  M  M  D  G  F  S  C  P  L  C  C  T  V
       M  V  G  F  Q  V  I  *  W  M  V  F  L  V  H  C  V  V  Q  F

1381 TTATGACTCTAGTGAAGTTAAAGCCCAATCATCTGGTGTTATTCCTGAGAATCCTGTGTT 1440
     L  *  L  *  *  S  *  S  P  I  I  W  C  Y  S  *  E  S  C  V
      Y  D  S  S  E  V  K  A  Q  S  S  G  V  I  P  E  N  P  V  L
       M  T  L  V  K  L  K  P  N  H  L  V  L  F  L  R  I  L  C  Y

1441 ATTTACTAATAGTACTGATACTGTTAACCCTGATTCTTTTAATTTGTATGGTTATTCTGT 1500
     I  Y  *  *  Y  *  Y  C  *  P  *  F  F  *  F  V  W  L  F  C
      F  T  N  S  T  D  T  V  N  P  D  S  F  N  L  Y  G  Y  S  V
       L  L  I  V  L  I  L  L  T  L  I  L  L  I  C  M  V  I  L  L

1501 TACACCATTTGGTTCTTGTATATATTGGTCACCGCGTCCTGGATTGTGGATTCCTATCAT 1560
     Y  T  I  W  F  L  Y  I  L  V  T  A  S  W  I  V  D  S  Y  H
      T  P  F  G  S  C  I  Y  W  S  P  R  P  G  L  W  I  P  I  I
       H  H  L  V  L  V  Y  I  G  H  R  V  L  D  C  G  F  L  S  L

1561 TAAATCTTCAGTCAAGTCTTATGATGATTTGGTTTATTCAGGTGTAGTAGGTTGTAAATC 1620
     *  I  F  S  Q  V  L  *  *  F  G  L  F  R  C  S  R  L  *  I
      K  S  S  V  K  S  Y  D  D  L  V  Y  S  G  V  V  G  C  K  S
       N  L  Q  S  S  L  M  M  I  W  F  I  Q  V  *  *  V  V  N  L
```

FIG. 9 CONT.

```
1621 TATTGTTAAAGAAACTGCTCTTATTACTCATGCACTTTACTTAGATTATGTTCAATGTAA 1680
     Y  C  *  R  N  C  S  Y  Y  S  C  T  L  L  R  L  C  S  M  *
      I  V  K  E  T  A  L  I  T  H  A  L  Y  L  D  Y  V  Q  C  K
       L  L  K  K  L  L  L  L  L  M  H  F  T  *  I  M  F  N  V  S

1681 GTGTGGTAATCTTGAACAAAATCATATTCTTGGTGTTAATAATTCTTGGTGTAGGCAACT 1740
     V  W  *  S  *  T  K  S  Y  S  W  C  *  *  F  L  V  *  A  T
      C  G  N  L  E  Q  N  H  I  L  G  V  N  N  S  W  C  R  Q  L
       V  V  I  L  N  K  I  I  F  L  V  L  I  I  L  G  V  G  N  C

1741 GTTGCTTAATAGAGGTGATTATAATATGCTTTTAAAAAATATTGACTTGTTTGTTAAGCG 1800
     V  A  *  *  R  *  L  *  Y  A  F  K  K  Y  *  L  V  C  *  A
      L  L  N  R  G  D  Y  N  M  L  L  K  N  I  D  L  F  V  K  R
       C  L  I  E  V  I  I  I  C  F  *  K  I  L  T  C  L  L  S  V

1801 TCGTGCTGATTTTGCTTGCAAGTTTGCAGTTTGTGGAGATGGTTTTGTACCTTTTTTACT 1860
     S  C  *  F  C  L  Q  V  C  S  L  W  R  W  F  C  T  F  F  T
      R  A  D  F  A  C  K  F  A  V  C  G  D  G  F  V  P  F  L  L
       V  L  I  L  L  A  S  L  Q  F  V  E  M  V  L  Y  L  F  Y  *

1861 AGATGGTTTAATTCCCCGTAGTTATTATCTAATTCAGAGTGGTATTTTCTTTACATCTTT 1920
     R  W  F  N  S  P  *  L  L  S  N  S  E  W  Y  F  L  Y  I  F
      D  G  L  I  P  R  S  Y  Y  L  I  Q  S  G  I  F  F  T  S  L
       M  V  *  F  P  V  V  I  I  *  F  R  V  V  F  S  L  H  L  *

1921 GATGTCTCAATTTTCACAAGAAGTTTCTGATATGTGTTTAAAAATGTGTATTTTGTTTAT 1980
     D  V  S  I  F  T  R  S  F  *  Y  V  F  K  N  V  Y  F  V  Y
      M  S  Q  F  S  Q  E  V  S  D  M  C  L  K  M  C  I  L  F  M
       C  L  N  F  H  K  K  F  L  I  C  V  *  K  C  V  F  C  L  W

1981 GGACAGAGTTTCAGTTGCTACATTTTATATAGAGCATTATGTTAATAGGTTGGTTACTCA 2040
     G  Q  S  F  S  C  Y  I  L  Y  R  A  L  C  *  *  V  G  Y  S
      D  R  V  S  V  A  T  F  Y  I  E  H  Y  V  N  R  L  V  T  Q
       T  E  F  Q  L  L  H  F  I  *  S  I  M  L  I  G  W  L  L  N

2041 ATTTAAGTTATTGGGTACTACACTTGTTAATAAAATGGTTAATTGGTTTAATACCATGTT 2100
     I  *  V  I  G  Y  Y  T  C  *  *  N  G  *  L  V  *  Y  H  V
      F  K  L  L  G  T  T  L  V  N  K  M  V  N  W  F  N  T  M  L
       L  S  Y  W  V  L  H  L  L  I  K  W  L  I  G  L  I  P  C  *

2101 AGATGCTAGTGCACCTGCTACAGGCTGGCTTCTTTACCAATTATTGAATGGTCTTTTTGT 2160
     R  C  *  C  T  C  Y  R  L  A  S  L  P  I  I  E  W  S  F  C
      D  A  S  A  P  A  T  G  W  L  L  Y  Q  L  L  N  G  L  F  V
       M  L  V  H  L  L  Q  A  G  F  F  T  N  Y  *  M  V  F  L  *
```

FIG. 9 CONT.

```
2161 AGTATCTCAAGCCAACTTTAATTTTGTTGCTTTAATACCTGATTATGCTAAAATTTTAGT 2220
     S  I  S  S  Q  L  *  F  C  C  F  N  T  *  L  C  *  N  F  S
      V  S  Q  A  N  F  N  F  V  A  L  I  P  D  Y  A  K  I  L  V
       Y  L  K  P  T  L  I  L  L  L  *  Y  L  I  M  L  K  F  *  L

2221 TAATAAATTTTACACTTTTTTTAAGTTATTATTAGAGTGTGTTACAGTTGATGTTTTAAA 2280
     *  *  I  L  H  F  F  *  V  I  I  R  V  C  Y  S  *  C  F  K
      N  K  F  Y  T  F  F  K  L  L  L  E  C  V  T  V  D  V  L  K
       I  N  F  T  L  F  L  S  Y  Y  *  S  V  L  Q  L  M  F  *  K

2281 AGATATGCCTGTTCTTAAAACTATTAATGGTTTAGTTTGTATTGTAGGCAATAAGTTTTA 2340
     R  Y  A  C  S  *  N  Y  *  W  F  S  L  Y  C  R  Q  *  V  L
      D  M  P  V  L  K  T  I  N  G  L  V  C  I  V  G  N  K  F  Y
       I  C  L  F  L  K  L  L  M  V  *  F  V  L  *  A  I  S  F  I

2341 TAACGTTAGTACAGGGTTAATTCCTGGTTTTGTTTTACCATGTAATGCACAGGAACAACA 2400
     *  R  *  Y  R  V  N  S  W  F  C  F  T  M  *  C  T  G  T  T
      N  V  S  T  G  L  I  P  G  F  V  L  P  C  N  A  Q  E  Q  Q
       T  L  V  Q  G  *  F  L  V  L  F  Y  H  V  M  H  R  N  N  K

2401 AATTTATTTTTTTGAAGGCGTTGCAGAATCTGTTATAGTAGAAGATGATGTTATTGAGAA 2460
     N  L  F  F  *  R  R  C  R  I  C  Y  S  R  R  *  C  Y  *  E
      I  Y  F  F  E  G  V  A  E  S  V  I  V  E  D  D  V  I  E  N
       F  I  F  L  K  A  L  Q  N  L  L  *  *  K  M  M  L  L  R  M

2461 TGTCAAATCTTCTTTATCATCTTATGAGTATTGTCAACCACCTAAATCTGTAGAAAAAAT 2520
     C  Q  I  F  F  I  I  L  *  V  L  S  T  T  *  I  C  R  K  N
      V  K  S  S  L  S  S  Y  E  Y  C  Q  P  P  K  S  V  E  K  I
       S  N  L  L  Y  H  L  M  S  I  V  N  H  L  N  L  *  K  K  F

2521 TTGTATTATAGATAATATGTACATGGGTAAGTGTGGTGATAAATTTTTCCCTATTGTCAT 2580
     L  Y  Y  R  *  Y  V  H  G  *  V  W  *  *  I  F  P  Y  C  H
      C  I  I  D  N  M  Y  M  G  K  C  G  D  K  F  F  P  I  V  M
       V  L  *  I  I  C  T  W  V  S  V  V  I  N  F  S  L  L  S  *

2581 GAATGATAAAAATATTTGTCTTTTAGATCAGGCTTGGCGTTTTCCATGTGCAGGTAGAAA 2640
     E  *  *  K  Y  L  S  F  R  S  G  L  A  F  S  M  C  R  *  K
      N  D  K  N  I  C  L  L  D  Q  A  W  R  F  P  C  A  G  R  K
       M  I  K  I  F  V  F  *  I  R  L  G  V  F  H  V  Q  V  E  K

2641 AGTTAATTTTAACGAGAAACCTGTTGTTATGGAGATTCCGTCTTTGATGACAGTTAAGGT 2700
     S  *  F  *  R  E  T  C  C  Y  G  D  S  V  F  D  D  S  *  G
      V  N  F  N  E  K  P  V  V  M  E  I  P  S  L  M  T  V  K  V
       L  I  L  T  R  N  L  L  L  W  R  F  R  L  *  *  Q  L  R  L
```

FIG. 9 CONT.

```
2701 TATGTTTGATTTAGATTCTACTTTTGATGATATTTTAGGTAAAGTTTGTTCAGAATTTGA 2760
     Y  V  *  F  R  F  Y  F  *  *  Y  F  R  *  S  L  F  R  I  *
      M  F  D  L  D  S  T  F  D  D  I  L  G  K  V  C  S  E  F  E
       C  L  I  *  I  L  L  L  M  I  F  *  V  K  F  V  Q  N  L  K

2761 AGTAGAAAAGGGTGTTACTGTAGATGATTTTGTCGCTGTTGTTTGTGATGCTATAGAGAA 2820
     S  R  K  G  C  Y  C  R  *  F  C  R  C  C  L  *  C  Y  R  E
      V  E  K  G  V  T  V  D  D  F  V  A  V  V  C  D  A  I  E  N
       *  K  R  V  L  L  *  M  I  L  S  L  L  F  V  M  L  *  R  M

2821 TGCTTTAAACTCTTGTAAAGATCATCCAGTGGTTGGTTATCAAGTTCGTGCATTTTTAAA 2880
     C  F  K  L  L  *  R  S  S  S  G  W  L  S  S  S  C  I  F  K
      A  L  N  S  C  K  D  H  P  V  V  G  Y  Q  V  R  A  F  L  N
       L  *  T  L  V  K  I  I  Q  W  L  V  I  K  F  V  H  F  *  I

2881 TAAACTTAATGAGAACGTTGTTTATTTATTTGATGAGGCTGGTGATGAAGCAATGGCCTC 2940
     *  T  *  *  E  R  C  L  F  I  *  *  G  W  *  *  S  N  G  L
      K  L  N  E  N  V  V  Y  L  F  D  E  A  G  D  E  A  M  A  S
       N  L  M  R  T  L  F  I  Y  L  M  R  L  V  M  K  Q  W  P  L

2941 TCGTATGTATTGTACTTTTGCTATTGAGGATGTTGAAGACGTTATCAGTAGTGAAGCTGT 3000
     S  Y  V  L  Y  F  C  Y  *  G  C  *  R  R  Y  Q  *  *  S  C
      R  M  Y  C  T  F  A  I  E  D  V  E  D  V  I  S  S  E  A  V
       V  C  I  V  L  L  L  L  R  M  L  K  T  L  S  V  V  K  L  L

3001 TGAAGATACTATTGATGGTGTCGTTGAAGACACTATTAATGATGATGAAGATGTTGTTAC 3060
     *  R  Y  Y  *  W  C  R  *  R  H  Y  *  *  *  *  R  C  C  Y
      E  D  T  I  D  G  V  V  E  D  T  I  N  D  D  E  D  V  V  T
       K  I  L  L  M  V  S  L  K  T  L  L  M  M  M  K  M  L  L  L

3061 TGGTGACAATGACGATGAAGATGTTGTTACTGGTGACAATGACGATGAAGATGTTGTTAC 3120
     W  *  Q  *  R  *  R  C  C  Y  W  *  Q  *  R  *  R  C  C  Y
      G  D  N  D  D  E  D  V  V  T  G  D  N  D  D  E  D  V  V  T
       V  T  M  T  M  K  M  L  L  L  V  T  M  T  M  K  M  L  L  L

3121 TGGTGACAATGACGATGAAGATGTTGTTACTGGTGACAATGACGATGAAGATGTTGTTAC 3180
     W  *  Q  *  R  *  R  C  C  Y  W  *  Q  *  R  *  R  C  C  Y
      G  D  N  D  D  E  D  V  V  T  G  D  N  D  D  E  D  V  V  T
       V  T  M  T  M  K  M  L  L  L  V  T  M  T  M  K  M  L  L  L

3181 TGGTGATAATGACGATGAAGATGTTGTTACTGGTGACAATGACGATGAAGATGTTGTTAC 3240
     W  *  *  *  R  *  R  C  C  Y  W  *  Q  *  R  *  R  C  C  Y
      G  D  N  D  D  E  D  V  V  T  G  D  N  D  D  E  D  V  V  T
       V  I  M  T  M  K  M  L  L  L  V  T  M  T  M  K  M  L  L  L
```

FIG. 9 CONT.

```
3241 TGGTGACAATGACGATGAAGATGTTGTTACTGGTGACAATGACGATGAAGATGTTGTTAC 3300
     W  *  Q  *  R  *  R  C  C  Y  W  *  Q  *  R  *  R  C  C  Y
      G  D  N  D  D  E  D  V  V  T  G  D  N  D  D  E  D  V  V  T
       V  T  M  T  M  K  M  L  L  L  V  T  M  T  M  K  M  L  L  L

3301 TGGTGACAATGACGATGAAGATGTTGTTACTGGTGACAATGACGATGAAGATGTTGTTAC 3360
     W  *  Q  *  R  *  R  C  C  Y  W  *  Q  *  R  *  R  C  C  Y
      G  D  N  D  D  E  D  V  V  T  G  D  N  D  D  E  D  V  V  T
       V  T  M  T  M  K  M  L  L  L  V  T  M  T  M  K  M  L  L  L

3361 TGGTGACAATGACGATGAAGAGATTGTTACTGGTGACAATGATGACCAAATTGTTGTTAC 3420
     W  *  Q  *  R  *  R  D  C  Y  W  *  Q  *  *  P  N  C  C  Y
      G  D  N  D  D  E  E  I  V  T  G  D  N  D  D  Q  I  V  V  T
       V  T  M  T  M  K  R  L  L  L  V  T  M  M  T  K  L  L  L  L

3421 TGGTGATGATGTAGATGATATTGAAAGTGTCTATGATTTTGATACTTATAAAGCTCTTTT 3480
     W  *  *  C  R  *  Y  *  K  C  L  *  F  *  Y  L  *  S  S  F
      G  D  D  V  D  D  I  E  S  V  Y  D  F  D  T  Y  K  A  L  L
       V  M  M  *  M  I  L  K  V  S  M  I  L  I  L  I  K  L  F  *

3481 AGTTTTTAATGATGTCTATAATGATGCTTTGTTTGTTAGTTATGGTTCTAGTGTTGAAAC 3540
     S  F  *  *  C  L  *  *  C  F  V  C  *  L  W  F  *  C  *  N
      V  F  N  D  V  Y  N  D  A  L  F  V  S  Y  G  S  S  V  E  T
       F  L  M  M  S  I  M  M  L  C  L  L  V  M  V  L  V  L  K  Q

3541 AGAAACATATTTTAAAGTTAATGGTTTATGGTCACCTACTATTACACATACTAACTGTTG 3600
     R  N  I  F  *  S  *  W  F  M  V  T  Y  Y  Y  T  Y  *  L  L
      E  T  Y  F  K  V  N  G  L  W  S  P  T  I  T  H  T  N  C  W
       K  H  I  L  K  L  M  V  Y  G  H  L  L  L  H  I  L  T  V  G

3601 GTTGCGTTCTGTGTTACTTGTAATGCAGAAATTACCTTTTAAGTTTAAGGATTTAGCTAT 3660
     V  A  F  C  V  T  C  N  A  E  I  T  F  *  V  *  G  F  S  Y
      L  R  S  V  L  L  V  M  Q  K  L  P  F  K  F  K  D  L  A  I
       C  V  L  C  Y  L  *  C  R  N  Y  L  L  S  L  R  I  *  L  L

3661 TGAAAATATGTGGTTATCTTATAAGGTGGGTTATAATCAAAGTTTTGTTGATTATTTACT 3720
     *  K  Y  V  V  I  L  *  G  G  L  *  S  K  F  C  *  L  F  T
      E  N  M  W  L  S  Y  K  V  G  Y  N  Q  S  F  V  D  Y  L  L
       K  I  C  G  Y  L  I  R  W  V  I  I  K  V  L  L  I  I  Y  *

3721 GACCACTATTCCTAAAGCTATTGTTTTGCCTCAAGGTGGTTATGTAGCTGACTTTGCTTA 3780
     D  H  Y  S  *  S  Y  C  F  A  S  R  W  L  C  S  *  L  C  L
      T  T  I  P  K  A  I  V  L  P  Q  G  G  Y  V  A  D  F  A  Y
       P  L  F  L  K  L  L  F  C  L  K  V  V  M  *  L  T  L  L  I
```

FIG. 9 CONT.

```
3781 TTGGTTTTTAAACCAGTTTGATATTAATGCGTATGCTAATTGGTGTTGTTTAAAATGTGG 3840
     L  V  F  K  P  V  *  Y  *  C  V  C  *  L  V  L  F  K  M  W
      W  F  L  N  Q  F  D  I  N  A  Y  A  N  W  C  C  L  K  C  G
       G  F  *  T  S  L  I  L  M  R  M  L  I  G  V  V  *  N  V  V

3841 TTTTTCTTTTGATTTAAATGGTTTGGATGCTGTGTTTTTTTATGGAGATATTGTGTCTCA 3900
     F  F  F  *  F  K  W  F  G  C  C  V  F  L  W  R  Y  C  V  S
      F  S  F  D  L  N  G  L  D  A  V  F  F  Y  G  D  I  V  S  H
       F  L  L  I  *  M  V  W  M  L  C  F  F  M  E  I  L  C  L  M

3901 TGTTTGTAAGTGTGGACATAATATGACTCTAATAGCAGCGGACTTACCTTGTACATTACA 3960
     C  L  *  V  W  T  *  Y  D  S  N  S  S  G  L  T  L  Y  I  T
      V  C  K  C  G  H  N  M  T  L  I  A  A  D  L  P  C  T  L  H
       F  V  S  V  D  I  I  *  L  *  *  Q  R  T  Y  L  V  H  Y  I

3961 TTTTTCATTATTTGATGACAATTTTTGTGCTTTTTGCACCCCTAAAAAAATTTTTATTGC 4020
     F  F  I  I  *  *  Q  F  L  C  F  L  H  P  *  K  N  F  Y  C
      F  S  L  F  D  D  N  F  C  A  F  C  T  P  K  K  I  F  I  A
       F  H  Y  L  M  T  I  F  V  L  F  A  P  L  K  K  F  L  L  L

4021 TGCATGTGCTGTGGATGTAAACGTTTGTCATTCTGTAGCTGTTATAGGTGATGAACAAAT 4080
     C  M  C  C  G  C  K  R  L  S  F  C  S  C  Y  R  *  *  T  N
      A  C  A  V  D  V  N  V  C  H  S  V  A  V  I  G  D  E  Q  I
       H  V  L  W  M  *  T  F  V  I  L  *  L  L  *  V  M  N  K  *

4081 AGATGGTAAGTTTGTTACTAAATTTAGTGGTGATAAATTTGATTTTATAGTAGGTTATGG 4140
     R  W  *  V  C  Y  *  I  *  W  *  *  I  *  F  Y  S  R  L  W
      D  G  K  F  V  T  K  F  S  G  D  K  F  D  F  I  V  G  Y  G
       M  V  S  L  L  L  N  L  V  V  I  N  L  I  L  *  *  V  M  E

4141 AATGTCATTTAGTATGTCTTCTTTTGAGTTAGCTCAATTGTATGGTTTGTGTATAACACC 4200
     N  V  I  *  Y  V  F  F  *  V  S  S  I  V  W  F  V  Y  N  T
      M  S  F  S  M  S  S  F  E  L  A  Q  L  Y  G  L  C  I  T  P
       C  H  L  V  C  L  L  L  S  *  L  N  C  M  V  C  V  *  H  L

4201 TAATGTATGTTTTGTTAAAGGTGATATTATAAATGTTGCTAGACTTGTTAAAGCTGATGT 4260
     *  C  M  F  C  *  R  *  Y  Y  K  C  C  *  T  C  *  S  *  C
      N  V  C  F  V  K  G  D  I  I  N  V  A  R  L  V  K  A  D  V
       M  Y  V  L  L  K  V  I  L  *  M  L  L  D  L  L  K  L  M  L

4261 TATTGTTAACCCTGCTAATGGGCATATGCTCCATGGTGGTGGAGTTGCAAAAGCTATAGC 4320
     Y  C  *  P  C  *  W  A  Y  A  P  W  W  W  S  C  K  S  Y  S
      I  V  N  P  A  N  G  H  M  L  H  G  G  G  V  A  K  A  I  A
       L  L  T  L  L  M  G  I  C  S  M  V  V  E  L  Q  K  L  *  L
```

FIG. 9 CONT.

```
4321 TGTAGCTGCAGGTAAAAAATTTTCTAAAGAAACTGCTGCTATGGTTAAATCTAAAGGTGT 4380
     C  S  C  R  *  K  I  F  *  R  N  C  C  Y  G  *  I  *  R  C
      V  A  A  G  K  K  F  S  K  E  T  A  A  M  V  K  S  K  G  V
       *  L  Q  V  K  N  F  L  K  K  L  L  L  W  L  N  L  K  V  F

4381 TTGCCAAGTAGGAGATTGTTATGTTTCTACCGGTGGTAAATTATGTAAAACAATTCTTAA 4440
     L  P  S  R  R  L  L  C  F  Y  R  W  *  I  M  *  N  N  S  *
      C  Q  V  G  D  C  Y  V  S  T  G  G  K  L  C  K  T  I  L  N
       A  K  *  E  I  V  M  F  L  P  V  V  N  Y  V  K  Q  F  L  I

4441 TATTGTAGGTCCTGATGCTAGACAAGATGGAAGACAATCTTATGTTTTGTTAGCACGTGC 4500
     Y  C  R  S  *  C  *  T  R  W  K  T  I  L  C  F  V  S  T  C
      I  V  G  P  D  A  R  Q  D  G  R  Q  S  Y  V  L  L  A  R  A
       L  *  V  L  M  L  D  K  M  E  D  N  L  M  F  C  *  H  V  L

4501 TTATAAGCATCTTAATAATTATGATTGTTGTTTGTCTACTCTCATATCGGCTGGTATATT 4560
     L  *  A  S  *  *  L  *  L  L  F  V  Y  S  H  I  G  W  Y  I
      Y  K  H  L  N  N  Y  D  C  C  L  S  T  L  I  S  A  G  I  F
       I  S  I  L  I  I  M  I  V  V  C  L  L  S  Y  R  L  V  Y  L

4561 TAGTGTTCCTGCTGATGTGTCATTAACTTACCTTCTAGGTGTTGTTGATAAACAAGTTAT 4620
     *  C  S  C  *  C  V  I  N  L  P  S  R  C  C  *  *  T  S  Y
      S  V  P  A  D  V  S  L  T  Y  L  L  G  V  V  D  K  Q  V  I
       V  F  L  L  M  C  H  *  L  T  F  *  V  L  L  I  N  K  L  S

4621 CCTTGTTAGTAATAATAAAGAAGATTTTGATATTATTCAAAAATGTCAAATTACTTCAGT 4680
     P  C  *  *  *  *  R  R  F  *  Y  Y  S  K  M  S  N  Y  F  S
      L  V  S  N  N  K  E  D  F  D  I  I  Q  K  C  Q  I  T  S  V
       L  L  V  I  I  K  K  I  L  I  L  F  K  N  V  K  L  L  Q  L

4681 TGTTGGTACTAAAGCATTGGCTGTTAGATTAACTGCTAATGTAGGCCGTGTTATTAAATT 4740
     C  W  Y  *  S  I  G  C  *  I  N  C  *  C  R  P  C  Y  *  I
      V  G  T  K  A  L  A  V  R  L  T  A  N  V  G  R  V  I  K  F
       L  V  L  K  H  W  L  L  D  *  L  L  M  *  A  V  L  L  N  L

4741 TGAGACAGATGCATACAAACTTTTCTTGAGTGGTGATGATTGTTTTGTTTCAAATTCTTC 4800
     *  D  R  C  I  Q  T  F  L  E  W  *  *  L  F  C  F  K  F  F
      E  T  D  A  Y  K  L  F  L  S  G  D  D  C  F  V  S  N  S  S
       R  Q  M  H  T  N  F  S  *  V  V  M  I  V  L  F  Q  I  L  L

4801 TGTTATACAAGAAGTTTTATTGCTTCGTCATGATATACAATTGAATAATGACGTTCGTGA 4860
     C  Y  T  R  S  F  I  A  S  S  *  Y  T  I  E  *  *  R  S  *
      V  I  Q  E  V  L  L  L  R  H  D  I  Q  L  N  N  D  V  R  D
       L  Y  K  K  F  Y  C  F  V  M  I  Y  N  *  I  M  T  F  V  I
```

FIG. 9 CONT.

```
4861 TTATTTGTTGTCTAAGATGACTAGTCTTCCCAAAGATTGGCGTCTTATCAATAAATTTGA 4920
      L  F  V  V  *  D  D  *  S  S  Q  R  L  A  S  Y  Q  *  I  *
       Y  L  L  S  K  M  T  S  L  P  K  D  W  R  L  I  N  K  F  D
        I  C  C  L  R  *  L  V  F  P  K  I  G  V  L  S  I  N  L  M

4921 TGTTATTAACGGTGTTAAAACTGTTAAGTACTTTGAGTGTCCTAATTCTATTTATATATG 4980
      C  Y  *  R  C  *  N  C  *  V  L  *  V  S  *  F  Y  L  Y  M
       V  I  N  G  V  K  T  V  K  Y  F  E  C  P  N  S  I  Y  I  C
        L  L  T  V  L  K  L  L  S  T  L  S  V  L  I  L  F  I  Y  V

4981 TAGTCAGGGTAAAGACTTTGGTTATGTATGTGATGGTTCTTTTTATAAAGCAACTGTTAA 5040
      *  S  G  *  R  L  W  L  C  M  *  W  F  F  L  *  S  N  C  *
       S  Q  G  K  D  F  G  Y  V  C  D  G  S  F  Y  K  A  T  V  N
        V  R  V  K  T  L  V  M  Y  V  M  V  L  F  I  K  Q  L  L  I

5041 TCAAGTTTGTGTGTTATTAGCTAAGAAGATAGATGTTTTGCTTACTGTAGATGGTGTTAA 5100
      S  S  L  C  V  I  S  *  E  D  R  C  F  A  Y  C  R  W  C  *
       Q  V  C  V  L  L  A  K  K  I  D  V  L  L  T  V  D  G  V  N
        K  F  V  C  Y  *  L  R  R  *  M  F  C  L  L  *  M  V  L  I

5101 TTTTAAATCTATTTCTCTTACTGTAGGTGAAGTTTTTGGTAAAATACTTGGTAATGTTTT 5160
      F  *  I  Y  F  S  Y  C  R  *  S  F  W  *  N  T  W  *  C  F
       F  K  S  I  S  L  T  V  G  E  V  F  G  K  I  L  G  N  V  F
        L  N  L  F  L  L  L  *  V  K  F  L  V  K  Y  L  V  M  F  S

5161 CTGTGATGGCATTGATGTTACTAAGTTAAAGTGTAGTGATTTTTATGCCGATAAAATTTT 5220
      L  *  W  H  *  C  Y  *  V  K  V  *  *  F  L  C  R  *  N  F
       C  D  G  I  D  V  T  K  L  K  C  S  D  F  Y  A  D  K  I  L
        V  M  A  L  M  L  L  S  *  S  V  V  I  F  M  P  I  K  F  Y

5221 ATATCAGTATGAAAATTTGTCTTTAGCTGATATTTCTGCTGTACAAAGTTCATTTGGGTT 5280
      I  S  V  *  K  F  V  F  S  *  Y  F  C  C  T  K  F  I  W  V
       Y  Q  Y  E  N  L  S  L  A  D  I  S  A  V  Q  S  S  F  G  F
        I  S  M  K  I  C  L  *  L  I  F  L  L  Y  K  V  H  L  G  L

5281 TGATCAGCAACAATTGCTTGCTTACTATAATTTTTTAACAGTATGTAAATGGTCTGTAGT 5340
      *  S  A  T  I  A  C  L  L  *  F  F  N  S  M  *  M  V  C  S
       D  Q  Q  Q  L  L  A  Y  Y  N  F  L  T  V  C  K  W  S  V  V
        I  S  N  N  C  L  L  T  I  I  F  *  Q  Y  V  N  G  L  *  L

5341 TGTTAACGGTCCATTTTTTTCTTTTGAACAGTCTCATAATAATTGTTATGTGAATGTAGC 5400
      C  *  R  S  I  F  F  F  *  T  V  S  *  *  L  L  C  E  C  S
       V  N  G  P  F  F  S  F  E  Q  S  H  N  N  C  Y  V  N  V  A
        L  T  V  H  F  F  L  L  N  S  L  I  I  I  V  M  *  M  *  L
```

FIG. 9 CONT.

```
5401 TTGTCTTATGTTGCAGCATATTAATCTTAAATTTAATAAATGGCAGTGGCAGGAAGCATG 5460
     L  S  Y  V  A  A  Y  *  S  *  I  *  *  M  A  V  A  G  S  M
      C  L  M  L  Q  H  I  N  L  K  F  N  K  W  Q  W  Q  E  A  W
       V  L  C  C  S  I  L  I  L  N  L  I  N  G  S  G  R  K  H  G

5461 GTATGAATTTCGTGCTGGCAGACCACATAGGTTAGTTGCTCTTGTTTTAGCTAAAGGTCA 5520
     V  *  I  S  C  W  Q  T  T  *  V  S  C  S  C  F  S  *  R  S
      Y  E  F  R  A  G  R  P  H  R  L  V  A  L  V  L  A  K  G  H
       M  N  F  V  L  A  D  H  I  G  *  L  L  L  F  *  L  K  V  I

5521 TTTTAAATTTGATGAACCATCAGATGCTACTGATTTTATTCGTGTTGTTTTGAAACAAGC 5580
     F  *  I  *  *  T  I  R  C  Y  *  F  Y  S  C  C  F  E  T  S
      F  K  F  D  E  P  S  D  A  T  D  F  I  R  V  V  L  K  Q  A
       L  N  L  M  N  H  Q  M  L  L  I  L  F  V  L  F  *  N  K  L

5581 TGATTTATCAGGTGCAATTTGTGAATTAGAACTTATTTGTGATTGTGGTATTAAACAAGA 5640
     *  F  I  R  C  N  L  *  I  R  T  Y  L  *  L  W  Y  *  T  R
      D  L  S  G  A  I  C  E  L  E  L  I  C  D  C  G  I  K  Q  E
       I  Y  Q  V  Q  F  V  N  *  N  L  F  V  I  V  V  L  N  K  K

5641 AAGTCGTGTTGGTGTTGATGCTGTTATGCATTTTGGTACATTAGCAAAGACTGATCTTTT 5700
     K  S  C  W  C  *  C  C  Y  A  F  W  Y  I  S  K  D  *  S  F
      S  R  V  G  V  D  A  V  M  H  F  G  T  L  A  K  T  D  L  F
       V  V  L  V  L  M  L  L  C  I  L  V  H  *  Q  R  L  I  F  L

5701 TAATGGTTATAAGATTGGCTGTAATTGTGCAGGTAGAATTGTCCATTGTACTAAATTGAA 5760
     *  W  L  *  D  W  L  *  L  C  R  *  N  C  P  L  Y  *  I  E
      N  G  Y  K  I  G  C  N  C  A  G  R  I  V  H  C  T  K  L  N
       M  V  I  R  L  A  V  I  V  Q  V  E  L  S  I  V  L  N  *  M

5761 TGTACCATTTTTGATTTGTTCTAATACTCCTCTGAGTAAGGATTTACCTGATGATGTTGT 5820
     C  T  I  F  D  L  F  *  Y  S  S  E  *  G  F  T  *  *  C  C
      V  P  F  L  I  C  S  N  T  P  L  S  K  D  L  P  D  D  V  V
       Y  H  F  *  F  V  L  I  L  L  *  V  R  I  Y  L  M  M  L  L

5821 TGCAGCTAACATGTTTATGGGTGTAGGTGTAGGCCATTATACACATTTGAAATGTGGTTC 5880
     C  S  *  H  V  Y  G  C  R  C  R  P  L  Y  T  F  E  M  W  F
      A  A  N  M  F  M  G  V  G  V  G  H  Y  T  H  L  K  C  G  S
       Q  L  T  C  L  W  V  *  V  *  A  I  I  H  I  *  N  V  V  H

5881 ACCTTACCAACATTATGATGCTTGTAGTGTTAAAAAATATACAGGTGTTAGTGGTTGTTT 5940
     T  L  P  T  L  *  C  L  *  C  *  K  I  Y  R  C  *  W  L  F
      P  Y  Q  H  Y  D  A  C  S  V  K  K  Y  T  G  V  S  G  C  L
       L  T  N  I  M  M  L  V  V  L  K  N  I  Q  V  L  V  V  V  *
```

FIG. 9 CONT.

```
5941 AACTGACTGCTTGTATCTTAAAAATTTAACCCAGACTTTTACATCTATGTTGACTAATTA 6000
     N  *  L  L  V  S  *  K  F  N  P  D  F  Y  I  Y  V  D  *  L
      T  D  C  L  Y  L  K  N  L  T  Q  T  F  T  S  M  L  T  N  Y
       L  T  A  C  I  L  K  I  *  P  R  L  L  H  L  C  *  L  I  I

6001 TTTTTTGGATGATGTTGAAATGGTTGCTTATAACCCTGATCTTTCACAATATTATTGTGA 6060
     F  F  G  *  C  *  N  G  C  L  *  P  *  S  F  T  I  L  L  *
      F  L  D  D  V  E  M  V  A  Y  N  P  D  L  S  Q  Y  Y  C  D
       F  W  M  M  L  K  W  L  L  I  T  L  I  F  H  N  I  I  V  I

6061 TAATGGTAAGTATTATACAAAACCTATTATAAAGGCTCAGTTTAAACCATTTGCTAAAGT 6120
     *  W  *  V  L  Y  K  T  Y  Y  K  G  S  V  *  T  I  C  *  S
      N  G  K  Y  Y  T  K  P  I  I  K  A  Q  F  K  P  F  A  K  V
       M  V  S  I  I  Q  N  L  L  *  R  L  S  L  N  H  L  L  K  L

6121 TGACGGTGTTTATACTAACTTTAAGTTAGTTGGACATGATATTTGTGCTCAATTGAATGA 6180
     *  R  C  L  Y  *  L  *  V  S  W  T  *  Y  L  C  S  I  E  *
      D  G  V  Y  T  N  F  K  L  V  G  H  D  I  C  A  Q  L  N  D
       T  V  F  I  L  T  L  S  *  L  D  M  I  F  V  L  N  *  M  I

6181 TAAGTTAGGTTTTAATGTAGATTTGCCGTTTGTTGAGTACAAAGTAACAGTCTGGCCTGT 6240
     *  V  R  F  *  C  R  F  A  V  C  *  V  Q  S  N  S  L  A  C
      K  L  G  F  N  V  D  L  P  F  V  E  Y  K  V  T  V  W  P  V
       S  *  V  L  M  *  I  C  R  L  L  S  T  K  *  Q  S  G  L  *

6241 AGCTACTGGTGATGTTGTTTTGGCATCTGATGATTTATATGTTAAACGTTATTTTAAAGG 6300
     S  Y  W  *  C  C  F  G  I  *  *  F  I  C  *  T  L  F  *  R
      A  T  G  D  V  V  L  A  S  D  D  L  Y  V  K  R  Y  F  K  G
       L  L  V  M  L  F  W  H  L  M  I  Y  M  L  N  V  I  L  K  D

6301 ATGTGAAACTTTTGGTAAGCCTGTTATTTGGCTTTGTCATGATGAAGCATCATTGAATTC 6360
     M  *  N  F  W  *  A  C  Y  L  A  L  S  *  *  S  I  I  E  F
      C  E  T  F  G  K  P  V  I  W  L  C  H  D  E  A  S  L  N  S
       V  K  L  L  V  S  L  L  F  G  F  V  M  M  K  H  H  *  I  L

6361 TCTTACTTATTTTAATAAACCTAGTTTTAAATCTGAAAATAGATATAGTGTTTTGTCTGT 6420
     S  Y  L  F  *  *  T  *  F  *  I  *  K  *  I  *  C  F  V  C
      L  T  Y  F  N  K  P  S  F  K  S  E  N  R  Y  S  V  L  S  V
       L  L  I  L  I  N  L  V  L  N  L  K  I  D  I  V  F  C  L  L

6421 TGATTCTGTATCTGAGGAGTCACAAGGTAATGTGGTTACTTCTGTTATGGAATCGCAGAT 6480
     *  F  C  I  *  G  V  T  R  *  C  G  Y  F  C  Y  G  I  A  D
      D  S  V  S  E  E  S  Q  G  N  V  V  T  S  V  M  E  S  Q  I
       I  L  Y  L  R  S  H  K  V  M  W  L  L  L  L  W  N  R  R  L
```

FIG. 9 CONT.

```
6481 TAGTACTAAAGAGGTTAAGTTAAAGGGTGTTAGAAAGACTGTTAAAATAGAAGATGCTAT 6540
     * Y * R G * V K G C * K D C * N R R C Y
      S T K E V K L K G V R K T V K I E D A I
       V L K R L S * R V L E R L L K * K M L L

6541 TATTGTTAATGATGAAAATAGTTCTATTAAGGTTGTTAAAAGTTTATCTTTAGTTGATGT 6600
     Y C * * * K * F Y * G C * K F I F S * C
      I V N D E N S S I K V V K S L S L V D V
       L L M M K I V L L R L L K V Y L * L M F

6601 TTGGGATATGTATTTGACAGGTTGTGATTATGTTGTTTGGGTTGCTAATGAATTGTCACG 6660
     L G Y V F D R L * L C C L G C * * I V T
      W D M Y L T G C D Y V V W V A N E L S R
       G I C I * Q V V I M L F G L L M N C H A

6661 CCTAGTTAAATCACCAACAGTTAGGGAATATATACGATATGGTATTAAACCTATTACTAT 6720
     P S * I T N S * G I Y T I W Y * T Y Y Y
      L V K S P T V R E Y I R Y G I K P I T I
       * L N H Q Q L G N I Y D M V L N L L L Y

6721 ACCTATAGATTTGTTATGTTTAAGAGATGATAATCAAACTCTTTTAGTTCCTAAAATTTT 6780
     T Y R F V M F K R * * S N S F S S * N F
      P I D L L C L R D D N Q T L L V P K I F
       L * I C Y V * E M I I K L F * F L K F L

6781 TAAAGCAAGAGCTATAGAATTTTATGGTTTTTTGAAGTGGTTGTTTATTTATGTTTTTAG 6840
     * S K S Y R I L W F F E V V V Y L C F *
      K A R A I E F Y G F L K W L F I Y V F S
       K Q E L * N F M V F * S G C L F M F L V

6841 TTTATTACATTTTACAAATGATAAAACCATTTTTTATACTACAGAAATAGCTTCTAAGTT 6900
     F I T F Y K * * N H F L Y Y R N S F * V
      L L H F T N D K T I F Y T T E I A S K F
       Y Y I L Q M I K P F F I L Q K * L L S L

6901 TACTTTTAATTTGTTTTGTTTGGCTCTTAAAAATGCTTTTCAGACATTTAGATGGAGTAT 6960
     Y F * F V L F G S * K C F S D I * M E Y
      T F N L F C L A L K N A F Q T F R W S I
       L L I C F V W L L K M L F R H L D G V Y

6961 ATTTATAAAAGGTTTTCTTGTTGTAGCCACTGTGTTTTTGTTTTGGTTTAATTTTTTGTA 7020
     I Y K R F S C C S H C V F V L V * F F V
      F I K G F L V V A T V F L F W F N F L Y
       L * K V F L L * P L C F C F G L I F C I
```

FIG. 9 CONT.

```
7021 TATAAATGTTATTTTTAGTGATTTTTATCTTCCTAATATTAGTGTTTTTCCTATTTTTGT 7080
     Y  K  C  Y  F  *  *  F  L  S  S  *  Y  *  C  F  S  Y  F  C
      I  N  V  I  F  S  D  F  Y  L  P  N  I  S  V  F  P  I  F  V
       *  M  L  F  L  V  I  F  I  F  L  I  L  V  F  F  L  F  L  W

7081 GGGAAGAATTGTTATGTGGATAAAGGCTACTTTTGGTTTGGTTACAATTTGTGATTTTTA 7140
     G  K  N  C  Y  V  D  K  G  Y  F  W  F  G  Y  N  L  *  F  L
      G  R  I  V  M  W  I  K  A  T  F  G  L  V  T  I  C  D  F  Y
       E  E  L  L  C  G  *  R  L  L  L  V  W  L  Q  F  V  I  F  I

7141 TTCTAAGTTAGGTGTAGGTTTTACAAGTCATTTTTGTAATGGTAGTTTTATATGTGAATT 7200
     F  *  V  R  C  R  F  Y  K  S  F  L  *  W  *  F  Y  M  *  I
      S  K  L  G  V  G  F  T  S  H  F  C  N  G  S  F  I  C  E  L
       L  S  *  V  *  V  L  Q  V  I  F  V  M  V  V  L  Y  V  N  C

7201 GTGTTATTCTGGTTTTGATATGTTGGATACATATGCAGCTATAGATTTTGTTCAGTATGA 7260
     V  L  F  W  F  *  Y  V  G  Y  I  C  S  Y  R  F  C  S  V  *
      C  Y  S  G  F  D  M  L  D  T  Y  A  A  I  D  F  V  Q  Y  E
       V  I  L  V  L  I  C  W  I  H  M  Q  L  *  I  L  F  S  M  K

7261 AGTAGATAGACGTGTTTTATTTGATTATGTTAGTTTAGTCAAATTAATTGTTGAACTCGT 7320
     S  R  *  T  C  F  I  *  L  C  *  F  S  Q  I  N  C  *  T  R
      V  D  R  R  V  L  F  D  Y  V  S  L  V  K  L  I  V  E  L  V
       *  I  D  V  F  Y  L  I  M  L  V  *  S  N  *  L  L  N  S  L

7321 TATTGGTTATTCATTATATACAGTATGGTTTTATCCATTATTTTGTCTTATTGGTTTACA 7380
     Y  W  L  F  I  I  Y  S  M  V  L  S  I  I  L  S  Y  W  F  T
      I  G  Y  S  L  Y  T  V  W  F  Y  P  L  F  C  L  I  G  L  Q
       L  V  I  H  Y  I  Q  Y  G  F  I  H  Y  F  V  L  L  V  Y  N

7381 ATTATTTACTACATGGTTGCCTGATTTGTTTATGTTAGAAACTATGCATTGGTTGATTAG 7440
     I  I  Y  Y  M  V  A  *  F  V  Y  V  R  N  Y  A  L  V  D  *
      L  F  T  T  W  L  P  D  L  F  M  L  E  T  M  H  W  L  I  R
       Y  L  L  H  G  C  L  I  C  L  C  *  K  L  C  I  G  *  L  D

7441 ATTTATTGTATTTGTAGCTAATATGTTACCTGCTTTTGTCTTGTTGCGGTTTTATATAGT 7500
     I  Y  C  I  C  S  *  Y  V  T  C  F  C  L  V  A  V  L  Y  S
      F  I  V  F  V  A  N  M  L  P  A  F  V  L  L  R  F  Y  I  V
       L  L  Y  L  *  L  I  C  Y  L  L  L  S  C  C  G  F  I  *  L

7501 TGTTACTGCTATGTATAAAGTAGTTGGTTTTATTAGGCATATTGTTTATGGTTGTAATAA 7560
     C  Y  C  Y  V  *  S  S  W  F  Y  *  A  Y  C  L  W  L  *  *
      V  T  A  M  Y  K  V  V  G  F  I  R  H  I  V  Y  G  C  N  K
       L  L  L  C  I  K  *  L  V  L  L  G  I  L  F  M  V  V  I  K
```

FIG. 9 CONT.

```
7561 AGCTGGTTGTTTGTTTTGTTATAAACGAAATTGTAGTGTTCGTGTTAAGTGTAGTACTAT 7620
     S  W  L  F  V  L  L  *  T  K  L  *  C  S  C  *  V  *  Y  Y
      A  G  C  L  F  C  Y  K  R  N  C  S  V  R  V  K  C  S  T  I
       L  V  V  C  F  V  I  N  E  I  V  V  F  V  L  S  V  V  L  L

7621 TGTTGGTGGTGTAATTCGTTATTATGATATTACTGCTAATGGTGGTACTGGTTTTTGTGT 7680
     C  W  W  C  N  S  L  L  *  Y  Y  C  *  W  W  Y  W  F  L  C
      V  G  G  V  I  R  Y  Y  D  I  T  A  N  G  G  T  G  F  C  V
       L  V  V  *  F  V  I  M  I  L  L  L  M  V  V  L  V  F  V  L

7681 TAAACATCAATGGAATTGTTTTAATTGCCATTCTTTTAAACCAGGTAACACTTTTATAAC 7740
     *  T  S  M  E  L  F  *  L  P  F  F  *  T  R  *  H  F  Y  N
      K  H  Q  W  N  C  F  N  C  H  S  F  K  P  G  N  T  F  I  T
       N  I  N  G  I  V  L  I  A  I  L  L  N  Q  V  T  L  L  *  L

7741 TGTAGAAGCTGCTATAGAACTTTCTAAAGAGCTTAAACGACCTGTAAACCCAACTGATGC 7800
     C  R  S  C  Y  R  T  F  *  R  A  *  T  T  C  K  P  N  *  C
      V  E  A  A  I  E  L  S  K  E  L  K  R  P  V  N  P  T  D  A
       *  K  L  L  *  N  F  L  K  S  L  N  D  L  *  T  Q  L  M  L

7801 TTCACATTATGTAGTTACTGATATTAAGCAAGTTGGTTGTATGATGCGTTTGTTCTATGA 7860
     F  T  L  C  S  Y  *  Y  *  A  S  W  L  Y  D  A  F  V  L  *
      S  H  Y  V  V  T  D  I  K  Q  V  G  C  M  M  R  L  F  Y  D
       H  I  M  *  L  L  I  L  S  K  L  V  V  *  C  V  C  S  M  I

7861 TAGAGATGGACAGCGTGTTTACGATGATGTTGATGCTAGTTTATTTGTAGATATTAATAA 7920
     *  R  W  T  A  C  L  R  *  C  *  C  *  F  I  C  R  Y  *  *
      R  D  G  Q  R  V  Y  D  D  V  D  A  S  L  F  V  D  I  N  N
       E  M  D  S  V  F  T  M  M  L  M  L  V  Y  L  *  I  L  I  I

7921 TCTGTTACATTCTAAAGTCAAAGTTGTTCCTAATTTGTATGTAGTTGTAGTAGAGAGTGA 7980
     S  V  T  F  *  S  Q  S  C  S  *  F  V  C  S  C  S  R  E  *
      L  L  H  S  K  V  K  V  V  P  N  L  Y  V  V  V  V  E  S  D
       C  Y  I  L  K  S  K  L  F  L  I  C  M  *  L  *  *  R  V  M

7981 TGCTGATAGAGCTAATTTTCTGAATGCTGTTGTGTTTTATGCACAATCATTGTATAGGCC 8040
     C  *  *  S  *  F  S  E  C  C  C  V  L  C  T  I  I  V  *  A
      A  D  R  A  N  F  L  N  A  V  V  F  Y  A  Q  S  L  Y  R  P
       L  I  E  L  I  F  *  M  L  L  C  F  M  H  N  H  C  I  G  L

8041 TATATTACTTGTAGACAAAAAGTTAATTACTACAGCTTGTAATGGTATCTCTGTAACCCA 8100
     Y  I  T  C  R  Q  K  V  N  Y  Y  S  L  *  W  Y  L  C  N  P
      I  L  L  V  D  K  K  L  I  T  T  A  C  N  G  I  S  V  T  Q
       Y  Y  L  *  T  K  S  *  L  L  Q  L  V  M  V  S  L  *  P  R
```

FIG. 9 CONT.

```
8101 GACTATGTTTGATGTTTATGTTGATACTTTTATGTCTCATTTTGATGTTGATAGAAAGAG 8160
     D  Y  V  *  C  L  C  *  Y  F  Y  V  S  F  *  C  *  *  K  E
      T  M  F  D  V  Y  V  D  T  F  M  S  H  F  D  V  D  R  K  S
       L  C  L  M  F  M  L  I  L  L  C  L  I  L  M  L  I  E  R  V

8161 TTTTAATAATTTTGTTAACATTGCTCATGCTTCTCTTAGAGAGGGTGTGCAATTAGAAAA 8220
     F  *  *  F  C  *  H  C  S  C  F  S  *  R  G  C  A  I  R  K
      F  N  N  F  V  N  I  A  H  A  S  L  R  E  G  V  Q  L  E  K
       L  I  I  L  L  T  L  L  M  L  L  L  E  R  V  C  N  *  K  R

8221 GGTTTTAGATACTTTTGTGGGATGTGTACGTAAATGTTGTTCCATTGATTCAGATGTTGA 8280
     G  F  R  Y  F  C  G  M  C  T  *  M  L  F  H  *  F  R  C  *
      V  L  D  T  F  V  G  C  V  R  K  C  C  S  I  D  S  D  V  E
       F  *  I  L  L  W  D  V  Y  V  N  V  V  P  L  I  Q  M  L  K

8281 AACAAGATTTATTACTAAATCTATGATATCTGCAGTAGCTGCTGGTTTGGAATTTACTGA 8340
     N  K  I  Y  Y  *  I  Y  D  I  C  S  S  C  W  F  G  I  Y  *
      T  R  F  I  T  K  S  M  I  S  A  V  A  A  G  L  E  F  T  D
       Q  D  L  L  L  N  L  *  Y  L  Q  *  L  L  V  W  N  L  L  M

8341 TGAAAATTATAACAATTTGGTACCTACATATTTAAAGAGTGATAATATTGTAGCTGCAGA 8400
     *  K  L  *  Q  F  G  T  Y  I  F  K  E  *  *  Y  C  S  C  R
      E  N  Y  N  N  L  V  P  T  Y  L  K  S  D  N  I  V  A  A  D
       K  I  I  T  I  W  Y  L  H  I  *  R  V  I  I  L  *  L  Q  I

8401 TTTAGGTGTTCTTATACAGAATGGTGCTAAGCATGTACAGGGTAATGTTGCTAAGGCAGC 8460
     F  R  C  S  Y  T  E  W  C  *  A  C  T  G  *  C  C  *  G  S
      L  G  V  L  I  Q  N  G  A  K  H  V  Q  G  N  V  A  K  A  A
       *  V  F  L  Y  R  M  V  L  S  M  Y  R  V  M  L  L  R  Q  L

8461 TAATATTTCTTGTATATGGTTTATTGACACTTTTAATCAACTTACTGCTGATTTACAGCA 8520
     *  Y  F  L  Y  M  V  Y  *  H  F  *  S  T  Y  C  *  F  T  A
      N  I  S  C  I  W  F  I  D  T  F  N  Q  L  T  A  D  L  Q  H
       I  F  L  V  Y  G  L  L  T  L  L  I  N  L  L  L  I  Y  S  I

8521 TAAATTAAAAAAAGCATGTGTTAAAACTGGCTTGAAGTTAAAATTGACTTTTAATAAGCA 8580
     *  I  K  K  S  M  C  *  N  W  L  E  V  K  I  D  F  *  *  A
      K  L  K  K  A  C  V  K  T  G  L  K  L  K  L  T  F  N  K  Q
       N  *  K  K  H  V  L  K  L  A  *  S  *  N  *  L  L  I  S  K

8581 AGAGGCAAGTGTTCCTATTCTTACAACGCCCTTTTCACTTAAAGGAGGTGTTGTATTGAG 8640
     R  G  K  C  S  Y  S  Y  N  A  L  F  T  *  R  R  C  C  I  E
      E  A  S  V  P  I  L  T  T  P  F  S  L  K  G  G  V  V  L  S
       R  Q  V  F  L  F  L  Q  R  P  F  H  L  K  E  V  L  Y  *  V
```

FIG. 9 CONT.

```
8641 TAATTTGTTATATATATTATTTTTTATTAGTTTAATCTGTTTTATATTATTGTGGGCTTT 8700
      *  F  V  I  Y  I  I  F  Y  *  F  N  L  F  Y  I  I  V  G  F
       N  L  L  Y  I  L  F  F  I  S  L  I  C  F  I  L  L  W  A  L
        I  C  Y  I  Y  Y  F  L  L  V  *  S  V  L  Y  Y  C  G  L  Y

8701 ACTGCCTACATATAGTGTTTATAAGTCTGATATTCATTTGCCTGCTTATGCTAGTTTTAA 8760
      T  A  Y  I  *  C  L  *  V  *  Y  S  F  A  C  L  C  *  F  *
       L  P  T  Y  S  V  Y  K  S  D  I  H  L  P  A  Y  A  S  F  K
        C  L  H  I  V  F  I  S  L  I  F  I  C  L  L  M  L  V  L  K

8761 AGTTATTGATAATGGTGTTGTTAGAGATATTTCAGTTAATGATTTATGTTTTGCTAATAA 8820
      S  Y  *  *  W  C  C  *  R  Y  F  S  *  *  F  M  F  C  *  *
       V  I  D  N  G  V  V  R  D  I  S  V  N  D  L  C  F  A  N  K
        L  L  I  M  V  L  L  E  I  F  Q  L  M  I  Y  V  L  L  I  N

8821 ATTTTTCCAATTTGATCAATGGTATGAGTCCACTTTTGGGTCTTTTTACTATCATAATTC 8880
      I  F  P  I  *  S  M  V  *  V  H  F  W  V  F  L  L  S  *  F
       F  F  Q  F  D  Q  W  Y  E  S  T  F  G  S  F  Y  Y  H  N  S
        F  S  N  L  I  N  G  M  S  P  L  L  G  L  F  T  I  I  I  L

8881 TATGGATTGCCCTATTGTTGTGGCAGTTATGGATGAAGATATTGGTTCTACTATGTTTAA 8940
      Y  G  L  P  Y  C  C  G  S  Y  G  *  R  Y  W  F  Y  Y  V  *
       M  D  C  P  I  V  V  A  V  M  D  E  D  I  G  S  T  M  F  N
        W  I  A  L  L  L  W  Q  L  W  M  K  I  L  V  L  L  C  L  M

8941 TGTTCCTACTAAAGTTTTGAGACATGGCTTTCATGTTTTACATTTTCTAACTTATGCATT 9000
      C  S  Y  *  S  F  E  T  W  L  S  C  F  T  F  S  N  L  C  I
       V  P  T  K  V  L  R  H  G  F  H  V  L  H  F  L  T  Y  A  F
        F  L  L  K  F  *  D  M  A  F  M  F  Y  I  F  *  L  M  H  L

9001 TGCTAGTGATAGTGTTCAGTGCTATACACCACATATTCAGATTTCTTATAATGATTTTTA 9060
      C  *  *  *  C  S  V  L  Y  T  T  Y  S  D  F  L  *  *  F  L
       A  S  D  S  V  Q  C  Y  T  P  H  I  Q  I  S  Y  N  D  F  Y
        L  V  I  V  F  S  A  I  H  H  I  F  R  F  L  I  M  I  F  M

9061 TGCTAGTGGTTGTGTTTTATCATCTTTGTGTACTATGTTTAAAAGAGGTGATGGTACACC 9120
      C  *  W  L  C  F  I  I  F  V  Y  Y  V  *  K  R  *  W  Y  T
       A  S  G  C  V  L  S  S  L  C  T  M  F  K  R  G  D  G  T  P
        L  V  V  V  F  Y  H  L  C  V  L  C  L  K  E  V  M  V  H  H

9121 ACATCCTTATTGTTATTCAGATGGTGTTATGAAGAATGCTTCTTTGTATACATCTTTGGT 9180
      T  S  L  L  L  F  R  W  C  Y  E  E  C  F  F  V  Y  I  F  G
       H  P  Y  C  Y  S  D  G  V  M  K  N  A  S  L  Y  T  S  L  V
        I  L  I  V  I  Q  M  V  L  *  R  M  L  L  C  I  H  L  W  F
```

FIG. 9 CONT.

```
9181 TCCACATACACGTTATAGCCTTGCTAATTCTAATGGTTTTATAAGATTTCCTGATGTTAT 9240
     S  T  Y  T  L  *  P  C  *  F  *  W  F  Y  K  I  S  *  C  Y
      P  H  T  R  Y  S  L  A  N  S  N  G  F  I  R  F  P  D  V  I
       H  I  H  V  I  A  L  L  I  L  M  V  L  *  D  F  L  M  L  L

9241 TAGTGAAGGTATTGTACGTATTGTAAGAACGCGCTCTATGACTTATTGTAGAGTGGGTGC 9300
     *  *  R  Y  C  T  Y  C  K  N  A  L  Y  D  L  L  *  S  G  C
      S  E  G  I  V  R  I  V  R  T  R  S  M  T  Y  C  R  V  G  A
       V  K  V  L  Y  V  L  *  E  R  A  L  *  L  I  V  E  W  V  H

9301 ATGTGAATATGCCGAAGAGGGTATATGTTTTAATTTTAATAGTTCCTGGGTTTTGAATAA 9360
     M  *  I  C  R  R  G  Y  M  F  *  F  *  *  F  L  G  F  E  *
      C  E  Y  A  E  E  G  I  C  F  N  F  N  S  S  W  V  L  N  N
       V  N  M  P  K  R  V  Y  V  L  I  L  I  V  P  G  F  *  I  M

9361 TGATTATTATAGAAGTATGCCTGGAACTTTTTGTGGTAGAGATCTTTTTGATTTGTTTTA 9420
     *  L  L  *  K  Y  A  W  N  F  L  W  *  R  S  F  *  F  V  L
      D  Y  Y  R  S  M  P  G  T  F  C  G  R  D  L  F  D  L  F  Y
       I  I  I  E  V  C  L  E  L  F  V  V  E  I  F  L  I  C  F  I

9421 TCAATTTTTTAGTAGTTTAATTCGTCCTATAGATTTCTTTTCTCTTACTGCTAGTTCTAT 9480
     S  I  F  *  *  F  N  S  S  Y  R  F  L  F  S  Y  C  *  F  Y
      Q  F  F  S  S  L  I  R  P  I  D  F  F  S  L  T  A  S  S  I
       N  F  L  V  V  *  F  V  L  *  I  S  F  L  L  L  L  V  L  F

9481 TTTTGGAGCTATATTGGCTATAGTCGTTGTCTTGGTTTTTATTATTTAATAAAACTTAA 9540
     F  W  S  Y  I  G  Y  S  R  C  L  G  F  L  L  F  N  K  T  *
      F  G  A  I  L  A  I  V  V  V  L  V  F  Y  Y  L  I  K  L  K
       L  E  L  Y  W  L  *  S  L  S  W  F  F  I  I  *  *  N  L  S

9541 GCGTGCTTTTGGAGATTATACTAGTGTTGTAGTTATAAATGTTATTGTTTGGTGTATTAA 9600
     A  C  F  W  R  L  Y  *  C  C  S  Y  K  C  Y  C  L  V  Y  *
      R  A  F  G  D  Y  T  S  V  V  V  I  N  V  I  V  W  C  I  N
       V  L  L  E  I  I  L  V  L  *  L  *  M  L  L  F  G  V  L  I

9601 TTTTCTTATGCTTTTTGTTTTTCAAGTTTATCCTATTTGTGCATGTGTCTATGCTTGTTT 9660
     F  S  Y  A  F  C  F  S  S  L  S  Y  L  C  M  C  L  C  L  F
      F  L  M  L  F  V  F  Q  V  Y  P  I  C  A  C  V  Y  A  C  F
       F  L  C  F  L  F  F  K  F  I  L  F  V  H  V  S  M  L  V  F

9661 TTATTTTTATGTAACATTGTATTTTCCTTCTGAAATTAGTGTAATTATGCATTTGCAATG 9720
     L  F  L  C  N  I  V  F  S  F  *  N  *  C  N  Y  A  F  A  M
      Y  F  Y  V  T  L  Y  F  P  S  E  I  S  V  I  M  H  L  Q  W
       I  F  M  *  H  C  I  F  L  L  K  L  V  *  L  C  I  C  N  G
```

FIG. 9 CONT.

```
9781 TATTGCAAACCATGTTTTATGGTTATTTTCATATTGTAGGAAAATTGGTGTTAATGTATG 9840
     Y  C  K  P  C  F  M  V  I  F  I  L  *  E  N  W  C  *  C  M
      I  A  N  H  V  L  W  L  F  S  Y  C  R  K  I  G  V  N  V  C
       L  Q  T  M  F  Y  G  Y  F  H  I  V  G  K  L  V  L  M  Y  V

9841 TAATGATAGTACATTTGAAGAAACATCTCTTACTACTTTTATGATTACTAAAGATTCTTA 9900
     *  *  *  Y  I  *  R  N  I  S  Y  Y  F  Y  D  Y  *  R  F  L
      N  D  S  T  F  E  E  T  S  L  T  T  F  M  I  T  K  D  S  Y
       M  I  V  H  L  K  K  H  L  L  L  L  L  *  L  L  K  I  L  I

9901 TTGTAGATTAAAGAATTCTGTTTCTGATGTTGCTTACAATAGATATTTGAGTTTGTATAA 9960
     L  *  I  K  E  F  C  F  *  C  C  L  Q  *  I  F  E  F  V  *
      C  R  L  K  N  S  V  S  D  V  A  Y  N  R  Y  L  S  L  Y  N
       V  D  *  R  I  L  F  L  M  L  L  T  I  D  I  *  V  C  I  I

9961 TAAGTATCGTTACTATAGTGGTAAAATGGATACTGCTGCCTATAGAGAAGCGGCGTGTTC 10020
     *  V  S  L  L  *  W  *  N  G  Y  C  C  L  *  R  S  G  V  F
      K  Y  R  Y  Y  S  G  K  M  D  T  A  A  Y  R  E  A  A  C  S
       S  I  V  T  I  V  V  K  W  I  L  L  P  I  E  K  R  R  V  L

10021 TCAGTTAGCTAAAGCTATGGAAACATTTAATCACAATAATGGTAATGATGTCTTATACCA 10080
      S  V  S  *  S  Y  G  N  I  *  S  Q  *  W  *  *  C  L  I  P
       Q  L  A  K  A  M  E  T  F  N  H  N  N  G  N  D  V  L  Y  Q
        S  *  L  K  L  W  K  H  L  I  T  I  M  V  M  M  S  Y  T  N

10081 ACCTCCTACAGCATCTGTTTCTACATCTTTTTTGCAATCAGGTATTGTAAAGATGGTATC 10140
      T  S  Y  S  I  C  F  Y  I  F  F  A  I  R  Y  C  K  D  G  I
       P  P  T  A  S  V  S  T  S  F  L  Q  S  G  I  V  K  M  V  S
        L  L  Q  H  L  F  L  H  L  F  C  N  Q  V  L  *  R  W  Y  L

10141 TCCTACGTCAAAAATTGAACCTTGTATTGTTAGTGTTACTTATGGTAGTATGACTTTGAA 10200
      S  Y  V  K  N  *  T  L  Y  C  *  C  Y  L  W  *  Y  D  F  E
       P  T  S  K  I  E  P  C  I  V  S  V  T  Y  G  S  M  T  L  N
        L  R  Q  K  L  N  L  V  L  L  V  L  L  M  V  V  *  L  *  M

10201 TGGTTTATGGTTAGATGACAAAGTTTATTGTCCTCGTCATGTTATATGTTTATCCTCTAA 10260
      W  F  M  V  R  *  Q  S  L  L  S  S  S  C  Y  M  F  I  L  *
       G  L  W  L  D  D  K  V  Y  C  P  R  H  V  I  C  L  S  S  N
        V  Y  G  *  M  T  K  F  I  V  L  V  M  L  Y  V  Y  P  L  I

10261 TATGAATGAACCTGATTATTCTGCCTTATTATGTAGAGTTACTCTAGGTGATTTTACTAT 10320
      Y  E  *  T  *  L  F  C  L  I  M  *  S  Y  S  R  *  F  Y  Y
       M  N  E  P  D  Y  S  A  L  L  C  R  V  T  L  G  D  F  T  I
        *  M  N  L  I  I  L  P  Y  Y  V  E  L  L  *  V  I  L  L  *
```

FIG. 9 CONT.

```
 9721 GATTGTTATGTATGGTGCTATAATGCCTTTTTGGTTTTGTGTCACATATGTAGCTATGGT 9780
      D  C  Y  V  W  C  Y  N  A  F  L  V  L  C  H  I  C  S  Y  G
       I  V  M  Y  G  A  I  M  P  F  W  F  C  V  T  Y  V  A  M  V
        L  L  C  M  V  L  *  C  L  F  G  F  V  S  H  M  *  L  W  L

10321 AATGTCTGGGCGGATGAGTTTAACAGTTGTGTCTTACCAGATGCAGGGCTGTCAACTTGT 10380
      N  V  W  A  D  E  F  N  S  C  V  L  P  D  A  G  L  S  T  C
       M  S  G  R  M  S  L  T  V  V  S  Y  Q  M  Q  G  C  Q  L  V
        C  L  G  G  *  V  *  Q  L  C  L  T  R  C  R  A  V  N  L  F

10381 TTTGACAGTCTCTTTACAAAATCCTTACACTCCAAAATATACTTTTGGTGTTGTTAAACC 10440
      F  D  S  L  F  T  K  S  L  H  S  K  I  Y  F  W  C  C  *  T
       L  T  V  S  L  Q  N  P  Y  T  P  K  Y  T  F  G  V  V  K  P
        *  Q  S  L  Y  K  I  L  T  L  Q  N  I  L  L  V  L  L  N  L

10441 TGGTGAAACTTTTACTGTTTTAGCTGCGTATAATGGCCGACCACAAGGGGCATTTCATGT 10500
      W  *  N  F  Y  C  F  S  C  V  *  W  P  T  T  R  G  I  S  C
       G  E  T  F  T  V  L  A  A  Y  N  G  R  P  Q  G  A  F  H  V
        V  K  L  L  L  F  *  L  R  I  M  A  D  H  K  G  H  F  M  L

10501 TACTATGCGTAGTAGTTATACTATTAAAGGTTCTTTTTTGTGTGGGTCATGTGGATCTGT 10560
      Y  Y  A  *  *  L  Y  Y  *  R  F  F  F  V  W  V  M  W  I  C
       T  M  R  S  S  Y  T  I  K  G  S  F  L  C  G  S  C  G  S  V
        L  C  V  V  V  I  L  L  K  V  L  F  C  V  G  H  V  D  L  L

10561 TGGTTATGTATTAACAGGTGATAGTGTTAAGTTTGTATATATGCATCAATTAGAGCTCAG 10620
      W  L  C  I  N  R  *  *  C  *  V  C  I  Y  A  S  I  R  A  Q
       G  Y  V  L  T  G  D  S  V  K  F  V  Y  M  H  Q  L  E  L  S
        V  M  Y  *  Q  V  I  V  L  S  L  Y  I  C  I  N  *  S  S  V

10621 TACTGGTTGTCACACTGGCACTGATTTTACTGGTAATTTTTATGGTCCATATAGAGATGC 10680
      Y  W  L  S  H  W  H  *  F  Y  W  *  F  L  W  S  I  *  R  C
       T  G  C  H  T  G  T  D  F  T  G  N  F  Y  G  P  Y  R  D  A
        L  V  V  T  L  A  L  I  L  L  V  I  F  M  V  H  I  E  M  L

10681 TCAAGTTGTACAGTTGCCAGTTAAGGACTACGTCCAAACTGTTAATGTTATTGCTTGGCT 10740
      S  S  C  T  V  A  S  *  G  L  R  P  N  C  *  C  Y  C  L  A
       Q  V  V  Q  L  P  V  K  D  Y  V  Q  T  V  N  V  I  A  W  L
        K  L  Y  S  C  Q  L  R  T  T  S  K  L  L  M  L  L  L  G  S

10741 CTATGCAGCTATACTTAATAATTGTGCTTGGTTTGTACAAAATGATGTTTGTTCTATTGA 10800
      L  C  S  Y  T  *  *  L  C  L  V  C  T  K  *  C  L  F  Y  *
       Y  A  A  I  L  N  N  C  A  W  F  V  Q  N  D  V  C  S  I  E
        M  Q  L  Y  L  I  I  V  L  G  L  Y  K  M  M  F  V  L  L  K
```

FIG. 9 CONT.

```
10801 AGATTTTAATGTTTGGGCTATGACAAATGGTTTTAGCCAAGTAAAAGCAGATCTTGTTTT 10860
      R  F  *  C  L  G  Y  D  K  W  F  *  P  S  K  S  R  S  C  F
       D  F  N  V  W  A  M  T  N  G  F  S  Q  V  K  A  D  L  V  L
        I  L  M  F  G  L  *  Q  M  V  L  A  K  *  K  Q  I  L  F  *

10861 AGATGCTTTGGCTTCAATGACAGGTGTTTCTATTGAAACTTTATTGGCTGCTATTAAGCG 10920
      R  C  F  G  F  N  D  R  C  F  Y  *  N  F  I  G  C  Y  *  A
       D  A  L  A  S  M  T  G  V  S  I  E  T  L  L  A  A  I  K  R
        M  L  W  L  Q  *  Q  V  F  L  L  K  L  Y  W  L  L  L  S  V

10921 TCTATATATGGGATTTCAAGGTCGTCAAATACTAGGAAGTTGTACTTTTGAAGATGAATT 10980
      S  I  Y  G  I  S  R  S  S  N  T  R  K  L  Y  F  *  R  *  I
       L  Y  M  G  F  Q  G  R  Q  I  L  G  S  C  T  F  E  D  E  L
        Y  I  W  D  F  K  V  V  K  Y  *  E  V  V  L  L  K  M  N  W

10981 GGCACCTTCTGACGTTTATCAACAATTGGCTGGTGTTAAATTGCAATCTAAAACAAAAAG 11040
      G  T  F  *  R  L  S  T  I  G  W  C  *  I  A  I  *  N  K  K
       A  P  S  D  V  Y  Q  Q  L  A  G  V  K  L  Q  S  K  T  K  R
        H  L  L  T  F  I  N  N  W  L  V  L  N  C  N  L  K  Q  K  D

11041 ATTTATTAAAGAAACAATTTATTGGATTTTGATATCTACATTTTTGTTTAGTTGTATAAT 11100
      I  Y  *  R  N  N  L  L  D  F  D  I  Y  I  F  V  *  L  Y  N
       F  I  K  E  T  I  Y  W  I  L  I  S  T  F  L  F  S  C  I  I
        L  L  K  K  Q  F  I  G  F  *  Y  L  H  F  C  L  V  V  *  F

11101 TTCTGCATTTGTTAAATGGACTATATTTATGTATATTAATACACATATGATTGGTGTTAC 11160
      F  C  I  C  *  M  D  Y  I  Y  V  Y  *  Y  T  Y  D  W  C  Y
       S  A  F  V  K  W  T  I  F  M  Y  I  N  T  H  M  I  G  V  T
        L  H  L  L  N  G  L  Y  L  C  I  L  I  H  I  *  L  V  L  H

11161 ATTATGTGTACTTTGTTTTGTTAGTTTTATGATGTTACTAGTTAAACATAAGCATTTTTA 11220
      I  M  C  T  L  F  C  *  F  Y  D  V  T  S  *  T  *  A  F  L
       L  C  V  L  C  F  V  S  F  M  M  L  L  V  K  H  K  H  F  Y
        Y  V  Y  F  V  L  L  V  L  *  C  Y  *  L  N  I  S  I  F  I

11221 TTTGACTATGTATATAATTCCTGTACTCTGTACCTTGTTTTATGTAAATTATTTAGTTGT 11280
      F  D  Y  V  Y  N  S  C  T  L  Y  L  V  L  C  K  L  F  S  C
       L  T  M  Y  I  I  P  V  L  C  T  L  F  Y  V  N  Y  L  V  V
        *  L  C  I  *  F  L  Y  S  V  P  C  F  M  *  I  I  *  L  S

11281 CTATAAGGAAGGTTTTAGAGGTCTTACTTATGTCTGGCTCTCATATTTTGTTCCTGCTGT 11340
      L  *  G  R  F  *  R  S  Y  L  C  L  A  L  I  F  C  S  C  C
       Y  K  E  G  F  R  G  L  T  Y  V  W  L  S  Y  F  V  P  A  V
        I  R  K  V  L  E  V  L  L  M  S  G  S  H  I  L  F  L  L  *
```

FIG. 9 CONT.

```
11341 GAATTTTACTTATGTTTATGAAGTATTTTATGGTTGTATTTTATGTGTTTTTGCTATTTT 11400
      E  F  Y  L  C  L  *  S  I  L  W  L  Y  F  M  C  F  C  Y  F
       N  F  T  Y  V  Y  E  V  F  Y  G  C  I  L  C  V  F  A  I  F
        I  L  L  M  F  M  K  Y  F  M  V  V  F  Y  V  F  L  L  F  L

11401 TATAACTATGCATAGTATTAATCATGACATTTTTTCTTTGATGTTTTTGGTTGGTAGAAT 11460
      Y  N  Y  A  *  Y  *  S  *  H  F  F  F  D  V  F  G  W  *  N
       I  T  M  H  S  I  N  H  D  I  F  S  L  M  F  L  V  G  R  I
        *  L  C  I  V  L  I  M  T  F  F  L  *  C  F  W  L  V  E  *

11461 AGTTACTTTAATTTCTATGTGGTATTTTGGGTCGAATTTAGAAGAGGATGTTTTGTTATT 11520
      S  Y  F  N  F  Y  V  V  F  W  V  E  F  R  R  G  C  F  V  I
       V  T  L  I  S  M  W  Y  F  G  S  N  L  E  E  D  V  L  L  F
        L  L  *  F  L  C  G  I  L  G  R  I  *  K  R  M  F  C  Y  L

11521 TATTACAGCCTTTTTAGGTACTTATACATGGACCACTATTTTGTCATTAGCTATAGCAAA 11580
      Y  Y  S  L  F  R  Y  L  Y  M  D  H  Y  F  V  I  S  Y  S  K
       I  T  A  F  L  G  T  Y  T  W  T  T  I  L  S  L  A  I  A  K
        L  Q  P  F  *  V  L  I  H  G  P  L  F  C  H  *  L  *  Q  K

11581 AATTGTTGCTAATTGGTTGTCTGTTAATATATTTTATTTTACAGATGTACCTTATATTAA 11640
      N  C  C  *  L  V  V  C  *  Y  I  L  F  Y  R  C  T  L  Y  *
       I  V  A  N  W  L  S  V  N  I  F  Y  F  T  D  V  P  Y  I  K
        L  L  L  I  G  C  L  L  I  Y  F  I  L  Q  M  Y  L  I  L  N

11641 ATTGATTCTTTTGAGTTACTTATTTATAGGGTATATTTTATCTTGTTATTGGGGATTTTT 11700
      I  D  S  F  E  L  L  I  Y  R  V  Y  F  I  L  L  L  G  I  F
       L  I  L  L  S  Y  L  F  I  G  Y  I  L  S  C  Y  W  G  F  F
        *  F  F  *  V  T  Y  L  *  G  I  F  Y  L  V  I  G  D  F  S

11701 CTCTCTTTTAAACAGTGTTTTTAGAATGCCTATGGGTGTTTATAATTATAAAATTTCTGT 11760
      L  S  F  K  Q  C  F  *  N  A  Y  G  C  L  *  L  *  N  F  C
       S  L  L  N  S  V  F  R  M  P  M  G  V  Y  N  Y  K  I  S  V
        L  F  *  T  V  F  L  E  C  L  W  V  F  I  I  I  K  F  L  F

11761 TCAAGAATTGCGTTATATGAATGCTAATGGCTTACGTCCACCCCGTAATAGTTTTGAGGC 11820
      S  R  I  A  L  Y  E  C  *  W  L  T  S  T  P  *  *  F  *  G
       Q  E  L  R  Y  M  N  A  N  G  L  R  P  P  R  N  S  F  E  A
        K  N  C  V  I  *  M  L  M  A  Y  V  H  P  V  I  V  L  R  L

11821 TATTTTGTTAAATTTAAAACTGCTTGGAATAGGTGGCGTGCCAGTTATTGAAGTTTCTCA 11880
      Y  F  V  K  F  K  T  A  W  N  R  W  R  A  S  Y  *  S  F  S
       I  L  L  N  L  K  L  L  G  I  G  G  V  P  V  I  E  V  S  Q
        F  C  *  I  *  N  C  L  E  *  V  A  C  Q  L  L  K  F  L  K
```

FIG. 9 CONT.

```
11881 AATTCAATCAAAATTGACTGATGTGAAATGTGCTAATGTTGTTTTGTTAAATTGTTTACA 11940
      N  S  I  K  I  D  *  C  E  M  C  *  C  C  F  V  K  L  F  T
       I  Q  S  K  L  T  D  V  K  C  A  N  V  V  L  L  N  C  L  Q
        F  N  Q  N  *  L  M  *  N  V  L  M  L  F  C  *  I  V  Y  S

11941 GCATTTGCATGTTGCTTCTAATTCTAGGTTGTGGCAGTATTGTAGTATTTTACATAATGA 12000
      A  F  A  C  C  F  *  F  *  V  V  A  V  L  *  Y  F  T  *  *
       H  L  H  V  A  S  N  S  R  L  W  Q  Y  C  S  I  L  H  N  E
        I  C  M  L  L  L  I  L  G  C  G  S  I  V  V  F  Y  I  M  K

12001 AATACTATCTACTTCAGATTTAAGTGTAGCTTTTGATAAGCTTGCTCAATTATTGATTGT 12060
      N  T  I  Y  F  R  F  K  C  S  F  *  *  A  C  S  I  I  D  C
       I  L  S  T  S  D  L  S  V  A  F  D  K  L  A  Q  L  L  I  V
        Y  Y  L  L  Q  I  *  V  *  L  L  I  S  L  L  N  Y  *  L  F

12061 TTTATTCGCCAATCCTGCTGCAGTTGATACTAAGTGTCTTGCAAGTATAGATGAAGTTAG 12120
      F  I  R  Q  S  C  C  S  *  Y  *  V  S  C  K  Y  R  *  S  *
       L  F  A  N  P  A  A  V  D  T  K  C  L  A  S  I  D  E  V  S
        Y  S  P  I  L  L  Q  L  I  L  S  V  L  Q  V  *  M  K  L  A

12121 CGATGATTATGTTCAAGATAGTACTGTTTTGCAGGCTTTGCAAAGTGAGTTTGTAAATAT 12180
      R  *  L  C  S  R  *  Y  C  F  A  G  F  A  K  *  V  C  K  Y
       D  D  Y  V  Q  D  S  T  V  L  Q  A  L  Q  S  E  F  V  N  M
        M  I  M  F  K  I  V  L  F  C  R  L  C  K  V  S  L  *  I  W

12181 GGCTAGTTTTGTTGAATATGAAGTCGCAAAGAAAAATTTGGCTGATGCTAAAAATAGTGG 12240
      G  *  F  C  *  I  *  S  R  K  E  K  F  G  *  C  *  K  *  W
       A  S  F  V  E  Y  E  V  A  K  K  N  L  A  D  A  K  N  S  G
        L  V  L  L  N  M  K  S  Q  R  K  I  W  L  M  L  K  I  V  V

12241 TTCTGTTAATCAACAACAGATAAAACAGTTAGAAAAGGCATGTAATATAGCTAAGTCTGT 12300
      F  C  *  S  T  T  D  K  T  V  R  K  G  M  *  Y  S  *  V  C
       S  V  N  Q  Q  Q  I  K  Q  L  E  K  A  C  N  I  A  K  S  V
        L  L  I  N  N  R  *  N  S  *  K  R  H  V  I  *  L  S  L  C

12301 GTATGAACGCGATAAAGCTGTAGCTCGCAAACTGGAACGTATGGCAGACCTAGCACTTAC 12360
      V  *  T  R  *  S  C  S  S  Q  T  G  T  Y  G  R  P  S  T  Y
       Y  E  R  D  K  A  V  A  R  K  L  E  R  M  A  D  L  A  L  T
        M  N  A  I  K  L  *  L  A  N  W  N  V  W  Q  T  *  H  L  L

12361 TAACATGTATAAAGAGGCTCGGATTAATGATAAGAAGAGTAAAGTTGTTTCCGCTTTGCA 12420
      *  H  V  *  R  G  S  D  *  *  *  E  E  *  S  C  F  R  F  A
       N  M  Y  K  E  A  R  I  N  D  K  K  S  K  V  V  S  A  L  Q
        T  C  I  K  R  L  G  L  M  I  R  R  V  K  L  F  P  L  C  R
```

FIG. 9 CONT.

```
12421 GACAATGCTTTTTAGCATGGTTCGTAAATTGGATAATCAGGCTTTAAATTCTATTCTGGA 12480
      D  N  A  F  *  H  G  S  *  I  G  *  S  G  F  K  F  Y  S  G
       T  M  L  F  S  M  V  R  K  L  D  N  Q  A  L  N  S  I  L  D
        Q  C  F  L  A  W  F  V  N  W  I  I  R  L  *  I  L  F  W  I

12481 TAATGCTGTTAAAGGTTGTGTACCTTTGAATGCTATTCCAGCGCTGGCTGCTAATACTTT 12540
      *  C  C  *  R  L  C  T  F  E  C  Y  S  S  A  G  C  *  Y  F
       N  A  V  K  G  C  V  P  L  N  A  I  P  A  L  A  A  N  T  L
        M  L  L  K  V  V  Y  L  *  M  L  F  Q  R  W  L  L  I  L  *

12541 AACTATAATAATACCAGATAAACAAGTTTTTGATAAAGTTGTTGATAATGTTTATGTTGC 12600
      N  Y  N  N  T  R  *  T  S  F  *  *  S  C  *  *  C  L  C  C
       T  I  I  I  P  D  K  Q  V  F  D  K  V  V  D  N  V  Y  V  A
        L  *  *  Y  Q  I  N  K  F  L  I  K  L  L  I  M  F  M  L  H

12601 ATATGCTGGTAGTGTATGGCATATACAGACTGTTCAAGATGCTGATGGTATTAATAAACA 12660
      I  C  W  *  C  M  A  Y  T  D  C  S  R  C  *  W  Y  *  *  T
       Y  A  G  S  V  W  H  I  Q  T  V  Q  D  A  D  G  I  N  K  Q
        M  L  V  V  Y  G  I  Y  R  L  F  K  M  L  M  V  L  I  N  S

12661 GTTAACTGATATTAGTGTTGATTCTAATTGGCCTCTTGTTATTATTGCTAACAGGTATAA 12720
      V  N  *  Y  *  C  *  F  *  L  A  S  C  Y  Y  C  *  Q  V  *
       L  T  D  I  S  V  D  S  N  W  P  L  V  I  I  A  N  R  Y  N
        *  L  I  L  V  L  I  L  I  G  L  L  L  L  L  L  T  G  I  M

12721 TGAAGTTGCTAATGCTGTTATGCAGAATAATGAGTTGATGCCTCATAAATTAAAAATACA 12780
      *  S  C  *  C  C  Y  A  E  *  *  V  D  A  S  *  I  K  N  T
       E  V  A  N  A  V  M  Q  N  N  E  L  M  P  H  K  L  K  I  Q
        K  L  L  M  L  L  C  R  I  M  S  *  C  L  I  N  *  K  Y  K

12781 AGTTGTTAATAGTGGTTCTGATATGAATTGTAACATTCCTACTCAATGTTATTATAATAA 12840
      S  C  *  *  W  F  *  Y  E  L  *  H  S  Y  S  M  L  L  *  *
       V  V  N  S  G  S  D  M  N  C  N  I  P  T  Q  C  Y  Y  N  N
        L  L  I  V  V  L  I  *  I  V  T  F  L  L  N  V  I  I  I  M

12841 TGGTAGTAGTGGTAGAATAGTTTATGCTGTTCTTAGTGATGTTGATGGTCTTAAGTATAC 12900
      W  *  *  W  *  N  S  L  C  C  S  *  *  C  *  W  S  *  V  Y
       G  S  S  G  R  I  V  Y  A  V  L  S  D  V  D  G  L  K  Y  T
        V  V  V  V  E  *  F  M  L  F  L  V  M  L  M  V  L  S  I  L

12901 TAAGATAATAAAAGATGATGGAAATTGTGTTGTTTTAGAGCTTGATCCTCCTTGTAAATT 12960
      *  D  N  K  R  *  W  K  L  C  C  F  R  A  *  S  S  L  *  I
       K  I  I  K  D  D  G  N  C  V  V  L  E  L  D  P  P  C  K  F
        R  *  *  K  M  M  E  I  V  L  F  *  S  L  I  L  L  V  N  F
```

FIG. 9 CONT.

```
12961 TTCTATACAAGATGTTAAGGGACTTAAAATTAAGTATCTTTATTTTATTAAAGGATGTAA 13020
      F  Y  T  R  C  *  G  T  *  N  *  V  S  L  F  Y  *  R  M  *
       S  I  Q  D  V  K  G  L  K  I  K  Y  L  Y  F  I  K  G  C  N
        L  Y  K  M  L  R  D  L  K  L  S  I  F  I  L  L  K  D  V  T

13021 CACTTTAGCTAGAGGGTGGGTTGTTGGTACTTTATCTTCAACAATTAGATTGCAGGCTGG 13080
      H  F  S  *  R  V  G  C  W  Y  F  I  F  N  N  *  I  A  G  W
       T  L  A  R  G  W  V  V  G  T  L  S  S  T  I  R  L  Q  A  G
        L  *  L  E  G  G  L  L  V  L  Y  L  Q  Q  L  D  C  R  L  V

13081 TGTTGCTACTGAGTATGCAGCTAATTCTTCTATACTTTCATTATGTGCATTTTCTGTAGA 13140
      C  C  Y  *  V  C  S  *  F  F  Y  T  F  I  M  C  I  F  C  R
       V  A  T  E  Y  A  A  N  S  S  I  L  S  L  C  A  F  S  V  D
        L  L  L  S  M  Q  L  I  L  L  Y  F  H  Y  V  H  F  L  *  I

13141 TCCTAAGAAAACTTATTTAGATTATATACAACAAGGTGGTGTACCTATAATTAATTGTGT 13200
      S  *  E  N  L  F  R  L  Y  T  T  R  W  C  T  Y  N  *  L  C
       P  K  K  T  Y  L  D  Y  I  Q  Q  G  G  V  P  I  I  N  C  V
        L  R  K  L  I  *  I  I  Y  N  K  V  V  Y  L  *  L  I  V  L

13201 TAAAATGCTCTGTGATCATGCTGGTACTGGTATGGCTATTACTATTAAACCTGAGGCTAC 13260
      *  N  A  L  *  S  C  W  Y  W  Y  G  Y  Y  Y  *  T  *  G  Y
       K  M  L  C  D  H  A  G  T  G  M  A  I  T  I  K  P  E  A  T
        K  C  S  V  I  M  L  V  L  V  W  L  L  L  L  N  L  R  L  L

13261 TATTAATCAAGATTCTTATGGTGGTGCCTCAGTTTGTATTTACTGCCGTGCACGTGTAGA 13320
      Y  *  S  R  F  L  W  W  C  L  S  L  Y  L  L  P  C  T  C  R
       I  N  Q  D  S  Y  G  G  A  S  V  C  I  Y  C  R  A  R  V  E
        L  I  K  I  L  M  V  V  P  Q  F  V  F  T  A  V  H  V  *  S

13321 GCATCCAGATGTAGATGGTTTGTGTAAATTACGTGGTAAATTTGTACAAGTCCCTTTGGG 13380
      A  S  R  C  R  W  F  V  *  I  T  W  *  I  C  T  S  P  F  G
       H  P  D  V  D  G  L  C  K  L  R  G  K  F  V  Q  V  P  L  G
        I  Q  M  *  M  V  C  V  N  Y  V  V  N  L  Y  K  S  L  W  V

13381 TATAAAAGATCCTATTCTCTATGTGTTAACACATGATGTTTGTCAAGTTTGTGGATTTTG 13440
      Y  K  R  S  Y  S  L  C  V  N  T  *  C  L  S  S  L  W  I  L
       I  K  D  P  I  L  Y  V  L  T  H  D  V  C  Q  V  C  G  F  W
        *  K  I  L  F  S  M  C  *  H  M  M  F  V  K  F  V  D  F  G

13441 GAGAGATGGCAGTTGTTCCTGTGTAGGTTCAGGTGTCGCTGTTCAATCTAAAGATTTAAA 13500
      E  R  W  Q  L  F  L  C  R  F  R  C  R  C  S  I  *  R  F  K
       R  D  G  S  C  S  C  V  G  S  G  V  A  V  Q  S  K  D  L  N
        E  M  A  V  V  P  V  *  V  Q  V  S  L  F  N  L  K  I  *  I
```

FIG. 9 CONT.

```
13501 TTTTTTAAACGGGTTCGGGGTACTAGTGTGAATGCCCGTCTAGTACCCTGTGCTAGTGGT 13560
      F  F  K  R  V  R  G  T  S  V  N  A  R  L  V  P  C  A  S  G
       F  L  N  G  F  G  V  L  V  *  M  P  V  *  Y  P  V  L  V  V
        F  *  T  G  S  G  Y  *  C  E  C  P  S  S  T  L  C  *  W  F

13561 TTATCTACTGATGTTCAATTAAGGGCATTTGATATTTGTAATACTAATAGAGCTGGTATA 13620
      L  S  T  D  V  Q  L  R  A  F  D  I  C  N  T  N  R  A  G  I
       Y  L  L  M  F  N  *  G  H  L  I  F  V  I  L  I  E  L  V  *
        I  Y  *  C  S  I  K  G  I  *  Y  L  *  Y  *  *  S  W  Y  R

13621 GGTTTATATTATAAAGTGAATTGTTGCCGTTTTCAGCGTATAGATGACGACGGTAATAAA 13680
      G  L  Y  Y  K  V  N  C  C  R  F  Q  R  I  D  D  D  G  N  K
       V  Y  I  I  K  *  I  V  A  V  F  S  V  *  M  T  T  V  I  N
        F  I  L  *  S  E  L  L  P  F  S  A  Y  R  *  R  R  *  *  I

13681 TTGGATAAGTTCTTTGTTGTTAAAAGAACTAATCTAGAAGTTTATAATAAAGAGAAAACT 13740
      L  D  K  F  F  V  V  K  R  T  N  L  E  V  Y  N  K  E  K  T
       W  I  S  S  L  L  L  K  E  L  I  *  K  F  I  I  K  R  K  L
        G  *  V  L  C  C  *  K  N  *  S  R  S  L  *  *  R  E  N  L

13741 TATTATGAGTTGACTAAAAGTTGTGGTGTTGTGGCTGAACATGATTTCTTTACATTTGAT 13800
      Y  Y  E  L  T  K  S  C  G  V  V  A  E  H  D  F  F  T  F  D
       I  M  S  *  L  K  V  V  V  L  W  L  N  M  I  S  L  H  L  I
        L  *  V  D  *  K  L  W  C  C  G  *  T  *  F  L  Y  I  *  Y

13801 ATTGATGGTAGTCGTGTGCCACATATAGTTCGTAAGAACCTCTCAAAGTATACTATGTTA 13860
      I  D  G  S  R  V  P  H  I  V  R  K  N  L  S  K  Y  T  M  L
       L  M  V  V  V  C  H  I  *  F  V  R  T  S  Q  S  I  L  C  *
        *  W  *  S  C  A  T  Y  S  S  *  E  P  L  K  V  Y  Y  V  R

13861 GATCTTTGCTATGCATTGCGCCATTTTGATTGTAATGATTGTTCAGTATTGTGTGAAATT 13920
      D  L  C  Y  A  L  R  H  F  D  C  N  D  C  S  V  L  C  E  I
       I  F  A  M  H  C  A  I  L  I  V  M  I  V  Q  Y  C  V  K  F
        S  L  L  C  I  A  P  F  *  L  *  *  L  F  S  I  V  *  N  S

13921 CTTTGTGAGTATGCTGATTGTAAAGAATCCTACTTTTCTAAGAAAGATTGGTATGATTTT 13980
      L  C  E  Y  A  D  C  K  E  S  Y  F  S  K  K  D  W  Y  D  F
       F  V  S  M  L  I  V  K  N  P  T  F  L  R  K  I  G  M  I  L
        L  *  V  C  *  L  *  R  I  L  L  F  *  E  R  L  V  *  F  C

13981 GTTGAAAATCCTGATATTATTAATATTTATAAAAAATTAGGCCCTATTTTTAATAGAGCT 14040
      V  E  N  P  D  I  I  N  I  Y  K  K  L  G  P  I  F  N  R  A
       L  K  I  L  I  L  L  I  F  I  K  N  *  A  L  F  L  I  E  L
        *  K  S  *  Y  Y  *  Y  L  *  K  I  R  P  Y  F  *  *  S  F
```

FIG. 9 CONT.

```
14041 TTACTTAATACTGTCAGTTTTGCAGATACTTTAGTAAAAGTAGGTTTAGTTGGTGTTTTA 14100
      L  L  N  T  V  S  F  A  D  T  L  V  K  V  G  L  V  G  V  L
       Y  L  I  L  S  V  L  Q  I  L  *  *  K  *  V  *  L  V  F  *
        T  *  Y  C  Q  F  C  R  Y  F  S  K  S  R  F  S  W  C  F  N

14101 ACTTTAGATAATCAAGACTTGTATGGTCAATGGTATGATTTTGGTGATTTTATACAAACA 14160
      T  L  D  N  Q  D  L  Y  G  Q  W  Y  D  F  G  D  F  I  Q  T
       L  *  I  I  K  T  C  M  V  N  G  M  I  L  V  I  L  Y  K  Q
        F  R  *  S  R  L  V  W  S  M  V  *  F  W  *  F  Y  T  N  S

14161 GCTCCAGGTTTTGGTGTGGCAGTTGCAGATTCTTACTATTCTTATATGATGCCTATGTTG 14220
      A  P  G  F  G  V  A  V  A  D  S  Y  Y  S  Y  M  M  P  M  L
       L  Q  V  L  V  W  Q  L  Q  I  L  T  I  L  I  *  C  L  C  *
        S  R  F  W  C  G  S  C  R  F  L  L  F  L  Y  D  A  Y  V  D

14221 ACTATGTGTCATGTATTAGATTGTGAATTATTTGTTAATGATAGTTATAGACAATTCGAT 14280
      T  M  C  H  V  L  D  C  E  L  F  V  N  D  S  Y  R  Q  F  D
       L  C  V  M  Y  *  I  V  N  Y  L  L  M  I  V  I  D  N  S  I
        Y  V  S  C  I  R  L  *  I  I  C  *  *  *  L  *  T  I  R  S

14281 CTTGTACAGTATGATTTTACTGATTATAAGTTAGAATTGTTTAATAAGTATTTTAAGTAT 14340
      L  V  Q  Y  D  F  T  D  Y  K  L  E  L  F  N  K  Y  F  K  Y
       L  Y  S  M  I  L  L  I  I  S  *  N  C  L  I  S  I  L  S  I
        C  T  V  *  F  Y  *  L  *  V  R  I  V  *  *  V  F  *  V  L

14341 TGGGGTATGAAGTATCATCCTAATACTGTGGATTGTGATAATGATAGGTGTATTATTCAT 14400
      W  G  M  K  Y  H  P  N  T  V  D  C  D  N  D  R  C  I  I  H
       G  V  *  S  I  I  L  I  L  W  I  V  I  M  I  G  V  L  F  I
        G  Y  E  V  S  S  *  Y  C  G  L  *  *  *  *  V  Y  Y  S  L

14401 TGTGCTAATTTTAATATATTATTTAGTATGGTCTTACCTAATACTTGTTTTGGTCCTCTT 14460
      C  A  N  F  N  I  L  F  S  M  V  L  P  N  T  C  F  G  P  L
       V  L  I  L  I  Y  Y  L  V  W  S  Y  L  I  L  V  L  V  L  L
        C  *  F  *  Y  I  I  *  Y  G  L  T  *  Y  L  F  W  S  S  C

14461 GTTAGACAAATTTTTGTAGATGGTGTTCCGTTTGTTGTTTCAATTGGTTACCATTATAAA 14520
      V  R  Q  I  F  V  D  G  V  P  F  V  V  S  I  G  Y  H  Y  K
       L  D  K  F  L  *  M  V  F  R  L  L  F  Q  L  V  T  I  I  K
        *  T  N  F  C  R  W  C  S  V  C  C  F  N  W  L  P  L  *  R

14521 GAGTTAGGTGTAGTTATGAACTTGGATGTTGATACACACCGCTATCGTTTGTCTCTTAAA 14580
      E  L  G  V  V  M  N  L  D  V  D  T  H  R  Y  R  L  S  L  K
       S  *  V  *  L  *  T  W  M  L  I  H  T  A  I  V  C  L  L  K
        V  R  C  S  Y  E  L  G  C  *  Y  T  P  L  S  F  V  S  *  R
```

FIG. 9 CONT.

```
14581 GACTTACTTCTTTATGCAGCAGATCCTGCTATGCATGTTGCATCTGCTAGTGCTCTGCTT 14640
      D  L  L  L  Y  A  A  D  P  A  M  H  V  A  S  A  S  A  L  L
       T  Y  F  F  M  Q  Q  I  L  L  C  M  L  H  L  L  V  L  C  L
        L  T  S  L  C  S  R  S  C  Y  A  C  C  I  C  *  C  S  A  *

14641 GATTTACGAACTTGTTGTTTTAGTGTAGCTGCCATTACAAGTGGTATAAAGTTTCAAACT 14700
      D  L  R  T  C  C  F  S  V  A  A  I  T  S  G  I  K  F  Q  T
       I  Y  E  L  V  V  L  V  *  L  P  L  Q  V  V  *  S  F  K  L
        F  T  N  L  L  F  *  C  S  C  H  Y  K  W  Y  K  V  S  N  C

14701 GTTAAACCAGGTAATTTTAACCAAGATTTTTATGAGTTTGTCAAAAGTAAAGGCTTGTTT 14760
      V  K  P  G  N  F  N  Q  D  F  Y  E  F  V  K  S  K  G  L  F
       L  N  Q  V  I  L  T  K  I  F  M  S  L  S  K  V  K  A  C  L
        *  T  R  *  F  *  P  R  F  L  *  V  C  Q  K  *  R  L  V  *

14761 AAAGAGGGTAGTACAGTTGATTTGAAACACTTTTTCTTTACTCAAGATGGTAATGCTGCA 14820
      K  E  G  S  T  V  D  L  K  H  F  F  F  T  Q  D  G  N  A  A
       K  R  V  V  Q  L  I  *  N  T  F  S  L  L  K  M  V  M  L  Q
        R  G  *  Y  S  *  F  E  T  L  F  L  Y  S  R  W  *  C  C  N

14821 ATTACTGATTATAATTATTATAAGTATAATTTACCTACTATGGTTGATATTAAGCAGTTA 14880
      I  T  D  Y  N  Y  Y  K  Y  N  L  P  T  M  V  D  I  K  Q  L
       L  L  I  I  I  I  I  S  I  I  Y  L  L  W  L  I  L  S  S  Y
        Y  *  L  *  L  L  *  V  *  F  T  Y  Y  G  *  Y  *  A  V  I

14881 TTGTTTGTATTAGAAGTTGTTTATAAGTATTTTGAAATTTATGATGGTGGTTGTATACCA 14940
      L  F  V  L  E  V  V  Y  K  Y  F  E  I  Y  D  G  G  C  I  P
       C  L  Y  *  K  L  F  I  S  I  L  K  F  M  M  V  V  V  Y  Q
        V  C  I  R  S  C  L  *  V  F  *  N  L  *  W  W  L  Y  T  S

14941 GCATCACAAGTTATTGTTAATAATTATGACAAAAGTGCTGGTTATCCATTTAATAAATTT 15000
      A  S  Q  V  I  V  N  N  Y  D  K  S  A  G  Y  P  F  N  K  F
       H  H  K  L  L  L  I  I  M  T  K  V  L  V  I  H  L  I  N  L
        I  T  S  Y  C  *  *  L  *  Q  K  C  W  L  S  I  *  *  I  W

15001 GGTAAAGCTAGACTTTATTATGAGGCATTATCATTTGAGGAGCAGAATGAAATTTATGCA 15060
      G  K  A  R  L  Y  Y  E  A  L  S  F  E  E  Q  N  E  I  Y  A
       V  K  L  D  F  I  M  R  H  Y  H  L  R  S  R  M  K  F  M  H
        *  S  *  T  L  L  *  G  I  I  I  *  G  A  E  *  N  L  C  I

15061 TATACTAAACGTAATGTGTTGCCCACTTTAACTCAAATGAATTTAAAATATGCTATTAGT 15120
      Y  T  K  R  N  V  L  P  T  L  T  Q  M  N  L  K  Y  A  I  S
       I  L  N  V  M  C  C  P  L  *  L  K  *  I  *  N  M  L  L  V
        Y  *  T  *  C  V  A  H  F  N  S  N  E  F  K  I  C  Y  *  C
```

FIG. 9 CONT.

```
15121 GCTAAGAATAGAGCTCGTACTGTTGCAGGTGTTTCCATTCTTAGTACTATGACAGGTCGA 15180
      A  K  N  R  A  R  T  V  A  G  V  S  I  L  S  T  M  T  G  R
       L  R  I  E  L  V  L  L  Q  V  F  P  F  L  V  L  *  Q  V  E
        *  E  *  S  S  Y  C  C  R  C  F  H  S  *  Y  Y  D  R  S  N

15181 ATGTTTCATCAAAAATGTTTGAAGAGTATAGCAGCTACTCGTGGTGTTCCTGTTGTTATA 15240
      M  F  H  Q  K  C  L  K  S  I  A  A  T  R  G  V  P  V  V  I
       C  F  I  K  N  V  *  R  V  *  Q  L  L  V  V  F  L  L  L  *
        V  S  S  K  M  F  E  E  Y  S  S  Y  S  W  C  S  C  C  Y  R

15241 GGAACTACTAAATTTTATGGTGGCTGGGATGATATGTTACGCCATCTTATAAAGGATGTT 15300
      G  T  T  K  F  Y  G  G  W  D  D  M  L  R  H  L  I  K  D  V
       E  L  L  N  F  M  V  A  G  M  I  C  Y  A  I  L  *  R  M  L
        N  Y  *  I  L  W  W  L  G  *  Y  V  T  P  S  Y  K  G  C  *

15301 GACAACCCTGTTCTTATGGGTTGGGATTATCCTAAATGTGATCGTGCCATGCCAAATATT 15360
      D  N  P  V  L  M  G  W  D  Y  P  K  C  D  R  A  M  P  N  I
       T  T  L  F  L  W  V  G  I  I  L  N  V  I  V  P  C  Q  I  F
        Q  P  C  S  Y  G  L  G  L  S  *  M  *  S  C  H  A  K  Y  F

15361 TTGCGTATTGTTAGTAGTTTAGTTTTGGCTCGTAAACATGAATTTTGTTGTTCACATGGT 15420
      L  R  I  V  S  S  L  V  L  A  R  K  H  E  F  C  C  S  H  G
       C  V  L  L  V  V  *  F  W  L  V  N  M  N  F  V  V  H  M  V
        A  Y  C  *  *  F  S  F  G  S  *  T  *  I  L  L  F  T  W  *

15421 GATAGATTCTATCGCCTTGCGAATGAATGTGCTCAAGTTTTGAGTGAAATAGTTATGTGT 15480
      D  R  F  Y  R  L  A  N  E  C  A  Q  V  L  S  E  I  V  M  C
       I  D  S  I  A  L  R  M  N  V  L  K  F  *  V  K  *  L  C  V
        *  I  L  S  P  C  E  *  M  C  S  S  F  E  *  N  S  Y  V  W

15481 GGCGGTTGCTATTATGTTAAGCCTGGTGGTACTAGCAGTGGTGATGCAACCACTGCTTTT 15540
      G  G  C  Y  Y  V  K  P  G  G  T  S  S  G  D  A  T  T  A  F
       A  V  A  I  M  L  S  L  V  V  L  A  V  V  M  Q  P  L  L  L
        R  L  L  L  C  *  A  W  W  Y  *  Q  W  *  C  N  H  C  F  C

15541 GCTAACTCTGTTTTTAATATATGTCAAGCTGTTACTGCTAATGTTTGTTCTCTTATGGCT 15600
      A  N  S  V  F  N  I  C  Q  A  V  T  A  N  V  C  S  L  M  A
       L  T  L  F  L  I  Y  V  K  L  L  L  L  M  F  V  L  L  W  L
        *  L  C  F  *  Y  M  S  S  C  Y  C  *  C  L  F  S  Y  G  L

15601 TGTAATGGCCATAAGATTGAAGATTTAAGTATACGCAATTTACAAAAACGCTTATACTCT 15660
      C  N  G  H  K  I  E  D  L  S  I  R  N  L  Q  K  R  L  Y  S
       V  M  A  I  R  L  K  I  *  V  Y  A  I  Y  K  N  A  Y  T  L
        *  W  P  *  D  *  R  F  K  Y  T  Q  F  T  K  T  L  I  L  *
```

FIG. 9 CONT.

```
15661 AATGTTTATCGTACAGATTATGTTGATTATACATTTGTTAATGAGTATTATGAATTTTTA 15720
      N  V  Y  R  T  D  Y  V  D  Y  T  F  V  N  E  Y  Y  E  F  L
       M  F  I  V  Q  I  M  L  I  I  H  L  L  M  S  I  M  N  F  Y
        C  L  S  Y  R  L  C  *  L  Y  I  C  *  *  V  L  *  I  F  M

15721 TGTAAGCATTTTAGTATGATGATTTTGAGTGATGATGGTGTTGTTTGTTATAACTCTGAT 15780
      C  K  H  F  S  M  M  I  L  S  D  D  G  V  V  C  Y  N  S  D
       V  S  I  L  V  *  *  F  *  V  M  M  V  L  F  V  I  T  L  I
        *  A  F  *  Y  D  D  F  E  *  *  W  C  C  L  L  *  L  *  L

15781 TATGCTAGTAAGGGTTATATAGCCAATATAAGTGTTTTTCAACAAGTTTTGTACTATCAG 15840
      Y  A  S  K  G  Y  I  A  N  I  S  V  F  Q  Q  V  L  Y  Y  Q
       M  L  V  R  V  I  *  P  I  *  V  F  F  N  K  F  C  T  I  R
        C  *  *  G  L  Y  S  Q  Y  K  C  F  S  T  S  F  V  L  S  E

15841 AATAACGTTTTTATGTCTGAATCTAAATGTTGGGTTGAAAATGATATTACTAATGGTCCT 15900
      N  N  V  F  M  S  E  S  K  C  W  V  E  N  D  I  T  N  G  P
       I  T  F  L  C  L  N  L  N  V  G  L  K  M  I  L  L  M  V  L
        *  R  F  Y  V  *  I  *  M  L  G  *  K  *  Y  Y  *  W  S  S

15901 CATGAATTCTGTTCACAACATACTATGTTGGTTAAGATAGATGGTGACTATGTTTATCTA 15960
      H  E  F  C  S  Q  H  T  M  L  V  K  I  D  G  D  Y  V  Y  L
       M  N  S  V  H  N  I  L  C  W  L  R  *  M  V  T  M  F  I  Y
        *  I  L  F  T  T  Y  Y  V  G  *  D  R  W  *  L  C  L  S  T

15961 CCCTATCCAGACCCTTCTAGAATTTTAGGAGCTGGTTGTTTTGTTGATGATTTATTGAAG 16020
      P  Y  P  D  P  S  R  I  L  G  A  G  C  F  V  D  D  L  L  K
       P  I  Q  T  L  L  E  F  *  E  L  V  V  L  L  M  I  Y  *  R
        L  S  R  P  F  *  N  F  R  S  W  L  F  C  *  *  F  I  E  D

16021 ACTGACAGTGTTCTTTTGATAGAGCGCTTTGTAAGTCTAGCTATAGATGCTTACCCTTTA 16080
      T  D  S  V  L  L  I  E  R  F  V  S  L  A  I  D  A  Y  P  L
       L  T  V  F  F  *  *  S  A  L  *  V  *  L  *  M  L  T  L  *
        *  Q  C  S  F  D  R  A  L  C  K  S  S  Y  R  C  L  P  F  S

16081 GTACACCATGAAAATGAAGAATACCAAAAAGTTTTTCGTGTATATTTAGAATATATAAAA 16140
      V  H  H  E  N  E  E  Y  Q  K  V  F  R  V  Y  L  E  Y  I  K
       Y  T  M  K  M  K  N  T  K  K  F  F  V  Y  I  *  N  I  *  K
        T  P  *  K  *  R  I  P  K  S  F  S  C  I  F  R  I  Y  K  K

16141 AAACTATATAATGATCTTGGTAATCAGATCTTAGATAGTTATAGTGTTATTTTAAGTACT 16200
      K  L  Y  N  D  L  G  N  Q  I  L  D  S  Y  S  V  I  L  S  T
       N  Y  I  M  I  L  V  I  R  S  *  I  V  I  V  L  F  *  V  L
        T  I  *  *  S  W  *  S  D  L  R  *  L  *  C  Y  F  K  Y  L
```

FIG. 9 CONT.

```
16201 TGTGATGGTTTAAAGTTCACTGATGAATCATTTTATAAGAATATGTATTTAAAAAGTGCC 16260
      C  D  G  L  K  F  T  D  E  S  F  Y  K  N  M  Y  L  K  S  A
       V  M  V  *  S  S  L  M  N  H  F  I  R  I  C  I  *  K  V  P
        *  W  F  K  V  H  *  *  I  I  L  *  E  Y  V  F  K  K  C  R

16261 GTGATGCAGAGTGTAGGTGCATGTGTTGTTTGTTCATCACAGACGTCTTTGCGTTGTGGC 16320
      V  M  Q  S  V  G  A  C  V  V  C  S  S  Q  T  S  L  R  C  G
       *  C  R  V  *  V  H  V  L  F  V  H  H  R  R  L  C  V  V  A
        D  A  E  C  R  C  M  C  C  L  F  I  T  D  V  F  A  L  W  Q

16321 AGTTGTATACGGAAGCCTTTGTTGTGTTGTAAATGTTGCTATGATCATGTTATGGCAACC 16380
      S  C  I  R  K  P  L  L  C  C  K  C  C  Y  D  H  V  M  A  T
       V  V  Y  G  S  L  C  C  V  V  N  V  A  M  I  M  L  W  Q  P
        L  Y  T  E  A  F  V  V  L  *  M  L  L  *  S  C  Y  G  N  Q

16381 AATCATAAATATGTTTTGAGTGTTTCACCTTATGTGTGTAATGCACCTAACTGTGATGTG 16440
      N  H  K  Y  V  L  S  V  S  P  Y  V  C  N  A  P  N  C  D  V
       I  I  N  M  F  *  V  F  H  L  M  C  V  M  H  L  T  V  M  *
        S  *  I  C  F  E  C  F  T  L  C  V  *  C  T  *  L  *  C  E

16441 AGTGATGTCACCAAATTATATTTGGGTGGTATGTCTTATTATTGTGAAAACCATAAACCT 16500
      S  D  V  T  K  L  Y  L  G  G  M  S  Y  Y  C  E  N  H  K  P
       V  M  S  P  N  Y  I  W  V  V  C  L  I  I  V  K  T  I  N  L
        *  C  H  Q  I  I  F  G  W  Y  V  L  L  L  *  K  P  *  T  S

16501 CATTATTCATTTAAGTTAGTTATGAATGGTATGGTCTTTGGTTTGTATAAACAATCTTGT 16560
      H  Y  S  F  K  L  V  M  N  G  M  V  F  G  L  Y  K  Q  S  C
       I  I  H  L  S  *  L  *  M  V  W  S  L  V  C  I  N  N  L  V
        L  F  I  *  V  S  Y  E  W  Y  G  L  W  F  V  *  T  I  L  Y

16561 ACAGGTTCACCTTATATAGATGATTTTAATAAGATAGCTAGTTGTAAATGGACAGAAGTT 16620
      T  G  S  P  Y  I  D  D  F  N  K  I  A  S  C  K  W  T  E  V
       Q  V  H  L  I  *  M  I  L  I  R  *  L  V  V  N  G  Q  K  L
        R  F  T  L  Y  R  *  F  *  *  D  S  *  L  *  M  D  R  S  *

16621 GATGATTATGTTCTGGCAAATGAGTGTATTGAACGTTTAAAGTTATTTGCTGCAGAAACT 16680
      D  D  Y  V  L  A  N  E  C  I  E  R  L  K  L  F  A  A  E  T
       M  I  M  F  W  Q  M  S  V  L  N  V  *  S  Y  L  L  Q  K  L
        *  L  C  S  G  K  *  V  Y  *  T  F  K  V  I  C  C  R  N  S

16681 CAAAAGGCAACTGAAGAAGCTTTTAAACAAAGCTATGCTTCTGCTACTATTCAAGAGATT 16740
      Q  K  A  T  E  E  A  F  K  Q  S  Y  A  S  A  T  I  Q  E  I
       K  R  Q  L  K  K  L  L  N  K  A  M  L  L  L  L  F  K  R  L
        K  G  N  *  R  S  F  *  T  K  L  C  F  C  Y  Y  S  R  D  C
```

FIG. 9 CONT.

```
16741 GTTAGTGATAGAGAAATTATTTTGTGTTGGGAGACAGGTAAAGTTAAACCACCACTTAAT 16800
      V  S  D  R  E  I  I  L  C  W  E  T  G  K  V  K  P  P  L  N
       L  V  I  E  K  L  F  C  V  G  R  Q  V  K  L  N  H  H  L  I
        *  *  *  R  N  Y  F  V  L  G  D  R  *  S  *  T  T  T  *  *

16801 AAAAATTATGTTTTCACTGGCTATCATTTTACTAGTACTGGTAAGACAGTTTTAGGTGAG 16860
      K  N  Y  V  F  T  G  Y  H  F  T  S  T  G  K  T  V  L  G  E
       K  I  M  F  S  L  A  I  I  L  L  V  L  V  R  Q  F  *  V  S
        K  L  C  F  H  W  L  S  F  Y  *  Y  W  *  D  S  F  R  *  V

16861 TATGTTTTTGATAAAAGTGAATTAACTAATGGTGTTTATTATCGCGCTACAACTACTTAC 16920
      Y  V  F  D  K  S  E  L  T  N  G  V  Y  Y  R  A  T  T  T  Y
       M  F  L  I  K  V  N  *  L  M  V  F  I  I  A  L  Q  L  L  T
        C  F  *  *  K  *  I  N  *  W  C  L  L  S  R  Y  N  Y  L  Q

16921 AAACTTTCTATAGGTGATGTTTTTGTCTTAACATCACATTCTGTAGCTAATCTAAGTGCA 16980
      K  L  S  I  G  D  V  F  V  L  T  S  H  S  V  A  N  L  S  A
       N  F  L  *  V  M  F  L  S  *  H  H  I  L  *  L  I  *  V  H
        T  F  Y  R  *  C  F  C  L  N  I  T  F  C  S  *  S  K  C  T

16981 CCTACACTTGTTCCACAAGAGAACTATGCTAGTATAAGATTTTCTAGTGTTTATAGCGTT 17040
      P  T  L  V  P  Q  E  N  Y  A  S  I  R  F  S  S  V  Y  S  V
       L  H  L  F  H  K  R  T  M  L  V  *  D  F  L  V  F  I  A  F
        Y  T  C  S  T  R  E  L  C  *  Y  K  I  F  *  C  L  *  R  S

17041 CCTTTGCTGTTTCAAACTAATGTTGCTAACTATCAGCACATTGGAATGAAACGTTATTGC 17100
      P  L  L  F  Q  T  N  V  A  N  Y  Q  H  I  G  M  K  R  Y  C
       L  C  C  F  K  L  M  L  L  T  I  S  T  L  E  *  N  V  I  A
        F  A  V  S  N  *  C  C  *  L  S  A  H  W  N  E  T  L  L  H

17101 ACTGTGCAAGGTCCTCCTGGTACGGGCAAGTCTCACCTTGCTATAGGTTTAGCTGTTTAT 17160
      T  V  Q  G  P  P  G  T  G  K  S  H  L  A  I  G  L  A  V  Y
       L  C  K  V  L  L  V  R  A  S  L  T  L  L  *  V  *  L  F  I
        C  A  R  S  S  W  Y  G  Q  V  S  P  C  Y  R  F  S  C  L  L

17161 TACTATACAGCACGTGTAGTTTATACTGCTGCTAGTCATGCTGCTGTAGATGCATTGTGT 17220
      Y  Y  T  A  R  V  V  Y  T  A  A  S  H  A  A  V  D  A  L  C
       T  I  Q  H  V  *  F  I  L  L  L  V  M  L  L  *  M  H  C  V
        L  Y  S  T  C  S  L  Y  C  C  *  S  C  C  C  R  C  I  V  *

17221 GAAAAAGCTTATAAGTTTTTAAATATTAATGACTGTACACGCATTATACCTGCTAAAGTT 17280
      E  K  A  Y  K  F  L  N  I  N  D  C  T  R  I  I  P  A  K  V
       K  K  L  I  S  F  *  I  L  M  T  V  H  A  L  Y  L  L  K  F
        K  S  L  *  V  F  K  Y  *  *  L  Y  T  H  Y  T  C  *  S  S
```

FIG. 9 CONT.

```
17281 CGTGTAGATTGTTATGATAAGTTTAAAATTAATGATACTACTTGTAAGTATGTTTTTACT 17340
      R  V  D  C  Y  D  K  F  K  I  N  D  T  T  C  K  Y  V  F  T
       V  *  I  V  M  I  S  L  K  L  M  I  L  L  V  S  M  F  L  L
        C  R  L  L  *  *  V  *  N  *  *  Y  Y  L  *  V  C  F  Y  Y

17341 ACAATAAATGCATTACCAGAGTTAGTCACAGATATTGTTGTTGTTGATGAAGTTAGTATG 17400
      T  I  N  A  L  P  E  L  V  T  D  I  V  V  V  D  E  V  S  M
       Q  *  M  H  Y  Q  S  *  S  Q  I  L  L  L  L  M  K  L  V  C
        N  K  C  I  T  R  V  S  H  R  Y  C  C  C  *  *  S  *  Y  A

17401 CTTACTAATTATGAATTGTCTGTTATAAATGCTCGTGTTAAAGCTAAACATTATGTATAT 17460
      L  T  N  Y  E  L  S  V  I  N  A  R  V  K  A  K  H  Y  V  Y
       L  L  I  M  N  C  L  L  *  M  L  V  L  K  L  N  I  M  Y  I
        Y  *  L  *  I  V  C  Y  K  C  S  C  *  S  *  T  L  C  I  Y

17461 ATTGGAGATCCTGCTCAGTTACCTGCACCACGTGTGCTATTGAGTAAGGGTTCTTTAGAA 17520
      I  G  D  P  A  Q  L  P  A  P  R  V  L  L  S  K  G  S  L  E
       L  E  I  L  L  S  Y  L  H  H  V  C  Y  *  V  R  V  L  *  N
        W  R  S  C  S  V  T  C  T  T  C  A  I  E  *  G  F  F  R  T

17521 CCTAGGCATTTTAATTCTATTACTAAAATAATGTGCTGTTTAGGTCCTGATATTTTTTTG 17580
      P  R  H  F  N  S  I  T  K  I  M  C  C  L  G  P  D  I  F  L
       L  G  I  L  I  L  L  L  K  *  C  A  V  *  V  L  I  F  F  W
        *  A  F  *  F  Y  Y  *  N  N  V  L  F  R  S  *  Y  F  F  G

17581 GGAAATTGTTATAGATGTCCTAAAGAAATTGTAGAAACTGTTTCAGCATTGGTTTATGAT 17640
      G  N  C  Y  R  C  P  K  E  I  V  E  T  V  S  A  L  V  Y  D
       E  I  V  I  D  V  L  K  K  L  *  K  L  F  Q  H  W  F  M  I
        K  L  L  *  M  S  *  R  N  C  R  N  C  F  S  I  G  L  *  *

17641 AATAAACTTAAGGCTAAGAATGATAATAGTTCATTATGCTTTAAAGTATATTTTAAGGGA 17700
      N  K  L  K  A  K  N  D  N  S  S  L  C  F  K  V  Y  F  K  G
       I  N  L  R  L  R  M  I  I  V  H  Y  A  L  K  Y  I  L  R  D
        *  T  *  G  *  E  *  *  *  F  I  M  L  *  S  I  F  *  G  T

17701 CAGACAACACATGAGAGTTCAAGTGCTGTAAATATTCAACAAATATATTTAATTAGTAAA 17760
      Q  T  T  H  E  S  S  S  A  V  N  I  Q  Q  I  Y  L  I  S  K
       R  Q  H  M  R  V  Q  V  L  *  I  F  N  K  Y  I  *  L  V  N
        D  N  T  *  E  F  K  C  C  K  Y  S  T  N  I  F  N  *  *  I

17761 TTTTTGAAAGCTAATCCAGTTTGGAATAGTGCTGTTTTTATTAGTCCTTATAATAGTCAG 17820
      F  L  K  A  N  P  V  W  N  S  A  V  F  I  S  P  Y  N  S  Q
       F  *  K  L  I  Q  F  G  I  V  L  F  L  L  V  L  I  I  V  R
        F  E  S  *  S  S  L  E  *  C  C  F  Y  *  S  L  *  *  S  E
```

FIG. 9 CONT.

```
17821 AACTATGTTGCTAAGCGTATTTTAGGTGTTCAAACACAAACTGTTGATTCTGCTCAAGGT 17880
      N  Y  V  A  K  R  I  L  G  V  Q  T  Q  T  V  D  S  A  Q  G
       T  M  L  L  S  V  F  *  V  F  K  H  K  L  L  I  L  L  K  V
        L  C  C  *  A  Y  F  R  C  S  N  T  N  C  *  F  C  S  R  F

17881 TCTGAATATGATTATGTTATATATTCACAAACAGCAGAAACAGCTCATTCTATTAATGTT 17940
      S  E  Y  D  Y  V  I  Y  S  Q  T  A  E  T  A  H  S  I  N  V
       L  N  M  I  M  L  Y  I  H  K  Q  Q  K  Q  L  I  L  L  M  L
        *  I  *  L  C  Y  I  F  T  N  S  R  N  S  S  F  Y  *  C  *

17941 AATCGATTTAATGTTGCCATAACTAGAGCCAAGAAGGGTATTTTCTGTGTTATGAGTAAT 18000
      N  R  F  N  V  A  I  T  R  A  K  K  G  I  F  C  V  M  S  N
       I  D  L  M  L  P  *  L  E  P  R  R  V  F  S  V  L  *  V  I
        S  I  *  C  C  H  N  *  S  Q  E  G  Y  F  L  C  Y  E  *  Y

18001 ATGCAATTATTTGAATCTCTTAATTTTATTACTTTACCTTTAGATAAAATTCAGAATCAA 18060
      M  Q  L  F  E  S  L  N  F  I  T  L  P  L  D  K  I  Q  N  Q
       C  N  Y  L  N  L  L  I  L  L  L  Y  L  *  I  K  F  R  I  K
        A  I  I  *  I  S  *  F  Y  Y  F  T  F  R  *  N  S  E  S  N

18061 ACTTTATCTCGTTTGCATTGTACTACTAATCTTTTTAAAGATTGTAGTAAAAATTTTTTA 18120
      T  L  S  R  L  H  C  T  T  N  L  F  K  D  C  S  K  N  F  L
       L  Y  L  V  C  I  V  L  L  I  F  L  K  I  V  V  K  I  F  *
        F  I  S  F  A  L  Y  Y  *  S  F  *  R  L  *  *  K  F  F  R

18121 GGTTACCACCCAGCTCATGCTCCTTCATTTTTATCAGTTGATGATAAATATAAGGTCAAC 18180
      G  Y  H  P  A  H  A  P  S  F  L  S  V  D  D  K  Y  K  V  N
       V  T  T  Q  L  M  L  L  H  F  Y  Q  L  M  I  N  I  R  S  T
        L  P  P  S  S  C  S  F  I  F  I  S  *  *  *  I  *  G  Q  R

18181 GAAGATTTGGCTGTTTGTTTAAACATTTGTGAACCTGTTTTAACATATTCTCGTTTAATA 18240
      E  D  L  A  V  C  L  N  I  C  E  P  V  L  T  Y  S  R  L  I
       K  I  W  L  F  V  *  T  F  V  N  L  F  *  H  I  L  V  *  Y
        R  F  G  C  L  F  K  H  L  *  T  C  F  N  I  F  S  F  N  I

18241 TCTCTCATGGGGTTTAAATTGGATTTGACTCTTGATGGTTATTCTAAATTTTTTATTACT 18300
      S  L  M  G  F  K  L  D  L  T  L  D  G  Y  S  K  F  F  I  T
       L  S  W  G  L  N  W  I  *  L  L  M  V  I  L  N  F  L  L  L
        S  H  G  V  *  I  G  F  D  S  *  W  L  F  *  I  F  Y  Y  *

18301 AAAGACGAAGCTATTAAACGTGTTAGAGGTTGGGTTGGTTTTGATGTAGAAGGAGCCCAT 18360
      K  D  E  A  I  K  R  V  R  G  W  V  G  F  D  V  E  G  A  H
       K  T  K  L  L  N  V  L  E  V  G  L  V  L  M  *  K  E  P  M
        R  R  S  Y  *  T  C  *  R  L  G  W  F  *  C  R  R  S  P  C
```

FIG. 9 CONT.

```
18361 GCTACGCGTGACAACATTGGAACAAACTTTCCATTGCAAATAGGTTTTTCAACTGGTGTT 18420
      A  T  R  D  N  I  G  T  N  F  P  L  Q  I  G  F  S  T  G  V
       L  R  V  T  T  L  E  Q  T  F  H  C  K  *  V  F  Q  L  V  L
        Y  A  *  Q  H  W  N  K  L  S  I  A  N  R  F  F  N  W  C  *

18421 GATTTTGTAGTTGAAGCTACTGGCTTATTTGCTGAGAGAGATTGTTATATATTTAAAAGA 18480
      D  F  V  V  E  A  T  G  L  F  A  E  R  D  C  Y  I  F  K  R
       I  L  *  L  K  L  L  A  Y  L  L  R  E  I  V  I  Y  L  K  E
        F  C  S  *  S  Y  W  L  I  C  *  E  R  L  L  Y  I  *  K  N

18481 ACTGTTGCTAAAGCTCCTCCTGGTGATAACTTTAAACATTTAATACCCCTTATGTCGAAA 18540
      T  V  A  K  A  P  P  G  D  N  F  K  H  L  I  P  L  M  S  K
       L  L  L  K  L  L  L  V  I  T  L  N  I  *  Y  P  L  C  R  K
        C  C  *  S  S  S  W  *  *  L  *  T  F  N  T  P  Y  V  E  R

18541 GGTCAAAAGTGGGATGTTGTTAGAATCAGAATTGTTCAAATGTTGTCTGATTATCTTTTG 18600
      G  Q  K  W  D  V  V  R  I  R  I  V  Q  M  L  S  D  Y  L  L
       V  K  S  G  M  L  L  E  S  E  L  F  K  C  C  L  I  I  F  W
        S  K  V  G  C  C  *  N  Q  N  C  S  N  V  V  *  L  S  F  G

18601 GATCTTTCTGATAGTGTAGTATTTATTACTTGGTCTGCCAGTTTTGAACTTACGTGTTTA 18660
      D  L  S  D  S  V  V  F  I  T  W  S  A  S  F  E  L  T  C  L
       I  F  L  I  V  *  Y  L  L  L  G  L  P  V  L  N  L  R  V  *
        S  F  *  *  C  S  I  Y  Y  L  V  C  Q  F  *  T  Y  V  F  K

18661 AGGTATTTTGCTAAATTAGGTAGAGAGCTCAATTGTGATGTGTGTCCTAATCGTGCAACA 18720
      R  Y  F  A  K  L  G  R  E  L  N  C  D  V  C  P  N  R  A  T
       G  I  L  L  N  *  V  E  S  S  I  V  M  C  V  L  I  V  Q  H
        V  F  C  *  I  R  *  R  A  Q  L  *  C  V  S  *  S  C  N  M

18721 TGCTATAATTCTAGAACTGGTTATTACGGTTGTTGGCGCCATAGTTATACTTGTGATTAT 18780
      C  Y  N  S  R  T  G  Y  Y  G  C  W  R  H  S  Y  T  C  D  Y
       A  I  I  L  E  L  V  I  T  V  V  G  A  I  V  I  L  V  I  M
        L  *  F  *  N  W  L  L  R  L  L  A  P  *  L  Y  L  *  L  C

18781 GTGTATAACCCGCTTATTGTAGATATACAACAGTGGGGTTACACAGGTTCTTTAACTAGT 18840
      V  Y  N  P  L  I  V  D  I  Q  Q  W  G  Y  T  G  S  L  T  S
       C  I  T  R  L  L  *  I  Y  N  S  G  V  T  Q  V  L  *  L  V
        V  *  P  A  Y  C  R  Y  T  T  V  G  L  H  R  F  F  N  *  *

18841 AATCATGATATAATTTGTAATGTACATAAAGGTGCACATGTTGCATCATCTGATGCAATT 18900
      N  H  D  I  I  C  N  V  H  K  G  A  H  V  A  S  S  D  A  I
       I  M  I  *  F  V  M  Y  I  K  V  H  M  L  H  H  L  M  Q  L
        S  *  Y  N  L  *  C  T  *  R  C  T  C  C  I  I  *  C  N  Y
```

FIG. 9 CONT.

```
18901 ATGACTCGGTGTTTAGCAATCTATGATTGTTTTTGTAAATCTGTTAATTGGAATTTAGAG 18960
      M  T  R  C  L  A  I  Y  D  C  F  C  K  S  V  N  W  N  L  E
       *  L  G  V  *  Q  S  M  I  V  F  V  N  L  L  I  G  I  *  S
        D  S  V  F  S  N  L  *  L  F  L  *  I  C  *  L  E  F  R  V

18961 TATCCAATAATTTCCAATGAGGTTAGTATAAATACATCTTGTAGGTTATTGCAGCGTGTT 19020
      Y  P  I  I  S  N  E  V  S  I  N  T  S  C  R  L  L  Q  R  V
       I  Q  *  F  P  M  R  L  V  *  I  H  L  V  G  Y  C  S  V  L
        S  N  N  F  Q  *  G  *  Y  K  Y  I  L  *  V  I  A  A  C  Y

19021 ATGCTTAAAGCTGCCATGCTATGTAATAGATACAATTTATGTTATGACATTGGCAATCCT 19080
      M  L  K  A  A  M  L  C  N  R  Y  N  L  C  Y  D  I  G  N  P
       C  L  K  L  P  C  Y  V  I  D  T  I  Y  V  M  T  L  A  I  L
        A  *  S  C  H  A  M  *  *  I  Q  F  M  L  *  H  W  Q  S  *

19081 AAAGGTATTGCTTGTGTCAAAGATTATGAATTTAAATTCTATGATGCTTCTCCTGTTGTC 19140
      K  G  I  A  C  V  K  D  Y  E  F  K  F  Y  D  A  S  P  V  V
       K  V  L  L  V  S  K  I  M  N  L  N  S  M  M  L  L  L  L  S
        R  Y  C  L  C  Q  R  L  *  I  *  I  L  *  C  F  S  C  C  Q

19141 AAGTCTGTTAAACAGTTGTTTTATGTTTATGATGTTCATAAAGATAATTTTAAGGATGGT 19200
      K  S  V  K  Q  L  F  Y  V  Y  D  V  H  K  D  N  F  K  D  G
       S  L  L  N  S  C  F  M  F  M  M  F  I  K  I  I  L  R  M  V
        V  C  *  T  V  V  L  C  L  *  C  S  *  R  *  F  *  G  W  F

19201 TTATGTATGTTTTGGAATTGTAATGTTGATAAATATCCATCTAATTCAATTGTTTGTAGA 19260
      L  C  M  F  W  N  C  N  V  D  K  Y  P  S  N  S  I  V  C  R
       Y  V  C  F  G  I  V  M  L  I  N  I  H  L  I  Q  L  F  V  D
        M  Y  V  L  E  L  *  C  *  *  I  S  I  *  F  N  C  L  *  I

19261 TTTGATACTCGGGTATTAAATAAATTAAACCTCCCTGGATGTAATGGTGGTAGTTTGTAT 19320
      F  D  T  R  V  L  N  K  L  N  L  P  G  C  N  G  G  S  L  Y
       L  I  L  G  Y  *  I  N  *  T  S  L  D  V  M  V  V  V  C  M
        *  Y  S  G  I  K  *  I  K  P  P  W  M  *  W  W  *  F  V  C

19321 GTTAATAAACATGCATTTCATACTAATCCTTTTACCAGAACGGTCTTTGAAAATCTTAAA 19380
      V  N  K  H  A  F  H  T  N  P  F  T  R  T  V  F  E  N  L  K
       L  I  N  M  H  F  I  L  I  L  L  P  E  R  S  L  K  I  L  N
        *  *  T  C  I  S  Y  *  S  F  Y  Q  N  G  L  *  K  S  *  T

19381 CCTATGCCATTTTTTTACTATTCAGATACTCCTTGTGTGTATGTAGATGGTTTGGAATCC 19440
      P  M  P  F  F  Y  Y  S  D  T  P  C  V  Y  V  D  G  L  E  S
       L  C  H  F  F  T  I  Q  I  L  L  V  C  M  *  M  V  W  N  P
        Y  A  I  F  L  L  F  R  Y  S  L  C  V  C  R  W  F  G  I  Q
```

FIG. 9 CONT.

```
19441 AAACAAGTTGATTATGTGCCTTTAAGAAGCGCTACTTGTATCACACGATGTAATTTAGGT 19500
      K  Q  V  D  Y  V  P  L  R  S  A  T  C  I  T  R  C  N  L  G
       N  K  L  I  M  C  L  *  E  A  L  L  V  S  H  D  V  I  *  V
        T  S  *  L  C  A  F  K  K  R  Y  L  Y  H  T  M  *  F  R  W

19501 GGTGCTGTTTGTTCTAAGCATGCTGAAGATTATTGTAAATATCTTGAGTCTTATAATGTA 19560
      G  A  V  C  S  K  H  A  E  D  Y  C  K  Y  L  E  S  Y  N  V
       V  L  F  V  L  S  M  L  K  I  I  V  N  I  L  S  L  I  M  *
        C  C  L  F  *  A  C  *  R  L  L  *  I  S  *  V  L  *  C  S

19561 GCTACTACAGCAGGCTTTACTTTTTGGGTTTATAAGACTTTTGATTTTTATAATTTATGG 19620
      A  T  T  A  G  F  T  F  W  V  Y  K  T  F  D  F  Y  N  L  W
       L  L  Q  Q  A  L  L  F  G  F  I  R  L  L  I  F  I  I  Y  G
        Y  Y  S  R  L  Y  F  L  G  L  *  D  F  *  F  L  *  F  M  E

19621 AATACTTTCACTATGTTGCAGAGCTTAGAAAATGTAATATATAATTTGGTTAATGCTGGT 19680
      N  T  F  T  M  L  Q  S  L  E  N  V  I  Y  N  L  V  N  A  G
       I  L  S  L  C  C  R  A  *  K  M  *  Y  I  I  W  L  M  L  V
        Y  F  H  Y  V  A  E  L  R  K  C  N  I  *  F  G  *  C  W  S

19681 CATTATGATGGACGTATAGGTGAATTGCCTTGTGCTATTATGAATGACAAAGTTGTTGTT 19740
      H  Y  D  G  R  I  G  E  L  P  C  A  I  M  N  D  K  V  V  V
       I  M  M  D  V  *  V  N  C  L  V  L  L  *  M  T  K  L  L  L
        L  *  W  T  Y  R  *  I  A  L  C  Y  Y  E  *  Q  S  C  C  *

19741 AAGATTAATAATGTAGATACTGTTATTTTTAAAAATAATACATCACTTCCTACTAATATA 19800
      K  I  N  N  V  D  T  V  I  F  K  N  N  T  S  L  P  T  N  I
       R  L  I  M  *  I  L  L  F  L  K  I  I  H  H  F  L  L  I  *
        D  *  *  C  R  Y  C  Y  F  *  K  *  Y  I  T  S  Y  *  Y  S

19801 GCTGTTGAATTATTTACAAAACGTAGTATTCGCCATCACCCTGAACTTAAGATTCTTAGA 19860
      A  V  E  L  F  T  K  R  S  I  R  H  H  P  E  L  K  I  L  R
       L  L  N  Y  L  Q  N  V  V  F  A  I  T  L  N  L  R  F  L  E
        C  *  I  I  Y  K  T  *  Y  S  P  S  P  *  T  *  D  S  *  K

19861 AATTTGAATATTGATATTTGTTGGAAGCATGTCCTTTGGGATTATGTTAAAGATAGTTTG 19920
      N  L  N  I  D  I  C  W  K  H  V  L  W  D  Y  V  K  D  S  L
       I  *  I  L  I  F  V  G  S  M  S  F  G  I  M  L  K  I  V  C
        F  E  Y  *  Y  L  L  E  A  C  P  L  G  L  C  *  R  *  F  V

19921 TTTTGTAGTTCTACCTATGGTGTCTGCAAATACACAGATTTAAATTTTATTGAAAATTTG 19980
      F  C  S  S  T  Y  G  V  C  K  Y  T  D  L  N  F  I  E  N  L
       F  V  V  L  P  M  V  S  A  N  T  Q  I  *  I  L  L  K  I  *
        L  *  F  Y  L  W  C  L  Q  I  H  R  F  K  F  Y  *  K  F  E
```

FIG. 9 CONT.

```
19981 AATGTACTTTTTGATGGTCGTGACAATGGTGCTTTAGAAGCTTTTAGAAAAGCAAGAAAT 20040
      N  V  L  F  D  G  R  D  N  G  A  L  E  A  F  R  K  A  R  N
       M  Y  F  L  M  V  V  T  M  V  L  *  K  L  L  E  K  Q  E  M
        C  T  F  *  W  S  *  Q  W  C  F  R  S  F  *  K  S  K  K  W

20041 GGTGTTTTTATTAGTACTGGAAAATTAAGTAGTTTGTCTATGATTAAAGGTCCGCAACGA 20100
      G  V  F  I  S  T  G  K  L  S  S  L  S  M  I  K  G  P  Q  R
       V  F  L  L  V  L  E  N  *  V  V  C  L  *  L  K  V  R  N  E
        C  F  Y  *  Y  W  K  I  K  *  F  V  Y  D  *  R  S  A  T  S

20101 GCTGATTTAAATGGCGTAATTGTGGATAAAGTTGGAGAACTCAATGTTGAGTTTTGGTTT 20160
      A  D  L  N  G  V  I  V  D  K  V  G  E  L  N  V  E  F  W  F
       L  I  *  M  A  *  L  W  I  K  L  E  N  S  M  L  S  F  G  L
        *  F  K  W  R  N  C  G  *  S  W  R  T  Q  C  *  V  L  V  C

20161 GCTATGAGAAAAGATGGTGACGATGTTATCTTCAGCCGTGCAGACAGCCTAAGCCCAAGC 20220
      A  M  R  K  D  G  D  D  V  I  F  S  R  A  D  S  L  S  P  S
       L  *  E  K  M  V  T  M  L  S  S  A  V  Q  T  A  *  A  Q  A
        Y  E  K  R  W  *  R  C  Y  L  Q  P  C  R  Q  P  K  P  K  P

20221 CATTACTGGAGCCCACAAGGTAATCTAGGTGGTAATTGTGCAGGTAATGCCAGCGGTAAT 20280
      H  Y  W  S  P  Q  G  N  L  G  G  N  C  A  G  N  A  S  G  N
       I  T  G  A  H  K  V  I  *  V  V  I  V  Q  V  M  P  A  V  M
        L  L  E  P  T  R  *  S  R  W  *  L  C  R  *  C  Q  R  *  *

20281 GATGCTCTAGCGCGTTTTACTATCTTTACTCAGAGTCGTGTATTGTCAACCTTTGAACCT 20340
      D  A  L  A  R  F  T  I  F  T  Q  S  R  V  L  S  T  F  E  P
       M  L  *  R  V  L  L  S  L  L  R  V  V  Y  C  Q  P  L  N  L
        C  S  S  A  F  Y  Y  L  Y  S  E  S  C  I  V  N  L  *  T  S

20341 CGCTCAGATTTAGAACGGGATTTTATTGATATGGAGGATAGTCTGTTTATAGCCAAATAT 20400
      R  S  D  L  E  R  D  F  I  D  M  E  D  S  L  F  I  A  K  Y
       A  Q  I  *  N  G  I  L  L  I  W  R  I  V  C  L  *  P  N  M
        L  R  F  R  T  G  F  Y  *  Y  G  G  *  S  V  Y  S  Q  I  W

20401 GGTTTAGAAGATTATGCATTTGATCATATAGTTTATGGTAGTTTTAATTATAAAGTTATA 20460
      G  L  E  D  Y  A  F  D  H  I  V  Y  G  S  F  N  Y  K  V  I
       V  *  K  I  M  H  L  I  I  *  F  M  V  V  L  I  I  K  L  *
        F  R  R  L  C  I  *  S  Y  S  L  W  *  F  *  L  *  S  Y  R

20461 GGAGGTTTGCACTTGCTTATAGGTTTATTTCGTAGACTAAAAAAATCTAATTTGGTAATT 20520
      G  G  L  H  L  L  I  G  L  F  R  R  L  K  K  S  N  L  V  I
       E  V  C  T  C  L  *  V  Y  F  V  D  *  K  N  L  I  W  *  F
        R  F  A  L  A  Y  R  F  I  S  *  T  K  K  I  *  F  G  N  S
```

FIG. 9 CONT.

```
20521 CAAGAGTTTTTGCAGTATGATTCTAGTATTCATTCATATTTCATTACTGATCAAGAGTGT 20580
      Q  E  F  L  Q  Y  D  S  S  I  H  S  Y  F  I  T  D  Q  E  C
       K  S  F  C  S  M  I  L  V  F  I  H  I  S  L  L  I  K  S  V
        R  V  F  A  V  *  F  *  Y  S  F  I  F  H  Y  *  S  R  V  W

20581 GGTAGTAGTAAGAGTGTTTGTACAGTTATTGATTTATTATTAGATGACTTTGTTGTTATT 20640
      G  S  S  K  S  V  C  T  V  I  D  L  L  L  D  D  F  V  V  I
       V  V  V  R  V  F  V  Q  L  L  I  Y  Y  *  M  T  L  L  L  L
        *  *  *  E  C  L  Y  S  Y  *  F  I  I  R  *  L  C  C  Y  C

20641 GTTAAGTCATTAAATTTGAATTGTGTTAGTAAAGTTGTTAATATTAATGTTGACTTTAAG 20700
      V  K  S  L  N  L  N  C  V  S  K  V  V  N  I  N  V  D  F  K
       L  S  H  *  I  *  I  V  L  V  K  L  L  I  L  M  L  T  L  R
        *  V  I  K  F  E  L  C  *  *  S  C  *  Y  *  C  *  L  *  G

20701 GACTTTCAATTTATGTTGTGGTGTAATGATAATAAAATTATGACTTTTTATCCTAAAATG 20760
      D  F  Q  F  M  L  W  C  N  D  N  K  I  M  T  F  Y  P  K  M
       T  F  N  L  C  C  G  V  M  I  I  K  L  *  L  F  I  L  K  C
        L  S  I  Y  V  V  V  *  *  *  *  N  Y  D  F  L  S  *  N  A

20761 CAAGCTACTAGTGACTGGAAACCTGGTTATTCTATGCCTGTTTTATATAAGTATTTGAAT 20820
      Q  A  T  S  D  W  K  P  G  Y  S  M  P  V  L  Y  K  Y  L  N
       K  L  L  V  T  G  N  L  V  I  L  C  L  F  Y  I  S  I  *  M
        S  Y  *  *  L  E  T  W  L  F  Y  A  C  F  I  *  V  F  E  C

20821 GTTCCATTAGAGAGAGTTTCTTTATGGAATTATGGTAAAGCTATTAATTTACCAACAGGT 20880
      V  P  L  E  R  V  S  L  W  N  Y  G  K  A  I  N  L  P  T  G
       F  H  *  R  E  F  L  Y  G  I  M  V  K  L  L  I  Y  Q  Q  V
        S  I  R  E  S  F  F  M  E  L  W  *  S  Y  *  F  T  N  R  L

20881 TGTATGATGAATGTTGCTAAGTATACTCAATTATGTCAGTATTTAAATACTACAACATTA 20940
      C  M  M  N  V  A  K  Y  T  Q  L  C  Q  Y  L  N  T  T  T  L
       V  *  *  M  L  L  S  I  L  N  Y  V  S  I  *  I  L  Q  H  *
        Y  D  E  C  C  *  V  Y  S  I  M  S  V  F  K  Y  Y  N  I  S

20941 GCTGTTCCTGTTAATATGCGTGTCTTACACTTAGGTGCAGGATCTGATAAAGAAGTAGCC 21000
      A  V  P  V  N  M  R  V  L  H  L  G  A  G  S  D  K  E  V  A
       L  F  L  L  I  C  V  S  Y  T  *  V  Q  D  L  I  K  K  *  P
        C  S  C  *  Y  A  C  L  T  L  R  C  R  I  *  *  R  S  S  P

21001 CCTGGTTCTGCTGTTTTAAGACAGTGGTTACCATCTGGTAGTATTCTTGTAGATAATGAT 21060
      P  G  S  A  V  L  R  Q  W  L  P  S  G  S  I  L  V  D  N  D
       L  V  L  L  F  *  D  S  G  Y  H  L  V  V  F  L  *  I  M  I
        W  F  C  C  F  K  T  V  V  T  I  W  *  Y  S  C  R  *  *  F
```

FIG. 9 CONT.

```
21061 TTAAATCCTTTTGTTAGTGATAGTTTAGTCACTTATTTTGGAGATTGTATGACTTTACCA 21120
      L  N  P  F  V  S  D  S  L  V  T  Y  F  G  D  C  M  T  L  P
       *  I  L  L  L  V  I  V  *  S  L  I  L  E  I  V  *  L  Y  H
        K  S  F  C  *  *  *  F  S  H  L  F  W  R  L  Y  D  F  T  I

21121 TTTGATTGTCATTGGGATCTGATAATATCTGATATGTATGATCCTCTTACTAAGAATATT 21180
      F  D  C  H  W  D  L  I  I  S  D  M  Y  D  P  L  T  K  N  I
       L  I  V  I  G  I  *  *  Y  L  I  C  M  I  L  L  L  R  I  L
        *  L  S  L  G  S  D  N  I  *  Y  V  *  S  S  Y  *  E  Y  W

21181 GGTGATTATAATGTGAGTAAGGATGGTTTCTTTACTTATATTTGTTATTTAATTCGTGAT 21240
      G  D  Y  N  V  S  K  D  G  F  F  T  Y  I  C  Y  L  I  R  D
       V  I  I  M  *  V  R  M  V  S  L  L  I  F  V  I  *  F  V  I
        *  L  *  C  E  *  G  W  F  L  Y  L  Y  L  L  F  N  S  *  *

21241 AAATTATCTTTGGGTGGTAGTGTTGCTATAAAAATTACAGAATTTTCTTGGAATGCTGAC 21300
      K  L  S  L  G  G  S  V  A  I  K  I  T  E  F  S  W  N  A  D
       N  Y  L  W  V  V  V  L  L  *  K  L  Q  N  F  L  G  M  L  T
        I  I  F  G  W  *  C  C  Y  K  N  Y  R  I  F  L  E  C  *  L

21301 TTATATAAATTAATGAGTTATTTTGCATTCTGGACAGTTTTTTGTACTAATGTAAATGCT 21360
      L  Y  K  L  M  S  Y  F  A  F  W  T  V  F  C  T  N  V  N  A
       Y  I  N  *  *  V  I  L  H  S  G  Q  F  F  V  L  M  *  M  L
        I  *  I  N  E  L  F  C  I  L  D  S  F  L  Y  *  C  K  C  F

21361 TCTTCTAGTGAAGGGTTTTTAATAGGTATAAATTATTTGGGTAAGTCCTGCTTTGAAATA 21420
      S  S  S  E  G  F  L  I  G  I  N  Y  L  G  K  S  C  F  E  I
       L  L  V  K  G  F  *  *  V  *  I  I  W  V  S  P  A  L  K  *
        F  *  *  R  V  F  N  R  Y  K  L  F  G  *  V  L  L  *  N  R

21421 GATGGCAATGTTATGCATGCCAACTATTTGTTTTGGAGAAATAGTACAACATGGAATGGT 21480
      D  G  N  V  M  H  A  N  Y  L  F  W  R  N  S  T  T  W  N  G
       M  A  M  L  C  M  P  T  I  C  F  G  E  I  V  Q  H  G  M  V
        W  Q  C  Y  A  C  Q  L  F  V  L  E  K  *  Y  N  M  E  W  W

21481 GGTGCTTATAGTTTATTTGATATGTCTAAATTTTCTTTGAAATTGGCTGGCACTGCTGTA 21540
      G  A  Y  S  L  F  D  M  S  K  F  S  L  K  L  A  G  T  A  V
       V  L  I  V  Y  L  I  C  L  N  F  L  *  N  W  L  A  L  L  *
        C  L  *  F  I  *  Y  V  *  I  F  F  E  I  G  W  H  C  C  S

21541 GTAAATTTAAGACCAGATCAATTAAATGATTTAGTTTATTCTCTTATTGAAAGAGGTAAG 21600
      V  N  L  R  P  D  Q  L  N  D  L  V  Y  S  L  I  E  R  G  K
       *  I  *  D  Q  I  N  *  M  I  *  F  I  L  L  L  K  E  V  S
        K  F  K  T  R  S  I  K  *  F  S  L  F  S  Y  *  K  R  *  V
```

FIG. 9 CONT.

```
21601 TTATTAGTGCGTGATACGCGTAAAGAAATTTTTGTTGGTGATAGTCTTGTAAACACTTGT 21660
       L  L  V  R  D  T  R  K  E  I  F  V  G  D  S  L  V  N  T  C
        Y  *  C  V  I  R  V  K  K  F  L  L  V  I  V  L  *  T  L  V
         I  S  A  *  Y  A  *  R  N  F  C  W  *  *  S  C  K  H  L  L

21661 TAGATCTTTCAGTTTGTTAATATTAAATCTAAACTATGTTAATTATATTTTTATTTTTTA 21720
       *  I  F  Q  F  V  N  I  K  S  K  L  C  *  L  Y  F  Y  F  L
        R  S  F  S  L  L  I  L  N  L  N  Y  V  N  Y  I  F  I  F  *
         D  L  S  V  C  *  Y  *  I  *  T  M  L  I  I  F  L  F  F  N

21721 ATTTTTGTTATGGTTTTAATGAACCTTTGAATGTTGTGTCTCATTTAAACCATGACTGGT 21780
       I  F  V  M  V  L  M  N  L  *  M  L  C  L  I  *  T  M  T  G
        F  L  L  W  F  *  *  T  F  E  C  C  V  S  F  K  P  *  L  V
         F  C  Y  G  F  N  E  P  L  N  V  V  S  H  L  N  H  D  W  F

21781 TTTTATTTGGTGATAGTCGTTCTGATTGTAACCATATTAATAATTTAAAAATTAAAAATT 21840
       F  Y  L  V  I  V  V  L  I  V  T  I  L  I  I  *  K  L  K  I
        F  I  W  *  *  S  F  *  L  *  P  Y  *  *  F  K  N  *  K  L
         L  F  G  D  S  R  S  D  C  N  H  I  N  N  L  K  I  K  N  Y

21841 ATGGTTATTTGGATATTCACCCTAGTTTGTGTAATAATGGTAAAATTTCATCTAGTGCTG 21900
       M  V  I  W  I  F  T  L  V  C  V  I  M  V  K  F  H  L  V  L
        W  L  F  G  Y  S  P  *  F  V  *  *  W  *  N  F  I  *  C  W
         G  Y  L  D  I  H  P  S  L  C  N  N  G  K  I  S  S  S  A  G

21901 GTGATTCTATTTTTAAGAGTTATCATTTTACCCGGTTTTATAATTACACTGGCGAGGGTG 21960
       V  I  L  F  L  R  V  I  I  L  P  G  F  I  I  T  L  A  R  V
        *  F  Y  F  *  E  L  S  F  Y  P  V  L  *  L  H  W  R  G  *
         D  S  I  F  K  S  Y  H  F  T  R  F  Y  N  Y  T  G  E  G  D

21961 ATCAAATTATTTTTTATGAGGGTGTTAATTTCAATCCTCATCATAGGTTTAAGTGCTTCT 22020
       I  K  L  F  F  M  R  V  L  I  S  I  L  I  I  G  L  S  A  S
        S  N  Y  F  L  *  G  C  *  F  Q  S  S  S  *  V  *  V  L  L
         Q  I  I  F  Y  E  G  V  N  F  N  P  H  H  R  F  K  C  F  F

22021 TTAATGGTAGTAATGATGTATGGATTTTTAACAAGGTGAGGTTTTATCGTGCTTTATATT 22080
       L  M  V  V  M  M  Y  G  F  L  T  R  *  G  F  I  V  L  Y  I
        *  W  *  *  *  C  M  D  F  *  Q  G  E  V  L  S  C  F  I  F
         N  G  S  N  D  V  W  I  F  N  K  V  R  F  Y  R  A  L  Y  S

22081 CTAATATGGCTCTTTTTCGCTATCTTACCTTTGTTGATATTCTTTACAATTTTTCTTTTT 22140
       L  I  W  L  F  F  A  I  L  P  L  L  I  F  F  T  I  F  L  F
        *  Y  G  S  F  S  L  S  Y  L  C  *  Y  S  L  Q  F  F  F  F
         N  M  A  L  F  R  Y  L  T  F  V  D  I  L  Y  N  F  S  F  S
```

FIG. 9 CONT.

```
22141 CTATTAAGGCTAATATTTGTAATAGTAATATTTTATCACTTAATAATCCTATTTTTATTA 22200
      L  L  R  L  I  F  V  I  V  I  F  Y  H  L  I  I  L  F  L  L
       Y  *  G  *  Y  L  *  *  *  Y  F  I  T  *  *  S  Y  F  Y  *
        I  K  A  N  I  C  N  S  N  I  L  S  L  N  N  P  I  F  I  S

22201 GTACTAATTATTCTAAGGACGTTTATTTCACTTTATCAGGGTGTTCTTTGTATTTAGTAC 22260
      V  L  I  I  L  R  T  F  I  S  L  Y  Q  G  V  L  C  I  *  Y
       Y  *  L  F  *  G  R  L  F  H  F  I  R  V  F  F  V  F  S  T
        T  N  Y  S  K  D  V  Y  F  T  L  S  G  C  S  L  Y  L  V  P

22261 CTCTTTGTCTTTTTAAATCTAATTTTAGTCAGTACTATTATAATATGGATACTGGCTTTG 22320
      L  F  V  F  L  N  L  I  L  V  S  T  I  I  I  W  I  L  A  L
       S  L  S  F  *  I  *  F  *  S  V  L  L  *  Y  G  Y  W  L  C
        L  C  L  F  K  S  N  F  S  Q  Y  Y  Y  N  M  D  T  G  F  A

22321 CTTATGGTTATTCTAATTTTGTTTCTTCTGATTTAGATTGTACATATATTTCTCTTAAAC 22380
      L  M  V  I  L  I  L  F  L  L  I  *  I  V  H  I  F  L  L  N
       L  W  L  F  *  F  C  F  F  *  F  R  L  Y  I  Y  F  S  *  T
        Y  G  Y  S  N  F  V  S  S  D  L  D  C  T  Y  I  S  L  K  P

22381 CTGGTTCTTATAAAATTTTTTCTACTGGTTTTGTTTTATCCATACCTACTAAAGCTCTTT 22440
      L  V  L  I  K  F  F  L  L  V  L  F  Y  P  Y  L  L  K  L  F
       W  F  L  *  N  F  F  Y  W  F  C  F  I  H  T  Y  *  S  S  L
        G  S  Y  K  I  F  S  T  G  F  V  L  S  I  P  T  K  A  L  C

22441 GCTTTAATAAATCTAAACAATTTGTACCCGTGCAGGTTGTTGATTCTAGGTGGAACAATC 22500
      A  L  I  N  L  N  N  L  Y  P  C  R  L  L  I  L  G  G  T  I
       L  *  *  I  *  T  I  C  T  R  A  G  C  *  F  *  V  E  Q  S
        F  N  K  S  K  Q  F  V  P  V  Q  V  V  D  S  R  W  N  N  L

22501 TTCGTGCATCGGATACTTCATTATCCGATGCATGTCAGTTGCCTTATTGTTATTTTCGCA 22560
      F  V  H  R  I  L  H  Y  P  M  H  V  S  C  L  I  V  I  F  A
       S  C  I  G  Y  F  I  I  R  C  M  S  V  A  L  L  L  F  S  Q
        R  A  S  D  T  S  L  S  D  A  C  Q  L  P  Y  C  Y  F  R  N

22561 ATTCTTCTGGTAATTATGTTGGCAAATATGATATTAATCATGGTGATAATGGTTTTACTT 22620
      I  L  L  V  I  M  L  A  N  M  I  L  I  M  V  I  M  V  L  L
       F  F  W  *  L  C  W  Q  I  *  Y  *  S  W  *  *  W  F  Y  F
        S  S  G  N  Y  V  G  K  Y  D  I  N  H  G  D  N  G  F  T  S

22621 CTATTCTATCTGGTCTTTTATATAATGTCTCTTGTATTTCTTATTATGGCTCCTTTTTGT 22680
      L  F  Y  L  V  F  Y  I  M  S  L  V  F  L  I  M  A  P  F  C
       Y  S  I  W  S  F  I  *  C  L  L  Y  F  L  L  W  L  L  F  V
        I  L  S  G  L  L  Y  N  V  S  C  I  S  Y  Y  G  S  F  L  Y
```

FIG. 9 CONT.

```
22681 ATGACAATTTTACATCAATTTGGCCTCGTTTTTCTTTTGGTAATTGTCCTACATCTGCTT 22740
      M  T  I  L  H  Q  F  G  L  V  F  L  L  V  I  V  L  H  L  L
       *  Q  F  Y  I  N  L  A  S  F  F  F  W  *  L  S  Y  I  C  L
        D  N  F  T  S  I  W  P  R  F  S  F  G  N  C  P  T  S  A  Y

22741 ATATTAAATTAAATTGTTTCTATGATCCTTTGCCTATTATTTTACAAGGTATTTTATTAT 22800
      I  L  N  *  I  V  S  M  I  L  C  L  L  F  Y  K  V  F  Y  Y
       Y  *  I  K  L  F  L  *  S  F  A  Y  Y  F  T  R  Y  F  I  I
        I  K  L  N  C  F  Y  D  P  L  P  I  I  L  Q  G  I  L  L  F

22801 TTTTAGCTTTATTGTTTATTGTGTTTTTACTTTTTCTAGTTTACCATGGCTAATATTAAA 22860
      F  *  L  Y  C  L  L  C  F  Y  F  F  *  F  T  M  A  N  I  K
       F  S  F  I  V  Y  C  V  F  T  F  S  S  L  P  W  L  I  L  N
        L  A  L  L  F  I  V  F  L  L  F  L  V  Y  H  G  *  Y  *  I

22861 TCTAAACATGTTTTTAATTATTTTTATTTTGCCTACAACACTAGCTGTTATAGGTGATTT 22920
      S  K  H  V  F  N  Y  F  Y  F  A  Y  N  T  S  C  Y  R  *  F
       L  N  M  F  L  I  I  F  I  L  P  T  T  L  A  V  I  G  D  F
        *  T  C  F  *  L  F  L  F  C  L  Q  H  *  L  L  *  V  I  L

22921 TAATTGTACTAACTCTTTTATTAATGATTATAATAAAACCATTCCGCGTATAAGCGAGGA 22980
      *  L  Y  *  L  F  Y  *  *  L  *  *  N  H  S  A  Y  K  R  G
       N  C  T  N  S  F  I  N  D  Y  N  K  T  I  P  R  I  S  E  D
        I  V  L  T  L  L  L  M  I  I  I  K  P  F  R  V  *  A  R  M

22981 TGTTGTTGATGTATCTCTTGGTTTGGGCACATATTATGTTCTTAACCGTGTTTATTTAAA 23040
      C  C  *  C  I  S  W  F  G  H  I  L  C  S  *  P  C  L  F  K
       V  V  D  V  S  L  G  L  G  T  Y  Y  V  L  N  R  V  Y  L  N
        L  L  M  Y  L  L  V  W  A  H  I  M  F  L  T  V  F  I  *  I

23041 TACTACCTTGTTATTTACAGGTTATTTTCCTAAATCTGGTGCTAATTTTAGAGACTTGGC 23100
      Y  Y  L  V  I  Y  R  L  F  S  *  I  W  C  *  F  *  R  L  G
       T  T  L  L  F  T  G  Y  F  P  K  S  G  A  N  F  R  D  L  A
        L  P  C  Y  L  Q  V  I  F  L  N  L  V  L  I  L  E  T  W  L

23101 TTTAAAGGGTTCTAAATATTTGAGTACTCTCTGGTATAAACCACCTTTTCTGTCAGATTT 23160
      F  K  G  F  *  I  F  E  Y  S  L  V  *  T  T  F  S  V  R  F
       L  K  G  S  K  Y  L  S  T  L  W  Y  K  P  P  F  L  S  D  F
        *  R  V  L  N  I  *  V  L  S  G  I  N  H  L  F  C  Q  I  L

23161 TAATAATGGTATTTTTTCTAAGGTTAAGAATACTAAGTTATATGTTAATAATACTTTGTA 23220
      *  *  W  Y  F  F  *  G  *  E  Y  *  V  I  C  *  *  Y  F  V
       N  N  G  I  F  S  K  V  K  N  T  K  L  Y  V  N  N  T  L  Y
        I  M  V  F  F  L  R  L  R  I  L  S  Y  M  L  I  I  L  C  I
```

FIG. 9 CONT.

```
23221 TAGTGAATTTAGTACTATAGTTATAGGTAGTGTTTTTGTTAATACTTCTTATACTATTGT 23280
      *  *  I  *  Y  Y  S  Y  R  *  C  F  C  *  Y  F  L  Y  Y  C
       S  E  F  S  T  I  V  I  G  S  V  F  V  N  T  S  Y  T  I  V
        V  N  L  V  L  *  L  *  V  V  F  L  L  I  L  L  I  L  L  L

23281 TGTTCAACCTCACAATGGTATTTTGGAGATTACAGCTTGTCAGTATACTATGTGTGAATA 23340
      C  S  T  S  Q  W  Y  F  G  D  Y  S  L  S  V  Y  Y  V  *  I
       V  Q  P  H  N  G  I  L  E  I  T  A  C  Q  Y  T  M  C  E  Y
        F  N  L  T  M  V  F  W  R  L  Q  L  V  S  I  L  C  V  N  I

23341 TCCTCACACTGTTTGTAAGTCTAAGGGTAGTATTCGTAATGAATCTTGGCACATTGATTC 23400
      S  S  H  C  L  *  V  *  G  *  Y  S  *  *  I  L  A  H  *  F
       P  H  T  V  C  K  S  K  G  S  I  R  N  E  S  W  H  I  D  S
        L  T  L  F  V  S  L  R  V  V  F  V  M  N  L  G  T  L  I  L

23401 TTCGGAACCTTTATGCTTGTTTAAGAAAAATTTTACTTATAATGTTTCTGCAGATTGGCT 23460
      F  G  T  F  M  L  V  *  E  K  F  Y  L  *  C  F  C  R  L  A
       S  E  P  L  C  L  F  K  K  N  F  T  Y  N  V  S  A  D  W  L
        R  N  L  Y  A  C  L  R  K  I  L  L  I  M  F  L  Q  I  G  C

23461 GTATTTTCATTTTTATCAAGAACGTGGTGTTTTTTATGCATATTATGCAGATGTAGGTAT 23520
      V  F  S  F  L  S  R  T  W  C  F  L  C  I  L  C  R  C  R  Y
       Y  F  H  F  Y  Q  E  R  G  V  F  Y  A  Y  Y  A  D  V  G  M
        I  F  I  F  I  K  N  V  V  F  F  M  H  I  M  Q  M  *  V  C

23521 GCCTACCACTTTCTTATTTAGTTTATATTTAGGTACTATTTTATCTCATTATTATGTTAT 23580
      A  Y  H  F  L  I  *  F  I  F  R  Y  Y  F  I  S  L  L  C  Y
       P  T  T  F  L  F  S  L  Y  L  G  T  I  L  S  H  Y  Y  V  M
        L  P  L  S  Y  L  V  Y  I  *  V  L  F  Y  L  I  I  M  L  C

23581 GCCTTTGACTTGTAAGGCTATATCTTCAAATACTGACAATGAAACTTTAGAATATTGGGT 23640
      A  F  D  L  *  G  Y  I  F  K  Y  *  Q  *  N  F  R  I  L  G
       P  L  T  C  K  A  I  S  S  N  T  D  N  E  T  L  E  Y  W  V
        L  *  L  V  R  L  Y  L  Q  I  L  T  M  K  L  *  N  I  G  L

23641 TACACCGCTATCTAGACGTCAGTATCTTCTTAATTTTGATGAGCACGGTGTTATTACTAA 23700
      Y  T  A  I  *  T  S  V  S  S  *  F  *  *  A  R  C  Y  Y  *
       T  P  L  S  R  R  Q  Y  L  L  N  F  D  E  H  G  V  I  T  N
        H  R  Y  L  D  V  S  I  F  L  I  L  M  S  T  V  L  L  L  M

23701 TGCCGTTGATTGTTCAAGTAGTTTTCTTAGTGAGATTCAATGTAAAACTCAATCTTTTGC 23760
      C  R  *  L  F  K  *  F  S  *  *  D  S  M  *  N  S  I  F  C
       A  V  D  C  S  S  S  F  L  S  E  I  Q  C  K  T  Q  S  F  A
        P  L  I  V  Q  V  V  F  L  V  R  F  N  V  K  L  N  L  L  H
```

FIG. 9 CONT.

```
23761 ACCTAATACTGGTGTTTATGATTTGTCTGGTTTTACTGTAAAGCCTGTTGCAACTGTTTA 23820
      T  *  Y  W  C  L  *  F  V  W  F  Y  C  K  A  C  C  N  C  L
       P  N  T  G  V  Y  D  L  S  G  F  T  V  K  P  V  A  T  V  Y
        L  I  L  V  F  M  I  C  L  V  L  L  *  S  L  L  Q  L  F  I

23821 TCGTCGGATTCCTAATTTACCTGATTGTGACATTGACAACTGGCTTAATAATGTTAGTGT 23880
      S  S  D  S  *  F  T  *  L  *  H  *  Q  L  A  *  *  C  *  C
       R  R  I  P  N  L  P  D  C  D  I  D  N  W  L  N  N  V  S  V
        V  G  F  L  I  Y  L  I  V  T  L  T  T  G  L  I  M  L  V  Y

23881 ACCTTCACCTCTTAATTGGGAACGTAGAATTTTTTCTAATTGTAACTTCAATTTAAGCAC 23940
      T  F  T  S  *  L  G  T  *  N  F  F  *  L  *  L  Q  F  K  H
       P  S  P  L  N  W  E  R  R  I  F  S  N  C  N  F  N  L  S  T
        L  H  L  L  I  G  N  V  E  F  F  L  I  V  T  S  I  *  A  L

23941 TTTACTTCGTCTAGTTCATGTTGATTCTTTTTCTTGTAATAATCTTGATAAATCTAAAAT 24000
      F  T  S  S  S  C  *  F  F  F  L  *  *  S  *  *  I  *  N
       L  L  R  L  V  H  V  D  S  F  S  C  N  N  L  D  K  S  K  I
        Y  F  V  *  F  M  L  I  L  F  L  V  I  I  L  I  N  L  K  F

24001 TTTTGGTAGTTGCTTTAATAGTATTACTGTTGACAAGTTTGCTATACCTAATCGCAGACG 24060
      F  W  *  L  L  *  *  Y  Y  C  *  Q  V  C  Y  T  *  S  Q  T
       F  G  S  C  F  N  S  I  T  V  D  K  F  A  I  P  N  R  R  R
        L  V  V  A  L  I  V  L  L  L  T  S  L  L  Y  L  I  A  D  E

24061 AGATGATTTGCAATTGGGCAGTTCTGGCTTTTTGCAATCATCTAATTACAAAATAGATAT 24120
      R  *  F  A  I  G  Q  F  W  L  F  A  I  I  *  L  Q  N  R  Y
       D  D  L  Q  L  G  S  S  G  F  L  Q  S  S  N  Y  K  I  D  I
        M  I  C  N  W  A  V  L  A  F  C  N  H  L  I  T  K  *  I  F

24121 TTCTTCTAGTTCTTGTCAATTGTATTATAGTTTACCTTTAGTTAATGTTACTATTAATAA 24180
      F  F  *  F  L  S  I  V  L  *  F  T  F  S  *  C  Y  Y  *  *
       S  S  S  S  C  Q  L  Y  Y  S  L  P  L  V  N  V  T  I  N  N
        L  L  V  L  V  N  C  I  I  V  Y  L  *  L  M  L  L  L  I  T

24181 CTTTAATCCATCTTCTTGGAATAGGAGGTATGGTTTTGGTAGTTTTAATGTGTCTTCTTA 24240
      L  *  S  I  F  L  E  *  E  V  W  F  W  *  F  *  C  V  F  L
       F  N  P  S  S  W  N  R  R  Y  G  F  G  S  F  N  V  S  S  Y
        L  I  H  L  L  G  I  G  G  M  V  L  V  V  L  M  C  L  L  M

24241 TGACGTTGTTTATTCTGATCATTGTTTTTCTGTTAACAGCGACTTTTGCCCTTGTGCAGA 24300
      *  R  C  L  F  *  S  L  F  F  C  *  Q  R  L  L  P  L  C  R
       D  V  V  Y  S  D  H  C  F  S  V  N  S  D  F  C  P  C  A  D
        T  L  F  I  L  I  I  V  F  L  L  T  A  T  F  A  L  V  Q  I
```

FIG. 9 CONT.

```
24301 TCCGTCTGTTGTTAATTCTTGTGTTAAATCTAAGCCTCTTTCTGCCATTTGTCCTGCTGG 24360
      S  V  C  C  *  F  L  C  *  I  *  A  S  F  C  H  L  S  C  W
       P  S  V  V  N  S  C  V  K  S  K  P  L  S  A  I  C  P  A  G
        R  L  L  L  I  L  V  L  N  L  S  L  F  L  P  F  V  L  L  V

24361 TACTAAATATCGTCATTGCGACTTGGATACTACTCTTTATGTTAATAACTGGTGTAGATG 24420
      Y  *  I  S  S  L  R  L  G  Y  Y  S  L  C  *  *  L  V  *  M
       T  K  Y  R  H  C  D  L  D  T  T  L  Y  V  N  N  W  C  R  C
        L  N  I  V  I  A  T  W  I  L  L  F  M  L  I  T  G  V  D  V

24421 TTCTTGTCTACCTGACCCCATTTCTACTTATTCTCCTAACACATGTCCTCAAAAGAAGGT 24480
      F  L  S  T  *  P  H  F  Y  L  F  S  *  H  M  S  S  K  E  G
       S  C  L  P  D  P  I  S  T  Y  S  P  N  T  C  P  Q  K  K  V
        L  V  Y  L  T  P  F  L  L  I  L  L  T  H  V  L  K  R  R  S

24481 CGTTGTTGGTATAGGTGAACATTGTCCAGGTCTTGGTATTAATGAGGAAAAATGTGGTAC 24540
      R  C  W  Y  R  *  T  L  S  R  S  W  Y  *  *  G  K  M  W  Y
       V  V  G  I  G  E  H  C  P  G  L  G  I  N  E  E  K  C  G  T
        L  L  V  *  V  N  I  V  Q  V  L  V  L  M  R  K  N  V  V  H

24541 ACAATTAAATCATAGTTCCTGTTCTTGTAGTCCTGATGCCTTTTTGGGTTGGTCTTTTGA 24600
      T  I  K  S  *  F  L  F  L  *  S  *  C  L  F  G  L  V  F  *
       Q  L  N  H  S  S  C  S  C  S  P  D  A  F  L  G  W  S  F  D
        N  *  I  I  V  P  V  L  V  V  L  M  P  F  W  V  G  L  L  I

24601 TAGTTGTATTAGTAATAATCGTTGCAATATTTTTTCTAATTTTATTTTTAATGGAATTAA 24660
      *  L  Y  *  *  *  S  L  Q  Y  F  F  *  F  Y  F  *  W  N  *
       S  C  I  S  N  N  R  C  N  I  F  S  N  F  I  F  N  G  I  N
        V  V  L  V  I  I  V  A  I  F  F  L  I  L  F  L  M  E  L  I

24661 TAGTGGCACCACTTGTTCTAATGATTTGTTATATTCTAACACTGAAGTTTCTACTGGTGT 24720
      *  W  H  H  L  F  *  *  F  V  I  F  *  H  *  S  F  Y  W  C
       S  G  T  T  C  S  N  D  L  L  Y  S  N  T  E  V  S  T  G  V
        V  A  P  L  V  L  M  I  C  Y  I  L  T  L  K  F  L  L  V  F

24721 TTGTGTTAATTATGATCTTTATGGCATCACAGGCCAAGGTATTTTTAAAGAAGTTTCTGC 24780
      L  C  *  L  *  S  L  W  H  H  R  P  R  Y  F  *  R  S  F  C
       C  V  N  Y  D  L  Y  G  I  T  G  Q  G  I  F  K  E  V  S  A
        V  L  I  M  I  F  M  A  S  Q  A  K  V  F  L  K  K  F  L  R

24781 GGCTTATTATAATAATTGGCAGAATCTTTTGTATGATTCTAATGGTAATATTATTGGTTT 24840
      G  L  L  *  *  L  A  E  S  F  V  *  F  *  W  *  Y  Y  W  F
       A  Y  Y  N  N  W  Q  N  L  L  Y  D  S  N  G  N  I  I  G  F
        L  I  I  I  I  G  R  I  F  C  M  I  L  M  V  I  L  L  V  L
```

FIG. 9 CONT.

```
24841 TAAAGATTTTTTGACTAATAAAACTTACACTATACTTCCTTGTTATTCTGGTAGAGTGTC 24900
      * R F F D * * N L H Y T S L L F W * S V
       K D F L T N K T Y T I L P C Y S G R V S
        K I F * L I K L T L Y F L V I L V E C L

24901 TGCTGCATTTTATCAAAATTCTTCTTCACCAGCTTTGCTTTATCGTAATTTAAAGTGTAG 24960
      C C I L S K F F F T S F A L S * F K V *
       A A F Y Q N S S S P A L L Y R N L K C S
        L H F I K I L L H Q L C F I V I * S V V

24961 TTATGTTTTGAATAATATTTCTTTTATCTCACAACCATTTTATTTTGATAGTTATCTTGG 25020
      L C F E * Y F F Y L T T I L F * * L S W
       Y V L N N I S F I S Q P F Y F D S Y L G
        M F * I I F L L S H N H F I L I V I L V

25021 TTGTGTTTTGAATGCTGTTAATTTAACTAGCTATTCTGTATCCTCTTGTGATTTGCGTAT 25080
      L C F E C C * F N * L F C I L L * F A Y
       C V L N A V N L T S Y S V S S C D L R M
        V F * M L L I * L A I L Y P L V I C V W

25081 GGGTAGTGGGTTTTGTATTGATTATGCTTTACCCTCTTCTCGGCGTAAGCGTAGAGGTAT 25140
      G * W V L Y * L C F T L F S A * A * R Y
       G S G F C I D Y A L P S S R R K R R G I
        V V G F V L I M L Y P L L G V S V E V F

25141 TTCTTCTCCTTATCGCTTTGTAACTTTTGAACCCTTTAATGTTAGTTTTGTTAACGATAG 25200
      F F S L S L C N F * T L * C * F C * R *
       S S P Y R F V T F E P F N V S F V N D S
        L L L I A L * L L N P L M L V L L T I V

25201 TGTTGAAACTGTTGGTGGTTTATTTGAGATTCAGATTCCTACTAACTTTACCATAGCTGG 25260
      C * N C W W F I * D S D S Y * L Y H S W
       V E T V G G L F E I Q I P T N F T I A G
        L K L L V V Y L R F R F L L T L P * L V

25261 TCATGAAGAATTTATTCAGACTAGTTCTCCTAAAGTTACTATTGATTGTTCAGCTTTTGT 25320
      S * R I Y S D * F S * S Y Y * L F S F C
       H E E F I Q T S S P K V T I D C S A F V
        M K N L F R L V L L K L L L I V Q L L F

25321 TTGCTCTAATTATGCTGCTTGTCATGATTTATTGTCGGAATATGGCACTTTTTGCGATAA 25380
      L L * L C C L S * F I V G I W H F L R *
       C S N Y A A C H D L L S E Y G T F C D N
        A L I M L L V M I Y C R N M A L F A I I
```

FIG. 9 CONT.

```
25381 TATTAATAGTATTTTAAATGAAGTCAATGATTTACTTGATATTACTCAGTTGCAGGTTGC 25440
      Y  *  *  Y  F  K  *  S  Q  *  F  T  *  Y  Y  S  V  A  G  C
       I  N  S  I  L  N  E  V  N  D  L  L  D  I  T  Q  L  Q  V  A
        L  I  V  F  *  M  K  S  M  I  Y  L  I  L  L  S  C  R  L  L

25441 TAATGCTTTAATGCAAGGTGTTACACTTAGTTCTAATCTTAATACTAATCTACACTCTGA 25500
      *  C  F  N  A  R  C  Y  T  *  F  *  S  *  Y  *  S  T  L  *
       N  A  L  M  Q  G  V  T  L  S  S  N  L  N  T  N  L  H  S  D
        M  L  *  C  K  V  L  H  L  V  L  I  L  I  L  I  Y  T  L  M

25501 TGTTGATAATATAGATTTTAAATCTCTTCTAGGTTGTTTAGGTTCACAATGTGGTTCTTC 25560
      C  *  *  Y  R  F  *  I  S  S  R  L  F  R  F  T  M  W  F  F
       V  D  N  I  D  F  K  S  L  L  G  C  L  G  S  Q  C  G  S  S
        L  I  I  *  I  L  N  L  F  *  V  V  *  V  H  N  V  V  L  R

25561 GTCTAGATCTTTGTTAGAGGATTTATTATTCAACAAGGTCAAACTTTCAGATGTAGGTTT 25620
      V  *  I  F  V  R  G  F  I  I  Q  Q  G  Q  T  F  R  C  R  F
       S  R  S  L  L  E  D  L  L  F  N  K  V  K  L  S  D  V  G  F
        L  D  L  C  *  R  I  Y  Y  S  T  R  S  N  F  Q  M  *  V  L

25621 TGTTGAAGCTTATAATAATTGCACTGGTGGTAGTGAAATTAGAGATCTTCTCTGTGTGCA 25680
      C  *  S  L  *  *  L  H  W  W  *  *  N  *  R  S  S  L  C  A
       V  E  A  Y  N  N  C  T  G  G  S  E  I  R  D  L  L  C  V  Q
        L  K  L  I  I  I  A  L  V  V  V  K  L  E  I  F  S  V  C  N

25681 ATCTTTTAATGGTATTAAAGTATTACCTCCCATTTTATCTGAGACTCAAATTTCTGGCTA 25740
      I  F  *  W  Y  *  S  I  T  S  H  F  I  *  D  S  N  F  W  L
       S  F  N  G  I  K  V  L  P  P  I  L  S  E  T  Q  I  S  G  Y
        L  L  M  V  L  K  Y  Y  L  P  F  Y  L  R  L  K  F  L  A  I

25741 TACTACAGCTGCTACTGTGGCGGCTATGTTTCCGCCATGGTCTGCTGCTGCTGGTGTACC 25800
      Y  Y  S  C  Y  C  G  G  Y  V  S  A  M  V  C  C  C  W  C  T
       T  T  A  A  T  V  A  A  M  F  P  P  W  S  A  A  A  G  V  P
        L  Q  L  L  L  W  R  L  C  F  R  H  G  L  L  L  L  V  Y  H

25801 ATTTTCTCTTAATGTACAATATAGAATTAATGGTTTGGGTGTTACTATGGATGTTCTTAA 25860
      I  F  S  *  C  T  I  *  N  *  W  F  G  C  Y  Y  G  C  S  *
       F  S  L  N  V  Q  Y  R  I  N  G  L  G  V  T  M  D  V  L  N
        F  L  L  M  Y  N  I  E  L  M  V  W  V  L  L  W  M  F  L  I

25861 TAAGAATCAAAAGTTAATAGCTAATGCTTTTAATAAAGCTCTTCTTTCTATCCAGAATGG 25920
      *  E  S  K  V  N  S  *  C  F  *  *  S  S  S  F  Y  P  E  W
       K  N  Q  K  L  I  A  N  A  F  N  K  A  L  L  S  I  Q  N  G
        R  I  K  S  *  *  L  M  L  L  I  K  L  F  F  L  S  R  M  V
```

FIG. 9 CONT.

```
25921 TTTTACTGCTACTAACTCTGCTCTTGCTAAAATTCAAAGTGTCGTTAATGCTAATGCTCA 25980
      F  Y  C  Y  *  L  C  S  C  *  N  S  K  C  R  *  C  *  C  S
       F  T  A  T  N  S  A  L  A  K  I  Q  S  V  V  N  A  N  A  Q
        L  L  L  L  T  L  L  L  L  K  F  K  V  S  L  M  L  M  L  K

25981 AGCACTTAATAGTTTGTTACAACAATTATTTAATAAATTTGGTGCTATTAGTTCTTCTTT 26040
      S  T  *  *  F  V  T  T  I  I  *  *  I  W  C  Y  *  F  F  F
       A  L  N  S  L  L  Q  Q  L  F  N  K  F  G  A  I  S  S  S  L
        H  L  I  V  C  Y  N  N  Y  L  I  N  L  V  L  L  V  L  L  Y

26041 ACAAGAAATTTTGTCTCGCCTTGATAATTTAGAAGCTCAGGTTCAGATTGATAGGCTCAT 26100
      T  R  N  F  V  S  P  *  *  F  R  S  S  G  S  D  *  *  A  H
       Q  E  I  L  S  R  L  D  N  L  E  A  Q  V  Q  I  D  R  L  I
        K  K  F  C  L  A  L  I  I  *  K  L  R  F  R  L  I  G  S  L

26101 TAATGGTCGTTTGACTGCTTTAAATGCTTATGTTTCTCAACAGCTTAGTGATATTACACT 26160
      *  W  S  F  D  C  F  K  C  L  C  F  S  T  A  *  *  Y  Y  T
       N  G  R  L  T  A  L  N  A  Y  V  S  Q  Q  L  S  D  I  T  L
        M  V  V  *  L  L  *  M  L  M  F  L  N  S  L  V  I  L  H  L

26161 TATTAAGGCTGGAGCTTCTCGTGCTATTGAGAAGGTTAATGAGTGTGTTAAAAGTCAATC 26220
      Y  *  G  W  S  F  S  C  Y  *  E  G  *  *  V  C  *  K  S  I
       I  K  A  G  A  S  R  A  I  E  K  V  N  E  C  V  K  S  Q  S
        L  R  L  E  L  L  V  L  L  R  R  L  M  S  V  L  K  V  N  P

26221 CCCTCGTATAAATTTTTGTGGCAATGGTAACCACATTTTATCATTGGTTCAAAATGCTCC 26280
      P  S  Y  K  F  L  W  Q  W  *  P  H  F  I  I  G  S  K  C  S
       P  R  I  N  F  C  G  N  G  N  H  I  L  S  L  V  Q  N  A  P
        L  V  *  I  F  V  A  M  V  T  T  F  Y  H  W  F  K  M  L  L

26281 TTATGGTTTGCTTTTCATTCATTTTAGTTATAAACCTACTTCTTTTAAAACTGTCTTAGT 26340
      L  W  F  A  F  H  S  F  *  L  *  T  Y  F  F  *  N  C  L  S
       Y  G  L  L  F  I  H  F  S  Y  K  P  T  S  F  K  T  V  L  V
        M  V  C  F  S  F  I  L  V  I  N  L  L  L  L  K  L  S  *  *

26341 AAGTCCAGGTTTATGTTTATCCGGTGATAGAGGTATTGCACCTAAGCAAGGTTATTTTAT 26400
      K  S  R  F  M  F  I  R  *  *  R  Y  C  T  *  A  R  L  F  Y
       S  P  G  L  C  L  S  G  D  R  G  I  A  P  K  Q  G  Y  F  I
        V  Q  V  Y  V  Y  P  V  I  E  V  L  H  L  S  K  V  I  L  L

26401 TAAACAAAATGATTCCTGGATGTTTACTGGTAGTTCCTATTATTACCCAGAACCAATTTC 26460
      *  T  K  *  F  L  D  V  Y  W  *  F  L  L  L  P  R  T  N  F
       K  Q  N  D  S  W  M  F  T  G  S  S  Y  Y  Y  P  E  P  I  S
        N  K  M  I  P  G  C  L  L  V  V  P  I  I  T  Q  N  Q  F  Q
```

FIG. 9 CONT.

```
26461 AGATAAAAATGTTGTTTTCATGAATAGTTGCTCTGTTAATTTTACTAAAGCTCCATTTAT 26520
      R  *  K  C  C  F  H  E  *  L  L  C  *  F  Y  *  S  S  I  Y
       D  K  N  V  V  F  M  N  S  C  S  V  N  F  T  K  A  P  F  I
        I  K  M  L  F  S  *  I  V  A  L  L  I  L  L  K  L  H  L  F

26521 TTATCTTAATAATTCTATACCAAATTTGTCTGATTTTGAAGCCGAGTTTTCTCTTTGGTT 26580
      L  S  *  *  F  Y  T  K  F  V  *  F  *  S  R  V  F  S  L  V
       Y  L  N  N  S  I  P  N  L  S  D  F  E  A  E  F  S  L  W  F
        I  L  I  I  L  Y  Q  I  C  L  I  L  K  P  S  F  L  F  G  L

26581 TAAAAATCATACTTCTATAGCACCTAATTTAACCTTTAATTCTCATATTAATGCTACTTT 26640
      *  K  S  Y  F  Y  S  T  *  F  N  L  *  F  S  Y  *  C  Y  F
       K  N  H  T  S  I  A  P  N  L  T  F  N  S  H  I  N  A  T  F
        K  I  I  L  L  *  H  L  I  *  P  L  I  L  I  L  M  L  L  F

26641 TTTAGATCTGTATTATGAAATGAATGTTATTCAGGAATCTATTAAATCTTTGAACAGTAG 26700
      F  R  S  V  L  *  N  E  C  Y  S  G  I  Y  *  I  F  E  Q  *
       L  D  L  Y  Y  E  M  N  V  I  Q  E  S  I  K  S  L  N  S  S
        *  I  C  I  M  K  *  M  L  F  R  N  L  L  N  L  *  T  V  V

26701 TTTTATTAATCTTAAAGAAATAGGTACTTATGAAATGTATGTTAAATGGCCTTGGTACAT 26760
      F  Y  *  S  *  R  N  R  Y  L  *  N  V  C  *  M  A  L  V  H
       F  I  N  L  K  E  I  G  T  Y  E  M  Y  V  K  W  P  W  Y  I
        L  L  I  L  K  K  *  V  L  M  K  C  M  L  N  G  L  G  T  F

26761 TTGGTTGTTAATTGTCATTTTATTTATAATTTTTCTTATGATACTTTTCTTTATATGCTG 26820
      L  V  V  N  C  H  F  I  Y  N  F  S  Y  D  T  F  L  Y  M  L
       W  L  L  I  V  I  L  F  I  I  F  L  M  I  L  F  F  I  C  C
        G  C  *  L  S  F  Y  L  *  F  F  L  *  Y  F  S  L  Y  A  A

26821 CTGTACTGGTTGTGGTTCAGCATGTTTTAGTAAATGTCATAATTGTTGTGATGAGTATGG 26880
      L  Y  W  L  W  F  S  M  F  *  *  M  S  *  L  L  *  *  V  W
       C  T  G  C  G  S  A  C  F  S  K  C  H  N  C  C  D  E  Y  G
        V  L  V  V  V  Q  H  V  L  V  N  V  I  I  V  V  M  S  M  G

26881 GGGTCACAATGATTTTGTTATTAAAGCATCTCATGATGATTAGATTTTAAATCTAAACTT 26940
      G  S  Q  *  F  C  Y  *  S  I  S  *  *  L  D  F  K  S  K  L
       G  H  N  D  F  V  I  K  A  S  H  D  D  *  I  L  N  L  N  F
        V  T  M  I  L  L  L  K  H  L  M  M  I  R  F  *  I  *  T  L

26941 TATATATGGAAGTTTGGAGGCCTAGCTATAAATATTCTCTTATTACTAGAGAATTTGGTG 27000
      Y  I  W  K  F  G  G  L  A  I  N  I  L  L  L  L  E  N  L  V
       I  Y  G  S  L  E  A  *  L  *  I  F  S  Y  Y  *  R  I  W  C
        Y  M  E  V  W  R  P  S  Y  K  Y  S  L  I  T  R  E  F  G  V
```

FIG. 9 CONT.

```
27001 TCACAGATCTTGAGGATTTGTGTTTTAAATATAATTATTGCCAACCTTGTGTTGGTTATT 27060
      S  Q  I  L  R  I  C  V  L  N  I  I  I  A  N  L  V  L  V  I
       H  R  S  *  G  F  V  F  *  I  *  L  L  P  T  L  C  W  L  L
        T  D  L  E  D  L  C  F  K  Y  N  Y  C  Q  P  C  V  G  Y  C

27061 GTATTGTACCTTTAAACGTTTGGTGTCGTAAGTTTGGTAAATTTGCTTCTTATTTTGTTT 27120
      V  L  Y  L  *  T  F  G  V  V  S  L  V  N  L  L  L  I  L  F
       Y  C  T  F  K  R  L  V  S  *  V  W  *  I  C  F  L  F  C  F
        I  V  P  L  N  V  W  C  R  K  F  G  K  F  A  S  Y  F  V  L

27121 TACGTAGTCATGACACCTCTCATAAGAATAATTTTGGTGTTATAACTAGTTTTACTAGTT 27180
      Y  V  V  M  T  P  L  I  R  I  I  L  V  L  *  L  V  L  L  V
       T  *  S  *  H  L  S  *  E  *  F  W  C  Y  N  *  F  Y  *  L
        R  S  H  D  T  S  H  K  N  N  F  G  V  I  T  S  F  T  S  Y

27181 ATGGTAACACTGTTTCTGAGGCTGTTTCTAAATTAGTTGAATCAGCATCTGATTTTATCG 27240
      M  V  T  L  F  L  R  L  F  L  N  *  L  N  Q  H  L  I  L  S
       W  *  H  C  F  *  G  C  F  *  I  S  *  I  S  I  *  F  Y  R
        G  N  T  V  S  E  A  V  S  K  L  V  E  S  A  S  D  F  I  A

27241 CTTGGCGAGCTGAAGCACTTAATAAGTATGGTTGATGTATTTTTCACTGATACTGCTTGG 27300
      L  G  E  L  K  H  L  I  S  M  V  D  V  F  F  T  D  T  A  W
       L  A  S  *  S  T  *  *  V  W  L  M  Y  F  S  L  I  L  L  G
        W  R  A  E  A  L  N  K  Y  G  *  C  I  F  H  *  Y  C  L  V

27301 TATGTAGGTCAGATTTTCTTTTTAGTTTTATCTTGTGTCATTTTCTTAATTTTTGTTGTT 27360
      Y  V  G  Q  I  F  F  L  V  L  S  C  V  I  F  L  I  F  V  V
       M  *  V  R  F  S  F  *  F  Y  L  V  S  F  S  *  F  L  L  L
        C  R  S  D  F  L  F  S  F  I  L  C  H  F  L  N  F  C  C  C

27361 GCACTTTTAGCAACTATTAAACTTTGTATTCAAATTTGTGGTTTTTGTAATATTTTTATT 27420
      A  L  L  A  T  I  K  L  C  I  Q  I  C  G  F  C  N  I  F  I
       H  F  *  Q  L  L  N  F  V  F  K  F  V  V  F  V  I  F  L  L
        T  F  S  N  Y  *  T  L  Y  S  N  L  W  F  L  *  Y  F  Y  Y

27421 ATTTCACCTTCTGCCTATGTTTATAATAGAGGTAGACAGTTGTATAAGTCTTATAGTGAA 27480
      I  S  P  S  A  Y  V  Y  N  R  G  R  Q  L  Y  K  S  Y  S  E
       F  H  L  L  P  M  F  I  I  E  V  D  S  C  I  S  L  I  V  N
        F  T  F  C  L  C  L  *  *  R  *  T  V  V  *  V  L  *  *  T

27481 CATGTCATACCTTCTACTTTAGATGATTTAATTTAAATCTAAACATCATGAATGAATCAA 27540
      H  V  I  P  S  T  L  D  D  L  I  *  I  *  T  S  *  M  N  Q
       M  S  Y  L  L  L  *  M  I  *  F  K  S  K  H  H  E  *  I  N
        C  H  T  F  Y  F  R  *  F  N  L  N  L  N  I  M  N  E  S  I
```

FIG. 9 CONT.

```
27541 TTTTTCCTCATTGGAATTCTGATCAAGCTATTACATTCTTAAAAGAATGGAATTTCTCTT 27600
      F  F  L  I  G  I  L  I  K  L  L  H  S  *  K  N  G  I  S  L
       F  S  S  L  E  F  *  S  S  Y  Y  I  L  K  R  M  E  F  L  F
        F  P  H  W  N  S  D  Q  A  I  T  F  L  K  E  W  N  F  S  L

27601 TGGGTGTAATATTACTTCTCATTACTATCATACTGCAGTTTGGTTATACGAGTCGTAGTA 27660
      W  V  *  Y  Y  F  S  L  L  S  Y  C  S  L  V  I  R  V  V  V
       G  C  N  I  T  S  H  Y  Y  H  T  A  V  W  L  Y  E  S  *  Y
        G  V  I  L  L  L  I  T  I  I  L  Q  F  G  Y  T  S  R  S  M

27661 TGTTTGTTTATCTTATTAAGATGATTATTCTTTGGCTTATGTGGCCATTGACCATTATCT 27720
      C  L  F  I  L  L  R  *  L  F  F  G  L  C  G  H  *  P  L  S
       V  C  L  S  Y  *  D  D  Y  S  L  A  Y  V  A  I  D  H  Y  L
        F  V  Y  L  I  K  M  I  I  L  W  L  M  W  P  L  T  I  I  L

27721 TGACTATATTTAATTGCTTTTATGCTTTGAATAATATCTTTCTTGGGCTTTCTATACTGT 27780
      *  L  Y  L  I  A  F  M  L  *  I  I  S  F  L  G  F  L  Y  C
       D  Y  I  *  L  L  L  C  F  E  *  Y  L  S  W  A  F  Y  T  V
        T  I  F  N  C  F  Y  A  L  N  N  I  F  L  G  L  S  I  L  F

27781 TTACTATTATTTCTATTGTTATATGGATTTTATATTTTGTCAACAGTATTCGGCTTTTTA 27840
      L  L  L  F  L  L  L  Y  G  F  Y  I  L  S  T  V  F  G  F  L
       Y  Y  Y  F  Y  C  Y  M  D  F  I  F  C  Q  Q  Y  S  A  F  Y
        T  I  I  S  I  V  I  W  I  L  Y  F  V  N  S  I  R  L  F  I

27841 TCAGAACTGGCAGTTGGTGGAGTTTTAACCCAGAGACTAATAATCTTATGTGTATTGATA 27900
      S  E  L  A  V  G  G  V  L  T  Q  R  L  I  I  L  C  V  L  I
       Q  N  W  Q  L  V  E  F  *  P  R  D  *  *  S  Y  V  Y  *  Y
        R  T  G  S  W  W  S  F  N  P  E  T  N  N  L  M  C  I  D  M

27901 TGAAAGGTAAGATGTATGTTAGGCCAGTTATTGAGGACTATCATACATTAACGGCTACTG 27960
      *  K  V  R  C  M  L  G  Q  L  L  R  T  I  I  H  *  R  L  L
       E  R  *  D  V  C  *  A  S  Y  *  G  L  S  Y  I  N  G  Y  C
        K  G  K  M  Y  V  R  P  V  I  E  D  Y  H  T  L  T  A  T  V

27961 TTATCCGTGGTCATCTTTATATACAGGGTGTTAAACTTGGCACTGGTTACACGCTTGCCG 28020
      L  S  V  V  I  F  I  Y  R  V  L  N  L  A  L  V  T  R  L  P
       Y  P  W  S  S  L  Y  T  G  C  *  T  W  H  W  L  H  A  C  R
        I  R  G  H  L  Y  I  Q  G  V  K  L  G  T  G  Y  T  L  A  D

28021 ATTTGCCTGTTTATGTTACTGTAGCTAAGGTGCAAGTCCTCTGTACTTATAAACGTGCCT 28080
      I  C  L  F  M  L  L  *  L  R  C  K  S  S  V  L  I  N  V  P
       F  A  C  L  C  Y  C  S  *  G  A  S  P  L  Y  L  *  T  C  L
        L  P  V  Y  V  T  V  A  K  V  Q  V  L  C  T  Y  K  R  A  F
```

FIG. 9 CONT.

```
28081 TTTTAGATAAGTTAGATGTTAATAGTGGTTTTGCTGTTTTTGTTAAGTCTAAAGTTGGTA 28140
      F  *  I  S  *  M  L  I  V  V  L  L  F  L  L  S  L  K  L  V
       F  R  *  V  R  C  *  *  W  F  C  C  F  C  *  V  *  S  W  *
        L  D  K  L  D  V  N  S  G  F  A  V  F  V  K  S  K  V  G  N

28141 ACTATCGTTTACCTTCTAGTAAATCTAGTGGTATGGATACTGCCTTGTTGAGAGCTTAAA 28200
      T  I  V  Y  L  L  V  N  L  V  V  W  I  L  P  C  *  E  L  K
       L  S  F  T  F  *  *  I  *  W  Y  G  Y  C  L  V  E  S  L  N
        Y  R  L  P  S  S  K  S  S  G  M  D  T  A  L  L  R  A  *  I

28201 TCTAAACTATTAGGATGTCTTATACTCCCGGTCATCATGCTGGAAGTAGAAGCTCCTCTG 28260
      S  K  L  L  G  C  L  I  L  P  V  I  M  L  E  V  E  A  P  L
       L  N  Y  *  D  V  L  Y  S  R  S  S  C  W  K  *  K  L  L  W
        *  T  I  R  M  S  Y  T  P  G  H  H  A  G  S  R  S  S  S  G

28261 GAAATCGTTCAGGAATCCTCAAGAAAACTTCTTGGGTTGACCAATCTGAGCGAAGCCATC 28320
      E  I  V  Q  E  S  S  R  K  L  L  G  L  T  N  L  S  E  A  I
       K  S  F  R  N  P  Q  E  N  F  L  G  *  P  I  *  A  K  P  S
        N  R  S  G  I  L  K  K  T  S  W  V  D  Q  S  E  R  S  H  Q

28321 AAACCTATAATAGAGGCAGAAAACCCCAACCCAAATTCACTGTGTCTACTCAACCACAAG 28380
      K  P  I  I  E  A  E  N  P  N  P  N  S  L  C  L  L  N  H  K
       N  L  *  *  R  Q  K  T  P  T  Q  I  H  C  V  Y  S  T  T  R
        T  Y  N  R  G  R  K  P  Q  P  K  F  T  V  S  T  Q  P  Q  G

28381 GAAACCCTATCCCACATTATTCCTGGTTCTCTGGGATTACCCAATTTCAAAAAGGTAGAG 28440
      E  T  L  S  H  I  I  P  G  S  L  G  L  P  N  F  K  K  V  E
       K  P  Y  P  T  L  F  L  V  L  W  D  Y  P  I  S  K  R  *  R
        N  P  I  P  H  Y  S  W  F  S  G  I  T  Q  F  Q  K  G  R  D

28441 ACTTTAAATTTCCAGATGGTCAAGGAGTACCCATTGCTTACGGGATACCCCCTTCTGAAG 28500
      T  L  N  F  Q  M  V  K  E  Y  P  L  L  T  G  Y  P  L  L  K
       L  *  I  S  R  W  S  R  S  T  H  C  L  R  D  T  P  F  *  S
        F  K  F  P  D  G  Q  G  V  P  I  A  Y  G  I  P  P  S  E  A

28501 CAAAAGGATATTGGTATAAACACAACCGGCGTTCTTTTAAAACAGCTGATGGTCAACAAA 28560
      Q  K  D  I  G  I  N  T  T  G  V  L  L  K  Q  L  M  V  N  K
       K  R  I  L  V  *  T  Q  P  A  F  F  *  N  S  *  W  S  T  K
        K  G  Y  W  Y  K  H  N  R  R  S  F  K  T  A  D  G  Q  Q  K

28561 AGCAGTTGTTACCAAGATGGTATTTCTACTATCTCGGTACCGGTCCATATGCCAGTTCAT 28620
      S  S  C  Y  Q  D  G  I  S  T  I  S  V  P  V  H  M  P  V  H
       A  V  V  T  K  M  V  F  L  L  S  R  Y  R  S  I  C  Q  F  I
        Q  L  L  P  R  W  Y  F  Y  Y  L  G  T  G  P  Y  A  S  S  S
```

FIG. 9 CONT.

```
28621 CCTATGGTGATGCCCACGAAGGTATCTTCTGGGTCGCTAGTCACCAAGCTGACACTTCTA 28680
      P  M  V  M  P  T  K  V  S  S  G  S  L  V  T  K  L  T  L  L
       L  W  *  C  P  R  R  Y  L  L  G  R  *  S  P  S  *  H  F  Y
        Y  G  D  A  H  E  G  I  F  W  V  A  S  H  Q  A  D  T  S  I

28681 TTCCCTCCGATGTTTCGGCAAGGGATCCTACTATTCAAGAAGCTATCCCTACTAGGTTTT 28740
      F  P  P  M  F  R  Q  G  I  L  L  F  K  K  L  S  L  L  G  F
       S  L  R  C  F  G  K  G  S  Y  Y  S  R  S  Y  P  Y  *  V  F
        P  S  D  V  S  A  R  D  P  T  I  Q  E  A  I  P  T  R  F  S

28741 CGCCTGGTACGATTTTGCCTCAAGGCTATTATGTTGAAGGCTCAGGAAGGTCTGCTTCTA 28800
      R  L  V  R  F  C  L  K  A  I  M  L  K  A  Q  E  G  L  L  L
       A  W  Y  D  F  A  S  R  L  L  C  *  R  L  R  K  V  C  F  *
        P  G  T  I  L  P  Q  G  Y  Y  V  E  G  S  G  R  S  A  S  N

28801 ATAGCCGGCCAGGTTCACGTTCTCAATCACGTGGACCCAATAATCGTTCATTAAGTAGAA 28860
      I  A  G  Q  V  H  V  L  N  H  V  D  P  I  I  V  H  *  V  E
       *  P  A  R  F  T  F  S  I  T  W  T  Q  *  S  F  I  K  *  K
        S  R  P  G  S  R  S  Q  S  R  G  P  N  N  R  S  L  S  R  S

28861 GTAATTCTAATTTTAGACATTCTGATTCTATAGTGAAACCTGATATGGCTGATGAGATTG 28920
      V  I  L  I  L  D  I  L  I  L  *  *  N  L  I  W  L  M  R  L
       *  F  *  F  *  T  F  *  F  Y  S  E  T  *  Y  G  *  *  D  C
        N  S  N  F  R  H  S  D  S  I  V  K  P  D  M  A  D  E  I  A

28921 CTAGTCTTGTCTTGGCCAAGCTTGGTAAAGATTCTAAACCTCAGCAAGTTACCAAGCAAA 28980
      L  V  L  S  W  P  S  L  V  K  I  L  N  L  S  K  L  P  S  K
       *  S  C  L  G  Q  A  W  *  R  F  *  T  S  A  S  Y  Q  A  K
        S  L  V  L  A  K  L  G  K  D  S  K  P  Q  Q  V  T  K  Q  N

28981 ATGCTAAGGAAATTAGGCATAAAATTTTAATGAAACCTCGCCAAAAGCGAACTCCTAATA 29040
      M  L  R  K  L  G  I  K  F  *  *  N  L  A  K  S  E  L  L  I
       C  *  G  N  *  A  *  N  F  N  E  T  S  P  K  A  N  S  *  *
        A  K  E  I  R  H  K  I  L  M  K  P  R  Q  K  R  T  P  N  K

29041 AATTTTGTAATGTTCAACAGTGTTTTGGTAAAAGAGGACCGCTCCAAAACTTTGGTAATT 29100
      N  F  V  M  F  N  S  V  L  V  K  E  D  R  S  K  T  L  V  I
       I  L  *  C  S  T  V  F  W  *  K  R  T  A  P  K  L  W  *  F
        F  C  N  V  Q  Q  C  F  G  K  R  G  P  L  Q  N  F  G  N  S

29101 CTGAAATGTTAAAGCTTGGTACTAATGATCCTCAATTTCCTATTCTTGCTGAATTAGCCC 29160
      L  K  C  *  S  L  V  L  M  I  L  N  F  L  F  L  L  N  *  P
       *  N  V  K  A  W  Y  *  *  S  S  I  S  Y  S  C  *  I  S  P
        E  M  L  K  L  G  T  N  D  P  Q  F  P  I  L  A  E  L  A  P
```

FIG. 9 CONT.

```
29161 CTACACCAGGTGCTTTTTTCTTTGGCTCTAAATTAGAGTTGTTTAAAAGAGACTCTGATG 29220
      L  H  Q  V  L  F  S  L  A  L  N  *  S  C  L  K  E  T  L  M
       Y  T  R  C  F  F  L  W  L  *  I  R  V  V  *  K  R  L  *  C
        T  P  G  A  F  F  F  G  S  K  L  E  L  F  K  R  D  S  D  A

29221 CTGATTCACCTTCTAAAGACACTTTTGAACTTCGTTATTCTGGTTCTATTAGGTTTGATa 29280
      L  I  H  L  L  K  T  L  L  N  F  V  I  L  V  L  L  G  L  I
       *  F  T  F  *  R  H  F  *  T  S  L  F  W  F  Y  *  V  *  *
        D  S  P  S  K  D  T  F  E  L  R  Y  S  G  S  I  R  F  D  S

29281 GTACTTTACCTGGTTTTGAGACAATTATGAAAGTTCTTAAAGAGAATTTAGATGCTTATG 29340
      V  L  Y  L  V  L  R  Q  L  *  K  F  L  K  R  I  *  M  L  M
       Y  F  T  W  F  *  D  N  Y  E  S  S  *  R  E  F  R  C  L  C
        T  L  P  G  F  E  T  I  M  K  V  L  K  E  N  L  D  A  Y  V

29341 TTAATTCTAATCAGAACACTGTTTCTGGTTCGCTGAGTCCTAAACCTCAGCGTAAAAGAG 29400
      L  I  L  I  R  T  L  F  L  V  R  *  V  L  N  L  S  V  K  E
       *  F  *  S  E  H  C  F  W  F  A  E  S  *  T  S  A  *  K  R
        N  S  N  Q  N  T  V  S  G  S  L  S  P  K  P  Q  R  K  R  G

29401 GTGTTAAACAATCACCTGAATCGTTTGACTCTCTTAATTTAAGTGCTGATACTCAGCACA 29460
      V  L  N  N  H  L  N  R  L  T  L  L  I  *  V  L  I  L  S  T
       C  *  T  I  T  *  I  V  *  L  S  *  F  K  C  *  Y  S  A  H
        V  K  Q  S  P  E  S  F  D  S  L  N  L  S  A  D  T  Q  H  I

29461 TTTCAAATGATTTTACTCCTGAGGATCATAGTTTACTTGCTACTCTTGATGATCCTTATG 29520
      F  Q  M  I  L  L  L  R  I  I  V  Y  L  L  L  L  M  I  L  M
       F  K  *  F  Y  S  *  G  S  *  F  T  C  Y  S  *  *  S  L  C
        S  N  D  F  T  P  E  D  H  S  L  L  A  T  L  D  D  P  Y  V

29521 TAGAAGACTCTGTTGCTTAATGAGAATGAATCCTAATTCGACACTAGGTGGTAACCCCTC 29580
      *  K  T  L  L  L  N  E  N  E  S  *  F  D  T  R  W  *  P  L
       R  R  L  C  C  L  M  R  M  N  P  N  S  T  L  G  G  N  P  S
        E  D  S  V  A  *  *  E  *  I  L  I  R  H  *  V  V  T  P  R

29581 GCTATTAGTCGGAATAGGACACTCTCTATCAGAATGAATTCTTGCTGTTACAACAGATAG 29640
      A  I  S  R  N  R  T  L  S  I  R  M  N  S  C  C  Y  N  R  *
       L  L  V  G  I  G  H  S  L  S  E  *  I  L  A  V  T  T  D  R
        Y  *  S  E  *  D  T  L  Y  Q  N  E  F  L  L  L  Q  Q  I  E

29641 AGTAGGTTGTTGCAGACTATATATTAATTAGTAGAAACTTTATATTTAAATATTTGATTG 29700
      S  R  L  L  Q  T  I  Y  *  L  V  E  T  L  Y  L  N  I  *  L
       V  G  C  C  R  L  Y  I  N  *  *  K  L  Y  I  *  I  F  D  C
        *  V  V  A  D  Y  I  L  I  S  R  N  F  I  F  K  Y  L  I  V
```

FIG. 9 CONT.

```
29701 TTAGAGTAGTTATAAGGTTTAGCTGTAGTATAAACGCCTCCGGGAAGAGCTAGCAATTAT 29760
      L  E  *  L  *  G  L  A  V  V  *  T  P  P  G  R  A  S  N  Y
       *  S  S  Y  K  V  *  L  *  Y  K  R  L  R  E  E  L  A  I  I
        R  V  V  I  R  F  S  C  S  I  N  A  S  G  K  S  *  Q  L  *

29761 AGTATTTAATATATATATTAGTATATGATTGAAATTAATTATAGCCTTTTGGAGGAATTA 29820
      S  I  *  Y  I  Y  *  Y  M  I  E  I  N  Y  S  L  L  E  E  L
       V  F  N  I  Y  I  S  I  *  L  K  L  I  I  A  F  W  R  N  Y
        Y  L  I  Y  I  L  V  Y  D  *  N  *  L  *  P  F  G  G  I  T

29821 CAAAAAAAAAAAAAAA                                             29836
      Q  K  K  K  K  X
       K  K  K  K  K
        K  K  K  K
```

FIG. 9 CONT.

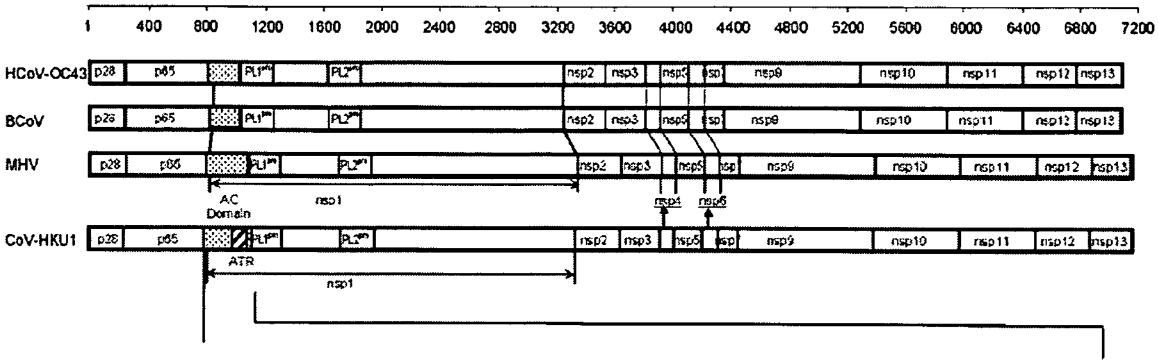

```
                                                             |<---- AC Domain
MHV                        VGEIEPAVFEDDVVDVVKAPLTYQGCCKPPTSFEKICIVDKLYMAKCGDQFYPVVVDNDT 819
BCoV                       KGSGSDFSLADSVVEVVTTSLTPCGYSEPPKVADKICIVDNVYMAKAGDKYYPVVVDG-H 838
HCoV-OC43                  KGSGSDFSLADSVVEVVTTSLTPCGYSEPPKVADKICIVDNVYMAKAGDKYYPVVVDD-H 838
CoV-HKU1(1st patient)      EGVAESVIVEDDVIENVKSSLSSYEYCQPPKSVEKICIIDNMYMGKCGDKFFPIVMNDKN 796
CoV-HKU1(2nd patient)      EGVAESVIVEDDVIENVKSSLSSYEYCQPPKSVEKICIIDNMYMGKCGDKFFPIVMNDKN 796
                           *  .    . *.*:: *.:.*:      .:**.   :****:*::**.*.**:::*:*::.

MHV                        VGVLDQCWRFPCAGKKVEFNDKPKVRKIPST-EKIKITFALDATFDSVLSKACSEFEVDK 878
BCoV                       VGLLDQAWRVPCAGRRVTFKEQPTVNEIASTPKTIKVFYELDKDFNTILNTACGVFEVDD 898
HCoV-OC43                  VGLLDQAWRVPCAGRRVTFKEQPTVKEIISMPKIIKVFYELDNDFNTILNTACGVFEVDD 898
CoV-HKU1(1st patient)      ICLLDQAWRFPCAGRKVNFNEKPVVMEIPSL-MTVKVMFDLDSTFDDILGKVCSEFEVEK 855
CoV-HKU1(2nd patient)      ICLLDQAWRFPCAGRKVNFNEKPVVMEIPSL-MTVKVMFDLDSTFDDILGKVCSEFEVEK 855
                           : :***.**.****::* *:::* * :* *     :*: : **  *: :*...*. ***:.

MHV                        DVTLDELLDVVLDAVESTLSPCKEHDVIGTKVCALLDRLAGDYVYLFDEGGDEVIAPRMY 938
BCoV                       TVDMEEFYAVVIDAIEEKLSPCKELEGVGAKVSAFLQKLEDNSLFLFDEAGEEVLASKLY 958
HCoV-OC43                  TVDMEEFYAVVIDAIEEKLSPCKELEGVGAKVSAFLQKLEDNPLFLFDEAGEEVLAPKLY 958
CoV-HKU1(1st patient)      GVTVDDFVAVVCDAIENALNSCKEHPVVGYQVRAFLNKLNENVVYLFDEAGDEAMASRMY 915
CoV-HKU1(2nd patient)      GVTVDDFVAVVCDAIENALNSCKDHPVVGYQVRAFLNKLNENVVYLFDEAGDEAMASRMY 915
                            * ::::  ** **:*. *..**:   :* :* *:*::*  : ::****.*:*.:*.::*

MHV                        CSFSAPDDEDCVAADVVDADEN-------QDD------DAEDSAVLVADTQEEDGVAKG- 984
BCoV                       CAFTAPEDDDFLEESGVE------------------------EDDVEGEETDLTVTSAG- 993
HCoV-OC43                  CAFTAPEDDDFLEESDVE------------------------EDDVEGEETDLTVTSAG- 993
CoV-HKU1(1st patient)      CTFAIEDVEDVISSEAVEDTIDGVVEDTINDDEDVVTGDNDDEDVVTGDNDDEDVVTGDN 975
CoV-HKU1(2nd patient)      CTFAIEDVEDVISSEAVEDTIDGVVEDTINDDEDVVTGDNDDEDVVTGDNDDEDVVTGDN 975
                           *:*:  : :* :  . *:                         .  : .:  :   .: .

MHV                        ------QVEADSEICVAHTGSQEELAEPDAVGSQTPIASAEETEVGEASDREGIAEAKAT 1038
BCoV                       ------------EPCVASEQEESSEILEDTLDDGPCVETSD-------SQVEEDVEMSDF 1034
HCoV-OC43                  ------------QPCVASEQEESSEVLEDTLDDGPSVETSD-------SQVEEDVEMSDF 1034
CoV-HKU1(1st patient)      DDEDVVTGDNDDEDVVTGDNDDEDVVTGDNDDEDVVTGDNDDEDVVTGDNDDEDVVTGDN 1035
CoV-HKU1(2nd patient)      DDEDVVTGDNDDEDVVTGDNDDEDVVTGDNDDEDVVTGDNDDEDVVTGDNDDEDVVTGDN 1035
                                  :  *:   .:..    *  ..       :        .: :  .

MHV                        VCADAVDACPDQVEAFSIEKVEDSILDELQTELNAPADK--------------------- 1077
BCoV                       ADLESVIQDYEN------------------------------------------------ 1046
HCoV-OC43                  VDLESVIQDYEN------------------------------------------------ 1046
CoV-HKU1(1st patient)      DDEDVVTGDNDDEDVVTGDNDDEDVVTGDNDDEDVVTGDNDDEDVVTGDNNDEEIVTGDN 1095
CoV-HKU1(2nd patient)      DDEDVVTGDNDDEDVVTGDNDDE------------------------------EIVTGDN 1065
                              :  *     ::

                                                 AC Domain  ---->|<---- PL1pro
MHV                        ---------------------TYEDVLAFDAVCSEALSAFYAVPSDETHF-KVCGFYSPA 1115
BCoV                       --------------------------------------VCFEFYTTEPEFVKVLDLYVPK 1068
HCoV-OC43                  --------------------------------------VCFEFYTTEPEFVKVLGLYVPK 1068
CoV-HKU1(1st patient)      DDQIVVTGDDVDDIESIYDFDTYKALLVFNDVYNDALFVSYGSSVETETYFKVNGLWSPT 1155
CoV-HKU1(2nd patient)      DDQIVVTGDDVDDIESIYDFDTYKALLVFNDVYNDALFVSYGSSVETETYFKVNGLWSPT 1125
                                                                  . :     .   ..**  .::  *
```

FIG. 10

Fig. 11. Multiple alignment of the replicase genes of CoV-HKU1 from patients 1, 2, 4, 5, 6, 7, 8, 9 and 10.

```
Patient 7     TCTAAAGATTTAAATTTTTTAAACCGGGTTCGGGGTACTAGTGTGAATGCCCGGCTAGTA 60
Patient 9     TCTAAAGATTTAAATTTTTTAAACCGGGTTCGGGGTACTAGTGTGAATGCCCGGCTAGTA 60
Patient 10    TCTAAAGATTTAAATTTTTTAAACCGGGTTCGGGGTACTAGTGTGAATGCCCGGCTAGTA 60
Patient 6     TCTAAAGATTTAAATTTTTTAAACCGGGTTCGGGGTACTAGTGTGAATGCCCGGCTAGTA 60
Patient 4     TCTAAAGATTTAAATTTTTTAAACCGGGTTCGGGGTACTAGTGTGAATGCCCGGCTAGTA 60
Patient 8     TCTAAAGATTTAAATTTTTTAAACCGGGTTAGGGGTACTAGTGTGAATGCCCGGCTAGTA 60
Patient 2     TCTAAAGATTTAAATTTTTTAAACCGGGTTCGGGGTACTAGTGTGAATGCCCGGCTAGTA 60
Patient 5     TCTAAAGATTTAAATTTTTTAAACCGGGTTCGGGGTACTAGTGTGAATGCCCGGCTAGTA 60
Patient 1     TCTAAAGATTTAAATTTTTTAAACCGGGTTCGGGGTACTAGTGTGAATGCCCGTCTAGTA 60
              ****************************** ********************** ******

Patient 7     CCCTGTGCTAGTGGTTTATCTACTGATGTTCAATTAAGGGCATTTGACATTTGTAATACC 120
Patient 9     CCCTGTGCTAGTGGTTTATCTACTGATGTTCAATTAAGGGCATTTGACATTTGTAATACC 120
Patient 10    CCCTGTGCTAGTGGTTTATCTACTGATGTTCAATTAAGGGCATTTGACATTTGTAATACC 120
Patient 6     CCCTGTGCTAGTGGTTTATCTACTGATGTTCAATTAAGGGCATTTGACATTTGTAATACC 120
Patient 4     CCCTGTGCTAGTGGTTTATCTACTGATGTTCAATTAAGGGCATTTGACATTTGTAATACC 120
Patient 8     CCCTGTGCTAGTGGTTTATCTACTGATGTTCAATTAAGGGCATTTGACATTTGTAATACC 120
Patient 2     CCCTGTGCTAGTGGTTTATCTACTGATGTTCAATTAAGGGCATTTGACATTTGTAATACC 120
Patient 5     CCCTGTGCTAGTGGTTTATCTACTGATGTTCAATTAAGGGCATTTGACATTTGTAATACC 120
Patient 1     CCCTGTGCTAGTGGTTTATCTACTGATGTTCAATTAAGGGCATTTGATATTTGTAATACT 120
              *********************************************** ***********

Patient 7     AATAGAGCTGGTATAGGTTTATATTATAAAGTGAATTGTTGCCGTTTTCAGCGTATAGAT 180
Patient 9     AATAGAGCTGGTATAGGTTTATATTATAAAGTGAATTGTTGCCGTTTTCAGCGTATAGAT 180
Patient 10    AATAGAGCTGGTATAGGTTTATATTATAAAGTGAATTGTTGCCGTTTTCAGCGTATAGAT 180
Patient 6     AATAGAGCTGGTATAGGTTTATATTATAAAGTGAATTGTTGCCGTTTTCAGCGTATAGAT 180
Patient 4     AATAGAGCTGGTATAGGTTTATATTATAAAGTGAATTGTTGCCGTTTTCAGCGTATAGAT 180
Patient 8     AATAGAGCTGGTATAGGTTTATATTATAAAGTGAATTGTTGCCGTTTTCAGCGTATAGAT 180
Patient 2     AATAGAGCTGGTATAGGTTTATATTATAAAGTGAATTGTTGCCGTTTTCAGCGTATAGAT 180
Patient 5     AATAGAGCTGGTATAGGTTTATATTATAAAGTGAATTGTTGCCGTTTTCAGCGTATAGAT 180
Patient 1     AATAGAGCTGGTATAGGTTTATATTATAAAGTGAATTGTTGCCGTTTTCAGCGTATAGAT 180
              ************************************************************

Patient 7     GACGACGGTAATAAATTGGATAAGTTCTTTGTTGTCAAAAGAACTAATTTAGAAGTTTAT 240
Patient 9     GACGACGGTAATAAATTGGATAAGTTCTTTGTTGTCAAAAGAACTAATTTAGAAGTTTAT 240
Patient 10    GACGACGGTAATAAATTGGATAAGTTCTTTGTTGTCAAAAGAACTAATTTAGAAGTTTAT 240
Patient 6     GACGACGGTAATAAATTGGATAAGTTCTTTGTTGTCAAAAGAACTAATTTAGAAGTTTAT 240
Patient 4     GACGACGGTAATAAATTGGATAAGTTCTTTGTTGTCAAAAGAACTAATTTAGAAGTTTAT 240
Patient 8     GACGACGGTAATAAATTGGATAAGTTCTTTGTTGTCAAAAGAACTAATTTAGAAGTTTAT 240
Patient 2     GACGACGGTAATAAATTGGATAAGTTCTTTGTTGTCAAAAGAACTAATTTAGAAGTTTAT 240
Patient 5     GACGACGGTAATAAATTGGATAAGTTCTTTGTTGTCAAAAGAACTAATTTAGAAGTTTAT 240
Patient 1     GACGACGGTAATAAATTGGATAAGTTCTTTGTTGTTAAAAGAACTAATCTAGAAGTTTAT 240
              *********************************** ************ ***********

Patient 7     AATAAAGAGAAAACTTATTATGAGTTGACTAAAAGTTGTGGTGTTGTGGCTGAACATGAT 300
Patient 9     AATAAAGAGAAAACTTATTATGAGTTGACTAAAAGTTGTGGTGTTGTGGCTGAACATGAT 300
Patient 10    AATAAAGAGAAAACTTATTATGAGTTGACTAAAAGTTGTGGTGTTGTGGCTGAACATGAT 300
Patient 6     AATAAAGAGAAAACTTATTATGAGTTGACTAAAAGTTGTGGTGTTGTGGCTGAACATGAT 300
Patient 4     AATAAAGAGAAAACTTATTATGAGTTGACTAAAAGTTGTGGTGTTGTGGCTGAACATGAT 300
Patient 8     AATAAAGAGAAAACTTATTATGAGTTGACTAAAAGTTGTGGTGTTGTGGCTGAACATGAT 300
Patient 2     AATAAAGAGAAAACTTATTATGAGTTGACTAAAAGTTGTGGTGTTGTGGCTGAACATGAT 300
Patient 5     AATAAAGAGAAAACTTATTATGAGTTGACTAAAAGTTGTGGTGTTGTGGCTGAACATGAT 300
Patient 1     AATAAAGAGAAAACTTATTATGAGTTGACTAAAAGTTGTGGTGTTGTGGCTGAACATGAT 300
              ************************************************************

Patient 7     TTCTTTATATTTGATATTGATGGTAGTCGCGTGCCACATATAGTTCGTAGGAATCTTTCA 360
Patient 9     TTCTTTACATTTGATATTGATGGTAGTCGCGTGCCACATATAGTTCGTAGGAATCTTTCA 360
Patient 10    TTCTTTACATTTGATATTGATGGTAGTCGCGTGCCACATATAGTTCGTAGGAATCTTTCA 360
Patient 6     TTCTTTACATTTGATATTGATGGTAGTCGCGTGCCACATATAGTTCGTAGGAATCTTTCA 360
Patient 4     TTCTTTACATTTGATATTGATGGTAGTCGCGTGCCACATATAGTTCGTAGGAATCTTTCA 360
Patient 8     TTCTTTACATTTGATATTGATGGTAGTCGCGTGCCACATATAGTTCGTAGGAATCTTTCA 360
Patient 2     TTCTTTACATTTGATATTGATGGTAGTCGCGTGCCACATATAGTTCGTAGGAATCTTTCA 360
Patient 5     TTCTTTACATTTGATATTGATGGTAGTCGCGTGCCACATATAGTTCGTAGGAATCTTTCA 360
Patient 1     TTCTTTACATTTGATATTGATGGTAGTCGTGTGCCACATATAGTTCGTAAGAACCTCTCA 360
              ******* ********************* ******************* *** ** ***

Patient 7     AAGTATACTATGTTAGATCTTTGCTATGCATTGCGTCATTTTGATCGTAATGATTGTTCA 420
Patient 9     AAGTATACTATGTTAGATCTTTGCTATGCATTGCGTCATTTTGATCGTAATGATTGTTCA 420
Patient 10    AAGTATACTATGTTAGATCTTTGCTATGCATTGCGTCATTTTGATCGTAATGATTGTTCA 420
Patient 6     AAGTATACTATGTTAGATCTTTGCTATGCATTGCGTCATTTTGATCGTAATGATTGTTCA 420
Patient 4     AAGTATACTATGTTAGATCTTTGCTATGCATTGCGTCATTTTGATCGTAATGATTGTTCA 420
Patient 8     AAGTATACTATGTTAGATCTTTGCTATGCATTGCGTCATTTTGATCGTAATGATTGTTCA 420
Patient 2     AAGTATACTATGTTAGATCTTTGCTATGCATTGCGTCATTTTGATCGTAATGATTGTTCA 420
Patient 5     AAGTATACTATGTTAGATCTTTGCTATGCATTGCGTCATTTTGATCGTAATGATTGTTCA 420
```

FIG. 11

```
Patient 1       AAGTATACTATGTTAGATCTTTGCTATGCATTGCGCCATTTTGATTGTAATGATTGTTCA 420
                *********************************** ********* **************

Patient 7       ATATTGTGTGAAATTCTTTGTGAGTATGCTGATTGTAAAGAATCCTACTTTTCTAAGAAA 480
Patient 9       ATATTGTGTGAAATTCTTTGTGAGTATGCTGATTGTAAAGAATCCTACTTTTCTAAGAAA 480
Patient 10      ATATTGTGTGAAATTCTTTGTGAGTATGCTGATTGTAAAGAATCCTACTTTTCTAAGAAA 480
Patient 6       ATATTGTGTGAAATTCTTTGTGAGTATGCTGATTGTAAAGAATCCTACTTTTCTAAGAAA 480
Patient 4       ATATTGTGTGAAATTCTTTGTGAGTATGCTGATTGTAAAGAATCCTACTTTTCTAAGAAA 480
Patient 8       ATATTGTGTGAAATTCTTTGTGAGTATGCTGATTGTAAAGAATCCTACTTTTCTAAGAAA 480
Patient 2       ATATTGTGTGAAATTCTTTGTGAGTATGCTGATTGTAAAGAATCCTACTTTTCTAAGAAA 480
Patient 5       ATATTGTGTGAAATTCTTTGTGAGTATGCTGATTGTAAAGAATCCTACTTTTCTAAGAAA 480
Patient 1       GTATTGTGTGAAATTCTTTGTGAGTATGCTGATTGTAAAGAATCCTACTTTTCTAAGAAA 480
                 ***********************************************************

Patient 7       GATTGGTATGATTTTGTTGAAAATCCTGATATTATTAATATATATAAAAAATTAGGCCCT 540
Patient 9       GATTGGTATGATTTTGTTGAAAATCCTGATATTATTAATATATATAAAAAATTAGGCCCT 540
Patient 10      GATTGGTATGATTTTGTTGAAAATCCTGATATTATTAATATATATAAAAAATTAGGCCCT 540
Patient 6       GATTGGTATGATTTTGTTGAAAATCCTGATATTATTAATATATATAAAAAATTAGGCCCT 540
Patient 4       GATTGGTATGATTTTGTTGAAAATCCTGATATTATTAATATATATAAAAAATTAGGCCCT 540
Patient 8       GATTGGTATGATTTTGTTGAAAATCCTGATATTATTAATATATATAAAAAATTAGGTCCT 540
Patient 2       GATTGGTATGATTTTGTTGAAAATCCTGATATTATTAATATATATAAAAAATTAGGCCCT 540
Patient 5       GATTGGTATGATTTTGTTGAAAATCCTGATATTATTAATATATATAAAAAATTAGGCCCT 540
Patient 1       GATTGGTATGATTTTGTTGAAAATCCTGATATTATTAATATTTATAAAAAATTAGGCCCT 540
                ***************************************** ************** ***

Patient 7       ATTTTTAATAGAGCTTTACTTAATACTGTCATTTTTGCAGACACCTTAGTTGAAGTAGGT 600
Patient 9       ATTTTTAATAGAGCTTTACTTAATACTGTCATTTTTGCAGACACCTTAGTTGAAGTAGGT 600
Patient 10      ATTTTTAATAGAGCTTTACTTAATACTGTCATTTTTGCAGACACCTTAGTTGAAGTAGGT 600
Patient 6       ATTTTTAATAGAGCTTTACTTAATACTGTCATTTTTGCAGACACCTTAGTTGAAGTAGGT 600
Patient 4       ATTTTTAATAGAGCTTTACTTAATACTGTCATTTTTGCAGACACCTTAGTTGAAGTAGGT 600
Patient 8       ATTTTTAATAGAGCTTTACTTAATACTGTCATTTTTGCAGACACCTTAGTTGAAGTAGGT 600
Patient 2       ATTTTTAATAGAGCTTTACTTAATACTGTCATTTTTGCAGACACCTTAGTTGAAGTAGGT 600
Patient 5       ATTTTTAATAGAGCTTTACTTAATACTGTCATTTTTGCAGACACCTTAGTTGAAGTAGGT 600
Patient 1       ATTTTTAATAGAGCTTTACTTAATACTGTCAGTTTTGCAGATACTTTAGTAAAAGTAGGT 600
                ******************************* ********* ** *****  ********

Patient 7       TTAGTTGGTGTTTTAACTTTAGATAACCAAGATTTGTATGGTCAATGGTATGATTTTGGT 660
Patient 9       TTAGTTGGTGTTTTAACTTTAGATAACCAAGATTTGTATGGTCAATGGTATGATTTTGGT 660
Patient 10      TTAGTTGGTGTTTTAACTTTAGATAACCAAGATTTGTATGGTCAATGGTATGATTTTGGT 660
Patient 6       TTAGTTGGTGTTTTAACTTTAGATAACCAAGATTTGTATGGTCAATGGTATGATTTTGGT 660
Patient 4       TTAGTTGGTGTTTTAACTTTAGATAACCAAGATTTGTATGGTCAATGGTATGATTTTGGT 660
Patient 8       TTAGTTGGTGTTTTAACTTTAGATAACCAAGATTTGTATGGTCAATGGTATGATTTTGGT 660
Patient 2       TTAGTTGGTGTTTTAACTTTAGATAACCAAGATTTGTATGGTCAATGGTATGATTTTGGT 660
Patient 5       TTAGTTGGTGTTTTAACTTTAGATAACCAAGATTTGTATGGTCAATGGTATGATTTTGGT 660
Patient 1       TTAGTTGGTGTTTTAACTTTAGATAATCAAGACTTGTATGGTCAATGGTATGATTTTGGT 660
                ************************** ***** ***************************

Patient 7       GATTTTATACAAACAGCCCCAGGATTTGGTGTGGCAGTCGCAGATTCTTACTATTCTTAT 720
Patient 9       GATTTTATACAAACAGCCCCAGGATTTGGTGTGGCAGTCGCAGATTCTTACTATTCTTAT 720
Patient 10      GATTTTATACAAACAGCCCCAGGATTTGGTGTGGCAGTCGCAGATTCTTACTATTCTTAT 720
Patient 6       GATTTTATACAAACAGCCCCAGGATTTGGTGTGGCAGTCGCAGATTCTTACTATTCTTAT 720
Patient 4       GATTTTATACAAACAGCCCCAGGATTTGGTGTGGCAGTCGCAGATTCTTACTATTCTTAT 720
Patient 8       GATTTTATACAAACAGCCCCAGGATTTGGTGTGGCAGTCGCAGATTCTTACTATTCTTAT 720
Patient 2       GATTTTATACAAACAGCCCCAGGGTTTGGTGTGGCAGTTGCAGATTCTTACTTTTCTTAT 720
Patient 5       GATTTTATACAAACAGCCCCAGGGTTTGGTGTGGCAGTTGCAGATTCTTACTATTCTTAT 720
Patient 1       GATTTTATACAAACAGCTCCAGGTTTTGGTGTGGCAGTTGCAGATTCTTACTATTCTTAT 720
                ***************** ***** ************** ************ ********

Patient 7       ATGATGCCTATGTTGACTATGTGTCATGTATTAGATTGTGAATTATTTGTTAATGATAGT 780
Patient 9       ATGATGCCTATGTTGACTATGTGTCATGTATTAGATTGTGAATTATTTGTTAATGATAGT 780
Patient 10      ATGATGCCTATGTTGACTATGTGTCATGTATTAGATTGTGAATTATTTGTTAATGATAGT 780
Patient 6       ATGATGCCTATGTTGACTATGTGTCATGTATTAGATTGTGAATTATTTGTTAATGATAGT 780
Patient 4       ATGATGCCTATGTTGACTATGTGTCATGTATTAGATTGTGAATTATTTGTTAATGATAGT 780
Patient 8       ATGATGCCTATGTTAACTATGTGTCATGTATTAGATTGTGAATTATTTGTTAATGATAGT 780
Patient 2       ATGATGCCTATGTTGACTATGTGTCATGTATTAGATTGTGAATTATTTGTTAATGATAGT 780
Patient 5       ATGATGCCTATGTTGACTATGTGTCATGTATTAGATTGTGAATTATTTGTTAATGATAGT 780
Patient 1       ATGATGCCTATGTTGACTATGTGTCATGTATTAGATTGTGAATTATTTGTTAATGATAGT 780
                ************** *********************************************

Patient 7       TATAGACAATTCGATCTTGTGCAGTATGATTTTACTGATTACAAGTTAGAGTTGTTTAAT 840
Patient 9       TATAGACAATTCGATCTTGTGCAGTATGATTTTACTGATTACAAGTTAGAGTTGTTTAAT 840
Patient 10      TATAGACAATTCGATCTTGTGCAGTATGATTTTACTGATTACAAGTTAGAGTTGTTTAAT 840
Patient 6       TATAGACAATTCGATCTTGTGCAGTATGATTTTACTGATTACAAGTTAGAGTTGTTTAAT 840
Patient 4       TATAGACAATTCGATCTTGTGCAGTATGATTTTACTGATTACAAGTTAGAGTTGTTTAAT 840
Patient 8       TATAGACAATTCGATCTTGTACAGTATGATTTTACTGATTACAAGTTAGAGTTGTTTAAT 840
Patient 2       TATAGACAATTCGATCTTGTACAGTATGATTTTACTGATTACAAGTTAGAGTTGTTTAAT 840
```

FIG. 11 CONT.

```
Patient 5     TATAGACAATTCGATCTTGTACAGTATGATTTTACTGATTACAAGTTAGAGTTGTTTAAT 840
Patient 1     TATAGACAATTCGATCTTGTACAGTATGATTTTACTGATTATAAGTTAGAATTGTTTAAT 840
              ******************** ******************** ******** *********

Patient 7     AAGTATTTTAAGTATTGGGGTATGAAGTATCATCCTAATACTGTGGATTGTGATAATGAT 900
Patient 9     AAGTATTTTAAGTATTGGGGTATGAAGTATCATCCTAATACTGTGGATTGTGATAATGAT 900
Patient 10    AAGTATTTTAAGTATTGGGGTATGAAGTATCATCCTAATACTGTGGATTGTGATAATGAT 900
Patient 6     AAGTATTTTAAGTATTGGGGTATGAAGTATCATCCTAATACTGTGGATTGTGATAATGAT 900
Patient 4     AAGTATTTTAAGTATTGGGGTATGAAGTATCATCCTAATACTGTGGATTGTGATAATGAT 900
Patient 8     AAGTATTTTAAGTATTGGGGTATGAAGTATCATCCTAATACTGTGGATTGTGATAATGAT 900
Patient 2     AAGTATTTTAAGTATTGGGGTATGAAGTATCATCCTAATACTGTGGATTGTGATAATGAT 900
Patient 5     AAGTATTTTAAGTATTGGGGTATGAAGTATCATCCTAATACTGTGGATTGTGATAATGAT 900
Patient 1     AAGTATTTTAAGTATTGGGGTATGAAGTATCATCCTAATACTGTGGATTGTGATAATGAT 900
              ************************************************************

Patient 7     AGGTGTATTATTCATTGTGCTAATTTTAATATACTATTTAGTATGGTTTTACCTAATACT 960
Patient 9     AGGTGTATTATTCATTGTGCTAATTTTAATATACTATTTAGTATGGTTTTACCTAATACT 960
Patient 10    AGGTGTATTATTCATTGTGCTAATTTTAATATACTATTTAGTATGGTTTTACCTAATACT 960
Patient 6     AGGTGTATTATTCATTGTGCTAATTTTAATATACTATTTAGTATGGTTTTACCTAATACT 960
Patient 4     AGGTGTATTATTCATTGTGCTAATTTTAATATACTATTTAGTATGGTTTTACCTAATACT 960
Patient 8     AGGTGTATTATTCATTGTGCTAATTTTAATATACTATTTAGTATGGTTTTACCTAATACT 960
Patient 2     AGGTGTATTATTCATTGTGCTAATTTTAATATACTATTTAGTATGGTTTTACCTAATACT 960
Patient 5     AGGTGTATTATTCATTGTGCTAATTTTAATATACTATTTAGTATGGTTTTACCTAATACT 960
Patient 1     AGGTGTATTATTCATTGTGCTAATTTTAATATATTATTTAGTATGGTCTTACCTAATACT 960
              ********************************* ************* ************

Patient 7     TGTTTTGGTCCCCTTGTTAGACAAATTTTTGTAGATGGTGTACCGTTTGTTGTTTCTATT 1020
Patient 9     TGTTTTGGTCCCCTTGTTAGACAAATTTTTGTAGATGGTGTACCGTTTGTTGTTTCTATT 1020
Patient 10    TGTTTTGGTCCCCTTGTTAGACAAATTTTTGTAGATGGTGTACCGTTTGTTGTTTCTATT 1020
Patient 6     TGTTTTGGTCCCCTTGTTAGACAAATTTTTGTAGATGGTGTACCGTTTGTTGTTTCTATT 1020
Patient 4     TGTTTTGGTCCCCTTGTTAGACAAATTTTTGTAGATGGTGTACCGTTTGTTGTTTCTATT 1020
Patient 8     TGTTTTGGTCCCCTTGTTAGACAAATTTTTGTAGATGGTGTACCGTTTGTTGTTTCTATT 1020
Patient 2     TGTTTTGGTCCCCTTGTTAGACAAATTTTTGTAGATGGTGTACCGTTTGTTGTTTCTATT 1020
Patient 5     TGTTTTGGTCCCCTTGTTAGACAAATTTTTGTAGATGGTGTACCGTTTGTTGTTTCTATT 1020
Patient 1     TGTTTTGGTCCTCTTGTTAGACAAATTTTTGTAGATGGTGTTCCGTTTGTTGTTTCAATT 1020
              *********** ***************************** ************** ***

Patient 7     GGTTACCATTACAAAGAGTTAGGTGTAGTTATGAACTTAGATGTTGACACACACCGTTAT 1080
Patient 9     GGTTACCATTACAAAGAGTTAGGTGTAGTTATGAACTTAGATGTTGACACACACCGTTAT 1080
Patient 10    GGTTACCATTACAAAGAGTTAGGTGTAGTTATGAACTTAGATGTTGACACACACCGTTAT 1080
Patient 6     GGTTACCATTACAAAGAGTTAGGTGTAGTTATGAACTTAGATGTTGACACACACCGTTAT 1080
Patient 4     GGTTACCATTACAAAGAGTTAGGTGTAGTTATGAACTTAGATGTTGACACACACCGTTAT 1080
Patient 8     GGTTACCATTACAAAGAGTTAGGTGTAGTTATGAACTTAGATGTTGACACACACCGTTAT 1080
Patient 2     GGTTACCATTACAAAGAGTTAGGTGTAGTTATGAACTTAGATGTTGACACACACCGTTAT 1080
Patient 5     GGTTACCATTACAAAGAGTTAGGTGTAGTTATGAACTTAGATGTTGACACACACCGTTAT 1080
Patient 1     GGTTACCATTATAAAGAGTTAGGTGTAGTTATGAACTTGGATGTTGATACACACCGCTAT 1080
              *********** ************************** ******** ******** ***

Patient 7     CGTTTGTCTCTTAAAGATTTACTTCTTTATGCAGCAGATCCTGCTATGCATGTTGCATCT 1140
Patient 9     CGTTTGTCTCTTAAAGATTTACTTCTTTATGCAGCAGATCCTGCTATGCATGTTGCATCT 1140
Patient 10    CGTTTGTCTCTTAAAGATTTACTTCTTTATGCAGCAGATCCTGCTATGCATGTTGCATCT 1140
Patient 6     CGTTTGTCTCTTAAAGATTTACTTCTTTATGCAGCAGATCCTGCTATGCATGTTGCATCT 1140
Patient 4     CGTTTGTCTCTTAAAGATTTACTTCTTTATGCAGCAGATCCTGCTATGCATGTTGCATCT 1140
Patient 8     CGCTTGTCTCTTAAAGATTTACTTCTTTATGCAGCAGATCCTGCTATGCATGTTGCATCT 1140
Patient 2     CGTTTGTCTCTTAAAGATTTACTTCTTTATGCAGCAGATCCTGCTATGCACGTTGCATCT 1140
Patient 5     CGTTTGTCTCTTAAAGATTTACTTCTTTATGCAGCAGATCCTGCTATGCACGTTGCATCT 1140
Patient 1     CGTTTGTCTCTTAAAGACTTACTTCTTTATGCAGCAGATCCTGCTATGCATGTTGCATCT 1140
              ** ************** ******************************** *********

Patient 7     GCTAGTGCTCTGCTTGATTTACGAACTTGTTGTTTTAGTGTAGCTGCCATTACAAGTGGT 1200
Patient 9     GCTAGTGCTCTGCTTGATTTACGAACTTGTTGTTTTAGTGTAGCTGCCATTACAAGTGGT 1200
Patient 10    GCTAGTGCTCTGCTTGATTTACGAACTTGTTGTTTTAGTGTAGCTGCCATTACAAGTGGT 1200
Patient 6     GCTAGTGCTCTGCTTGATTTACGAACTTGTTGTTTTAGTGTAGCTGCCATTACAAGTGGT 1200
Patient 4     GCTAGTGCTCTGCTTGATTTACGAACTTGTTGTTTTAGTGTAGCTGCCATTACAAGTGGT 1200
Patient 8     GCTAGTGCTCTGCTTGATTTACGAACTTGTTGTTTTAGTGTAGCTGCCATTACAAGTGGT 1200
Patient 2     GCTAGTGCTCTGCTTGATTTACGAACTTGTTGTTTTAGTGTAGCTGCCATTACAAGTGGT 1200
Patient 5     GCTAGTGCTCTGCTTGATTTACGAACTTGTTGTTTTAGTGTAGCTGCCATTACAAGTGGT 1200
Patient 1     GCTAGTGCTCTGCTTGATTTACGAACTTGTTGTTTTAGTGTAGCTGCCATTACAAGTGGT 1200
              ************************************************************

Patient 7     ATAAAATTTCAAACTGTAAAACCAGGTAACTTTAACCAAGACTTTTACGAGTTTGTTAAA 1260
Patient 9     ATAAAATTTCAAACTGTAAAACCAGGTAACTTTAACCAAGACTTTTACGAGTTTGTTAAA 1260
Patient 10    ATAAAATTTCAAACTGTAAAACCAGGTAACTTTAACCAAGACTTTTACGAGTTTGTTAAA 1260
Patient 6     ATAAAATTTCAAACTGTAAAACCAGGTAACTTTAACCAAGACTTTTACGAGTTTGTTAAA 1260
Patient 4     ATAAAATTTCAAACTGTAAAACCAGGTAACTTTAACCAAGACTTTTACGAGTTTGTTAAA 1260
Patient 8     ATAAAATTTCAAACTGTTAAACCAGGTAACTTTAACCAAGACTTTTACGAGTTTGTTAAA 1260
```

FIG. 11 CONT.

```
Patient 2     ATAAAATTTCAAACTGTAAAACCAGGTAACTTTAACCAAGACTTTTACGAGTTTGTTAAA 1260
Patient 5     ATAAAATTTCAAACTGTAAAACCAGGTAACTTTAACCAAGACTTTTACGAGTTTGTTAAA 1260
Patient 1     ATAAAGTTTCAAACTGTTAAACCAGGTAATTTTAACCAAGATTTTTATGAGTTTGTCAAA 1260
              ***** *********** *********** *********** ***** ******** ***

Patient 7     AGTAAAGGCTTGTTTAAAGAGGGTAGTACAGTTGATTTGAAACATTTTTTCTTTACTCAA 1320
Patient 9     AGTAAAGGCTTGTTTAAAGAGGGTAGTACAGTTGATTTGAAACATTTTTTCTTTACTCAA 1320
Patient 10    AGTAAAGGCTTGTTTAAAGAGGGTAGTACAGTTGATTTGAAACATTTTTTCTTTACTCAA 1320
Patient 6     AGTAAAGGCTTGTTTAAAGAGGGTAGTACAGTTGATTTGAAACATTTTTTCTTTACTCAA 1320
Patient 4     AGTAAAGGCTTGTTTAAAGAGGGTAGTACAGTTGATTTGAAACATTTTTTCTTTACTCAA 1320
Patient 8     AGTAAAGGCTTGTTTAAAGAGGGTAGTACAGTTGATTTGAAACATTTTTTCTTTACTCAA 1320
Patient 2     AGTAAAGGCTTGTTTAAAGAGGGTAGTACAGTTGATTTGAAACATTTTTTCTTTACTCAA 1320
Patient 5     AGTAAAGGCTTGTTTAAAGAGGGTAGTACAGTTGATTTGAAACATTTTTTCTTTACTCAA 1320
Patient 1     AGTAAAGGCTTGTTTAAAGAGGGTAGTACAGTTGATTTGAAACACTTTTTCTTTACTCAA 1320
              ******************************************** ***************

Patient 7     GATGGTAATGCTGCAATTACTGATTATAATTATTATAAGTATAATTTACCTACTATGGTT 1380
Patient 9     GATGGTAATGCTGCAATTACTGATTATAATTATTATAAGTATAATTTACCTACTATGGTT 1380
Patient 10    GATGGTAATGCTGCAATTACTGATTATAATTATTATAAGTATAATTTACCTACTATGGTT 1380
Patient 6     GATGGTAATGCTGCAATTACTGATTATAATTATTATAAGTATAATTTACCTACTATGGTT 1380
Patient 4     GATGGTAATGCTGCAATTACTGATTATAATTATTATAAGTATAATTTACCTACTATGGTT 1380
Patient 8     GATGGTAATGCTGCAATTACTGATTATAATTATTATAAGTATAATTTACCTACTATGGTT 1380
Patient 2     GATGGTAATGCTGCAATTACTGATTATAATTATTATAAGTATAATTTACCTACTATGGTT 1380
Patient 5     GATGGTAATGCTGCAATTACTGATTATAATTATTATAAGTATAATTTACCTACTATGGTT 1380
Patient 1     GATGGTAATGCTGCAATTACTGATTATAATTATTATAAGTATAATTTACCTACTATGGTT 1380
              ************************************************************

Patient 7     GATATTAAGCAGTTATTGTTTGTATTAGAAGTTGTTTATAAATATTTTGAAATTTATGAT 1440
Patient 9     GATATTAAGCAGTTATTGTTTGTATTAGAAGTTGTTTATAAATATTTTGAAATTTATGAT 1440
Patient 10    GATATTAAGCAGTTATTGTTTGTATTAGAAGTTGTTTATAAATATTTTGAAATTTATGAT 1440
Patient 6     GATATTAAGCAGTTATTGTTTGTATTAGAAGTTGTTTATAAATATTTTGAAATTTATGAT 1440
Patient 4     GATATTAAGCAGTTATTGTTTGTATTAGAAGTTGTTTATAAATATTTTGAAATTTATGAT 1440
Patient 8     GATATTAAGCAGTTATTGTTTGTATTAGAAGTTGTTTATAAATATTTTGAAATTTATGAT 1440
Patient 2     GATATTAAGCAGTTATTGTTTGTATTAGAAGTTGTTTATAAATATTTTGAAATTTATGAT 1440
Patient 5     GATATTAAGCAGTTATTGTTTGTATTAGAAGTTGTTTATAAATATTTTGAAATTTATGAT 1440
Patient 1     GATATTAAGCAGTTATTGTTTGTATTAGAAGTTGTTTATAAGTATTTTGAAATTTATGAT 1440
              ****************************************** *****************

Patient 7     GGTGGTTGTATACCAGCATCACAAGTTATTGTTAATAATTATGATAAAAGTGCTGGTTAT 1500
Patient 9     GGTGGTTGTATACCAGCATCACAAGTCATTGTTAATAATTATGATAAAAGTGCTGGTTAT 1500
Patient 10    GGTGGTTGTATACCAGCATCACAAGTTATTGTTAATAATTATGATAAAAGTGCTGGTTAT 1500
Patient 6     GGTGGTTGTATACCAGCATCACAAGTTATTGTTAATAATTATGATAAAAGTGCTGGTTAT 1500
Patient 4     GGTGGTTGTATACCAGCATCACAAGTTATTGTTAATAATTATGATAAAAGTGCTGGTTAT 1500
Patient 8     GGTGGTTGTATACCAGCATCACAAGTTATTGTTAATAATTATGATAAAAGTGCTGGTTAT 1500
Patient 2     GGTGGTTGTATACCAGCATCACAAGTTATTGTTAATAATTATGATAAAAGTGCTGGTTAT 1500
Patient 5     GGTGGTTGTATACCAGCATCACAAGTTATTGTTAATAATTATGATAAAAGTGCTGGTTAT 1500
Patient 1     GGTGGTTGTATACCAGCATCACAAGTTATTGTTAATAATTATGACAAAAGTGCTGGTTAT 1500
              ************************** ***************** ***************

Patient 7     CCATTTAATAAATTTGGTAAAGCCAGACTTTATTATGAGGCATTATCATTTGAAGAACAG 1560
Patient 9     CCATTTAATAAATTTGGTAAAGCCAGACTTTATTATGAGGCATTATCATTTGAAGAACAG 1560
Patient 10    CCATTTAATAAATTTGGTAAAGCCAGACTTTATTATGAGGCATTATCATTTGAAGAACAG 1560
Patient 6     CCATTTAATAAATTTGGTAAAGCCAGACTTTATTATGAGGCATTATCATTTGAAGAACAG 1560
Patient 4     CCATTTAATAAATTTGGTAAAGCCAGACTTTATTATGAGGCATTATCATTTGAAGAACAG 1560
Patient 8     CCATTTAATAAATTTGGTAAAGCCAGACTTTATTATGAGGCATTATCATTTGAGGAACAG 1560
Patient 2     CCATTTAATAAATTTGGTAAAGCCAGACTTTATTATGAGGCATTATCATTTGAGGAACAG 1560
Patient 5     CCATTTAATAAATTTGGTAAAGCCAGACTTTATTATGAGGCATTATCATTTGAGGAACAG 1560
Patient 1     CCATTTAATAAATTTGGTAAAGCTAGACTTTATTATGAGGCATTATCATTTGAGGAGCAG 1560
              ********************** ***************************** ** ****

Patient 7     AATGAAATTTATGCATATACTAAACGTAATGTTCTGCCCACCTTAACTCAAATGAATTTA 1620
Patient 9     AATGAAATTTATGCATATACTAAACGTAATGTTCTGCCCACCTTAACTCAAATGAATTTA 1620
Patient 10    AATGAAATTTATGCATATACTAAACGTAATGTTCTGCCCACCTTAACTCAAATGAATTTA 1620
Patient 6     AATGAAATTTATGCATATACTAAACGTAATGTTCTGCCCACCTTAACTCAAATGAATTTA 1620
Patient 4     AATGAAATTTATGCATATACTAAACGTAATGTTCTGCCCACCTTAACTCAAATGAATTTA 1620
Patient 8     AATGAAATTTATGCATATACTAAACGTAATGTTCTGCCCACCTTAACTCAAATGAATTTA 1620
Patient 2     AATGAAATTTATGCATATACTAAACGTAATGTTCTGCCCACCTTAACTCAAATGAATTTA 1620
Patient 5     AATGAAATTTATGCATATACTAAACGTAATGTTCTGCCCACCTTAACTCAAATGAATTTA 1620
Patient 1     AATGAAATTTATGCATATACTAAACGTAATGTGTTGCCCACTTTAACTCAAATGAATTTA 1620
              ********************************  ******* ******************

Patient 7     AAATATGCTATCAGTGCTAAGAATAGAGCTCGCACTGTAGCAGGTGTTTCTATTCTTAGT 1680
Patient 9     AAATATGCTATCAGTGCTAAGAATAGAGCTCGCACTGTAGCAGGTGTTTCTATTCTTAGT 1680
Patient 10    AAATATGCTATCAGTGCTAAGAATAGAGCTCGCACTGTAGCAGGTGTTTCTATTCTTAGT 1680
Patient 6     AAATATGCTATCAGTGCTAAGAATAGAGCTCGCACTGTAGCAGGTGTTTCTATTCTTAGT 1680
Patient 4     AAATATGCTATCAGTGCTAAGAATAGAGCTCGCACTGTAGCAGGTGTTTCTATTCTTAGT 1680
```

FIG. 11 CONT.

```
Patient 8     AAATATGCTATCAGTGCTAAGAATAGAGCTCGCACTGTAGCAGGTGTTTCTATTCTTAGT 1680
Patient 2     AAATATGCTATCAGTGCTAAGAATAGAGCTCGCACTGTAGCAGGTGTTTCTATTCTTAGT 1680
Patient 5     AAATATGCTATCAGTGCTAAGAATAGAGCTCGCACTGTAGCAGGTGTTTCTATTCTTAGT 1680
Patient 1     AAATATGCTATTAGTGCTAAGAATAGAGCTCGTACTGTTGCAGGTGTTTCCATTCTTAGT 1680
              *********** ******************** ***** *********** *********

Patient 7     ACTATGACAGGCCGAATGTTCCATCAAAAATGTTTGAAGAGTATAGCAGCTACCCGAGGT 1740
Patient 9     ACTATGACAGGCCGAATGTTCCATCAAAAATGTTTGAAGAGTATAGCAGCTACCCGAGGT 1740
Patient 10    ACTATGACAGGCCGAATGTTCCATCAAAAATGTTTGAAGAGTATAGCAGCTACCCGAGGT 1740
Patient 6     ACTATGACAGGCCGAATGTTCCATCAAAAATGTTTGAAGAGTATAGCAGCTACCCGAGGT 1740
Patient 4     ACTATGACAGGCCGAATGTTCCATCAAAAATGTTTGAAGAGTATAGCAGCTACCCGAGGT 1740
Patient 8     ACTATGACAGGCCGAATGTTCCATCAAAAATGTTTGAAGAGTATAGCAGCCACCCGAGGT 1740
Patient 2     ACTATGACAGGCCGAATGTTCCATCAAAAATGTTTGAAGAGTATAGCAGCTACCCGAGGT 1740
Patient 5     ACTATGACAGGCCGAATGTTCCATCAAAAATGTTTGAAGAGTATAGCAGCTACCCGAGGT 1740
Patient 1     ACTATGACAGGTCGAATGTTTCATCAAAAATGTTTGAAGAGTATAGCAGCTACTCGTGGT 1740
              *********** ******** ***************************** ** ** ***

Patient 7     GTTCCTGTTGTTATAGGAACCACTAAATTTTATGGTGGTTGGGACGATATGTTACGTCAT 1800
Patient 9     GTTCCTGTTGTTATAGGAACCACTAAATTTTATGGTGGTTGGGACGATATGTTACGTCAT 1800
Patient 10    GTTCCTGTTGTTATAGGAACCACTAAATTTTATGGTGGTTGGGACGATATGTTACGTCAT 1800
Patient 6     GTTCCTGTTGTTATAGGAACCACTAAATTTTATGGTGGTTGGGACGATATGTTACGTCAT 1800
Patient 4     GTTCCTGTTGTTATAGGAACCACTAAATTTTATGGTGGTTGGGACGATATGTTACGTCAT 1800
Patient 8     GTTCCTGTTGTTATAGGAACCACTAAATTTTATGGTGGTTGGGACGATATGTTACGTCAT 1800
Patient 2     GTTCCTGTTGTTATAGGAACCACTAAATTTTATGGTGGTTGGGACGATATGTTACGTCAT 1800
Patient 5     GTTCCTGTTGTTATAGGAACCACTAAATTTTATGGTGGTTGGGACGATATGTTACGTCAT 1800
Patient 1     GTTCCTGTTGTTATAGGAACTACTAAATTTTATGGTGGCTGGGATGATATGTTACGCCAT 1800
              ******************** ***************** ***** *********** ***

Patient 7     CTTATAAAGGATGTTGACAACCCTGTTCTTATGGGTTGGGATTATCCTAAATGTGATCGT 1860
Patient 9     CTTATAAAGGATGTTGACAACCCTGTTCTTATGGGTTGGGATTATCCTAAATGTGATCGT 1860
Patient 10    CTTATAAAGGATGTTGACAACCCTGTTCTTATGGGTTGGGATTATCCTAAATGTGATCGT 1860
Patient 6     CTTATAAAGGATGTTGACAACCCTGTTCTTATGGGTTGGGATTATCCTAAATGTGATCGT 1860
Patient 4     CTTATAAAGGATGTTGACAACCCTGTTCTTATGGGTTGGGATTATCCTAAATGTGATCGT 1860
Patient 8     CTTATAAAGGATGTTGACAACCCTGTTCTTATGGGTTGGGATTATCCTAAATGTGATCGT 1860
Patient 2     CTTATAAAGGATGTTGACAACCCTGTTCTTATGGGTTGGGATTATCCTAAATGTGATCGT 1860
Patient 5     CTTATAAAGGATGTTGACAACCCTGTTCTTATGGGTTGGGATTATCCTAAATGTGATCGT 1860
Patient 1     CTTATAAAGGATGTTGACAACCCTGTTCTTATGGGTTGGGATTATCCTAAATGTGATCGT 1860
              ************************************************************

Patient 7     GCTATGCCAAATATTTTGCGTATTGTTAGTAGTTTAGTTTTGGCCCGCAAACATGAATTT 1920
Patient 9     GCTATGCCAAATATTTTGCGTATTGTTAGTAGTTTAGTTTTGGCCCGCAAACATGAATTT 1920
Patient 10    GCTATGCCAAATATTTTGCGTATTGTTAGTAGTTTAGTTTTGGCCCGCAAACATGAATTT 1920
Patient 6     GCTATGCCAAATATTTTGCGTATTGTTAGTAGTTTAGTTTTGGCCCGCAAACATGAATTT 1920
Patient 4     GCTATGCCAAATATTTTGCGTATTGTTAGTAGTTTAGTTTTGGCCCGCAAACATGAATTT 1920
Patient 8     GCTATGCCAAATATTTTGCGTATTGTTAGTAGTTTAGTTTTGGCCCGCAAACATGAATTT 1920
Patient 2     GCTATGCCAAATATTTTGCGTATTGTTAGTAGTTTAGTTTTGGCCCGCAAACATGAATTT 1920
Patient 5     GCTATGCCAAATATTTTGCGTATTGTTAGTAGTTTAGTTTTGGCCCGCAAACATGAATTT 1920
Patient 1     GCCATGCCAAATATTTTGCGTATTGTTAGTAGTTTAGTTTTGGCTCGTAAACATGAATTT 1920
              ** ***************************************** ** ************

Patient 7     TGTTGTTCACATGGTGATAGATTTTATCGCCTTGCGAATGAATGTGCTCAAGTTTTGAGT 1980
Patient 9     TGTTGTTCACATGGTGATAGATTTTATCGCCTTGCGAATGAATGTGCTCAAGTTTTGAGT 1980
Patient 10    TGTTGTTCACATGGTGATAGATTTTATCGCCTTGCGAATGAATGTGCTCAAGTTTTGAGT 1980
Patient 6     TGTTGTTCACATGGTGATAGATTTTATCGCCTTGCGAATGAATGTGCTCAAGTTTTGAGT 1980
Patient 4     TGTTGTTCACATGGTGATAGATTTTATCGCCTTGCGAATGAATGTGCTCAAGTTTTGAGT 1980
Patient 8     TGTTGTTCACATGGTGATAGATTCTATCGCCTTGCGAATGAATGTGCACAAGTTTTGAGT 1980
Patient 2     TGTTGTTCACATGGTGATAGATTTTATCGCCTTGCGAATGAATGTGCTCAAGTTTTGAGT 1980
Patient 5     TGTTGTTCACATGGTGATAGATTTTATCGCCTTGCGAATGAATGTGCTCAAGTTTTGAGT 1980
Patient 1     TGTTGTTCACATGGTGATAGATTCTATCGCCTTGCGAATGAATGTGCTCAAGTTTTGAGT 1980
              *********************** *********************** ************

Patient 7     GAAATAGTTATGTGTGGCGGTTGCTATTATGTTAAGCCTGGTGGTACTAGCAGTGGTGAT 2040
Patient 9     GAAATAGTTATGTGTGGCGGTTGCTATTATGTTAAGCCTGGTGGTACTAGCAGTGGTGAT 2040
Patient 10    GAAATAGTTATGTGTGGCGGTTGCTATTATGTTAAGCCTGGTGGTACTAGCAGTGGTGAT 2040
Patient 6     GAAATAGTTATGTGTGGCGGTTGCTATTATGTTAAGCCTGGTGGTACTAGCAGTGGTGAT 2040
Patient 4     GAAATAGTTATGTGTGGCGGTTGCTATTATGTTAAGCCTGGTGGTACTAGCAGTGGTGAT 2040
Patient 8     GAAATAGTTATGTGTGGCGGTTGCTATTATGTTAAGCCTGGTGGTACTAGCAGTGGTGAT 2040
Patient 2     GAAATAGTTATGTGTGGCGGTTGCTATTATGTTAAGCCTGGTGGTACTAGCAGTGGTGAT 2040
Patient 5     GAAATAGTTATGTGTGGCGGTTGCTATTATGTTAAGCCTGGTGGTACTAGCAGTGGTGAT 2040
Patient 1     GAAATAGTTATGTGTGGCGGTTGCTATTATGTTAAGCCTGGTGGTACTAGCAGTGGTGAT 2040
              ************************************************************

Patient 7     GCAACTACTGCTTTTGCTAATTCTGTTTTTAATATATGTCAGGCTGTTACTGCTAACGTT 2100
Patient 9     GCAACTACTGCTTTTGCTAATTCTGTTTTTAATATATGTCAGGCTGTTACTGCTAACGTT 2100
Patient 10    GCAACTACTGCTTTTGCTAATTCTGTTTTTAATATATGTCAGGCTGTTACTGCTAACGTT 2100
Patient 6     GCAACTACTGCTTTTGCTAATTCTGTTTTTAATATATGTCAGGCTGTTACTGCTAACGTT 2100
```

FIG. 11 CONT.

| | | |
|---|---|---|
| Patient 4  | GCAACTACTGCTTTTGCTAATTCTGTTTTTAATATATGTCAGGCTGTTACTGCTAACGTT | 2100 |
| Patient 8  | GCAACTACTGCTTTTGCTAATTCTGTTTTTAATATATGTCAGGCTGTTACTGCTAATGTT | 2100 |
| Patient 2  | GCAACTACTGCTTTTGCTAATTCTGTTTTTAATATATGTCAGGCTGTTACTGCTAATGTT | 2100 |
| Patient 5  | GCAACTACTGCTTTTGCTAATTCTGTTTTTAATATATGTCAGGCTGTTACTGCTAATGTT | 2100 |
| Patient 1  | GCAACCACTGCTTTTGCTAACTCTGTTTTTAATATATGTCAAGCTGTTACTGCTAATGTT | 2100 |
| | ***** ************* ********************* ************* *** | |
| | | |
| Patient 7  | TGTTCTCTTATGGCCTGTAATGGCCATAAGATTGAAGATTTAAGTATACGCAATTTACAA | 2160 |
| Patient 9  | TGTTCTCTTATGGCCTGTAATGGCCATAAGATTGAAGATTTAAGTATACGCAATTTACAA | 2160 |
| Patient 10 | TGTTCTCTTATGGCCTGTAATGGCCATAAGATTGAAGATTTAAGTATACGCAATTTACAA | 2160 |
| Patient 6  | TGTTCTCTTATGGCCTGTAATGGCCATAAGATTGAAGATTTAAGTATACGCAATTTACAA | 2160 |
| Patient 4  | TGTTCTCTTATGGCCTGTAATGGCCATAAGATTGAAGATTTAAGTATACGCAATTTACAA | 2160 |
| Patient 8  | TGTTCTCTTATGGCCTGTAATGGCCATAAGATTGAAGATTTAAGTATACGCAATTTACAA | 2160 |
| Patient 2  | TGTTCTCTTATGGCCTGTAATGGCCATAAGATTGAAGATTTAAGTATACGCAATTTACAA | 2160 |
| Patient 5  | TGTTCTCTTATGGCCTGTAATGGCCATAAGATTGAAGATTTAAGTATACGCAATTTACAA | 2160 |
| Patient 1  | TGTTCTCTTATGGCTTGTAATGGCCATAAGATTGAAGATTTAAGTATACGCAATTTACAA | 2160 |
| | ************** ********************************************* | |
| | | |
| Patient 7  | AAACGCTTATACTCTAATGTTTATCGTACAGATTATGTTGATTATACATTTGTTAATGAG | 2220 |
| Patient 9  | AAACGCTTATACTCTAATGTTTATCGTACAGATTATGTTGATTATACATTTGTTAATGAG | 2220 |
| Patient 10 | AAACGCTTATACTCTAATGTTTATCGTACAGATTATGTTGATTATACATTTGTTAATGAG | 2220 |
| Patient 6  | AAACGCTTATACTCTAATGTTTATCGTACAGATTATGTTGATTATACATTTGTTAATGAG | 2220 |
| Patient 4  | AAACGCTTATACTCTAATGTTTATCGTACAGATTATGTTGATTATACATTTGTTAATGAG | 2220 |
| Patient 8  | AAACGCTTATACTCTAATGTTTATCGTACAGATTATGTTGATTATACATTTGTTAATGAG | 2220 |
| Patient 2  | AAACGCTTATACTCTAATGTTTATCGTACAGATTATGTTGATTATACATTTGTTAATGAG | 2220 |
| Patient 5  | AAACGCTTATACTCTAATGTTTATCGTACAGATTATGTTGATTATACATTTGTTAATGAG | 2220 |
| Patient 1  | AAACGCTTATACTCTAATGTTTATCGTACAGATTATGTTGATTATACATTTGTTAATGAG | 2220 |
| | ************************************************************ | |
| | | |
| Patient 7  | TATTATGAATTTTTATGTAAGCATTTTAGTATGATGATTTTGAGTGATGATGGTGTTGTC | 2280 |
| Patient 9  | TATTATGAATTTTTATGTAAGCATTTTAGTATGATGATTTTGAGTGATGATGGTGTTGTC | 2280 |
| Patient 10 | TATTATGAATTTTTATGTAAGCATTTTAGTATGATGATTTTGAGTGATGATGGTGTTGTC | 2280 |
| Patient 6  | TATTATGAATTTTTATGTAAGCATTTTAGTATGATGATTTTGAGTGATGATGGTGTTGTC | 2280 |
| Patient 4  | TATTATGAATTTTTATGTAAGCATTTTAGTATGATGATTTTGAGTGATGATGGTGTTGTC | 2280 |
| Patient 8  | TATTATGAATTTTTATGTAAGCATTTTAGTATGATGATTTTGAGTGATGATGGTGTTGTC | 2280 |
| Patient 2  | TATTATGAATTTTTATGTAAGCATTTTAGTATGATGATTTTGAGTGATGATGGTGTTGTC | 2280 |
| Patient 5  | TATTATGAATTTTTATGTAAGCATTTTAGTATGATGATTTTGAGTGATGATGGTGTTGTC | 2280 |
| Patient 1  | TATTATGAATTTTTATGTAAGCATTTTAGTATGATGATTTTGAGTGATGATGGTGTTGTT | 2280 |
| | *********************************************************** | |
| | | |
| Patient 7  | TGTTATAACTCTGATTATGCTAGTAAGGGTTATATAGCTAATATAAGTGTTTTTCAACAA | 2340 |
| Patient 9  | TGTTATAACTCTGATTATGCTAGTAAGGGTTATATAGCTAATATAAGTGTTTTTCAACAA | 2340 |
| Patient 10 | TGTTATAACTCTGATTATGCTAGTAAGGGTTATATAGCTAATATAAGTGTTTTTCAACAA | 2340 |
| Patient 6  | TGTTATAACTCTGATTATGCTAGTAAGGGTTATATAGCTAATATAAGTGTTTTTCAACAA | 2340 |
| Patient 4  | TGTTATAACTCTGATTATGCTAGTAAGGGTTATATAGCTAATATAAGTGTTTTTCAACAA | 2340 |
| Patient 8  | TGTTATAACTCTGATTATGCTAATAAGGGTTATATAGCTAATATAAGTGCTTTTCAACAA | 2340 |
| Patient 2  | TGTTATAACTCTGATTATGCTAGTAAGGGTTATATAGCTAATATAAGTGTTTTTCAACAA | 2340 |
| Patient 5  | TGTTATAACTCTGATTATGCTAGTAAGGGTTATATAGCTAATATAAGTGTTTTTCAACAA | 2340 |
| Patient 1  | TGTTATAACTCTGATTATGCTAGTAAGGGTTATATAGCCAATATAAGTGTTTTTCAACAA | 2340 |
| | ********************** *************** ********* ********* | |
| | | |
| Patient 7  | GTTTTGTACTATCAGAATAATGTTTTTATGTCTGAATCTAAATGTTGGGTTGAAAATGAT | 2400 |
| Patient 9  | GTTTTGTACTATCAGAATAATGTTTTTATGTCTGAATCTAAATGTTGGGTTGAAAATGAT | 2400 |
| Patient 10 | GTTTTGTACTATCAGAATAATGTTTTTATGTCTGAATCTAAATGTTGGGTTGAAAATGAT | 2400 |
| Patient 6  | GTTTTGTACTATCAGAATAATGTTTTTATGTCTGAATCTAAATGTTGGGTTGAAAATGAT | 2400 |
| Patient 4  | GTTTTGTACTATCAGAATAATGTTTTTATGTCTGAATCTAAATGTTGGGTTGAAAATGAT | 2400 |
| Patient 8  | GTTTTGTACTATCAGAATAATGTCTTTATGTCTGAATCTAAATGTTGGGTTGAAAATGAT | 2400 |
| Patient 2  | GTTTTGTACTATCAGAATAATGTCTTTATGTCTGAATCTAAATGTTGGGTTGAAAATGAT | 2400 |
| Patient 5  | GTTTTGTACTATCAGAATAATGTCTTTATGTCTGAATCTAAATGTTGGGTTGAAAATGAT | 2400 |
| Patient 1  | GTTTTGTACTATCAGAATAACGTTTTTATGTCTGAATCTAAATGTTGGGTTGAAAATGAT | 2400 |
| | ******************** ** ************************************ | |
| | | |
| Patient 7  | ATTACTAATGGTCCTCATGAATTTTGTTCCCAACATACTATGTTGGTTAAGATAGATGGT | 2460 |
| Patient 9  | ATTACTAATGGTCCTCATGAATTTTGTTCCCAACATACTATGTTGGTTAAGATAGATGGT | 2460 |
| Patient 10 | ATTACTAATGGTCCTCATGAATTTTGTTCCCAACATACTATGTTGGTTAAGATAGATGGT | 2460 |
| Patient 6  | ATTACTAATGGTCCTCATGAATTTTGTTCCCAACATACTATGTTGGTTAAGATAGATGGT | 2460 |
| Patient 4  | ATTACTAATGGTCCTCATGAATTTTGTTCCCAACATACTATGTTGGTTAAGATAGATGGT | 2460 |
| Patient 8  | ATTACTAATGGTCCTCATGAATTTTGTTCCCAACATACTATGTTGGTTAAGATAGATGGT | 2460 |
| Patient 2  | ATTACTAATGGTCCTCATGAATTTTGTTCCCAACATACTATGTTAGTTAAGATAGATGGT | 2460 |
| Patient 5  | ATTACTAATGGTCCTCATGAATTTTGTTCCCAACATACTATGTTAGTTAAGATAGATGGT | 2460 |
| Patient 1  | ATTACTAATGGTCCTCATGAATTCTGTTCACAACATACTATGTTGGTTAAGATAGATGGT | 2460 |
| | *********************** ***** ************** ************** | |
| | | |
| Patient 7  | GATTATGTTTATTTACCATATCCAGATCCTTCTAGAATTCTAGGAGCTGGTTGTTTTGTT | 2520 |
| Patient 9  | GATTATGTTTATTTACCATATCCAGATCCTTCTAGAATTCTAGGAGCTGGTTGTTTTGTT | 2520 |
| Patient 10 | GATTATGTTTATTTACCATATCCAGATCCTTCTAGAATTCTAGGAGCTGGTTGTTTTGTT | 2520 |

FIG. 11 CONT.

```
Patient 6       GATTATGTTTATTTACCATATCCAGATCCTTCTAGAATTCTAGGAGCTGGTTGTTTTGTT 2520
Patient 4       GATTATGTTTATTTACCATATCCAGATCCTTCTAGAATTCTAGGAGCTGGTTGTTTTGTT 2520
Patient 8       GATTATGTTTATTTACCATATCCAGATCCTTCTAGAATCTTAGGAGCTGGTTGTTTTGTT 2520
Patient 2       GATTATGTTTATTTACCATATCCAGATCCTTCTAGAATTTTAGGAGCTGGTTGTTTTGTT 2520
Patient 5       GATTATGTTTATTTACCATATCCAGATCCTTCTAGAATTTTAGGAGCTGGTTGTTTTGTT 2520
Patient 1       GACTATGTTTATCTACCCTATCCAGACCCTTCTAGAATTTTAGGAGCTGGTTGTTTTGTT 2520
                ** ********* **** ******** ***********  ********************

Patient 7       GATGATTTATTGAAGACTGACAGTGTTCTTTTGATAGAGCGCTTTGTAAGTCTAGCTATA 2580
Patient 9       GATGATTTATTGAAGACTGATAGTGTTCTTTTGATAGAGCGCTTTGTAAGTCTAGCTATA 2580
Patient 10      GATGATTTATTGAAGACTGACAGTGTTCTTTTGATAGAGCGCTTTGTAAGTCTAGCTATA 2580
Patient 6       GATGATTTATTGAAGACTGACAGTGTTCTTTTGATAGAGCGCTTTGTAAGTCTAGCTATA 2580
Patient 4       GATGATTTATTGAAGACTGACAGTGTTCTTTTGATAGAGCGCTTTGTAAGTCTAGCTATA 2580
Patient 8       GATGATTTATTGAAGACTGACAGTGTTCTTTTGATAGAGCGCTTTGTAAGTCTAGCTATA 2580
Patient 2       GATGATTTATTGAAGACTGACAGTATTCTTTTGATAGAGCGCTTTGTAAGTCTAGCTATA 2580
Patient 5       GATGATTTATTGAAGACTGACAGTGTTCTTTTGATAGAGCGCTTTGTAAGTCTAGCTATA 2580
Patient 1       GATGATTTATTGAAGACTGACAGTGTTCTTTTGATAGAGCGCTTTGTAAGTCTAGCTATA 2580
                ******************** *** ***********************************

Patient 7       GATGCTTACCCTTTAGTATATCATGAAAATGAAGAATACCAAAAAGTCTTTCGTGTATAT 2640
Patient 9       GATGCTTACCCTTTAGTATATCATGAAAATGAAGAATACCAAAAAGTCTTTCGTGTATAT 2640
Patient 10      GATGCTTACCCTTTAGTATATCATGAAAATGAAGAATACCAAAAAGTCTTTCGTGTATAT 2640
Patient 6       GATGCTTACCCTTTAGTATATCATGAAAATGAAGAATACCAAAAAGTCTTTCGTGTATAT 2640
Patient 4       GATGCTTACCCTTTAGTATATCATGAAAATGAAGAATACCAAAAAGTCTTTCGTGTATAT 2640
Patient 8       GATGCTTACCCTTTAGTATATCATGAAAATGAAGAATACCAAAAAGTCTTTCGCGTATAT 2640
Patient 2       GATGCTTACCCTTTAGTACATCATGAAAATGAAGAATACCAAAAAGTCTTTCGTGTATAT 2640
Patient 5       GATGCTTACCCTTTAGTACATCATGAAAATGAAGAATACCAAAAAGTCTTTCGTGTATAT 2640
Patient 1       GATGCTTACCCTTTAGTACACCATGAAAATGAAGAATACCAAAAAGTTTTTCGTGTATAT 2640
                ****************** * ************************** ***** ******

Patient 7       TTAGAATATATAAAAAAACTGTATAATGATCTTGGTACTCAGATCTTAGATAGTTATAGT 2700
Patient 9       TTAGAATATATAAAAAAACTGTATAATGATCTTGGTACTCAGATCTTAGATAGTTATAGT 2700
Patient 10      TTAGAATATATAAAAAAACTGTATAATGATCTTGGTACTCAGATCTTAGATAGTTATAGT 2700
Patient 6       TTAGAATATATAAAAAAACTGTATAATGATCTTGGTACTCAGATCTTAGATAGTTATAGT 2700
Patient 4       TTAGAATATATAAAAAAACTGTATAATGATCTTGGTACTCAGATCTTAGATAGTTATAGT 2700
Patient 8       TTAGAATATATAAAAAAACTGTATAATGATCTTGGTACTCAGATCTTAGATAGTTATAGT 2700
Patient 2       TTAGAATATATAAAAAAACTGTATAATGATCTTGGTACTCAGATCTTAGATAGTTATAGT 2700
Patient 5       TTAGAATATATAAAAAAACTGTATAATGATCTTGGTACTCAGATCTTAGATAGTTATAGT 2700
Patient 1       TTAGAATATATAAAAAAACTATATAATGATCTTGGTAATCAGATCTTAGATAGTTATAGT 2700
                ******************** **************** **********************

Patient 7       GTTATTTTAAGTACTTGTGATGGTTTAAAGTTTACTGAAGAATCATTTTACAAGAATATG 2760
Patient 9       GTTATTTTAAGTACTTGTGATGGTTTAAAGTTTACTGAAGAATCATTTTACAAGAATATG 2760
Patient 10      GTTATTTTAAGTACTTGTGATGGTTTAAAGTTTACTGAAGAATCATTTTACAAGAATATG 2760
Patient 6       GTTATTTTAAGTACTTGTGATGGTTTAAAGTTTACTGAAGAATCATTTTACAAGAATATG 2760
Patient 4       GTTATTTTAAGTACTTGTGATGGTTTAAAGTTTACTGAAGAATCATTTTACAAGAATATG 2760
Patient 8       GTTATTTTAAGTACTTGTGATGGTTTAAAGTTTACTGAAGAATCATTTTACAAGAATATG 2760
Patient 2       GTTATTTTAAGTACTTGTGATGGTTTAAAGTTTACTGAAGAATCATTTTACAAGAATATG 2760
Patient 5       GTTATTTTAAGTACTTGTGATGGTTTAAAGTTTACTGAAGAATCATTTTACAAGAATATG 2760
Patient 1       GTTATTTTAAGTACTTGTGATGGTTTAAAGTTCACTGATGAATCATTTTATAAGAATATG 2760
                ******************************** ***** *********** *********

Patient 7       TATTTAAAAAGTGCCGTGATGCAG 2784
Patient 9       TATTTAAAAAGTGCCGTGATGCAG 2784
Patient 10      TATTTAAAAAGTGCCGTGATGCAG 2784
Patient 6       TATTTAAAAAGTGCCGTGATGCAG 2784
Patient 4       TATTTAAAAAGTGCCGTGATGCAG 2784
Patient 8       TATTTAAAAAGTGCCGTGATGCAG 2784
Patient 2       TATTTAAAAAGTGCCGTGATGCAG 2784
Patient 5       TATTTAAAAAGTGCCGTGATGCAG 2784
Patient 1       TATTTAAAAAGTGCCGTGATGCAG 2784
                ************************
```

FIG. 11 CONT.

Fig. 13. Multiple alignment of the spike genes of CoV-HKU1 from patients 1, 2, 4, 5, 6, 7, 8, 9, and 10.

```
Patient 6       ATGTTATTAATTATTTTTATTTTGCCTACAACATTAGCTGTTATAGGTGATTTTAATTGT 60
Patient 9       ATGTTATTAATTATTTTTATTTTGCCTACAACATTAGCTGTTATAGGTGATTTTAATTGT 60
Patient 10      ATGTTATTAATTATTTTTATTTTGCCTACAACATTAGCTGTTATAGGTGATTTTAATTGT 60
Patient 5       ATGTTATTAATTATTTTTATTTTGCCTACAACATTAGCTGTTATAGGTGATTTTAATTGT 60
Patient 4       ATGTTATTAATTATTTTTATTTTGCCTACAACATTAGCTGTTATAGGTGATTTTAATTGT 60
Patient 7       ATGTTATTAATTATTTTTATTTTGCCTACAACATTAGCTGTTATAGGTGATTTTAATTGT 60
Patient 2       ATGTTATTAATTATTTTTATTTTGCCTACAACATTAGCTGTTATAGGTGATTTTAATTGT 60
Patient 1       ATGTTTTTAATTATTTTTATTTTGCCTACAACACTAGCTGTTATAGGTGATTTTAATTGT 60
Patient 8       ATGTTTTTAATTATTTTTATTTTGCCTACAACACTAGCTGTTATAGGTGATTTTAATTGT 60
                ***** *************************** **************************

Patient 6       ACTAATTTTGCTATTAATGATTTAAACACCACAGTTCCTCGCATAAGTGAGTATGTTGTG 120
Patient 9       ACTAATTTTGCTATTAATGATTTAAACACCACAGTTCCTCGCATAAGTGAGTATGTTGTG 120
Patient 10      ACTAATTTTGCTATTAATGATTTAAACACCACAGTTCCTCGCATAAGTGAGTATGTTGTG 120
Patient 5       ACTAATTTTGCTATTAATGATTTAAACACCACAGTTCCTCGCATAAGTGAGTATGTTGTG 120
Patient 4       ACTAATTTTGCTATTAATGATTTAAACACCACAGTTCCTCGCATAAGTGAGTATGTTGTG 120
Patient 7       ACTAATTTTGCTATTAATGATTTAAACACCACAGTTCCTCGCATAAGTGAGTATGTTGTG 120
Patient 2       ACTAATTTTGCTATTAATGATTTAAACACCACAGTTCCTCGCATAAGTGAGTATGTTGTG 120
Patient 1       ACTAACTCTTTTATTAATGATTATAATAAAACCATTCCGCGTATAAGCGAGGATGTTGTT 120
Patient 8       ACTAACTCTTTTATTAATGATTATAATAAAACCATTCCGCGTATAAGCGAGGATGTTGTT 120
                ***** * *  ***********  ** *  **  **** ** ***** *** ******* 

Patient 6       GATGTTTCTTATGGTTTGGGTACATATTATATACTTGATCGTGTTTATTTAAATACTACT 180
Patient 9       GATGTTTCTTATGGTTTGGGTACATATTATATACTTGATCGTGTTTATTTAAATACTACT 180
Patient 10      GATGTTTCTTATGGTTTGGGTACATATTATATACTTGATCGTGTTTATTTAAATACTACT 180
Patient 5       GATGTTTCTTATGGTTTGGGTACATATTATATACTTGATCGTGTTTATTTAAATACTACT 180
Patient 4       GATGTTTCTTATGGTTTGGGTACATATTATATACTTGATCGTGTTTATTTAAATACTACT 180
Patient 7       GATGTTTCTTATGGTTTGGGTACATATTATATACTTGATCGTGTTTATTTAAATACTACT 180
Patient 2       GATGTTTCTTATGGTTTGGGTACATATTATATACTTGATCGTGTTTATTTAAATACTACT 180
Patient 1       GATGTATCTCTTGGTTTGGGCACATATTATGTTCTTAACCGTGTTTATTTAAATACTACC 180
Patient 8       GATGTATCTCTTGGTTTGGGCACATATTATGTTCTTAACCGTGTTTATTTAAATACTACC 180
                ***** ***  ********* ********* * *** * ******************** 

Patient 6       ATATTATTTACTGGTTATTTCCCTAAATCTGGTGCCAATTTTAGGGATCTATCTTTAAAA 240
Patient 9       ATATTATTTACTGGTTATTTCCCTAAATCTGGTGCCAATTTTAGGGATCTATCTTTAAAA 240
Patient 10      ATATTATTTACTGGTTATTTCCCTAAATCTGGTGCCAATTTTAGGGATCTATCTTTAAAA 240
Patient 5       ATATTATTTACTGGTTATTTCCCTAAATCTGGTGCCAATTTTAGGGATCTATCTTTAAAA 240
Patient 4       ATATTATTTACTGGTTATTTCCCTAAATCTGGTGCCAATTTTAGGGATCTATCTTTAAAA 240
Patient 7       ATATTATTTACTGGTTATTTCCCTAAATCTGGTGCCAATTTTAGGGATCTATCTTTAAAA 240
Patient 2       ATATTATTTACTGGTTATTTCCCTAAATCTGGTGCCAATTTTAGGGATCTATCTTTAAAA 240
Patient 1       TTGTTATTTACAGGTTATTTTCCTAAATCTGGTGCTAATTTTAGAGACTTGGCTTTAAAG 240
Patient 8       TTGTTATTTACGGGTTATTTTCCTAAATCTGGTGCTAACTTTAGAGACTTGGCTTTAAAG 240
                 * ******** ******** ************** ** ***** **  *  ******* 

Patient 6       GGTACTACATATTTGAGTACTCTTTGGTATCAGAAACCCTTTTTATCTGATTTTAATAAT 300
Patient 9       GGTACTACATATTTGAGTACTCTTTGGTATCAGAAACCCTTTTTATCTGATTTTAATAAT 300
Patient 10      GGTACTACATATTTGAGTACTCTTTGGTATCAGAAACCCTTTTTATCTGATTTTAATAAT 300
Patient 5       GGTACTACATATTTGAGTACTCTTTGGTATCAGAAACCCTTTTTATCTGATTTTAATAAT 300
Patient 4       GGTACTACATATTTGAGTACTCTTTGGTATCAGAAACCCTTTTTATCTGATTTTAATAAT 300
Patient 7       GGTACTACATATTTGAGTACTCTTTGGTATCAGAAACCCTTTTTATCTGATTTTAATAAT 300
Patient 2       GGTACTACATATTTGAGTACTCTTTGGTATCAGAAACCCTTTTTATCTGATTTTAATAAT 300
Patient 1       GGTTCTAAATATTTGAGTACTCTCTGGTATAAACCACCTTTTCTGTCAGATTTTAATAAT 300
Patient 8       GGTTCTATATATTTGAGTACTCTCTGGTATAAACCACCTTTTCTGTCAGATTTTAATAAT 300
                *** *** *************** ****** *   *** *** * ** ************

Patient 6       GGTATTTTTTCTAGAGTTAAGAATACTAAGTTGTATGTTAATAAAACTTTGTATAGTGAG 360
Patient 9       GGTATTTTTTCTAGAGTTAAGAATACTAAGTTGTATGTTAATAAAACTTTGTATAGTGAG 360
Patient 10      GGTATTTTTTCTAGAGTTAAGAATACTAAGTTGTATGTTAATAAAACTTTGTATAGTGAG 360
Patient 5       GGTATTTTTTCTAGAGTTAAGAATACTAAGTTGTATGTTAATAAAACTTTGTATAGTGAG 360
Patient 4       GGTATTTTTTCTAGAGTTAAGAATACTAAGTTGTATGTTAATAAAACTTTGTATAGTGAG 360
Patient 7       GGTATTTTTTCTAGAGTTAAGAATACTAAGTTGTATGTTAATAAAACTTTGTATAGTGAG 360
Patient 2       GGTATTTTTTCTAGAGTTAAGAATACTAAGTTGTATGTTAATAAAACTTTGTATAGTGAG 360
Patient 1       GGTATTTTTTCTAAGGTTAAGAATACTAAGTTATATGTTAATAATACTTTGTATAGTGAA 360
Patient 8       GGTATTTTTTCTAAGGTTAAGAATACTAAGTTATATGTTAATAATACTTTGTATAGTGAA 360
                *************  ***************** *********** ************** 

Patient 6       TTTAGTACTATAGTTATAGGTAGTGTTTTTATTAACAACTCTTATACTATTGTTGTTCAA 420
Patient 9       TTTAGTACTATAGTTATAGGTAGTGTTTTTATTAACAACTCTTATACTATTGTTGTTCAA 420
Patient 10      TTTAGTACTATAGTTATAGGTAGTGTTTTTATTAACAACTCTTATACTATTGTTGTTCAA 420
Patient 5       TTTAGTACTATAGTTATAGGTAGTGTTTTTATTAACAACTCTTATACTATTGTTGTTCAA 420
Patient 4       TTTAGTACTATAGTTATAGGTAGTGTTTTTATTAACAACTCTTATACTATTGTTGTTCAA 420
Patient 7       TTTAGTACTATAGTTATAGGTAGTGTTTTTATTAACAACTCTTATACTATTGTTGTTCAA 420
Patient 2       TTTAGTACTATAGTTATAGGTAGTGTTTTTATTAACAACTCTTATACTATTGTTGTTCAA 420
Patient 1       TTTAGTACTATAGTTATAGGTAGTGTTTTTGTTAATACTTCTTATACTATTGTTGTTCAA 420
```

FIG. 13

```
Patient 8     TTTAGTACTATAGTTATAGGTAGTGTTTTTGTTAATACTTCTTATACTATTGTTGTTCAA 420
              ****************************** **** *  *********************

Patient 6     CCTCATAATGGTGTTTTGGAGATTACAGCTTGTCAATACACTATGTGTGAGTATCCTCAT 480
Patient 9     CCTCATAATGGTGTTTTGGAGATTACAGCTTGTCAATACACTATGTGTGAGTATCCTCAT 480
Patient 10    CCTCATAATGGTGTTTTGGAGATTACAGCTTGTCAATACACTATGTGTGAGTATCCTCAT 480
Patient 5     CCTCATAATGGTGTTTTGGAGATTACAGCTTGTCAATACACTATGTGTGAGTATCCTCAT 480
Patient 4     CCTCATAATGGTGTTTTGGAGATTACAGCTTGTCAATACACTATGTGTGAGTATCCTCAT 480
Patient 7     CCTCATAATGGTGTTTTGGAGATTACAGCTTGTCAATACACTATGTGTGAGTATCCTCAT 480
Patient 2     CCTCATAATGGTGTTTTGGAGATTACAGCTTGTCAATACACTATGTGTGAGTATCCTCAT 480
Patient 1     CCTCACAATGGTATTTTGGAGATTACAGCTTGTCAGTATACTATGTGTGAATATCCTCAC 480
Patient 8     CCTCATAATGGTATTTTGGAGATTACAGCTTGTCAGTATACTATGTGTGAATATCCTCAC 480
              ***** ****** ********************** ** *********** ******** 

Patient 6     ACTATTTGTAAATCTAAAGGTAGTTCTCGTAATGAATCTTGGCATTTTGATAAATCTGAA 540
Patient 9     ACTATTTGTAAATCTAAAGGTAGTTCTCGTAATGAATCTTGGCATTTTGATAAATCTGAA 540
Patient 10    ACTATTTGTAAATCTAAAGGTAGTTCTCGTAATGAATCTTGGCATTTTGATAAATCTGAA 540
Patient 5     ACTATTTGTAAATCTAAAGGTAGTTCTCGTAATGAATCTTGGCATTTTGATAAATCTGAA 540
Patient 4     ACTATTTGTAAATCTAAAGGTAGTTCTCGTAATGAATCTTGGCATTTTGATAAATCTGAA 540
Patient 7     ACTATTTGTAAATCTAAAGGTAGTTCTCGTAATGAATCTTGGCATTTTGATAAATCTGAA 540
Patient 2     ACTATTTGTAAATCTAAAGGTAGTTCTCGTAATGAATCTTGGCATTTTGATAAATCTGAA 540
Patient 1     ACTGTTTGTAAGTCTAAGGGTAGTATTCGTAATGAATCTTGGCACATTGATTCTTCGGAA 540
Patient 8     ACTGTTTGTAAGTCTAAGGGTAGTATTCGTAATGAATCTTGGCACATTGATTCTTCGGAA 540
              *** ******* ***** ******  ******************  *****   ** ***

Patient 6     CCTTTGTGTCTGTTCAAGAAAAATTTTACTTATAATGTTTCTACAGATTGGTTGTATTTT 600
Patient 9     CCTTTGTGTCTGTTCAAGAAAAATTTTACTTATAATGTTTCTACAGATTGGTTGTATTTT 600
Patient 10    CCTTTGTGTCTGTTCAAGAAAAATTTTACTTATAATGTTTCTACAGATTGGTTGTATTTT 600
Patient 5     CCTTTGTGTCTGTTCAAGAAAAATTTTACTTATAATGTTTCTACAGATTGGTTGTATTTT 600
Patient 4     CCTTTGTGTCTGTTCAAGAAAAATTTTACTTATAATGTTTCTACAGATTGGTTGTATTTT 600
Patient 7     CCTTTGTGTCTGTTCAAGAAAAATTTTACTTATAATGTTTCTACAGATTGGTTGTATTTT 600
Patient 2     CCTTTGTGTCTGTTCAAGAAAAATTTTACTTATAATGTTTCTACAGATTGGTTGTATTTT 600
Patient 1     CCTTTATGCTTGTTTAAGAAAAATTTTACTTATAATGTTTCTGCAGATTGGCTGTATTTT 600
Patient 8     CCTTTATGCTTGTTTAAGAAAAATTTTACTTATAATGTTTCTGCAGATTGGCTGTATTTT 600
              ***** **  **** *************************** ******** ********

Patient 6     CATTTTTATCAAGAACGTGGCACTTTTTATGCTTATTATGCTGATTCTGGCATGCCTACT 660
Patient 9     CATTTTTATCAAGAACGTGGCACTTTTTATGCTTATTATGCTGATTCTGGCATGCCTACT 660
Patient 10    CATTTTTATCAAGAACGTGGCACTTTTTATGCTTATTATGCTGATTCTGGCATGCCTACT 660
Patient 5     CATTTTTATCAAGAACGTGGCACTTTTTATGCTTATTATGCTGATTCTGGCATGCCTACT 660
Patient 4     CATTTTTATCAAGAACGTGGCACTTTTTATGCTTATTATGCTGATTCTGGCATGCCTACT 660
Patient 7     CATTTTTATCAAGAACGTGGCACTTTTTATGCTTATTATGCTGATTCTGGCATGCCTACT 660
Patient 2     CATTTTTATCAAGAACGTGGCACTTTTTATGCTTATTATGCTGATTCTGGCATGCCTACT 660
Patient 1     CATTTTTATCAAGAACGTGGTGTTTTTTATGCATATTATGCAGATGTAGGTATGCCTACC 660
Patient 8     CATTTTTATCAAGAACGTGGTGTTTTTTATGCATATTATGCAGATGTAGGTATGCCTACC 660
              ********************   ********* ******** ***   ** ******** 

Patient 6     ACTTTTTTATTTAGTTTGTATCTTGGTACTCTTTTATCTCATTATTATGTTTTGCCTTTG 720
Patient 9     ACTTTTTTATTTAGTTTGTATCTTGGTACTCTTTTATCTCATTATTATGTTTTGCCTTTG 720
Patient 10    ACTTTTTTATTTAGTTTGTATCTTGGTACTCTTTTATCTCATTATTATGTTTTGCCTTTG 720
Patient 5     ACTTTTTTATTTAGTTTGTATCTTGGTACTCTTTTATCTCATTATTATGTTTTGCCTTTG 720
Patient 4     ACTTTTTTATTTAGTTTGTATCTTGGTACTCTTTTATCTCATTATTATGTTTTGCCTTTG 720
Patient 7     ACTTTTTTATTTAGTTTGTATCTTGGTACTCTTTTATCTCATTATTATGTTTTGCCTTTG 720
Patient 2     ACTTTTTTATTTAGTTTGTATCTTGGTACTCTTTTATCTCATTATTATGTTTTGCCTTTG 720
Patient 1     ACTTTCTTATTTAGTTTATATTTAGGTACTATTTTATCTCATTATTATGTTATGCCTTTG 720
Patient 8     ACTTTCTTATTTAGTCTATATTTAGGTACTATTTTATCTCATTATTATGTTATGCCTTTG 720
              ***** ********* * *** * ****** ******************** ********

Patient 6     ACTTGTAATGCTATATCTTCTAATACTGATAATGAGACTTTACAATATTGGGTCACACCT 780
Patient 9     ACTTGTAATGCTATATCTTCTAATACTGATAATGAGACTTTACAATATTGGGTCACACCT 780
Patient 10    ACTTGTAATGCTATATCTTCTAATACTGATAATGAGACTTTACAATATTGGGTCACACCT 780
Patient 5     ACTTGTAATGCTATATCTTCTAATACTGATAATGAGACTTTACAATATTGGGTCACACCT 780
Patient 4     ACTTGTAATGCTATATCTTCTAATACTGATAATGAGACTTTACAATATTGGGTCACACCT 780
Patient 7     ACTTGTAATGCTATATCTTCTAATACTGATAATGAGACTTTACAATATTGGGTCACACCT 780
Patient 2     ACTTGTAATGCTATATCTTCTAATACTGATAATGAGACTTTACAATATTGGGTTACACCT 780
Patient 1     ACTTGTAAGGCTATATCTTCAAATACTGACAATGAAACTTTAGAATATTGGGTTACACCG 780
Patient 8     ACTTGTAATGCTATATCTTCAAATACTGACAATGAAACTTTAGAATATTGGGTTACACCG 780
              ******** *********** ******** ***** ****** ********** ***** 

Patient 6     TTGTCTAAACGCCAATATCTTCTTAAATTTGACAACCGTGGTGTTATTACTAATGCTGTT 840
Patient 9     TTGTCTAAACGCCAATATCTTCTTAAATTTGACAACCGTGGTGTTATTACTAATGCTGTT 840
Patient 10    TTGTCTAAACGCCAATATCTTCTTAAATTTGACAACCGTGGTGTTATTACTAATGCTGTT 840
Patient 5     TTGTCTAAACGCCAATATCTTCTTAAATTTGACAACCGTGGTGTTATTACTAATGCTGTT 840
Patient 4     TTGTCTAAACGCCAATATCTTCTTAAATTTGACAACCGTGGTGTTATTACTAATGCTGTT 840
Patient 7     TTGTCTAAACGCCAATATCTTCTTAAATTTGACAACCGTGGTGTTATTACTAATGCTGTT 840
Patient 2     TTGTCTAAACGCCAATATCTTCTTAAATTTGACAACCGTGGTGTTATTACTAATGCTGTT 840
```

FIG. 13 CONT.

```
Patient 1     CTATCTAGACGTCAGTATCTTCTTAATTTTGATGAGCACGGTGTTATTACTAATGCCGTT 840
Patient 8     CTATCTAGACGTCAGTATCTTCTTAATTTTGATGAGCACGGTGTTATTACTAATGCCGTT 840
               * **** *** ** *********** *****  * *  **************** ***

Patient 6     GATTGTTCTAGTAGTTTCTTTAGCGAGATTCAATGTAAAACTAAATCTTTATTACCTAAT 900
Patient 9     GATTGTTCTAGTAGTTTCTTTAGCGAGATTCAATGTAAAACTAAATCTTTATTACCTAAT 900
Patient 10    GATTGTTCTAGTAGTTTCTTTAGCGAGATTCAATGTAAAACTAAATCTTTATTACCTAAT 900
Patient 5     GATTGTTCTAGTAGTTTCTTTAGCGAGATTCAATGTAAAACTAAATCTTTATTACCTAAT 900
Patient 4     GATTGTTCTAGTAGTTTCTTTAGCGAGATTCAATGTAAAACTAAATCTTTATTACCTAAT 900
Patient 7     GATTGTTCTAGTAGTTTCTTTAGCGAGATTCAATGTAAAACTAAATCTTTATTACCTAAT 900
Patient 2     GATTGTTCTAGTAGTTTCTTTAGCGAGATTCAATGTAAAACTAAATCTTTATTACCTAAT 900
Patient 1     GATTGTTCAAGTAGTTTTCTTAGTGAGATTCAATGTAAAACTCAATCTTTTGCACCTAAT 900
Patient 8     GATTGTTCAAGTAGTTTTCTTAGTGAGATTCAATGTAAAACTCAATCTTTTGCACCTAAT 900
              ******** ********  **** ****************** *******   *******

Patient 6     ACTGGTGTTTATGACTTATCTGGTTTTACTGTTAAGCCTGTTGCAACTGTACATCGTCGT 960
Patient 9     ACTGGTGTTTATGACTTATCTGGTTTTACTGTTAAGCCTGTTGCAACTGTACATCGTCGT 960
Patient 10    ACTGGTGTTTATGACTTATCTGGTTTTACTGTTAAGCCTGTTGCAACTGTACATCGTCGT 960
Patient 5     ACTGGTGTTTATGACTTATCTGGTTTTACTGTTAAGCCTGTTGCAACTGTACATCGTCGT 960
Patient 4     ACTGGTGTTTATGACTTATCTGGTTTTACTGTTAAGCCTGTTGCAACTGTACATCGTCGT 960
Patient 7     ACTGGTGTTTATGACTTATCTGGTTTTACTGTTAAGCCTGTTGCAACTGTACATCGTCGT 960
Patient 2     ACTGGTGTTTATGACTTATCTGGTTTTACTGTTAAGCCTGTTGCAACTGTACATCGTCGT 960
Patient 1     ACTGGTGTTTATGATTTGTCTGGTTTTACTGTAAAGCCTGTTGCAACTGTTTATCGTCGG 960
Patient 8     ACTGGTGTTTATGATTTGTCTGGTTTTACTGTAAAGCCTGTTGCAACTGTTTATCGTCGG 960
              ************** ** ************** ****************  *******

Patient 6     ATTCCTGATTTACCTGATTGTGACATTGATAAATGGCTTAACAATTTTAATGTACCCTCA 1020
Patient 9     ATTCCTGATTTACCTGATTGTGACATTGATAAATGGCTTAACAATTTTAATGTACCCTCA 1020
Patient 10    ATTCCTGATTTACCTGATTGTGACATTGATAAATGGCTTAACAATTTTAATGTACCCTCA 1020
Patient 5     ATTCCTGATTTACCTGATTGTGACATTGATAAATGGCTTAACAATTTTAATGTACCCTCA 1020
Patient 4     ATTCCTGATTTACCTGATTGTGACATTGATAAATGGCTTAACAATTTTAATGTACCCTCA 1020
Patient 7     ATTCCTGATTTACCTGATTGTGACATTGATAAATGGCTTAACAATTTTAATGTACCCTCA 1020
Patient 2     ATTCCTGATTTACCTGATTGTGACATTGATAAATGGCTTAACAATTTTAATGTACCCTCA 1020
Patient 1     ATTCCTAATTTACCTGATTGTGACATTGACAACTGGCTTAATAATGTTAGTGTACCTTCA 1020
Patient 8     ATTCCTAATTTACCTGATTGTGACATTGACAACTGGCTTAATAATGTTAGTGTACCTTCA 1020
              ****** ********************** ** ******** *** *** ****** ***

Patient 6     CCTCTTAATTGGGAACGTAAAATTTTTTCTAATTGCAACTTTAATTTGAGTACTTTGCTT 1080
Patient 9     CCTCTTAATTGGGAACGTAAAATTTTTTCTAATTGCAACTTTAATTTGAGTACTTTGCTT 1080
Patient 10    CCTCTTAATTGGGAACGTAAAATTTTTTCTAATTGCAACTTTAATTTGAGTACTTTGCTT 1080
Patient 5     CCTCTTAATTGGGAACGTAAAATTTTTTCTAATTGCAACTTTAATTTGAGTACTTTGCTT 1080
Patient 4     CCTCTTAATTGGGAACGTAAAATTTTTTCTAATTGCAACTTTAATTTGAGTACTTTGCTT 1080
Patient 7     CCTCTTAATTGGGAACGTAAAATTTTTTCTAATTGCAACTTTAATTTGAGTACTTTGCTT 1080
Patient 2     CCTCTTAATTGGGAACGTAAAATTTTTTCTAATTGCAACTTTAATTTGAGTACTTTGCTT 1080
Patient 1     CCTCTTAATTGGGAACGTAGAATTTTTTCTAATTGTAACTTCAATTTAAGCACTTTACTT 1080
Patient 8     CCTCTTAATTGGGAACGTAGAATTTTTTCTAATTGTAACTTTAACTTAAGCACTTTACTT 1080
              ******************* *************** ***** ** ** ** ***** ***

Patient 6     CGTTTAGTTCATACTGATTCTTTTTCTTGTAATAATTTTGATGAATCTAAGATATATGGT 1140
Patient 9     CGTTTAGTTCATACTGATTCTTTTTCTTGTAATAATTTTGATGAATCTAAGATATATGGT 1140
Patient 10    CGTTTAGTTCATACTGATTCTTTTTCTTGTAATAATTTTGATGAATCTAAGATATATGGT 1140
Patient 5     CGTTTAGTTCATACTGATTCTTTTTCTTGTAATAATTTTGATGAATCTAAGATATATGGT 1140
Patient 4     CGTTTAGTTCATACTGATTCTTTTTCTTGTAATAATTTTGATGAATCTAAGATATATGGT 1140
Patient 7     CGTTTAGTTCATACTGATTCTTTTTCTTGTAATAATTTTGATGAATCTAAGATATATGGT 1140
Patient 2     CGTTTAGTTCATACTGATTCTTTTTCTTGTAATAATTTTGATGAATCTAAGATATATGGT 1140
Patient 1     CGTCTAGTTCATGTTGATTCTTTTTCTTGTAATAATCTTGATAAATCTAAAATTTTTGGT 1140
Patient 8     CGTCTAGTTCATGTTGATTCTTTTTCTTGTAATAATCTTGATAAATCTAAAATTTTTGGT 1140
              *** ********  ********************** ***** ******* ** * ****

Patient 6     AGTTGTTTTAAGAGTATTGTTTTAGATAAATTTGCCATACCCAACTCCAGACGATCTGAT 1200
Patient 9     AGTTGTTTTAAGAGTATTGTTTTAGATAAATTTGCCATACCCAACTCCAGACGATCTGAT 1200
Patient 10    AGTTGTTTTAAGAGTATTGTTTTAGATAAATTTGCCATACCCAACTCCAGACGATCTGAT 1200
Patient 5     AGTTGTTTTAAGAGTATTGTTTTAGATAAATTTGCCATACCCAACTCCAGACGATCTGAT 1200
Patient 4     AGTTGTTTTAAGAGTATTGTTTTAGATAAATTTGCTATACCCAACTCCAGACGATCTGAT 1200
Patient 7     AGTTGTTTTAAGAGTATTGTTTTAGATAAATTTGCTATACCCAACTCCAGACGATCTGAT 1200
Patient 2     AGTTGTTTTAAGAGTATTGTTTTAGATAAATTTGCCATACCCAACTCCAGACGATCTGAT 1200
Patient 1     AGTTGCTTTAATAGTATTACTGTTGACAAGTTTGCTATACCTAATCGCAGACGAGATGAT 1200
Patient 8     AGTTGCTTTAATAGTATTACTGTTGACAAGTTTGCTATACCTAATCGCAGACGAGATGAT 1200
              ***** ***** ******  * * ** ** ***** ***** **   *******  ****

Patient 6     TTGCAGTTGGGCAGTTCTGGTTTTCTGCAATCTTCTAATTATAAAATTGACACTACTTCT 1260
Patient 9     TTGCAGTTGGGCAGTTCTGGTTTTCTGCAATCTTCTAATTATAAAATTGACACTACTTCT 1260
Patient 10    TTGCAGTTGGGCAGTTCTGGTTTTCTGCAATCTTCTAATTATAAAATTGACACTACTTCT 1260
Patient 5     TTGCAGTTGGGCAGTTCTGGTTTTCTGCAATCTTCTAATTATAAAATTGACACTACTTCT 1260
Patient 4     TTGCAGTTGGGCAGTTCTGGTTTTCTGCAATCTTCTAATTATAAAATTGACACTACTTCT 1260
Patient 7     TTGCAGTTGGGCAGTTCTGGTTTTCTGCAATCTTCTAATTATAAAATTGACACTACTTCT 1260
```

FIG. 13 CONT.

```
Patient 2     TTGCAGTTGGGCAGTTCTGGTTTTCTGCAATCTTCTAATTATAAAATTGACACTACTTCT 1260
Patient 1     TTGCAATTGGGCAGTTCTGGCTTTTGCAATCATCTAATTACAAAATAGATATTTCTTCT 1260
Patient 8     TTGCAATTGGGCAGTTCTGGCTTTTGCAATCATCTAATTACAAAATAGATATTTCTTCT 1260
              ***** ************** *** ******* ******** ***** ** * * *****

Patient 6     AGTTCTTGTCAATTGTATTATAGTTTGCCTGCAATTAATGTTACTATTAATAATTATAAT 1320
Patient 9     AGTTCTTGTCAATTGTATTATAGTTTGCCTGCAATTAATGTTACTATTAATAATTATAAT 1320
Patient 10    AGTTCTTGTCAATTGTATTATAGTTTGCCTGCAATTAATGTTACTATTAATAATTATAAT 1320
Patient 5     AGTTCTTGTCAATTGTATTATAGTTTGCCTGCAATTAATGTTACTATTAATAATTATAAT 1320
Patient 4     AGTTCTTGTCAATTGTATTATAGTTTGCCTGCAATTAATGTTACTATTAATAATTATAAT 1320
Patient 7     AGTTCTTGTCAATTGTATTATAGTTTGCCTGCAATTAATGTTACTATTAATAATTATAAT 1320
Patient 2     AGTTCTTGTCAATTGTATTATAGTTTGCCTGCAATTAATGTTACTATTAATAATTATAAT 1320
Patient 1     AGTTCTTGTCAATTGTATTATAGTTTACCTTTAGTTAATGTTACTATTAATAACTTTAAT 1320
Patient 8     AGTTCTTGTCAATTGTATTATAGTTTACCTTTAGTTAATGTTACTATTAATAACTTTAAT 1320
              ************************** ***  * ******************* * ****

Patient 6     CCTTCTTCTTGGAATAGAAGGTATGGTTTTAATAATTTTAATTTGAGCTCTCATAGTGTT 1380
Patient 9     CCTTCTTCTTGGAATAGAAGGTATGGTTTTAATAATTTTAATTTGAGCTCTCATAGTGTT 1380
Patient 10    CCTTCTTCTTGGAATAGAAGGTATGGTTTTAATAATTTTAATTTGAGCTCTCATAGTGTT 1380
Patient 5     CCTTCTTCTTGGAATAGAAGGTATGGTTTTAATAATTTTAATTTGAGCTCTCATAGTGTT 1380
Patient 4     CCTTCTTCTTGGAATAGAAGGTATGGTTTTAATAATTTTAATTTGAGCTCTCATAGTGTT 1380
Patient 7     CCTTCTTCTTGGAATAGAAGGTATGGTTTTAATAATTTTAATTTGAGCTCTCATAGTGTT 1380
Patient 2     CCTTCTTCTTGGAATAGAAGGTATGGTTTTAATAATTTTAATTTGAGCTCTCATAGTGTT 1380
Patient 1     CCATCTTCTTGGAATAGGAGGTATGGTTTTGGTAGTTTTAATGTGTCTTCTTATGACGTT 1380
Patient 8     CCATCTTCTTGGAATAGGAGGTATGGTTTTGGTAGTTTTAATTTGTCTTCTTATGACGTT 1380
              ** ************** ************  ** ******* **   *** **   ***

Patient 6     GTTTACTCACGTTATTGTTTTTCTGTTAATAATACTTTTTGTCCTTGTGCTAAACCTTCT 1440
Patient 9     GTTTACTCACGTTATTGTTTTTCTGTTAATAATACTTTTTGTCCTTGTGCTAAACCTTCT 1440
Patient 10    GTTTACTCACGTTATTGTTTTTCTGTTAATAATACTTTTTGTCCTTGTGCTAAACCTTCT 1440
Patient 5     GTTTACTCACGTTATTGTTTTTCTGTTAATAATACTTTTTGTCCTTGTGCTAAACCTTCT 1440
Patient 4     GTTTACTCACGTTATTGTTTTTCTGTTAATAATACTTTTTGTCCTTGTGCTAAACCTTCT 1440
Patient 7     GTTTACTCACGTTATTGTTTTTCTGTTAATAATACTTTTTGTCCTTGTGCTAAACCTTCT 1440
Patient 2     GTTTACTCACGTTATTGTTTTTCTGTTAATAATACTTTTTGTCCTTGTGCTAAACCTTCT 1440
Patient 1     GTTTATTCTGATCATTGTTTTTCTGTTAACAGCGACTTTTGCCCTTGTGCAGATCCGTCT 1440
Patient 8     GTTTATTCTGATCATTGTTTTTCTGTTAACAGCGACTTTTGCCCTTGTGCAGATCCGTCT 1440
              ***** **   * **************** *     ***** ********  * ** ***

Patient 6     TTTGCTTCAAGTTGCAAGAGTCATAAACCACCTTCTGCTTCCTGTCCTATTGGTACTAAT 1500
Patient 9     TTTGCTTCAAGTTGCAAGAGTCATAAACCACCTTCTGCTTCCTGTCCTATTGGTACTAAT 1500
Patient 10    TTTGCTTCAAGTTGCAAGAGTCATAAACCACCTTCTGCTTCCTGTCCTATTGGTACTAAT 1500
Patient 5     TTTGCTTCAAGTTGCAAGAGTCATAAACCACCTTCTGCTTCCTGTCCTATTGGTACTAAT 1500
Patient 4     TTTGCTTCAAGTTGCAAGAGTCATAAACCACCTTCTGCTTCCTGTCCTATTGGTACTAAT 1500
Patient 7     TTTGCTTCAAGTTGCAAGAGTCATAAACCACCTTCTGCTTCCTGTCCTATTGGTACTAAT 1500
Patient 2     TTTGCTTCAAGTTGCAAGAGTCATAAACCACCTTCTGCTTCCTGTCCTATTGGTACTAAT 1500
Patient 1     GTTGTTAATTCTTGTGTTAAATCTAAGCCTCTTTCTGCCATTTGTCCTGCTGGTACTAAA 1500
Patient 8     GTTGTTAATTCTTGTGCTAAATCTAAGCCTCCTTCTGCCATTTGTCCTGCTGGTACTAAA 1500
               *** *     ***    *    *** ** * ******    ******  *********

Patient 6     TATCGTTCTTGTGAGAGTACTACTGTACTCGACCACACTGATTGGTGTAGGTGTTCTTGT 1560
Patient 9     TATCGTTCTTGTGAGAGTACTACTGTACTCGACCACACTGACTGGTGTAGGTGTTCTTGT 1560
Patient 10    TATCGTTCTTGTGAGAGTACTACTGTACTCGACCACACTGACTGGTGTAGGTGTTCTTGT 1560
Patient 5     TATCGTTCTTGTGAGAGTACTACTGTACTCGACCACACTGACTGGTGTAGGTGTTCTTGT 1560
Patient 4     TATCGTTCTTGTGAGAGTACTACTGTACTCGACCACACTGACTGGTGTAGGTGTTCTTGT 1560
Patient 7     TATCGTTCTTGTGAGAGTACTACTGTACTCGACCACACTGACTGGTGTAGGTGTTCTTGT 1560
Patient 2     TATCGTTCTTGTGAGAGTACTACTGTACTCGACCACACTGACTGGTGTAGGTGTTCTTGT 1560
Patient 1     TATCGTCATTGCGACTTGGATACTACTCTTTATGTTAATAACTGGTGTAGATGTTCTTGT 1560
Patient 8     TATCGTCATTGCGACTTGGATACTACTCTTTATGTTAAAAACTGGTGTAGATGTTCTTGT 1560
              ******  *** **      ****   **  *    *   * ******** *********

Patient 6     TTACCTGATCCTATAACTGCTTATGACCCTAGGTCTTGTTCTCAAAAAAAGTCTCTGGTT 1620
Patient 9     TTACCTGATCCTATAACTGCTTATGACCCTAGGTCTTGTTCTCAAAAAAAGTCTCTGGTC 1620
Patient 10    TTACCTGATCCTATAACTGCTTATGACCCTAGGTCTTGTTCTCAAAAAAAGTCTCTGGTT 1620
Patient 5     TTACCTGATCCTATAACTGCTTATGACCCTAGGTCTTGTTCTCAAAAAAAGTCTCTGGTT 1620
Patient 4     TTACCTGATCCTATAACTGCTTATGACCCTAGGTCTTGTTCTCAAAAAAAGTCTCTGGTT 1620
Patient 7     TTACCTGATCCTATAACTGCTTATGACCCTAGGTCTTGTTCTCAAAAAAAGTCTCTGGTT 1620
Patient 2     TTACCTGATCCTATAACTGCTTATGACCCTAGGTCTTGTTCTCAAAAAAAGTCTCTGGTT 1620
Patient 1     CTACCTGACCCCATTTCTACTTATTCTCCTAACACATGTCCTCAAAAGAAGGTCGTTGTT 1620
Patient 8     CTACCTGACCCCATTTCTACTTATTCTCCTAACACATGTCCTCAAAAGAAGGTCGTTGTT 1620
               ******* ** **  ** *****   ****   * *** ******* ***    * **

Patient 6     GGTGTTGGTGAACATTGTGCAGGGTTCGGTGTTGATGAAGAAAAGTGTGGTGTATTGGAT 1680
Patient 9     GGTGTTGGTGAACATTGTGCAGGGTTCGGTGTTGATGAAGAAAAGTGTGGTGTATTGGAT 1680
Patient 10    GGTGTTGGTGAACATTGTGCAGGGTTCGGTGTTGATGAAGAAAAGTGTGGTGTATTGGAT 1680
Patient 5     GGTGTTGGTGAACATTGTGCAGGGTTCGGTGTTGATGAAGAAAAGTGTGGTGTATTGGAT 1680
Patient 4     GGTGTTGGTGAACATTGTGCAGGGTTCGGTGTTGATGAAGAAAAGTGTGGTGTATTGGAT 1680
```

FIG. 13 CONT.

```
Patient 7     GGTGTTGGTGAACATTGTGCAGGGTTCGGTGTTGATGAAGAAAAGTGTGGTGTATTGGAT 1680
Patient 2     GGTGTTGGTGAACATTGTGCAGGGTTCGGTGTTGATGAAGAAAAGTGTGGTGTATTGGAT 1680
Patient 1     GGTATAGGTGAACATTGTCCAGGTCTTGGTATTAATGAGGAAAAATGTGGTACAC----- 1675
Patient 8     GGTATAGGTGAACATTGTCCAGGTCTTGGTATTAATGAGGAAAAATGTGGTACAC----- 1675
              *** * ************ ****  * *** ** **** ***** ******  *

Patient 6     GGATCATATAATGTTTCTTGTCTTTGTAGTACTGATGCCTTTCTAGGTTGGTCTTATGAC 1740
Patient 9     GGATCATATAATGTTTCTTGTCTTTGTAGTACTGATGCCTTTCTAGGTTGGTCTTATGAC 1740
Patient 10    GGATCATATAATGTTTCTTGTCTTTGTAGTACTGATGCCTTTCTAGGTTGGTCTTATGAC 1740
Patient 5     GGATCATATAATGTTTCTTGTCTTTGTAGTACTGATGCCTTTCTAGGTTGGTCTTATGAC 1740
Patient 4     GGATCATATAATGTTTCTTGTCTTTGTAGTACTGATGCCTTTCTAGGTTGGTCTTATGAC 1740
Patient 7     GGATCATATAATGTTTCTTGTCTTTGTAGTACTGATGCCTTTCTAGGTTGGTCTTATGAC 1740
Patient 2     GGATCATATAATGTTTCTTGTCTTTGTAGTACTGATGCCTTTCTAGGTTGGTCTTATGAC 1740
Patient 1     -AATTAAATCATAGTTCCTGTTCTTGTAGTCCTGATGCCTTTTTGGGTTGGTCTTTTGAT 1734
Patient 8     -AATTAAATCATAGTTCCTGTTTTTGTAGTCCTGATGCCTTTTTGGGTTGGTCTTTTGAT 1734
                ** * ** **  *** ***  ******* *********** * ********** ***

Patient 6     ACTTGCGTCAGTAACAACCGTTGTAATATTTTTTCTAATTTTATTTTAAATGGTATCAAT 1800
Patient 9     ACTTGCGTCAGTAACAACCGTTGTAATATTTTTTCTAATTTTATTTTAAATGGTATCAAT 1800
Patient 10    ACTTGCGTCAGTAACAACCGTTGTAATATTTTTTCTAATTTTATTTTAAATGGTATCAAT 1800
Patient 5     ACTTGCGTCAGTAACAACCGTTGTAATATTTTTTCTAATTTTATTTTAAATGGTATCAAT 1800
Patient 4     ACTTGCGTCAGTAACAACCGTTGTAATATTTTTTCTAATTTTATTTTAAATGGTATCAAT 1800
Patient 7     ACTTGCGTCAGTAACAACCGTTGTAATATTTTTTCTAATTTTATTTTAAATGGTATCAAT 1800
Patient 2     ACTTGCGTCAGTAACAACCGTTGTAATATTTTTTCTAATTTTATTTTAAATGGTATCAAT 1800
Patient 1     AGTTGTATTAGTAATAATCGTTGCAATATTTTTTCTAATTTTATTTTTAATGGAATTAAT 1794
Patient 8     AGTTGTATTAGTAATAATCGTTGCAATATTTTTTCTAATTTTATTTTTAATGGAATTAAT 1794
              * ***  * ***** ** ***** *********************** ***** ** ***

Patient 6     AGTGGTACCACTTGTTCTAATGATTTATTGCAGCCTAATACTGAAGTTTTTACTGATGTT 1860
Patient 9     AGTGGTACCACTTGTTCTAATGATTTATTGCAGCCTAATACTGAAGTTTTTACTGATGTT 1860
Patient 10    AGTGGTACCACTTGTTCTAATGATTTATTGCAGCCTAATACTGAAGTTTTTACTGATGTT 1860
Patient 5     AGTGGTACCACTTGTTCTAATGATTTATTGCAGCCTAATACTGAAGTTTTTACTGATGTT 1860
Patient 4     AGTGGTACCACTTGTTCTAATGATTTATTGCAGCCTAATACTGAAGTTTTTACTGATGTT 1860
Patient 7     AGTGGTACCACTTGTTCTAATGATTTATTGCAGCCTAATACTGAAGTTTTTACTGATGTT 1860
Patient 2     AGTGGTACCACTTGTTCTAATGATTTATTGCAGCCTAATACTGAAGTTTTTACTGATGTT 1860
Patient 1     AGTGGCACCACTTGTTCTAATGATTTGTTATATTCTAACACTGAAGTTTCTACTGGTGTT 1854
Patient 8     AGTGGCACCACTTGTTCTAATGATTTGTTATATTCTAACACTGAAATTTCTACTGGTGTT 1854
              ***** ******************** **  *  **** ****** *** ***** ****

Patient 6     TGTGTTGATTACGACCTTTATGGTATTACAGGACAAGGTATTTTTAAAGAAGTTTCTGCT 1920
Patient 9     TGTGTTGATTACGACCTTTATGGTATTACAGGACAAGGTATTTTTAAAGAAGTTTCTGCT 1920
Patient 10    TGTGTTGATTACGACCTTTATGGTATTACAGGACAAGGTATTTTTAAAGAAGTTTCTGCT 1920
Patient 5     TGTGTTGATTACGACCTTTATGGTATTACAGGACAAGGTATTTTTAAAGAAGTTTCTGCT 1920
Patient 4     TGTGTTGATTACGACCTTTATGGTATTACAGGACAAGGTATTTTTAAAGAAGTTTCTGCT 1920
Patient 7     TGTGTTGATTACGACCTTTATGGTATTACAGGACAAGGTATTTTTAAAGAAGTTTCTGCT 1920
Patient 2     TGTGTTGATTACGACCTTTATGGTATTACAGGACAAGGTATTTTTAAAGAAGTTTCTGCT 1920
Patient 1     TGTGTTAATTATGATCTTTATGGCATCACAGGCCAAGGTATTTTTAAAGAAGTTTCTGCG 1914
Patient 8     TGTGTTAATTATGATCTTTATGGCATCACAGGCCAAGGTATTTTTAAAGAAGTTTCTGCG 1914
              ****** **** ** ******** ** ***** **************************

Patient 6     GTTTATTATAATAGTTGGCAAAATCTTTTGTATGATTCTAATGGCAACATTATTGGTTTT 1980
Patient 9     GTTTATTATAATAGTTGGCAAAATCTTTTGTATGATTCTAATGGCAACATTATTGGTTTT 1980
Patient 10    GTTTATTATAATAGTTGGCAAAATCTTTTGTATGATTCTAATGGCAACATTATTGGTTTT 1980
Patient 5     GTTTATTATAATAGTTGGCAAAATCTTTTGTATGATTCTAATGGCAACATTATTGGTTTT 1980
Patient 4     GTTTATTATAATAGTTGGCAAAATCTTTTGTATGATTCTAATGGCAACATTATTGGTTTT 1980
Patient 7     GTTTATTATAATAGTTGGCAAAATCTTTTGTATGATTCTAATGGCAACATTATTGGTTTT 1980
Patient 2     GTTTATTATAATAGTTGGCAAAATCTTTTGTATGATTCTAATGGCAACATTATTGGTTTT 1980
Patient 1     GCTTATTATAATAATTGGCAGAATCTTTTGTATGATTCTAATGGTAATATTATTGGTTTT 1974
Patient 8     GCTTATTATAATAATTGGCAGAATCTTTTGTATGATTCTAATGGTAATATTATTGGTTTT 1974
              * *********** ****** *********************** ** ************

Patient 6     AAAGATTTTGTTACTAATAAAACATATAATATTTTCCCTTGTTATGCAGGAAGAGTTTCT 2040
Patient 9     AAAGATTTTGTTACTAATAAAACATATAATATTTTCCCTTGTTATGCAGGAAGAGTTTCT 2040
Patient 10    AAAGATTTTGTTACTAATAAAACATATAATATTTTCCCTTGTTATGCAGGAAGAGTTTCT 2040
Patient 5     AAAGATTTTGTTACTAATAAAACATATAATATTTTCCCTTGTTATGCAGGAAGAGTTTCT 2040
Patient 4     AAAGATTTTGTTACTAATAAAACATATAATATTTTCCCTTGTTATGCAGGAAGAGTTTCT 2040
Patient 7     AAAGATTTTGTTACTAATAAAACATATAATATTTTCCCTTGTTATGCAGGAAGAGTTTCT 2040
Patient 2     AAAGATTTTGTTACTAATAAAACATATAATATTTTCCCTTGTTATGCAGGAAGAGTTTCT 2040
Patient 1     AAAGATTTTTTGACTAATAAAACTTACACTATACTTCCTTGTTATTCTGGTAGAGTGTCT 2034
Patient 8     AAAGATTTTTTGACTAATAAAACTTACACTATACTTCCTTGTTATTCTGGTAGAGTGTCT 2034
              ********* * *********** ** * ***  * ********* * ** ***** ***

Patient 6     GCTGCTTTTCATCAAAATGCTTCCTCTTTGGCTTTACTTTATCGTAATTTAAAATGTAGC 2100
Patient 9     GCTGCTTTTCATCAAAATGCTTCCTCTTTGGCTTTACTTTATCGTAATTTAAAATGTAGC 2100
Patient 10    GCTGCTTTTCATCAAAATGCTTCCTCTTTGGCTTTACTTTATCGTAATTTAAAATGTAGC 2100
Patient 5     GCTGCTTTTCATCAAAATGCTTCCTCTTTGGCTTTACTTTATCGTAATTTAAAATGTAGC 2100
```

FIG. 13 CONT.

```
Patient 4      GCTGCTTTTCATCAAAATGCTTCCTCTTTGGCTTTACTTTATCGTAATTTAAAATGTAGC 2100
Patient 7      GCTGCTTTTCATCAAAATGCTTCCTCTTTGGCTTTACTTTATCGTAATTTAAAATGTAGC 2100
Patient 2      GCTGCTTTTCATCAAAATGCTTCCTCTTTGGCTTTACTTTATCGTAATTTAAAATGTAGC 2100
Patient 1      GCTGCATTTTATCAAAATTCTTCTTCACCAGCTTTGCTTTATCGTAATTTAAAGTGTAGT 2094
Patient 8      GCTGCATTTTATCAAAATTCTTCCTCACCAGCTTTGCTTTATCGTAATTTAAAGTGTAGT 2094
               ***** *** ******** **** **    ***** ***************** *****

Patient 6      TATGTTTTGAATAATATTTCTTTAGCTACTCAGCCAT---ATTTTGATAGTTATCTTGGT 2157
Patient 9      TATGTTTTGAATAATATTTCTTTAGCTACTCAGCCAT---ATTTTGATAGTTATCTTGGT 2157
Patient 10     TATGTTTTGAATAATATTTCTTTAGCTACTCAGCCAT---ATTTTGATAGTTATCTTGGT 2157
Patient 5      TATGTTTTGAATAATATTTCTTTAACTACTCAGCCAT---ATTTTGATAGTTATCTTGGT 2157
Patient 4      TATGTTTTGAATAATATTTCTTTAGCTACTCAGCCAT---ATTTTGATAGTTATCTTGGT 2157
Patient 7      TATGTTTTGAATAATATTTCTTTAGCTACTCAGCCAT---ATTTTGATAGTTATCTTGGT 2157
Patient 2      TATGTTTTGAATAATATTTCTTTAGCTACTCAGCCAT---ATTTTGATAGTTATCTTGGT 2157
Patient 1      TATGTTTTGAATAATATTTCTTTTATCTCACAACCATTTTATTTTGATAGTTATCTTGGT 2154
Patient 8      TATGTTTTGAATAATATTTCTTTTATCTCACAACCATTTTATTTCGATAGTTATCTTGGT 2154
               ***********************     * ** ****   **** ***************

Patient 6      TGCGTTTTTAATGCTGATAATTTAACTGATTATTCTGTTTCTTCTTGTGCTCTTCGCATG 2217
Patient 9      TGCGTTTTTAATGCTGATAATTTAACTGATTATTCTGTTTCTTCTTGTGCTCTTCGCATG 2217
Patient 10     TGCGTTTTTAATGCTGATAATTTAACTGATTATTCTGTTTCTTCTTGTGCTCTTCGCATG 2217
Patient 5      TGCGTTTTTAATGCTGATAATTTAACTGATTATTCTGTTTCTTCTTGTGCTCTTCGCATG 2217
Patient 4      TGCGTTTTTAATGCTGATAATTTAACTGATTATTCTGTTTCTTCTTGTGCTCTTCGCATG 2217
Patient 7      TGCGTTTTTAATGCTGATAATTTAACTGATTATTCTGTTTCTTCTTGTGCTCTTCGCATG 2217
Patient 2      TGCGTTTTTAATGCTGATAATTTAACTGATTATTCTGTTTCTTCTTGTGCTCTTCGCATG 2217
Patient 1      TGTGTTTTGAATGCTGTTAATTTAACTAGCTATTCTGTATCCTCTTGTGATTTGCGTATG 2214
Patient 8      TGTGTTTTGAATGCTGTTAATTTAACTAGCTATTCTGTATCCTCTTGTGATTTGCGTATG 2214
               ** ***** ******* **********   ******** ** ******* * * ** ***

Patient 6      GGTAGTGGTTTTTGTGTTGATTATAACTCACCTTCTTCTTCCTCTTCGCGTCGTAAACGT 2277
Patient 9      GGTAGTGGTTTTTGTGTTGATTATAACTCACCTTCTTCTTCCTCTTCGCGTCGTAAACGT 2277
Patient 10     GGTAGTGGTTTTTGTGTTGATTATAACTCACCTTCTTCTTCCTCTTCGCGTCGTAAACGT 2277
Patient 5      GGTAGTGGTTTTTGTGTTGATTATAACTCACCTTCTTCTTCCTCTTCGCGTCGTAAACGT 2277
Patient 4      GGTAGTGGTTTTTGTGTTGATTATAACTCACCTTCTTCTTCCTCTTCGCGTCGTAAACGT 2277
Patient 7      GGTAGTGGTTTTTGTGTTGATTATAACTCACCTTCTTCTTCCTCTTCGCGTCGTAAACGT 2277
Patient 2      GGTAGTGGTTTTTGTGTTGATTATAACTCACCTTCTTCTTCCTCTTCGCGTCGTAAACGT 2277
Patient 1      GGTAGTGGGTTTTGTATTGATTATGCTTTACCCTCTTCT---------CGGCGTAAGCGT 2265
Patient 8      GGTAGTGGATTTTGTATTGATTATGCTTTACCCTCTTCT---------CGGCGTAAGCGT 2265
               ******** ****** ********   * *** ******         ** ***** ***

Patient 6      AGAAGTATTTCTGCTTCTTATCGTTTTGTTACTTTTGAACCCTTTAATGTCAGTTTTGTT 2337
Patient 9      AGAAGTATTTCTGCTTCTTATCGTTTTGTTACTTTTGAACCCTTTAATGTCAGTTTTGTT 2337
Patient 10     AGAAGTATTTCTGCTTCTTATCGTTTTGTTACTTTTGAACCCTTTAATGTCAGTTTTGTT 2337
Patient 5      AGAAGTATTTCTGCTTCTTATCGTTTTGTTACTTTTGAACCCTTTAATGTCAGTTTTGTT 2337
Patient 4      AGAAGTATTTCTGCTTCTTATCGTTTTGTTACTTTTGAACCCTTTAATGTCAGTTTTGTT 2337
Patient 7      AGAAGTATTTCTGCTTCTTATCGTTTTGTTACTTTTGAACCCTTTAATGTCAGTTTTGTT 2337
Patient 2      AGAAGTATTTCTGCTTCTTATCGTTTTGTTACTTTTGAACCCTTTAATGTCAGTTTTGTT 2337
Patient 1      AGAGGTATTTCTTCTCCTTATCGCTTTGTAACTTTTGAACCCTTTAATGTTAGTTTTGTT 2325
Patient 8      AGAGGTATTTCTTCTCCTTATCGCTTTGTAACTTTTGAACCCTTTAATGTTAGTTTTGTT 2325
               *** ******** ** ******* ***** ******************** *********

Patient 6      AATGACAGTATTGAGTCTGTGGGTGGTCTTTATGAGATCAAAATTCCCACTAACTTTACT 2397
Patient 9      AATGACAGTATTGAGTCTGTGGGTGGTCTTTATGAGATCAAAATTCCCACTAACTTTACT 2397
Patient 10     AATGACAGTATTGAGTCTGTGGGTGGTCTTTATGAGATCAAAATTCCCACTAACTTTACT 2397
Patient 5      AATGACAGTATTGAGTCTGTGGGTGGTCTTTATGAGATCAAAATTCCCACTAACTTTACT 2397
Patient 4      AATGACAGTATTGAGTCTGTGGGTGGTCTTTATGAGATCAAAATTCCCACTAACTTTACT 2397
Patient 7      AATGACAGTATTGAGTCTGTGGGTGGTCTTTATGAGATCAAAATTCCCACTAACTTTACT 2397
Patient 2      AATGACAGTATTGAGTCTGTGGGTGGTCTTTATGAGATCAAAATTCCCACTAACTTTACT 2397
Patient 1      AACGATAGTGTTGAAACTGTTGGTGGTTTATTTGAGATTCAGATTCCTACTAACTTTACC 2385
Patient 8      AACGATAGTGTTGAAACTGTTGGTGGTTTATTTGAGATTCAGATTCCTACTAACTTTACC 2385
               ** ** *** ****  **** ****** * * ******  * ***** *********** 

Patient 6      ATAGTTGGTCAAGAGGAATTTATTCAAACTAATTCTCCTAAAGTTACTATTGATTGTTCT 2457
Patient 9      ATAGTTGGTCAAGAGGAATTTATTCAAACTAATTCTCCTAAAGTTACTATTGATTGTTCT 2457
Patient 10     ATAGTTGGTCAAGAGGAATTTATTCAAACTAATTCTCCTAAAGTTACTATTGATTGTTCT 2457
Patient 5      ATAGTTGGTCAAGAGGAATTTATTCAAACTAATTCTCCTAAAGTTACTATTGATTGTTCT 2457
Patient 4      ATAGTTGGTCAAGAGGAATTTATTCAAACTAATTCTCCTAAAGTTACTATTGATTGTTCT 2457
Patient 7      ATAGTTGGTCAAGAGGAATTTATTCAAACTAATTCTCCTAAAGTTACTATTGATTGTTCT 2457
Patient 2      ATAGTTGGTCAAGAGGAATTTATTCAAACTAATTCTCCTAAAGTTACTATTGATTGTTCT 2457
Patient 1      ATAGCTGGTCATGAAGAATTTATTCAGACTAGTTCTCCTAAAGTTACTATTGATTGTTCA 2445
Patient 8      ATAGCTGGTCATGAAGAATTTATTCAGACTAGTTCTCCTAAAGTTACTATTGATTGTTCA 2445
               **** ****** ** *********** **** ***************************

Patient 6      TTATTTGTCTGTTCTAATTATGCAGCTTGCCATGACTTATTGTCAGAGTATGGCACTTTT 2517
Patient 9      TTATTTGTCTGTTCTAATTATGCAGCTTGCCATGACTTATTGTCAGAGTATGGCACTTTT 2517
Patient 10     TTATTTGTCTGTTCTAATTATGCAGCTTGCCATGACTTATTGTCAGAGTATGGCACTTTT 2517
```

FIG. 13 CONT.

```
Patient 5       TTATTTGTCTGTTCTAATTATGCAGCTTGCCATGACTTATTGTCAGAGTATGGCACTTTT 2517
Patient 4       TTATTTGTCTGTTCTAATTATGCAGCTTGCCATGACTTATTGTCAGAGTATGGCACTTTT 2517
Patient 7       TTATTTGTCTGTTCTAATTATGCAGCTTGCCATGACTTATTGTCAGAGTATGGCACTTTT 2517
Patient 2       TTATTTGTCTGTTCTAATTATGCAGCTTGCCATGACTTATTGTCAGAGTATGGCACTTTT 2517
Patient 1       GCTTTTGTTTGCTCTAATTATGCTGCTTGTCATGATTTATTGTCGGAATATGGCACTTTT 2505
Patient 8       GCTTTTGTTTGCTCTAACTATGCTGCTTGTCATGATTTATTGTCGGAATATGGCACTTTT 2505
                   ***** ** ***** ***** ***** ***** ******** ** ************

Patient 6       TGTGATAATATTAATAGTATTTTAGATGAAGTTAATGGTTTACTTGATACTACTCAATTG 2577
Patient 9       TGTGATAATATTAATAGTATTTTAGATGAAGTTAATGGTTTACTTGATACTACTCAATTG 2577
Patient 10      TGTGATAATATTAATAGTATTTTAGATGAAGTTAATGGTTTACTTGATACTACTCAATTG 2577
Patient 5       TGTGATAATATTAATAGTATTTTAGATGAAGTTAATGGTTTACTTGATACTACTCAATTG 2577
Patient 4       TGTGATAATATTAATAGTATTTTAGATGAAGTTAATGGTTTACTTGATACTACTCAATTG 2577
Patient 7       TGTGATAATATTAATAGTATTTTAGATGAAGTTAATGGTTTACTTGATACTACTCAATTG 2577
Patient 2       TGTGATAATATTAATAGTATTTTAGATGAAGTTAATGGTTTACTTGATACTACTCAATTG 2577
Patient 1       TGCGATAATATTAATAGTATTTTAAATGAAGTCAATGATTTACTTGATATTACTCAGTTG 2565
Patient 8       TGCGATAATATTAATAGTATTTTAAATGAAGTCAATGATTTACTTGATATTACTCAGTTG 2565
                ** ********************* ******* **** *********** ****** ***

Patient 6       CATGTAGCTGATACTCTTATGCAAGGTGTCACACTTAGCTCCAATCTTAATACTAATTTG 2637
Patient 9       CATGTAGCTGATACTCTTATGCAAGGTGTCACACTTAGCTCCAATCTTAATACTAATTTG 2637
Patient 10      CATGTAGCTGATACTCTTATGCAAGGTGTCACACTTAGCTCCAATCTTAATACTAATTTG 2637
Patient 5       CATGTAGCTGATACTCTTATGCAAGGTGTCACACTTAGCTCCAATCTTAATACTAATTTG 2637
Patient 4       CATGTAGCTGATACTCTTATGCAAGGTGTCACACTTAGCTCCAATCTTAATACTAATTTG 2637
Patient 7       CATGTAGCTGATACTCTTATGCAAGGTGTCACACTTAGCTCCAATCTTAATACTAATTTG 2637
Patient 2       CATGTAGCTGATACTCTTATGCAAGGTGTCACACTTAGCTCCAATCTTAATACTAATTTG 2637
Patient 1       CAGGTTGCTAATGCTTTAATGCAAGGTGTTACACTTAGTTCTAATCTTAATACTAATCTA 2625
Patient 8       CAGGTTGCTAATGCTCTAATGCAAGGTGTTACACTTAGTTCTAATCTTAATACTAATCTA 2625
                ** ** *** ** ** * *********** ******** ** *************** *

Patient 6       CATTTTGATGTTGATAATATTAATTTTAAATCCCTAGTTGGATGTTTAGGTCCACACTGC 2697
Patient 9       CATTTTGATGTTGATAATATTAATTTTAAATCCCTAGTTGGATGTTTAGGTCCACACTGC 2697
Patient 10      CATTTTGATGTTGATAATATTAATTTTAAATCCCTAGTTGGATGTTTAGGTCCACACTGC 2697
Patient 5       CATTTTGATGTTGATAATATTAATTTTAAATCCCTAGTTGGATGTTTAGGTCCACACTGC 2697
Patient 4       CATTTTGATGTTGATAATATTAATTTTAAATCCCTAGTTGGATGTTTAGGTCCACACTGC 2697
Patient 7       CATTTTGATGTTGATAATATTAATTTTAAATCCCTAGTTGGATGTTTAGGTCCACACTGC 2697
Patient 2       CATTTTGATGTTGATAATATTAATTTTAAATCCCTAGTTGGATGTTTAGGTCCACACTGC 2697
Patient 1       CACTCTGATGTTGATAATATAGATTTTAAATCTCTTCTAGGTTGTTTAGGTTCACAATGT 2685
Patient 8       CACTCTGATGTTGATAATATAGATTTTAAATCTCTTCTAGGTTGTTTAGGTTCACAATGT 2685
                ** * ***************  ********** **  * ** ********* **** **

Patient 6       GGTTCTTCTTCTCGTTCTTTTTTTGAAGATTTATTGTTTGACAAAGTTAAACTTTCAGAT 2757
Patient 9       GGTTCTTCTTCTCGTTCTTTTTTTGAAGATTTATTGTTTGACAAAGTTAAACTTTCAGAT 2757
Patient 10      GGTTCTTCTTCTCGTTCTTTTTTTGAAGATTTATTGTTTGACAAAGTTAAACTTTCAGAT 2757
Patient 5       GGTTCTTCTTCTCGTTCTTTTTTTGAAGATTTATTGTTTGACAAAGTTAAACTTTCAGAT 2757
Patient 4       GGTTCTTCTTCTCGTTCTTTTTTTGAAGATTTATTGTTTGACAAAGTTAAACTTTCAGAT 2757
Patient 7       GGTTCTTCTTCTCGTTCTTTTTTTGAAGATTTATTGTTTGACAAAGTTAAACTTTCAGAT 2757
Patient 2       GGTTCTTCTTCTCGTTCTTTTTTTGAAGATTTATTGTTTGACAAAGTTAAACTTTCAGAT 2757
Patient 1       GGTTCTTCGTCTAGATCTTTGTTAGAGGATTTATTATTCAACAAGGTCAAACTTTCAGAT 2745
Patient 8       GGTTCTTCGTCTAGATCTTTGTTAGAGGATTTATTATTCAACAAAGTCAAACTTTCAGAT 2745
                ******** *** * ***** ** ** ******** **  **** ** ************

Patient 6       GTTGGTTTTGTTGAAGCTTATAACAATTGTACTGGTGGTAGTGAAATTAGAGATCTTCTT 2817
Patient 9       GTTGGTTTTGTTGAAGCTTATAACAATTGTACTGGTGGTAGTGAAATTAGAGATCTTCTT 2817
Patient 10      GTTGGTTTTGTTGAAGCTTATAACAATTGTACTGGTGGTAGTGAAATTAGAGATCTTCTT 2817
Patient 5       GTTGGTTTTGTTGAAGCTTATAACAATTGTACTGGTGGTAGTGAAATTAGAGATCTTCTT 2817
Patient 4       GTTGGTTTTGTTGAAGCTTATAACAATTGTACTGGTGGTAGTGAAATTAGAGATCTTCTT 2817
Patient 7       GTTGGTTTTGTTGAAGCTTATAACAATTGTACTGGTGGTAGTGAAATTAGAGATCTTCTT 2817
Patient 2       GTTGGTTTTGTTGAAGCTTATAACAATTGTACTGGTGGTAGTGAAATTAGAGATCTTCTT 2817
Patient 1       GTAGGTTTTGTTGAAGCTTATAATAATTGCACTGGTGGTAGTGAAATTAGAGATCTTCTC 2805
Patient 8       GTAGGTTTTGTTGAAGCTTATAATAATTGCACTGGTGGTAGTGAAATTAGAGATCTTCTC 2805
                ** ******************** ***** *****************************

Patient 6       TGTGTACAATCCTTTAATGGTATTAAAGTTTTGCCTCCTATTTTGTCTGAATCTCAAATT 2877
Patient 9       TGTGTACAATCCTTTAATGGTATTAAAGTTTTGCCTCCTATTTTGTCTGAATCTCAAATT 2877
Patient 10      TGTGTACAATCCTTTAATGGTATTAAAGTTTTGCCTCCTATTTTGTCTGAATCTCAAATT 2877
Patient 5       TGTGTACAATCCTTTAATGGTATTAAAGTTTTGCCTCCTATTTTGTCTGAATCTCAAATT 2877
Patient 4       TGTGTACAATCCTTTAATGGTATTAAAGTTTTGCCTCCTATTTTGTCTGAATCTCAAATT 2877
Patient 7       TGTGTACAATCCTTTAATGGTATTAAAGTTTTGCCTCCTATTTTGTCTGAATCTCAAATT 2877
Patient 2       TGTGTACAATCCTTTAATGGTATTAAAGTTTTGCCTCCTATTTTGTCTGAATCTCAAATT 2877
Patient 1       TGTGTGCAATCTTTTAATGGTATTAAAGTATTACCTCCCATTTTATCTGAGACTCAAATT 2865
Patient 8       TGTGTGCAATCTTTTAATGGTATTAAAGTATTACCTCCCATTTTATCTGAGACTCAAATT 2865
                ***** ***** ***************** ** ***** ***** *****  ********

Patient 6       TCTGGTTACACCACAGCCGCTACTGTTGCTGCTATGTTTCCACCATGGTCAGCAGCAGCT 2937
Patient 9       TCTGGTTACACCACAGCCGCTACTGTTGCTGCTATGTTTCCACCATGGTCAGCAGCAGCT 2937
```

FIG. 13 CONT.

```
Patient 10      TCTGGTTACACCACAGCCGCTACTGTTGCTGCTATGTTTCCACCATGGTCAGCAGCAGCT 2937
Patient 5       TCTGGTTACACCACAGCCGCTACTGTTGCTGCTATGTTTCCACCATGGTCAGCAGCAGCT 2937
Patient 4       TCTGGTTACACCACAGCCGCTACTGTTGCTGCTATGTTTCCACCATGGTCAGCAGCAGCT 2937
Patient 7       TCTGGTTACACCACAGCCGCTACTGTTGCTGCTATGTTTCCACCATGGTCAGCAGCAGCT 2937
Patient 2       TCTGGTTACACCACAGCCGCTACTGTTGCTGCTATGTTTCCACCATGGTCAGCAGCAGCT 2937
Patient 1       TCTGGCTATACTACAGCTGCTACTGTGGCGGCTATGTTTCCGCCATGGTCTGCTGCTGCT 2925
Patient 8       TCTGGCTATACTACAGCTGCTACTGTGGCGGCTATGTTTCCGCCATGGTCTGCTGCTGCT 2925
                ***** ** ** ***** ******** ** *********** ******** ** ** ***

Patient 6       GGCATACCATTTTCTCTTAATGTACAATATAGAATTAATGGTTTGGGTGTTACTATGGAT 2997
Patient 9       GGCATACCATTTTCTCTTAATGTACAATATAGAATTAATGGTTTGGGTGTTACTATGGAT 2997
Patient 10      GGCATACCATTTTCTCTTAATGTACAATATAGAATTAATGGTTTGGGTGTTACTATGGAT 2997
Patient 5       GGCATACCATTTTCTCTTAATGTACAATATAGAATTAATGGTTTGGGTGTTACTATGGAT 2997
Patient 4       GGCATACCATTTTCTCTTAATGTACAATATAGAATTAATGGTTTGGGTGTTACTATGGAT 2997
Patient 7       GGCATACCATTTTCTCTTAATGTACAATATAGAATTAATGGTTTGGGTGTTACTATGGAT 2997
Patient 2       GGCATACCATTTTCTCTTAATGTACAATATAGAATTAATGGTTTGGGTGTTACTATGGAT 2997
Patient 1       GGTGTACCATTTTCTCTTAATGTACAATATAGAATTAATGGTTTGGGTGTTACTATGGAT 2985
Patient 8       GGTGTACCATTTTCTCTTAATGTACAATATAGAATTAATGGTTTGGGTGTTACTATGGAT 2985
                **  ********************************************************

Patient 6       GTTCTTAATAAAAATCAAAAGTTGATAGCTACTGCTTTTAATAATGCTCTTCTTTCTATT 3057
Patient 9       GTTCTTAATAAAAATCAAAAGTTGATAGCTACTGCTTTTAATAATGCTCTTCTTTCTATT 3057
Patient 10      GTTCTTAATAAAAATCAAAAGTTGATAGCTACTGCTTTTAATAATGCTCTTCTTTCTATT 3057
Patient 5       GTTCTTAATAAAAATCAAAAGTTGATAGCTACTGCTTTTAATAATGCTCTTCTTTCTATT 3057
Patient 4       GTTCTTAATAAAAATCAAAAGTTGATAGCTACTGCTTTTAATAATGCTCTTCTTTCTATT 3057
Patient 7       GTTCTTAATAAAAATCAAAAGTTGATAGCTACTGCTTTTAATAATGCTCTTCTTTCTATT 3057
Patient 2       GTTCTTAATAAAAATCAAAAGTTGATAGCTACTGCTTTTAATAATGCTCTTCTTTCTATT 3057
Patient 1       GTTCTTAATAAGAATCAAAAGTTAATAGCTAATGCTTTTAATAAAGCTCTTCTTTCTATC 3045
Patient 8       GTTCTTAATAAGAATCAAAAGTTAATAGCTAATGCTTTTAATAAAGCTCTTCTTTCTATC 3045
                *********** *********** ******* ************ ************** 

Patient 6       CAGAATGGTTTTAGTGCTACCAACTCTGCACTTGCTAAAATACAAAGTGTTGTTAATTCT 3117
Patient 9       CAGAATGGTTTTAGTGCTACCAACTCTGCACTTGCTAAAATACAAAGTGTTGTTAATTCT 3117
Patient 10      CAGAATGGTTTTAGTGCTACCAACTCTGCACTTGCTAAAATACAAAGTGTTGTTAATTCT 3117
Patient 5       CAGAATGGTTTTAGTGCTACCAACTCTGCACTTGCTAAAATACAAAGTGTTGTTAATTCT 3117
Patient 4       CAGAATGGTTTTAGTGCTACCAACTCTGCACTTGCTAAAATACAAAGTGTTGTTAATTCT 3117
Patient 7       CAGAATGGTTTTAGTGCTACCAACTCTGCACTTGCTAAAATACAAAGTGTTGTTAATTCT 3117
Patient 2       CAGAATGGTTTTAGTGCTACCAACTCTGCACTTGCTAAAATACAAAGTGTTGTTAATTCT 3117
Patient 1       CAGAATGGTTTTACTGCTACTAACTCTGCTCTTGCTAAAATTCAAAGTGTCGTTAATGCT 3105
Patient 8       CAGAATGGTTTTACTGCTACTAACTCTGCTCTTGCTAAAATTCAAAGTGTCGTTAATGCT 3105
                ************* ****** ******** *********** ******** ****** **

Patient 6       AATGCTCAAGCACTTAATAGTTTGTTACAGCAATTATTTAATAAATTTGGTGCAATTAGT 3177
Patient 9       AATGCTCAAGCACTTAATAGTTTGTTACAGCAATTATTTAATAAATTTGGTGCAATTAGT 3177
Patient 10      AATGCTCAAGCACTTAATAGTTTGTTACAGCAATTATTTAATAAATTTGGTGCAATTAGT 3177
Patient 5       AATGCTCAAGCACTTAATAGTTTGTTACAGCAATTATTTAATAAATTTGGTGCAATTAGT 3177
Patient 4       AATGCTCAAGCACTTAATAGTTTGTTACAGCAATTATTTAATAAATTTGGTGCAATTAGT 3177
Patient 7       AATGCTCAAGCACTTAATAGTTTGTTACAGCAATTATTTAATAAATTTGGTGCAATTAGT 3177
Patient 2       AATGCTCAAGCACTTAATAGTTTGTTACAGCAATTATTTAATAAATTTGGTGCAATTAGT 3177
Patient 1       AATGCTCAAGCACTTAATAGTTTGTTACAACAATTATTTAATAAATTTGGTGCTATTAGT 3165
Patient 8       AATGCTCAAGCACTTAATAGTTTGTTACAACAATTATTTAATAAATTTGGTGCTATTAGT 3165
                ***************************** *********************** ******

Patient 6       TCTTCTTTACAAGAAATTTTATCTCGTCTCGATGCTTTAGAGGCTCAGGTTCAGATTGAT 3237
Patient 9       TCTTCTTTACAAGAAATTTTATCTCGTCTCGATGCTTTAGAGGCTCAGGTTCAGATTGAT 3237
Patient 10      TCTTCTTTACAAGAAATTTTATCTCGTCTCGATGCTTTAGAGGCTCAGGTTCAGATTGAT 3237
Patient 5       TCTTCTTTACAAGAAATTTTATCTCGTCTCGATGCTTTAGAGGCTCAGGTTCAGATTGAT 3237
Patient 4       TCTTCTTTACAAGAAATTTTATCTCGTCTCGATGCTTTAGAGGCTCAGGTTCAGATTGAT 3237
Patient 7       TCTTCTTTACAAGAAATTTTATCTCGTCTCGATGCTTTAGAGGCTCAGGTTCAGATTGAT 3237
Patient 2       TCTTCTTTACAAGAAATTTTATCTCGTCTCGATGTTTTAGAGGCTCAGGTTCAGATTGAT 3237
Patient 1       TCTTCTTTACAAGAAATTTTGTCTCGCCTTGATAATTTAGAAGCTCAGGTTCAGATTGAT 3225
Patient 8       TCTTCTTTACAAGAAATTTTGTCTCGCCTTGATAATTTAGAAGCTCAGGTTCAGATTGAT 3225
                ******************** ***** ** ***  ****** ******************

Patient 6       AGGCTTATTAATGGTCGTTTAACTGCTTTAAATGCTTATGTCTCTCAACAGCTTAGTGAT 3297
Patient 9       AGGCTTATTAATGGTCGTTTAACTGCTTTAAATGCTTATGTCTCTCAACAGCTTAGTGAT 3297
Patient 10      AGGCTTATTAATGGTCGTTTAACTGCTTTAAATGCTTATGTCTCTCAACAGCTTAGTGAT 3297
Patient 5       AGGCTTATTAATGGTCGTTTAACTGCTTTAAATGCTTATGTCTCTCAACAGCTTAGTGAT 3297
Patient 4       AGGCTTATTAATGGTCGTTTAACTGCTTTAAATGCTTATGTCTCTCAACAGCTTAGTGAT 3297
Patient 7       AGGCTTATTAATGGTCGTTTAACTGCTTTAAATGCTTATGTCTCTCAACAGCTTAGTGAT 3297
Patient 2       AGGCTTATTAATGGTCGTTTAACTGCTTTAAATGCTTATGTCTCTCAACAGCTTAGTGAT 3297
Patient 1       AGGCTCATTAATGGTCGTTTGACTGCTTTAAATGCTTATGTTTCTCAACAGCTTAGTGAT 3285
Patient 8       AGGCTCATTAATGGTCGTTTGACTGCTTTAAATGCTTATGTTTCTCAACAGCTTAGTGAT 3285
                ***** ************** ******************** ******************

Patient 6       ATTTCTCTTGTAAAATTTGGTGCTGCTTTAGCTATGGAGAAGGTTAATGAGTGTGTTAAA 3357
```

FIG. 13 CONT.

```
Patient 9     ATTTCTCTTGTAAAATTTGGTGCTGCTTTAGCTATGGAGAAGGTTAATGAGTGTGTTAAA 3357
Patient 10    ATTTCTCTTGTAAAATTTGGTGCTGCTTTAGCTATGGAGAAGGTTAATGAGTGTGTTAAA 3357
Patient 5     ATTTCTCTTGTAAAATTTGGTGCTGCTTTAGCTATGGAGAAGGTTAATGAGTGTGTTAAA 3357
Patient 4     ATTTCTCTTGTAAAATTTGGTGCTGCTTTAGCTATGGAGAAGGTTAATGAGTGTGTTAAA 3357
Patient 7     ATTTCTCTTGTAAAATTTGGTGCTGCTTTAGCTATGGAGAAGGTTAATGAGTGTGTTAAA 3357
Patient 2     ATTTCTCTTGTAAAATTTGGTGCTGCTTTAGCTATGGAGAAGGTTAATGAGTGTGTTAAA 3357
Patient 1     ATTACACTTATTAAGGCTGGAGCTTCTCGTGCTATTGAGAAGGTTAATGAGTGTGTTAAA 3345
Patient 8     ATTACACTTATTAAGGCTGGAGCTTCTCGTGCTATTGAGAAGGTTAATGAGTGTGTTAAA 3345
              *** * *** * **   *** *** **   ***** ************************

Patient 6     AGTCAATCTCCTCGTATTAATTTTTGTGGTAATGGTAATCATATTTTGTCATTAGTTCAA 3417
Patient 9     AGTCAATCTCCTCGTATTAATTTTTGTGGTAATGGTAATCATATTTTGTCATTAGTTCAA 3417
Patient 10    AGTCAATCTCCTCGTATTAATTTTTGTGGTAATGGTAATCATATTTTGTCATTAGTTCAA 3417
Patient 5     AGTCAATCTCCTCGTATTAATTTTTGTGGTAATGGTAATCATATTTTGTCATTAGTTCAA 3417
Patient 4     AGTCAATCTCCTCGTATTAATTTTTGTGGTAATGGTAATCATATTTTGTCATTAGTTCAA 3417
Patient 7     AGTCAATCTCCTCGTATTAATTTTTGTGGTAATGGTAATCATATTTTGTCATTAGTTCAA 3417
Patient 2     AGTCAATCTCCTCGTATTAATTTTTGTGGTAATGGTAATCATATTTTGTCATTAGTTCAA 3417
Patient 1     AGTCAATCCCCTCGTATAAATTTTTGTGGCAATGGTAACCACATTTTATCATTGGTTCAA 3405
Patient 8     AGTCAATCCCCTCGTATAAATTTTTGTGGCAATGGTAACCACATTTTATCATTGGTTCAA 3405
              ******** ******** *********** ******** ** ***** ***** ******

Patient 6     AATGCTCCTTATGGTTTGTTGTTTATGCATTTTAGTTATAAACCTATTTCTTTTAAAACT 3477
Patient 9     AATGCTCCTTATGGTTTGTTGTTTATGCATTTTAGTTATAAACCTATTTCTTTTAAAACT 3477
Patient 10    AATGCTCCTTATGGTTTGTTGTTTATGCATTTTAGTTATAAACCTATTTCTTTTAAAACT 3477
Patient 5     AATGCTCCTTATGGTTTGTTGTTTATGCATTTTAGTTATAAACCTATTTCTTTTAAAACT 3477
Patient 4     AATGCTCCTTATGGTTTGTTGTTTATGCATTTTAGTTATAAACCTATTTCTTTTAAAACT 3477
Patient 7     AATGCTCCTTATGGTTTGTTGTTTATGCATTTTAGTTATAAACCTATTTCTTTTAAAACT 3477
Patient 2     AATGCTCCTTATGGTTTGTTGTTTATGCATTTTAGTTATAAACCTATTTCTTTTAAAACT 3477
Patient 1     AATGCTCCTTATGGTTTGCTTTTCATTCATTTTAGTTATAAACCTACTTCTTTTAAAACT 3465
Patient 8     AATGCTCCTTATGGTTTGCTTTTCATTCATTTTAGTTATAAACCTACTTCTTTTAAAACT 3465
              ****************** * ** ** ******************* *************

Patient 6     GTTTTAGTAAGTCCTGGTTTGTGTATATCAGGTGATGTAGGTATTGCACCTAAACAAGGG 3537
Patient 9     GTTTTAGTAAGTCCTGGTTTGTGTATATCAGGTGATGTAGGTATTGCACCTAAACAAGGG 3537
Patient 10    GTTTTAGTAAGTCCTGGTTTGTGTATATCAGGTGATGTAGGTATTGCACCTAAACAAGGG 3537
Patient 5     GTTTTAGTAAGTCCTGGTTTGTGTATATCAGGTGATGTAGGTATTGCACCTAAACAAGGG 3537
Patient 4     GTTTTAGTAAGTCCTGGTTTGTGTATATCAGGTGATGTAGGTATTGCACCTAAACAAGGG 3537
Patient 7     GTTTTAGTAAGTCCTGGTTTGTGTATATCAGGTGATGTAGGTATTGCACCTAAACAAGGG 3537
Patient 2     GTTTTAGTAAGTCCTGGTTTGTGTATATCAGGTGATGTAGGTATTGCACCTAAACAAGGG 3537
Patient 1     GTCTTAGTAAGTCCAGGTTTATGTTTATCCGGTGATAGAGGTATTGCACCTAAGCAAGGT 3525
Patient 8     GTCTTAGTAAGTCCAGGTTTATGTTTATCCGGTGATAGAGGTATTGCACCTAAGCAAGGT 3525
              ** *********** ***** *** **** ******  *************** *****

Patient 6     TATTTTATTAAACATAATGATCATTGGATGTTCACTGGTAGTTCTTACTATTATCCTGAA 3597
Patient 9     TATTTTATTAAACATAATGATCATTGGATGTTCACTGGTAGTTCTTACTATTATCCTGAA 3597
Patient 10    TATTTTATTAAACATAATGATCATTGGATGTTCACTGGTAGTTCTTACTATTATCCTGAA 3597
Patient 5     TATTTTATTAAACATAATGATCATTGGATGTTCACTGGTAGTTCTTACTATTATCCTGAA 3597
Patient 4     TATTTTATTAAACATAATGATCATTGGATGTTCACTGGTAGTTCTTACTATTATCCTGAA 3597
Patient 7     TATTTTATTAAACATAATGATCATTGGATGTTCACTGGTAGTTCTTACTATTATCCTGAA 3597
Patient 2     TATTTTATTAAACATAATGATCATTGGATGTTCACTGGTAGTTCTTACTATTATCCTGAA 3597
Patient 1     TATTTTATTAAACAAAATGATTCCTGGATGTTTACTGGTAGTTCCTATTATTACCCAGAA 3585
Patient 8     TATTTTATTAAACAAAATGATTCCTGGATGTTTACTGGTAGTTCCTATTATTATCCAGAA 3585
              ************** ******   ******** *********** ** ***** ** ***

Patient 6     CCAATTTCAGATAAAAATGTTGTTTTTATGAATACTTGTTCTGTTAATTTTACTAAAGCG 3657
Patient 9     CCAATTTCAGATAAAAATGTTGTTTTTATGAATACTTGTTCTGTTAATTTTACTAAAGCG 3657
Patient 10    CCAATTTCAGATAAAAATGTTGTTTTTATGAATACTTGTTCTGTTAATTTTACTAAAGCG 3657
Patient 5     CCAATTTCAGATAAAAATGTTGTTTTTATGAATACTTGTTCTGTTAATTTTACTAAAGCG 3657
Patient 4     CCAATTTCAGATAAAAATGTTGTTTTTATGAATACTTGTTCTGTTAATTTTACTAAAGCG 3657
Patient 7     CCAATTTCAGATAAAAATGTTGTTTTTATGAATACTTGTTCTGTTAATTTTACTAAAGCG 3657
Patient 2     CCAATTTCAGATAAAAATGTTGTTTTTATGAATACTTGTTCTGTTAATTTTACTAAAGCG 3657
Patient 1     CCAATTTCAGATAAAAATGTTGTTTTCATGAATAGTTGCTCTGTTAATTTTACTAAAGCT 3645
Patient 8     CCAATTTCAGATAAAAATGTTGTTTTCATGAATAGTTGCTCTGTTAATTTTACTAAAGCT 3645
              ************************** ******* *** ********************

Patient 6     CCTCTTGTTTATTTGAATCATTCTGTACCAAAATTGTCTGATTTTGAATCTGAGTTATCT 3717
Patient 9     CCTCTTGTTTATTTGAATCATTCTGTACCAAAATTGTCTGATTTTGAATCTGAGTTATCT 3717
Patient 10    CCTCTTGTTTATTTGAATCATTCTGTACCAAAATTGTCTGATTTTGAATCTGAGTTATCT 3717
Patient 5     CCTCTTGTTTATTTGAATCATTCTGTACCAAAATTGTCTGATTTTGAATCTGAGTTATCT 3717
Patient 4     CCTCTTGTTTATTTGAATCATTCTGTACCAAAATTGTCTGATTTTGAATCTGAGTTATCT 3717
Patient 7     CCTCTTGTTTATTTGAATCATTCTGTACCAAAATTGTCTGATTTTGAATCTGAGTTATCT 3717
Patient 2     CCTCTTGTTTATTTGAATCATTCTGTACCAAAATTGTCTGATTTTGAATCTGAGTTATCT 3717
Patient 1     CCATTTATTTATCTTAATAATTCTATACCAAATTTGTCTGATTTTGAAGCCGAGTTTTCT 3705
Patient 8     CCATTTATTTATCTTAATAATTCTATACCAAATTTGTCTGATTTTGAAGCCGAGTTATCT 3705
              **  ** ***** * *** ***** ******* *************** * ***** ***
```

FIG. 13 CONT.

```
Patient 6     CATTGGTTTAAAAATCAAACATCCATTGCGCCTAATTTGACTTTAAATCTTCATACTATT 3777
Patient 9     CATTGGTTTAAAAATCAAACATCCATTGCGCCTAATTTGACTTTAAATCTTCATACTATT 3777
Patient 10    CATTGGTTTAAAAATCAAACATCCATTGCGCCTAATTTGACTTTAAATCTTCATACTATT 3777
Patient 5     CATTGGTTTAAAAATCAAACATCCATTGCGCCTAATTTGACTTTAAATCTTCATACTATT 3777
Patient 4     CATTGGTTTAAAAATCAAACATCCATTGCGCCTAATTTGACTTTAAATCTTCATACTATT 3777
Patient 7     CATTGGTTTAAAAATCAAACATCCATTGCGCCTAATTTGACTTTAAATCTTCATACTATT 3777
Patient 2     CATTGGTTTAAAAATCAAACATCCATTGCGCCTAATTTGACTTTAAATCTTCATACTATT 3777
Patient 1     CTTTGGTTTAAAAATCATACTTCTATAGCACCTAATTTAACCTTTAATTCTCATA---TT 3762
Patient 8     CTTTGGTTTAAAAATCATACTTCTATAGCACCTAATTTAACCTTTAATTCTCATA---TT 3762
              * *************** ** ** ** ** ******** ** ** ***  *****   **

Patient 6     AATGCTACTTTTTTAGATTTGTATTATGAGATGAATCTTATTCAAGAGTCTATTAAGTCT 3837
Patient 9     AATGCTACTTTTTTAGATTTGTATTATGAGATGAATCTTATTCAAGAGTCTATTAAGTCT 3837
Patient 10    AATGCTACTTTTTTAGATTTGTATTATGAGATGAATCTTATTCAAGAGTCTATTAAGTCT 3837
Patient 5     AATGCTACTTTTTTAGATTTGTATTATGAGATGAATCTTATTCAAGAGTCTATTAAGTCT 3837
Patient 4     AATGCTACTTTTTTAGATTTGTATTATGAGATGAATCTTATTCAAGAGTCTATTAAGTCT 3837
Patient 7     AATGCTACTTTTTTAGATTTGTATTATGAGATGAATCTTATTCAAGAGTCTATTAAGTCT 3837
Patient 2     AATGCTACTTTTTTAGATTTGTATTATGAGATGAATCTTATTCAAGAGTCTATTAAGTCT 3837
Patient 1     AATGCTACTTTTTTAGATCTGTATTATGAAATGAATGTTATTCAGGAATCTATTAAATCT 3822
Patient 8     AATGCTACTTTTTTAGATCTGTATTATGAAATGAATGTTATTCAGGAATCTATTAAATCT 3822
              ****************** ********** ****** ******* ** ******** ***

Patient 6     TTGAATAATAGTTATATCAATCTTAAAGATATAGGTACATATGAAATGTATGTAAAATGG 3897
Patient 9     TTGAATAATAGTTATATCAATCTTAAAGATATAGGTACATATGAAATGTATGTAAAATGG 3897
Patient 10    TTGAATAATAGTTATATCAATCTTAAAGATATAGGTACATATGAAATGTATGTAAAATGG 3897
Patient 5     TTGAATAATAGTTATATCAATCTTAAAGATATAGGTACATATGAAATGTATGTAAAATGG 3897
Patient 4     TTGAATAATAGTTATATCAATCTTAAAGATATAGGTACATATGAAATGTATGTAAAATGG 3897
Patient 7     TTGAATAATAGTTATATCAATCTTAAAGATATAGGTACATATGAAATGTATGTAAAATGG 3897
Patient 2     TTGAATAATAGTTATATCAATCTTAAAGATATAGGTACATATGAAATGTATGTAAAATGG 3897
Patient 1     TTGAACAGTAGTTTTATTAATCTTAAAGAAATAGGTACTTATGAAATGTATGTTAAATGG 3882
Patient 8     TTGAACAGTAGTTTTATTAATCTTAAAGAAATAGGTACTTATGAAATGTATGTTAAATGG 3882
              ***** * ***** *** *********** ******** ************** ******

Patient 6     CCTTGGTATGTTTGGCTACTAATTTCTTTTTCATTTATAATATTCCTTGTATTGCTCTTT 3957
Patient 9     CCTTGGTATGTTTGGCTACTAATTTCTTTTTCATTTATAATATTCCTTGTATTGCTCTTT 3957
Patient 10    CCTTGGTATGTTTGGCTACTAATTTCTTTTTCATTTATAATATTCCTTGTATTGCTCTTT 3957
Patient 5     CCTTGGTATGTTTGGCTACTAATTTCTTTTTCATTTATAATATTCCTTGTATTGCTCTTT 3957
Patient 4     CCTTGGTATGTTTGGCTACTAATTTCTTTTTCATTTATAATATTCCTTGTATTGCTCTTT 3957
Patient 7     CCTTGGTATGTTTGGCTACTAATTTCTTTTTCATTTATAATATTCCTTGTATTGCTCTTT 3957
Patient 2     CCTTGGTATGTTTGGCTACTAATTTCTTTTTCATTTATAATATTCCTTGTATTGCTCTTT 3957
Patient 1     CCTTGGTACATTTGGTTGTTAATTGTCATTTTATTTATAATTTTTCTTATGATACTTTTC 3942
Patient 8     CCTTGGTACATTTGGTTGTTAATTGTCATTTTATTTATAATTTTTCTTATGATACTTTTC 3942
              ********  ***** *  *****    *** ********* ** *** *  * ** **

Patient 6     TTTATATGTTGTTGTACTGGTTGTGGTTCTGCATGTTTTAGTAAATGTCATAATTGTTGT 4017
Patient 9     TTTATATGTTGTTGTACTGGTTGTGGTTCTGCATGTTTTAGTAAATGTCATAATTGTTGT 4017
Patient 10    TTTATATGTTGTTGTACTGGTTGTGGTTCTGCATGTTTTAGTAAATGTCATAATTGTTGT 4017
Patient 5     TTTATATGTTGTTGTACTGGTTGTGGTTCTGCATGTTTTAGTAAATGTCATAATTGTTGT 4017
Patient 4     TTTATATGTTGTTGTACTGGTTGTGGTTCTGCATGTTTTAGTAAATGTCATAATTGTTGT 4017
Patient 7     TTTATATGTTGTTGTACTGGTTGTGGTTCTGCATGTTTTAGTAAATGTCATAATTGTTGT 4017
Patient 2     TTTATATGTTGTTGTACTGGTTGTGGTTCTGCATGTTTTAGTAAATGTCATAATTGTTGT 4017
Patient 1     TTTATATGCTGCTGTACTGGTTGTGGTTCAGCATGTTTTAGTAAATGTCATAATTGTTGT 4002
Patient 8     TTTATATGCTGCTGTACTGGTTGTGGTTCAGCATGTTTTAGTAAATGTCATAATTGTTGT 4002
              ******** ** ***************** ******************************

Patient 6     GATGAGTATGGTGGTCATCATGATTTTGTTATCAAAACATCTCATGATGATTAG 4071
Patient 9     GATGAGTATGGTGGTCATCATGATTTTGTTATCAAAACATCTCATGATGATTAG 4071
Patient 10    GATGAGTATGGTGGTCATCATGATTTTGTTATCAAAACATCTCATGATGATTAG 4071
Patient 5     GATGAGTATGGTGGTCATCATGATTTTGTTATCAAAACATCTCATGATGATTAG 4071
Patient 4     GATGAGTATGGTGGTCATCATGATTTTGTTATCAAAACATCTCATGATGATTAG 4071
Patient 7     GATGAGTATGGTGGTCATCATGATTTTGTTATCAAAACATCTCATGATGATTAG 4071
Patient 2     GATGAGTATGGTGGTCATCATGATTTTGTTATCAAAACATCTCATGATGATTAG 4071
Patient 1     GATGAGTATGGGGGTCACAATGATTTTGTTATTAAAGCATCTCATGATGATTAG 4056
Patient 8     GATGAGTATGGGGGTCACAATGATTTTGTTATTAAAGCATCTCATGATGATTAG 4056
              *********** ***** ************** *** *****************
```

FIG. 13 CONT.

Fig. 14. Multiple alignment of the nucleocapsid genes of CoV-HKU1 from patients 1, 2, 4, 5, 6, 7, 8, 9, and 10.

```
Patient 4       ATGTCTTATACTCCCGGTCATTATGCTGGAAGTAGAAGCTCCTCTGGAAATCGTTCAGGA 60
Patient 6       ATGTCTTATACTCCCGGTCATTATGCTGGAAGTAGAAGCTCCTCTGGAAATCGTTCAGGA 60
Patient 7       ATGTCTTATACTCCCGGTCATTATGCTGGAAGTAGAAGCTCCTCTGGAAATCGTTCAGGA 60
Patient 9       ATGTCTTATACTCCCGGTCATTATGCTGGAAGTAGAAGCTCCTCTGGAAATCGTTCAGGA 60
Patient 10      ATGTCTTATACTCCCGGTCATTATGCTGGAAGTAGAAGCTCCTCTGGAAATCGTTCAGGA 60
Patient 2       ATGTCTTATACTCCCGGTCATTATGCTGGAAGTAGAAGCTCCTCTGGAAATCGTTCAGGA 60
Patient 5       ATGTCTTATACTCCCGGTCATTATGCTGGAAGTAGAAGCTCCTCTGGAAATCGTTCAGGA 60
Patient 1       ATGTCTTATACTCCCGGTCATCATGCTGGAAGTAGAAGCTCCTCTGGAAATCGTTCAGGA 60
Patient 8       ATGTCTTATACTCCCGGTCATCATGCTGGAAGTAGAAGCTCCTCTGGAAATCGTTCAGGA 60
                ********************* **************************************

Patient 4       ATCCTCAAGAAAACTTCTTGGGCTGACCAATCTGAACGAAATTACCAAACCTTTAATAGA 120
Patient 6       ATCCTCAAGAAAACTTCTTGGGCTGACCAATCTGAACGAAATTACCAAACCTTTAATAGA 120
Patient 7       ATCCTCAAGAAAACTTCTTGGGCTGACCAATCTGAACGAAATTACCAAACCTTTAATAGA 120
Patient 9       ATCCTCAAGAAAACTTCTTGGGCTGACCAATCTGAACGAAATTACCAAACCTTTAATAGA 120
Patient 10      ATCCTCAAGAAAACTTCTTGGGCTGACCAATCTGAACGAAATTACCAAACCTTTAATAGA 120
Patient 2       ATCCTCAAGAAAACTTCTTGGGCTGACCAATCTGAGCGAAATTACCAAACCTTTAATAGA 120
Patient 5       ATCCTCAAGAAAACTTCTTGGGCTGACCAATCTGAGCGAAATTACCAAACCTTTAATAGA 120
Patient 1       ATCCTCAAGAAAACTTCTTGGGTTGACCAATCTGAGCGAAGCCATCAAACCTATAATAGA 120
Patient 8       ATCCTCAAGAAAACTTCTTGGGTTGACCAATCTGAGCGAAGCCATCAAACCTATAATAGA 120
                ********************** ************ ****   * ******* *******

Patient 4       GGCAGAAAAACCCAACCTAAATTCACTGTGTCTACTCAACCACAAGGAAATACTATCCCA 180
Patient 6       GGCAGAAAAACCCAACCTAAATTCACTGTGTCTACTCAACCACAAGGAAATACTATCCCA 180
Patient 7       GGCAGAAAAACCCAACCTAAATTCACTGTGTCTACTCAACCACAAGGAAATACTATCCCA 180
Patient 9       GGCAGAAAAACCCAACCTAAATTCACTGTGTCTACTCAACCACAAGGAAATACTATCCCA 180
Patient 10      GGCAGAAAAACCCAACCTAAATTCACTGTGTCTACTCAACCACAAGGAAATACTATCCCA 180
Patient 2       GGCAGAAAAACCCAACCTAAATTCACTGTGTCTACTCAACCACAAGGAAATACTATCCCA 180
Patient 5       GGCAGAAAAACCCAACCTAAATTCACTGTGTCTACTCAACCACAAGGAAATACTATCCCA 180
Patient 1       GGCAGAAAACCCCAACCCAAATTCACTGTGTCTACTCAACCACAAGGAAACCCTATCCCA 180
Patient 8       GGCAGAAAACCCCAACCAAAATTCACTGTGTCTACTCAACCACAAGGAAACCCTATCCCA 180
                ********* ******* ********************************  ********

Patient 4       CATTATTCCTGGTTCTCCGGGATCACTCAATTTCAAAAAGGTAGAGACTTTAAATTTTCA 240
Patient 6       CATTATTCCTGGTTCTCCGGGATCACTCAATTTCAAAAAGGTAGAGACTTTAAATTTTCA 240
Patient 7       CATTATTCCTGGTTCTCCGGGATCACTCAATTTCAAAAAGGTAGAGACTTTAAATTTTCA 240
Patient 9       CATTATTCCTGGTTCTCCGGGATCACTCAATTTCAAAAAGGTAGAGACTTTAAATTTTCA 240
Patient 10      CATTATTCCTGGTTCTCCGGGATCACTCAATTTCAAAAAGGTAGAGACTTTAAATTTTCA 240
Patient 2       CATTATTCCTGGTTCTCCGGGATCACTCAATTTCAAAAAGGTAGAGACTTTAAATTTTCA 240
Patient 5       CATTATTCCTGGTTCTCCGGGATCACTCAATTTCAAAAAGGTAGAGACTTTAAATTTTCA 240
Patient 1       CATTATTCCTGGTTCTCTGGGATTACCCAATTTCAAAAAGGTAGAGACTTTAAATTTCCA 240
Patient 8       CATTATTCCTGGTTCTCTGGGATTACCCAATTTCAAAAAGGTAGAGACTTTAAATTTCCA 240
                ***************** ***** ** ****************************** **

Patient 4       GATGGTCAAGGAGTTCCCATTGCTTTCGGAGTACCCCCTTCTGAAGCAAAAGGATATTGG 300
Patient 6       GATGGTCAAGGAGTTCCCATTGCTTTCGGAGTACCCCCTTCTGAAGCAAAAGGATATTGG 300
Patient 7       GATGGTCAAGGAGTTCCCATTGCTTTCGGAGTACCCCCTTCTGAAGCAAAAGGATATTGG 300
Patient 9       GATGGTCAAGGAGTTCCCATTGCTTTCGGAGTACCCCCTTCTGAAGCAAAAGGATATTGG 300
Patient 10      GATGGTCAAGGAGTTCCCATTGCTTTCGGAGTACCCCCTTCTGAAGCAAAAGGATATTGG 300
Patient 2       GATGGTCAAGGAGTTCCCATTGCTTTCGGAGTACCCCCTTCTGAAGCAAAAGGATATTGG 300
Patient 5       GATGGTCAAGGAGTTCCCATTGCTTTCGGAGTACCCCCTTCTGAAGCAAAAGGATATTGG 300
Patient 1       GATGGTCAAGGAGTACCCATTGCTTACGGGATACCCCCTTCTGAAGCAAAAGGATATTGG 300
Patient 8       GATGGTCAAGGAGTACCCATTGCTTACGGGATACCCCCTTCTGAAGCAAAAGGATATTGG 300
                ************** ********** ***  *****************************

Patient 4       TATAGACACAGCCGGCGTTCTTTTAAAACAGCTGATGGTCAACAAAAGCAGTTGTTACCG 360
Patient 6       TATAGACACAGCCGGCGTTCTTTTAAAACAGCTGATGGTCAACAAAAGCAGTTGTTACCG 360
Patient 7       TATAGACACAGCCGGCGTTCTTTTAAAACAGCTGATGGTCAACAAAAGCAGTTGTTACCG 360
Patient 9       TATAGACACAACCGGCGTTCTTTTAAAACAGCTGATGGTCAACAAAAGCAGTTGTTACCG 360
Patient 10      TATAGACACAGCCGGCGTTCTTTTAAAACAGCTGATGGTCAACAAAAGCAGTTGTTACCG 360
Patient 2       TATAGACACAGCCGGCGTTCTTTTAAAACAGCTGATGGTCAACAAAAGCAGTTGTTACCG 360
Patient 5       TATAGACACAGCCGGCGTTCTTTTAAAACAGCTGATGGTCAACAAAAGCAGTTGTTACCG 360
Patient 1       TATAAACACAACCGGCGTTCTTTTAAAACAGCTGATGGTCAACAAAAGCAGTTGTTACCA 360
Patient 8       TATAAACACAACCGGCGTTCTTTTAAAACAGCTGATGGTCAACAAAAGCAGTTGTTACCA 360
                **** ***** ************************************************ 

Patient 4       AGATGGTATTTCTACTATCTCGGTACCGGCCCATATGCCAATGCATCCTATGGTGAATCC 420
Patient 6       AGATGGTATTTCTACTATCTCGGTACCGGCCCATATGCCAATGCATCCTATGGTGAATCC 420
Patient 7       AGATGGTATTTCTACTATCTCGGTACCGGCCCATATGCCAATGCATCCTATGGTGAATCC 420
Patient 9       AGATGGTATTTCTACTATCTCGGTACCGGCCCATATGCCAATGCATCCTATGGTGAATCC 420
Patient 10      AGATGGTATTTCTACTATCTCGGTACCGGCCCATATGCCAATGCATCCTATGGTGAATCC 420
Patient 2       AGATGGTATTTCTACTATCTCGGTACCGGCCCATATGCCAATGCATCCTATGGTGAATCC 420
Patient 5       AGATGGTATTTCTACTATCTCGGTACCGGCCCATATGCCAATGCATCCTATGGTGAATCC 420
Patient 1       AGATGGTATTTCTACTATCTCGGTACCGGTCCATATGCCAGTTCATCCTATGGTGATGCC 420
```

FIG. 14

```
Patient 8     AGATGGTATTTCTACTATCTCGGTACCGGTCCATATGCCAGTTCATCCTATGGTGATGCC 420
              ***************************** ********** * *************  **

Patient 4     CTCGAAGGGGTCTTCTGGGTTGCTAATCACCAAGCTGACACTTCTACTCCCTCCGATGTT 480
Patient 6     CTCGAAGGGGTCTTCTGGGTTGCTAATCACCAAGCTGACACTTCTACTCCCTCCGATGTT 480
Patient 7     CTCGAAGGGGTCTTCTGGGTTGCTAATCACCAAGCTGACACTTCTACTCCCTCCGATGTT 480
Patient 9     CTCGAAGGGGTCTTCTGGGTTGCTAATCACCAAGCTGACACTTCTACTCCCTCCGATGTT 480
Patient 10    CTCGAAGGGGTCTTCTGGGTTGCTAATCACCAAGCTGACACTTCTACTCCCTCCGATGTT 480
Patient 2     CTCGAAGGGGTCTTCTGGGTTGCTAATCACCAAGCTGACACTTCTACTCCCTCCGATGTT 480
Patient 5     CTCGAAGGGGTCTTCTGGGTTGCTAATCACCAAGCTGACACTTCTACTCCCTCCGATGTT 480
Patient 1     CACGAAGGTATCTTCTGGGTCGCTAGTCACCAAGCTGACACTTCTATTCCCTCCGATGTT 480
Patient 8     CACGAAGGTATCTTCTGGGTCGCTAGTCACCAAGCTGATACTTCTATTCCCTCCGATGTT 480
              * ******  ********** **** ************ ******* *************

Patient 4     TCGTCAAGGGATCCTACTACTCAAGAAGCTATCCCTACTAGGTTTCCGCCTGGTACGATT 540
Patient 6     TCGTCAAGGGATCCTACTACTCAAGAAGCTATCCCTACTAGGTTTCCGCCTGGTACGATT 540
Patient 7     TCGTCAAGGGATCCTACTACTCAAGAAGCTATCCCTACTAGGTTTCCGCCTGGTACGATT 540
Patient 9     TCGTCAAGGGATCCTACTACTCAAGAAGCTATCCCTACTAGGTTTCCGCCTGGTACGATT 540
Patient 10    TCGTCAAGGGATCCTACTACTCAAGAAGCTATCCCTACTAGGTTTCCGCCTGGTACGATT 540
Patient 2     TCGTCAAGGGATCCTACTACTCAAGAAGCTATCCCTACTAGGTTTCCGCCTGGTACGATT 540
Patient 5     TCGTCAAGGGATCCTACTACTCAAGAAGCTATCCCTACTAGGTTTCCGCCTGGTACGATT 540
Patient 1     TCGGCAAGGGATCCTACTATTCAAGAAGCTATCCCTACTAGGTTTTCGCCTGGTACGATT 540
Patient 8     TCGGCAAGGGATCCTACTATTCAAGAAGCTATCCCTACTAGGTTTTCGCCTGGTACGATT 540
              *** *************** ************************* **************

Patient 4     TTGCCTCAAGGCTATTATGTTGAAGGCTCAGGAAGGTCTGCTTCTAATAGTCGACCAGGT 600
Patient 6     TTGCCTCAAGGCTATTATGTTGAAGGCTCAGGAAGGTCTGCTTCTAATAGTCGACCAGGT 600
Patient 7     TTGCCTCAAGGCTATTATGTTGAAGGCTCAGGAAGGTCTGCTTCTAATAGTCGACCAGGT 600
Patient 9     TTGCCTCAAGGCTATTATGTTGAAGGCTCAGGAAGGTCTGCTTCTAATAGTCGACCAGGT 600
Patient 10    TTGCCTCAAGGCTATTATGTTGAAGGCTCAGGAAGGTCTGCTTCTAATAGTCGACCAGGT 600
Patient 2     TTGCCTCAAGGCTATTATGTTGAAGGCTCAGGAAGGTCTGCTTCTAATAGTCGACCAGGT 600
Patient 5     TTGCCTCAAGGCTATTATGTTGAAGGCTCAGGAAGGTCTGCTTCTAATAGTCGACCAGGT 600
Patient 1     TTGCCTCAAGGCTATTATGTTGAAGGCTCAGGAAGGTCTGCTTCTAATAGCCGGCCAGGT 600
Patient 8     TTGCCTCAAGGCTATTATGTTGAAGGCTCAGGAAGGTCTGCTTCTAATAGCCGGCCAGGT 600
              ************************************************** ** ******

Patient 4     TCACGTTCTCAATCACGTGGACCCAATAATCGTTCATTAAGTAGAAGTAATTCTAATTTT 660
Patient 6     TCACGTTCTCAATCACGTGGACCCAATAATCGTTCATTAAGTAGAAGTAATTCTAATTTT 660
Patient 7     TCACGTTCTCAATCACGTGGACCCAATAATCGTTCATTAAGTAGAAGTAATTCTAATTTT 660
Patient 9     TCACGTTCTCAATCACGTGGACCCAATAATCGTTCATTAAGTAGAAGTAATTCCAATTTT 660
Patient 10    TCACGTTCTCAATCACGTGGACCCAATAATCGTTCATTAAGTAGAAGTAATTCTAATTTT 660
Patient 2     TCACGTTCTCAATCACGTGGACCCAATAATCGTTCATTAAGTAGAAGTAATTCTAATTTT 660
Patient 5     TCACGTTCTCAATCACGTGGACCCAATAATCGTTCATTAAGTAGAAGTAATTCTAATTTT 660
Patient 1     TCACGTTCTCAATCACGTGGACCCAATAATCGTTCATTAAGTAGAAGTAATTCTAATTTT 660
Patient 8     TCACGTTCTCAATCACGTGGACCCAATAATCGTTCATTAAGTAGAAGTAATTCTAATTTT 660
              ***************************************************** ******

Patient 4     AGACATTCAGATTCTATAGTAAAACCTGATATGGCTGATGAGATTGCTAATCTTGTTTTA 720
Patient 6     AGACATTCAGATTCTATAGTAAAACCTGATATGGCTGATGAGATTGCTAATCTTGTTTTA 720
Patient 7     AGACATTCAGATTCTATAGTAAAACCTGATATGGCTGATGAGATTGCTAATCTTGTTTTA 720
Patient 9     AGACATTCAGATTCTATAGTAAAACCTGATATGGCTGATGAGATTGCTAATCTTGTTTTA 720
Patient 10    AGACATTCAGATTCTATAGTAAAACCTGATATGGCTGATGAGATTGCTAATCTTGTTTTA 720
Patient 2     AGACATTCAGATTCTATAGTAAAACCTGATATGGCTGATGAGATCGCTAATCTTGTTTTA 720
Patient 5     AGACATTCAGATTCTATAGTAAAACCTGATATGGCTGATGAGATCGCTAATCTTGTTTTA 720
Patient 1     AGACATTCTGATTCTATAGTGAAACCTGATATGGCTGATGAGATTGCTAGTCTTGTCTTG 720
Patient 8     AGACATTCTGATTCTATAGTGAAACCTGATATGGCTGATGAGATTGCTAGTCTTGTCTTA 720
              ******** *********** *********************** **** ****** **

Patient 4     GCCAAGCTTGGTAAAGAATCTAAACCTCAGCAAGTCACTAAGCAAAATGCCAAGGAAATT 780
Patient 6     GCCAAGCTTGGTAAAGAATCTAAACCTCAGCAAGTCACTAAGCAAAATGCCAAGGAAATT 780
Patient 7     GCCAAGCTTGGTAAAGAATCTAAACCTCAGCAAGTCACTAAGCAAAATGCCAAGGAAATT 780
Patient 9     GCCAAGCTTGGTAAAGAATCTAAACCTCAGCAAGTCACTAAGCAAAATGCCAAGGAAATT 780
Patient 10    GCCAAGCTTGGTAAAGAATCTAAACCTCAGCAAGTCACTAAGCAAAATGCCAAGGAAATT 780
Patient 2     GCCAAGCTTGGTAAAGATTCTAAACCTCAGCAAGTCACTAAGCAAAATGCCAAGGAAATC 780
Patient 5     GCCAAGCTTGGTAAAGATTCTAAACCTCAGCAAGTCACTAAGCAAAATGCCAAGGAAATC 780
Patient 1     GCCAAGCTTGGTAAAGATTCTAAACCTCAGCAAGTTACCAAGCAAAATGCTAAGGAAATT 780
Patient 8     GCCAAGCTTGGTAAAGATTCTAAACCTCAGCAAGTTACCAAGCAAAATGCTAAGGAAATT 780
              ***************** ***************** ** *********** ********

Patient 4     AGGCATAAAATTTTAACAAAACCTCGCCAAAAGCGAACTCCTAATAAACATTGTAATGTT 840
Patient 6     AGGCATAAAATTTTAACAAAACCTCGCCAAAAGCGAACTCCTAATAAACATTGTAATGTT 840
Patient 7     AGGCATAAAATTTTAACAAAACCTCGCCAAAAGCGAACTCCTAATAAACATTGTAATGTT 840
Patient 9     AGGCATAAAATTTTAACAAAACCTCGCCAAAAGCGAACTCCTAATAAACATTGTAATGTT 840
Patient 10    AGGCATAAAATTTTAACAAAACCTCGCCAAAAGCGAACTCCTAATAAACATTGTAATGTT 840
Patient 2     AGGCATAAAATTTTAACAAAACCTCGCCAAAAGCGAACTCCTAATAAACATTGTAATGTT 840
Patient 5     AGGCATAAAATTTTAACAAAACCTCGCCAAAAGCGAACTCCTAATAAACATTGTAATGTT 840
```

FIG. 14 CONT.

```
Patient 1     AGGCATAAAATTTTAATGAAACCTCGCCAAAAGCGAACTCCTAATAAATTTTGTAATGTT 840
Patient 8     AGGCATAAAATTTTAATGAAACCTCGCCAAAAGCGAACTCCTAATAAATTTTGTAATGTT 840
              ****************  ******************************  **********

Patient 4     CAACAGTGTTTTGGTAAAAGAGGACCTTCTCAAAATTTTGGTAATGCTGAAATGTTAAAG 900
Patient 6     CAACAGTGTTTTGGTAAAAGAGGACCTTCTCAAAATTTTGGTAATGCTGAAATGTTAAAG 900
Patient 7     CAACAGTGTTTTGGTAAAAGAGGACCTTCTCAAAATTTTGGTAATGCTGAAATGTTAAAG 900
Patient 9     CAACAGTGTTTTGGTAAAAGAGGACCTTCTCAAAATTTTGGTAATGCTGAAATGTTAAAG 900
Patient 10    CAACAGTGTTTTGGTAAAAGAGGACCTTCTCAAAATTTTGGTAATGCTGAAATGTTAAAG 900
Patient 2     CAACAGTGTTTTGGTAAAAGAGGACCTTCTCAAAATTTTGGTAATGCTGAAATGTTAAAG 900
Patient 5     CAACAGTGTTTTGGTAAAAGAGGACCTTCTCAAAATTTTGGTAATGCTGAAATGTTAAAG 900
Patient 1     CAACAGTGTTTTGGTAAAAGAGGACCGCTCCAAAACTTTGGTAATTCTGAAATGTTAAAG 900
Patient 8     CAACAGTGTTTTGGTAAAAGAGGACCGCTCCAAAACTTTGGTAATTCTGAAATGTTAAAG 900
              **************************    ***** ********* **************

Patient 4     CTTGGTACTAATGATCCTCAGTTTCCTATTCTTGCAGAATTAGCTCCTACACCAGGTGCT 960
Patient 6     CTTGGTACTAATGATCCTCAGTTTCCTATTCTTGCAGAATTAGCTCCTACACCAGGTGCT 960
Patient 7     CTTGGTACTAATGATCCTCAGTTTCCTATTCTTGCAGAATTAGCTCCTACACCAGGTGCT 960
Patient 9     CTTGGTACTAATGATCCTCAGTTTCCTATTCTTGCAGAATTAGCTCCTACACCAGGTGCT 960
Patient 10    CTTGGTACTAATGATCCTCAGTTTCCTATTCTTGCAGAATTAGCTCCTACACCAGGTGCT 960
Patient 2     CTTGGTACTAATGATCCTCAGTTTCCTATTCTTGCAGAATTAGCTCCTACACCAGGTGCT 960
Patient 5     CTTGGTACTAATGATCCTCAGTTTCCTATTCTTGCAGAATTAGCTCCTACACCAGGTGCT 960
Patient 1     CTTGGTACTAATGATCCTCAATTTCCTATTCTTGCTGAATTAGCCCCTACACCAGGTGCT 960
Patient 8     CTTGGTACTAATGATCCTCAATTTCCTATTCTTGCTGAATTAGCTCCTACACCAGGTGCT 960
              ******************** ************** ******** ***************

Patient 4     TTTTTCTTTGGTTCTAAATTAGACTTGGTTAAAAGAGATTCCGAGGCTGACTCACCTGTT 1020
Patient 6     TTTTTCTTTGGTTCTAAATTAGACTTGGTTAAAAGAGATTCCGAGGCTGACTCACCTGTT 1020
Patient 7     TTTTTCTTTGGTTCTAAATTAGACTTGGTTAAAAGAGATTCCGAGGCTGACTCACCTGTT 1020
Patient 9     TTTTTCTTTGGTTCTAAATTAGACTTGGTTAAAAGAGATTCCGAGGCTGACTCACCTGTT 1020
Patient 10    TTTTTCTTTGGTTCTAAATTAGACTTGGTTAAAAGAGATTCCGAGGCTGACTCACCTGTT 1020
Patient 2     TTTTTCTTTGGTTCTAAATTAGACTTGGTTAAAAGAGATTCCGAGGCTGACTCACCTGTT 1020
Patient 5     TTTTTCTTTGGTTCTAAATTAGACTTGGTTAAAAGAGATTCCGAGGCTGACTCACCTGTT 1020
Patient 1     TTTTTCTTTGGCTCTAAATTAGAGTTGTTTAAAAGAGACTCTGATGCTGATTCACCTTCT 1020
Patient 8     TTTTTCTTTGGCTCTAAATTAGAGTTGTTTAAAAGAGACTCTGATGCTGATTCACCTTCT 1020
              *********** *********** *** ********** ** ** ***** ******  *

Patient 4     AAAGATGTTTTTGAACTTCATTATTCTGGTTCTATTAGGTTTGATAGTACTTTACCAGGC 1080
Patient 6     AAAGATGTTTTTGAACTTCATTATTCTGGTTCTATTAGGTTTGATAGTACTTTACCAGGC 1080
Patient 7     AAAGATGTTTTTGAACTTCATTATTCTGGTTCTATTAGGTTTGATAGTACTTTACCAGGC 1080
Patient 9     AAAGATGTTTTTGAACTTCATTATTCTGGTTCTATTAGGTTTGATAGTACTTTACCAGGC 1080
Patient 10    AAAGATGTTTTTGAACTTCATTATTCTGGTTCTATTAGGTTTGATAGTACTTTACCAGGC 1080
Patient 2     AAAGATGTTTTTGAACTTCATTATTCTGGTTCTATTAGGTTTGATAGTACTTTACCAGGC 1080
Patient 5     AAAGATGTTTTTGAACTTCATTATTCTGGTTCTATTAGGTTTGATAGTACTTTACCAGGC 1080
Patient 1     AAAGACACTTTTGAACTTCGTTATTCTGGTTCTATTAGGTTTGATAGTACTTTACCTGGT 1080
Patient 8     AAAGACACTTTTGAACTTCGTTATTCTGGTTCTATTAGGTTTGATAGTACTTTACCTGGT 1080
              *****   *********** ************************************ ** 

Patient 4     TTTGAGACAATTATGAAAGTTCTTGAAGAGAATTTAAATGCTTATGTTAATTCTAATCAG 1140
Patient 6     TTTGAGACAATTATGAAAGTTCTTGAAGAGAATTTAAATGCTTATGTTAATTCTAATCAG 1140
Patient 7     TTTGAGACAATTATGAAAGTTCTTGAAGAGAATTTAAATGCTTATGTTAATTCTAATCAG 1140
Patient 9     TTTGAGACAATTATGAAAGTTCTTGAAGAGAACTTAAATGCTTATGTTAATTCTAATCAG 1140
Patient 10    TTTGAGACAATTATGAAAGTTCTTGAAGAGAACTTAAATGCTTATGTTAATTCTAATCAG 1140
Patient 2     TTTGAGACAATTATGAAAGTTCTTGAAGAGAATTTAAATGCTTACGTTAATTCTAATCAG 1140
Patient 5     TTTGAGACAATTATGAAAGTTCTTGAAGAGAATTTAAATGCTTACGTTAATTCTAATCAG 1140
Patient 1     TTTGAGACAATTATGAAAGTTCTTAAAGAGAATTTAGATGCTTATGTTAATTCTAATCAG 1140
Patient 8     TTTGAGACAATTATGAAAGTTCTTAAAGAGAATTTAGATGCTTATGTTAATTCTAATCAG 1140
              ************************ ******* *** ******* ***************

Patient 4     AACACTGATTCTGATTCGTTGAGTTCTAAACCTCAGCGTAAAAGAGGTGTTAAACAATTA 1200
Patient 6     AACACTGATTCTGATTCGTTGAGTTCTAAACCTCAGCGTAAAAGAGGTGTTAAACAATTA 1200
Patient 7     AACACTGATTCTGATTCGTTGAGTTCTAAACCTCAGCGTAAAAGAGGTGTTAAACAATTA 1200
Patient 9     AACACTGATTCTGATTCGTTGAGTTCTAAACCTCAGCGTAAAAGAGGTGTTAAACAATTA 1200
Patient 10    AACACTGATTCTGATTCGTTGAGTTCTAAACCTCAGCGTAAAAGAGGTGTTAAACAATTA 1200
Patient 2     AACACTGATTCTGATTCGTTGAGTTCTAAACCTCAGCGTAAAAGAGGTGTTAAACAATTA 1200
Patient 5     AACACTGATTCTGATTCGTTGAGTTCTAAACCTCAGCGTAAAAGAGGTGTTAAACAATTA 1200
Patient 1     AACACTGTTTCTGGTTCGCTGAGTCCTAAACCTCAGCGTAAAAGAGGTGTTAAACAATCA 1200
Patient 8     AACACTGTTTCTGGTTCGCTGAGTCCTAAACCTCAGCGTAAAAGAGGTGTTAAACAATCA 1200
              ******* ***** **** ***** ********************************* *

Patient 4     CCAGAACAGTTTGACTCTCTTAATTTAAGTGCTGGTACTCAGCACATTTCAAATGATTTT 1260
Patient 6     CCAGAACAGTTTGACTCTCTTAATTTAAGTGCTGGTACTCAGCACATTTCAAATGATTTT 1260
Patient 7     CCAGAACAGTTTGACTCTCTTAATTTAAGTGCTGGTACTCAGCACATTTCAAATGATTTT 1260
Patient 9     CCAGAACAGTTTGACTCTCTTAATTTAAGTGCTGGTACTCAGCACATTTCAAATGATTTT 1260
Patient 10    CCAGAACAGTTTGACTCTCTTAATTTAAGTGCTGGTACTCAGCACATTTCAAATGATTTT 1260
Patient 2     CCAGAACAGTTTGACTCTCTTAATTTAAGTGCTGGTACTCAGCACATTTCAAATGATTTT 1260
```

FIG. 14 CONT.

```
Patient 5     CCAGAACAGTTTGACTCTCTTAATTTAAGTGCTGGTACTCAGCACATTTCAAATGATTTT 1260
Patient 1     CCTGAATCGTTTGACTCTCTTAATTTAAGTGCTGATACTCAGCACATTTCAAATGATTTT 1260
Patient 8     CCTGAATCGTTTGACTCTCTTAATTTAAGTGCTGATACTCAGCACATTTCAAATGATTTT 1260
              ** ***  ************************* **************************

Patient 4     ACTCCTGAGGATCATAGTTTACTTGCTACTCTTGACGATCCTTATGTAGAAGACTCTGTT 1320
Patient 6     ACTCCTGAGGATCATAGTTTACTTGCTACTCTTGACGATCCTTATGTAGAAGACTCTGTT 1320
Patient 7     ACTCCTGAGGATCATAGTTTACTTGCTACTCTTGACGATCCTTATGTAGAAGACTCTGTT 1320
Patient 9     ACTCCTGAGGATCATAGTTTACTTGCTACTCTTGACGATCCTTATGTAGAAGACTCTGTT 1320
Patient 10    ACTCCTGAGGATCATAGTTTACTTGCTACTCTTGACGATCCTTATGTAGAAGACTCTGTT 1320
Patient 2     ACTCCTGAGGATCATAGTTTACTTGCTACTCTTGATGATCCTTATGTAGAAGACTCTGTT 1320
Patient 5     ACTCCTGAGGATCATAGTTTACTTGCTACTCTTGATGATCCTTATGTAGAAGACTCTGTT 1320
Patient 1     ACTCCTGAGGATCATAGTTTACTTGCTACTCTTGATGATYCTTATGTAGAAGACTCTGTT 1320
Patient 8     ACTCCTGAGGATCATAGTTTACTTGCTACTCTTGATGATCCTTATGTAGAAGACTCTGTT 1320
              *********************************** *** ********************

Patient 4     GCTTAA 1326
Patient 6     GCTTAA 1326
Patient 7     GCTTAA 1326
Patient 9     GCTTAA 1326
Patient 10    GCTTAA 1326
Patient 2     GCTTAA 1326
Patient 5     GCTTAA 1326
Patient 1     GCTTAA 1326
Patient 8     GCTTAA 1326
              ******
```

FIG. 14 CONT.

| | | LPW1926 | | LPW1927 | |
|---|---|---|---|---|---|
| .CoV-HKU1 | (Patient 1) | AAAGGATGTTGACAACCCTGTT | CTTATGGG/…/ATTTTTA | TGTAAGCATTTTAGTATGATGAT | 2258 |
| .CoV-HKU1 | (Patient 2) | AAAGGATGTTGACAACCCTGTT | CTTATGGG/…/ATTTTTA | TGTAAGCATTTTAGTATGATGAT | 2258 |
| .CoV-HKU1 | (Patient 4) | AAAGGATGTTGACAACCCTGTT | CTTATGGG/…/ATTTTTA | TGTAAGCATTTTAGTATGATGAT | 2258 |
| .CoV-HKU1 | (Patient 5) | AAAGGATGTTGACAACCCTGTT | CTTATGGG/…/ATTTTTA | TGTAAGCATTTTAGTATGATGAT | 2258 |
| .CoV-HKU1 | (Patient 6) | AAAGGATGTTGACAACCCTGTT | CTTATGGG/…/ATTTTTA | TGTAAGCATTTTAGTATGATGAT | 2258 |
| .CoV-HKU1 | (Patient 7) | AAAGGATGTTGACAACCCTGTT | CTTATGGG/…/ATTTTTA | TGTAAGCATTTTAGTATGATGAT | 2258 |
| .CoV-HKU1 | (Patient 8) | AAAGGATGTTGACAACCCTGTT | CTTATGGG/…/ATTTTTA | TGTAAGCATTTTAGTATGATGAT | 2258 |
| .CoV-HKU1 | (Patient 9) | AAAGGATGTTGACAACCCTGTT | CTTATGGG/…/ATTTTTA | TGTAAGCATTTTAGTATGATGAT | 2258 |
| .CoV-HKU1 | (Patient 10) | AAAGGATGTTGACAACCCTGTT | CTTATGGG/…/ATTTTTA | TGTAAGCATTTTAGTATGATGAT | 2258 |
| HCoV-OC43 | (NC_005147) | TAAAGATGTTGACAATCCTGTA | CTTATGGG/…/ATTTTTA | AATAAGCATTTTAGTATGATGAT | 2258 |
| SARS-CoV | (NC_004718) | CAGTGATGTAGAAACTCCACAC | CTTATGGG/…/TTACCTG | CGTAAACATTTCTCCATGATGAT | 2270 |
| HCoV-229E | (NC_002645) | GGCCGATGTTGATGATCCTAAA | TTGATGGG/…/TTATTTG | CAAAAGCATTTTTCTATGATGAT | 2255 |
| HCoV-NL63 | (NC_005831) | TGATGGTGTTGAAAACCCTATG | CTTATGGG/…/TTATCTT | AGGAAACATTTTTCAATGATGAT | 2255 |

FIG. 16

HUMAN VIRUS CAUSING RESPIRATORY TRACT INFECTION AND USES THEREOF

This is a continuation-in-part application of U.S. patent application Ser. No. 10/895,064 filed Jul. 21, 2004, which is incorporated by reference in its entirety.

SEQUENCE LISTING

The instant application contains a "lengthy" Sequence Listing which has been submitted via CD-R in lieu of a printed paper copy, and is hereby incorporated by reference in its entirety. Said CD-R, recorded on Mar. 21, 2005, are labeled "CRF", "Copy 1" and "Copy 2", respectively, and each contains only one identical 2.84 MB file (V0690044.APP).

1. INTRODUCTION

The present invention relates to a novel virus causing respiratory tract infection in humans ["coronavirus-HKU1 (CoV-HKU1)"]. Phylogenetic analysis has revealed that the CoV-HKU1 is a new group 2 coronavirus, which has, at least, two (2) genotypes, A and B. The present invention relates to nucleotide sequences comprising the complete genomic sequences of the CoV-HKU1. The invention further relates to nucleotide sequences comprising a portion of the genomic sequences of the CoV-HKU1. The invention also relates to the deduced amino acid sequences of the complete genomes of the CoV-HKU1. The invention further relates to the nucleic acids and peptides encoded by and/or derived from these sequences and their use in diagnostic methods and therapeutic methods, such as for immunogens. The invention further encompasses chimeric or recombinant viruses encoded by said nucleotide sequences and antibodies directed against polypeptides encoded by the nucleotide sequence. Furthermore, the invention relates to vaccine preparations comprising the CoV-HKU1 recombinant and chimeric forms of said virus as well as protein extracts and subunits of said virus.

2. BACKGROUND OF THE INVENTION

Since no microbiological cause has been identified in a significant proportion of patients with respiratory tract infections (Macfarlane, J. T. et al., 1993, Prospective study of aetiology and outcome of adult lower-respiratory-tract infections in the community, *Lancet* 341:511-514; Ruiz, M., S. et al., 1990, Etiology of community-acquired pneumonia: impact of age, comorbidity, and severity, *Am. J. Respir. Crit. Care Med.* 160:397-405), research has been conducted to identify possible novel agent(s). Of the three novel agents identified in the recent three years, including human metapneumovirus (Van den Hoogen, et al., 2001, A newly discovered human pneumovirus isolated from young children with respiratory tract disease, *Nat. Med.* 7:719-724), Severe Acute Respiratory Syndrome (SARS) coronavirus (SARS-CoV) (Peiris, J. S. et al., 2003, Coronavirus as a possible cause of severe acute respiratory syndrome, *Lancet* 361:1319-1325) and human coronavirus NL63 (HCoV-NL63) (Fouchier, R. A. et al., 2004, A previously undescribed coronavirus associated with respiratory disease in humans, *Proc. Natl. Acad. Sci. USA*. 101:6212-6216; van der Hoek, et al., 2004, Identification of a new human coronavirus, *Nat. Med*. 10:368-373), two were coronaviruses. Coronaviruses possess the largest genome of about 30 kb among all RNA viruses. As a result of the unique mechanism of viral replication, coronaviruses have a high frequency of recombination.

Based on genotypic and serological characterization, coronaviruses were divided into three distinct groups, with human coronavirus 229E (HCoV-229E) being a group 1 coronavirus and HCoV-OC43 a group 2 coronavirus (Lai, M. M. et al., 1997, The molecular biology of coronaviruses, *Adv. Virus Res*. 48:1-100). They account for 5-30% of human respiratory tract infections. In late 2002 and 2003, the epidemic caused by SARS-CoV affected over 8000 people with 750 deaths (for example, Peiris, J. S. et al., 2003, Clinical progression and viral load in a community outbreak of coronavirus-associated SARS pneumonia: a prospective study, *Lancet* 361:1767-1772). We have also reported the isolation of SARS-CoV-like viruses from Himalayan palm civets, which suggested that animals could be the reservoir for the ancestor of SARS-CoV (Guan, Y. et al., 2003, Isolation and characterization of viruses related to the SARS coronavirus from animals in southern China, *Science* 302:276-278). On the basis of genome analysis, SARS-CoV belongs to a fourth group of coronavirus, or alternatively, a distant relative of group 2 coronaviruses (Eickmann, M. et al., 2003, Phylogeny of the SARS coronavirus, *Science* 302:1504-1505; Marra, M. A. et al., 2003, The Genome sequence of the SARS-associated coronavirus, *Science* 300:1399-1404; Rota, P. A. et al., 2003, Characterization of a novel coronavirus associated with severe acute respiratory syndrome, *Science* 300:1394-1399; Snijder, E. J. et al., 2003, Unique and conserved features of genome and proteome of SARS-coronavirus, an early split-off from the coronavirus group 2 lineage, *J. Mol. Biol*. 331:991-1004; Yeh, S. H. et al., 2004, Characterization of severe acute respiratory syndrome coronavirus genomes in Taiwan: molecular epidemiology and genome evolution, *Proc. Natl. Acad. Sci. USA*. 101:2542-2547). Recently, a novel group 1 human coronavirus associated with respiratory tract infections, HCoV-NL63, has been discovered, and its genome sequenced (37).

In January, 2004, a 71-year-old Chinese man was admitted to hospital because of fever and chills for two days associated with sore throat, rhinorrhoea, productive cough with purulent sputum, headache and nausea. He had history of pulmonary tuberculosis more than 40 years ago complicated by cicatrization of right upper lobe and bronchiectasis with chronic *Pseudomonas aeruginosa* colonization of airways. He was a chronic smoker and also had chronic obstructive airway disease, hyperlipidemia, and asymptomatic abdominal aortic aneurysm. He had just returned from Shenzhen of China three days before admission. During his three-day trip to Shenzhen, he had no history of contact with or consumption of wild animals. On admission, his oral temperature was 37.6° C. Physical examination showed tracheal deviation to the right and inspiratory crackles over the anterior left lower zone. His haemoglobin level was 14.7 g/dL, total white cell count $12.1\times10^9$/L, with neutrophil $9.7\times10^9$/L, lymphocyte $1.6\times10^9$/L and monocyte $0.5\times10^9$/L, and plate count $303\times10^9$/L. His liver and renal function tests were within normal limits. Chest radiograph showed right upper lobe collapse and new patchy infiltrates over the left lower zone. Blood culture was performed. Empirical oral amoxicillin/clavulanate and azithromycin were commenced. Nasopharyngeal aspirates for direct antigen detection for respiratory viruses, RT-PCR for influenza A virus, human metapneumovirus and SARS-CoV, and viral cultures were negative. Sputum for bacterial culture only recovered *P. aeruginosa*. Sputum for mycobacterial culture was negative.

Blood culture was negative. Paired sera for antibodies against *Mycoplasma, Chlamydia, Legionella*, and SARS-CoV did not show any rise in antibody titres. His fever subsided two days after admission. His cough improved and he was discharged after five days of hospitalization. Amoxicillin/clavulanate and azithromycin were continued for a total of seven days. The present inventors were the group involved in the investigation of this patient. All tests for identifying commonly recognized viruses and bacteria were negative in these patients. The etiologic agent responsible for this disease was not known until the complete genome of CoV-HKU1 from this patient by the present inventors as disclosed herein. Further studies disclosed herein have revealed that CoV-HKU1 is a human coronavirus and there are, at least, two (2) genotypes, A and B, within CoV-HKU1. The invention is useful in both clinical and scientific research applications.

3. SUMMARY OF INVENTION

The present invention is based upon the inventor's complete genome sequencing of a novel virus ("CoV-HKU1") causing pneumonia in humans. The virus was first discovered from a patient suffering from pneumonia in Hong Kong. The virus is a single-stranded RNA virus of positive polarity which belongs to the order, Nidovirales, of the family, Coronaviridae. Further studies based on prospectively collected nasopharyngeal aspirates (NPAs) from patients with community-acquired pneumonia during a 12-month period, have revealed that there are, at least, two (2) genotypes for CoV-HKU1. Accordingly, the invention relates to CoV-HKU1 that phylogenetically relates to known members of Coronaviridae and specifically belongs to group 2 coronavirus. In a specific embodiment, the invention provides complete genomic sequences of two (2) genotypes of CoV-HKU1. In a preferred embodiment, the virus comprises a nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966. In another specific embodiment, the invention provides nucleic acids isolated from the virus. The virus preferably comprises a nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, in its genome. In a specific embodiment, the present invention provides isolated nucleic acid molecules comprising or, alternatively, consisting of the nucleotide sequence of SEQ ID NO:1, 2920, 2922, 2924, 2926, 2928, 2930, 2932, or 2934, a complement thereof or a portion thereof, preferably at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, 2,100, 2,200, 2,300, 2,400, 2,500, 2,600, 2,700, or more contiguous nucleotides of the nucleotide sequence of SEQ ID NO:1, 2920, 2922, 2924, 2926, 2928, 2930, 2932, or 2934, or a complement thereof. In another specific embodiment, the present invention provides isolated nucleic acid molecules comprising or, alternatively, consisting of the nucleotide sequence of SEQ ID NO:3 or 2919, a complement thereof or a portion thereof, preferably at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:3, or 2919, or a complement thereof. In yet another specific embodiment, the present invention provides isolated nucleic acid molecules comprising or, alternatively, consisting of the nucleotide sequence of SEQ ID NO:2936, 2938, 2940, 2942, 2944, 2946, 2948, or 2950, a complement thereof, or a portion thereof, preferably at least 5, 10, 15, 20, 25, 30, 35, 40, 45, 100, 150, 200, 250, 300, 350, 400, 450, 500, 550, 600, 650, 700, 750, 800, 850, 900, 950, 1000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, or more contiguous nucleotides of the nucleotide sequence of SEQ ID NO:2936, 2938, 2940, 2942, 2944, 2946, 2948, or 2950, or a complement thereof. In yet another specific embodiment, the present invention provides isolated nucleic acid molecules comprising or, alternatively, consisting of the nucleotide sequence of SEQ ID NO:2952, 2954, 2956, 2958, 2960, 2962, 2964, or 2966, a complement thereof, or a portion thereof, preferably at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, or more contiguous nucleotides of the nucleotide sequence of SEQ ID NO:2952, 2954, 2956, 2958, 2960, 2962, 2964, or 2966, or a complement thereof. Furthermore, in another specific embodiment, the invention provides isolated nucleic acid molecules which hybridize under stringent conditions, as defined herein, to a nucleic acid molecule having the sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a complement thereof. In preferred embodiments, such nucleic acid molecules encode amino acid sequences that have biological activities exhibited by the polypeptides encoded by the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966. In another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, 2,100, 2,200, 2,300, 2,400, 2,500, 2,600, 2,700, or more contiguous nucleotides of the nucleotide sequence of SEQ ID NO:1, 2920, 2922, 2924, 2926, 2928, 2930, 2932, or 2934, or a complement thereof. In yet another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, or more contiguous nucleotides of the nucleotide sequence of SEQ ID NO:2936, 2938, 2940, 2942, 2944, 2946, 2948, or 2950, or a complement thereof. In yet another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, or more contiguous nucleotides of the nucleotide sequence of SEQ ID NO:2952, 2954, 2956, 2958, 2960, 2962, 2964, or 2966, a complement thereof. In yet another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:3 or 2919, or a complement thereof. The polypeptides or proteins include those having the amino acid sequences of SEQ ID NO:2, 34-2918 shown in FIGS. 2 and 3, and SEQ ID NOS:2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and 2970-4236 shown in FIG. 9. The invention further provides proteins or polypeptides that are isolated from the CoV-HKU1, including viral proteins isolated from cells infected with the virus but not present in comparable uninfected cells. The polypeptides or the proteins of the present invention preferably have a biological activity of the protein (including antigenicity and/or immunogenicity) encoded by the nucleotide sequence that is at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, 2,100, 2,200, 2,300, 2,400, 2,500, 2,600, 2,700, or more contiguous nucleotides of the nucleotide sequence of SEQ ID NO:1, 2920, 2922, 2924, 2926, 2928, 2930, 2932, or 2934. In another embodiment, the polypeptides or the proteins of the present invention have a biological activity of the protein (including antigenicity and/or immunogenicity) encoded by a nucleotide sequence that is at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, or more contiguous nucleotides of the nucleotide sequence of SEQ ID NO:2936, 2938, 2940, 2942, 2944, 2946, 2948, or 2950, or a complement thereof. Furthermore, in another embodiment, the polypeptides or the proteins of the present invention have a biological activity of the protein (including antigenicity and/or immunogenicity) encoded by a nucleotide sequence that is at least 5, 10, 15, 20, 25, 30, 35, 40, 45, 100, 150, 200, 300, 350, 400, 450, 500, 550, 600, 650, 700, 750, 800, 850, 900, 950, 1,000, 1,050, 1,100, 1,150, 1,200, 1,250, 1,300, or more contiguous nucleotides of the nucleotide sequence of SEQ ID NO:2952, 2954, 2956, 2958, 2960, 2962, 2964, or 2966, or a complement thereof. In other embodiments, the polypeptides or the proteins of the present invention have a biological activity of the protein (including antigenicity and/or immunogenicity) encoded by a nucleotide sequence that is at least 5, 10, 15, 20, 25, 30, 35, 40, 45, 100, 150, 200, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:3 or 2919, or a complement thereof.

In one aspect, the invention relates to the use of CoV-HKU1 for diagnostic methods. In a specific embodiment, the invention provides a method of detecting in a biological sample an antibody that immunospecifically binds to the CoV-HKU1, or any proteins or polypeptides thereof. In another specific embodiment, the invention provides a method of detecting in a biological sample an antibody that immunospecifically binds to the CoV-HKU1-infected cells. In yet another specific embodiment, the invention provides a method of screening for an antibody that immunospecifically binds and neutralizes CoV-HKU1. Such an antibody is useful for a passive immunization or immunotherapy of a subject infected with CoV-HKU1.

The invention further relates to the use of the sequence information of the isolated virus for diagnostic methods. In a specific embodiment, the invention provides nucleic acid molecules which are suitable for use as primers consisting of or comprising the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, a complement thereof, or at least a portion of the nucleotide sequence thereof. In another specific embodiment, the invention provides nucleic acid molecules which are suitable for hybridization to CoV-HKU1 nucleic acid, including, but not limited to, as PCR primers, Reverse Transcriptase primers, probes for Southern or Northern analysis or other nucleic acid hybridization analysis for the detection of CoV-HKU1 nucleic acids, e.g., consisting of or comprising the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, a complement thereof, or a portion thereof.

The invention further provides antibodies that specifically bind a polypeptide of the invention encoded by the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a fragment thereof, including the polypeptide having the amino acid sequence of SEQ ID NO:2 or any one of SEQ ID NOS:34-2918 shown in FIGS. 2 and 3, 2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and 2970-4236 shown in FIG. 9, or encoded by a nucleic acid comprising a nucleotide sequence that hybridizes under stringent conditions to the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, and/or any CoV-HKU1 epitope, having one or more biological activities of a polypeptide of the invention. The invention further provides antibodies that specifically bind cells or tissues that are infected by CoV-HKU1. Such antibodies include, but are not limited to polyclonal, monoclonal, bi-specific, multi-specific, human, humanized, chimeric antibodies, single chain antibodies, Fab fragments, F(ab')$_2$ fragments, disulfide-linked Fvs, intrabodies and fragments containing either a VL or VH domain or even a complementary determining region (CDR) that specifically binds to a polypeptide of the invention.

In one embodiment, the invention provides methods for detecting the presence, activity or expression of the CoV-HKU1 of the invention in a biological material, such as cells, blood, saliva, urine, and so forth. The increased or decreased activity or expression of the CoV-HKU1 in a sample relative to a control sample can be determined by contacting the biological material with an agent which can detect directly or indirectly the presence, activity or expression of the CoV-HKU1. In a specific embodiment, the detecting agents are the antibodies or nucleic acid molecules of the present invention. Antibodies of the invention may also be used to detect and/or treat other coronaviruses, such as Severe Acute Respiratory Syndrome ("SARS") viruses.

In another embodiment, the invention provides vaccine preparations, comprising the CoV-HKU1 recombinant and chimeric forms of said virus, or protein subunits of the virus. In a specific embodiment, the present invention provides methods of preparing recombinant or chimeric forms of CoV-HKU1. In another specific invention, the vaccine preparations of the present invention comprise a nucleic acid or fragment of the CoV-HKU1, or nucleic acid molecules having the sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a fragment thereof. In another embodiment, the invention provides vaccine preparations comprising one or more polypeptides isolated from or produced from nucleic acid of CoV-HKU1. In a specific embodiment, the vaccine preparations comprise a polypeptide of the invention encoded by the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a fragment thereof, including the polypeptides having the amino acid sequences of SEQ ID NO:2 or any one of SEQ ID NOS:34-2918, 2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and 2970-4236. Furthermore, the present invention provides methods for treating, ameliorating, managing or preventing respiratory tract infections caused by CoV-HKU1 by administering to a subject in need thereof the anti-viral agents of the present invention, alone or in combination with various anti-viral agents as well as adjuvants, and/or other pharmaceutically acceptable excipients.

In another aspect, the present invention provides methods for preventing or inhibiting, under a physiological condition, binding to a host cell, or infection of a host cell, or replication in a host cell, of CoV-HKU1 or a virus comprising a nucleic acid molecule comprising the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a complement thereof, by administering to the host cell the anti-viral agents of the present invention, alone or in combination with other anti-viral agents. In a specific embodiment, the anti-viral agent of the invention includes the immunogenic preparations of the invention or an antibody that immunospecifically binds CoV-HKU1 or any CoV-HKU1 epitope and/or neutralizes CoV-HKU1. In another specific embodiment, the anti-viral agent is a polypeptide or protein of the present invention or a nucleic acid molecule of the invention. In a specific embodiment, the host cell is a mammalian cell, including a cell of human, primates, cows, horses, sheep, pigs, fowl (e.g., chickens), goats, cats, dogs, hamsters, mice and rats. Preferably a host cell is a primate cell, and most preferably a human cell. Furthermore, the present invention provides pharmaceutical compositions comprising anti-viral agents of the present invention and a pharmaceutically acceptable carrier. The invention also provides kits containing a pharmaceutical composition of the present invention.

3.1 Definitions

The term "an antibody or an antibody fragment that immunospecifically binds a polypeptide of the invention" as used herein refers to an antibody or a fragment thereof that immunospecifically binds to the polypeptide encoded by the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a fragment thereof, and does not non-specifically bind to other polypeptides. An antibody or a fragment thereof that immunospecifically binds to the polypeptide of the invention may cross-react with other antigens. Preferably, an antibody or a fragment thereof that immunospecifically binds to a polypeptide of the invention does not cross-react with other antigens. An antibody or a fragment thereof that immunospecifically binds to the polypeptide of the invention, can be identified by, for example, immunoassays or other techniques known to those skilled in the art.

An "isolated" or "purified" peptide or protein is substantially free of cellular material or other contaminating proteins from the cell or tissue source from which the protein is derived, or substantially free of chemical precursors or other chemicals when chemically synthesized. The language "substantially free of cellular material" includes preparations of a polypeptide/protein in which the polypeptide/protein is separated from cellular components of the cells from which it is isolated or recombinantly produced. Thus, a polypeptide/protein that is substantially free of cellular material includes preparations of the polypeptide/protein having less than about 30%, 20%, 10%, 5%, 2.5%, or 1%, (by dry weight) of contaminating protein. When the polypeptide/protein is recombinantly produced, it is also preferably substantially free of culture medium, i.e., culture medium represents less than about 20%, 10%, or 5% of the volume of the protein preparation. When polypeptide/protein is produced by chemical synthesis, it is preferably substantially free of chemical precursors or other chemicals, i.e., it is separated from chemical precursors or other chemicals which are involved in the synthesis of the protein. Accordingly, such preparations of the polypeptide/protein have less than about 30%, 20%, 10%, 5% (by dry weight) of chemical precursors or compounds other than polypeptide/protein fragment of interest. In a preferred embodiment of the present invention, polypeptides/proteins are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a preferred embodiment of the invention, nucleic acid molecules encoding polypeptides/proteins of the invention are isolated or purified. The term "isolated" nucleic acid molecule does not include a nucleic acid that is a member of a library that has not been purified away from other library clones containing other nucleic acid molecules.

The term "portion" or "fragment" as used herein refers to a fragment of a nucleic acid molecule containing at least about 10, 15, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,500, 2,000, 2,500, 3,000, 3,500, 4,000, 4,500, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, or more contiguous nucleic acids in length of the relevant nucleic acid molecule and having at least one functional feature of the nucleic acid molecule (or the encoded protein has one functional feature of the protein encoded by the nucleic acid molecule); or a fragment of a protein or a polypeptide containing at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, 360, 380, 400, 500, 600, 700, 800, 900, 1,000, 1,500, 2,000, 2,500, 3,000, 3,500, 4,000, 4,100, 4,200, 4,300, 4,350, 4,360, 4,370, 4,380 amino acid residues in length of the relevant protein or polypeptide and having at least one functional feature of the protein or polypeptide.

The term "having a biological activity of the protein" or "having biological activities of the polypeptides of the invention" refers to the characteristics of the polypeptides or proteins having a common biological activity similar or identical structural domain and/or having sufficient amino acid identity to the polypeptide encoded by the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or the polypeptide having any one of the amino acid sequences of SEQ ID NOS:2, 34-2918, 2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and 2970-4236, or a complement thereof. Such common biological activities of the polypeptides of the invention include antigenicity and immunogenicity.

The term "under stringent condition" refers to hybridization and washing conditions under which nucleotide sequences having at least 70%, at least 75%, at least 80%, at least 85%, at least 90%, or at least 95% identity to each other remain hybridized to each other. Such hybridization conditions are described in, for example but not limited to, Current Protocols in Molecular Biology, John Wiley & Sons, N.Y. (1989), 6.3.1-6.3.6.; Basic Methods in Molecular Biology, Elsevier Science Publishing Co., Inc., N.Y. (1986), pp. 75-78, and 84-87; and Molecular Cloning, Cold Spring Harbor Laboratory, N.Y. (1982), pp. 387-389, and are well known to those skilled in the art. A preferred, non-limiting example of stringent hybridization conditions is hybridization in 6× sodium chloride/sodium citrate (SSC), 0.5% SDS at about 68° C. followed by one or more washes (e.g., about 5 to 30 min each) in 2×SSC, 0.5% SDS at room temperature. Another preferred, non-limiting example of stringent hybridization conditions is hybridization in 6×SSC at about 45° C. followed by one or more washes (e.g., about 5 to 30 min each) in 0.2×SSC, 0.1% SDS at about 45-65° C.

The term "variant" as used herein refers either to a naturally occurring genetic mutant of CoV-HKU1 or a recombinantly prepared variation of CoV-HKU1 each of which contain one or more mutations in its genome compared to CoV-HKU1. The term "variant" may also refers either to a naturally occurring variation of a given peptide or a recombinantly prepared variation of a given peptide or protein in which one or more amino acid residues have been modified by amino acid substitution, addition, or deletion.

4. BRIEF DESCRIPTION OF FIGURES

FIG. 1 shows a partial DNA sequence (SEQ ID NO:1) and its deduced amino acid sequence (SEQ ID NO:2) obtained from CoV-HKU1 that has 91% amino acid identity to the RNA-dependent RNA polymerase protein of known *Coronaviruses.*

FIG. 2 shows the entire genomic DNA sequence (SEQ ID NO:3) of the first isolate of CoV-HKU1 and its deduced amino acid sequences therefrom in three frames. An asterisk (*) indicates a stop codon which marks the end of a peptide. The first-frame translation and amino acid sequences: SEQ ID NOS:34-456; the second-frame translation and amino acid sequences: SEQ ID NOS:457-723; and the third-frame translation and amino acid sequences: SEQ ID NOS:724-1318.

FIG. 3 shows the complement (SEQ ID NO:1319) of the entire genomic DNA sequence (SEQ ID NO:3) of CoV-HKU1 in 3'→5' orientation and its deduced amino acid sequences therefrom in three frames. An asterisk (*) indicates a stop codon which marks the end of a peptide. The first-frame translation and amino acid sequences: SEQ ID NOS:1319-1907; the second-frame translation and amino acid sequences: SEQ ID NO:1908-2453; and the third-frame translation and amino acid sequences: SEQ ID NOS:2454-2918.

FIG. 4 shows genome organization of CoV-HKU1. Overall organization of the 29926-nucleotide CoV-HKU1 genomic RNA. Predicted ORFs 1a and 1b, encoding the nonstructural polyproteins (p28, p65 and nsp1-13) and those encoding the hemagglutinin-esterase, spike, envelope, membrane and nucleocapsid structural proteins are indicated. Arrows indicate putative cleavage sites (with the corresponding nucleotide positions) of the replicase polyprotein encoded by ORF 1a and ORF 1b. ATR, PL1$^{pro}$ and PL2$^{pro}$ represent the acidic tandem repeat and the two papain-like proteases, respectively, in nsp1.

Figure 5A:
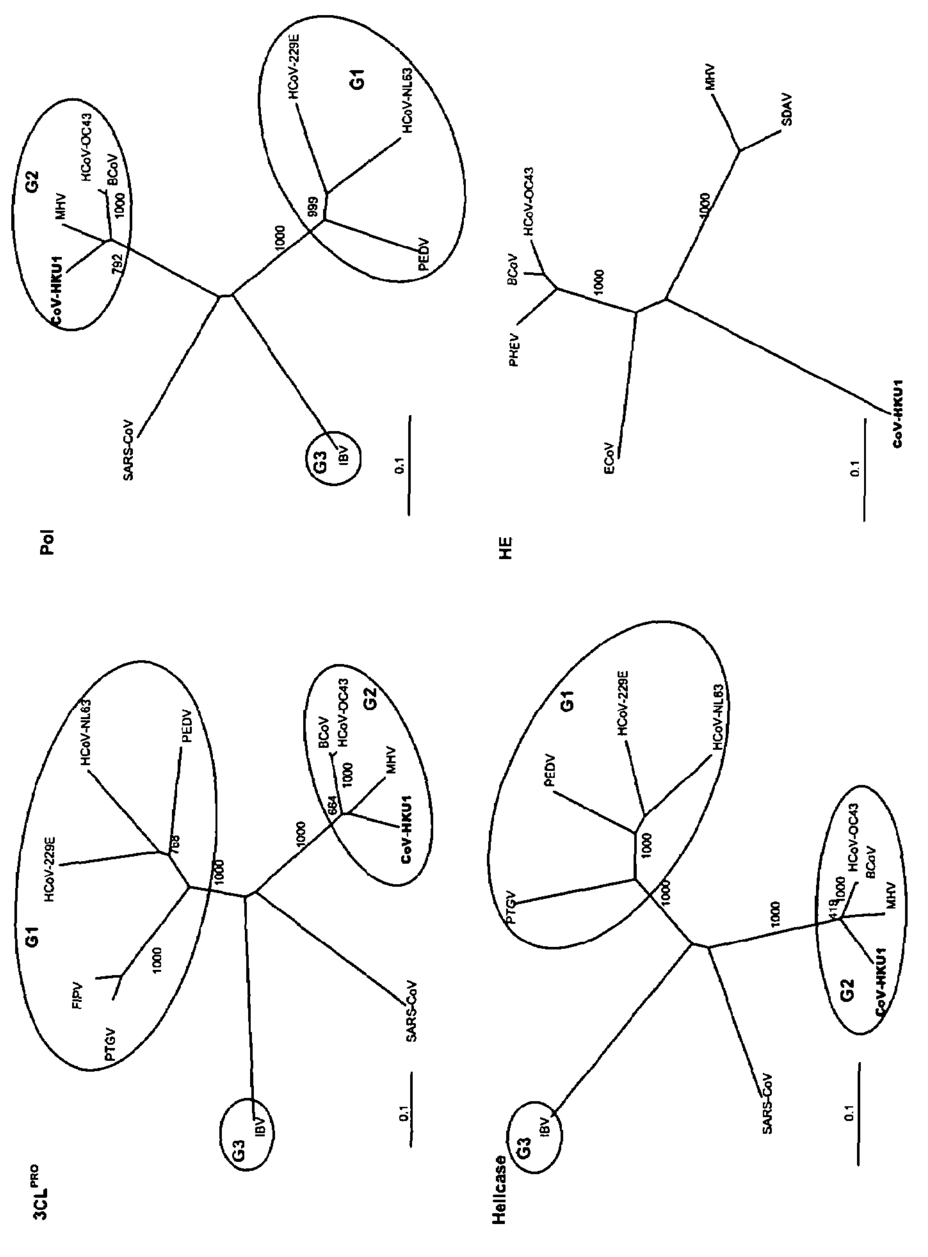
Figure 5B:
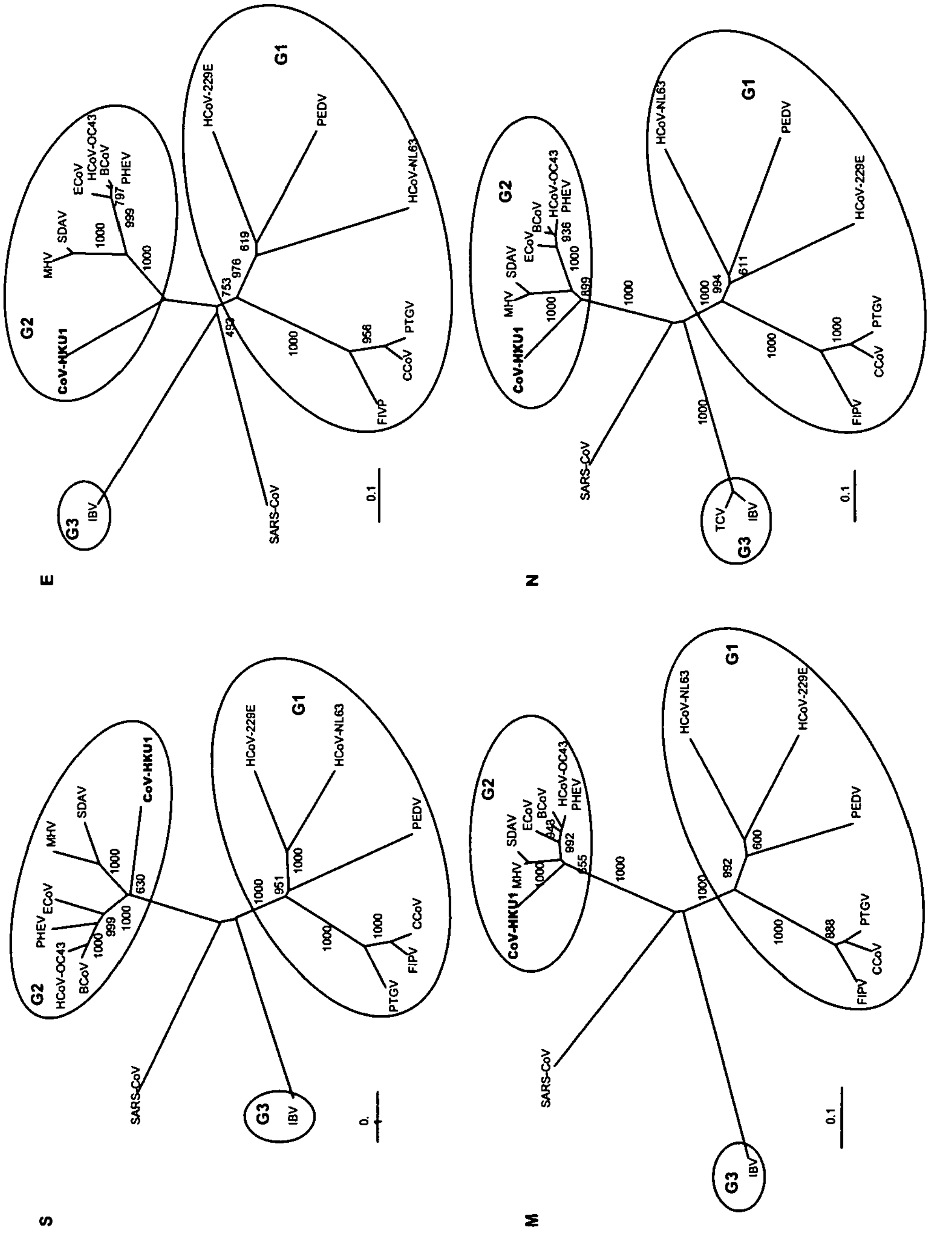

FIG. 5A shows the phylogenetic analysis of the chymotrypsin like protease (3CL$^{pro}$), RNA-dependent RNA polymerase (Pol), helicase, and hemagglutinin-esterase (HE); and FIG. 5B shows that of the spike (S), envelope (E), membrane (M), and nucleocapsid (N) proteins of CoV-HKU1. The trees were constructed by the neighbor joining method using the Jukes-Cantor correction and bootstrap values were calculated from 1000 trees. A total of 303, 928, 595, 418, 1356, 75, 225 and 406 amino acid positions in 3CL$^{pro}$, Pol, helicase, HE, S, E, M, and N, respectively, were included in the analysis. The scale bar indicates the estimated number of substitutions per 10 amino acids. HCoV-229E: human coronavirus 229E; PEDV: porcine epidemic diarrhea virus; PTGV: porcine transmissible gastroenteritis virus; CCoV, canine enteric coronavirus; HCoV-NL63: human coronavirus NL63; HCoV-OC43: human coronavirus OC43; MHV: murine hepatitis virus; BCoV: bovine coronavirus; SDAV: rat sialodacryoadnitis coronavirus; ECoV: equine coronavirus NC99; PHEV: porcine hemagglutinating encephalomyelitis virus; IBV: infectious bronchitis virus; SARS-CoV: SARS coronavirus.

Figure 6:
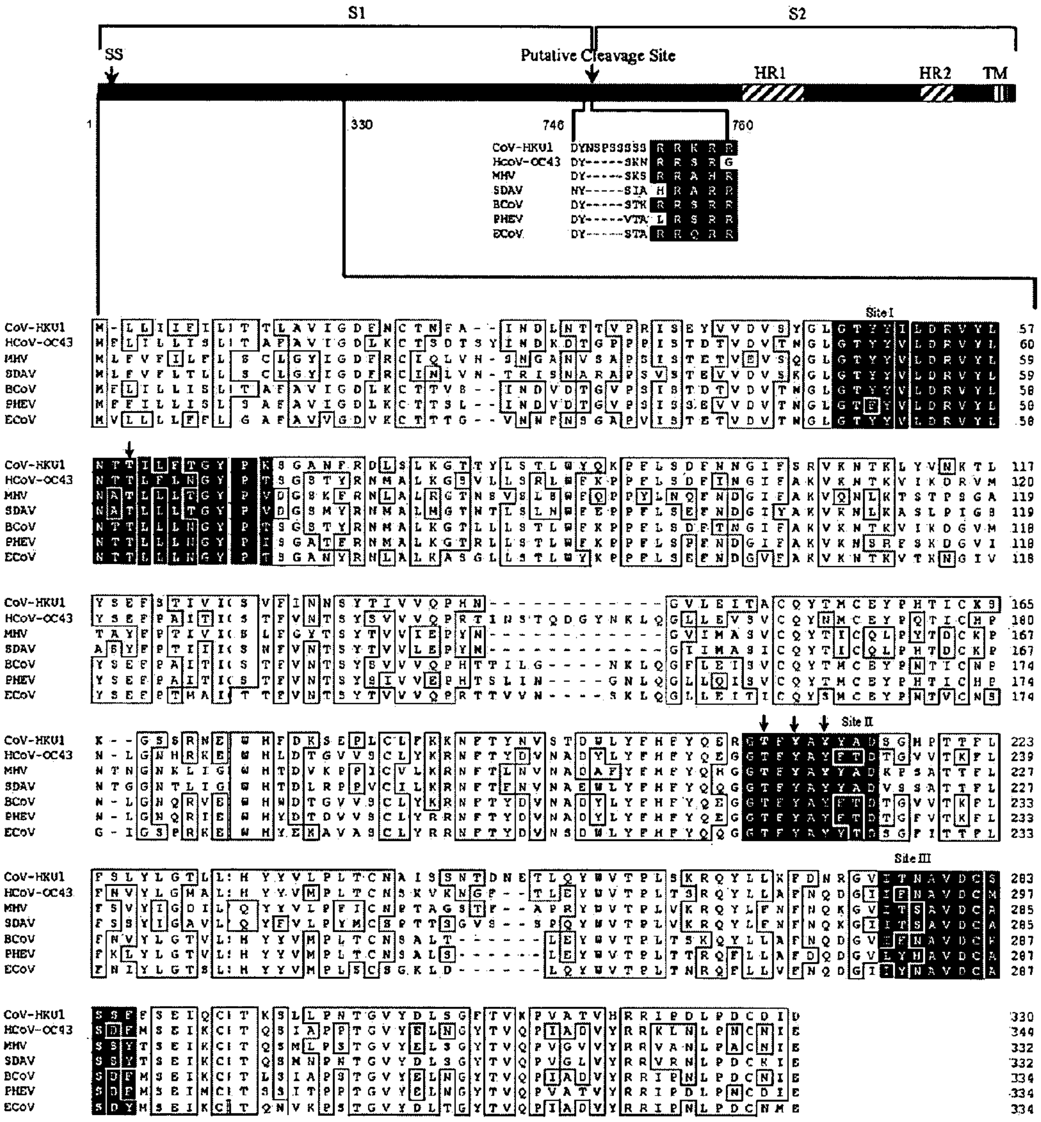

FIG. 6 shows the spike protein of CoV-HKU1 (residues 7-336 of SEQ ID NO: 420) and those of other group 2 coronaviruses (SEQ ID NOS 21-26, respectively, in order of appearance). The spike protein (1356 amino acids) of CoV-HKU1 is depicted by the horizontal bar [SS=N terminal signal sequence (amino acid residues 1 to 13), HR1=heptad repeat 1 (amino acid residues 982 to 1083), HR2=heptad repeat 2 (amino acid residues 1250 to 1297), TM=transmembrane domain (amino acid residues 1301 to 1323)], (the seven sequences below the horizontal bar disclose residues 752-766 of SEQ ID NO: 420 and SEQ ID NOS 28-33, respectively, in order of appearance). Alignment of the N-terminal region important for receptor binding (amino acid residues 1 to 330) and the region upstream to the cleavage site between S1 and S2 of CoV-HKU1 and other group 2 coronaviruses was generated with ClustalX 1.83. Residues that match the CoV-HKU1 exactly are boxed. The three conserved regions (sites I, II, and III) for receptor binding in MHV are shaded. The positions of the four conserved amino acids important for receptor binding in MHV are indicated with arrows. (GenBank accession nos. MHV: P11224; BCoV: NP 150077; HCoV-OC43: NP 937950; SDAV: AAF97738; PHEV: AAL80031; ECoV: AAQ67205).

Figure 7:
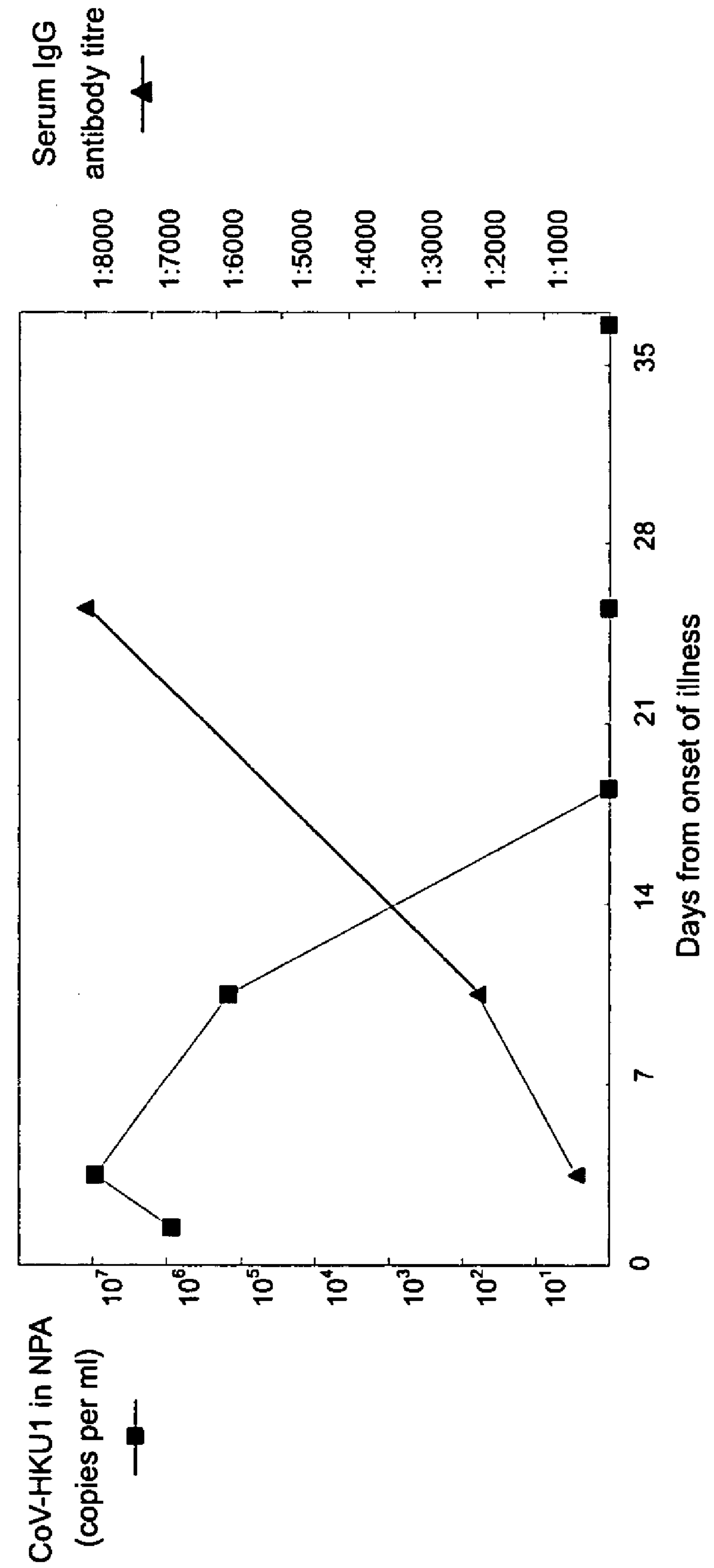

FIG. 7 shows the sequential quantitative RT-PCR (closed squares; copies/ml) for CoV-HKU1 in nasopharyngeal aspirates; and serum IgG antibody titers against N protein of CoV-HKU1 (closed triangles).

Figure 8:
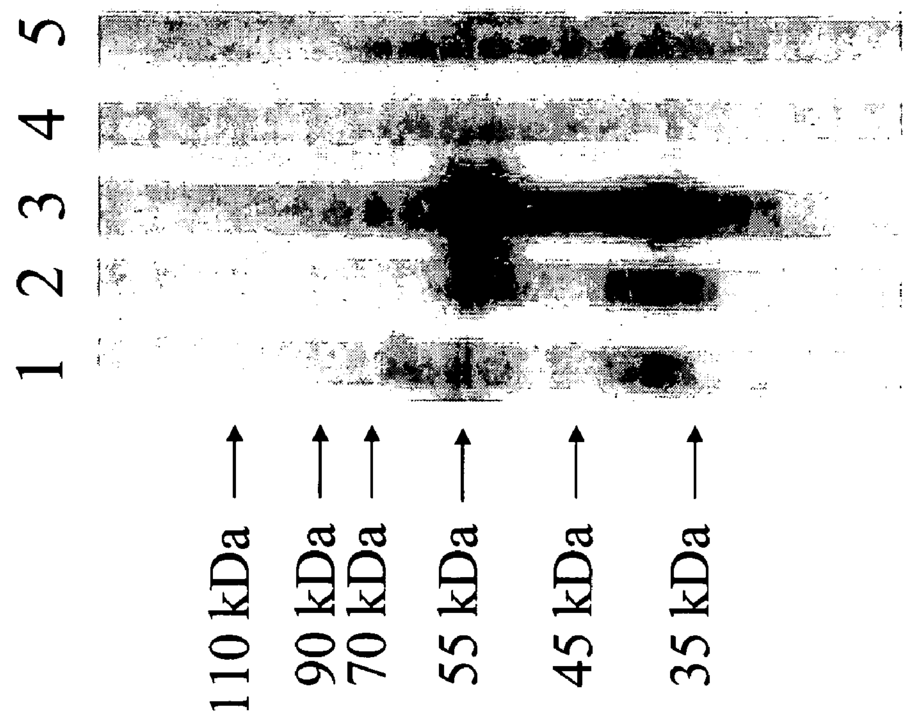

FIG. 8 shows the Western blot analysis of purified recombinant CoV-HKU1 N protein antigen. Prominent immunoreactive protein bands of about 53 kDa (i.e., purified recombinant CoV-HKU1 N protein) were detected by the Western blot using the patient's sera obtained during the second and fourth weeks of the illness (lanes 2 and 3). Only very faint bands were observed with the serum samples obtained from the patient during the first week of the illness (lane 1) and two healthy blood donors (lane 4 and 5), respectively.

FIG. 9 shows the entire genomic DNA sequence (SEQ ID NO:2919) of CoV-HKU1 and its deduced amino acid sequences therefrom in three frames. An asterisk (*) indicates a stop codon which marks the end of a peptide. The first-frame translation and amino acid sequences: SEQ ID NOS: 2970-3474; the second-frame translation and amino acid sequences: SEQ ID NOS: 3475-3721; and the third-frame translation and amino acid sequences: SEQ ID NOS: 3722-4236.

FIG. 10 shows arrangements of proteins in replicase polyprotein in CoV-HKU1 compared with those in HCoV-OC43, BCoV, and MHV. Alignment of the AC domains of HCoV-OC43 (SEQ ID NO: 4239), BCoV (SEQ ID NO: 4238), and MHV (SEQ ID NO: 4237) and the AC domains and ATR (underlined) of CoV-HKU1 in the two patients (SEQ ID NOS 4240 and 4241) was generated with ClustalX 1.83. AC domain=acidic domain, ATR=acidic tandem repeat. (GenBank accession no. MHV: NC_001846; BCoV: NC_003045; HCoV-OC43: AY585229).

FIG. 11 shows the multiple alignments of the replicase genes of CoV-HKU1 from patients 1 (SEQ ID NO: 2920 which encodes SEQ ID NO: 2921), 2 (SEQ ID NO: 2922 which encodes SEQ ID NO: 2923), 4 (SEQ ID NO: 2924 which encodes SEQ ID NO: 2925), 5 (SEQ ID NO: 4242 which encodes SEQ ID NO: 4243), 6 (SEQ ID NO: 2926 which encodes SEQ ID NO: 2927), 7 (SEQ ID NO: 2928 which encodes SEQ ID NO: 2929), 8 (SEQ ID NO: 2930 which encodes SEQ ID NO: 2931), 9 (SEQ ID NO: 2932 which encodes SEQ ID NO: 2933) and 10 (SEQ ID NO: 2934 which encodes SEQ ID NO: 2935).

Figure 12:
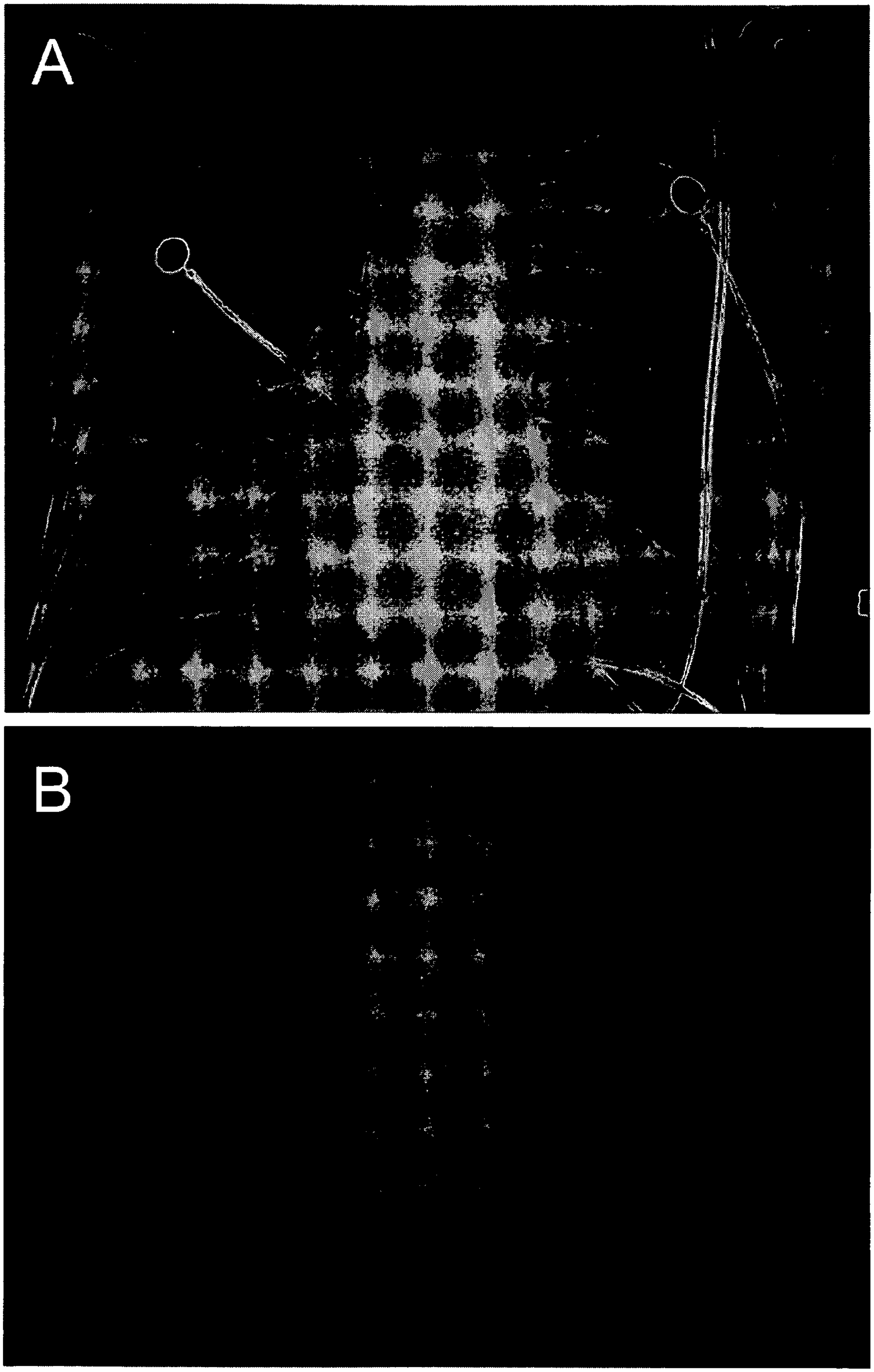

FIG. 12 shows the chest radiographs of the two patients who died of community acquired pneumonia associated with CoV-HKU1. The chest radiograph of the first patient (FIG. 12A; patient no. 2 in Table 5) showed patchy airspace shadows in both lungs with predominant involvement of the lower zones. The chest radiograph of the second patient (FIG. 12B; patient no. 10 in Table 5), with Luque instrumentation in situ, showed extensive airspace shadows in both lungs with the middle zones more severely involved.

FIG. 13 shows the multiple alignments of the spike genes of CoV-HKU1 from patients 1 (SEQ ID NO: 2936 which encodes SEQ ID NO: 2937), 2 (SEQ ID NO: 2938 which encodes SEQ ID NO: 2939), 4 (SEQ ID NO: 2940 which encodes SEQ ID NO: 2941), 5 (SEQ ID NO: 4244 which encodes SEQ ID NO: 4245), 6 (SEQ ID NO: 2942 which encodes SEQ ID NO: 2943), 7 (SEQ ID NO: 2944 which encodes SEQ ID NO: 2945), 8 (SEQ ID NO: 2946 which encodes SEQ ID NO: 2947), 9 (SEQ ID NO: 2948 which encodes SEQ ID NO: 2949) and 10 (SEQ ID NO: 2950 which encodes SEQ ID NO: 2951).

FIG. 14 shows the multiple alignments of the nucleocapsid genes of CoV-HKU1 from patients 1 (SEQ ID NO: 2952 which encodes SEQ ID NO: 2953), 2 (SEQ ID NO: 2954 which encodes SEQ ID NO: 2955), 4 (SEQ ID NO: 2956 which encodes SEQ ID NO: 2957), 5 (SEQ ID NO: 4246 which encodes SEQ ID NO: 4247), 6 (SEQ ID NO: 2958 which encodes SEQ ID NO: 2959), 7 (SEQ ID NO: 2960 which encodes SEQ ID NO: 2961), 8 (SEQ ID NO: 2962 which encodes SEQ ID NO: 2963), 9 (SEQ ID NO: 2964 which encodes SEQ ID NO: 2965) and 10 (SEQ ID NO: 2966 which encodes SEQ ID NO: 2967).

Figure 15:
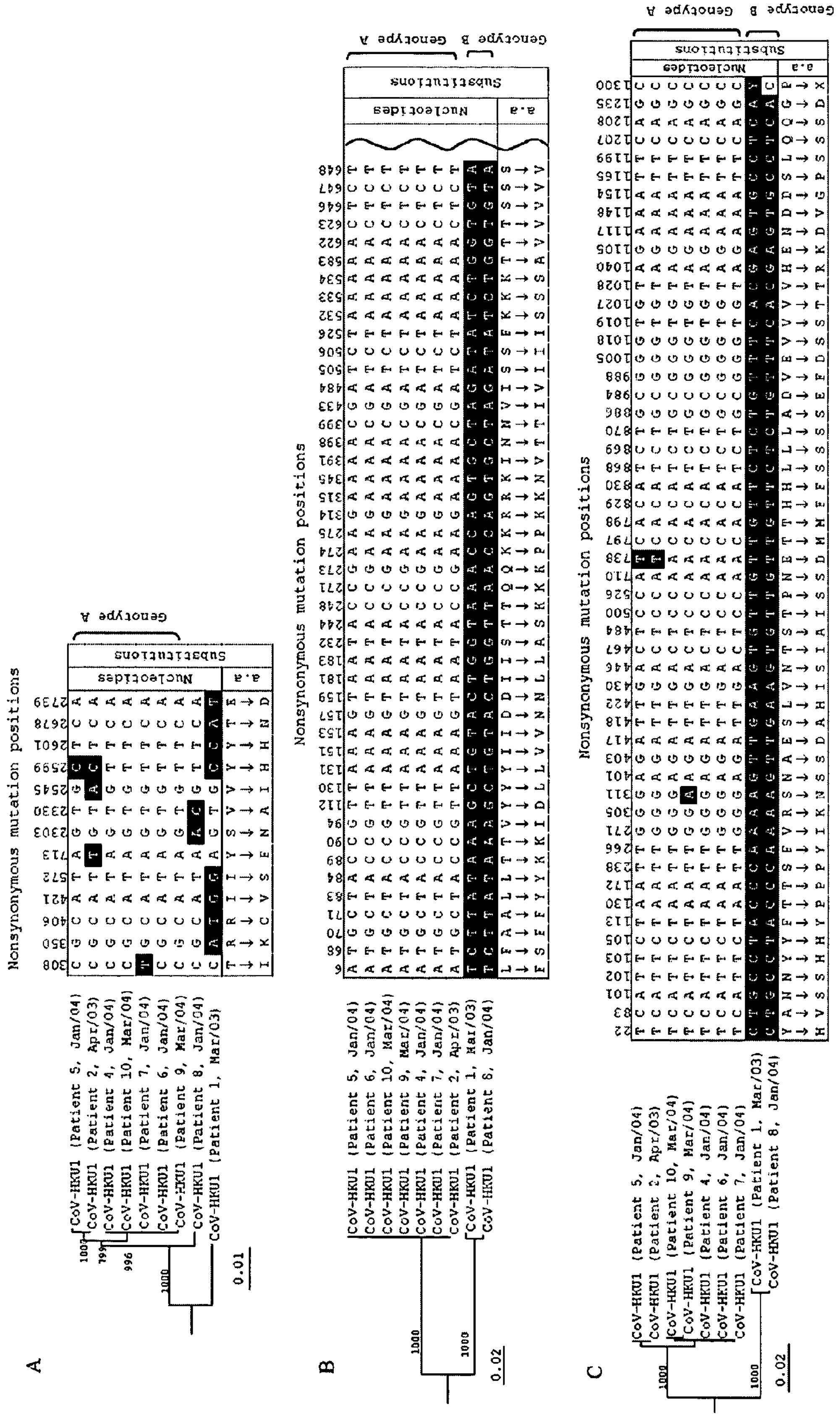

FIG. 15 shows phylogenetic trees and non-synonymous mutations and corresponding amino acid changes of complete pol, S and N gene sequences of CoV-HKU1 from nine patients with community acquired pneumonia. The trees were inferred from pol (FIG. 15A), S (FIG. 15B) and N (FIG. 15C) gene data by the neighbor-joining method and bootstrap values calculated from 1000 trees. The trees were rooted using pol, S and N gene sequences of HCoV-OC43, respectively. 2784 nucleotide positions in each pol gene, 4071 nucleotide positions in each S gene, and 1326 nucleotide positions in each N gene, were included in the analysis. The scale bar indicates the estimated number of substitutions per 100 (FIG. 15A) and 50 (FIGS. 15B and 15C) bases, respectively, using Jukes-Cantor correction. The shaded nucleotides are those that differ from the majority at the corresponding locations. Due to the large number of non-synonymous mutations in the S gene, only the $NH_2$ terminal 45, out of the total of 306, non-synonymous mutations are shown.

FIG. 16 shows the multiple alignments of nucleotides 1806-1835 and 2229-2258 of the pol genes in the nine CoV-HKU1 and those of HCoV-OC43, HCoV-229E, HCoV-NL63 and SARS-CoV. Marked differences between the 3' ends of the two primers for RT-PCR (LPW1926; SEQ ID NO: 2968 and LPW1927; SEQ ID NO: 2969) and the corresponding bases in HCoV-OC43 (SEQ ID NOS 4250 and 4251), HCoV-229E (SEQ ID NOS: 4254 and 4255), HCoV-NL63 (SEQ ID NOS: 4256 and 4257) and SARS-CoV (SEQ ID NOS: 4252 and 4253) are observed, indicating the high specificity of the two primers for CoV-HKU1. The positions of LPW1926 (SEQ ID NO: 2968) and LPW1927 (SEQ ID NO: 2969) are boxed. The bases in HCoV-OC43, HCoV-229E, HCoV-NL63 and SARS-CoV that were different from those in the sequence of the primers, were shaded.

Figure 17:
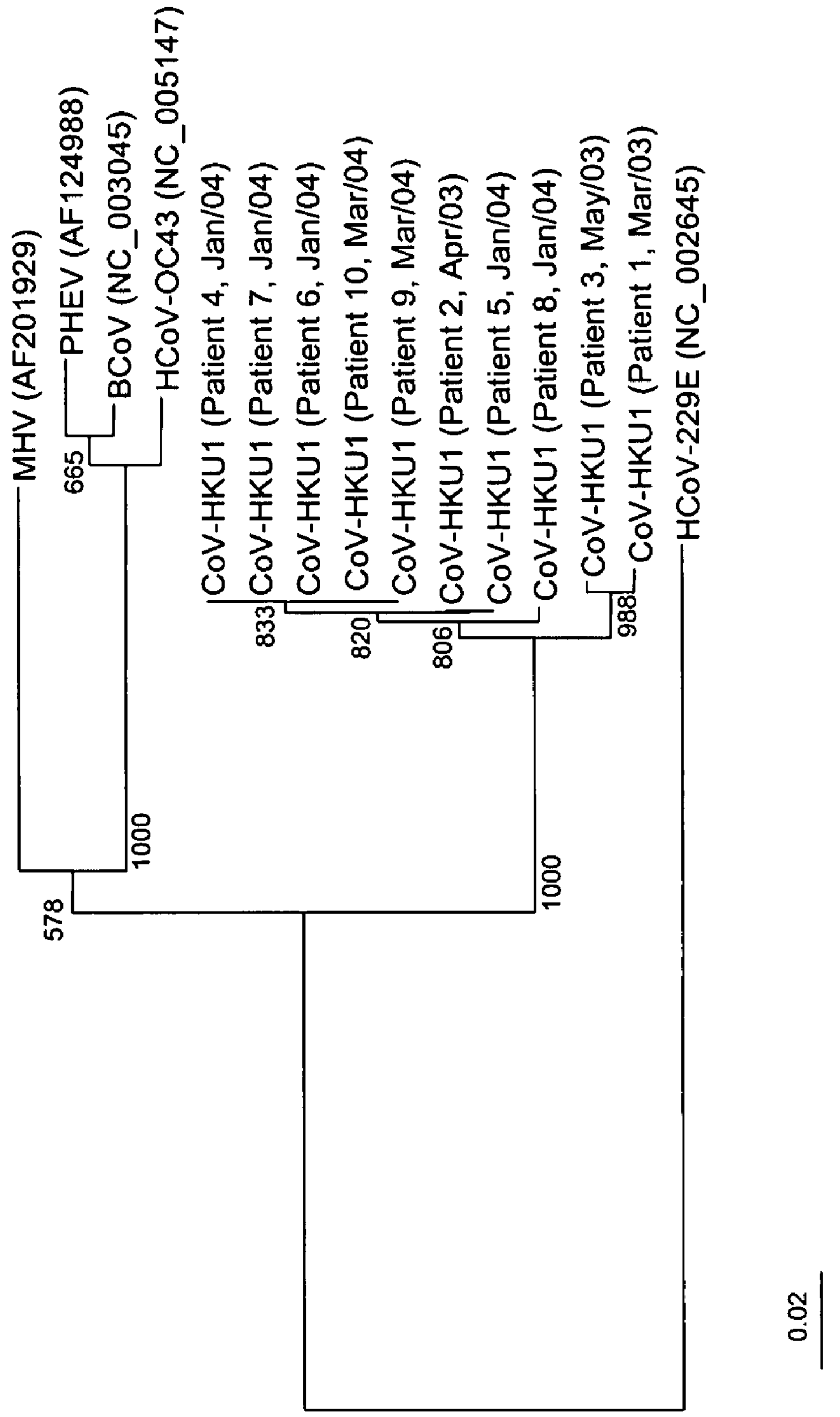

FIG. 17 show a phylogenetic tree of pol gene sequences of the 10 CoV-HKU1 from patients with community acquired pneumonia. The tree was inferred from pol gene data by the neighbor-joining method and bootstrap values calculated from 1000 trees. The tree was rooted using pol gene sequence of HCoV:229E and 393 nucleotide positions (primer sequences excluded) in each pol gene were included in the analysis. The scale bar indicates the estimated number of substitutions per 50 bases using Jukes-Cantor correction. CoV-HKU1: human coronavirus HKU1; HCoV-229E: human coronavirus 229E; HCoV-OC43: human coronavirus OC43; MHV: murine hepatitis virus; BCoV: bovine coronavirus; PHEV: porcine hemagglutinating encephalomyelitis virus.

5. DETAILED DESCRIPTION OF THE INVENTION

The present invention relates to the CoV-HKU1 that phylogenetically relates to known *Coronaviruses*. In a specific embodiment, CoV-HKU1 comprises a nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966. In a specific embodiment, the present invention provides isolated nucleic acid molecules of the CoV-HKU1, comprising, or, alternatively, consisting of the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, a complement thereof or a portion thereof. In another specific embodiment, the invention provides isolated nucleic acid molecules which hybridize under stringent conditions, as defined herein, to a nucleic acid molecule having the sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or specific genes of known member of Coronaviridae, or a complement thereof. In another specific embodiment, the invention provides isolated polypeptides or proteins that are encoded by a nucleic acid molecule comprising a nucleotide sequence that is at least about 5, 10, 15, 20, 25, 30, 35, 40, 45, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2,100, 2,200, 2,300, 2,400, 2,500, 2,600, 2,700, or more contiguous nucleotides of the nucleotide sequence of SEQ ID NO:1, 2920, 2922, 2924, 2926, 2928, 2930, 2932, or 2934, or a complement thereof. In yet another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, or more contiguous nucleotides of the nucleotide sequence of SEQ ID NO:2936, 2938, 2940, 2942, 2944, 2946, 2948, or 2950, or a complement thereof. In yet another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, or more contiguous nucleotides of the nucleotide sequence of SEQ ID NO:2952, 2954, 2956, 2958, 2960, 2962, 2964, or 2966, a complement thereof. In yet another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 100, 150, 200, 250, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:3 or 2919, or a complement thereof. The polypeptides or the proteins of the present invention preferably have one or more biological activities of the proteins encoded by the sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or the native viral proteins containing the amino acid sequences encoded by the sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a portion thereof.

The invention further relates to the use of the sequence information of the isolated virus for diagnostic and therapeutic methods. In a specific embodiment, the invention provides the entire nucleotide sequence of CoV-HKU1 (SEQ ID NO:3 or 2919), or fragments, or complement thereof. Furthermore, the present invention relates to a nucleic acid molecule that hybridizes any portion of the genome of the CoV-HKU1 (SEQ ID NO:3 or 2919) under the stringent conditions. In a specific embodiment, the invention provides nucleic acid molecules which are suitable for use as primers consisting of or comprising the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a complement thereof, or a portion thereof. In another specific embodiment, the invention provides nucleic acid molecules which are suitable for use as hybridization probes for the detection of nucleic acids encoding a polypeptide of the invention, consisting of or comprising the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, a complement thereof, or a portion thereof. The invention further encompasses chimeric or recombinant viruses or viral proteins encoded by said nucleotide sequences.

The invention further provides antibodies that specifically bind a polypeptide of the invention encoded by the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a fragment thereof, or any CoV-HKU1 epitope as well as the polypeptides having the amino acid sequqences of any one of SEQ ID NO:2, SEQ ID NOS:34-2918 shown in FIGS. 2 and 3, SEQ ID NOS:2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and 2970-4236 shown in FIG. 9. Such antibodies include, but are not limited to polyclonal, monoclonal, bi-specific, multi-specific, human, humanized, chimeric antibodies, single chain antibodies, Fab fragments, $F(ab')_2$ fragments, disulfide-linked Fvs, intrabodies and fragments containing either a VL or VH domain or even a complementary determining region (CDR) that specifically binds to a polypeptide of the invention.

In one embodiment, the invention provides methods for detecting the presence, activity or expression of the CoV-HKU1 of the invention in a biological material, such as cells, blood, saliva, urine, sputum, nasopharyngeal aspirates, and so forth. The presence of the CoV-HKU1 in a sample can be determined by contacting the biological material with an agent which can detect directly or indirectly the presence, activity or expression of the CoV-HKU1. In a specific embodiment, the detection agents are the antibodies of the present invention. In another embodiment, the detection agent is a nucleic acid of the present invention.

In another embodiment, the invention provides vaccine preparations comprising the CoV-HKU1 recombinant and chimeric forms of said virus, or subunits of the virus.

The present invention further provides methods of preparing recombinant or chimeric forms of CoV-HKU1. In another specific embodiment, the vaccine preparations of the present invention comprise one or more nucleic acid molecules comprising or consisting of the sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a fragment thereof. In another embodiment, the invention provides vaccine preparations comprising one or more polypeptides of the invention encoded by a nucleotide sequence comprising or consisting of the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a fragment thereof, including the polypeptides having the amino acid sequences of SEQ ID NO:2, SEQ ID NOS:34-2918, 2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and/or 2970-4236. Furthermore, the present invention provides methods for treating, ameliorating, managing, or preventing respiratory tract infections by administering to a subject in need thereof the anti-viral agents of the present invention, alone or in combination with other antivirals [e.g., amantadine, rimantadine, gancyclovir, acyclovir, ribavirin, penciclovir, oseltamivir, foscarnet zidovudine (AZT), didanosine (ddI), lamivudine (3TC), zalcitabine (ddC), stavudine (d4T), nevirapine, delavirdine, indinavir, ritonavir, vidarabine, nelfinavir, saquinavir, relenza, tamiflu, pleconaril, interferons, etc.], steroids and corticosteroids such as prednisone, cortisone, fluticasone and glucocorticoid, antibiotics, analgesics, bronchodialaters, or other treatments for respiratory and/or viral infections. In one aspect, the anti-viral agent of the present invention prevents or inhibit the binding of the virus or viral proteins to a host cell under a physiological condition, thereby preventing or inhibiting the infection of the host cell by the virus. In another aspect, the anti-viral agent of the invention prevents or inhibits replication of the viral nucleic acid molecules in the host cell under a physiological condition by interacting with the viral nucleic acid molecules or its transcription mechanisms. In a specific embodiment, the anti-viral agent of the invention includes the vaccine or immunogenic preparations of the invention or an antibody that immunospecifically binds CoV-HKU1 or any CoV-HKU1 epitope and may neutralizes CoV-HKU1. In another specific embodiment, the anti-viral agent is a polypeptide or protein of the invention or a nucleic acid molecule of the invention. In addition, the present invention provides a method of preventing or inhibiting replication in a host cell of a nucleic acid molecule having the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or inhibiting the activities of the polypeptides encoded by the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, a complement thereof, or a portion thereof, including the polypeptides having the amino acid sequence of SEQ ID NO:2, SEQ ID NO:34-2918, 2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and/or 2970-4236, by administering to said host cell the anti-viral agent of the invention. In a specific embodiment the host cell is a mammalian cell, such as a cell of humans, primates, horses, cows, sheep, pigs, goats, dogs, cats, arivan species and rodents. Preferably, the cell is a primate cell and most preferably a human cell.

Furthermore, the present invention provides pharmaceutical compositions comprising anti-viral agents of the present invention and a pharmaceutically acceptable carrier. The present invention also provides kits comprising pharmaceutical compositions of the present invention.

5.1 Recombinant and Chimeric CoV-HKU1

The present invention encompasses recombinant or chimeric viruses encoded by viral vectors derived from the genome of CoV-HKU 1 or natural variants thereof. In a specific embodiment, a recombinant virus is one derived from the CoV-HKU1. In a specific embodiment, the virus has a nucleotide sequence of SEQ ID NO:3 or 2919. In another specific embodiment, a recombinant virus is one derived from a natural variant of CoV-HKU1. A natural variant of CoV-HKU1 has a sequence that is different from the genomic sequence (SEQ ID NO:3 or 2919) of CoV-HKU1, due to one or more naturally occurred mutations, including, but not limited to, point mutations, rearrangements, insertions, deletions etc., to the genomic sequence that may or may not result in a phenotypic change. In accordance with the present invention, a viral vector which is derived from the genome of the CoV-HKU, is one that contains a nucleic acid sequence that encodes at least a part of one ORF of the CoV-HKU1. In a specific embodiment, the ORF comprises or consists of a nucleotide sequence of SEQ ID NO:1, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a fragment thereof. In a specific embodiment, there are more than one ORF within the nucleotide sequence of SEQ ID NO:3 or 2919, or a fragment thereof. In another embodiment, the polypeptides encoded by the ORF comprises or consists of amino acid sequences of SEQ ID NO:34-2918 shown in FIGS. 2 and 8, or SEQ ID NO:2, SEQ ID NO:2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and/or 2970-4236, or a fragment thereof. In accordance with the present invention these viral vectors may or may not include nucleic acids that are non-native to the viral genome.

In another specific embodiment, a chimeric virus of the invention is a recombinant CoV-HKU1 which further comprises a heterologous nucleotide sequence. In accordance with the invention, a chimeric virus may be encoded by a nucleotide sequence in which heterologous nucleotide sequences have been added to the genome or in which endogenous or native nucleotide sequences have been replaced with heterologous nucleotide sequences.

According to the present invention, the chimeric viruses are encoded by the viral vectors of the invention which further comprise a heterologous nucleotide sequence. In accordance with the present invention a chimeric virus is encoded by a viral vector that may or may not include nucleic acids that are non-native to the viral genome. In accordance with the invention a chimeric virus is encoded by a viral vector to which heterologous nucleotide sequences have been added, inserted or substituted for native or non-native sequences. In accordance with the present invention, the chimeric virus may be encoded by nucleotide sequences derived from different strains or variants of CoV-HKU1. In particular, the chimeric virus is encoded by nucleotide sequences that encode antigenic polypeptides derived from different strains or variants of CoV-HKU1.

A chimeric virus may be of particular use for the generation of recombinant vaccines protecting against two or more viruses (Tao et al., J. Virol. 72, 2955-2961; Durbin et al., 2000, J. Virol. 74, 6821-6831; Skiadopoulos et al., 1998, J. Virol. 72, 1762-1768 (1998); Teng et al., 2000, J. Virol. 74, 9317-9321). For example, it can be envisaged that a virus vector derived from the CoV-HKU1 expressing one or more proteins of variants of CoV-HKU1, or vice versa, will protect a subject vaccinated with such vector against infections by both the native CoV-HKU1 and the variant. Attenuated and replication-defective viruses may be of use for vaccination purposes with live vaccines as has been suggested for other viruses.

In accordance with the present invention the heterologous sequence to be incorporated into the viral vectors encoding the recombinant or chimeric viruses of the invention include sequences obtained or derived from different strains or variants of CoV-HKU1.

In certain embodiments, the chimeric or recombinant viruses of the invention are encoded by viral vectors derived from viral genomes wherein one or more sequences, intergenic regions, termini sequences, or portions or entire ORF have been substituted with a heterologous or non-native sequence. In certain embodiments of the invention, the chimeric viruses of the invention are encoded by viral vectors derived from viral genomes wherein one or more heterologous sequences have been inserted or added to the vector.

The selection of the viral vector may depend on the species of the subject that is to be treated or protected from a viral infection.

In accordance with the present invention, the viral vectors can be engineered to provide antigenic sequences which confer protection against infection by the CoV-HKU1 and natural variants thereof. The viral vectors may be engineered to provide one, two, three or more antigenic sequences. In accordance with the present invention the antigenic sequences may be derived from the same virus, from different strains or variants of the same type of virus, or from different viruses.

The expression products and/or recombinant or chimeric virions obtained in accordance with the invention may advantageously be utilized in vaccine formulations. The expression products and chimeric virions of the present invention may be engineered to create vaccines against a broad range of pathogens, including viral and bacterial antigens, tumor antigens, allergen antigens, and auto antigens involved in autoimmune disorders. In particular, the chimeric virions of the present invention may be engineered to create vaccines for the protection of a subject from infections with CoV-HKU1 and variants thereof.

In certain embodiments, the expression products and recombinant or chimeric virions of the present invention may be engineered to create vaccines against a broad range of pathogens, including viral antigens, tumor antigens and autoantigens involved in autoimmune disorders. One way to achieve this goal involves modifying existing CoV-HKU1 genes to contain foreign sequences in their respective external domains. Where the heterologous sequences are epitopes or antigens of pathogens, these chimeric viruses may be used to induce a protective immune response against the disease agent from which these determinants are derived.

Thus, the present invention relates to the use of viral vectors and recombinant or chimeric viruses to formulate vaccines against a broad range of viruses and/or antigens. The present invention also encompasses recombinant viruses comprising a viral vector derived from the CoV-HKU1 or variants thereof which contains sequences which result in a virus having a phenotype more suitable for use in vaccine formulations. The mutations and modifications can be in coding regions, in intergenic regions and in the leader and trailer sequences of the virus.

The invention provides a host cell comprising a nucleic acid or a vector according to the invention. Plasmid or viral vectors containing the polymerase components of CoV-HKU1 are generated in prokaryotic cells for the expression of the components in relevant cell types (bacteria, insect cells, eukaryotic cells). Plasmid or viral vectors containing full-length or partial copies of the CoV-HKU1 genome will be generated in prokaryotic cells for the expression of viral nucleic acids in-vitro or in-vivo. The latter vectors may contain other viral sequences for the generation of chimeric viruses or chimeric virus proteins, may lack parts of the viral genome for the generation of replication defective virus, and may contain mutations, deletions or insertions for the generation of attenuated viruses.

In addition, eukaryotic cells, transiently or stably expressing one or more full-length or partial CoV-HKU1 proteins can be used. Such cells can be made by transfection (proteins or nucleic acid vectors), infection (viral vectors) or transduction (viral vectors) and may be useful for complementation of mentioned wild type, attenuated, replication-defective or chimeric viruses.

The viral vectors and chimeric viruses of the present invention may be used to modulate a subject's immune system by stimulating a humoral immune response, a cellular immune response or by stimulating tolerance to an antigen. As used herein, a subject means: humans, primates, horses, cows, sheep, pigs, goats, dogs, cats, avian species and rodents.

5.2 Formulation of Vaccines and Antivirals

In a preferred embodiment, the invention provides a proteinaceous molecule or CoV-HKU1 specific viral protein or functional fragment thereof encoded by a nucleic acid according to the invention. Useful proteinaceous molecules are for example derived from any of the genes or genomic fragments derivable from the virus according to the invention, including envelop protein (E protein), integral membrane protein (M protein), spike protein (S protein), nucleocapsid protein (N protein), hemagglutinin esterase (HE protein), and RNA-dependent RNA polymerase. Such molecules, or antigenic fragments thereof, as provided herein, are for example useful in diagnostic methods or kits and in pharmaceutical compositions such as subunit vaccines. Particularly useful are polypeptides encoded by the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, including the polypeptides having the amino acid sequences of SEQ ID NOS:34-2918 in FIGS. 2 and 3, or SEQ ID NO:2, 2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and/or 2970-4236 in FIG. 9, or antigenic fragments thereof for inclusion as antigen or subunit immunogen, but inactivated whole virus can also be used. Particularly useful are also those proteinaceous substances that are encoded by recombinant nucleic acid fragments of the CoV-HKU1 genome; of course preferred are those that are within the preferred bounds and metes of ORFs, in particular, for eliciting CoV-HKU1 specific antibody or T cell responses, whether in vivo (e.g. for protective or therapeutic purposes or for providing diagnostic antibodies) or in vitro (e.g. by phage display technology or another technique useful for generating synthetic antibodies).

The invention provides vaccine formulations for the prevention and treatment of infections with CoV-HKU1. In certain embodiments, the vaccine of the invention comprises recombinant and chimeric viruses of the CoV-HKU1.

In another aspect, the present invention also provides DNA vaccine formulations comprising a nucleic acid or fragment of the CoV-HKU1, or nucleic acid molecules having the sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a fragment thereof. In another specific embodiment, the DNA vaccine formulations of the present invention comprises a nucleic acid or fragment thereof encoding the antibodies which immunospecifically binds CoV-HKU1. In DNA vaccine formulations, a vaccine DNA comprises a viral vector, such as that derived from the CoV-HKU1, bacterial plasmid, or other expression vector, bearing an insert comprising a nucleic acid molecule of the present invention operably linked to one or more control elements, thereby allowing expression of the vaccinating proteins encoded by said nucleic acid molecule in a vaccinated subject. Such vectors can be prepared by recombinant DNA technology as recombinant or chimeric viral vectors carrying a nucleic acid molecule of the present invention.

Various heterologous vectors are described for DNA vaccinations against viral infections. For example, the vectors described in the following references may be used to express CoV-HKU1 sequences instead of the sequences of the viruses or other pathogens described; in particular, vectors described for hepatitis B virus (Michel, M. L. et al., 1995, DAN-mediated immunization to the hepatitis B surface antigen in mice: Aspects of the humoral response mimic hepatitis B viral infection in humans, *Proc. Natl. Aca. Sci. USA* 92:5307-5311; Davis, H. L. et al., 1993, DNA-based immunization induces continuous seretion of hepatitis B surface antigen and high levels of circulating antibody, *Human Molec. Genetics* 2:1847-1851), HIV virus (Wang, B. et al., 1993, Gene inoculation generates immune responses against human imunodeficiency virus type 1, *Proc. Natl. Acad. Sci. USA* 90:4156-4160; Lu, S. et al., 1996, Simian immunodeficiency virus DNA vaccine trial in macques, *J. Virol*. 70:3978-3991; Letvin, N. L. et al., 1997, Potent, protective anti-HIV immune responses generated by bimodal HIV envelope DNA plus protein vaccination, *Proc Natl Acad Sci USA*. 94(17):9378-83), and influenza viruses (Robinson, H L et al., 1993, Protection against a lethal influenza virus challenge by immunization with a haemagglutinin-expressing plasmid DNA, *Vaccine* 11:957-960; Ulmer, J. B. et al., Heterologous protection against influenza by injection of DNA encoding a viral protein, *Science* 259:1745-1749), as well as bacterial infections, such as tuberculosis (Tascon, R. E. et al., 1996, Vaccination against tuberculosis by DNA injection, *Nature Med*. 2:888-892; Huygen, K. et al., 1996, Immunogenicity and protective efficacy of a tuberculosis DNA vaccine, *Nature Med*., 2:893-898), and parasitic infection, such as malaria (Sedegah, M., 1994, Protection against malaria by immunization with plasmid DNA encoding circumsporozoite protein, *Proc. Natl. Acad. Sci. USA* 91:9866-9870; Doolan, D. L. et al., 1996, Circumventing genetic restriction of protection against malaria with multigene DNA immunization: CD8+ T cell-interferon δ, and nitric oxide-dependent immunity, *J. Exper. Med*., 1183:1739-1746).

Many methods may be used to introduce the vaccine formulations described above. These include, but are not limited to, oral, intradermal, intramuscular, intraperitoneal, intravenous, subcutaneous, and intranasal routes. Alternatively, it may be preferable to introduce the chimeric virus vaccine formulation via the natural route of infection of the pathogen for which the vaccine is designed. The DNA vaccines of the present invention may be administered in saline solutions by injections into muscle or skin using a syringe and needle (Wolff J. A. et al., 1990, Direct gene transfer into mouse muscle in vivo, *Science* 247:1465-1468; Raz, E., 1994, Intradermal gene immunization: The possible role of DNA uptake in the induction of cellular immunity to viruses, *Proc. Natl. Acd. Sci. USA* 91:9519-9523). Another way to administer DNA vaccines is called "gene gun" method, whereby microscopic gold beads coated with the DNA molecules of interest is fired into the cells (Tang, D. et al., 1992, Genetic immunization is a simple method for eliciting an immune response, *Nature* 356:152-154). For general reviews of the methods for DNA vaccines, see Robinson, H. L., 1999, DNA vaccines: basic mechanism and immune responses (Review), *Int. J. Mol. Med*. 4(5):549-555; Barber, B., 1997, Introduction: Emerging vaccine strategies, *Seminars in Immunology* 9(5):269-270; and Robinson, H. L. et al., 1997, DNA vaccines, *Seminars in Immunology* 9(5):271-283.

5.3 Adjuvants and Carrier Molecules

CoV-HKU1-associated antigens are administered with one or more adjuvants. In one embodiment, the CoV-HKU1-associated antigen is administered together with a mineral salt adjuvants or mineral salt gel adjuvant. Such mineral salt and mineral salt gel adjuvants include, but are not limited to, aluminum hydroxide (ALHYDROGEL, REHYDRAGEL), aluminum phosphate gel, aluminum hydroxyphosphate (ADJU-PHOS), and calcium phosphate.

In another embodiment, CoV-HKU1-associated antigen is administered with an immunostimulatory adjuvant. Such class of adjuvants, include, but are not limited to, cytokines (e.g., interleukin-2, interleukin-7, interleukin-12, granulocyte-macrophage colony stimulating factor (GM-CSF), interfereon-γinterleukin-1β (IL-1β), and IL-1β peptide or Sclavo Peptide), cytokine-containing liposomes, triterpenoid glycosides or saponins (e.g., QuilA and QS-21, also sold under the trademark STIMULON, ISCOPREP), Muramyl Dipeptide (MDP) derivatives, such as N-acetyl-muramyl-L-threonyl-D-isoglutamine (Threonyl-MDP, sold under the trademark TERMURTIDE), GMDP, N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxy phosphoryloxy)-ethylamine, muramyl tripeptide phosphatidylethanolamine (MTP-PE), unmethylated CpG dinucleotides and oligonucleotides, such as bacterial DNA and fragments thereof, LPS, monophosphoryl Lipid A (3D-MLA sold under the trademark MPL), and polyphosphazenes.

In another embodiment, the adjuvant used is a particular adjuvant, including, but not limited to, emulsions, e.g., Freund's Complete Adjuvant, Freund's Incomplete Adjuvant, squalene or squalane oil-in-water adjuvant formulations, such as SAF and MF59, e.g., prepared with block-copolymers, such as L-121 (polyoxypropylene/polyoxyetheylene) sold under the trademark PLURONIC L-121, Liposomes, Virosomes, cochleates, and immune stimulating complex, which is sold under the trademark ISCOM.

In another embodment, a microparticular adjuvant is used. Microparticulare adjuvants include, but are not limited to biodegradable and biocompatible polyesters, homo- and copolymers of lactic acid (PLA) and glycolic acid (PGA), poly(lactide-co-glycolides) (PLGA) microparticles, polymers that self-associate into particulates (poloxamer particles), soluble polymers (polyphosphazenes), and virus-like particles (VLPs) such as recombinant protein particulates, e.g., hepatitis B surface antigen (HbsAg).

Yet another class of adjuvants that may be used include mucosal adjuvants, including but not limited to heat-labile enterotoxin from *Escherichia coli* (LT), cholera holotoxin (CT) and cholera Toxin B Subunit (CTB) from *Vibrio cholerae*, mutant toxins (e.g., LTK63 and LTR72), microparticles, and polymerized liposomes.

In other embodiments, any of the above classes of adjuvants may be used in combination with each other or with other adjuvants. For example, non-limiting examples of combination adjuvant preparations that can be used to administer the CoV-HKU1-associated antigens of the invention include liposomes containing immunostimulatory protein, cytokines, or T-cell and/or B-cell peptides, or microbes with or without entrapped IL-2 or microparticles containing enterotoxin. Other adjuvants known in the art are also included within the scope of the invention (see *Vaccine Design: The Subunit and Adjuvant Approach*, Chap. 7, Michael F. Powell and Mark J. Newman (eds.), Plenum Press, New York, 1995, which is incorporated herein in its entirety).

The effectiveness of an adjuvant may be determined by measuring the induction of antibodies directed against an immunogenic polypeptide containing a CoV-HKU1 polypeptide epitope, the antibodies resulting from administration of this polypeptide in vaccines which are also comprised of the various adjuvants.

The polypeptides may be formulated into the vaccine as neutral or salt forms. Pharmaceutically acceptable salts include the acid additional salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The vaccines of the invention may be multivalent or univalent. Multivalent vaccines are made from recombinant viruses that direct the expression of more than one antigen.

Many methods may be used to introduce the vaccine formulations of the invention; these include but are not limited to oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but can also be a non-human animal including but not limited to cows, horses, sheep, pigs, fowl (e.g., chickens), goats, cats, dogs, hamsters, mice and rats.

5.4 Preparation of Antibodies

Antibodies which specifically recognize a polypeptide of the invention, such as, but not limited to, polypeptides comprising the sequence of SEQ ID NO:2 or any of SEQ ID NOS: 34-2918, 2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and/or 2970-4236, or CoV-HKU1 epitope, or antigen-binding fragments thereof, can be used for detecting, screening, and isolating the polypeptide of the invention or fragments thereof, or similar sequences that might encode similar enzymes from the other organisms. For example, in one specific embodiment, an antibody which immunospecifically binds CoV-HKU1 epitope, or a fragment thereof, can be used for various in vitro detection assays, including enzyme-linked immunosorbent assays (ELISA), radioimmunoassays, Western blot, etc., for the detection of a polypeptide of the invention or, preferably, CoV-HKU1, in samples, for example, a biological material, including cells, cell culture media (e.g., bacterial cell culture media, mammalian cell culture media, insect cell culture media, yeast cell culture media, etc.), blood, plasma, serum, tissues, sputum, naseopharyngeal aspirates, etc.

Antibodies specific for a polypeptide of the invention or any epitope of CoV-HKU1 may be generated by any suitable method known in the art. Polyclonal antibodies to an antigen-of-interest, for example, the CoV-HKU1 epitopes or polypeptides encoded by a nucleotide sequence of SEQ ID NO:1 or 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, including the polypeptides shown in FIG. 2 (SEQ ID NOS: 34-1318), FIG. 3 (SEQ ID NOS:1319-2918), as well as SEQ ID NO:2, 2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and/or 2970-4236, can be produced by various procedures well known in the art. For example, an antigen can be administered to various host animals including, but not limited to, rabbits, mice, rats, etc., to induce the production of antisera containing polyclonal antibodies specific for the antigen. Various adjuvants may be used to increase the immunological response, depending on the host species, and include but are not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calnette-Guerin) and *Corynebacterium parvum*. Such adjuvants are also well known in the art (see Section 5.4, supra).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by known techniques. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the complete light chain, and the variable region, the CH1 region and the hinge region of the heavy chain.

The antibodies of the invention or fragments thereof can be also produced by any method known in the art for the synthesis of antibodies, in particular, by chemical synthesis or preferably, by recombinant expression techniques.

The nucleotide sequence encoding an antibody may be obtained from any information available to those skilled in the art (i.e., from Genbank, the literature, or by routine cloning and sequence analysis). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., supra; and Ausubel et al., eds., 1998, Current Protocols in Molecular Biology, John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies or any portion of antibodies which may enhance or reduce biological activities of the antibodies.

Recombinant expression of an antibody requires construction of an expression vector containing a nucleotide sequence that encodes the antibody. Once a nucleotide sequence encoding an antibody molecule or a heavy or light chain of an antibody, or portion thereof has been obtained, the vector for the production of the antibody molecule may be produced by recombinant DNA technology using techniques well known in the art as discussed in the previous sections. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression. Thus-prepared expression vector can be then introduced into appropriate host cells for the expression of the antibody. Accordingly, the invention includes host cells containing a polynucleotide encoding an antibody specific for the polypeptides of the invention or fragments thereof.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature, 322:52, 1986; and Kohler, Proc. Natl. Acad. Sci. USA, 77:2 197, 1980). The coding sequences for the heavy and light chains may comprise cDNA or genomic DNA.

In another embodiment, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., J. Immunol. Methods, 182:41-50, 1995; Ames et al., J. Immunol. Methods, 184: 177-186, 1995; Kettleborough et al., Eur. J. Immunol., 24:952-958, 1994; Persic et al., Gene, 187:9-18, 1997; Burton et al., Advances in Immunology, 57:191-280, 1994; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques, 12(6):864-869, 1992; and Sawai et al., AJRI, 34:26-34, 1995; and Better et al., Science, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., Methods in Enzymology, 203:46-88, 1991; Shu et al., PNAS, 90:7995-7999, 1993; and Skerra et al., Science, 240:1038-1040, 1988.

Once an antibody molecule of the invention has been produced by any methods described above, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, Science, 229:1202, 1985; Oi et al., BioTechniques, 4:214 1986; Gillies et al., J. Immunol. Methods, 125:191-202, 1989; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., Nature, 332:323, 1988, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, Molecular Immunology, 28(4/5):489-498, 1991; Studnicka et al., Protein Engineering, 7(6):805-814, 1994; Roguska et al., Proc Natl. Acad. Sci. USA, 91:969-973, 1994), and chain shuffling (U.S. Pat. No. 5,565,332), all of which are hereby incorporated by reference in their entireties.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, Int. Rev. Immunol., 13:65-93, 1995. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Fremont, Calif.), Medarex (NJ) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology, 12:899-903, 1988).

Antibodies fused or conjugated to heterologous polypeptides may be used in in vitro immunoassays and in purification methods (e.g., affinity chromatography) well known in the art. See e.g., PCT publication Number WO 93/21232; EP 439,095; Naramura et al., Immunol. Lett., 39:91-99, 1994; U.S. Pat. No. 5,474,981; Gillies et al., PNAS, 89:1428-1432, 1992; and Fell et al., J. Immunol., 146:2446-2452, 1991, which are incorporated herein by reference in their entireties.

Antibodies may also be attached to solid supports, which are particularly useful for immunoassays or purification of the polypeptides of the invention or fragments, derivatives, analogs, or variants thereof, or similar molecules having the similar enzymatic activities as the polypeptide of the invention. Such solid supports include, but are not limited to, glass, cellulose, polyacrylamide, nylon, polystyrene, polyvinyl chloride or polypropylene.

5.5 Pharmaceutical Compositions and Kits

The present invention encompasses pharmaceutical compositions comprising anti-viral agents of the present invention. In a specific embodiment, the anti-viral agent is an antibody which immunospecifically binds CoV-HKU1 or variants thereof, or any proteins derived therefrom. In another specific embodiment, the anti-viral agent is a polypeptide or nucleic acid molecule of the invention. The pharmaceutical compositions have utility as an anti-viral prophylactic agent and may be administered to a subject where the subject has been exposed or is expected to be exposed to a virus.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu and Wu, 1987, J. Biol. Chem. 262:4429 4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In a preferred embodiment, it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, by means of nasal spray, or by means of an implant, said implant being of a porous, non porous, or gelatinous material, including membranes, such as sialastic membranes, or fibers. In one embodiment, administration can be by direct injection at the site (or former site) infected tissues.

In another embodiment, the pharmaceutical composition can be delivered in a vesicle, in particular a liposome (see Langer, 1990, Science 249:1527-1533; Treat et al., in Liposomes in the Therapy of Infectious Disease and Cancer, Lopez Berestein and Fidler (eds.), Liss, New York, pp. 353-365 (1989); Lopez-Berestein, ibid. , pp. 317-327; see generally ibid.).

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al.,1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

The pharmaceutical compositions of the present invention comprise a therapeutically effective amount of recombinant or chimeric CoV-HKU1, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2 ethylamino ethanol, histidine, procaine, etc.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a preferred embodiment, the kit contains an antiviral agent of the invention, e.g., an antibody specific for the polypeptides encoded by a nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966 or any CoV-HKU1 epitope, or a polypeptide or protein of the present invention, including those shown in FIG. 2 (SEQ ID NOS:34-1318), FIG. 3 (SEQ ID NOS:1319-2918), FIG. 9 (SEQ ID NOS:2970-4236) and SEQ ID NO:2, or a nucleic acid molecule of the invention, alone or in combination with adjuvants, antivirals, antibiotics, analgesic, bronchodialaters, or other pharmaceutically acceptable excipients.

The present invention further encompasses kits comprising a container containing a pharmaceutical composition of the present invention and instructions for use.

5.6 Detection Assays

The present invention provides a method for detecting an antibody, which immunospecifically binds to the CoV-HKU1, in a biological sample, for example blood, serum, plasma, saliva, urine, etc., from a patient suffering from respiratory tract infection. In a specific embodiment, the method comprising contacting the sample with the polypeptides or protein encoded by the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, including the polypeptides having the amino acid sequences of SEQ ID NOS:34-1318 shown in FIG. 2, SEQ ID NOS:1319-2918 shown in FIG. 3, or SEQ ID NO:2, 2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, and/or 2970-4236 shown in FIG. 9, directly immobilized on a substrate and detecting the virus-bound antibody directly or indirectly by a labeled heterologous anti-isotype antibody. In another specific embodiment, the sample is contacted with a host cell comprising a nucleic acid molecule having the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, and expressing the polypeptides encoded thereby, and the bound antibody can be detected by immunofluorescent assay.

An exemplary method for detecting the presence or absence of a polypeptide or nucleic acid of the invention in a biological sample involves obtaining a biological sample from various sources and contacting the sample with a compound or an agent capable of detecting an epitope or nucleic acid (e.g., mRNA, genomic RNA) of CoV-HKU1 such that the presence of CoV-HKU1 is detected in the sample. A preferred agent for detecting CoV-HKU1 mRNA or genomic RNA of the invention is a labeled nucleic acid probe capable of hybridizing to mRNA or genomic RNA encoding a polypeptide of the invention. The nucleic acid probe can be, for example, a nucleic acid molecule comprising or consisting of the nucleotide sequence of SEQ ID NO:1, 3, 2919, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966, or a portion thereof, or a complement thereof, such as an oligonucleotide of at least 15, 20, 25, 30, 50, 100, 250, 500, 750, 1,000 or more contiguous nucleotides in length and sufficient to specifically hybridize under stringent conditions to a CoV-HKU1 mRNA or genomic RNA.

In another preferred specific embodiment, the presence of CoV-HKU1 is detected in the sample by an reverse transcription polymerase chain reaction (RT-PCR) using the primers that are constructed based on a partial nucleotide sequence of the genome of CoV-HKU1 or a genomic nucleic acid sequence of SEQ ID NO:3 or 2919, or based on a nucleotide sequence of SEQ ID NO:1, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964 and/or 2966. In a non-limiting specific embodiment, preferred primers to be used in a RT-PCR method are: 5'-GGTTGGGACTATCCTAAGTGTGA-3' (SEQ ID NO:4) and 5'-CCATCATCAGATAGAATCATCATA-3' (SEQ ID NO:5), or 5'-AAAGGATGTTGACAACCCTGTT-3' (LPW1926; SEQ ID NO: 2968) and 5'-ATCATCATACTAAAATGCTTACA-3' (LPW1927; SEQ ID NO: 2969), in the presence of 3 mM $MgCl_2$ and the thermal cycles are, for example, but not limited to, 94° C. for 8 min followed by 40 cycles of 94° C. for 1 min, 50° C. for 1 min, 72° C. for 1 min. In more preferred specific embodiment, the present invention provides a real-time quantitative PCR assay to detect the presence of CoV-HKU1 in a biological sample by subjecting the cDNA obtained by reverse transcription of the extracted total RNA from the sample to PCR reactions using the specific primers, such as those having nucleotide sequences of SEQ ID NOS:4, 5, 2968 and 2969, and a fluorescence dye, such as SYBR® Green I, which fluoresces when bound non-specifically to double-stranded DNA. The fluorescence signals from these reactions are captured at the end of extension steps as PCR product is generated over a range of the thermal cycles, thereby allowing the quantitative determination of the viral load in the sample based on an amplification plot.

A preferred agent for detecting CoV-HKU1 is an antibody that specifically binds a polypeptide of the invention or any CoV-HKU1 epitope, preferably an antibody with a detectable label. Antibodies can be polyclonal, or more preferably, monoclonal. An intact antibody, or a fragment thereof (e.g., Fab or $F(ab')_2$) can be used.

The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The detection method of the invention can be used to detect mRNA, protein (or any epitope), or genomic RNA in a sample in vitro as well as in vivo. For example, in vitro techniques for detection of mRNA include northern hybridizations, in situ hybridizations, RT-PCR, and RNase protection. In vitro techniques for detection of an epitope of CoV-HKU1 include enzyme linked immunosorbent assays (ELISAs), Western blots, immunoprecipitations and immunofluorescence. In vitro techniques for detection of genomic RNA include northern hybridizations, RT-PCR, and RNase protection. Furthermore, in vivo techniques for detection of CoV-HKU1 include introducing into a subject organism a labeled antibody directed against the polypeptide. For example, the antibody can be labeled with a radioactive marker whose presence and location in the subject organism can be detected by standard imaging techniques, including autoradiography.

In a specific embodiment, the methods further involve obtaining a control sample from a control subject, contacting the control sample with a compound or agent capable of detecting CoV-HKU1, e.g., a polypeptide of the invention or mRNA or genomic RNA encoding a polypeptide of the invention, such that the presence of CoV-HKU1 or the polypeptide or mRNA or genomic RNA encoding the polypeptide is detected in the sample, and comparing the absence of CoV-HKU1 or the polypeptide or mRNA or genomic RNA encoding the polypeptide in the control sample with the presence of CoV-HKU1, or the polypeptide or mRNA or genomic DNA encoding the polypeptide in the test sample.

The invention also encompasses kits for detecting the presence of CoV-HKU1 or a polypeptide or nucleic acid of the invention in a test sample. The kit, for example, can comprise a labeled compound or agent capable of detecting CoV-HKU1 or the polypeptide or a nucleic acid molecule encoding the polypeptide in a test sample and, in certain embodiments, a means for determining the amount of the polypeptide or mRNA in the sample (e.g., an antibody which binds the polypeptide or an oligonucleotide probe which binds to DNA or mRNA encoding the polypeptide). Kits can also include instructions for use.

For antibody-based kits, the kit can comprise, for example: (1) a first antibody (e.g., attached to a solid support) which binds to a polypeptide of the invention or CoV-HKU1 epitope; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or to a sequence within the CoV-HKU1 genome or (2) a pair of primers useful for amplifying a nucleic acid molecule containing an CoV-HKU1 sequence. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for use.

6. EXAMPLES

The following examples illustrate the identification of the novel CoV-HKU1. These examples should not be construed as limiting.

METHODS AND RESULTS

As a general reference, Wiedbrauk D L & Johnston S L G. (Manual of Clinical Virology, Raven Press, New York, 1993) was used.

6.1 Example 1

6.1.1 Clinical Subject

The patient is an in-patient of the United Christian Hospital in Hong Kong. Nasopharyngeal aspirates were collected from the patient weekly from the first till the fifth week of the illness, stool and urine in the first and second week of the illness, and sera in the first, second, and fourth weeks of the illness.

6.1.2 Antibody Detection

To produce a fusion plasmid for protein purification, primers, 5'-TTTTCCTTTTGCGGCCGCTTAAGCAACA-GAGTCTTCTA-3' (SEQ ID NO:6) and 5'-CGGAATTC-GATGTCTTATACTCCCGGT-3'(SEQ ID NO:7) were used to amplify the gene encoding the N protein of the CoV-HKU1 by RT-PCR. The sequence coding for amino acid residues 1 to 441 of the N protein was amplified and cloned into the EcoRI and NotI sites of expression vector pET-28b (+) (Novagen, Madison, Wis., USA) in frame and downstream of the series of six histidine residues. The $(His)_6$-tagged (SEQ ID NO:27) recombinant N protein was expressed in *E. coli* and purified using the $Ni^{2+}$-loaded HiTrap Chelating System (Amersham Pharmacia, USA) according to the manufacturer's instructions.

Western blot analysis was performed as follows: Two-hundred ng of purified $(His)_6$-tagged (SEQ ID NO:27) recombinant N protein of CoV-HKU1 were loaded into each well of a sodium dodecyl sulfate (SDS)—10% polyacrylamide gel and subsequently electroblotted onto a nitrocellulose membrane (Bio-Rad, Hercules, Calif., USA). The blot was cut into strips and the strips were incubated separately with 1:2000 dilution of serum samples obtained during the first, second, and fourth weeks of the patient's illness. Serum samples of two healthy blood donors were used as controls. Antigen-antibody interaction was detected with an ECL fluorescence system (Amersham Life Science, Buckinghamshire, UK).

Several prominent immunoreactive bands were visible for serum samples collected during the second and fourth weeks of the patient's illness (FIG. 8, lanes 2 and 3). The sizes of the largest bands were about 53 kDa, consistent with the expected size of 52.8 kDa for the full-length $(His)_6$-tagged (SEQ ID NO:27) N protein, whereas the other bands were consistent with the degradation products of the $(His)_6$-tagged (SEQ ID NO:27) N protein. Only very faint bands were observed for serum samples obtained from the patient during the first week of the illness (FIG. 8, lane 1) and two healthy blood donors (FIG. 8, lanes 4 and 5).

ELISA was performed using the recombinant N protein of CoV-HKU1 prepared as described above. Each well of a Nunc immunoplate (Roskilde, Denmark) was coated with 20 ng of purified $(His)_6$-tagged (SEQ ID NO:27) recombinant N protein for 12 h and then blocked in phosphate-buffered saline with 2% bovine serum albumin. The serum samples obtained from the patient during the first, second, and fourth weeks of the illness were serially diluted and were added to the wells of the (His)6-tagged (SEQ ID NO:27) recombinant N protein-coated plates in a total volume of 100 μl per well and incubated at 37° C. for 2 h. After washing with washing buffer five times, 100 μl per well of 1:4000 diluted horse radish peroxidase-conjugated goat anti-human IgG antibody (Zymed Laboratories Inc., South San Francisco, Calif., USA) were added to the wells and incubated at 37° C. for 1 h. After washing with washing buffer five times, 100 μl of diluted 3,3',5,5'-tetramethylbenzidine (Zymed Laboratories Inc.) were added to each well and incubated at room temperature for 15 min. One hundred microliters of 0.3 M $H_2SO_4$ were added and the absorbance at 450 nm of each well was measured. Each sample was tested in duplicate and the mean absorbance for each serum was calculated.

Box titration was carried out with different dilutions of $(His)_6$-tagged (SEQ ID NO:27) recombinant N protein coating antigen and serum obtained from the fourth week of the patient's illness. The results identified 20 ng and 80 ng of purified $(His)_6$-tagged recombinant N protein per ELISA well as the ideal amount for plate coating and 1:1000 and 1:20 as the most optimal serum dilution for IgG and IgM detection, respectively.

To establish the baseline for the tests, serum samples (diluted at 1:1000 and 1:20 for IgG and IgM, respectively) from 100 healthy blood donors were tested in the CoV-HKU1 antibody ELISA. For the 100 sera from healthy blood donors, the mean ELISA $OD_{450}$ values for IgG and IgM detection were 0.178 and 0.224, with standard deviations of 0.070 and 0.117. Absorbance values of 0.387 and 0.576 were selected as the cutoff values (that equal the sum of the mean value from the healthy control and three times the standard deviation) for IgG and IgM, respectively. Using these cutoff values, the titers for IgG of the patient's serum samples obtained during the first, second, and fourth weeks of the illness were<1:1000, 1:2000, and 1:8000, respectively (FIG. 7), and those for IgM were 1:20, 1:40, and 1:80, respectively (data not shown).

6.1.3 RT-PCR and Real Time Quantitative PCR

RT-PCR Assay

An RT-PCR was developed to detect the CoV-HKU1 sequence from NPA samples. Total RNA from clinical samples was reverse transcribed using random hexamers and cDNA was amplified using primers 5'-GGTTGGGACTATCCTAAGTGTGA-3' (SEQ ID NO:4) and 5'-CCATCATCAGATAGAATCATCATA-3' (SEQ ID NO:5), which were constructed based on the RNA-dependent RNA polymerase-encoding sequence (SEQ ID NO:1) of the CoV-HKU1 in the presence of 2.5 mM $MgCl_2$ (94° C. for 8 min followed by 40 cycles of 94° C. for 1 min, 50° C. for 1 min, 72° C. for 1 min).

The summary of a typical RT-PCR protocol is as follows:

1. RNA Extraction

RNA from 140 μl of NPA samples was extracted by QIAquick® viral RNA extraction kit and was eluted in 50 μl of elution buffer.

2. Reverse Transcription

| | |
|---|---|
| RNA | 11.5 μl |
| 0.1 M DTT | 2 μl |
| 5 × buffer | 4 μl |
| 10 mM dNTP | 1 μl |
| Superscript II, 200 U/μl (Invitrogen) | 1 μl |
| Random hexamers, 0.3 μg/μl | 0.5 μl |
| Reaction condition | 42° C., 50 min<br>94° C., 3 min<br>4° C. |

3. PCR cDNA generated by random primers was amplified in a 50 μl reaction as follows:

| | |
|---|---|
| cDNA | 2 μl |
| 10 mM dNTP | 0.5 μl |
| 10 × buffer | 5 μl |
| 25 mM $MgCl_2$ | 5 μl |
| 25 μM Forward primer | 0.5 μl |
| 25 μM Reverse primer | 0.5 μl |
| AmpliTaq Gold ® polymerase, 5 U/μl (Applied Biosystems) | 0.25 μl |
| Water | 36.25 μl |

Thermal-cycle condition: 95° C., 10 min, followed by 40 cycles of 95° C., 1 min; 50° C. 1 min; 72° C., 1 min.

4. Primer Sequences

Primers were designed based on the RNA-dependent RNA polymerase encoding sequence (SEQ ID NO:1) of the CoV-HKU1.

```
Forward primer:
5'-GGTTGGGACTATCCTAAGTGTGA-3'      (SEQ ID NO: 4)

Reverse primer: and
5'-CCATCATCAGATAGAATCATCATA-3'     (SEQ ID NO: 5)

Product size:
440 bps
```

Real-Time Quantitative PCR Assay

Total RNA from 140 μl of nasopharyngeal aspirate (NPA) was extracted by QIAamp® virus RNA mini kit (Qiagen) as instructed by the manufacturer. Ten μl of eluted RNA samples were reverse transcribed by 200 U of Superscript® II reverse transcriptase (Invitrogen) in a 20 μl reaction mixture containing 0.15 µg of random hexamers, 10 mmol/L DTT, and 0.5 mmol/L dNTP, as instructed. Complementary DNA was then amplified in a SYBR® Green I fluorescence reaction (Roche, Ind.) mixtures. Briefly, 20 µl reaction mixtures containing 2 µl of cDNA, 3.5 mmol/L $MgCl_2$, 0.25 µmol/L of forward primer [5'-GGTTGGGACTATCCTAAGTGTGA-3' (SEQ ID NO:4)] and 0.25 µmol/L reverse primer [5'-CCATCATCAGATAGAATCATCATA-3' (SEQ ID NO:5)] were thermal-cycled by a LightCycler® (Roche) with the PCR program, [95° C., 10 min followed by 50 cycles of 95° C., 10 min; 57° C., 5 sec; 72° C. 9 sec]. Plasmids containing the target sequence were used as positive controls. Fluorescence signals from these reactions were captured at the end of extension step in each cycle. To determine the specificity of the assay, PCR products (440 base pairs) were subjected to a melting curve analysis at the end of the assay (65° C. to 95° C., 0.1° C. per second) (data not shown).

The amount of CoV-HKU1 RNA in the nasopharyngeal aspirates was followed weekly. Quantitative RT-PCR showed that the amounts of CoV-HKU1 RNA were $8.5\times10^5$ and $9.6\times10^6$ copies per ml in two nasopharyngeal aspirates collected in the first week of the illness, 1.5x105 copies per ml of NPA, respectively, at two time points collected in the second week of the illness, but CoV-HKU1 RNA was undetectable in the NPA collected in the third, fourth and fifth weeks of the illness (FIG. 7). CoV-HKU1 RNA was also undetectable in the urine and stool of the patient collected in the first and second weeks of the illness.

Discussion

The genome of CoV-HKU1 is a 29926-nucleotide long, polyadenylated RNA. The G+C content is 32%, which is the lowest among all known coronaviruses with genome sequences available, with a GC skew of 0.19. Table 1 shows comparison of genomic features of CoV-HKU1 and other coronaviruses and amino acid identities between the predicted chymotrypsin-like protease ($3CL^{pro}$), RNA dependent RNA polymerase (Pol), helicase (Hel), hemagglutinin-esterase (HE), spike (S), envelope (E), membrane (M), and nucleocapsid (N) proteins of CoV-HKU1 and the corresponding proteins of other coronaviruses

TABLE 1

| | Genome features | | Pairwise amino acid identity (%) | | | | | | | |
|---|---|---|---|---|---|---|---|---|---|---|
| Coronaviruses[a] | Size (bases) | G + C content | $3CL^{pro}$ | Pol | Hel | HE | S | E | M | N |
| Group 1 | | | | | | | | | | |
| HCoV-229E | 27317 | 0.38 | 45 | 54 | 55 | — | 31 | 26 | 35 | 28 |
| PEDV | 28033 | 0.42 | 44 | 56 | 55 | — | 30 | 34 | 37 | 37 |
| PTGV | 28586 | 0.38 | 45 | 57 | 57 | — | 32 | 34 | 37 | 27 |
| CCoV | — | — | — | — | — | — | 31 | 32 | 36 | 27 |
| HCoV-NL63 | 27553 | 0.34 | 43 | 54 | 54 | — | 30 | 28 | 32 | 28 |
| Group 2 | | | | | | | | | | |
| CoV-HKU1 | 29926 | 0.32 | — | — | — | — | — | — | — | — |
| HCoV-OC43 | 30738 | 0.37 | 82 | 87 | 88 | 57 | 60 | 54 | 76 | 58 |
| MHV | 31357 | 0.42 | 85 | 90 | 89 | 50 | 61 | 57 | 84 | 68 |
| BCoV | 31028 | 0.37 | 84 | 88 | 88 | 56 | 61 | 55 | 76 | 57 |
| SDAV | — | — | — | — | — | 50 | 61 | 60 | 77 | 62 |
| ECoV | — | — | — | — | — | 53 | 61 | 56 | 78 | 59 |
| PHEV | — | — | — | — | — | 54 | 61 | 54 | 77 | 57 |
| Group 3 | | | | | | | | | | |
| IBV | 27608 | 0.38 | 41 | 60 | 57 | — | 32 | 28 | 38 | 27 |
| SARS-CoV | 29751 | 0.41 | 48 | 65 | 63 | — | 33 | 27 | 34 | 31 |

[a]HCoV-229E, human coronavirus 229E; PEDV, porcine epidemic diarrhea virus; PTGV, porcine transmissible gastroenteritis virus; CCoV, canine enteric coronavirus; HCoV-NL63, human coronavirus NL63; HCoV-OC43, human coronavirus OC43; MHV, murine hepatitis virus;BCoV, bovine coronavirus; SDAV, rat sialodacryoadenitis coronavirus; ECoV, equine coronavirus NC99; PHEV, porcine hemagglutinating encephalomyelitis virus; IBV, infectious bronchitis virus; SARS-CoV, SARS coronavirus The genome organization is the same as other coronaviruses, with the characteristic gene order 5'-replicase, S, E, M, N-3'. Both 5' and 3' ends contain short untranslated regions. The 5' end of the genome consists of a putative 5' leader sequence. A putative transcription regulatory sequences (TRS) motif, 5'-CUAAAC-3', was found at the 3' end of the leader sequence and precedes each translated ORF except ORF5 which encodes the putative E protein. Table 2 shows the putative transcription regulatory sequences in the genome of CoV-HKU1.

TABLE 2

| Number of base up-stream of AUG | ORF | TRS sequence | SEQ ID NO. |
|---|---|---|---|
| -140 | Leader | UUAAAUCUAAACUUUUUAA (127) **AUG** | 8 |
| -7 | Hemagglutinin esterase | UUAAAUCUAAACU **AUG** | 9 |
| -6 | Spike | UUAAAUCUAAAC **AUG** | 10 |
| -13 | ORF 4 | UUAAAUCUAAACUUUAUUU **AUG** | 11 |
| -9 | Membrane | CUAAAUCUAAACAUU **AUG** | 12 |
| -13 | Nucleocapsid | UUAAAUCUAAACUAUUAGG **AUG** | 13 |

TABLE 2-continued

| Number of base up-stream of AUG | ORF | TRS sequence | SEQ ID NO. |
|---|---|---|---|
| -35 | ORF 8 | UUAAAUCUAAACUAUUAGGAUGUCUUAU ACUCCCGGUCAUU **AUG** | 14 |

As in SDAV (Sialodacryoadenitis virus) and MHV (mouse hepatitis virus), ORF5 may share the same TRS with ORF 4, suggesting that the translation of the E protein is cap-independent, possibly via an internal ribosomal entry site. The 3' untranslated region contains a predicted pseudoknot structure 59-119 bp downstream of N gene. This pseudoknot structure is highly conserved among coronaviruses and plays a role in coronavirus RNA replication.

The coding potential of the CoV-HKU1 genome is shown in FIG. 4 and Table 3 and the phylogenetic analyses of the chymotrypsin-like protease (3CL$^{pro}$), replicase, helicase, haemagglutinin-esterase (HE), S, E, M and N, are shown in FIGS. 5A and 5B.

TABLE 3

| ORFs | Start-end (base) | No. of bases | No. of amino acids | Frame | Candidate TRS |
|---|---|---|---|---|---|
| ORF 1a | 206-13600 | 13395 | 4465 | +2 | — |
| ORF 1b | 13600-21753 | 8154 | 2717 | +1 | — |
| HE (ORF 2) | 21773-22933 | 1161 | 386 | +2 | Strong |
| S (ORF 3) | 22942-27012 | 4071 | 1356 | +1 | Strong |
| ORF 4 | 27051-27380 | 330 | 109 | +3 | Strong |
| E (ORF 5) | 27373-27621 | 249 | 82 | +1 | None |
| M (ORF 6) | 27633-28304 | 672 | 223 | +3 | Strong |
| N (ORF 7) | 28320-29645 | 1326 | 441 | +3 | Strong |
| ORF 8 | 28342-28959 | 618 | 205 | +1 | Strong |

The replicase 1a ORF (bases 206-13600) and replicase 1b ORF (bases 13600-21753) occupy 21.5 kb of the CoV-HKU1 genome. Similar to other coronaviruses, a frame shift interrupts the protein-coding regions and separates the 1a and 1b ORFs. This ORF encodes a number of putative proteins, including papain-like protease (PLP) with two copies of the PLP domain, PLP1$^{pro}$ and PLP2$^{pro}$, 3CL$^{pro}$, replicase, helicase, and other proteins of unknown functions. These proteins are produced by proteolytic cleavages of a large polyprotein (FIG. 4). The sequence of the resulting putative proteins is the same as that in the MHV genome. This polyprotein is synthesized by a −1 ribosomal frameshift at a conserved site (UUUAAAC) upstream of a pseudoknot structure at the junction of ORF 1 a and ORF 1b. This ribosomal frameshift would result in a polyprotein of 7182 amino acids, which has 75-77% amino acid identities with the polyprotein in other Group 2 coronaviruses and 43-47% amino acid identities with the polyprotein in other non-Group 2 coronaviruses. The replicase gene of CoV-HKU1, which encodes 928 amino acids, has 87-89% amino acid identities with the replicase of other Group 2 coronaviruses and 54-65% amino acid identities with the replicase of other non-Group 2 coronaviruses (Table 4 and FIG. 5A). Table 4 shows amino acid identities between the predicted chymotrypsin-like protease (3CL$^{pro}$), replicase (Rep), helicase (Hel), hemagglutinin-esterase (HE), spike (S), envelope (E), membrane (M), and nucleocapsid (N) proteins of CoV-HKU1 and the corresponding proteins of other coronaviruses.

TABLE 4

| | | Pairwise amino acid identity (%) | | | | | | | |
|---|---|---|---|---|---|---|---|---|---|
| Group | Virus | 3CL$^{pro}$ | Rep | Hel | HE | S | E | M | N |
| 1 | HCoV-229E | 45 | 54 | 55 | — | 31 | 26 | 35 | 28 |
| | PEDV | 44 | 56 | 55 | — | 30 | 34 | 37 | 37 |
| | PTGV | 45 | 57 | 57 | — | 32 | 34 | 37 | 27 |
| | CCoV | — | — | — | — | 31 | 32 | 36 | 27 |
| | HCoV-NL63 | 43 | 54 | 54 | — | 30 | 28 | 32 | 28 |
| 2 | HCoV-OC43 | 82 | 87 | 88 | 57 | 60 | 54 | 76 | 58 |
| | MHV | 85 | 89 | 87 | 50 | 58 | 55 | 78 | 60 |
| | BCoV | 84 | 88 | 88 | 56 | 61 | 55 | 76 | 57 |
| | SDAV | — | — | — | 50 | 61 | 60 | 77 | 62 |
| | ECoV | — | — | — | 53 | 61 | 56 | 78 | 59 |
| | PHEV | — | — | — | 54 | 61 | 54 | 77 | 57 |
| 3 | IBV | 41 | 60 | 57 | — | 32 | 28 | 38 | 27 |
| SARS-CoV | SARS-CoV | 48 | 65 | 63 | — | 33 | 27 | 34 | 31 |

HCoV-229E = human coronavirus 229E;
PEDV = porcine epidemic diarrhea virus;
PTGV = porcine transmissible gastroenteritis virus;
CCoV = canine enteric coronavirus;
HCoV-NL63 = human coronavirus NL63;
HCoV-OC43 = human coronavirus OC43;
MHV = murine hepatitis virus;
BCoV = bovine coronavirus;
SDAV = rat sialodacryoadenitis coronavirus;
ECoV = equine coronavirus NC99;
PHEV = porcine hemagglutinating encephalomyelitis virus;
IBV = infectious bronchitis virus;
SARS-CoV = SARS coronavirus The catalytic histidine and cysteine amino acid residues, conserved among the 3CL$^{pro}$ in all coronaviruses, are present in the predicted 3CL$^{pro}$ of CoV-HKU1 (amino acids His$^{3375}$ and Cys$^{3479}$ of ORF 1a). In the N-terminal of the putative PLP (amino acid residues 945 to 1104 of ORF 1a), there are 14 tandem copies of a 30-base repeat, which encode NDDEDVVTGD (SEQ ID NO:15), followed by two 30-base regions that encode NNDEEIVTGD (SEQ ID NO:16) and NDDQIVVTGD (SEQ ID NO:17), located upstream to the first copy of PLP domain, PLP1$^{pro}$. This repeat is not observed in other coronaviruses.

ORF 2 (bases 21773-22933) encodes the predicted HE glycoprotein with 386 amino acids. The HE protein of CoV-HKU1 has 50-57% amino acid identities with the HE proteins of other Group 2 coronaviruses (Table 4 and FIG. 5A). PFAM and InterProScan analyses of the ORF show that amino acid residues 1 to 349 of the predicted protein is a member of the haemagglutinin esterase family (PFAM accession no.: PF03996 and INTERPRO accession no. IPR007142). This family contains membrane glycoproteins that are present on viral surface and are involved with the cell infection process. It contains haemagglutinin chain 1 (HE1) and haemagglutinin chain 2 (HE2), and forms a homotrimer with each monomer being formed by two chains linked by a disulphide bond. Furthermore, PFAM and InterProScan analyses of the ORF show that amino acid residues 122 to 236 of the predicted protein are the haemagglutinin domain of HE-fusion glycoprotein family (PFAM accession no.: PF02710 and INTERPRO accession no. IPR003860). HE is also present in other Group 2 coronaviruses and influenza C virus. SignalP analysis reveals a signal peptide probability of 0.738, with a cleavage site between residues 13 and 14. Although TMpred and TMHMM analyses of the ORF show four and three transmembrane domains, respectively, PHDhtm analysis of the ORF shows only one transmembrane domain at positions 354 to 376. This concurs with only one transmembrane region reported in the C terminal of the HE of BCoV (bovine coronavirus) and puffinosis virus. PrositeScan analysis of the HE protein of CoV-HKU1 reveals eight potential N-linked glycosylation (six NXS and two NXT) sites. These are located at positions 83 (NYT), 110, (NGS), 145 (NVS), 168 (NYS), 193 (NFS), 286 (NSS), 314 (NVS, and 328 (NFT). The putative active site for neuraminate O-acetyl-esterase activity, FGDS (SEQ ID NO:18), is located at positions 31-34.

ORF 3 (bases 22942-27012) encodes the predicted S glycoprotein (PFAM accession no. PF01601) with 1356 amino acids. The S protein of CoV-HKU1 has 58-61% amino acid identities with the S proteins of other Group 2 coronaviruses, but has fewer than 35% amino acid identities with the S proteins of Group 1, Group 3, and SARS-CoV (Table 4 and FIG. 5B). InterProScan analysis predicts it as a type I membrane glycoprotein. Important features of the S protein of CoV-HKU1 are depicted in FIG. 6. PrositeScan of the S protein of CoV-HKU1 reveals 28 potential N-linked glycosylation (12 NXS and 16 NXT) sites. SignalP analysis reveals a signal peptide probability of 0.909, with a cleavage site between residues 13 and 14. By multiple alignments with the S proteins of other Group 2 coronaviruses, a potential cleavage site located after RRKRR (SEQ ID NO:19), between residues 760 and 761, where S will be cleaved into S1 and S2, is identified. Immediately upstream to RRKRR (SEQ ID NO:19), there is a series of five serine residues that are not present in any other known coronaviruses (FIG. 6). Most of the S protein (residues 15 to 1300) is exposed on the outside of the virus, with a transmembrane domain at the C terminus (TMHMM analysis of the ORF shows one transmembrane domain at positions 1301 to 1356), followed by a cytoplasmic tail rich in cysteine residues. Two heptad repeats (HR), located at residues 982 to 1083 (HR1) and 1250 to 1297 (HR2), identified by multiple alignments with other coronaviruses, are present. In MHV, it has been confirmed that the receptor for its S protein binding is CEACAMI, a member of the carcinoembryonic antigen (CEA) family of glycoproteins in the immunoglobulin superfamily. Furthermore, it has been shown, by site-directed mutagenesis, that three conserved regions (sites I, II, and III) and some amino acid residues ($Thr^{62}$, $Thr^{212}$, $Tyr^{214}$, and $Tyr^{216}$ in MHV) in the N-terminal of the S protein are particularly important for its receptor-binding activity. By multiple alignments with the N-terminal 330 amino acids of the S protein of MHV and other group 2 coronaviruses, it is observed that these conserved regions and amino acids are present in CoV-HKU1 (FIG. 6). This infers that the receptor for CoV-HKU1 could be a member of the CEA family on the surface of the cells in the respiratory tract. On the other hand, for HCoV-OC43, it has been shown in vitro that the receptor for the S protein is a sialic acid. However, the amino acid residues on the S protein of HCoV-OC43 that are important for receptor binding are not well defined.

ORF 4 (bases 27051-27380) encodes a predicted protein with 109 amino acids. This ORF overlaps with the ORF that encodes the E protein. PFAM analysis of the ORF shows that the predicted protein is a member of the coronavirus non-structural protein NS2 family (PFAM accession no.: PF04753). TMpred and TMHMM analysis do not reveal any transmembrane helix. This predicted protein of CoV-HKU1 has 44-51% amino acid identities with the corresponding proteins of other Group 2 coronaviruses.

ORF 5 (bases 27373-27621) encodes the predicted E protein with 82 amino acids. The E protein of CoV-HKU1 has 54-60% amino acid identities with the E proteins of other Group 2 coronaviruses, but has fewer than 35% amino acid identities with the E proteins of Group 1, Group 3, and SARS-CoV (Table 4 and FIG. 5B). PFAM and InterProScan analyses of the ORF show that the predicted E protein is a member of the non-structural protein NS3/Small envelope protein E (NS3_envE) family (PFAM accession no.: PF02723). SignalP analysis predicts the presence of a transmembrane anchor (probability 0.995). TMpred analysis of the ORF shows two transmembrane domains at positions 16 to 34 and 39 to 59, and TMHMM analysis of the ORF shows two transmembrane domains at positions 10 to 32 and 39 to 58, consistent with the anticipated association of the E protein with the viral envelope. Both programs predict that both the N and C termini are located on the surface of the virus.

ORF 6 (bases 27633-28304) encodes the predicted M protein with 223 amino acids. The M protein of CoV-HKU1 has 76-78% amino acid identities with the M proteins of other Group 2 coronavirus, but has fewer than 40% amino acid identities with the M proteins of Group 1, Group 3, and SARS-CoV (Table 4 and FIG. 5B). PFAM analysis of the ORF shows that the predicted M protein is a member of the coronavirus matrix glycoprotein (Corona_M) family (PFAM accession no.: PF01635). SignalP analysis predicts the presence of a transmembrane anchor (probability 0.926). TMpred analysis of the ORF shows three transmembrane domains at positions 21 to 42, 53 to 74, and 77 to 98. TMHMM analysis of the ORF shows three transmembrane domains at positions 20 to 39, 46 to 68, and 78 to 100. The N terminal 19-20 amino acids are located on the outside and the C terminal 123-125-amino acid hydrophilic domain on the inside of the virus.

ORF 7 (bases 28320-29645) encodes the predicted N protein (PFAM accession no.: PF00937) with 441 amino acids. The N protein of CoV-HKU1 has 57-62% amino acid identities with the N proteins of other Group 2 coronaviruses, but has fewer than 40% amino acid identities with the N proteins of Group 1, Group 3, and SARS-CoV (Table 4 and FIG. 5B).

ORF 8 (bases 28342-28959) encodes a hypothetical protein (N2) of 205 amino acids within the ORF that encodes the predicted N protein. PFAM analysis of the ORF shows that the predicted protein is a member of the coronavirus nucleocapsid I protein (Corona_I) family (PFAM accession no.: PF03187). This hypothetical N2 protein of CoV-HKU1 has 32-39% amino acid identities with the N2 proteins of other Group 2 coronaviruses.

We report the characterization and complete genome sequence of a novel coronavirus detected in the nasopharyngeal aspirates of patients with pneumonia. The clinical significance of the virus in the first patient was evident by the high viral loads in the patient's nasopharyngeal aspirates during the first week of his illness, which coincided with the acute symptoms developed in the patient. The viral load decreased during the second week of the illness and was undetectable in the third week of the illness. In addition, the fall in viral load was accompanied by the recovery from the illness and development of specific antibody response to the recombinant N protein of the virus. Similar to other recently discovered viruses, such as hepatitis C virus, GB virus C, transfusion transmitted virus, and SEN virus, the present virus could not be recovered from cell cultures using the standard cell lines. This could be related to the inherently low recovery rate of coronaviruses. Human coronaviruses are particularly difficult to culture in vitro. Many decades after the recognition of HCoV-229E and HCoV-OC43, there are still only a handful of primary virus isolates available and organ culture is required for primary isolation of HCoV-OC43. In our experience, SARS-CoV can only be recovered from less than 20% of patients with serologically and RT-PCR documented SARS-CoV pneumonia. Therefore, it is not surprising that the new coronavirus CoV-HKU1 has been so far proven difficult to culture in vitro. After the discovery of CoV-HKU1 in the first patient, we conducted a preliminary study on 400 nasopharyngeal aspirates that were collected last year during the SARS epidemic period. Among these 400 nasopharyngeal aspirates, CoV-HKU1 was detected in one specimen, with a viral load comparable to that of the first patient. These results have suggested that CoV-HKU1 is not only incidentally found in one patient, but a previously unrecognized coronavirus associated with pneumonia.

Genomic analysis has reveals that CoV-HKU1 is a Group 2 coronavirus. The genome organization of CoV-HKU1 concurs with those of other coronaviruses, with the characteristic gene order, i.e., 5'-replicase, S, E, M, N-3', short untranslated regions in both 5' and 3' ends, 5' conserved coronavirus core leader sequence, putative TRS upstream to multiple ORFs, and conserved pseudoknot in the 3' untranslated region. In contrast to coronaviruses of other groups, CoV-HKU1 contains certain features that are characteristics of Group 2 coronaviruses, including the presence of HE, ORF 4, and N2. Phylogenetic analysis of the $3CL^{pro}$, replicase, helicase, S, E, M, and N proteins showed that these genes of CoV-HKU1 were clustered with the corresponding genes in other Group 2 coronaviruses. However, the proteins of CoV-HKU1 formed distinct branches in the phylogenetic trees, indicating that CoV-HKU1 is a distinct member of the group, and is not very closely related to any other known members of Group 2 coronaviruses (FIGS. 4A and 4B).

In addition to phylogenetic analysis of the putative proteins, CoV-HKU1 exhibits certain features that are distinct from other Group 2 coronaviruses. Compared to other Group 2 coronaviruses, there is a deletion of about 800 bps between the replicase ORF 1b and the HE ORF 2 in CoV-HKU1. In other Group 2 coronaviruses, including MHV, SDAV, HCoV-OC43 and BCoV, an ORF of 798-837 bp (273-278 amino acids) is present between the replicase 1b ORF and the HE ORF 2. This ORF encodes a protein of the coronavirus non-structural protein NS2a family (PFAM accession no.: PF05213). The absence of this ORF in CoV-HKU1 indicates that this is probably a non-essential gene of coronavirus. In addition to the deletion, the N-terminal of the putative PLP in ORF 1a contains 14 tandem copies of a 30-bp repeat that codes for a highly acidic domain. Similar repeats, with different amino acid compositions, have been found in the genomes of human, rat and parasites, but have not been found in other coronaviruses. The function of these repeats is not well understood, although some authors have suggested that the repeats could be important antigens, and their biological role may be related to their special three-dimensional structures. The vitellaria antigenic protein of *Clonorchis sinensis* contains 23 tandem copies of a 30-bp repeat that codes for DGGAQP-PKSG (SEQ ID NO:20). In the case of *Plasmodium falciparum*, it has been shown that the antigenicity of the circumsporozoite protein is due to its repeating epitope structure. It has also been suggested that the tandemly repeated peptide may induce strong humoral immune response in the infected host and thus may also be useful in serological diagnosis. Further experiments should be performed to delineate the antigenic properties, biological role, and possible clinical usefulness of the repeat in the PLP of CoV-HKU1.

The geographical, political, and economic location of Hong Kong makes it a unique place for the study of emerging infectious disease. Hong Kong, as the gateway of southern China, with thousands of people crossing the border on surface and by air every day, has a high potential of importing and exporting infectious diseases to and from China, countries in Southeast Asia and from the rest of the world. In 1997, the first 18 human cases of avian influenza A H5N1 virus infection were reported in Hong Kong. In early 2003, two cases of human infection caused by avian influenza A (H5N1) that was acquired in Fujian, were diagnosed in Hong Kong, which provided an early warning of the impending disease threat for humans and poultry in Southeast Asia that followed in 2004. For the SARS epidemic, although both epidemiological and genomic evidence revealed that the disease had first occurred in southern China in November 2002, it did not receive as much international attention until the disease was spread to Hong Kong and through Hong Kong to Singapore, Toronto, Vietnem, and the United States of America. As for emerging bacterial infections, 50% of the patients with gastroenteritis associated with the recovery of *Laribacter hongkongensis* had recent history of travel to southern China. In this report, one of the patients also had recent history of travel to Shenzhen of China prior to the development of the respiratory illness. We speculate that he might have contacted the virus in Shenzhen. More intensive surveillance of emerging infectious pathogens in this locality is warranted.

6.2 Example 2

We prospectively collected nasopharyngeal aspirates (NPAs) from patients with community-acquired pneumonia during a 12-month period. A 453-bp fragment of the pol gene of CoV-HKU1 was amplified from the extracted RNA by RT-PCR using CoV-HKU1 specific primers. The epidemiological, clinical, laboratory and radiological features of patients with pneumonia associated with CoV-HKU1 were analyzed. Specific antibodies were detected using a recombinant CoV-HKU1 N protein based ELISA. The complete pol, S and N genes of the CoV-HKU1 were amplified and sequenced. RNA extracted from 208 nasopharyngeal swabs and fecal samples from 56 wild and domestic animals in Hong Kong and southern China were subject to RT-PCR of pol gene of CoV-HKU1 using CoV-HKU1 specific primers.

6.2.1 Patients and Microbiological Methods

All prospectively collected NPAs from patients with community-acquired pneumonia sent to the clinical microbiology laboratories of four regional hospitals in Hong Kong during a 12-month period [Mar. 22, 2003 (beginning of SARS epidemic in Hong Kong)—Mar. 21, 2004] for detection of SARS-CoV but negative for SARS-CoV RNA by RT-PCR were included in the study. Community-acquired pneumonia is defined as symptoms and signs consistent with an acute lower respiratory tract infection associated with new radiographic shadowing for which there is no other explanation that develop prior to or within 48 h after presentation to hospital. Once CoV-HKU1 was detected from NPAs, the hospital records, laboratory results and chest radiographs of the corresponding patients were retrieved and examined by two infectious disease physicians. The RNA extracted from the NPAs was subject to RT-PCR for influenza A virus and human metapneumovirus (Peiris J S M et. al., *Lancet* 2003; 361: 1319-25). Available stored serum samples were subject to serological assays for detection of antibodies against *Mycoplasma, Chlamydia, Legionella* and SARS-CoV by SERODIA-MYCO II (Fujirebio Inc., Tokyo, Japan), *Chlamydia pneumoniae* MIF IgG (Focus technologies, Cypress, Calif., USA), indirect immunofluorescence (MRL, San Diego, Calif., USA) and our recently developed enzyme-linked immunosorbent assay (ELISA), respectively (Woo P C Y et al., *Lancet* 2004; 363:841-5).

To determine the possible risk factors associated with CoV-HKU1 pneumonia, two age- and sex-matched controls per patient with CoV-HKU1 pneumonia were randomly selected from those with community-acquired pneumonia but their NPAs negative for CoV-HKU1. Controls were within five years older or younger than the corresponding patients with CoV-HKU1 pneumonia, and were admitted within 15 days before or after admission of the corresponding patients with CoV-HKU1 pneumonia. The hospital records, laboratory results and chest radiographs of the controls were retrieved and examined by the two infectious disease physicians.

6.2.2 RNA Extraction

Viral RNA was extracted from NPAs using QIAamp Viral RNA Mini Kit (QIAgen, Hilden, Germany) according to the manufacturer's instructions within 10 h upon receipt of specimens. The eluted RNA was used as the template for RT-PCR. All extracted RNA was stored immediately at −70° C. until use.

6.2.3 RT-PCR of RNA-Dependent RNA Polymerase Gene of Coronavirus-HKU1 Using Coronavirus-HKU1 Specific Primers and DNA Sequencing A 453-bp fragment of the RNA dependent RNA polymerase (pol) gene of CoV-HKU1 was amplified by RT-PCR using CoV-HKU1 specific primers, 5'-AAAGGATGTTGACAACCCTGTT-3' (LPW1926; SEQ ID NO:2968) and 5'-ATCATCATACTAAAATGCTTACA-3' (LPW1927; SEQ ID NO:2969) designed by multiple alignment of the nucleotide sequences of the pol genes of the two CoV-HKU1 (Woo, P C. et al., *J. of Virol*., 2005, p. 884-895) and those of the available pol genes of other known human coronaviruses. RT was performed using the SuperScript II kit (Invitrogen, San Diego, Calif., USA) according to manufacturer's instructions. The PCR mixture (50 μl) contained cDNA, PCR buffer (10 mM Tris-HCl pH 8.3, 50 mM KCl, 3 mM $MgCl_2$ and 0.01% gelatin), 200 μM of each dNTPs and 1.0 U Taq polymerase (Boehringer Mannheim, Germany). The mixtures were amplified in 40 cycles of 94° C. for 1 min, 48° C. for 1 min and 72° C. for 1 min, and a final extension at 72° C. for 10 min in an automated thermal cycler (Perkin-Elmer Cetus, Gouda, The Netherlands). Distilled water was used as the negative control. To ensure the high specificity of the CoV-HKU1 specific primers, RNA extracted from 200 NPAs positive for influenza A and B viruses, parainfluenza viruses 1-3, respiratory syncytial virus (RSV), or adenovirus antigens and RNA of HCoV-229E, HCoV-OC43, HCoV-NL63 and SARS-CoV were also subject to RT-PCR using the two CoV-HKU1 specific primers.

Ten microlitres of each amplified product was electrophoresed in 1.5% (w/v) agarose gel, with a molecular size marker (ΦX-174 DNA HaeIII digest, Boehringer Mannheim, Germany) in parallel. Electrophoresis in Tris-borate-EDTA buffer was performed at 100 V for 1.5 h. The gel was stained with ethidium bromide (0.5 μg/ml) for 15 minutes, rinsed and photographed under ultraviolet light illumination.

The PCR products were gel-purified using the QIAquick gel extraction kit (QIAgen, Hilden, Germany). Both strands of the PCR products were sequenced twice with an ABI Prism 3700 DNA Analyzer according to manufacturers' instructions (Applied Biosystems, Foster City, Calif., USA), using the two PCR primers. The sequences of the PCR products were compared with the sequences of the pol genes of the two CoV-HKU1 (Woo, P C. et al., *J. of Virol*., 2005, p. 884-895) and those of the pol genes of coronaviruses in the GenBank database.

6.2.4 ELISA Using Recombinant Nucleocapsid Protein of CoV-HKU1

The ELISA-based IgG and IgM antibody tests were performed according to our published protocol (Woo, P C. et al., *J. of Virol*., 2005, p. 884-895). Briefly, each well of a Nunc immunoplate (Roskilde, Denmark) was coated with purified $(His)_6$-tagged recombinant N protein (20 ng for IgG and 80 ng for IgM) for 1 h and then blocked in phosphate-buffered saline with 5% skim milk. The serum samples obtained from the patients during the acute and convalescent phase of the illness were serially diluted and were added to the wells of the $(His)_6$-tagged (SEQ ID NO: 27) recombinant N protein-coated plates in a total volume of 100 μl and incubated at 37° C. for 2 h. After washing with washing buffer five times, 100 μl of diluted horse radish peroxidase-conjugated goat anti-human IgG (1:4000) and mouse anti-human IgM (1:1000) antibodies (Zymed Laboratories Inc., South San Francisco, Calif., USA) were added to the wells and incubated at 37° C. for 1 h. After washing with washing buffer five times, 100 μl diluted 3,3',5,5'-tetramethylbenzidine (Zymed Laboratories Inc.) were added to each well and incubated at room temperature for 15 min. One hundred microlitres of 0.3 M $H_2SO_4$ were added and the absorbance at 450 nm of each well was measured. Each sample was tested in duplicate and the mean absorbance for each serum was calculated.

6.2.5 RT-PCR and Sequencing of the Complete RNA-Dependent RNA Polymerase, Spike and Nuclocapsid Genes of Coronavirus-HKU1 and Phylogenetic Analysis The complete pol, spike (S) and N genes of CoV-HKU1 from NPAs of nine of the 10 patients, with adequate amount of RNA available, were amplified and sequenced using the RNA extracted from the NPAs as template. The RNA was converted to cDNA by a combined random-priming and oligo(dT) priming strategy. The cDNA was amplified by degenerate primers designed by multiple alignment of the regions encoding the pol, S and N genes in the genomes of the two CoV-HKU1 (Woo, P C. et al., *J. of Virol*., 2005, p. 884-895) and those of other group 2 coronaviruses and additional primers designed from the results of the first and subsequent rounds of sequencing. Sequences were assembled and manually edited to produce the complete sequences of the pol, S and N genes of CoV-HKU1 from different patients. The nucleotide and the deduced amino acid sequences of the pol, S and N genes were compared to those of the two CoV-HKU1 (Woo, P C. et al., *J. of Virol*., 2005, p. 884-895) and other group 2 coronaviruses. Phylogenetic tree construction was performed using PileUp method with GrowTree (Genetics Computer Group, Inc.).

6.2.6 Animal Surveillance

Two hundred and eight nasopharyngeal swabs and faecal samples from 56 wild and domestic animals [including Chinese ferret-badger (*Melogale moschata*), domestic cat (*Felis catus*), hog-badger (*Arctonyx collaris*), masked palm civet (*Paguma larvata*), racoon dog (*Nyctereutes procyonoides*), Chinese pygmy dormouse (*Typhlomys cinereus*), common pangolin (*Manis pentadactyla*), nutria (*Myocastor coypus*), dog (*Canis familiaris*), rabbit (Leporidae family), snake (Serpentes suborder) and bat (Microchiroptera suborder)] in Hong Kong and southern China (Guan Y, et al., *Science* 2003; 302: 276-8) were subjected to RNA extraction and RT-PCR of pol gene of CoV-HKU1 using the CoV-HKU1 specific primers (LPW1926; SEQ ID NO:2968 and LPW1927; SEQ ID NO:2969) and protocol described above.

6.2.7 Results

Clinical and Laboratory Characteristics

During the 12-month period, NPAs from 418 patients [male:female=198:220, age (mean±SD)=49±26] with community-acquired pneumonia, for detection of SARS-CoV but were negative for SARS-CoV RNA by RT-PCR, were identified in the four hospitals. A 453-bp fragment of the pol gene of CoV-HKU1 was amplified and sequenced in 10 (2.5%) patients. Sequence analysis revealed 0-2% nucleotide differences between the sequences of the fragments and the sequence of the pol gene of the CoV-HKU1 from the reported index patient (patient no. 5) described in Example 1 above (FIG. 11) (Woo, P C. et al., *J. of Virol*., 2005, p. 884-895). In contrast, using our CoV-HKU1 specific primers, none of the 200 NPAs that were positive for influenza A and B viruses, parainfluenza viruses 1-3, RSV, or adenovirus antigens and RNA of HCoV-229E, HCoV-OC43, HCoV-NL63 and SARS-CoV, was RT-PCR positive.

The epidemiological, clinical and radiological characteristics of the 10 patients, including patient no. 5 (Woo, P C. et al., *J. of Virol*., 2005, p. 884-895), with community-acquired pneumonia associated with CoV-HKU1 are summarized in Table 5. No epidemiological linkage was identified among the 10 cases. All cases occurred in either winter or spring (January-May). The median age was 71.5 (range: 13-96). Seven were males and three were females. Nine were Chinese and one was an Arabian. Eight had underlying diseases, and four had underlying diseases of the respiratory tract. Four had recent travel histories to southern China. Five were smokers. Clinically, the illness was not distinguishable from other community-acquired pneumonia. Fever, productive cough and dyspnoea were common presenting symptoms. Upper respiratory tract symptoms were present in only two patients (patient nos. 1 and 5). One patient (patient no. 7) had loose stool diarrhea. Oxygen saturation on room air upon admission was <95% in two. Airspace shadows were observed in the right lungs of six patients and the left lungs of six patients. The upper, middle and lower zones were affected in two, four and nine patients respectively. All patients, except patient no. 10, had normal platelet counts and normal liver and renal function tests. Bacterial or mycobacterial pathogens were not detected in any of the sputum samples from the patients. Direct antigen detection for influenza A and B viruses, parainfluenza viruses 1-3, RSV, adenovirus (Woo P C Y et al., *J Clin Microbiol* 1997; 35: 1579-81) and RT-PCR for influenza A virus and metapneumovirus, was negative in all NPAs. Antibodies against *M. pneumoniae, C. pneumoniae, C. psittaci, L. pneumophila* and SARS-CoV were negative in all the six patients (patient nos. 1, 4, 5, 6, 8 and 9) whose serum samples were available. All these six patients showed a four-fold change in IgG titer (patient nos. 4, 5 and 6) and/or the presence of IgM (patient nos. 1, 5, 8 and 9) against CoV-HKU1.

TABLE 5

| | Patient no. | | | | |
|---|---|---|---|---|---|
| Characteristics | 1 | 2 | 3 | 4 | 5 |
| Month/Year | Mar/03 | Apr/03 | May/03 | Jan/04 | Jan/04 |
| Sex/Age | F/35 | M/66 | M/13 | M/75 | M/71 |
| Ethnic origin | Chinese | Arabian | Chinese | Chinese | Chinese |
| Underlying diseases | – | Diabetes mellitus, old myocardial infarction, gastric lymphoma | Asthma, situs inversus, dextrocardia | Hypertension | Chronic obstructive airway disease, hyperlipidaemia, abdominal aortic aneurysm |
| History of travel within two weeks of disease onset | – | – | Shenzhen, China | Guangdong, China | Shenzhen, China |
| History of smoking | – | – | – | + | + |
| Clinical features | | | | | |
| Fever | + | – | + | – | + |
| Chills | – | – | – | – | + |
| Rigor | – | – | – | – | – |
| Myalgia | – | – | – | – | – |
| Headache | – | – | – | – | + |
| Cough | + | – | + | + | + |
| Sputum | – | – | + | + | + |

TABLE 5-continued

| | | | | | |
|---|---|---|---|---|---|
| production | | | | | |
| Dyspnoea | – | + | – | + | – |
| Pleurisy | – | – | – | – | – |
| Rhinorrhoea | – | – | – | – | + |
| Sore throat | + | – | – | – | + |
| Oxygen saturation on room air (%) | 99 | 83 | 100 | 99 | 99 |
| Chest radiograph features | RLZ airspace shadows | Bilateral airspace shadows | LMZ and LLZ airspace shadows | LLZ airspace shadows | LLZ airspace shadows |
| Outcome | Survived | Died | Survived | Survived | Survived |
| Duration of hospitalization (no. of days) | 2 | Died on day 12 | 3 | 7 | 5 |

| | Patient no. | | | | |
|---|---|---|---|---|---|
| Characteristics | 6 | 7 | 8 | 9 | 10 |
| Month/Year | Jan/04 | Jan/04 | Jan/04 | Mar/04 | Mar/04 |
| Sex/Age | F/96 | M/78 | M/68 | F/83 | M/72 |
| Ethnic origin | Chinese | Chinese | Chinese | Chinese | Chinese |
| Underlying diseases | Hypertension | Chronic obstructive airway disease, diabetes mellitus | – | Chronic obstructive airway disease, parathyroid adenoma, dementia | Prostate carcinoma, cerebrovascular accident, diabetes mellitus |
| History of travel within two weeks of disease onset | – | – | Guangdong, China | – | – |
| History of smoking | – | + | – | + | + |
| Clinical features | | | | | |
| Fever | + | + | + | + | + |
| Chills | – | – | – | – | – |
| Rigor | – | – | – | – | – |
| Myalgia | – | – | – | – | – |
| Headache | – | – | – | – | – |
| Cough | – | + | + | – | + |
| Sputum production | – | + | + | – | + |
| Dyspnoea | – | + | + | + | + |
| Pleurisy | – | – | – | – | – |
| Rhinorrhoea | – | – | – | – | |
| Sore throat | – | – | – | – | – |
| Oxygen saturation on room air (%) | 97 | 97 | 95 | 99 | 88 |
| Chest radiograph features | RLZ airspace shadows | LLZ airspace shadows | RMZ airspace shadows | RLZ airspace shadows | Bilateral airspace shadows |
| Outcome | Survived | Survived | Survived | Survived | Died |
| Duration of hospitalization (no. of days) | 7 | 13 | 5 | 6 | Died on day 6 |

+ = present;
– = absent;
RUZ = right upper zone;
LUZ = left upper zone;
RMZ = right middle zone;
LMZ = left middle zone;
RLZ = right lower zone;
LLZ = left lower zone In comparison with age- and sex-matched controls with non-CoV-HKU1 pneumonia, no epidemiological, clinical, haematological, serum biochemical and radiological risk factors were identified in patients with CoV-HKU1 pneumonia (Table 6).

TABLE 6

| | Pneumonia* | | |
|---|---|---|---|
| | CoV-HKU1 (n = 10) | Non-CoV-HKU1 (n = 20) | P value |
| Characteristics | | | |
| Underlying diseases | 8 | 12 | 0.42 |
| History of travel within two weeks of disease onset | 4 | 6 | 0.69 |
| History of smoking | 5 | 7 | 0.46 |
| Clinical features | | | |
| Fever | 8 | 14 | 0.68 |
| Cough | 7 | 17 | 0.37 |
| Sputum production | 6 | 12 | 1.00 |
| Dyspnoea | 6 | 6 | 0.12 |
| Rhinorrhoea | 1 | 2 | 1.00 |
| Sore throat | 2 | 2 | 0.58 |
| Haematological features | | | |
| Haemoglobin (g/dl) | 12.4 | 13.2 | 0.27 |
| Leukocyte count ($\times 10^9$/l) | 9.9 | 9.7 | 0.95 |
| Neutrophil count ($\times 10^9$/l) | 7.35 | 7.4 | 0.71 |
| Lymphocyte count ($\times 10^9$/l) | 0.95 | 1.02 | 0.48 |
| Monocyte count ($\times 10^9$/l) | 0.55 | 0.65 | 0.35 |
| Platelet count ($\times 10^9$/l) | 240 | 292 | 0.20 |
| Serum biochemical features | | | |
| Sodium (mmol/l) | 136 | 137 | 0.59 |
| Potassium (mmol/l) | 3.9 | 4.0 | 0.42 |
| Creatinine (μmol/l) | 92 | 76.5 | 0.06 |
| Urea (mmol/l) | 5.25 | 4.9 | 0.62 |
| Albumin (g/l) | 37 | 38 | 0.59 |
| Globulin (g/l) | 36.5 | 30 | 0.07 |
| Bilirubin (μmol/l) | 12 | 10 | 1.00 |
| ALT (U/l) | 20 | 17 | 0.42 |
| Alkaline phosphatase (U/l) | 102 | 91 | 0.95 |
| Oxygen saturation on room air (%) | 96 | 98 | 0.86 |
| Radiological features | | | |
| Bilateral involvement | 2 | 5 | 1.00 |
| No. of zones involved | 1 | 1 | 0.81 |
| Mortality | 2 | 0 | 0.10 |

*Continuous variables are expressed as median and categorical variables as no. of patients with the presence of the characteristics.

Two of the 10 patients died of CoV-HKU1 pneumonia. The first patient (patient no. 2) was a 66-year old man who presented with dyspnoea for one day. He had type 2 diabetes mellitus, old myocardial infarction and gastric lymphoma with total gastrectomy in 2002 and was put on chemotherapy. He had severe lymphopenia ($0.2\times10^9$/L) and an oxygen saturation of only 83% on admission. Chest radiograph revealed patchy airspace shadows in both lungs with predominant involvement of the lower zones (FIG. 12A). He died 11 days after admission. The other patient (patient no. 10) was a 72-year old man who presented with fever and productive cough for one week. He had type 2 diabetes mellitus, cerebrovascular accident and prostatic carcinoma with bone metastasis complicated by spinal cord compression with laminectomy and Luque instrumentation performed. He had lymphopenia ($0.9\times10^9$/L), thrombocytopenia ($33\times10^9$/L), deranged liver and renal function tests and an oxygen saturation of only 88% on admission. Chest radiograph revealed extensive airspace shadows in both lungs, with the middle zones more severely involved (FIG. 12B). He died 5 days after admission.

The clinical, laboratory and radiological characteristics of patients who survived and those who died with community acquired pneumonia associated with CoV-HKU1 were compared (Table 7). Patients who died had lower hemoglobin concentration (P=0.04), monocyte count (P=0.04), serum albumin (P=0.04) and oxygen saturation on admission (P=0.03) and bilateral involvement (P=0.003) and more number of zones involved (P=0.01) on chest radiograph.

TABLE 7

| | Outcome* | | |
|---|---|---|---|
| | Survived (n = 8) | Died (n = 2) | P value |
| Characteristics | | | |
| Sex (M:F) | 5:3 | 2:0 | 1.00 |
| Age | 73 | 69 | 0.60 |
| Underlying diseases | 6 | 2 | 0.45 |
| History of travel within two weeks of disease onset | 4 | 0 | 0.24 |
| History of smoking | 4 | 1 | 1.00 |
| Clinical features | | | |
| Fever | 7 | 1 | 0.26 |
| Cough | 6 | 1 | 0.51 |
| Sputum production | 5 | 1 | 0.76 |
| Dyspnoea | 4 | 2 | 0.22 |
| Rhinorrhoea | 1 | 0 | 0.62 |
| Sore throat | 2 | 0 | 0.45 |
| Haematological features | | | |
| Haemoglobin (g/dl) | 13.4 | 9 | 0.04 |
| Leukocyte count ($\times 10^9$/l) | 9.7 | 7.85 | 0.43 |
| Neutrophil count ($\times 10^9$/l) | 7.4 | 6.9 | 0.79 |
| Lymphocyte count ($\times 10^9$/l) | 1.35 | 0.55 | 0.15 |
| Monocyte count ($\times 10^9$/l) | 0.7 | 0.3 | 0.04 |
| Platelet count ($\times 10^9$/l) | 292 | 200.5 | 0.79 |
| Serum biochemical features | | | |
| Sodium (mmol/l) | 137.5 | 134 | 0.11 |
| Potassium (mmol/l) | 3.9 | 4.5 | 0.06 |
| Creatinine (μmol/l) | 79 | 76.5 | 0.69 |
| Urea (mmol/l) | 4.6 | 10.75 | 0.19 |
| Albumin (g/l) | 38.5 | 26 | 0.04 |
| Globulin (g/l) | 30 | 30 | 1.00 |
| Bilirubin (μmol/l) | 10 | 30.5 | 0.79 |
| ALT (U/l) | 16.5 | 30.5 | 0.36 |
| Alkaline phosphatase (U/l) | 86 | 190.5 | 0.07 |
| Oxygen saturation on room air (%) | 99 | 85.5 | 0.03 |
| Radiological features | | | |
| Bilateral involvement | 0 | 2 | 0.003 |
| No. of zones involved | 1 | 6 | 0.01 |

*Continuous variables are expressed as median and categorical variables as no. of patients with the presence of the characteristics.

RT-PCR and Sequencing of the Complete RNA-Dependent RNA Polymerase, Spike and Nucleocapsid Genes of Coronavirus-HKU1 and Phylogenetic Analysis The complete pol (FIG. 11), S (FIG. 13) and N (FIG. 14) genes of CoV-HKU1 from NPAs of nine of the 10 patients, with adequate amount of RNA available, were amplified and sequenced. The phylogenetic trees and non-synonymous mutations and the corresponding amino acid changes are shown in FIG. 15. In all three genes, the phylogenetic trees using nucleotides or amino acids for construction showed the same topologies. For the S gene, there were 317 and 306 nucleotide positions with synonymous and non-synonymous mutations respectively (FIG. 15B). For the N gene, there were 42 and 53 nucleotide positions with synonymous and non-synonymous mutations respectively (FIG. 15C). The nucleotide sequences of seven of the nine S or N genes showed similar sequences (genotype A, FIGS. 15B and 15C) and those of the other two also showed similar sequences (genotype B, FIGS. 15B and 15C). For the CoV-HKU1 from patient 1, two peaks (T and C) were consistently observed at nucleotide position 1300 of the N gene, suggesting the presence of quasi-species (FIG. 15C). For the pol gene, there were 95 and 13 nucleotide positions with synonymous and non-synonymous mutations respectively (FIG. 15A). The nucleotide sequences of the pol genes in the seven CoV-HKU1 of genotype A were also clustered together (FIG. 15A). Interestingly, the seven CoV-HKU1 of genotype A were from seven patients with underlying diseases and the two of genotype B were from the two patients without underlying diseases (Table 5). Furthermore, multiple alignments of the nucleotides sequences of the pol genes of the nine CoV-HKU1 and those of HCoV-OC43, HCoV-229E, HCoV-NL63 and SARS-CoV revealed that the primers we used in the present study should be specific for CoV-HKU1 (FIG. 16).

Animal Surveillance

None of the 208 nasopharyngeal swabs and faecal samples from 56 wild and domestic animals in Hong Kong and southern China was positive for CoV-HKU1 RNA.

6.2.8 Discussion

CoV-HKU1, a novel group 2 coronavirus, is associated with community-acquired pneumonia. Since the SARS epidemic in 2003, we have started to prospectively collect NPAs and store the extracted RNA from patients with community-acquired pneumonia so that when a novel virus is discovered, the epidemiology and hence the clinical, laboratory and radiological features of the disease can be studied timely. In January 2004, we discovered a novel coronavirus, CoV-HKU1, from a patient with community-acquired pneumonia (Woo, P C. et al., *J. of Virol*., 2005, p. 884-895). The RNA extracted from prospectively collected NPAs were immediately retrieved and the presence of CoV-HKU1 RNA looked for. Ten of the 418 NPAs were positive for RNA of CoV-HKU1, giving an incidence of 2.5%. The presence of CoV-HKU1 RNA in these specimens was genuine, instead of due to contamination, as amplification and sequencing of multiple genes (pol, S and N) of CoV-HKU1 indicated the presence of CoV-HKU1 with different nucleotide sequences in the NPAs from the different patients. Moreover, the clinical significance of CoV-HKU1 was further confirmed by the presence of specific antibody responses in all six patients whose serum samples were available.

Similar to HCoV-229E, HCoV-OC43 and HCoV-NL63, CoV-HKU1 is probably a human coronavirus that is endemic in human. Similar to other human coronavirus infections, cases of CoV-HKU1 pneumonia also occurred in winter and spring. Most patients with CoV-HKU1 pneumonia were old (80% older than 65) with major underlying diseases, especially those of the respiratory and cardiovascular systems. In order to study the phylogeny and relationships among the 10 CoV-HKU1, we sequenced the pol, S and N genes of the nine CoV-HKU1 cases which provided adequate amount of RNA. Combined with the data of partial sequencing of the pol genes of the 10 CoV-HKU1 (FIG. 17), results showed that unlike the epidemiology of SARS-CoV, the 10 CoV-HKU1 were not clonal and the topology of the phylogenetic trees did not follow the pattern of a clonal outbreak (FIG. 15). Interestingly, the phylogenetic tress constructed using the sequences of both the S and N genes showed that CoV-HKU1 of genotype B was associated with the two patients without underlying diseases, but CoV-HKU1 of genotype A was associated with patients with underlying diseases (Table 5; and FIGS. 16B and 16C). Sequencing of more CoV-HKU1 may reveal the presence of genotypes or clades of CoV-HKU1 with differential virulence. To investigate for the possibility of an animal reservoir of CoV-HKU1, we tried to look for the presence of CoV-HKU1 RNA from wild and domestic animals in Hong Kong and southern China by RT-PCR. Our results revealed that none of the specimens showed the presence of CoV-HKU1 RNA. With the results of these clinical epidemiology, molecular epidemiology and eco-epidemiology studies, we conclude that CoV-HKU1 is probably a human coronavirus.

Compared with SARS-CoV pneumonia, CoV-HKU1 pneumonia is a monophasic disease and most patients had relatively mild symptoms that were localized to the respiratory tract and were only briefly hospitalized. SARS-CoV pneumonia is often described as a biphasic disease, with the first phase due to cell lysis as a result of active viral replication, and the second phase may be due to immunopathological damage (Peiris J S M et al., *Lancet* 2003; 361: 1319-25; Peiris J S M et al., *Lancet* 2003; 361: 1767-72). On the other hand, all 10 patients with CoV-HKU1 pneumonia showed the pattern of a monophasic disease. Although dyspnoea was present in half of the patients with CoV-HKU1 pneumonia at initial presentation, as compared to only about 20% of patients with SARS-CoV pneumonia at initial presentation (Peiris J S M et al., *Lancet* 2003; 361: 1319-25), patients with CoV-HKU1 pneumonia often recovered quickly, but patients with SARS-CoV pneumonia deteriorated after 7-10 days (Peiris J S M et al., *Lancet* 2003; 361:1319-25; Peiris J S M et al., *Lancet* 2003; 361: 1767-72). For the eight patients who recovered, the median duration of hospitalization was only 5.5 days. This rapid recovery of patients with CoV-HKU1 pneumonia could be related to the rapid control of the virus by the immune system. This is in line with our previous study showing the index patient (patient 5) with CoV-HKU1 pneumonia had his peak viral load at around day 3 after onset of illness (Woo, P C. et al., *J. of Virol*., 2005, p. 884-895). Moreover, only one of the patients had extrapulmonary symptoms and all available extrapulmonary specimens (stool, urine and serum) were RT-PCR negative for CoV-HKU1 (unpublished data). On the other hand, for SARS-CoV pneumonia, patients usually had their peak viral loads 7-10 days after the onset of illness (Peiris J S M et al., *Lancet* 2003; 361: 1767-72). Furthermore, the virus can be readily detected in extrapulmonary specimens, in which the viral loads correlated with the manifestations in the corresponding systems (Hung, I F N et al., *Emerg Infect Dis* 2004; 10: 1550-1557). These imply that the virus was not well controlled by the immune system in the initial phase of the illness.

Despite the relatively mild disease in most patients, CoV-HKU1 pneumonia is associated with mortality in a minority of patients who had lower haemoglobin concentration, monocyte count, serum albumin and oxygen saturation on admission and more extensive involvement on chest radiograph. As in most cases of pneumonia, more extensive involvement in the lungs will result in poor gaseous exchange and hence hypoxia and eventually fatality. The lower haemoglobin concentration, monocyte count and serum albumin could represent poorer premorbid states and narrower margins to fight against infections. Both patients who died had underlying diabetes mellitus, malignancy (gastric lymphoma in one and carcinoma of the prostate in the other) and cardiovascular disease (old myocardial infarct in one and cerebrovascular accident in the other).

7. MARKET POTENTIAL

The two genomic types of CoV-HKU1 are completely sequenced. These sequences allow the development of various diagnostic tests and therapeutic methods as described hereinabove. In addition, the genetic information of CoV-HKU1 is extremely important and valuable for clinical and scientific research applications.

8. EQUIVALENTS

Those skilled in the art will recognize, or be able to ascertain many equivalents to the specific embodiments of the invention described herein using no more than routine experimentation. Such equivalents are intended to be encompassed by the following claims.

All publications, patents and patent applications mentioned in this specification are herein incorporated by reference into the specification.

Citation or discussion of a reference herein shall not be construed as an admission that such is prior art to the present invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07371837B2). An electronic copy of the "Sequence Listing" will also be available from the USPTO upon request and payment of the fee set forth in 37 CFR 1.19(b)(3).

What is claimed:

1. An isolated nucleic acid molecule comprising the nucleotide sequence of SEQ ID NO:2919, or the full length complement thereof.

2. An isolated nucleic acid molecule comprising a replicase gene of coronavirus HKU1 strain (CoV-HKU1), wherein the said replicase gene comprises a nucleotide sequence selected from the group consisting of SEQ ID NO:2920, 2922, 2924, 2926, 2928, 2930, 2932 and 2934.

3. A vector comprising the nucleic acid molecule of claim 1.

4. A vector comprising the nucleic acid molecule of claim 2.

5. An isolated host cell comprising the vector of claim 3.

6. An isolated host cell comprising the vector of claim 4.

7. An isolated replicase polypeptide encoded by the nucleic acid molecule of claim 2.

8. An isolated nucleic acid molecule encoding the polypeptide of claim 7.

* * * * *